(12) United States Patent
Pittman et al.

(10) Patent No.: US 7,251,568 B2
(45) Date of Patent: Jul. 31, 2007

(54) METHODS AND COMPOSITIONS FOR REGULATING BONE AND CARTILAGE FORMATION

(75) Inventors: Debra D. Pittman, Windham, NH (US); Brian M. Clancy, Ashland, MA (US)

(73) Assignee: Wyeth, Madison, NJ (US)

( * ) Notice: Subject to any disclaimer, the term of this patent is extended or adjusted under 35 U.S.C. 154(b) by 452 days.

(21) Appl. No.: 10/329,056

(22) Filed: Dec. 23, 2002

(65) Prior Publication Data

US 2004/0073377 A1    Apr. 15, 2004

Related U.S. Application Data

(63) Continuation-in-part of application No. 10/125,691, filed on Apr. 18, 2002, now abandoned.

(60) Provisional application No. 60/284,786, filed on Apr. 18, 2001.

(51) Int. Cl.
    *G01N 33/48* (2006.01)
(52) U.S. Cl. .......................... 702/19; 702/20; 435/6; 435/7.1; 436/501; 703/11
(58) Field of Classification Search ............... None
    See application file for complete search history.

(56) References Cited

U.S. PATENT DOCUMENTS

| | | | |
|---|---|---|---|
| 5,631,142 A * | 5/1997 | Wang et al. | 435/69.1 |
| 5,928,940 A | 7/1999 | Sampath et al. | 435/325 |
| 5,966,711 A | 10/1999 | Adams | 707/104 |
| 6,071,695 A | 6/2000 | Ozkaynak et al. | 435/6 |
| 6,083,690 A | 7/2000 | Harris et al. | 435/6 |
| 6,706,867 B1 * | 3/2004 | Lorenz | 536/23.1 |

FOREIGN PATENT DOCUMENTS

WO    WO 99/05323    2/1999

OTHER PUBLICATIONS

Elson et al.; "Cytokine-Like Factor-1, a Novel Soluble Protein, Shares Homology with Members of the Cytokine Type 1 Receptor Family[1]", The Journal of Immunology 161: 1371-1379, (1998).

Elson et al.; "CLF Associates with CLC TO Form a Functional Heteromeric Ligand for the CNTF Receptor Complex", Nature Neuroscience 3(9): 867-872, (Sep. 2000).

Heller et al.; "Discovery and Analysis of Inflammatory Disease-related Genes Using cDNA Microarrays", Proc. Natl. Acad. Sci. USA, 94: 2150-2155, (Mar. 1997).

Lelievre et al.; "Signaling Pathways Recruited by the Cardiotrophin-like Cytokine/Cytokine-like Factor-1 Composite Cytokine", The Journal of Biological Chemistry, 276(25): 22476-22484, (Jun. 22, 2001).

Velasco et al.; "Cloning and Characterization of Human MMP-23, a New Matrix Metalloproteinase Predomonantly Expressed in Reproductive Tissues and Lacking Conserved Domains in Other Family Members", The Journal of Biological Chemistry, 274(8): 4570-4576, (1999).

Database Caplus, DN 133:84852, Van Steenseli et al. Probing the Gene Expression Database for Candidate Genes. European Journal of Human Genetics. 1999, vol. 7(8):910-919.

Database GenBank, Accession No. AB040038, Mus Musculus CRLM3 mRNA for Cytokine Receptor like Molecule 3, Complete eds. Mar. 16, 2000.

International Search Report Completed on Oct. 11, 2002 and Mailed on Dec. 19, 2002.

* cited by examiner

*Primary Examiner*—Mary K. Zeman
(74) *Attorney, Agent, or Firm*—Fitzpatrick, Cella, Harper & Scinto

(57) ABSTRACT

The invention provides methods and compositions for diagnostic assays for detecting bone and cartilage formation and therapeutic methods and compositions for treating disease and disorders related to bone and cartilage formation or resorption, such as osteoporosis and bone fractions. The invention also provides therapeutic methods for diseases related to bone or cartilage formation or resorption. Methods for identifying therapeutics for such diseases are also provided.

8 Claims, 3 Drawing Sheets

METHODS AND COMPOSITIONS FOR REGULATING BONE AND CARTILAGE FORMATION

CROSS-REFERENCE TO RELATED APPLICATIONS

This application is a continuation-in-part of application Ser. No. 10/125,691, entitled "Methods and Compositions for Regulating Bone and Cartilage Formation", filed Apr. 18, 2002, now abondaned which application claims the benefit of U.S. Provisional Application No. 60/284,786, filed on Apr. 18, 2001. The contents of both applications are specifically incorporated by reference herein.

BACKGROUND OF THE INVENTION

Bone formation is an essential process in embryonic development and plays a critical role in many diseases and conditions which affect millions of humans. For example, osteoporosis is a debilitating disease characterized by excessive bone loss that affects approximately 14 million Americans and costs the U.S. health care system nearly $10 billion annually. In about 40 percent of women and 13 percent of men over 50, osteoporosis is the underlying cause of most hip, spine, and wrist fractures. Recent studies estimate that as much as 70 percent of the variation in bone density is inherited. Bone density reaches adult levels at approximately 18–22 years of life and remains relatively stable until middle age. Loss of bone density in the elderly is the consequence of known factors such as menopause, inadequate nutrition, specific medical conditions, and unknown factors such as a person's genetic constitution. Physicians have very few available drugs to treat declining bone density and need drugs that will promote bone formation in patients.

Bone is continuously remodeled through a coupled process of bone resorption and bone formation. During bone resorption, osteoclasts attach to the mineralized bone matrix and excavate small pits on the bone surface, releasing bone collagen and minerals in the circulation. Subsequently, cross-linked N-telopeptides are released into the bloodstream during osteoclastic activity. During bone formation, osteoblasts are recruited to the newly resorbed areas on the bone where they deposit new collagen. When resorption and formation are in balance, there is no net change in bone mass. After a resting phase during which the bone is mineralized, the remodeling cycle begins again.

In addition to bone formation, another important role for osteoprogenitor cells is in vascular calcification (see, e.g. Curr Opin Nephrol Hypertens (2000) 9: 11–15). Calcification is a component of vascular disease that usually occurs in concert with atheroma formation but through distinct pathophysiological processes. Vessel wall osteoprogenitor cells known as calcifying vascular cells can form bone matrix proteins and calcified nodules, analogous to osteoblastic differentiation in bone. These cells have been isolated from the tunica media of bovine and human arteries, and both in-vitro tissue culture models and mouse models of vascular calcification have been established. Studies of the effects of diabetes mellitus, hyperlipidemia, estrogens and glucocorticoids on calcifying vascular cell function provide insight into the relationship between common human disease states and vascular calcification.

While endochondral bone formation has been fairly well characterized from a morphological perspective, this process remains largely undefined at a gene transcriptional level. In vitro and in vivo studies have suggested that bone morphogenetic protein-2 (BMP-2) plays an important role in bone formation, however a detailed understanding of the molecular mechanisms involved would be useful to identify potential genetic targets for controlling bone formation. Accordingly, an understanding of the biochemical and molecular events underlying bone formation, and in particular the identity of the gene(s) expressed during bone and cartilage formation, would provide significant diagnostic and therapeutic applications for the treatment of diseases relating to bone and cartilage formation or resorption, such as osteoporosis, bone fractures and rheumatoid arthritis.

SUMMARY OF THE INVENTION

In one embodiment, the invention provides computer-readable media comprising a plurality of digitally encoded values representing the levels of expression of a plurality of genes listed in Table 1, 2, 5, 6 and/or 7 during bone or cartilage formation. The computer-readable medium may comprise values representing levels of expression of at least 5 genes listed in Table 1, 2, 5, 6 and/or 7. The computer-readable medium may comprise values representing levels of expression of CLF-1 and MMP23 during bone or cartilage formation. The computer-readable medium may comprise values representing levels of expression of a plurality of genes listed in Table 6. The computer-readable medium may further comprise at least one value representing a level of expression of at least one gene that is up-or down-regulated during bone or cartilage formation in a precursor cell. In other embodiments, the computer-readable medium may comprise at least one value representing a level of expression of at least one gene that is up-or down-regulated during a particular stage of bone or cartilage formation. Further, the computer-readable medium may comprise values representing levels of expression of at least one of Cyr61, Col2a1, Runx2, and Ctsk during bone or cartilage formation. In certain embodiments, the computer-readable medium may comprise values representing levels of expression of a plurality of genes listed in Table 7. In still other embodiments, the computer-readable medium may comprise at least one value representing a level of expression of at least one gene that is co-regulated or functionally connected with a gene that is up-or down-regulated during a particular stage of bone or cartilage formation. The values on the computer-readable medium may represent ratios of, or differences between, a level of expression of a gene in one sample and the level of expression of the gene in another sample. In certain embodiments, less than about 50% of the values in the computer-readable medium represent expression levels of genes which are not listed in Table 1, 2, 5, 6 and/or 7.

In another embodiment, the invention provides computer systems, comprising, e.g., a database comprising values representing expression levels of a plurality of genes listed in Table 1, 2, 5, 6 and/or 7 during bone or cartilage formation; and, a processor having instructions to, receive at least one query value representing at least one level of expression of at least one gene listed in Table 1, 2, 5, 6 and/or 7; and, compare the at least one query value and the at least one database value. The query value may represent the level of expression of a gene listed in Table 1, 2, 5, 6 and/or 7 in a diseased cell of a subject having or susceptible of having a disease selected from the group consisting of osteodystrophy, osteohypertrophy, osteoblastoma, osteopertrusis, osteogenesis imperfecta, osteoporosis, osteopenia, osteoma and osteoblastoma; periondontal disease; hyperparathyroidism; hypercalcemia of malignancy; Paget's disease;

osteolytic lesions produced by bone metastasis; bone loss due to immobilization or sex hormone deficiency; bone and cartilage loss caused by an inflammatory disease, rheumatoid arthritis, osteoarthritis and bone fractures. Further, the query value may represent the level of expression of a gene listed in Table 1, 2, 5, 6 and/or 7 in a precursor cell for which the stage of bone or cartilage formation is unknown.

The invention further provides computer programs for analyzing levels of expression of a plurality of genes listed in Table 1, 2, 5, 6 and/or 7 in a cell, the computer program being disposed on a computer readable medium and including instructions for causing a processor to: receive query values representing levels of expression of a plurality of genes listed in Table 1, 2, 5, 6 and/or 7 in a query cell, and, compare the query values with levels of expression of the plurality of genes listed in Table 1, 2, 5, 6 and/or 7 in a reference cell.

Also provided by the invention are compositions comprising a plurality of detection agents of genes listed in Table 1, 2, 5, 6 and/or 7, which detection agents are capable of detecting the expression of the genes or the polypeptides encoded by the genes, and wherein, e.g., less than about 50% of the detection agents are of genes which are not listed in Table 1, 2, 5, 6 and/or 7. The composition may comprise detection agents of CLF-1 or MMP23. Other compositions comprise detection agents of Cyr61, Col2a1, Runx2, or Ctsk. Still other compositions comprise detection agents of genes having expression profiles similar to Cyr61, Col2a1, Runx2, or Ctsk. The detection agents may be isolated nucleic acids that hybridize specifically to nucleic acids corresponding to the genes, e.g., at least about 5, 10 or 100 genes of Table 6. Other compositions comprise a plurality of antagonists of a plurality of genes listed in Table 1, 2, 5, 6 and/or 7, e.g., antisense nucleic acids, siRNAs, ribozymes or dominant negative mutants. Yet other compositions comprise a plurality of agonists of a plurality of genes listed in Table 1, 2, 5, 6 and/or 7.

Also within the scope of the invention are solid surfaces to which are linked a plurality of detection agents of genes which are listed in Table 1, 2, 5, 6 and/or 7, which detection agents are capable of detecting the expression of the genes or the polypeptides encoded by the genes, and wherein, e.g., less than about 50% of the detection agents are not detecting genes listed in Table 1, 2, 5, 6 and/or 7. The detection agents may be isolated nucleic acids that hybridize specifically to the genes. The detection agents may be covalently linked to the solid surface.

Also provided are methods for determining the difference between levels of expression of a plurality of genes in Table 1, 2, 5, 6 and/or 7 in a cell and reference levels of expression of the genes, comprising, e.g., providing RNA from the cell; determining levels of RNA of a plurality of genes listed in Table 1, 2, 5, 6 and/or 7 to obtain the levels of expression of the plurality of genes in the cell; and comparing the levels of expression of the plurality of genes in the cell to a set of reference levels of expression of the genes, to thereby determine the difference between levels of expression of the plurality of genes listed in Table 1, 2, 5, 6 and/or 7 in the cell and reference levels of expression of the genes. The set of reference levels of expression may include the levels of expression of the genes during bone or cartilage formation. The set of reference levels of expression may also include the levels of expression of the genes during a particular stage of bone or cartilage formation. The set of reference levels of expression may further include the levels of expression of the genes in a precursor cell. The set of reference levels of expression may further include the levels of expression of the genes during a stage of bone or cartilage formation in a precursor cell. The cell may be a cell of a subject having or susceptible of having a disease selected from the group consisting of osteodystrophy, osteohypertrophy, osteoblastoma, osteopertrusis, osteogenesis imperfecta, osteoporosis, osteopenia, osteoma and osteoblastoma; periondontal disease; hyperparathyroidism; hypercalcemia of malignancy; Paget's disease; osteolytic lesions produced by bone metastasis; bone loss due to immobilization or sex hormone deficiency; bone and cartilage loss caused by an inflammatory disease, rheumatoid arthritis, osteoarthritis and bone fractures. The method may comprise incubating a nucleic acid sample derived from the RNA of the cell of the subject with nucleic acids corresponding to the genes, under conditions wherein two complementary nucleic acids hybridize to each other. The nucleic acids corresponding to the genes may be attached to a solid surface. The method may comprise entering the levels of expression of the plurality of genes into a computer that comprises a memory with values representing the set of reference levels of expression. Comparing the level may comprise providing to the computer instructions to perform.

In another embodiment, the invention provides methods for determining whether a subject has or is likely to develop a disease related to bone or cartilage resorption, comprising, e.g., obtaining a biological sample from the subject and comparing gene expression levels in the biological sample to those of a set of reference levels of expression during normal bone and cartilage formation, wherein significant differences in the levels of expression of the plurality of genes indicates that the subject has or is likely to develop a disease related to bone or cartilage resorption. The disease may be selected from the group consisting of osteoporosis, osteopenia, periondontal disease; osteolytic lesions produced by bone metastasis; bone loss due to immobilization or sex hormone deficiency; bone and cartilage loss caused by an inflammatory disease, rheumatoid arthritis and osteoarthritis.

In another embodiment, the invention provides methods for determining whether a subject has or is likely to develop a disease related to bone or cartilage formation, comprising, e.g., obtaining a biological sample from the subject and comparing gene expression levels in the biological sample to those of a set of reference levels of expression during normal bone and cartilage formation, wherein significant similarities in the levels of expression of the plurality of genes indicates that the subject has or is likely to develop a disease related to bone or cartilage formation. The disease may be selected from the group consisting of osteodystrophy, osteohypertrophy, osteoblastoma, osteopertrusis, osteogenesis imperfecta, osteoma and osteoblastoma, hyperparathyroidism; hypercalcemia of malignancy; and Paget's disease.

In yet another embodiment, the invention provides methods for determining the effectiveness of a treatment intended to stimulate bone or cartilage formation, comprising, e.g., obtaining a biological sample from the subject and comparing gene expression levels in the biological sample to those of a set of reference levels of expression during normal bone and cartilage formation, wherein significant similarities in the levels of expression of the plurality of genes indicates that the treatment is effective. The biological sample may be obtained from the healing region of a bone fracture and a similarity in levels of expression of the plurality of genes in the cell of the subject and the reference levels of expression indicates that the fracture is healing. The method may further comprise iteratively providing a biological sample from the subject, such as to determine an evolution of the levels of expression of the genes in the subject. The set of reference levels of expression may be in the form of a database. The database may be included in a computer-readable medium. The database may be in communications with a microprocessor and microprocessor instructions for providing a user interface to receive expression level data of a subject and to compare the expression level data with the database.

The invention also provides methods for determining the effectiveness of a treatment intended to reduce bone or cartilage formation, comprising, e.g., obtaining a biological sample from the subject and comparing gene expression levels in the biological sample to those of a set of reference levels of expression during normal bone and cartilage formation, wherein significant differences in the levels of expression of the plurality of genes indicates that the treatment is effective.

The methods of the invention may comprise obtaining a sample; identifying expression levels of a plurality of genes listed in Table 1, 2, 5, 6 and/or 7 from the sample; determining whether the levels of expression of the genes in the patient sample are more similar to those of a cell differentiating into bone or cartilage or to those of a precursor cell; and transmitting the results. The results may be transmitted across a network.

The invention also provides methods for identifying a compound for treating a disease related to bone or cartilage formation, comprising, e.g., providing levels of expression of a plurality of genes listed in Table 1, 2, 5, 6 and/or 7 in a cell of a subject incubated with a test compound; providing levels of expression of a cell differentiating into bone or cartilage; and comparing the two levels of expression, wherein significantly different levels of expression in the two cells indicates that the compound is likely to be effective for treating a disease related to bone or cartilage formation. Also provided are methods for identifying a compound for treating a disease related to bone or cartilage resorption, comprising, e.g., providing levels of expression of a plurality of genes listed in Table 1, 2, 5, 6 and/or 7 in a cell of a subject incubated with a test compound; providing levels of expression of a cell differentiating into bone or cartilage; and comparing the two levels of expression, wherein significantly similar levels of expression in the two cells indicates that the compound is likely to be effective for treating a disease related to bone or cartilage formation.

In yet another embodiment, the invention provides a method for identifying a compound that modulates bone or cartilage formation, comprising, e.g., contacting a precursor cell with an agent that stimulates bone or cartilage formation and a test compound; and determining the level of expression of one or more genes of Tables 1, 2, 6 and 7 during the bone or cartilage formation; wherein a significant similarity or difference between the expression level of the genes in the cell and reference expression levels of the genes during bone or cartilage formation indicates that the test compound modulates bone or cartilage formation. The reference expression levels may be essentially identical to the levels set forth in Table 1, 2, 5, 6 and/or 7. Other methods for identifying a compound that stimulates bone or cartilage formation, comprises, e.g., contacting a precursor cell with a test compound; and determining the level of expression of one or more genes of Tables 1, 2, 6 and 7 in the cell over time; wherein a similarity between the expression level of the genes in the cell and reference expression levels of the genes during bone or cartilage formation indicates that the test compound stimulates bone or cartilage formation. The reference expression levels may be levels set forth in Table 1, 2, 5, 6 and/or 7.

Also provided are methods for identifying a compound that binds to a polypeptide encoded by a gene listed in Table 1, 2, 5, 6 and/or 7, comprising, e.g., contacting a polypeptide encoded by a gene listed in Table 1, 2, 5, 6 and/or 7 with a test compound under essentially physiological conditions; and determining whether the compound binds to the polypeptide. In another embodiment, the invention provides a method for identifying a compound that modulates a biological activity of a polypeptide encoded by a gene listed in Table 1, 2, 5, 6 and/or 7, comprising, e.g., contacting a polypeptide encoded by a gene listed in Table 1, 2, 5, 6 and/or 7 with a test compound under essentially physiological conditions; and determining the biological activity of the polypeptide, wherein a higher or lower biological activity of the polypeptide in the presence of the test compound relative to the absence of the test compound indicates that the test compound modulates the biological activity of the polypeptide. The gene may be CLF-1 or MMP23. Other methods for identifying a compound for treating a disease related to bone or cartilage formation or resorption, comprise, e.g., identifying a compound that modulates the activity of a polypeptide encoded by a gene listed in Table 1, 2, 6 or 7; and contacting a precursor cell with the compound in the presence or absence of an agent that stimulates the differentiation into bone or cartilage, wherein stimulation or inhibition of bone or cartilage formation from the cell indicates that the test compound is effective for treating a disease related to bone or cartilage formation or resorption.

The invention also provides methods of treatment, e.g., methods for treating a disease related to bone or cartilage formation or resorption, comprising administering to a subject having a disease related to bone or cartilage formation or resorption a compound that modulates the biological activity of a polypeptide encoded by a gene listed in Table 1, 2, 5, 6 and/or 7 and thereby modulates bone or cartilage formation, to thereby treat the disease in the subject.

Also within the scope of the invention are diagnostic or drug discovery kits, e.g., comprising a computer-readable medium, a composition a solid surface as described herein, and optionally instructions for use.

BRIEF DESCRIPTION OF THE FIGURES

FIG. 3A shows changes in expression for Cyr61; FIG. 3B shows changes in expression for Col2a1; FIG. 3C shows changes in expression for Runx2; and FIG. 3D shows changes in expression for Ctsk.

BRIEF DESCRIPTION OF THE TABLES

Table 1 lists genes on the U74 microarrays for which BMP-2 induced at least a two-fold increase in expression at any time point.

Table 2 lists genes on the U74 microarrays for which BMP-2 induced at least a two-fold decrease in expression at any time point.

Table 3 summarizes the cells stained with an antisense riboprobe for CLF-1 mRNA.

Table 4 summarizes the cells stained with an antisense riboprobe for MMP23 mRNA.

Table 5 lists genes, previously associated with bone or cartilage metabolism, on the Mu1a microarray for which BMP-2 induced at least a four-fold change in expression at any time point.

Table 6 lists genes, not associated with bone or cartilage metabolism, on the Mula microarray for which BMP-2 induced at least a four-fold change in expression at any time point.

Table 7 lists genes from Tables 5 and 6 whose expression profiles correlate with those of selected gene markers for processes contributing to bone formation.

DETAILED DESCRIPTION OF THE INVENTION

The invention is based at least in part on the identification of genes which are up- and down-regulated during bone and cartilage formation, in particular, during endochondral or ectopic bone formation. Genes which are modulated include cell surface proteins, cytokines, extracellular matrix proteins, extracellular proteins, intracellular proteins, proteases, receptors, signal transduction proteins and transcription factors. In these expression profiles, certain genes are significantly up-regulated, e.g., MMP23, CLF-1, cadherin 11, and CD68 antigen, and certain genes are significantly down-regulated, e.g., vascular endothelial growth factor B and fatty acid synthase, during differentiation. Tables 1 and 2 list genes which are modulated by a factor of at least about 2 and Tables 5 and 6 list genes which are modulated by a factor of at least about 4. Genes of particular interest are indicated in italics and in bold in the Tables.

Whereas some of the genes listed in the Tables may have been known to be potentially involved in bone and cartilage formation, many other genes listed in the Tables have never before been associated with these processes.

Figure 1:
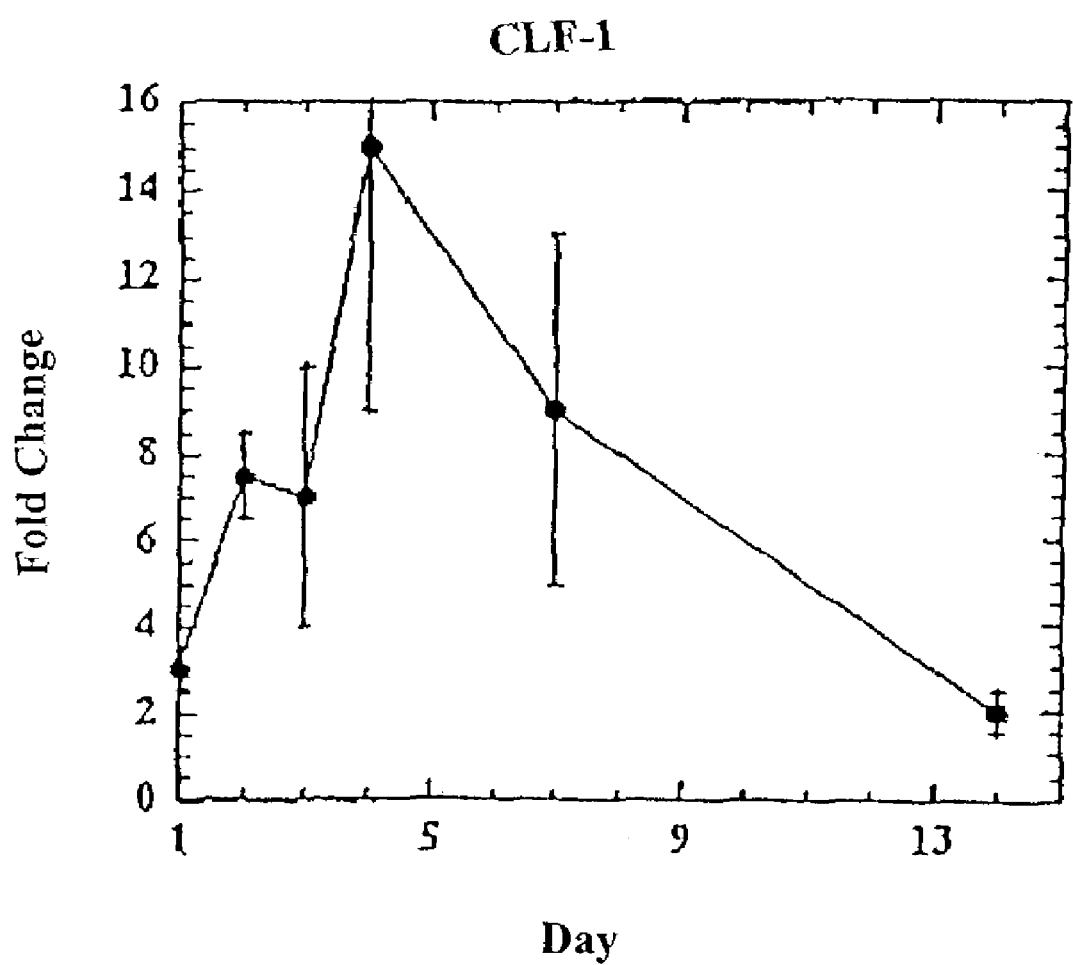
FIG. 1 shows a time course for BMP-2 induction of cytokine receptor-like factor 1 expression (CLF-1) in a mouse model of ectopic bone formation.

One of the genes not previously known to be associated with bone or cartilage formation that was found to be significantly up-regulated and then down-regulated during the mesenchymal cell differentiation into bone and cartilage is Cytokine Receptor-Like Factor 1 (CLF-1 or CRLF-1, as in Table 6) (see, FIG. 1). Its up-regulation during bone formation is shown in FIG. 1. The mouse CLF-1 gene (also known as CRLM3 mRNA for cytokine receptor like molecule 3) is transcribed into a 1646 bp mRNA (GenBank Accession No. AB040038) which encodes a mouse protein of 425 amino acids (GenBank Accession No. BAA92777). The nucleotide and amino acid sequences of human CLF-1 are set forth as GenBank Accession Nos. NM_004750 (SEQ ID NO: 1) and NP_004741 (SEQ ID NO: 2) (Elson et al. (1998) J. Immunol. 161:1371). Other human nucleotide sequences have GenBank Accession Nos. AX205046 and AF073515. Other human amino acid sequences include GenBank Accession No. AAD39681. The protein is secreted and dimerizes with cardiotrophin-like cytokine (CLC) (Elson et al. (2000) Nature Neuroscience 3(9): 867–872). This heterodimer is also a cytokine (Elson, et al. Nature Neuroscience 3(9):867–872, 2000). The CLC/CLF-1 heterodimeric cytokine binds to ciliary neurotrophic factor receptor (CNTFR) (Elson, et al. Nature Neuroscience 3(9): 867–872, 2000). Ligation of CNTFR activates STAT3 (Lelievre et al., J. Biol. Chem. 276(25):22476–22484, 2001). STAT3 activation is tied to the differentiation of a number of cell types such as osteoblasts and osteoclasts. CLF-1 plays a role in promoting the differentiation of mesenchymal progenitor cells towards either chondrocytes or osteoblasts.

Figure 2:
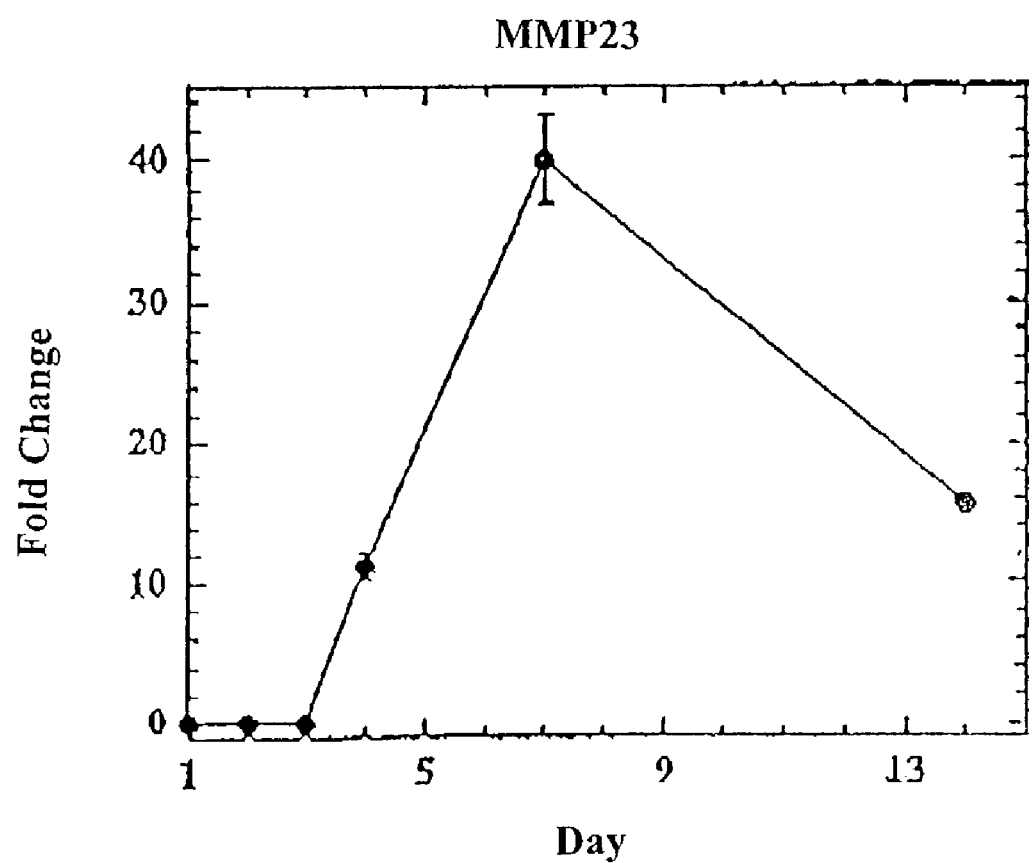
FIG. 2 shows a time course for BMP-2 induction of matrix metalloproteinase 23 expression (MMP23) in a mouse model of ectopic bone formation.

Another gene that was not previously known to be associated with bone or catilage formation that found to be up- and then down-regulated during bone and cartilage formation is Matrix Metalloproteinse 23 (MMP23) (see FIG. 2). Its upregulation during bone development is set forth in FIG. 2. The gene is transcribed into a mRNA of 1434 base pairs (GenBank Accession No. AF085742), which encodes a protein of 391 amino acid (GenBank Accession No. AAC34886). The nucleotide and amino acid sequences of human MMP23 have GenBank Accession No. AJ005256 (SEQ ID NO: 3) and CAB38176 (SEQ ID NO: 4) (Velasco et al. (1999) J. Biol. Chem. 274:4570. The MMP23 protein is a secreted and also membrane bound protease. Unlike other MMPs it is secreted as an active protease. MMP23 plays a role in normal tissue remodeling (which is part of the bone formation) and in pathological erosion of extracellular matrix proteins (which is part of an arthritic disease).

In another aspect, the invention is based at least in part on the identification of genes which are up- and down-regulated during particular phases of bone and cartilage formation. Table 7 contains genes whose time-dependent expression profiles correlate with the profiles of four phenotypic markers (Cyr 61, Col2a1, Runx2, and Ctsk) of one or more phases of endochondral bone formation. Cyr61 is a member of the CCN family of growth factors and is believed to regulate the proliferation and differentiation of various connective tissue cell types. Col2a1, Runx2 and Ctsk are well-defined markers for chondrocytes, osteoblasts and osteoclasts, respectively. Such genes may also be markers of bone formation phases, or have a functional connection to the markers with whose expression they correlate.

Although at least some of the genes listed in Tables 1, 2, 5, 6 and/or 7 may not be human genes, corresponding human genes are available or can be obtained within undue experimentation by a person of skill in the art. Methods of the invention may use human or non-human genes, depending on the similarity between the two and the particular use of the genes. A person of skill in the art can determine whether a nucleic acid or protein of a human or non-human gene can be used.

1. Definitions:

As used herein, the following terms and phrases shall have the meanings set forth below. Unless defined otherwise, all technical and scientific terms used herein have the same meaning as commonly understood to one of ordinary skill in the art to which this invention belongs.

The singular forms "a," "an," and "the" include plural reference unless the context clearly dictates otherwise.

The phrase "a corresponding normal cell of" or "normal cell corresponding to" or "normal counterpart cell of" a diseased cell refers to a normal cell of the same type as that of the diseased cell.

The term "agonist," as used herein, is meant to refer to an agent that mimics or upregulates (e.g., potentiates or supplements) the bioactivity of a protein. An agonist can be a wild-type protein or derivative thereof having at least one bioactivity of the wild-type protein. An agonist can also be a compound that upregulates expression of a gene or which increases at least one bioactivity of a protein. An agonist can also be a compound which increases the interaction of a polypeptide with another molecule, e.g., a target peptide or nucleic acid.

"Antagonist" as used herein is meant to refer to an agent that downregulates (e.g., suppresses or inhibits) at least one bioactivity of a protein. An antagonist can be a compound which inhibits or decreases the interaction between a protein and another molecule, e.g., a target peptide or enzyme substrate. An antagonist can also be a compound that downregulates expression of a gene or which reduces the amount of expressed protein present.

By "array" or "matrix" is meant an arrangement of addressable locations or "addresses" on a device. The locations can be arranged in two dimensional arrays, three dimensional arrays, or other matrix formats. The number of locations can range from several to at least hundreds of thousands. Most importantly, each location represents a totally independent reaction site. A "nucleic acid array" refers to an array containing nucleic acid probes, such as oligonucleotides or larger portions of genes. The nucleic acid on the array is preferably single stranded. Arrays wherein the probes are oligonucleotides are referred to as "oligonucleotide arrays" or "oligonucleotide chips." A "microarray," also referred to herein as a "biochip" or "biological chip" is an array of regions having a density of discrete regions of at least about 100/cm$^2$, and preferably at least about 1000/cm$^2$. The regions in a microarray have typical dimensions, e.g., diameters, in the range of between about 10–250 μm, and are separated from other regions in the array by about the same distance.

The term "biological sample", as used herein, refers to a sample obtained from a subject, e.g., a human or from components (e.g., tissues) of a subject. The sample may be of any biological tissue or fluid. Frequently the sample will be a "clinical sample" which is a sample derived from a patient. Such samples include, but are not limited to bodily fluids which may or may not contain cells, e.g., blood, synovial fluid; tissue or fine needle biopsy samples, such as from bone, cartilage or tissues containing mesenchymal cells. Biological samples may also include sections of tissues such as frozen sections taken for histological purposes.

The term "biomarker" of a disease related to bone or cartilage formation or resorption refers to a gene which is up- or down-regulated in a diseased cell of a subject having such a disease, relative to a counterpart normal cell, which gene is sufficiently specific to the diseased cell that it can be used, optionally with other genes, to identify or detect the disease. Generally, a biomarker is a gene that is characteristic of the disease.

"Bone formation" or "bone development" refers to ossification or osteogenesis, such as by endochondral bone formation or intramembraneous bone formation. In intramembraneous bone formation, osteogenesis occurs directly in the condensed mesenchymal cells. In endochondral ossification, mesenchymal cells first condense to form a cartilage model, and then bone formation occurs replacing the cartilage. Osteoprogenitor cells include mesenchymal and skeletal mesenchymal cells. Angiogenesis is part of bone formation. Thus, inhibiting or stimulating angiogenesis may inhibit or stimulate bone formation.

A "cell characteristic of a disease" also referred to as a "diseased cell" refers to a cell of a subject having a disease, which cell is affected by the disease, and is therefore different from the corresponding cell in a non-diseased subject. A diseased cell can also be a cell that is present in significantly higher or lower numbers in a subject having the disease relative to a healthy subject. For example a cell characteristic of cancer is a cancer cell or tumor cell. A diseased cell may also differ from a normal cell in its gene expression profile. A disease cell of a disease relating to bone or cartilage formation or resorption can be a mesenchymal cell, a chondroblast, a chondrocyte, an osteoblast, an osteocyte, a fibroblast or other cells present in bone or cartilage or in bone or cartilage forming tissues.

A "cell sample characteristic of a disease" or a "tissue sample characteristic of a disease" refers to a sample of cells, such as a tissue, that contains at least one cell characteristic of the disease.

A "computer readable medium" is any medium that can be used to store data which can be accessed by a computer. Exemplary media include: magnetic storage media, such as a diskettes, hard drives, and magnetic tape; optical storage media such as CD-ROMs; electrical storage media such as RAM and ROM; and hybrids of these media, such as magnetic/optical storage medium.

The term "derivative" refers to the chemical modification of a compound, e.g., a polypeptide, or a polynucleotide. Chemical modifications of a polynucleotide can include, for example, replacement of hydrogen by an alkyl, acyl, or amino group. A derivative polynucleotide encodes a polypeptide which retains at least one biological or immunological function of the natural molecule. A derivative polypeptide can be one modified by glycosylation, pegylation, or any similar process that retains at least one biological or immunological function of the polypeptide from which it was derived.

A disease, disorder, or condition "associated with" or "characterized by" or "relating to bone or cartilage formation or resorption" refers to a disease, condition or disorder involving cells that are associated with bone or cartilage formation or resorption. Exemplary diseases include osteodystrophy, osteohypertrophy, osteoblastoma, osteopertrusis, osteogenesis imperfecta, osteoporosis, osteopenia, osteoma and osteoblastoma; periondontal disease; hyperparathyroidism; hypercalcemia of malignancy; Paget's disease; osteolytic lesions produced by bone metastasis; bone loss due to immobilization or sex hormone deficiency; bone and cartilage loss cause by an inflammatory disease, e.g., rheumatoid arthritis and osteoarthritis; wound healing and related tissue repair (e.g., burns, incisions and ulcers) and bone fractures. A "disease relating to bone or cartilage formation" refers to a disease, disorder or condition that can be treated by inhibiting bone or cartilage formation. A "disease relating to bone or cartilage resorption" refers to a disease, disorder or condition that can be treated by stimulating bone or cartilage formation.

A "detection agent of a gene" refers to an agent that can be used to specifically detect a gene or other biological molecule relating to it, e.g., RNA transcribed from the gene and polypeptides encoded by the gene. Exemplary detection agents are nucleic acid probes which hybridize to nucleic acids corresponding to the gene, polypeptide probes, polypeptides, such asantibodies, and small molecules.

The term "equivalent" is understood to include nucleotide sequences encoding functionally equivalent polypeptides. Equivalent nucleotide sequences will include sequences that differ by one or more nucleotide substitutions, additions or deletions, such as allelic variants; and will, therefore, include sequences that differ from the nucleotide sequence of the nucleic acids referred to in Any of Tables 1–5 due to the degeneracy of the genetic code.

The term "expression profile," which is used interchangeably herein with "gene expression profile," "finger print" and "expression pattern" refers to a set of values representing the activity of about 10 or more genes. An expression profile preferably comprises values representing expression levels of at least about 20 genes, preferably at least about 30, 50, 100, 200 or more genes.

"Genes that are up- or down-regulated" in a particular process, e.g., bone and cartilage formation, refer to genes which are up- or down-regulated by, e.g., a factor of at least about 1.1 fold, 1.25 fold, 1.5 fold, 2 fold, 5 fold, 10 fold or more. Exemplary genes that are up- or down-regulated during bone and cartilage formation are set forth in Tables 1, 2, 5, 6 and/or 7. "Genes that are up- or down-regulated in a disease" refer to the genes which are up- or down-regulated by, e.g., at least about 1.1 fold, 1.25 fold, 1.5 fold, 2 fold, 5 fold, 10 fold or more in at least about 50%, preferably 60%, 70%, 80%, or 90% of the patients having the disease.

"Hybridization" refers to any process by which a strand of nucleic acid binds with a complementary strand through base pairing. Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. Hybridization also includes the formation of duplexes which contain certain mismatches, provided that the two strands are still forming a double stranded helix. "Stringent hybridization conditions" refers to hybridization conditions resulting in essentially specific hybridization.

The term "isolated" as used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

As used herein, the terms "label" and "detectable label" refer to a molecule capable of detection, including, but not limited to, radioactive isotopes, fluorophores, chemiluminescent moieties, enzymes, enzyme substrates, enzyme cofactors, enzyme inhibitors, dyes, metal ions, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH, alpha-beta-galactosidase and horseradish peroxidase.

The "level of expression of a gene" refers to the activity of a gene, which can be indicated by the level of mRNA, as well as pre-mRNA nascent transcript(s), transcript processing intermediates, mature mRNA(s) and degradation products, and polypeptides encoded by the gene. Accordingly, the level of expression of a gene also refers to the amount of polypeptide encoded by the gene.

The phrase "normalizing expression of a gene" in a diseased cell refers to an action to compensate for the altered expression of the gene in the diseased cell, so that it is essentially expressed at the same level as in the corresponding non diseased cell. For example, where the gene is over-expressed in the diseased cell, normalization of its expression in the diseased cell refers to treating the diseased cell in such a way that its expression becomes essentially the same as the expression in the counterpart normal cell. "Normalization" preferably brings the level of expression to within approximately a 50% difference in expression, more preferably to within approximately a 25%, and even more preferably 10% difference in expression. The required level of closeness in expression will depend on the particular gene, and can be determined as described herein. The phrase "normalizing gene expression in a diseased cell" refers to an action to normalize the expression of a substantial number of genes in the diseased cell.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The phrase "nucleic acid corresponding to a gene" refers to a nucleic acid that can be used for detecting the gene, e.g., a nucleic acid which is capable of hybridizing specifically to the gene.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases. Databases with individual sequences are described in Methods in Enzymology, ed. Doolittle, supra. Databases include Genbank, EMBL, and DNA Database of Japan (DDBJ).

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. A mismatch in a duplex between a target polynucleotide and an oligonucleotide or olynucleotide means that a pair of nucleotides in the duplex fails to undergo Watson-Crick bonding. In reference to a triplex, the term means that the triplex consists of a perfectly matched duplex and a third strand in which every nucleotide undergoes Hoogsteen or reverse Hoogsteen association with a basepair of the perfectly matched duplex.

A "plurality" refers to two or more.

A "precursor cell", or "progenitor cell", refers to a cell that has the capacity to create progeny that are more differentiated than itself. For example, the term may refer to an undifferentiated cell or cell differentiated to an extent short of final differentiation which is capable of proliferation and giving rise to more progenitor cells having the ability to generate a large number of mother cells that can in turn give rise to differentiated, or differentiable daughter cells. In certain embodiments, the term progenitor cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. By this definition, stem cells may also be progenitor cells, as well as the more immediate precursors to terminally differentiated cells. Exemplary precursor cells involved in bone and cartilage formation include osteoprogenitor cells such as for example mesenchymal precursors cells, osteoblasts, and chondroblasts. As used herein, a nucleic acid or other molecule attached to an array, is referred to as a "probe" or "capture probe." When an array contains several probes corresponding to one gene, these probes are referred to as "gene-probe set." A gene-probe set can consist of, e.g., 2 to 10 probes, preferably from 2 to 5 probes and most preferably about 5 probes.

A "significant similarity" between the level of expression of a gene in two cells or tissues generally refers to a difference in expression levels of a factor of at most about 10% (i.e., 1.1 fold), 25% (i.e., 1.25 fold), 50% (i.e., 1.5 fold), 75% (i.e., 1.75 fold), 90% (i.e., 1.9 fold), 2 fold, 2.5 fold, 3 fold, 5 fold, or 10 fold. Expression levels can be raw data or they can averaged or normalized data, e.g., normalized relative to normal controls. A "significant difference" between the level of expression of a gene in two cells or tissues generally refers to a difference in expression levels of a factor of at least about 10% (i.e., 1.1 fold), 25% (i.e., 1.25 fold), 50% (i.e., 1.5 fold), 75% (i.e., 1.75 fold), 90% (i.e., 1.9 fold), 2 fold, 2.5 fold, 3 fold, 5 fold, 10 fold, 50 fold or 100 fold. Whether the expression of a particular gene in two samples is significantly different or similar also depends on the gene itself and, e.g., its variability in expression between different individuals. It is within the skill in the art to determine whether expression levels are significantly similar or different.

An expression profile in one cell or tissue is "significantly similar" to an expression profile in another cell or tissue when the level of expression of the genes in the two expression profiles are sufficiently similar that the similarity is indicative of a common characteristic, e.g., being of the same cell type, or being characteristic of a disease. "Similarity" between an expression profile of a cell or tissue, e.g., of a subject, and a set of data representing an expression profile characteristic of a disease can be based on the presence or absence in the cell or tissue of certain RNAs and/or certain levels of certain RNAs of genes having a high probability of being associated with the disease. A high probability of being associated with a disease can be, e.g., the presence of RNA or of certain levels of RNA of particular genes which are over-expressed or under-expressed, in at least about 50%, 60%, 70%, 80%, 90%, or 100% of patients having the disease. A similarity with an expression profile of a patient can be based on higher or lower expression levels of a factor of at most about 10%, 25%, 50%, 75%, 1.5 fold, 2 fold, 2.5 fold, 3 fold, 5 fold or 10 fold of at least about 50%, 60%, 70%, 80%, 90%, or 100% of genes, or at least about 10, 50, 100, 200, 300 genes, that are up- or down-regulated in at least about 50%, 60%, 70%, 80%, 90%, or 100% of patients.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

The term "specific hybridization" of a probe to a target site of a template nucleic acid refers to hybridization of the probe predominantly to the target, such that the hybridization signal can be clearly interpreted. As further described herein, such conditions resulting in specific hybridization vary depending on the length of the region of homology, the GC content of the region, the melting temperature "Tm" of the hybrid. Hybridization conditions will thus vary in the salt content, acidity, and temperature of the hybridization solution and the washes.

A "subject" can be a mammal, e.g., a human, primate, ovine, bovine, porcine, equine, feline, canine and a rodent (rat or mouse).

The term "treating" a disease in a subject or "treating" a subject having a disease refers to providing the subject with a pharmaceutical treatment, e.g., the administration of a drug, such that at least one symptom of the disease is decreased. Treating a disease can be preventing the disease, improving the disease or curing the disease.

The phrase "value representing the level of expression of a gene" refers to a raw number which reflects the mRNA or polypeptide level of a particular gene in a cell or biological sample, e.g., obtained from analytical tools for measuring RNA or polypeptide levels.

A "variant" of a polypeptide refers to a polypeptide having the amino acid sequence of the polypeptide, in which one or more amino acid residues are altered. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR). The term "variant," when used in the context of a polynucleotide sequence, encompasses a polynucleotide sequence related to that of a gene of interest or the coding sequence thereof. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

2. Diagnostic and Prognostic Methods and Compositions

The invention provides gene expression profiles over time during bone formation, e.g., endochondral bone formation induced by BMP-2. Since these expression profiles are characteristic of bone and cartilage formation, measuring the level of expression or level of product of one or more genes identified in these expression profiles, e.g., genes set forth in Tables 1, 2, 5, 6 and/or 7, during bone or cartilage formation is expected to reveal any abnormalities in these processes. Abnormalities can then be treated appropriately, such as described below.

Exemplary situations in which one may wish to monitor bone or cartilage formation or resorption include diseases relating to bone or cartilage formation or bone or cartilage resorption, such as osteodystrophy, osteohypertrophy, osteoblastoma, osteopertrusis, osteogenesis imperfecta, osteoporosis, osteopenia, osteoma and osteoblastoma; periondontal disease; hyperparathyroidism; hypercalcemia of malignancy; Paget's disease; osteolytic lesions produced by bone metastasis; bone loss due to immobilization or sex hormone deficiency; bone and cartilage loss cause by an inflammatory disease, e.g., rheumatoid arthritis and osteoarthritis; wound healing and related tissue repair (e.g., burns, incisions and ulcers) and bone fractures. Bone or cartilage formation or resoption can also be monitored during treatment of any of the above-mentioned diseases and any conditions in which bone or cartilage formation is induced, such as by therapeutics, e.g., bone morphogenetic proteins. Situations in which bone or cartilage formation may be induced include healing of fractures, e.g., in closed and open fracture reduction; improved fixation of artificial joints; repair of congenital, trauma induced, or oncologic resection induced craniofacial defects; tooth repair processes and plastic, e.g., cosmetic plastic, surgery.

Accordingly, the invention provides methods for diagnosing and monitoring the development of any disease relating to bone or cartilage formation or resorption, such as the diseases set forth above. The methods of the invention also allow to distinguish one disease from another, where such distinction is not possible based on phenotypic or histologic examination.

In yet another embodiment, the methods of the invention allow the determination of the stage of a particular disease. For example, by knowing the level of expression of certain genes, the state of bone or cartilage development can be established.

The methods of the invention can also be used to monitor the treatment of a disease. Monitoring will reveal whether a subject is responsive to a treatment or whether the treatment should be modified.

Measuring the level of expression or the level of product of one or more genes described herein can also be used in prognostics, such as to determine whether a subject is likely to develop a disease relating to bone or cartilage formation or resorption. For example a subject whose family is associated with such disorders can be monitored to determine whether he or she will develop such a disorder.

Another situation during which gene expression can be monitored is during in vitro bone or cartilage formation, e.g., induced by a bone morphogenetic protein. In vitro synthesized bone or cartilage can be used for implanting into subject in need thereof, such as subjects having suffered bone loss, e.g., resulting from cancer or osteoporosis.

In one embodiment, a sample is obtained from a subject, e.g., a human subject, and the level of expression of one or more genes, such as genes listed in any of Tables 1, 2, 5, 6 and/or 7, is determined. The particular method used for obtaining a sample will depend on the site of the sample to be obtained. Samples can be obtained according to methods known in the art. As few as one cell may be sufficient for determining gene expression. In other embodiments, the presence of proteins is determined in a bodily fluid, e.g., blood or synovial fluid. Gene expression can be determined according to methods known in the art, such as reverse transcriptase polymerase chain reaction (RT-PCR); nucleic acid arrays; dotblots; and in situ hybridization, as further described herein. In other embodiments, the level of protein is measured, such as by immunohistochemistry, ELISA, or immunoprecipitation.

In certain embodiments, several samples are obtained consecutively, and a change of expression is monitored over time. For example, samples may be obtained about every 1, 2, 3, 5, 6, 12, 24, 36 or 48 hours.

Figure 3:
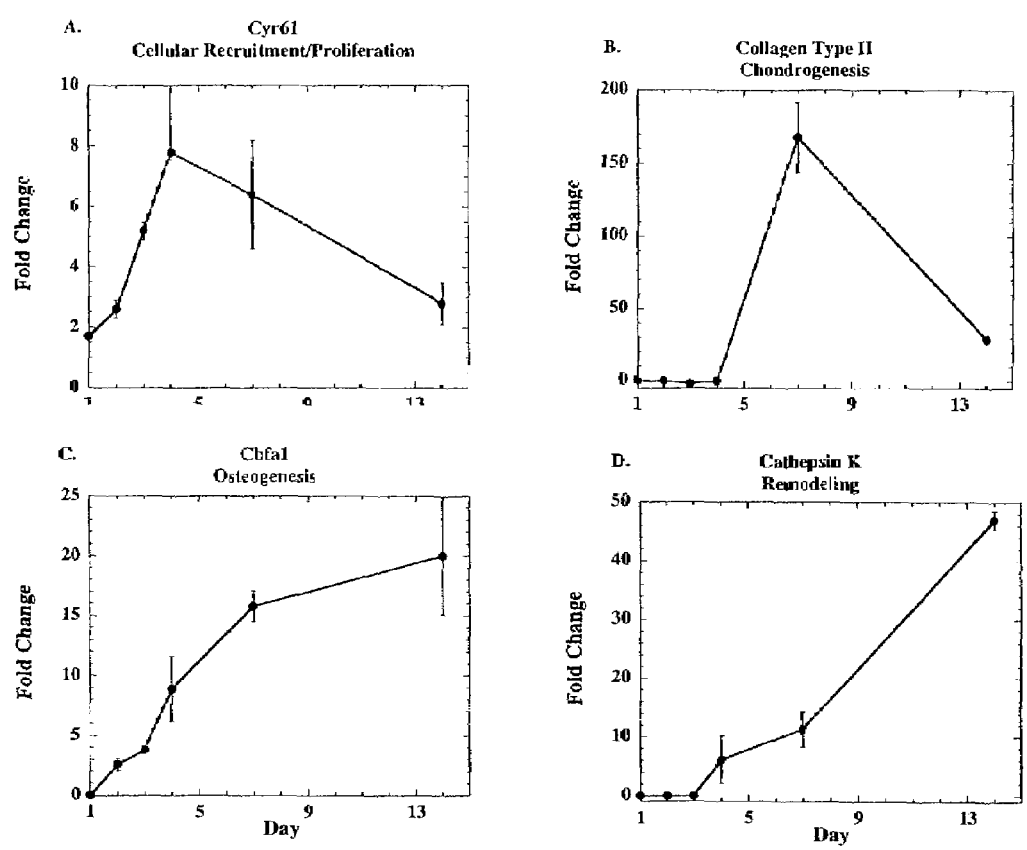
FIG. 3 shows time-dependent changes in the expression of selected marker genes of endochondral bone formation.

The level of expression of one or more genes in a sample can be compared to the level of expression of these genes in a control sample. A control sample may be obtained, e.g., from the same patient, but at a different site, or from a healthy subject. Alternatively, the level of expression of the genes in the sample is compared to values stored in a data-readable medium, such as the values set forth in Tables 1, 2, 5, 6 and/or 7 or in FIG. 1 or 2 or 3. The comparison can be conducted visually, or via a computer.

The presence of a bone or cartilage related disease or a defect in the treatment of such a disease may be indicated by differences in the level of expression of one or more genes in a sample and in the control sample. The differences in gene expression may be a difference of a factor of at least about 50%; 2; 3; 5; 10; 20; 50; or 100 fold. In other embodiments, an abnormality is revealed by comparing the level of expression of one or more genes over time with their expression in a control or healthy subject.

The diagnostic and prognostic assays may indicate a defect in cartilage or bone formation or the existence of inefficient treatment of a disease or healing, e.g., bone fracture healing. The assays may thus be followed by a proper treatment or correction of treatment. Exemplary treatments are provided below. Generally, any therapeutic known to correct the diagnosed abnormality can be used. For example, defective bone or cartilage formation may be corrected by administration of a bone morphogenetic protein (BMP), e.g., BMP-2 or BMP-4. The nucleic acid sequence for human BMP-2 is set forth in SEQ ID NO:5, and the corresponding amino acid sequence is set forth in SEQ ID NO:6.

2.1. Use of Arrays for Determining the Level of Expression of Genes

Generally, determining expression profiles with arrays involves the following steps: (a) obtaining a mRNA sample from a subject and preparing labeled nucleic acids therefrom (the "target nucleic acids" or "targets"); (b) contacting the target nucleic acids with the array under conditions sufficient for target nucleic acids to bind with corresponding probes on the array, e.g. by hybridization or specific binding; (c) optionally removing unbound targets from the array; (d) detecting bound targets, and (e) analyzing the results. As used herein, "nucleic acid probes", or "probes" are nucleic acids attached to the array, whereas "target nucleic acids" are nucleic acids that are hybridized to the array. Each of these steps is described in more detail below.

(i) Obtaining a mRNA Sample of a Subject

In one embodiment, one or more cells from the subject to be tested are obtained and RNA is isolated from the cells. In a preferred embodiment, a sample of bone, cartilage, mesenchymal cells, synovial fluid, synovium, tumor or other tissue likely to be affected by the disorder to be diagnosed or monitored, are obtained from the subject according to methods known in the art. Cells from which expression levels may be obtained include macrophages, fibroblasts, chondrocyte-like cells, chondrocytes, chondroblasts, bone marrow cells, osteoblast, osteocytes, osteoclasts, and osteogenic precursor cells, e.g., mesenchymal cells. When obtaining the cells, it is preferable to obtain a sample containing predominantly cells of the desired type, e.g., a sample of cells in which at least about 50%, preferably at least about 60%, even more preferably at least about 70%, 80% and even more preferably, at least about 90% of the cells are of the desired type. A higher percentage of cells of the desired type is preferable, since such a sample is more likely to provide clear gene expression data.

It is also possible to obtain a cell sample from a subject, and then to enrich it for a desired cell type. Cells can also be isolated from other cells using a variety of techniques, such as isolation with an antibody binding to an epitope on the cell surface of the desired cell type. Another method that can be used includes negative selection using antibodies to cell surface markers to selectively enrich for a specific cell type without activating the cell by receptor engagement. Where the desired cells are in a solid tissue, particular cells can be dissected out, e.g., by microdissection. Exemplary cells that one may want to enrich for include mesenchymal cells, such as muscular mesenchymal cells, osteoblasts, osteocytes, chondroblasts, chondrocytes, tumor cells and other bone or cartilage cells.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., those described in the Examples or guanidium thiocyanate lysis followed by CsCl centrifugation (Chirgwin et al., 1979, Biochemistry 18:5294–5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized on a solid support to serve as affinity ligands for mRNA. Kits for this purpose are commercially available, e.g., the MessageMaker kit (Life Technologies, Grand Island, N.Y.).

In a preferred embodiment, the RNA population is enriched in sequences of interest, such as those of genes listed in Tables 1, 2, 5, 6 and/or 7. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. Such amplification is particularly important when using RNA from a single or a few cells. A variety of amplification methods are suitable for use in the methods of the invention, including, e.g., PCR; ligase chain reaction (LCR) (See, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); nucleic acid based sequence amplification (NASBA) and transcription amplification (see, e.g., Kwoh et al., Proc. Natl. Acad. Sci. USA 86, 1173 (1989)). For PCR technology, see, e.g., PCR Technology: Principles and Applications for DNA Amplification (ed. H. A. Erlich, Freeman Press, N.Y., N.Y., 1992); PCR Protocols: A Guide to Methods and applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202. Methods of amplification are described, e.g., in Ohyama et al. (2000) BioTechniques 29:530; Luo et al. (1999) Nat. Med. 5, 117; Hegde et al. (2000) BioTechniques 29:548; Kacharmina et al. (1999) Meth. Enzymol. 303:3; Livesey et al. (2000) Curr. Biol. 10:301; Spirin et al. (1999) Invest. Ophtalmol. Vis. Sci. 40:3108; and Sakai et al. (2000) Anal. Biochem. 287:32. RNA amplification and cDNA synthesis can also be conducted in cells in situ (see, e.g., Eberwine et al. (1992) PNAS 89:3010).

One of skill in the art will appreciate that whatever amplification method is used, if a quantitative result is desired, care must be taken to use a method that maintains or controls for the relative frequencies of the amplified nucleic acids to achieve quantitative amplification. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. A high density array may then include probes specific to the internal standard for quantification of the amplified nucleic acid.

One preferred internal standard is a synthetic AW106 cRNA. The AW106 ERNA is combined with RNA isolated from the sample according to standard techniques known to those of skilled in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al., Academic Press, Inc. N.Y., (1990).

In a preferred embodiment, a sample mRNA is reverse transcribed with a reverse transcriptase and a primer consisting of oligo(dT) and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (See, e.g., Sambrook, (supra) and this particular method is described in detail by Van Gelder, et al., Proc. Natl. Acad. Sci. USA, 87: 1663–1667 (1990) who demonstrate that in vitro amplification according to this method preserves the relative frequencies of the various RNA transcripts). Moreover, Eberwine et al. Proc. Natl. Acad. Sci. USA, 89: 3010–3014 provide a protocol that uses two rounds of amplification via in vitro transcription to achieve greater than 106 fold amplification of the original starting material, thereby permitting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

(ii) Labeling of the Nucleic Acids to be Analyzed

Generally, the target molecules will be labeled to permit detection of hybridization of target molecules to a microarray. By "labeled" is meant that the probe comprises a member of a signal producing system and is thus detectable, either directly or through combined action with one or more additional members of a signal producing system. Examples of directly detectable labels include isotopic and fluorescent moieties incorporated into, usually covalently bonded to, a moiety of the probe, such as a nucleotide monomeric unit, e.g. dNMP of the primer, or a photoactive or chemically active derivative of a detectable label which can be bound to a functional moiety of the probe molecule.

Nucleic acids can be labeled after or during enrichment and/or amplification of RNAs. For example, labeled cDNA can be prepared from mRNA by oligo dT-primed or random-primed reverse transcription, both of which are well known in the art (see, e.g., Klug and Berger, 1987, Methods Enzymol. 152:316–325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, Nature Biotech. 14:1675). In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

In one embodiment, labeled cDNA is synthesized by incubating a mixture containing RNA and 0.5 mM dGTP, dATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., SuperScript.™0.11, LTI Inc.) at 42° C. for 60 min.

Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. Texas red, tetramethylrhodamine, eosins and erythrosins, cyanine dyes, e.g. Cy2, Cy3, Cy3.5, Cy5, Cy5.5, Cy7, Fluor X, macrocyclic chelates of lanthanide ions, e.g. quantum dye™, fluorescent energy transfer dyes, such as thiazole orange-ethidium heterodimer, TOTAB, dansyl, etc. Individual fluorescent compounds which have functionalities for linking to an element desirably detected in an apparatus or assay of the invention, or which can be modified to incorporate such functionalities include, e.g., dansyl chloride; fluoresceins such as 3,6-dihydroxy-9-phenylxanthydrol; rhodamineisothiocyanate; N-phenyl 1-amino-8-sulfonatonaphthalene; N-phenyl 2-amino-6-sulfonatonaphthalene; 4-acetamido-4-isothiocyanatostilbene-2,2'-disulfonic acid; pyrene-3-sulfonic acid; 2-toluidinonaphthalene-6-sulfonate; Nphenyl-N-methyl-2-aminoaphthalene-6-sulfonate;

ethidium bromide; stebrine; auromine-0,2-(9'-anthroyl) palmitate; dansyl phosphatidylethanolamine; N,N'-dioctadecyl oxacarbocyanine: N,N'-dihexyl oxacarbocyanine; merocyanine, 4-(3'-pyrenyl)stearate; d-3-aminodesoxy-equilenin; 12-(9'-anthroyl)stearate; 2-methylanthracene; 9-vinylanthracene; 2,2'(vinylene-p-phenylene)bisbenzoxazole; p-bis (2--methyl-5-phenyl-oxazolyl))benzene; 6-dimethylamino-1,2-benzophenazin; retinol; bis(3'-aminopyridinium) 1,10-decandiyl dilodide; sulfonaphthylhydrazone of hellibrienin; chlorotetracycline; N-(7-dimethylamino-4-methyl-2-oxo-3-chromenyl)maleimide; N-(p-(2benzimidazolyl)-phenyl)maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone. (see, e.g., Kricka, 1992, Nonisotopic DNA Probe Techniques, Academic Press San Diego, Calif.). Many fluorescent tags are commercially available from SIGMA chemical company (Saint Louis, Mo.), Amersham, Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.) as well as other commercial sources known to one of skill.

Chemiluminescent labels include luciferin and 2,3-dihydrophthalazinediones, e.g., luminol.

Isotopic moieties or labels of interest include $^{32}P$, $^{33}P$, $^{35}S$, $^{125}I$, $^{2}H$, $^{14}C$, and the like (see Zhao et al., 1995, High density cDNA filter analysis: a novel approach for large-scale, quantitative analysis of gene expression, Gene 156: 207; Pietu et al., 1996, Novel gene transcripts preferentially expressed in human muscles revealed by quantitative hybridization of a high density cDNA array, Genome Res. 6:492).

Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody and the like.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

In some cases, hybridized target nucleic acids may be labeled following hybridization. For example, where biotin labeled dNTPs are used in, e.g., amplification or transcription, streptavidin linked reporter groups may be used to label hybridized complexes.

In other embodiments, the target nucleic acid is not labeled. In this case, hybridization can be determined, e.g., by plasmon resonance, as described, e.g., in Thiel et al. (1997) Anal. Chem. 69:4948.

In one embodiment, a plurality (e.g., 2, 3, 4, 5 or more) of sets of target nucleic acids are labeled and used in one hybridization reaction ("multiplex" analysis). For example, one set of nucleic acids may correspond to RNA from one cell or tissue sample and another set of nucleic acids may correspond to RNA from another cell or tissue sample. The plurality of sets of nucleic acids can be labeled with different labels, e.g., different fluorescent labels which have distinct emission spectra so that they can be distinguished. The sets can then be mixed and hybridized simultaneously to one microarray.

For example, the two different cells can be a cell of a subject suspected of having a disease related to bone or cartilage formation or resoprtion and a counterpart normal cell. In another embodiment, e.g., for identifying drugs modulating bone formation, one biological sample contains cells that were exposed to a drug and the other biological sample contains cells that were not exposed to the drug. The cDNA derived from each of the two cell types are differently labeled so that they can be distinguished. In one embodiment, for example, cDNA from one sample is synthesized using a fluorescein-labeled dNTP, and cDNA from the second sample is synthesized using a rhodamine-labeled dNTP. When the two cDNAs are mixed and hybridized to the microarray, the relative intensity of signal from each cDNA set is determined for each site on the array, and any relative difference in abundance of a particular mRNA detected.

In the example described above, the cDNA from one sample will fluoresce green when the fluorophore is stimulated and the cDNA from the second sample will fluoresce red. As a result, if the two cells are essentially the same, the particular mRNA will be equally prevalent in both cells and, upon reverse transcription, red-labeled and green-labeled cDNA will be equally prevalent. When hybridized to the microarray, the binding site(s) for that species of RNA will emit wavelengths characteristic of both fluorophores (and appear brown in combination). In contrast, if the two cells are different, the ratio of green to red fluorescence will be different.

The use of a two-color fluorescence labeling and detection scheme to define alterations in gene expression has been described, e.g., in Shena et al., 1995, Quantitative monitoring of gene expression patterns with a complementary DNA microarray, Science 270:467–470. An advantage of using cDNA labeled with two different fluorophores is that a direct and internally controlled comparison of the mRNA levels corresponding to each arrayed gene in two cell states can be made, and variations due to minor differences in experimental conditions (e.g, hybridization conditions) will not affect subsequent analyses.

Examples of distinguishable labels for use when hybridizing a plurality of target nucleic acids to one array are well known in the art and include: two or more different emission wavelength fluorescent dyes, like Cy3 and Cy5, combination of fluorescent proteins and dyes, like phicoerythrin and Cy5, two or more isotopes with different energy of emission, like $^{32}P$ and $^{33}P$, gold or silver particles with different scattering spectra, labels which generate signals under different treatment conditions, like temperature, pH, treatment by additional chemical agents, etc., or generate signals at different time points after treatment. Using one or more enzymes for signal generation allows for the use of an even greater variety of distinguishable labels, based on different substrate specificity of enzymes (alkaline phosphatase/peroxidase).

Further, it is preferable in order to reduce experimental error to reverse the fluorescent labels in two-color differential hybridization experiments to reduce biases peculiar to individual genes or array spot locations. In other words, it is preferable to first measure gene expression with one labeling (e.g., labeling nucleic acid froma first cell with a first fluorochrome and nucleic acid from a second cell with a second fluorochrome) of the mRNA from the two cells being measured, and then to measure gene expression from the two cells with reversed labeling (e.g., labeling nucleic acid from the first cell with the second fluorochrome and nucleic acid from the second cell with the first fluorochrome). Multiple measurements over exposure levels and perturbation control parameter levels provide additional experimental error control.

The quality of labeled nucleic acids can be evaluated prior to hybridization to an array. For example, a sample of the labeled nucleic acids can be hybridized to probes derived from the 5', middle and 3' portions of genes known to be or suspected to be present in the nucleic acid sample. This will be indicative as to whether the labeled nucleic acids are full length nucleic acids or whether they are degraded. In one embodiment, the GeneChip® Test3 Array from Affymetrix (Santa Clara, Calif.) can be used for that purpose. This array contains probes representing a subset of characterized genes from several organisms including mammals. Thus, the quality of a labeled nucleic acid sample can be determined by hybridization of a fraction of the sample to an array, such as the GeneChip® Test3 Array from Affymetrix (Santa Clara, Calif.).

(iii) Exemplary Arrays

Preferred arrays, e.g., microarrays, for use according to the invention include one or more probes of genes which are up- or down-regulated during bone or cartilage formation, such as one or more genes listed in any of Tables 1, 2, 5, 6 and/or 7. The array may comprise probes corresponding to at least 10, preferably at least 20, at least 50, at least 100 or at least 1000 genes. The array may comprise probes corresponding to about 10%, 20%, 50%, 70%, 90% or 95% of the genes listed in any of Tables 1, 2, 5, 6 and/or 7. The array may comprise probes corresponding to about 10%, 20%, 50%, 70%, 90% or 95% of the genes listed in any of Tables 1, 2, 5, 6 and/or 7 whose expression increases or decreases at least about 2 fold, preferably at least about 3 fold, more preferably at least about 4 fold, 5 fold, 7 fold and most preferably at least about 10 fold during bone or cartilage formation. One array that can be used is the array used and described in the Examples.

There can be one or more than one probe corresponding to each gene on a microarray. For example, a microarray may contain from 2 to 20 probes corresponding to one gene and preferably about 5 to 10. The probes may correspond to the full length RNA sequence or complement thereof of genes that are up- or down-regulated during bone or cartilage formation, or they may correspond to a portion thereof, which portion is of sufficient length for permitting specific hybridization. Such probes may comprise from about 50 nucleotides to about 100, 200, 500, or 1000 nucleotides or more than 1000 nucleotides. As further described herein, microarrays may contain oligonucleotide probes, consisting of about 10 to 50 nucleotides, preferably about 15 to 30 nucleotides and even more preferably 20–25 nucleotides. The probes are preferably single stranded. The probe will have sufficient complementarity to its target to provide for the desired level of sequence specific hybridization (see below).

Typically, the arrays used in the present invention will have a site density of greater than 100 different probes per $cm^2$. Preferably, the arrays will have a site density of greater than 500/$cm^2$, more preferably greater than about 1000/$cm^2$, and most preferably, greater than about 10,000/$cm^2$. Preferably, the arrays will have more than 100 different probes on a single substrate, more preferably greater than about 1000 different probes still more preferably, greater than about 10,000 different probes and most preferably, greater than 100,000 different probes on a single substrate.

Microarrays can be prepared by methods known in the art, as described below, or they can be custom made by companies, e.g., Affymetrix (Santa Clara, Calif.).

Generally, two types of microarrays can be used. These two types are referred to as "synthesis" and "delivery." In the synthesis type, a microarray is prepared in a step-wise fashion by the in situ synthesis of nucleic acids from nucleotides. With each round of synthesis, nucleotides are added to growing chains until the desired length is achieved. In the delivery type of microarray, preprepared nucleic acids are deposited onto known locations using a variety of delivery technologies. Numerous articles describe the different microarray technologies, e.g., Shena et al. (1998) Tibtech 16: 301; Duggan et al. (1999) Nat. Genet. 21:10; Bowtell et al. (1999) Nat. Genet. 21: 25.

One novel synthesis technology is that developed by Affymetrix (Santa Clara, Calif.), which combines photolithography technology with DNA synthetic chemistry to enable high density oligonucleotide microarray manufacture. Such chips contain up to 400,000 groups of oligonucleotides in an area of about 1.6 $cm^2$. Oligonucleotides are anchored at the 3' end thereby maximizing the availability of single-stranded nucleic acid for hybridization. Generally such chips, referred to as "GeneChipso®" contain several oligonucleotides of a particular gene, e.g., between 15–20, such as 16 oligonucleotides. Since Affymetrix (Santa Clara, Calif.) sells custom made microarrays, microarrays containing genes which are up- or down-regulated during bone formation can be ordered for purchase from Affymetrix (Santa Clara, Calif.).

Microarrays can also be prepared by mechanical microspotting, e.g., those commercialized at Synteni (Fremont, Calif.). According to these methods, small quantities of nucleic acids are printed onto solid surfaces. Microspotted arrays prepared at Synteni contain as many as 10,000 groups of cDNA in an area of about 3.6 $cm^2$.

A third group of microarray technologies consist in the "drop-on-demand" delivery approaches, the most advanced of which are the ink-jetting technologies, which utilize piezoelectric and other forms of propulsion to transfer nucleic acids from miniature nozzles to solid surfaces. Inkjet technologies is developed at several centers including Incyte Pharmaceuticals (Palo Alto, Calif.) and Protogene (Palo Alto, Calif.). This technology results in a density of 10,000 spots per $cm^2$. See also, Hughes et al. (2001) Nat. Biotechn. 19:342.

Arrays preferably include control and reference nucleic acids. Control nucleic acids are nucleic acids which serve to indicate that the hybridization was effective. For example, all Affymetrix (Santa Clara, Calif.) expression arrays contain sets of probes for several prokaryotic genes, e.g., bioB, bioC and bioD from biotin synthesis of *E. coli* and cre from P1 bacteriophage. Hybridization to these arrays is conducted in the presence of a mixture of these genes or portions thereof, such as the mix provided by Affymetrix (Santa Clara, Calif.) to that effect (Part Number 900299), to thereby confirm that the hybridization was effective. Control nucleic acids included with the target nucleic acids can also be mRNA synthesized from cDNA clones by in vitro transcription. Other control genes that may be included in arrays are polyA controls, such as dap, lys, phe, thr, and trp (which are included on Affymetrix GeneChips®)

Reference nucleic acids allow the normalization of results from one experiment to another, and to compare multiple experiments on a quantitative level. Exemplary reference nucleic acids include housekeeping genes of known expression levels, e.g., GAPDH, hexokinase and actin.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases.

Arrays may also contain probes that hybridize to more than one allele of a gene. For example the array can contain one probe that recognizes allele 1 and another probe that recognizes allele 2 of a particular gene.

Microarrays can be prepared as follows. In one embodiment, an array of oligonucleotides is synthesized on a solid support. Exemplary solid supports include glass, plastics, polymers, metals, metalloids, ceramics, organics, etc. Using chip masking technologies and photoprotective chemistry it is possible to generate ordered arrays of nucleic acid probes. These arrays, which are known, e.g., as "DNA chips," or as very large scale immobilized polymer arrays ("VLSIPS™" arrays) can include millions of defined probe regions on a substrate having an area of about 1 cm$^2$ to several cm$^2$, thereby incorporating sets of from a few to millions of probes (see, e.g., U.S. Pat. No. 5,631,734).

The construction of solid phase nucleic acid arrays to detect target nucleic acids is well described in the literature. See, Fodor et al. (1991) Science, 251: 767–777; Sheldon et al. (1993) Clinical Chemistry 39(4): 718–719; Kozal et al. (1996) Nature Medicine 2(7): 753–759 and Hubbell U.S. Pat. No. 5,571,639; Pinkel et al. PCT/US95/16155 (WO 96/17958); U.S. Pat. Nos. 5,677,195; 5,624,711; 5,599,695; 5,451,683; 5,424,186; 5,412,087; 5,384,261; 5,252,743 and 5,143,854; PCT Patent Publication Nos. 92/10092 and 93/09668; and PCT WO 97/10365. In brief, a combinatorial strategy allows for the synthesis of arrays containing a large number of probes using a minimal number of synthetic steps. For instance, it is possible to synthesize and attach all possible DNA 8 mer oligonucleotides (4$^8$, or 65,536 possible combinations) using only 32 chemical synthetic steps. In general, VLSIPS™ procedures provide a method of producing 4n different oligonucleotide probes on an array using only 4n synthetic steps (see, e.g., U.S. Pat. No. 5,631,734 5,143,854 and PCT Patent Publication Nos. WO 90/15070; WO 95/11995 and WO 92/10092).

Light-directed combinatorial synthesis of oligonucleotide arrays on a glass surface can be performed with automated phosphoramidite chemistry and chip masking techniques similar to photoresist technologies in the computer chip industry. Typically, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface.

Algorithms for design of masks to reduce the number of synthesis cycles are described by Hubbel et al., U.S. Pat. No. 5,571,639 and U.S. Pat. No. 5,593,839. A computer system may be used to select nucleic acid probes on the substrate and design the layout of the array as described in U.S. Pat. No. 5,571,639.

Another method for synthesizing high density arrays is described in U.S. Pat. No. 6,083,697. This method utilizes a novel chemical amplification process using a catalyst system which is initiated by radiation to assist in the synthesis the polymer sequences. Such methods include the use of photosensitive compounds which act as catalysts to chemically alter the synthesis intermediates in a manner to promote formation of polymer sequences. Such photosensitive compounds include what are generally referred to as radiation-activated catalysts (RACs), and more specifically photo activated catalysts (PACs). The RACs can by themselves chemically alter the synthesis intermediate or they can activate an autocatalytic compound which chemically alters the synthesis intermediate in a manner to allow the synthesis intermediate to chemically combine with a later added synthesis intermediate or other compound.

Arrays can also be synthesized in a combinatorial fashion by delivering monomers to cells of a support by mechanically constrained flowpaths. See Winkler et al., EP 624,059. Arrays can also be synthesized by spotting monomers reagents on to a support using an ink jet printer. See id. and Pease et al., EP 728,520.

cDNA probes can be prepared according to methods known in the art and further described herein, e.g., reverse-transcription PCR (RT-PCR) of RNA using sequence specific primers. Oligonucleotide probes can be synthesized chemically. Sequences of the genes or cDNA from which probes are made can be obtained, e.g., from GenBank, other public databases or publications.

Nucleic acid probes can be natural nucleic acids, chemically modified nucleic acids, e.g., composed of nucleotide analogs, as long as they have activated hydroxyl groups compatible with the linking chemistry. The protective groups can, themselves, be photolabile. Alternatively, the protective groups can be labile under certain chemical conditions, e.g., acid. In this example, the surface of the solid support can contain a composition that generates acids upon exposure to light. Thus, exposure of a region of the substrate to light generates acids in that region that remove the protective groups in the exposed region. Also, the synthesis method can use 3'-protected 5'-0-phosphoramidite-activated deoxynucleoside. In this case, the oligonucleotide is synthesized in the 5' to 3' direction, which results in a free 5' end.

Oligonucleotides of an array can be synthesized using a 96 well automated multiplex oligonucleotide synthesizer (A.M.O.S.) that is capable of making thousands of oligonucleotides (Lashkari et al. (1995) PNAS 93: 7912) can be used.

It will be appreciated that oligonucleotide design is influenced by the intended application. For example, it may be desirable to have similar melting temperatures for all of the probes. Accordingly, the length of the probes are adjusted so that the melting temperatures for all of the probes on the array are closely similar (it will be appreciated that different lengths for different probes may be needed to achieve a particular T[m] where different probes have different GC contents). Although melting temperature is a primary consideration in probe design, other factors are optionally used to further adjust probe construction, such as selecting against primer self-complementarity and the like.

Arrays, e.g., microarrrays, may conveniently be stored following fabrication or purchase for use at a later time. Under appropriate conditions, the subject arrays are capable of being stored for at least about 6 months and may be stored for up to one year or longer. Arrays are generally stored at temperatures between about −20° C. to room temperature, where the arrays are preferably sealed in a plastic container, e.g. bag, and shielded from light.

(iv) Hybridization of the Target Nucleic Acids to the Microarray

The next step is to contact the target nucleic acids with the array under conditions sufficient for binding between the target nucleic acids and the probes of the array. In a preferred embodiment, the target nucleic acids will be contacted with the array under conditions sufficient for hybridization to occur between the target nucleic acids and probes on the microarray, where the hybridization conditions will be selected in order to provide for the desired level of hybridization specificity.

Contact of the array and target nucleic acids involves contacting the array with an aqueous medium comprising the target nucleic acids. Contact may be achieved in a variety of different ways depending on specific configuration of the array. For example, where the array simply comprises the pattern of size separated probes on the surface of a "plate-like" rigid substrate, contact may be accomplished by simply placing the array in a container comprising the target nucleic acid solution, such as a polyethylene bag, and the like. In other embodiments where the array is entrapped in a separation media bounded by two rigid plates, the opportunity exists to deliver the target nucleic acids via electrophoretic means. Alternatively, where the array is incorporated into a biochip device having fluid entry and exit ports, the target nucleic acid solution can be introduced into the chamber in which the pattern of target molecules is presented through the entry port, where fluid introduction could be performed manually or with an automated device. In multiwell embodiments, the target nucleic acid solution will be introduced in the reaction chamber comprising the array, either manually, e.g. with a pipette, or with an automated fluid handling device.

Contact of the target nucleic acid solution and the probes will be maintained for a sufficient period of time for binding between the target and the probe to occur. Although dependent on the nature of the probe and target, contact will generally be maintained for a period of time ranging from about 10 min to 24 hrs, usually from about 30 min to 12 hrs and more usually from about 1 hr to 6 hrs.

When using commercially available microarrays, adequate hybridization conditions are provided by the manufacturer. When using non-commercial microarrays, adequate hybridization conditions can be determined based on the following hybridization guidelines, as well as on the hybridization conditions described in the numerous published articles on the use of microarrays.

Nucleic acid hybridization and wash conditions are optimally chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls.

Hybridization is carried out in conditions permitting essentially specific hybridization. The length of the probe and GC content will determine the Tm of the hybrid, and thus the hybridization conditions necessary for obtaining specific hybridization of the probe to the template nucleic acid. These factors are well known to a person of skill in the art, and can also be tested in assays. An extensive guide to the hybridization of nucleic acids is found in Tijssen (1993), "Laboratory Techniques in biochemistry and molecular biology-hybridization with nucleic acid probes." Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Highly stringent conditions are selected to be equal to the Tm point for a particular probe. Sometimes the term "Td" is used to define the temperature at which at least half of the probe dissociates from a perfectly matched target nucleic acid. In any case, a variety of estimation techniques for estimating the Tm or Td are available, and generally described in Tijssen, supra. Typically, G-C base pairs in a duplex are estimated to contribute about 3° C. to the Tm, while A-T base pairs are estimated to contribute about 2° C., up to a theoretical maximum of about 80–100° C. However, more sophisticated models of Tm and Td are available and appropriate in which G-C stacking interactions, solvent effects, the desired assay temperature and the like are taken into account. For example, probes can be designed to have a dissociation temperature (Td) of approximately 60° C., using the formula: $Td=(((((3\times\#GC)+(2\times\#AT))\times37)-562)/\#bp)-5$; where #GC, #AT, and #bp are the number of guanine-cytosine base pairs, the number of adenine-thymine base pairs, and the number of total base pairs, respectively, involved in the annealing of the probe to the template DNA.

The stability difference between a perfectly matched duplex and a mismatched duplex, particularly if the mismatch is only a single base, can be quite small, corresponding to a difference in Tm between the two of as little as 0.5 degrees. See Tibanyenda, N. et al., Eur. J. Biochem. 139:19 (1984) and Ebel, S. et al., Biochem. 31:12083 (1992). More importantly, it is understood that as the length of the homology region increases, the effect of a single base mismatch on overall duplex stability decreases.

Theory and practice of nucleic acid hybridization is described, e.g., in S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, New York provide a basic guide to nucleic acid hybridization.

Certain microarrays are of "active" nature, i.e., they provide independent electronic control over all aspects of the hybridization reaction (or any other affinity reaction) occurring at each specific microlocation. These devices provide a new mechanism for affecting hybridization reactions which is called electronic stringency control (ESC). Such active devices can electronically produce "different stringency conditions" at each microlocation. Thus, all hybridizations can be carried out optimally in the same bulk solution. These arrays are described in U.S. Pat. No. 6,051,380 by Sosnowski et al.

In a preferred embodiment, background signal is reduced by the use of a detergent (e.g, C-TAB) or a blocking reagent (e.g., sperm DNA, cot-1 DNA, etc.) during the hybridization to reduce non-specific binding. In a particularly preferred (embodiment, the hybridization is performed in the presence of about 0.5 mg/ml DNA (e.g., herring sperm DNA). The use of blocking agents in hybridization is well known to those of skill in the art (see, e.g., Chapter 8 in Laboratory Techniques in Biochemistry and Molecular Biology, Vol. 24: Hybridization With Nucleic Acid Probes, P. Tijssen, ed. Elsevier, N.Y., (1993)).

The method may or may not further comprise a non-bound label removal step prior to the detection step, depending on the particular label employed on the target nucleic acid. For example, in certain assay formats (e.g., "homogenous assay formats") a detectable signal is only generated upon specific binding of target to probe. As such, in these assay formats, the hybridization pattern may be detected without a non-bound label removal step. In other embodiments, the label employed will generate a signal whether or not the target is specifically bound to its probe. In such embodiments, the non-bound labeled target is removed from the support surface. One means of removing the non-bound labeled target is to perform the well known technique of washing, where a variety of wash solutions and protocols for their use in removing non-bound label are known to those of skill in the art and may be used. Alternatively, non-bound labeled target can be removed by electrophoretic means.

Where all of the target sequences are detected using the same label, different arrays will be employed for each physiological source or time point (where different could include using the same array at different times). The above methods can be varied to provide for multiplex analysis, by employing different and distinguishable labels for the different target populations (representing each of the different physiological sources or time points being assayed). According to this multiplex method, the same array is used at the same time for each of the different target populations.

In another embodiment, hybridization is monitored in real time using a charge-coupled device (CCD) imaging camera (Guschin et al. (1997) Anal. Biochem. 250:203). Synthesis of arrays on optical fibre bundles allows easy and sensitive reading (Healy et al. (1997) Anal. Biochem. 251:270). In another embodiment, real time hybridization detection is carried out on microarrays without washing using evanescent wave effect that excites only fluorophores that are bound to the surface (see, e.g., Stimpson et al. (1995) PNAS 92:6379).

(v) Detection of Hybridization and Analysis of Results

The above steps result in the production of hybridization patterns of target nucleic acid on the array surface. These patterns may be visualized or detected in a variety of ways, with the particular manner of detection being chosen based on the particular label of the target nucleic acid. Representative detection means include scintillation counting, autoradiography, fluorescence measurement, colorimetric measurement, light emission measurement, light scattering, and the like.

One method of detection includes an array scanner that is commercially available from Affymetrix (Santa Clara, Calif.), e.g., the 417™ Arrayer, the 418™ Array Scanner, or the Agilent GeneArray™ Scanner. This scanner is controlled from the system computer with a Windows$^R$ interface and easy-to-use software tools. The output is a 16-bit.tif file that can be directly imported into or directly read by a variety of software applications. Preferred scanning devices are described in, e.g., U.S. Pat. Nos. 5,143,854 and 5,424,186.

When fluorescently labeled probes are used, the fluorescence emissions at each site of a transcript array can be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, A DNA microarray system for analyzing complex DNA samples using two-color fluorescent probe hybridization, Genome Research 6:639–645). In a preferred embodiment, the arrays are scanned with a laser fluorescent scanner with a computer controlled X-Y stage and a microscope objective. Sequential excitation of the two fluorophores can be achieved with a multi-line, mixed gas laser and the emitted light is split by wavelength and detected with two photomultiplier tubes. In one embodiment in which fluorescent target nucleic acids are used, the arrays may be scanned using lasers to excite fluorescently labeled targets that have hybridized to regions of probe arrays, which can then be imaged using charged coupled devices ("CCDs") for a wide field scanning of the array. Fluorescence laser scanning devices are described, e.g., in Schena et al., 1996, Genome Res. 6:639–645. Alternatively, the fiber-optic bundle described by Ferguson et al., 1996, Nature Biotech. 14:1681–1684, may be used to monitor mRNA abundance levels.

Following the data gathering operation, the data will typically be reported to a data analysis operation. To facilitate the sample analysis operation, the data obtained by the reader from the device will typically be analyzed using a digital computer. Typically, the computer will be appropriately programmed for receipt and storage of the data from the device, as well as for analysis and reporting of the data gathered, e.g., subtrackion of the background, deconvolution multi-color images, flagging or removing artifacts, verifying that controls have performed properly, normalizing the signals, interpreting fluorescence data to determine the amount of hybridized target, normalization of background and single base mismatch hybridizations, and the like. In a preferred embodiment, a system comprises a search function that allows one to search for specific patterns, e.g., patterns relating to differential gene expression of genes which are up- or down-regulated during bone or cartilage formation. A system preferably allows one to search for patterns of gene expression between more than two samples.

A desirable system for analyzing data is a general and flexible system for the visualization, manipulation, and analysis of gene expression data. Such a system preferably includes a graphical user interface for browsing and navigating through the expression data, allowing a user to selectively view and highlight the genes of interest. The system also preferably includes sort and search functions and is preferably available for general users with PC, Mac or Unix workstations. Also preferably included in the system are clustering algorithms that are qualitatively more efficient than existing ones. The accuracy of such algorithms is preferably hierarchically adjustable so that the level of detail of clustering can be systematically refined as desired.

Various algorithms are available for analyzing the gene expression profile data, e.g., the type of comparisons to perform. In certain embodiments, it is desirable to group genes that are co-regulated. This allows the comparison of large numbers of profiles. A preferred embodiment for identifying such groups of genes involves clustering algorithms (for reviews of clustering algorithms, see, e.g., Fukunaga, 1990, Statistical Pattern Recognition, 2nd Ed., Academic Press, San Diego; Everitt, 1974, Cluster Analysis, London: Heinemann Educ. Books; Hartigan, 1975, Clustering Algorithms, New York: Wiley; Sneath and Sokal, 1973, Numerical Taxonomy, Freeman; Anderberg, 1973, Cluster Analysis for Applications, Academic Press: New York).

Clustering analysis is useful in helping to reduce complex patterns of thousands of time curves into a smaller set of representative clusters. Some systems allow the clustering and viewing of genes based on sequences. Other systems allow clustering based on other characteristics of the genes, e.g., their level of expression (see, e.g., U.S. Pat. No. 6,203,987). Other systems permit clustering of time curves (see, e.g. U.S. Pat. No. 6,263,287). Cluster analysis can be performed using the hclust routine (see, e.g., "hclust" routine from the software package S-Plus, MathSoft, Inc., Cambridge, Mass.).

In some specific embodiments, genes are grouped according to the degree of co-variation of their transcription, presumably co-regulation, as described in U.S. Pat. No. 6,203,987. Groups of genes that have co-varying transcripts are termed "genesets." Cluster analysis or other statistical classification methods can be used to analyze the co-variation of transcription of genes in response to a variety of perturbations, e.g. caused by a disease or a drug. In one specific embodiment, clustering algorithms are applied to expression profiles to construct a "similarity tree" or "clustering tree" which relates genes by the amount of co-regulation exhibited. Genesets are defined on the branches of a clustering tree by cutting across the clustering tree at different levels in the branching hierarchy.

In some embodiments, a gene expression profile is converted to a projected gene expression profile. The projected gene expression profile is a collection of geneset expression values. The conversion is achieved, in some embodiments, by averaging the level of expression of the genes within each geneset. In some other embodiments, other linear projection processes may be used. The projection operation expresses the profile on a smaller and biologically more meaningful set of coordinates, reducing the effects of measurement errors by averaging them over each cellular constituent sets and aiding biological interpretation of the profile.

Values that can be compared include gross expression levels; averages of expression levels, e.g., from different experiments, different samples from the same subject or samples from different subjects; and ratios of expression levels, e.g., between patients and normal controls.

A variety of other statistical methods are available to assess the degree of relatedness in expression patterns of different genes. Certain statistical methods may be broken into two related portions: metrics for determining the relatedness of the expression pattern of one or more gene, and clustering methods, for organizing and classifying expression data based on a suitable metric (Sherlock, 2000, Curr. Opin. Immunol. 12:201–205; Butte et al., 2000, Pacific Symposium on Biocomputing, Hawaii, World Scientific, p. 418–29).

In one embodiment, Pearson correlation may be used as a metric. In brief, for a given gene, each data point of gene expression level defines a vector describing the deviation of the gene expression from the overall mean of gene expression level for that gene across all conditions. Each gene's expression pattern can then be viewed as a series of positive and negative vectors. A Pearson correlation coefficient can then be calculated by comparing the vectors of each gene to each other. An example of such a method is described in Eisen et al. (1998, supra). Pearson correlation coefficients account for the direction of the vectors, but not the magnitudes.

In another embodiment, Euclidean distance measurements may be used as a metric. In these methods, vectors are calculated for each gene in each condition and compared on the basis of the absolute distance in multidimensional space between the points described by the vectors for the gene.

In a further embodiment, the relatedness of gene expression patterns may be determined by entropic calculations (Butte et al. 2000, supra). Entropy is calculated for each gene's expression pattern. The calculated entropy for two genes is then compared to determine the mutual information. Mutual information is calculated by subtracting the entropy of the joint gene expression patterns from the entropy for calculated for each gene individually. The more different two gene expression patterns are, the higher the joint entropy will be and the lower the calculated mutual information. Therefore, high mutual information indicates a non-random relatedness between the two expression patterns.

The different metrics for relatedness may be used in various ways to identify clusters of genes. In one embodiment, comprehensive pairwise comparisons of entropic measurements will identify clusters of genes with particularly high mutual information. In preferred embodiments, expression patterns for two genes are correlated if the normalized mutual information score is greater than or equal to 0.7, and preferably greater than 0.8, greater than 0.9 or greater than 0.95. In alternative embodiments, a statistical significance for mutual information may be obtained by randomly permuting the expression measurements 30 times and determining the highest mutual information measurement obtained from such random associations. All clusters with a mutual information higher than can be obtained randomly after 30 permutations are statistically significant. In a further embodiment, expression patterns for two genes are correlated if the correlation coefficient is greater than or equal to 0.8, and preferably greater than 0.85, 0.9 or, most preferably greater than 0.95.

In another embodiment, agglomerative clustering methods may be used to identify gene clusters. In one embodiment, Pearson correlation coefficients or Euclidean metrics are determined for each gene and then used as a basis for forming a dendrogram. In one example, genes were scanned for pairs of genes with the closest correlation coefficient. These genes are then placed on two branches of a dendrogram connected by a node, with the distance between the depth of the branches proportional to the degree of correlation. This process continues, progressively adding branches to the tree. Ultimately a tree is formed in which genes connected by short branches represent clusters, while genes connected by longer branches represent genes that are not clustered together. The points in multidimensional space by Euclidean metrics may also be used to generate dendrograms.

In yet another embodiment, divisive clustering methods may be used. For example, vectors are assigned to each gene's expression pattern, and two random vectors are generated. Each gene is then assigned to one of the two random vectors on the basis of probability of matching that vector. The random vectors are iteratively recalculated to generate two centroids that split the genes into two groups. This split forms the major branch at the bottom of a dendrogram. Each group is then further split in the same manner, ultimately yielding a fully branched dendrogram.

In a further embodiment, self-organizing maps (SOM) may be used to generate clusters. In general, the gene expression patterns are plotted in n-dimensional space, using a metric such as the Euclidean metrics described above. A grid of centroids is then placed onto the n-dimensional space and the centroids are allowed to migrate towards clusters of points, representing clusters of gene expression. Finally the centroids represent a gene expression pattern that is a sort of average of a gene cluster. In certain embodiments, SOM may be used to generate centroids, and the genes clustered at each centroid may be further represented by a dendrogram. An exemplary method is described in Tamayo et al., 1999, PNAS 96:2907–12. Once centroids are formed, correlation must be evaluated by one of the methods described supra.

2.2. Other Methods for Determining Gene Expression Levels

In certain embodiments, it is sufficient to determine the expression of one or only a few genes, as opposed to hundreds or thousands of genes. Although microarrays can be used in these embodiments, various other methods of detection of gene expression are available. This section describes a few exemplary methods for detecting and quantifying mRNA or polypeptide encoded thereby. Where the first step of the methods includes isolation of mRNA from cells, this step can be conducted as described above. Labeling of one or more nucleic acids can be performed as described above.

In one embodiment, mRNA obtained form a sample is reverse transcribed into a first cDNA strand and subjected to PCR, e.g., RT-PCR. House keeping genes, or other genes whose expression does not vary can be used as internal controls and controls across experiments. Following the PCR reaction, the amplified products can be separated by electrophoresis and detected. By using quantitative PCR, the level of amplified product will correlate with the level of RNA that was present in the sample. The amplified samples can also be separated on a agarose or polyacrylamide gel, transferred onto a filter, and the filter hybridized with a probe specific for the gene of interest. Numerous samples can be analyzed simultaneously by conducting parallel PCR amplification, e.g., by multiplex PCR.

A quantitative PCR technique that can be used is based on the use of TaqMan™ probes. Specific sequence detection occurs by amplification of target sequences in the PE Applied Biosystems 7700 Sequence Detection System in the presence of an oligonucleotide probe labeled at the 5' and 3' ends with a reporter and quencher fluorescent dye, respectively (FQ probe), which anneals between the two PCR primers. Only specific product will be detected when the probe is bound between the primers. As PCR amplification proceeds, the 5'-nuclease activity of Taq polymerase initially cleaves the reporter dye from the probe. The signal generated when the reporter dye is physically separated from the quencher dye is detected by measuring the signal with an attached CCD camera. Each signal generated equals one probe cleaved which corresponds to amplification of one target strand. PCR reactions may be set up using the PE Applied Biosystem TaqMan PCR Core Reagent Kit according to the instructions supplied. This technique is further described, e.g., in U.S. Pat. No. 6,326,462.

In another embodiment, mRNA levels is determined by dotblot analysis and related methods (see, e.g., G. A. Beltz et al., in Methods in Enzymology, Vol. 100, Part B, R. Wu, L. Grossmam, K. Moldave, Eds., Academic Press, New York, Chapter 19, pp. 266–308, 1985). In one embodiment, a specified amount of RNA extracted from cells is blotted (i.e., non-covalently bound) onto a filter, and the filter is hybridized with a probe of the gene of interest. Numerous RNA samples can be analyzed simultaneously, since a blot can comprise multiple spots of RNA. Hybridization is detected using a method that depends on the type of label of the probe. In another dotblot method, one or more probes of one or more genes which are up- or down-regulated during bone or cartilage formation are attached to a membrane, and the membrane is incubated with labeled nucleic acids obtained from and optionally derived from RNA of a cell or tissue of a subject. Such a dotblot is essentially an array comprising fewer probes than a microarray.

"Dot blot" hybridization gained wide-spread use, and many versions were developed (see, e.g., M. L. M. Anderson and B. D. Young, in Nucleic Acid Hybridization-A Practical Approach, B. D. Hames and S. J. Higgins, Eds., IRL Press, Washington D.C., Chapter 4, pp. 73–111, 1985).

Another format, the so-called "sandwich" hybridization, involves covalently attaching oligonucleotide probes to a solid support and using them to capture and detect multiple nucleic acid targets (see, e.g., M. Ranki et al., Gene, 21, pp. 77–85, 1983; A. M. Palva, T. M. Ranki, and H. E. Soderlund, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R. B. Wallace et al. 6 Nucleic Acid Res. 11, p. 3543, 1979; and B. J. Connor et al., 80 Proc. Natl. Acad. Sci. USA pp. 278–282, 1983). Multiplex versions of these formats are called "reverse dot blots."

mRNA levels can also be determined by Northern blots. Specific amounts of RNA are separated by gel electrophoresis and transferred onto a filter which is then hybridized with a probe corresponding to the gene of interest. This method, although more burdensome when numerous samples and genes are to be analyzed provides the advantage of being very accurate.

A preferred method for high throughput analysis of gene expression is the serial analysis of gene expression (SAGE) technique, first described in Velculescu et al. (1995) Science 270, 484–487. Among the advantages of SAGE is that it has the potential to provide detection of all genes expressed in a given cell type, provides quantitative information about the relative expression of such genes, permits ready comparison of gene expression of genes in two cells, and yields sequence information that can be used to identify the detected genes. Thus far, SAGE methodology has proved itself to reliably detect expression of regulated and nonregulated genes in a variety of cell types (Velculescu et al. (1997) *Cell* 88, 243–251; Zhang et al. (1997) *Science* 276, 1268–1272 and Velculescu et al. (1999) *Nat. Genet.* 23, 387–388).

Techniques for producing and probing nucleic acids are further described, for example, in Sambrook et al., "Molecular Cloning: A Laboratory Manual" (New York, Cold Spring Harbor Laboratory, 1989).

Alternatively, the level of expression of one or more genes which are up- or down-regulated during bone or cartilage formation is determined by in situ hybridization. In one embodiment, a tissue sample is obtained from a subject, the tissue sample is sliced, and in situ hybridization is performed according to methods known in the art, to determine the level of expression of the genes of interest.

In other methods, the level of expression of a gene is detected by measuring the level of protein encoded by the gene. This can be done, e.g., by immunoprecipitation, ELISA, or immunohistochemistry using an agent, e.g., an antibody, that specifically detects the protein encoded by the gene. Other techniques include Western blot analysis. Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In the case of polypeptides which are secreted from cells, the level of expression of these polypeptides can be measured in biological fluids.

2.3. Data Analysis Methods

Comparison of the expression levels of one or more genes which are up- or down-regulated in a sample, e.g., of a patient, with reference expression levels, e.g., in normal cells undergoing bone or cartilage formation, is preferably conducted using computer systems. In one embodiment, one or more expression levels are obtained in two cells and these two sets of expression levels are introduced into a computer system for comparison. In a preferred embodiment, one set of one or more expression levels is entered into a computer system for comparison with values that are already present in the computer system, or in computer-readable form that is then entered into the computer system.

In one embodiment, the invention provides a computer readable form of the gene expression profile data of the invention, or of values corresponding to the level of expression of at least one gene which is up- or down-regulated during bone or cartilage formation. The values can be mRNA expression levels obtained from experiments, e.g., microarray analysis. The values can also be mRNA levels normalized relative to a reference gene whose expression is constant in numerous cells under numerous conditions, e.g., GAPDH. In other embodiments, the values in the computer are ratios of, or differences between, normalized or non-normalized mRNA levels in different samples.

The computer readable medium may comprise values of at least 2, at least 3, at least 5, 10, 20, 50, 100, 200, 500 or more genes, e.g., genes listed in Tables 1, 2, 5, 6 and/or 7. In a preferred embodiment, the computer readable medium comprises at least one expression profile.

Gene expression data can be in the form of a table, such as an Excel table. The data can be alone, or it can be part of a larger database, e.g., comprising other expression profiles, e.g., publicly available database. The computer readable form can be in a computer. In another embodiment, the invention provides a computer displaying the gene expression profile data.

Although the invention provides methods in which the level of expression of a single gene can be compared in two or more cells or tissue samples, in a preferred embodiment, the level of expression of a plurality of genes is compared.

For example, the level of expression of at least 2, at least 3, at least 5, 10, 20, 50, 100, 200, 500 or more genes, e.g., genes listed in Tables 1, 2, 5, 6 and/or 7 can be compared. In a preferred embodiment, expression profiles are compared.

In one embodiment, the invention provides a method for determining the similarity between the level of expression of one or more genes which are up- or down-regulated during bone or cartilage formation in a first cell, e.g., a cell of a subject, and that in a second cell. The method preferably comprises obtaining the level of expression of one or more genes which are up- or down-regulated during bone or cartilage formation in a first cell and entering these values into a computer comprising (i) a database including records comprising values corresponding to levels of expression of one or more genes which are up- or down-regulated during bone or cartilage formation in a second cell, and (ii) processor instructions, e.g., a user interface, capable of receiving a selection of one or more values for comparison purposes with data that is stored in the computer. The computer may further comprise a means for converting the comparison data into a diagram or chart or other type of output.

In another embodiment, values representing expression levels of one or more genes which are up- or down-regulated during bone or cartilage formation are entered into a computer system that comprises one or more databases with reference expression levels obtained from more than one cell. For example, the computer may comprise expression data of diseased, e.g., bone or cartilage cells of an osteoporosis patient, and normal cells. The computer may also comprise expression data of genes at different time points during bone or cartilage formation, e.g., the data set forth in Tables 1, 2, 5, 6 and/or 7. Instructions are provided to the computer, and the computer is capable of comparing the data entered with the data in the computer to determine whether the data entered is more similar to one or the other gene expression data stored in the computer.

In another embodiment, the computer comprises values of expression levels in cells of subjects at different stages of a disease relating to bone or cartilage formation or resorption, and the computer is capable of comparing expression data entered into the computer with the data stored, and produce results indicating to which of the expression data in the computer, the one entered is most similar, such as to determine the stage of the disease in the subject.

In yet another embodiment, the reference expression data in the computer are expression data from cells of one or more subjects having a disease relating to bone or cartilage formation or resorption, which cells are treated in vivo or in vitro with a drug used for therapy of the disease. Upon entering of expression data of a cell of a subject treated in vitro or in vivo with the drug, the computer is instructed to compare the data entered with the data in the computer, and to provide results indicating whether the expression data input into the computer are more similar to those of a cell of a subject that is responsive to the drug or more similar to those of a cell of a subject that is not responsive to the drug. Thus, the results indicate whether the subject is likely to respond to the treatment with the drug or unlikely to respond to it.

The reference expression data may also be from cells of subjects responding or not responding to several different treatments, and the computer system indicates a preferred treatment for the subject. Accordingly, the invention provides a method for selecting a therapy for a patient having a disease relating to bone or cartilage formation or resorption, the method comprising: (i) providing the level of expression of one or more genes which are up- or down-regulated during bone or cartilage formation in a diseased cell of the patient; (ii) providing a plurality of reference expression levels, each associated with a therapy, wherein the subject expression levels and each reference expression level has a plurality of values, each value representing the level of expression of a gene that is up- or down-regulated during bone or cartilage formation; and (iii) selecting the reference expression levels most similar to the subject expression levels, to thereby select a therapy for said patient. In a preferred embodiment step (iii) is performed by a computer. The most similar reference profile may be selected by weighing a comparison value of the plurality using a weight value associated with the corresponding expression data.

In one embodiment, the invention provides a system that comprises a means for receiving gene expression data for one or a plurality of genes; a means for comparing the gene expression data from each of said one or plurality of genes to a common reference frame; and a means for presenting the results of the comparison. This system may further comprise a means for clustering the data.

In another embodiment, the invention provides a computer program for analyzing gene expression data comprising (i) a computer code that receives as input gene expression data for a plurality of genes and (ii) a computer code that compares said gene expression data from each of said plurality of genes to a common reference frame.

The invention also provides a machine-readable or computer-readable medium including program instructions for performing the following steps: (i) comparing a plurality of values corresponding to expression levels of one or more genes which are up- or down-regulated during bone or cartilage formation in a query cell with a database including records comprising reference expression of one or more reference cells and an annotation of the type of cell; and (ii) indicating to which cell the query cell is most similar based on similarities of expression levels.

The relative levels of expression, e.g., abundance of an mRNA, in two biological samples can be scored as a perturbation (relative abundance difference) or as not perturbed (i.e., the relative abundance is the same). For example, a perturbation can be a difference in expression levels between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant). Perturbations can be used by a computer for calculating and expressing comparisons.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

The computer readable medium may further comprise a pointer to a descriptor of the level of expression or expression profile, e.g., from which source it was obtained, e.g., from which patient it was obtained. A descriptor can reflect the stage of a disease, the therapy that a patient is undergoing or any other descriptions of the source of expression levels.

In operation, the means for receiving gene expression data, the means for comparing the gene expression data, the means for presenting, the means for normalizing, and the means for clustering within the context of the systems of the present invention can involve a programmed computer with the respective functionalities described herein, implemented in hardware or hardware and software; a logic circuit or other component of a programmed computer that performs the operations specifically identified herein, dictated by a computer program; or a computer memory encoded with executable instructions representing a computer program that can cause a computer to function in the particular fashion described herein.

Those skilled in the art will understand that the systems and methods of the present invention may be applied to a variety of systems, including IBM-compatible personal computers running MS-DOS or Microsoft Windows.

The computer may have internal components linked to external components. The internal components may include a processor element interconnected with a main memory. The computer system can be an Intel Pentium®-based processor of 200 MHz or greater clock rate and with 32 MB or more of main memory. The external component may comprise a mass storage, which can be one or more hard disks (which are typically packaged together with the processor and memory). Such hard disks are typically of 1 GB or greater storage capacity. Other external components include a user interface device, which can be a monitor, together with an inputing device, which can be a "mouse", or other graphic input devices, and/or a keyboard. A printing device can also be attached to the computer.

Typically, the computer system is also linked to a network link, which can be part of an Ethernet link to other local computer systems, remote computer systems, or wide area communication networks, such as the Internet. This network link allows the computer system to share data and processing tasks with other computer systems.

Loaded into memory during operation of this system are several software components, which are both standard in the art and special to the instant invention. These software components collectively cause the computer system to function according to the methods of this invention. These software components are typically stored on a mass storage. A software component represents the operating system, which is responsible for managing the computer system and its network interconnections. This operating system can be, for example, of the Microsoft Windows' family, such as Windows 95, Windows 98, or Windows NT. A software component represents common languages and functions conveniently present on this system to assist programs implementing the methods specific to this invention. Many high or low level computer languages can be used to program the analytic methods of this invention. Instructions can be interpreted during run-time or compiled. Preferred languages include C/C++, and JAVA®. Most preferably, the methods of this invention are programmed in mathematical software packages which allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, Ill.), or S-Plus from Math Soft (Cambridge, Mass.). Accordingly, a software component represents the analytic methods of this invention as programmed in a procedural language or symbolic package. In a preferred embodiment, the computer system also contains a database comprising values representing levels of expression of one or more genes which are up- or down-regulated during bone or cartilage formation. The database may contain one or more expression profiles of genes which are up- or down-regulated during bone or cartilage formation in different cells.

In an exemplary implementation, to practice the methods of the present invention, a user first loads expression data into the computer system. These data can be directly entered by the user from a monitor and keyboard, or from other computer systems linked by a network connection, or on removable storage media such as a CD-ROM or floppy disk or through the network. Next the user causes execution of expression profile analysis software which performs the steps of comparing and, e.g., clustering co-varying genes into groups of genes.

In another exemplary implementation, expression profiles are compared using a method described in U.S. Pat. No. 6,203,987. A user first loads expression profile data into the computer system. Geneset profile definitions are loaded into the memory from the storage media or from a remote computer, preferably from a dynamic geneset database system, through the network. Next the user causes execution of projection software which performs the steps of converting expression profile to projected expression profiles. The projected expression profiles are then displayed.

In yet another exemplary implementation, a user first leads a projected profile into the memory. The user then causes the loading of a reference profile into the memory. Next, the user causes the execution of comparison software which performs the steps of objectively comparing the profiles.

3. Exemplary Diagnostic and Prognostic Compositions and Devices of the Invention Any composition and device (e.g., an array or microarray) for use in the above-described methods are within the scope of the invention.

In one embodiment, the invention provides a composition comprising a plurality of detection agents for detecting expression of genes which are up- or down-regulated during bone or cartilage formation. In a preferred embodiment, the composition comprises at least 2, preferably at least 3, 5, 10, 20, 50, or 100 different detection agents, such as to genes listed in Tables 1, 2, 5, 6 and/or 7. In certain embodiments, the composition comprises at most about 1000, 500, 300, 100, 50, 30, 10, 5 or 3 detection agents. Certain composition may comprise no more than about 1, 2, 3, 5, or 10 detection agents of genes which are not listed in Tables 1, 2, 5, 6 and/or 7. In certain compositions, less than about 1%, 3%, 5%, 10%, 30% or 50% of the detection agents are to genes that are not listed in Tables 1, 2, 5, 6 and/or 7. A detection agent can be a nucleic acid probe, e.g., DNA or RNA, or it can be a polypeptide, e.g., as antibody that binds to the polypeptide encoded by a gene that is up- or down-regulated during bone or cartilage formation. The probes can be present in equal amount or in different amounts in the solution.

A nucleic acid probe can be at least about 10 nucleotides long, preferably at least about 15, 20, 25, 30, 50, 100 nucleotides or more, and can comprise the full length gene. Preferred probes are those that hybridize specifically to genes listed in any of Tables 1, 2, 5, 6 and/or 7. If the nucleic acid is short (i.e., 20 nucleotides or less), the sequence is preferably perfectly complementary to the target gene (i.e., a gene that is up- or down-regulated during bone or cartilage formation), such that specific hybridization can be obtained. However, nucleic acids, even short ones that are not perfectly complementary to the target gene can also be included in a composition of the invention, e.g., for use as a negative control. Certain compositions may also comprise nucleic acids that are complementary to, and capable of detecting, an allele of a gene.

In a preferred embodiment, the invention provides nucleic acids which hybridize under high stringency conditions of 0.2 to 1×SSC at 65° C. followed by a wash at 0.2×SSC at 65° C. to genes which are up- or down-regulated during bone or cartilage formation. In another embodiment, the invention provides nucleic acids which hybridize under low stringency conditions of 6×SSC at room temperature followed by a wash at 2×SSC at room temperature. Other nucleic acids probes hybridize to their target in 3×SSC at 40 or 50° C., followed by a wash in 1 or 2×SSC at 20, 30, 40, 50, 60, or 65° C.

Nucleic acids which are at least about 80%, preferably at least about 90%, even more preferably at least about 95% and most preferably at least about 98% identical to genes which are up- or down-regulated during bone or cartilage formation or cDNAs thereof, complements thereof, fragments and variants are also within the scope of the invention.

Nucleic acid probes can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments. Computer programs can be used in the design of primers with the required specificity and optimal amplification properties. See, e.g., Oligo version 5.0 (National Biosciences). Factors which apply to the design and selection of primers for amplification are described, for example, by Rylchik, W. (1993) "Selection of Primers for Polymerase Chain Reaction," in Methods in Molecular Biology, Vol. 15, White B. ed., Humana Press, Totowa, N.J. Sequences can be obtained from GenBank or other public sources.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Nat. Acad. Sci. U.S.A. 85: 7448–7451), etc. In another embodiment, the oligonucleotide is a 2'-0-methylribonucleotide (Inoue et al., 1987, Nucl. Acids Res. 15: 6131–6148), or a chimeric RNA-DNA analog (Inoue et al., 1987, FEBS Lett. 215: 327–330).

"Rapid amplification of cDNA ends," or RACE, is a PCR method that can be used for amplifying cDNAs from a number of different RNAs. The cDNAs may be ligated to an oligonucleotide linker and amplified by PCR using two primers. One primer may be based on sequence from the instant nucleic acids, for which full length sequence is desired, and a second primer may comprise a sequence that hybridizes to the oligonucleotide linker to amplify the cDNA. A description of this method is reported in PCT Pub. No. WO 97/19110.

In another embodiment, the invention provides a composition comprising a plurality of agents which can detect a polypeptide encoded by a gene that is up- or down-regulated during bone or cartilage formation. An agent can be, e.g., an antibody. Antibodies to polypeptides described herein can be obtained commercially, or they can be produced according to methods known in the art.

The probes can be attached to a solid support, such as paper, membranes, filters, chips, pins or glass slides, or any other appropriate substrate, such as those further described herein. For example, probes of genes which are up- or down-regulated during bone or cartilage formation can be attached covalently or non covalently to membranes for use, e.g., in dotblots, or to solids such as to create arrays, e.g., microarrays. Exemplary solid surfaces, e.g., arrays, comprise probes corresponding to all or a portion of the genes listed in Tables 1, 2, 5, 6 and/or 7. Solid surfaces may comprise at least about 1, 2, 3, 5, 10, 20, 30, or 100 probes corresponding to genes listed in Tables 1, 2, 5, 6 and/or 7. In certain embodiments, solid surfaces comprise less than about 1, 2, 3, 5, 10, 20, 30, or 100 probes corresponding to genes that are not listed in Tables 1, 2, 5, 6 and/or 7. In certain solid surfaces, less than about 1%, 2%, 3%, 5%, 10%, 20%, 30%, or 50% of the probes are probes that correspond to genes that are not listed in any of Tables 1, 2, 5, 6 and/or 7.

The invention also provides computer-readable media and computers comprising expression values of all or a portion of the genes set forth in Tables 1, 2, 5, 6 and/or 7 during bone and cartilage development, such as the values set forth in Tables 1, 2, 5, 6 and/or 7. The media and computers may comprise at least about 1, 2, 3, 5, 10, 20, 30, or 100 values of genes listed in Tables 1, 2, 5, 6 and/or 7. In certain embodiments, media and computers comprise less than about 1, 2, 3, 5, 10, 20, 30, or 100 values of genes that are not listed in Tables 1, 2, 5, 6 and/or 7. In certain media and computers, less than about 1%, 2%, 3%, 5%, 10%, 20%, 30%, or 50% of the values correspond to genes that are not listed in Tables 1, 2, 5, 6 and/or 7.

Methods for preparing compositions and devices, e.g., computer readable media, are also within the scope of the invention.

4. Therapeutic Methods and Compositions

Up- or down-regulation of genes which have been shown to be down- and up-regulated during bone formation, respectively, can be used as a therapeutic method in various situations, e.g., diseases relating to bone and cartilage formation, such as osteodystrophy, osteohypertrophy, osteoblastoma, osteopertrusis, osteogenesis imperfecta, osteoporosis, osteopenia, osteoma and osteoblastoma; inflammatory diseases, such as rheumatoid arthritis and osteoarthritis; periodontal disease or other teeth related diseases; hyperparathyroidism; hypercalcemia of malignancy; Paget's disease; osteolytic lesions produced by bone metastasis; bone loss due to immobilization or sex hormone deficiency; wound healing and related tissue repair (e.g., burns, incisions and ulcers); healing of fractures, e.g., in closed and open fracture reduction; improved fixation of artificial joints; repair of congenital, trauma induced, or oncologic resection induced craniofacial defects; tooth repair processes and plastic, e.g., cosmetic plastic, surgery.

Accordingly, in certain diseases, e.g., osteoporosis, which can be treated by stimulating bone or cartilage formation, the invention provides methods for stimulating bone or cartilage formation. In other diseases, e.g., osteodystrophy, osteohypertrophy, osteoma, osteoblastoma and cancers, which can be treated by inhibiting bone or cartilage formation, the invention provides methods for inhibiting bone or cartilage formation.

Certain genes have been shown herein to be expressed maximally in differentiated bone cells (see, e.g., genes represented in bold and italics in Table 1). Such genes are likely to be markers of osteoclast formation, differentiation or activity. Thus, inhibiting the expression of one or more of these genes or reducing the activity of level of the protein encoded thereby, will reduce osteoclast activity, and could thus be used in treating diseases relating to excessive osteoclast activity, e.g., osteopenia, osteoporosis and erosion associated with arthritis.

In other embodiments, the invention is used for stimulating in vitro formation of bone or cartilage that can then be implanted into subjects.

In one embodiment, a therapeutic method includes increasing or decreasing the level of expression of one or more genes whose expression is abnormally low or high, respectively, relatively to that in a normal subject. For example, the invention may comprise first determining the level of expression of one or more genes that are up- or down-regulated during bone or cartilage formation, e.g., genes in any of the Tables described herein, and then bringing the level of expression of the genes whose level of expression differs from the control to about the level in the control.

Gene expression may be normalized, i.e., brought to within a similar level relative to a control, by various ways. For example, gene expression may be normalized by administering the protein that is encoded by the gene; by administering a nucleic acid encoding the protein that is encoded by the gene; or by stimulating expression of the gene. Reducing gene expression can be achieved, e.g., by administration of antisense, siRNA, ribozymes or aptamers directed to the gene or antibodies or other molecules that bind and, e.g., inactivate the protein encoded by the gene.

In certain embodiments, osteogenic, cartilage-inducing or bone inducing factors can be co-administered together with a gene-specific therapeutic to a subject. For example, a growth or differentiation factor or bone morphogenetic protein, e.g., BMP-2 can be co-administered. Other factors that can be co-administered include those described in European patent applications 148,155 and 169,016.

4.1. Methods for Confirming that Modulation of the Expression of a Gene Improves a Disease Relating to Bone or Cartilage Formation or Resorption In one embodiment, the effect of up- or down-regulating the level of expression of a gene which is down- or up-regulated, respectively, in a cell of a subject having a disease relating to bone or cartilage formation or resorption can be confirmed by phenotypic analysis of the cell characteristic of the disease, in particular by determining whether the cell adopts a phenotype that is more reminiscent of that of a normal cell than that of a cell characteristic of the disease relating to bone or cartilage formation or resorption. A "cell characteristic of a disease" also referred to as a "diseased cell" refers to a cell of a subject having a disease, which cell is affected by the disease, and is therefore different from the corresponding cell in a non-diseased subject. For example a cell characteristic of cancer is a cancer cell or tumor cell.

The effect on the cell can also be confirmed by measuring the level of expression of one or more genes which are up- or down-regulated during bone or cartilage formation, and preferably at least about 10, or at least about 100 genes which are up- or down-regulated during bone or cartilage formation. In a preferred embodiment, the level of expression of a gene is modulated, and the level of expression of at least one gene that is up- or down-regulated during bone or cartilage formation is determined, e.g., by using a microarray having probes to the one or more genes. If the normalization of expression of the gene results in at least some normalization of the gene expression profile in the diseased cell, then normalizing the expression of the gene in the subject having the disease is expected to improve the disease. The term "normalization of the expression of a gene in a diseased cell" refers to bringing the level of expression of that gene in the diseased cell to a level that is similar to that in the corresponding normal cell. "Normalization of the gene expression profile in a diseased cell" refers to bringing the expression profile in a diseased cell essentially to that in the corresponding non-diseased cell. If, however, the normalization of expression of the gene does not result in at least some normalization of the gene expression profile in the diseased cell, normalizing the expression of the gene in a subject having a disease relating to bone or cartilage formation or resorption is not expected to improve the disease. In certain embodiments, the expression level of two or more genes which are up- or down-regulated during bone or cartilage formation is modulated and the effect on the diseased cell is determined.

A preferred cell for use in these assays is a cell characteristic of a disease relating to bone or cartilage formation or resorption that can be obtained from a subject and, e.g., established as a primary cell culture. The cell can be immortalized by methods known in the art, e.g., by expression of an oncogene or large T antigen of SV40. Alternatively, cell lines corresponding to such a diseased cell can be used. Examples include RAW cells and THPI cells. However, prior to using such cell lines, it may be preferably to confirm that the gene expression profile of the cell line corresponds essentially to that of a cell characteristic of a disease related to bone or cartilage formation or resorption. This can be done as described in details herein.

Modulating the expression of a gene in a cell can be achieved, e.g., by contacting the cell with an agent that increases the level of expression of the gene or the activity of the polypeptide encoded by the gene. Increasing the level of a polypeptide in a cell can also be achieved by transfecting the cell, transiently or stably, with a nucleic acid encoding the polypeptide. Decreasing the expression of a gene in a cell can be achieved by inhibiting transcription or translation of the gene or RNA, e.g., by introducing antisense nucleic acids, ribozymes or siRNAs into the cells, or by inhibiting the activity of the polypeptide encoded by the gene, e.g., by using antibodies or dominant negative mutants. These methods are further described below in the context of therapeutic methods.

A nucleic acid encoding a particular polypeptide can be obtained, e.g., by RT-PCR from a cell that is known to express the gene. Primers for the RT-PCR can be derived from the nucleotide sequence of the gene encoding the polypeptide. The nucleotide sequence of the gene is available, e.g., in GenBank or in the publications. GenBank Accession numbers of the genes listed in Tables 1, 2, 5, 6 and/or 7 are provided in the tables. Amplified DNA can then be inserted into an expression vector, according to methods known in the art and transfected into diseased cells of a disease related to bone or cartilage formation or resorption. In a control experiment, normal counterpart cells can also be transfected. The level of expression of the polypeptide in the transfected cells can be determined, e.g., by electrophoresis and staining of the gel or by Western blot using an a agent that binds the polypeptide, e.g., an antibody. The level of expression of one or more genes which are up- or down-regulated during bone or cartilage formation can then be determined in the transfected cells having elevated levels of the polypeptide. In a preferred embodiment, the level of expression is determined by using a microarray. For example, RNA is extracted from the transfected cells, and used as target DNA for hybridization to a microarray, as further described herein.

These assays will allow the identification of genes which are up- or down-regulated during bone or cartilage formation that can be used as therapeutic targets for developing therapeutics for diseases relating to bone or cartilage formation or resorption.

4.2. Therapeutic Methods 4.2.1. Methods for Reducing Expression of a Gene or the Activity or Level of the Protein Encoded Thereby in a Patient Genes that are expressed at higher levels in diseased cells of subjects having a disease relating to bone or cartilage formation or resorption relative to their expression level in a normal cell undergoing bone or cartilage formation may be used as therapeutic targets for treating the disease. For example, it is possible to treat such a disease by decreasing the level of the polypeptides in diseased cells. Similarly, where bone or cartilage formation is undesired, it may be inhibited by blocking or reducing the expression of a gene or the activity or level of the encoded polypeptide that is modulated, e.g., up-regulated, during normal bone or cartilage formation. Bone and cartilage formation may also be stimulated by blocking or reducing the expression of a gene or the activity or level of the encoded polypeptide that is modulated, e.g., down-regulated, during normal bone or cartilage formation.

(i) Antisense Nucleic Acids

One method for decreasing the level of expression of a gene is to introduce into the cell antisense molecules which are complementary to at least a portion of the gene or RNA of the gene. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553–6556; Lemaitre et al., 1987, Proc. Natl. Acad. Sci. 84: 648–652: PCT Publication No. WO 88/09810, published Dec. 15, 1988), hybridization-triggered cleavage agents (see, e.g., Krol et al., 1988, BioTechniques 6: 958–976) or intercalating agents (see, e.g., Zon, 1988, Pharm. Res. 5: 539–549).

In a preferred aspect of the invention, an antisense oligonucleotide is provided, preferably as single-stranded DNA. The oligonucleotide may be modified at any position on its structure with constituents generally known in the art. For example, the antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent transport agent, hybridization-triggered cleavage agent, etc. An antisense molecule can be a "peptide nucleic acid" (PNA). PNA refers to an antisense molecule or antigene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Other usable promoters for mammalian cells include, but are not limited to: the SV40 early promoter region (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42), etc.

Antisense therapy for a variety of cancers is in clinical phase and has been discussed extensively in the literature. Reed reviewed antisense therapy directed at the Bcl-2 gene in tumors; gene transfer-mediated overexpression of Bcl-2 in tumor cell lines conferred resistance to many types of cancer drugs. (Reed, J. C., *N. C. I.* (1997) 89:988–990). The potential for clinical development of antisense inhibitors of ras is discussed by Cowsert, L. M., *Anti-Cancer Drug Design* (1997) 12:359–371. Additional important antisense targets include leukemia (Geurtz, A. M., *Anti-Cancer Drug Design* (1997) 12:341–358); human C-ref kinase (Monia, B. P., *Anti-Cancer Drug Design* (1997) 12:327–339); and protein kinase C (McGraw et al., *Anti-Cancer Drug Design* (1997) 12:315–326.

(ii) Ribozymes

In another embodiment, the level of a particular mRNA or polypeptide in a cell is reduced by introduction of a ribozyme into the cell or nucleic acid encoding such. Ribozyme molecules designed to catalytically cleave mRNA transcripts can also be introduced into, or expressed, in cells to inhibit expression of the gene (see, e.g., Sarver et al., 1990, *Science* 247:1222–1225 and U.S. Pat. No. 5,093,246). One commonly used ribozyme motif is the hammerhead, for which the substrate sequence requirements are minimal. Design of the hammerhead ribozyme is disclosed in Usman et al., *Current Opin. Struct. Biol.* (1996) 6:527–533. Usman also discusses the therapeutic uses of ribozymes. Ribozymes can also be prepared and used as described in Long et al., *FASEB J.* (1993) 7:25; Symons, *Ann. Rev. Biochem.* (1992) 61:641; Perrotta et al., *Biochem.* (1992) 31:16–17; Ojwang et al., *Proc. Natl. Acad. Sci.* (*USA*) (1992) 89:10802–10806 and U.S. Pat. No. 5,254,678. Ribozyme cleavage of HIV-I RNA is described in U.S. Pat. No. 5,144,019; methods of cleaving RNA using ribozymes is described in U.S. Pat. No. 5,116,742; and methods for increasing the specificity of ribozymes are described in U.S. Pat. No. 5,225,337 and Koizumi et al., *Nucleic Acid Res.* (1989) 17:7059–7071. Preparation and use of ribozyme fragments in a hammerhead structure are also described by Koizumi et al., *Nucleic Acids Res.* (1989) 17:7059–7071. Preparation and use of ribozyme fragments in a hairpin structure are described by Chowrira and Burke, *Nucleic Acids Res.* (1992) 20:2835. Ribozymes can also be made by rolling transcription as described in Daubendiek and Kool, *Nat. Biotechnol.* (1997) 15(3):273–277.

(iii) siRNAs

Another method for decreasing or blocking gene expression is by introducing double stranded small interfering RNAs (siRNAs), which mediate sequence specific mRNA degradation. RNA interference (RNAi) is the process of sequence-specific, post-transcriptional gene silencing in animals and plants, initiated by double-stranded RNA (dsRNA) that is homologous in sequence to the silenced gene. In vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. Nature 2001 ;411(6836):494–8).

(iv) Triplex Formation

Gene expression can be reduced by targeting deoxyribonucleotide sequences complementary to the regulatory region of the target gene (i.e., the gene promoter and/or enhancers) to form triple helical structures that prevent transcription of the gene in target cells in the body. (See generally, Helene, C. 1991, Anticancer Drug Des., 6(6): 569–84; Helene, C., et al., 1992, Ann, N.Y. Accad. Sci., 660:27–36; and Maher, L. J., 1992, Bioassays 14(12):807–15).

(v) Aptamers

In a further embodiment, RNA aptamers can be introduced into or expressed in a cell. RNA aptamers are specific RNA ligands for proteins, such as for Tat and Rev RNA (Good et al., 1997, Gene Therapy 4: 45–54) that can specifically inhibit their translation.

(vi) Dominant Negative Mutants

Another method of decreasing the biological activity of a polypeptide is by introducing into the cell a dominant negative mutant. A dominant negative mutant polypeptide will interact with a molecule with which the polypeptide normally interacts, thereby competing for the molecule, but since it is biologically inactive, it will inhibit the biological activity of the polypeptide. A dominant negative mutant can be created by mutating the substrate-binding domain, the catalytic domain, or a cellular localization domain of the polypeptide. Preferably, the mutant polypeptide will be overproduced. Point mutations are made that have such an effect. In addition, fusion of different polypeptides of various lengths to the terminus of a protein can yield dominant negative mutants. General strategies are available for making dominant negative mutants. See Herskowitz, *Nature* (1987) 329:219–222.

(vi) Use of Agents Inhibiting Transcription or Polypeptide Activity

In another embodiment, a compound decreasing the expression of the gene of interest or the activity of the polypeptide is administered to a subject having a disease relating to bone or cartilage formation or resorption, such that the level or activity of the polypeptide in the diseased cells decreases, and the disease is improved. Compounds may be known in the art or can be identified as further described herein. For example, where the gene encodes a polypeptide that is a protease, the activity of the protease can be inhibited, e.g., by a compound that binds an active site of the enzyme, by a compound that inhibits the interaction of the protease with its target, or by a compound that decreases the stability of the protease.

4.2.2. Methods for Increasing the Expression of a Gene or the Activity or Level of the Protein Encoded Thereby in a Patient Genes which are expressed at lower levels in diseased cells of subjects having a disease relating to bone or cartilage formation or resorption relative to their expression level in a normal cell undergoing bone or cartilage formation may be used as therapeutic targets for treating such diseases. For example, it may be possible to treat such a disease by increasing the level of the polypeptides in diseased cells. Similarly, where on wishes to stimulate bone formation, one may increase the level of expression of a gene or the activity or level of protein encoded by the gene that is modulated, e.g., up-regulated, during bone or cartilage formation. If one wishes to inhibit bone or cartilage formation, one may increase the level of expression of a gene or the activity or level of protein encoded by the gene that is modulated, e.g., down-regulated, during bone or cartilage formation.

(i) Administration of a Nucleic Acid Encoding a Polypeptide of Interest to a Subject In one embodiment, a nucleic acid encoding a polypeptide of interest, or an equivalent thereof, such as a functionally active fragment of the polypeptide, is administered to a subject, such that the nucleic acid arrives at the site of the diseased cells, traverses the cell membrane and is expressed in the diseased cell.

A nucleic acid encoding a polypeptide of interest can be obtained as described herein, e.g., by RT-PCR, or from publicly available DNA clones. It may not be necessary to express the full length polypeptide in a cell of a subject, and a functional fragment thereof may be sufficient. Similarly, it is not necessary to express a polypeptide having an amino acid sequence that is identical to that of the wild-type polypeptide. Certain amino acid deletions, additions and substitutions are permitted, provided that the polypeptide retains most of its biological activity. For example, it is expected that polypeptides having conservative amino acid substitutions will have the same activity as the polypeptide. Polypeptides that are shorter or longer than the wild-type polypeptide or which contain from one to 20 amino acid deletions, insertions or substitutions and which have a biological activity that is essentially identical to that of the wild-type polypeptide are referred to herein as "equivalents of the polypeptide." Equivalent polypeptides also include polypeptides having an amino acid sequence which is at least 80%, preferably at least about 90%, even more preferably at least about 95% and most preferably at least 98% identical or similar to the amino acid sequence of the wild-type polypeptide.

Determining which portion of the polypeptide is sufficient for improving a disease relating to bone or cartilage formation or which polypeptides derived from the polypeptide are "equivalents" which can be used for treating the disease, can be done in in vitro assays. For example, expression plasmids encoding various portions of the polypeptide can be transfected into cells, e.g., diseased cells of patients, and the effect of the expression of the portion of the polypeptide in the cells can be determined, e.g., by visual inspection of the phenotype of the cell or by obtaining the expression profile of the cell, as further described herein.

Any means for the introduction of polynucleotides into mammals, human or non-human, may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126–139, 1995). Formulation of DNA, e.g. with various lipid or liposome materials, may then be effected using known methods and materials and delivered to the recipient mammal. See, e.g., Canonico et al, Am J Respir Cell Mol Biol 10:24–29, 1994; Tsan et al, Am J Physiol 268; Alton et al., Nat Genet. 5:135–142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

In a preferred method of the invention, the DNA constructs are delivered using viral vectors. The transgene may be incorporated into any of a variety of viral vectors useful in gene therapy, such as recombinant retroviruses, adenovirus, adeno-associated virus (AAV), and herpes simplex virus-1, or recombinant bacterial or eukaryotic plasmids. While various viral vectors may be used in the practice of this invention, AAV- and adenovirus-based approaches are of particular interest. Such vectors are generally understood to be the recombinant gene delivery system of choice for the transfer of exogenous genes in vivo, particularly into humans.

It is possible to limit the infection spectrum of viruses by modifying the viral packaging proteins on the surface of the viral particle (see, for example PCT publications WO93/25234, WO94/06920, and WO94/11524). For instance, strategies for the modification of the infection spectrum of viral vectors include: coupling antibodies specific for cell surface antigens to envelope protein (Roux et al., (1989) PNAS USA 86:9079–9083; Julan et al., (1992) J. Gen Virol 73:3251–3255; and Goud et al., (1983) Virology 163:251–254); or coupling cell surface ligands to the viral envelope proteins (Neda et al., (1991) J. Biol. Chem. 266: 14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

The expression of a polypeptide of interest or equivalent thereof in cells of a patient to which a nucleic acid encoding the polypeptide was administered can be determined, e.g., by obtaining a sample of the cells of the patient and determining the level of the polypeptide in the sample, relative to a control sample. The successful administration to a patient and expression of the polypeptide or an equivalent thereof in the cells of the patient can be monitored by determining the expression of at least one gene that is up- or down-regulated during bone or cartilage formation, and preferably by determining an expression profile including most of the genes which are up- or down-regulated during bone or cartilage formation, as described herein.

(ii) Administration of a Polypeptide of Interest to a Subject

In another embodiment, a polypeptide of interest, or an equivalent or variant thereof, e.g., a functional fragment thereof, is administered to the subject such that it reaches the diseased cells of a disease related to bone or cartilage formation or resorption, and traverses the cellular membrane. Polypeptides can be synthesized in prokaryotes or eukaryotes or cells thereof and purified according to methods known in the art. For example, recombinant polypeptides can be synthesized in human cells, mouse cells, rat cells, insect cells, yeast cells, and plant cells. Polypeptides can also be synthesized in cell free extracts, e.g., reticulocyte lysates or wheat germ extracts. Purification of proteins can be done by various methods, e.g., chromatographic methods (see, e.g., Robert K Scopes "Protein Purification: Principles and Practice" Third Ed. Springer-Verlag, N.Y. 1994). In one embodiment, the polypeptide is produced as a fusion polypeptide comprising an epitope tag consisting of about six consecutive histidine residues. The fusion polypeptide can then be purified on a $Ni^{++}$ column. By inserting a protease site between the tag and the polypeptide, the tag can be removed after purification of the peptide on the $Ni^{++}$ column. These methods are well known in the art and commercial vectors and affinity matrices are commercially available.

Administration of polypeptides can be done by mixing them with liposomes, as described above. The surface of the liposomes can be modified by adding molecules that will target the liposome to the desired physiological location.

In one embodiment, a polypeptide is modified so that its rate of traversing the cellular membrane is increased. For example, the polypeptide can be fused to a second peptide which promotes "transcytosis," e.g., uptake of the peptide by cells. In one embodiment, the peptide is a portion of the HIIV transactivator (TAT) protein, such as the fragment corresponding to residues 37–62 or 48–60 of TAT, portions which are rapidly taken up by cell in vitro (Green and Loewenstein, (1989) Cell 55:1179–1188). In another embodiment, the internalizing peptide is derived from the Drosophila antennapedia protein, or homologs thereof. The 60 amino acid long homeodomain of the homeo-protein antennapedia has been demonstrated to translocate through biological membranes and can facilitate the translocation of heterologous polypeptides to which it is couples. Thus, polypeptides can be fused to a peptide consisting of about amino acids 42–58 of Drosophila antennapedia or shorter fragments for transcytosis. See for example Derossi et al. (1996) J Biol Chem 271:18188–18193; Derossi et al. (1994) J Biol Chem 269:10444–10450; and Perez et al. (1992) J Cell Sci 102:717–722.

(iii) Use of Agents Stimulating Transcription or Polypeptide Activity

In another embodiment, a pharmaceutical composition comprising a compound that stimulates the level of expression of a gene of interest or the activity of the polypeptide in a cell is administered to a subject, such that the level of expression of the gene or polypeptide level or activity in the diseased cells is increased or even restored, and the disease is improving in the subject. Compounds may be known in the art or can be identified as further described herein. Compounds may increase the activity of a polypeptide by stabilizing the polypeptide.

4.3. Drug Design and Discovery of Therapeutics

The invention further provides methods for identifying therapeutics that modulate bone and cartilage formation. For example, therapeutics that inhibit bone or cartilage formation can be identified by treating precursor cells with an agent, such as a bone mophogenetic protein, e.g., BMP-2, in the presence or absence of a test compound and determining whether bone or cartilage formation is inhibited or not by the presence of the test compound. The effect on bone or cartilage formation can be measured by determining the level of expression of one or more genes that are up- or down-regulated during bone or cartilage formation, e.g., genes set forth in Tables 1, 2, 5, 6 and/or 7. The assay that is described in the Examples can be used in such assays.

In another embodiment, therapeutics which stimulate bone formation can be identified by contacting precursor cells with a test compound and determining whether bone or cartilage formation is stimulated in the presence of the test compound. A positive control for this assay can be cells treated with an agent known to cause bone or cartilage formation or differentiation, such as BMP-2. Alternatively, gene expression levels can be measured over a time course and the levels compared to those set forth in Tables 1, 2, 5, 6 and/or 7.

As described above, genes whose modulation of expression improve a disease related to bone or cartilage formation or resorption can be used as targets in drug design and discovery. For example, assays can be conducted to identify molecules that modulate the expression and or activity of genes which are up- or down-regulated during bone or cartilage formation.

In one embodiment, the invention provides methods for identifying an agonist or antagonist of a polypeptide, comprising contacting the polypeptide with a test compound under essentially physiological conditions, and determining whether the test compound binds to the polypeptide or not. In another embodiment, the invention provides a method for identifying an agonist or antagonist of a polypeptide, comprising contacting the polypeptide with a test compound under essentially physiological conditions; and determining a biological activity of the polypeptide in the presence of the test compound, wherein a higher or lower biological activity in the presence relative to the absence of the test compound indicates that the test compound is an agonist or antagonist of the polypeptide. Other assays may be based on a change in the polypeptide, e.g., a change in its phosphorylation level.

In another embodiment, an agent that modulates the expression of a gene that is up- or down-regulated during bone or cartilage formation is identified by contacting cells expressing the gene with one or more test compounds, and monitoring the level of expression of the gene, e.g., by directly or indirectly determining the level of the protein encoded by the gene. Alternatively, compounds which modulate the expression of the gene can be identified by conducting assays using the promoter region of a gene and screening for compounds which modify binding of proteins to the promoter region. The nucleotide sequence of the promoter may be described in a publication or available in GenBank. Alternatively, the promoter region of the gene can be isolated, e.g., by screening a genomic library with a probe corresponding to the gene. Such methods are known in the art.

Inhibitors of the polypeptide can also be agents which bind to the polypeptide, and thereby prevent it from functioning normally, or which degrades or causes the polypeptide to be degraded. For example, such an agent can be an antibody or derivative thereof which interacts specifically with the polypeptide. Preferred antibodies are monoclonal antibodies, humanized antibodies, human antibodies, and single chain antibodies. Such antibodies can be prepared and tested as known in the art.

If a polypeptide of interest binds to another polypeptide, drugs can be developed which modulate the activity of the polypeptide by modulating its binding to the other polypeptide (referred to herein as "binding partner"). Cell-free assays can be used to identify compounds which are capable of interacting with the polypeptide or binding partner, to thereby modify the activity of the polypeptide or binding partner. Such a compound can, e.g., modify the structure of the polypeptide or binding partner and thereby effect its activity. Cell-free assays can also be used to identify compounds which modulate the interaction between the polypeptide and a binding partner. In a preferred embodiment, cell-free assays for identifying such compounds consist essentially in a reaction mixture containing the polypeptide and a test compound or a library of test compounds in the presence or absence of a binding partner. A test compound can be, e.g., a derivative of a binding partner, e.g., a biologically inactive peptide, or a small molecule.

Accordingly, one exemplary screening assay of the present invention includes the steps of contacting the polypeptide or functional fragment thereof or a binding partner with a test compound or library of test compounds and detecting the formation of complexes. For detection purposes, the molecule can be labeled with a specific marker and the test compound or library of test compounds labeled with a different marker. Interaction of a test compound with a polypeptide or fragment thereof or binding partner can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the polypeptide, functional fragment thereof, polypeptide analog or binding partner is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) a polypeptide of interest, (ii) a binding partner, and (iii) a test compound; and (b) detecting interaction of the polypeptide and the binding partner. The polypeptide and binding partner can be produced recombinantly, purified from a source, e.g., plasma, or chemically synthesized, as described herein. A statistically significant change (potentiation or inhibition) in the interaction of the polypeptide and binding partner in the presence of the test compound, relative to the interaction in the absence of the test compound, indicates a potential agonist (mimetic or potentiator) or antagonist (inhibitor) of the polypeptide bioactivity for the test compound. The compounds of this assay can be contacted simultaneously. Alternatively, the polypeptide can first be contacted with a test compound for an appropriate amount of time, following which the binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified polypeptide or binding partner is added to a composition containing the binding partner or polypeptide, and the formation of a complex is quantified in the absence of the test compound.

Complex formation between a polypeptide and a binding partner may be detected by a variety of techniques. Modulation of the formation of complexes can be quantitated using, for example, detectably labeled proteins such as radiolabeled, fluorescently labeled, or enzymatically labeled polypeptides or binding partners, by immunoassay, or by chromatographic detection.

For processes that rely on immunodetection for quantitating one of the proteins trapped in the complex, antibodies against the protein can be used. Alternatively, the protein to be detected in the complex can be "epitope tagged" in the form of a fusion protein which includes, in addition to the polypeptide sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharmacia, NJ).

Similar assays can be used to identify compounds that bind a protein of interest and thereby inhibit the activity of the protein.

In another embodiment, drugs are designed or optimized by monitoring the level of expression of a plurality of genes, e.g., with microarrays. In one embodiment, compounds are screened by comparing the expression level of one or more genes which are up- or down-regulated (e.g., expression profile) during bone or cartilage formation in a cell, e.g., a cell characteristic of a disease relating to bone or cartilage formation or resorption treated with a drug, relative to their expression in a reference cell, e.g., a normal cell. Optionally the expression profile is also compared to that of a cell characteristic of the disease. The comparisons are preferably done by introducing the gene expression profile data of the cell treated with the drug into a computer system comprising reference gene expression profiles which are stored in a computer readable form, using appropriate algorithms. Test compounds will be screened for those which alter the level of expression of genes, so as to bring them to a level that is similar to that in a reference or normal cell of the same type as a cell characteristic of the disease. Compounds which are capable of normalizing the expression of at least about 10%, preferably at least about 20%, 50%, 70%, 80% or 90% of the genes which are up- or down-regulated during bone or cartilage formation, are candidate therapeutics.

The efficacy of the compounds can then be tested in additional in vitro assays and in vivo, in animal models, such as the one described in the Examples. The test compound is administered to the test animal and one or more symptoms of the disease are monitored for improvement of the condition of the animal. Expression of one or more genes which are up- or down-regulated during bone or cartilage formation can also be measured before and after administration of the test compound to the animal. A normalization of the expression of one or more of these genes is indicative of the efficiency of the compound for treating a disease relating to bone or cartilage formation or resorption.

The toxicity, such as resulting from a stress-related response, of a candidate therapeutic compound can be evaluated, e.g., by determining whether it induces the expression of genes known to be associated with a toxic response. Expression of such toxicity related genes may be determined in different cell types, preferably those that are known to express the genes. In a preferred method, microarrays are used for detecting changes in gene expression of genes known to be associated with a toxic response. Changes in gene expression may be a more sensitive marker of human toxicity than routine preclinical safety studies. It was shown, e.g., that a drug which was found not be to toxic in laboratory animals was toxic when administered to humans. When gene profiling was studied in cells contacted with the drug, however, it was found that a gene, whose expression is known to correlate to liver toxicity, was expressed (see below).

Such microarrays will comprise genes which are modulated in response to toxicity or stress. An exemplary array that can be used for that purpose is the Affymetrix Rat Toxicology U34 array, which contains probes of the following genes: metabolism enzymes, e.g., CYP450s, acetyltransferases, and sulfotransferases; growth factors and their receptors, e.g., IGFs, interleukins, NGTs, TGFs, and VEGT; kinases and phosphatases, e.g., lipid kinases, MAFKs, and stress-activated kinases; nuclear receptors, e.g., retinoic acid, retinoid X and PPARs; transcription factors, e.g., oncogenes, STATs, NF-kB, and zinc finger proteins; apoptosis genes, e.g., Bcl-2 genes, Bad, Bax, Caspases and Fas;

stress response genes, e.g., heat-shock proteins and drug transporters; membrane proteins, e.g., gap-junction proteins and selectins; and cell-cycle regulators, e.g., cyclins and cyclin-associated proteins. Other genes included in the microarrays are only known because they contain the nucleotide sequence of an EST and because they have a connection with toxicity.

In one embodiment, a drug of interest is incubated with a cell, e.g., a cell in culture, the RNA is extracted, and expression of genes is analyzed with an array containing genes which have been shown to be up- or down-regulated in response to certain toxins. The results of the hybridization are then compared to databases containing expression levels of genes in response to certain known toxins in certain organisms. For example, the GeneLogic ToxExpress™ database can be used for that purpose. The information in this database was obtained in least in part from the use of the Affymetrix GeneChip® rat and human probe arrays with samples treated in vivo or in vitro with known toxins. The database contains levels of expression of liver genes in response to known liver toxins. These data were obtained by treating liver samples from rats treated in vivo with known toxins, and comparing the level of expression of numerous genes with that in rat or human primary hepatocytes treated in vitro with the same toxin. Data profiles can be retrieved and analyzed with the GeneExpress™ database tools, which are designed for complex data management and analysis. As indicated on the Affymetrix (Santa Clara, Calif.) website, the GeneLogic, Inc. (Gaithersburg, Md.) has preformed proof of concept studies showing the changes in gene expression levels can predict toxic events that were not identified by routine preclinical safety testing. GeneLogic tested a drug that had shown no evidence of liver toxicity in rats, but that later showed toxicity in humans. The hybridization results using the Affymetrix GeneChip® and GeneExpress™ tools showed that the drug caused abnormal elevations of alanine aminotransferase (ALT), which indicates liver injury, in half of the patients who had used the drug.

In one embodiment of the invention, the drug of interest is administered to an animal, such as a mouse or a rat, at different doses. As negative controls, animals are administered the vehicle alone, e.g., buffer or water. Positive controls can consist of animals treated with drugs known to be toxic. The animals can then be sacrificed at different times, e.g., at 3, 6, and 24 hours, after administration of the drug, vehicle alone or positive control drug, mRNA extracted from a sample of their liver; and the mRNA analyzed using arrays containing nucleic acids of genes which are likely to be indicative of toxicity, e.g., the Affymetrix Rat Toxicology U34 assay. The hybridization results can then be analyzed using computer programs and databases, as described above.

In addition, toxicity of a drug in a subject can be predicted based on the alleles of drug metabolizing genes that are present in a subject. Accordingly, it is known that certain enzymes, e.g., cytochrome p450 enzymes, i.e., CYP450, metabolize drugs, and thereby may render drugs which are innocuous in certain subjects, toxic in others. A commercially available array containing probes of different alleles of such drug metabolizing genes can be obtained, e.g., from Affymetrix (Santa Clara, Calif.), under the name of GeneChip® CYP450 assay.

Thus, a drug for a disease relating to bone or cartilage development identified as described herein can be optimized by reducing any toxicity it may have. Compounds can be derivatized in vitro using known chemical methods and tested for expression of toxicity related genes. The derivatized compounds must also be retested for normalization of expression levels of genes which are up- or down-regulated during bone or cartilage formation. For example, the derivatized compounds can be incubated with diseased cells of a disease relating to bone or cartilage formation or resorption, and the gene expression profile determined using microarrays. Thus, incubating cells with derivatized compounds and measuring gene expression levels with a microarray that contains the genes which are up- or down-regulated during bone or cartilage formation and a microarray containing toxicity related genes, compounds which are effective in treating diseases relating to bone or cartilage formation or resorption and which are not toxic can be developed. Such compounds can further be tested in animal models as described above.

In another embodiment of the invention, a drug is developed by rational drug design, i.e., it is designed or identified based on information stored in computer readable form and analyzed by algorithms. More and more databases of expression profiles are currently being established, numerous ones being publicly available. By screening such databases for the description of drugs affecting the expression of at least some of the genes which are up- or down-regulated during bone or cartilage formation in a manner similar to the change in gene expression profile from a cell characteristic of a disease related to bone or cartilage formation or resorption to that of a normal counterpart cell, compounds can be identified which normalize gene expression in a cell characteristic of such a disease. Derivatives and analogues of such compounds can then be synthesized to optimize the activity of the compound, and tested and optimized as described above.

Compounds identified by the methods described above are within the scope of the invention. Compositions comprising such compounds, in particular, compositions comprising a pharmaceutically efficient amount of the drug in a pharmaceutically acceptable carrier are also provided. Certain compositions comprise one or more active compounds for treating diseases relating to bone or cartilage development.

4.4. Exemplary Therapeutic Compositions

Therapeutic compositions include the compounds described herein, e.g., in the context of therapeutic treatments of diseases relating to bone or cartilage formation or resorption. Therapeutic compositions may comprise one or more nucleic acids encoding a polypeptide characteristic of a disease relating to bone or cartilage formation or resorption, or equivalents thereof. The nucleic acids may be in expression vectors, e.g., viral vectors. Other compositions comprise one or more polypeptides that are up- or down-regulated during bone or cartilage formation, or equivalents thereof. Yet other compositions comprise nucleic acids encoding antisense RNA, or ribozymes, siRNAs or RNA aptamers. Also within the scope of the invention are compositions comprising compounds identified by the methods described herein. The compositions may comprise pharmaceutically acceptable excipients, and may be contained in a device for their administration, e.g., a syringe.

4.5. Administration of Compounds and Compositions of the Invention

In a preferred embodiment, the invention provides a method for treating a subject having a disease relating to bone or cartilage formation or resorption, comprising administering to the subject a therapeutically effective amount of a pharmaceutical composition comprising a compound of the invention.

4.5.1. Effective Dose

Compounds of the invention refer to small molecules, polypeptides, peptide mimetics, nucleic acids or any other molecule identified as potentially useful for treating diseases relating to bone or cartilage formation or resorption.

Toxicity and therapeutic efficacy of compounds can be determined by standard pharmaceutical procedures in cell cultures or experimental animals, e.g., for determining the LD50 (The Dose Lethal To 50% Of The Population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to healthy cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.5.2. Formulation

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration. In one embodiment, the compound is administered locally, at the site where the diseased cells are present, e.g., in bone, cartilage, mesenchymal tissue, muscular tissue or in a joint.

The compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Administration, e.g., systemic administration, can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the compounds of the invention can be formulated into ointments, salves, gels, or creams as generally known in the art. A wash solution can be used locally to treat an injury or inflammation to accelerate healing.

In clinical settings, a gene delivery system for a gene of interest can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the subject or animal being quite localized. For example, the gene delivery vehicle can be introduced by catheter (see U.S. Pat. No. 5,328,470) or by stereotactic injection (e.g., Chen et al. (1994) PNAS 91: 3054–3057). A nucleic acid, such as one encoding a polypeptide of interest or homologue thereof can be delivered in a gene therapy construct by electroporation using techniques described, for example, by Dev et al. ((1994) Cancer Treat Rev 20:105–115). Gene therapy can be conducted in vivo or ex vivo.

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The therapeutic method may include administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage, tissue damage or diseased cells. Topical administration may be suitable for wound healing and tissue repair. Therapeutically useful agents other than the gene-specific therapeutics which may also optionally be included in the composition as described above, may alternatively or additionally, be administered simultaneously or sequentially with a composition of the invention. The compositions of the invention may be employed in association with surgery. Preferably for bone and/or cartilage formation, the composition would include a matrix capable of delivering the therapeutics to the site of bone and/or cartilage damage or other target site, providing a structure for the developing bone and cartilage and optimally capable of being resorbed into the body. Such matrices may be formed of materials presently in use for other implanted medical applications.

The choice of matrix material may be based on biocompatibility, biodegradability, mechanical properties, cosmetic appearance and interface properties. The particular application of the compositions of the invention will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the therapeutics, e.g. amount of bone weight desired to be formed, the site of bone damage or diseased cells, the condition of the damaged bone, the type of disease, the size of a wound, type of damaged tissue, the patient's age, sex, and diet, the severity of any infection, time of administration and other clinical factors. The dosage may vary with the type of matrix used in the reconstitution and the types of therapeutics in the composition. The addition of other known growth factors, such as BMP-2 and IGF I (insulin like growth factor I), to the final composition, may also effect the dosage. Progress can be monitored by periodic assessment of bone growth and/or repair, for example, x-rays, histomorphometric determinations and tetracycline labeling.

5. Exemplary Kits

The invention further provides kits for determining the expression level of genes which are up- or down-regulated during bone or cartilage formation or resorption. The kits may be useful for identifying subjects that are predisposed to developing or who have a disease relating to bone or cartilage formation or resorption, as well as for identifying and validating therapeutics for such diseases. In one embodiment, the kit comprises a computer readable medium on which is stored one or more gene expression profiles, e.g., of cells differentiating into bone or cartilage cells, or of diseased cells of a disease relating to bone or cartilage formation or resorption, or at least values representing levels of expression of one or more genes which are up- or down-regulated during bone or cartilage formation. The computer readable medium can also comprise gene expression profiles of counterpart normal cells, such as the expression profiles set forth in Tables 1, 2, 5, 6 and/or 7; diseased cells treated with a drug, and any other gene expression profile described herein. The kit can comprise expression profile analysis software capable of being loaded into the memory of a computer system.

A kit can comprise a microarray comprising probes of genes which are up- or down-regulated during bone or cartilage formation. A kit can comprise one or more probes or primers for detecting the expression level of one or more genes which are up- or down-regulated during bone or cartilage formation and/or a solid support on which probes are attached and which can be used for detecting expression of one or more genes which are up- or down-regulated during bone or cartilage formation in a sample. A kit may further comprise nucleic acid controls, buffers, and instructions for use.

Other kits provide compositions for treating a disease relating to bone or cartilage formation or resorption. For example, a kit may comprise one or more nucleic acids corresponding to one or more genes which are up- or down-regulated during bone or cartilage formation, e.g., for use in treating a patient having a disease relating to bone or cartilage formation or resorption. The nucleic acids can be included in a plasmid or a vector, e.g., a viral vector. Other kits comprise a polypeptide encoded by a gene that is up- or down-regulated during bone or cartilage formation or an antibody to a polypeptide. Yet other kits comprise compounds identified herein as agonists or antagonists of genes which are up- or down-regulated during bone or cartilage formation. The compositions may be pharmaceutical compositions comprising a pharmaceutically acceptable excipient.

Yet other kits comprise components for the identification of drugs that modulate the activity of a protein encoded by a gene that is up- or down-regulated during bone or cartilage formation. Exemplary kits may comprise a polypeptide encoded by a gene or a nucleic acid encoding such a polypeptide that is listed in any of the Tables described herein.

The present invention is further illustrated by the following examples which should not be construed as limiting in any way. The contents of all cited references including literature references, issued patents, published and non published patent applications as cited throughout this application, as well as those listed below, are hereby expressly incorporated by reference.

Bork, P. (1993) FEBS Lett. 327:125–130; Kothapalli, D., et al. (1998) FASEB J. 12:1151–1161; Bond, J. S. and Benyon, R. J. (1995) Protein Sci. 4:1247–1261; Stocker, W., et al. (1995) Protein Sci. 4:823–840; Kessler, E., et al. (2001) J. Biol. Chem. 276: 27051–27057; Kessler, E., et al. (1996) Science 271: 360–362; Jakob, M., et al. (2001) J. Cell Biochem. 81: 368–377; Hiraki, Y., et al. (1988) Biochim. Biophys. Acta 969: 91–99; Scott, I. C., et al. (2000) J. Biol. Chem. 275: 30504–30511; Hansen, K., et al. (1997) FEBS Lett. 409: 195–200, 1997; Hansen, K., et al. (1997) Biochem. Biophys. Res. Commun. 241: 355–362, 1997; Jahner, D. and Hunter, T. (1991) Mol. Cell Biol. 11: 3682–3690.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); Oligonucleotide Synthesis (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986) (Cold Spring Harbor Laboratory Press, Cold Spring Harbor, N.Y., 1986).

EXAMPLES

Example 1

This Example describes the identification of genes which are up- and down-regulated during hBMP-2 induced ectopic bone formation in mouse quadriceps muscles The following animal model of ectopic bone formation was used. Human BMP-2 (Wyeth Research Division of Wyeth Pharmaceuticals, Inc.) was diluted to a final concentration of 1 mg/ml in formulation buffer (0.5% sucrose, 2.5% glycine, 5 mM L-glutamic acid, 5 mM NaCl, 0.01% polysorbate 80, pH 4.5) (Wyeth Research Division of Wyeth Pharmaceuticals, Inc., MFR00842). Female B6.CB17-Prkdc<SCID>SzJ mice (14 weeks of age; Jackson Lab.) were randomly assigned to either a control or an experimental group. Mice in the control group were injected with 50 µl of formulation buffer into the quadriceps muscle of each leg. Similarly, mice in the experimental group were injected with 50 µg of recombinant human BMP-2 (hBMP-2) in formulation buffer. Care was taken to ensure that each injection was made into the middle of the muscle mass. In both groups, three mice were used for each time point. Mice were euthanized on days 1, 2, 3, 4, 7 and 14. The entire quadriceps muscle was removed from each leg and muscles selected for RNA analysis were snap frozen in liquid nitrogen and stored at −80 degrees Celsius. Total RNA was prepared for each sample. Equal amounts of RNA from the three control samples were pooled to create a single control sample for each time point.

GeneChip (Affymetrix, San Jose, Calif.) hybridization solutions were prepared as described previously (Lockhart, D. J., et al. (1996) Nature Biotechnol. 14:1675–1680 and Wilson, S. B., et al. (2000) Proc. Nat. Acad Sci. USA 97:7411–7416). Murine Genome U74 chips (Affymetrix cat. # 900322, 900324, 900326) were scanned with the use of protocols recommended by Affymetrix and data was collected/reduced with the use of the GeneChip 3.1 application (Affymetrix). To identify differentially expressed genes, GeneChip 3.1 was used to make three separate, time-matched, comparisons between a "pooled" buffer (control) and three hBMP-2 (experimental) samples.

Changes in gene expression, for each day of the experiment, were compiled into an Excel table. This table contained only those genes that satisfied the following two criteria for at least one time point of the experiment: i) the gene was Present in either or both the control and experimental samples; and ii) relative to the control sample, gene expression in the experimental sample was called Increasing or Decreasing. This composite table was imported into GeneSpring 3.2.12 (Silicon Genetics) for graphical analysis and for the creation of the expression profile gene lists. Table 1 lists genes on the U74 arrays that show at least a two-fold increase in gene expression on at least one day of the experiment. Table 2 lists genes on the U74 arrays that show at least a two-fold decrease in gene expression on at least one day of the experiment.

An expression analysis using the RNA obtained as described above was also conducted on another gene microarray design called Mula (Wyeth Research Division of Wyeth Pharmaceuticals, Inc.). Genes which were found to be up- or down-regulated by a factor of at least about 4 are set forth in Tables 5 and 6. The numbers represent fold change (Gene Frequency$_{BMP-2}$/Gene Frequency$_{Buffer}$) in gene expression+the standard deviation (n=3). The genes listed in Table 6 and many others listed in Tables 1 and 2 do not appear to have been associated with bone or cartilage formation before.

Example 2

MMP23 and CLF-1 are Up-Regulated During Bone and Cartilage Formation

Two genes which have not previously been known to be associated with bone or cartilage development appear to be up-regulated at very high levels. The first gene is Cytokine Receptor-like Factor 1 (CLF-1) and the second gene is Matrix MetalloProtease 23 (MMP23). Graphs representing the change in gene expression of each of these genes over time during bone formation in the above-described animal model are set forth in FIGS. 1 and 2. These graphs show that CLF-1 is maximally up-regulated about 15 fold and MMP23 is maximally upregulated about 40 fold.

To identify cells that express MMP23 and CLF-1, in situ hybridization was performed on tissue sections from mucles of mice injected or not with recombinant hBMP-2. No signal was detected with a sense or antisense probe directed against the message for CLF-1 in any cell type or at any time point in sections from muscles injected with buffer only. In contrast, the anti-sense probe was detected in sections from muscle injected with hBMP-2. Staining was detected at all time points in this treatment group, and these results are summarized in Table 3. In particular, staining was observed in hypertrophic chondrocytes on day 7 and osteoblasts and some marrow cells on day 14.

No signal was detected with a sense or antisense probe directed against the message for MMP23 in any cell type or at any time point in sections from muscles injected with buffer only. In contrast, the anti-sense probe detected MMP23 mRNA in sections from muscles injected with hBMP-2. Staining was detected at all time points in this treatment group, and these results are summarized in Table 4. Staining was observed in hypertrophic chondrocytes and osteblasts on days 7 and 14, respectively.

TABLE 3

Summary of cells stained with an antisense probe for CLF-1 mRNA*

| Treatment | CLF-1 mRNA Positive Cell | Day 1 | 2 | 3 | 4 | 7 | 14 |
|---|---|---|---|---|---|---|---|
| BUFFER | Fibroblast | | | | | | |
| | Macrophage | | | | | | |
| | Chondrocyte-like | N/A | N/A | N/A | N/A | N/A | N/A |
| | Chondrocyte | N/A | N/A | N/A | N/A | N/A | N/A |
| | Marrow cell | N/A | N/A | N/A | N/A | N/A | N/A |
| | Osteoblast/Osteocyte | N/A | N/A | N/A | N/A | N/A | N/A |
| HBMP-2 | Fibroblast | + | ++ | ++ | ++ | − | − |
| | Macrophage | ++ | + | ++ | ++ | − | − |
| | Chondrocyte-like | N/A | N/A | N/A | ++ | N/A | N/A |
| | Chondrocyte | N/A | N/A | N/A | N/A | + | N/A |
| | Marrow cell | N/A | N/A | N/A | N/A | N/A | + |
| | Osteoblast/Osteocyte | N/A | N/A | N/A | N/A | N/A | + |

*Binding of sense probe was not detected in either treatment group.
N/A: Cell type not present in section.
+: Slight staining intensity
++: Mild staining intensity
−: Staining not detected

TABLE 4

Summary of cells stained with an antisense probe for MMP23 mRNA*

| Treatment | MMP23 mRNA Positive Cell | Day 1 | 2 | 3 | 4 | 7 | 14 |
|---|---|---|---|---|---|---|---|
| BUFFER | Fibroblast | | | | | | |
| | Macrophage | | | | | | |
| | Chondrocyte-like | N/A | N/A | N/A | N/A | N/A | N/A |
| | Chondrocyte | N/A | N/A | N/A | N/A | N/A | N/A |
| | Marrow cell | N/A | N/A | N/A | N/A | N/A | N/A |
| | Osteoblast/Osteocyte | N/A | N/A | N/A | N/A | N/A | N/A |
| HBMP-2 | Fibroblast | + | − | − | − | − | − |
| | Macrophage | + | − | − | − | − | − |
| | Chondrocyte-like | N/A | N/A | N/A | + | N/A | N/A |
| | Chondrocyte | N/A | N/A | N/A | N/A | + | N/A |
| | Marrow cell | N/A | N/A | N/A | N/A | N/A | − |
| | Osteoblast/Osteocyte | N/A | N/A | N/A | N/A | N/A | + |

*Binding of sense probe was not detected in either treatment group.
N/A: Cell type not present in section.
+: Slight staining intensity
++: Mild staining intensity
−: Staining not detected Accordingly, the results show for the first time that CLF-1 and MMP23 are expressed in cells associated with bone and cartilage. These genes will thus be useful targets in diagnostics and in drug design for diseases relating to bone and cartilage formation.

Example 3

Patterns of Gene Expression During Particular Phases of Bone Formation

To identify genes with a particular expression profile, genes in Tables 5 and 6 were analyzed with the use of GeneSpring, a data analysis program (Silicon Genetics, Redwood City, Calif.). GeneSpring identified genes whose time-dependent expression profiles correlated with the profiles of an exemplar gene. The correlation was based upon the program's standard correlation calculation, within the "Find Similar" function, and the confidence level was set to 95%. Four exemplar genes, cysteine rich protein 61 (Cyr61), procollagen type II alpha I (Col2a1), runt related transcription factor 2 (Runx2), and cathepsin K (Ctsk), were selected because their protein products appear to be phenotypic markers of one or more phases of endochondral bone formation. Cyr61 is a member of the CCN family of growth factors and is believed to regulate the proliferation and differentiation of various connective tissue cell types. Col2a1, Runx2 and Ctsk are well-defined markers for chondrocytes, osteoblasts and osteoclasts, respectively. The four lists (one for each exemplar gene) of genes were compiled to create Table 7 and all genes were segregated according to their membership in either Tables 5 or 6.

The temporal patterns of gene expression (Tables 5 and 6) suggest at least two possibilities. The first possibility for the observed temporal patterns of gene expression is that there is some role for the gene products during the phase of bone formation in this model system. The second possibility is that patterns similar to the profiles of the exemplar genes in FIG. 3 may reveal some degree of gene co-regulation or functional connections between gene products. This comparative analysis can be made qualitatively, by a visual inspection of the time-dependent expression profiles in Tables 5 and 6, or quantitatively. Quantitatively, a data analysis program called GeneSpring identified genes having expression profiles similar those of Cyr61, Col2a1, Runx2 and Ctsk and these genes are listed in Table 7. Of the four exemplar genes, the correlation with Runx2 yielded the highest number of genes. It is interesting to note that several of the Runx2-like gene products from Table 5 (Bmp1, Pcolce, Col5a1 and Bgn) have been functionally linked in earlier studies of extracellular matrix proteins. For example, bone morphogenetic protein-1 (Bmp1), a member of the astacin family of proteases, is also known as procollagen C-proteinase and is capable of processing several forms of procollagen. Procollagen C-proteinase enhancer (Pcolce) is an extracellular matrix glycoprotein that binds to procollagen I and enhances the proteolytic activity of Bmp1 (which is also capable of processing procollagen, type V alpha 1 (Col5a1) and probiglycan (Bgn)). Similarly, several Runx2-like gene products from Table 6 (Pdgfrb, Fyn and Arhb) have been functionally linked. Platelet-derived growth factor receptor beta (pdgfrb) initiates a signaling cascade when activated by ligand. PDGF-BB, one of several ligands for Pdgfrb, has been shown to be an important growth factor for many cell types, including chondrocytes. Once activated by ligand, Pdgfrb has been shown to induce the phosphorylation and activation of Fyn, a member of the Src family of protein tyrosine kinases, in porcine aortic endothelial cells. In addition, Rat-2 fibroblasts exposed to PDGF showed an increase in rhoB (Arhb; a member of the ras gene superfamily whose products are GTP binding proteins) gene expression.

EQUIVALENTS

Those skilled in the art will recognize, or be able to ascertain using no more than routine experimentation, many equivalents of the specific embodiments of the invention described herein. Such equivalents are intended to be encompassed by the following claims.

TABLE 1

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 110451_at | 2.76 | 4.33 | 4.35 | 2.49 | 0.00 | 3.90 | UNK_AI646968 | AI646968 |
| 92315_at | 2.86 | 0.00 | 6.24 | 8.35 | 0.00 | 3.87 | SLFN4 | AF099977 |
| 93285_at | 0.00 | 2.14 | 2.31 | 2.81 | 0.00 | 2.94 | UNK_AI845584 | AI845584 |
| 103563_at | 0.00 | 4.54 | 5.11 | 2.68 | 0.00 | 5.42 | UNK_AW125713 | AW125713 |
| 107566_at | 0.00 | 1.55 | 3.55 | 3.44 | 2.08 | 17.15 | UNK_AI849532 | AI849532 |
| 115395_at | 0.00 | 2.23 | 3.68 | 2.97 | 0.00 | 2.37 | UNK_AW208422 | AW208422 |
| 92718_at | 0.00 | 1.68 | 2.17 | 3.31 | 0.00 | 2.34 | UNK_AI158810 | AI158810 |
| 93975_at | 0.00 | 1.77 | 2.83 | 3.21 | 0.00 | 3.81 | 33 POLYPEPTIDE [R. NORVEGICUS] | AI853531 |
| 96752_at | 1.65 | 2.58 | 0.00 | 3.13 | 0.00 | 2.46 | ICAM1 | M90551 |
| 103446_at | 0.00 | 0.00 | 3.81 | 5.48 | 0.00 | 3.13 | UNK_AA959954 | AA959954 |
| 104177_at | 0.00 | 0.00 | 3.59 | 2.98 | 0.00 | 2.50 | UNK_AA204579 | AA204579 |
| 104252_at | 0.00 | 0.00 | 2.17 | 2.34 | 0.00 | 2.47 | UNK_AW123823 | AW123823 |
| 108877_at | 0.00 | 0.00 | 2.69 | 2.18 | 0.00 | 2.40 | UNK_AI790579 | AI790579 |
| 109102_r_at | 0.00 | 1.67 | 2.79 | 2.38 | 0.00 | 2.61 | UNK_AI838972 | AI838972 |
| 109922_at | 0.00 | 3.60 | 0.00 | 4.21 | 0.00 | 3.09 | UNK_AW122872 | AW122872 |
| 112478_at | 0.00 | 0.00 | 2.02 | 2.33 | 0.00 | 2.33 | UNK_AI853409 | AI853409 |
| 112671_at | 0.00 | 0.00 | 2.84 | 5.17 | 0.00 | 3.73 | UNK_AW122101 | AW122101 |
| 113758_at | 0.00 | 0.00 | 0.00 | 3.78 | 3.50 | 23.28 | UNK_AI843230 | AI843230 |
| 115573_at | 0.00 | 4.17 | 3.10 | 0.00 | 0.00 | 2.99 | UNK_AW047581 | AW047581 |
| 130459_at | 0.00 | 2.06 | 3.92 | 4.75 | −1.78 | 0.00 | UNK_AI845691 | AI845691 |
| 136655_f_at | 0.00 | 0.00 | 2.87 | 3.14 | 0.00 | 2.39 | UNK_AI841502 | AI841502 |
| 94354_at | 0.00 | 0.00 | 0.00 | 2.22 | 0.00 | 3.75 | UNK_AI845514 | AI845514 |
| 95303_at | 1.49 | 2.01 | 0.00 | 0.00 | 0.00 | 2.63 | 0 | AA144469 |
| *96481_at* | *0.00* | *0.00* | *0.00* | *0.00* | *2.83* | *36.90* | *UNK_AV251613* | *AV251613* |
| 97448_at | 0.00 | 0.00 | 0.00 | 2.66 | 0.00 | 2.62 | UNK_AI845165 | AI845165 |
| 100880_at | 0.00 | 0.00 | 0.00 | 2.42 | 0.00 | 4.34 | UNK_AA816121 | AA816121 |
| 101327_at | 0.00 | 0.00 | 0.00 | 2.17 | 0.00 | 4.31 | UNK_U82610 | U82610 |
| 103672_at | 0.00 | 0.00 | 0.00 | 2.19 | 0.00 | 2.02 | UNK_AW122572 | AW122572 |
| 104193_at | 0.00 | 0.00 | 0.00 | 2.01 | 0.00 | 2.39 | UNK_AW047583 | AW047583 |
| 104195_at | 0.00 | 1.87 | 0.00 | 3.08 | 0.00 | 2.77 | UNK_AA939440 | AA939440 |
| 106500_f_at | 0.00 | 0.00 | 0.00 | 2.13 | 0.00 | 2.86 | UNK_AI642841 | AI642841 |
| 106583_at | 0.00 | 1.46 | 0.00 | 2.34 | 0.00 | 2.21 | UNK_AI851530 | AI851530 |
| 106644_at | 0.00 | 0.00 | 0.00 | 2.64 | 0.00 | 6.71 | UNK_AW047110 | AW047110 |
| 106957_f_at | 0.00 | 0.00 | 2.15 | 0.00 | 0.00 | 3.34 | UNK_AI790368 | AI790368 |
| 108494_at | 0.00 | 0.00 | 0.00 | 2.39 | 0.00 | 3.23 | UNK_AW123118 | AW123118 |
| 109099_at | 0.00 | 0.00 | 2.31 | 0.00 | 0.00 | 2.30 | UNK_AW049860 | AW049860 |
| 109345_at | 1.60 | 2.28 | 2.23 | 1.95 | 0.00 | 1.75 | UNK_AA711635 | AA711635 |
| 112015_at | 0.00 | 0.00 | 0.00 | 2.37 | 0.00 | 5.77 | UNK_AI551067 | AI551067 |
| 112908_at | 0.00 | 0.00 | 0.00 | 2.18 | 0.00 | 2.63 | UNK_AI849021 | AI849021 |
| 113181_r_at | 0.00 | 0.00 | 0.00 | 2.41 | 0.00 | 3.28 | UNK_AW125085 | AW125085 |
| 113248_at | 0.00 | 1.70 | 2.32 | 0.00 | 0.00 | 3.11 | UNK_AI837648 | AI837648 |
| 113724_at | 0.00 | 0.48 | 2.16 | 1.55 | 1.17 | 7.05 | UNK_AI848964 | AI848964 |
| 113865_at | 0.00 | 0.00 | 0.00 | 2.39 | 0.00 | 2.52 | UNK_AA231562 | AA231562 |
| 114306_at | 0.00 | 0.00 | 2.13 | 0.00 | 0.00 | 2.92 | UNK_AI593556 | AI593556 |
| 114380_at | 0.00 | 1.57 | 0.00 | 2.43 | 0.00 | 3.41 | UNK_AA959464 | AA959464 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 115397_at | 0.00 | 0.00 | 0.00 | 3.18 | 0.00 | 4.45 | UNK_AA727857 | AA727857 |
| 115453_at | 0.00 | 0.00 | 0.00 | 0.00 | 2.04 | 23.84 | UNK_AA764584 | AA764584 |
| 115520_at | 0.00 | 0.00 | 0.00 | 2.91 | 0.00 | 3.20 | UNK_AA163981 | AA163981 |
| 115874_at | 0.00 | 0.00 | 0.00 | 2.93 | 0.00 | 3.18 | UNK_AW046286 | AW046286 |
| 116418_at | 0.00 | 0.00 | 0.00 | 3.54 | 0.00 | 5.07 | UNK_AA839780 | AA839780 |
| 117265_at | 0.00 | 0.00 | 2.93 | 0.00 | 0.00 | 4.66 | UNK_AI853644 | AI853644 |
| 134205_at | 0.00 | 0.00 | 0.00 | 2.79 | 0.00 | 2.04 | UNK_AI482096 | AI482096 |
| 134405_at | 0.00 | 0.00 | 0.00 | 2.03 | 0.00 | 3.36 | UNK_AI662230 | AI662230 |
| 138037_at | 0.00 | 0.00 | 0.00 | 2.32 | 0.00 | 2.43 | UNK_AI851460 | AI851460 |
| *92378_at* | *0.00* | *0.00* | *0.00* | *0.00* | *0.00* | *4.69* | *UNK_AI849305* | *AI849305* |
| 92474_at | 0.00 | 0.00 | 0.00 | 0.00 | 0.00 | 2.13 | UNK_AF083497 | AF083497 |
| 93153_at | 0.00 | 0.00 | 0.00 | 0.00 | 0.40 | 2.46 | UNK_AW124433 | AW124433 |
| 93475_at | 0.00 | 0.00 | 0.00 | 0.00 | 0.00 | 2.60 | UNK_AI845581 | AI845581 |
| 93482_at | 0.00 | 0.00 | 0.00 | 0.00 | 0.00 | 2.28 | UNK_AI117835 | AI117835 |
| 93647_at | 0.00 | 0.00 | 0.00 | 0.00 | 0.00 | 3.25 | UNK_AI152195 | AI152195 |
| 93837_at | 0.00 | 0.00 | 0.00 | 0.00 | 0.00 | 3.92 | UNK_AI786089 | AI786089 |
| 94347_i_at | 0.00 | 0.00 | 0.00 | 0.00 | 0.00 | 2.23 | UNK_AW124044 | AW124044 |
| 94352_at | 0.00 | 0.00 | 0.00 | 0.00 | 0.00 | 2.50 | UNK_AI850675 | AI850675 |
| 94362_at | 0.00 | 1.77 | 0.00 | 2.00 | 0.00 | 1.81 | UNK_AI843682 | AI843682 |
| 94364_at | 0.00 | 0.00 | 0.00 | 0.00 | 0.00 | 2.74 | UNK_AI847926 | AI847926 |
| 94460_at | 0.00 | 0.00 | 0.00 | 1.78 | 0.00 | 2.16 | UNK_AA691445 | AA691445 |
| 94471_r_at | 0.00 | 0.00 | 0.00 | 0.00 | 0.00 | 2.86 | UNK_AW045974 | AW045974 |
| 94512_f_at | 0.00 | 0.00 | 0.00 | 1.95 | 0.00 | 2.91 | UNK_AI843210 | AI843210 |
| 95165_at | 0.00 | 0.00 | 0.00 | 0.00 | 0.00 | 3.48 | 0 | AA409156 |
| *95620_at* | *0.00* | *0.00* | *0.00* | *0.00* | *0.00* | *5.11* | *UNK_AW120882* | *AW120882* |
| 95914_at | 0.00 | 0.00 | 0.00 | 0.00 | 0.00 | 2.09 | UNK_AA177382 | AA177382 |
| 96165_at | 0.00 | 0.00 | 0.00 | 0.00 | 0.00 | 2.08 | UNK_AW125109 | AW125109 |
| 96172_at | 0.00 | 0.00 | 0.00 | 0.00 | 0.00 | 3.73 | UNK_AA795946 | AA795946 |
| 96187_at | 0.00 | 0.00 | 0.00 | 0.00 | 0.00 | 2.40 | UNK_AI837021 | AI837021 |
| 96785_at | 0.00 | 0.00 | 0.00 | 0.00 | 0.00 | 2.14 | UNK_AF110520 | AF110520 |
| 96790_f_at | 0.00 | 0.00 | 0.00 | 0.00 | 0.00 | 2.16 | UNK_AW125222 | AW125222 |
| 96806_at | 0.00 | 0.00 | 0.00 | 0.00 | 0.00 | 2.70 | UNK_AI843802 | AI843802 |
| 96862_at | 0.00 | 0.00 | 0.00 | 1.98 | 0.00 | 2.03 | UNK_AI848584 | AI848584 |
| 96881_at | 0.00 | 0.00 | 0.00 | 1.79 | 0.00 | 2.31 | UNK_AW049394 | AW049394 |
| 97131_at | 0.00 | 0.00 | 0.00 | 0.00 | 0.00 | 2.66 | UNK_AW124615 | AW124615 |
| 97197_r_at | 0.00 | 0.00 | 0.00 | 2.21 | 0.00 | 1.78 | UNK_C78850 | C78850 |
| 97386_at | 0.00 | 0.00 | 0.00 | 0.00 | 0.00 | 2.29 | UNK_AI853294 | AI853294 |
| 97598_at | 0.00 | 0.00 | 0.00 | 0.00 | 0.00 | 3.27 | UNK_AW209139 | AW209139 |
| 97864_at | 0.00 | 0.00 | 0.00 | 0.00 | 0.00 | 2.90 | UNK_AW258842 | AW258842 |
| 97866_at | 0.00 | 0.00 | 0.00 | 0.00 | 0.00 | 2.12 | UNK_AI842858 | AI842858 |
| 97944_f_at | 0.00 | 0.00 | 0.00 | 0.00 | 0.00 | 3.30 | UNK_AF099808 | AF099808 |
| *97967_at* | *0.00* | *0.00* | *0.00* | *0.00* | *0.00* | *4.08* | *UNK_AA881438* | *AA881438* |
| 98104_at | 0.00 | 0.00 | 0.00 | 0.00 | 0.00 | 2.65 | UNK_AI842889 | AI842889 |
| 98154_at | 0.00 | 0.00 | 0.00 | 2.56 | 0.00 | 1.79 | UNK_AW050133 | AW050133 |
| 98572_at | 0.00 | 0.00 | 1.76 | 2.55 | 0.00 | 1.86 | UNK_AW122551 | AW122551 |
| 98849_at | 0.00 | 0.00 | 0.00 | 0.00 | 0.00 | 2.52 | UNK_AI463656 | AI463656 |
| 98908_at | 0.00 | 0.00 | 0.00 | 1.67 | 0.00 | 2.04 | UNK_AW125510 | AW125510 |
| 98988_at | 0.00 | 0.00 | 0.00 | 2.11 | 0.00 | 1.77 | 0 | AA614971 |
| 99178_at | 0.00 | 0.00 | 0.00 | 0.00 | 0.00 | 2.09 | UNK_AI845652 | AI845652 |
| *99379_f_at* | *0.00* | *0.00* | *0.00* | *0.00* | *0.00* | *4.39* | *0* | *M27034* |
| 99592_f_at | 0.00 | 0.00 | 0.00 | 0.00 | 0.00 | 2.16 | UNK_AB030505 | AB030505 |
| 100297_at | 0.00 | 0.00 | 0.00 | 0.00 | 0.00 | 2.38 | UNK_AA693125 | AA693125 |
| 100890_at | 0.00 | 0.00 | 0.00 | 0.00 | 0.00 | 2.48 | UNK_AI173038 | AI173038 |
| 101221_at | 0.00 | 1.67 | 1.61 | 2.10 | 0.00 | 1.90 | 0 | C76746 |
| 102009_at | 0.00 | 0.00 | 0.00 | 0.00 | 0.00 | 3.95 | UNK_AI835274 | AI835274 |
| 102348_at | 0.00 | 0.00 | 0.00 | 1.85 | 0.00 | 2.42 | XDH | AI551087 |
| 102383_at | 0.00 | 0.00 | 0.00 | 0.00 | 0.00 | 3.66 | UNK_AW048977 | AW048977 |
| 102863_at | 0.00 | 0.00 | 0.00 | 0.00 | 0.00 | 2.16 | UNK_AI550530 | AI550530 |
| 103356_at | 0.00 | 0.00 | 0.00 | 0.00 | 0.00 | 2.97 | UNK_AI843267 | AI843267 |
| *103424_at* | *0.00* | *0.00* | *0.00* | *0.00* | *0.00* | *4.23* | *UNK_AI844839* | *AI844839* |
| 103451_at | 0.00 | 0.00 | 0.00 | 0.00 | 0.00 | 2.30 | UNK_AI835159 | AI835159 |
| *103493_at* | *0.00* | *0.00* | *0.00* | *0.00* | *0.00* | *7.57* | *UNK_AW045989* | *AW045989* |
| 103582_r_at | 0.00 | 0.00 | 0.00 | 0.00 | 0.00 | 2.59 | UNK_AI845633 | AI845633 |
| 103678_at | 0.00 | 0.00 | 0.00 | 0.00 | 0.00 | 2.22 | UNK_AI841139 | AI841139 |
| 103697_at | 0.00 | 0.00 | 0.00 | 0.00 | 0.00 | 3.81 | UNK_AW061234 | AW061234 |
| 103901_at | 0.00 | 0.00 | 0.00 | 0.00 | 0.00 | 2.52 | UNK_AW213777 | AW213777 |
| *103923_at* | *0.00* | *0.00* | *0.00* | *0.00* | *0.00* | *13.09* | *UNK_AA656014* | *AA656014* |
| 103957_at | 0.00 | 0.00 | 0.00 | 0.00 | −2.38 | 2.04 | Trfr | X57349 |
| 104036_at | 0.00 | 0.00 | 0.00 | 0.00 | 0.00 | 2.39 | UNK_AI845447 | AI845447 |
| 104058_at | 0.00 | 0.00 | 0.00 | 1.82 | 0.00 | 2.49 | UNK_AW047528 | AW047528 |
| 104118_at | 0.00 | 0.00 | 0.00 | 0.00 | 0.00 | 2.29 | UNK_AW123781 | AW123781 |
| 104150_at | 0.00 | 2.31 | 0.00 | 0.00 | 0.00 | 1.72 | UNK_AW121957 | AW121957 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 104274_at | 0.00 | 0.00 | 0.00 | 0.00 | 0.00 | 2.47 | UNK_AW124843 | AW124843 |
| 104316_at | 0.00 | 0.00 | 0.00 | 0.00 | 0.00 | 2.69 | UNK_AI646098 | AI646098 |
| 104326_at | 0.00 | 0.00 | 0.04 | 0.00 | 0.00 | 2.48 | UNK_AI838951 | AI838951 |
| 104477_at | 0.00 | 0.00 | 0.00 | 0.00 | 0.00 | 3.25 | UNK_AW047643 | AW047643 |
| 104494_at | 0.00 | 0.00 | 0.00 | 0.00 | 0.00 | 2.16 | UNK_AI642098 | AI642098 |
| 104513_at | 0.00 | 0.00 | 0.00 | 0.00 | 0.00 | 2.22 | EST; unknown | AA688938 |
| 104550_at | 0.00 | 0.00 | 0.00 | 0.00 | 0.00 | 2.32 | UNK_AW123273 | AW123273 |
| 105005_at | 0.00 | 0.00 | 0.00 | 0.00 | 0.00 | 2.02 | UNK_AI020518 | AI020518 |
| 105143_at | 0.00 | 0.00 | 0.00 | 0.00 | 0.00 | 2.81 | UNK_AI852801 | AI852801 |
| 105159_at | 0.00 | 0.00 | 0.00 | 0.00 | 0.00 | 2.62 | UNK_AI843003 | AI843003 |
| 105317_at | 0.00 | 0.00 | 0.00 | 0.00 | 0.00 | 2.61 | UNK_AI876413 | AI876413 |
| 105455_at | 0.00 | 0.00 | 0.00 | 0.00 | 0.00 | 2.53 | UNK_AI606142 | AI606142 |
| 105554_at | 0.00 | 0.00 | 0.00 | 0.00 | 0.00 | 2.08 | UNK_AA177721 | AA177721 |
| 105574_i_at | 0.00 | 0.00 | 0.00 | 2.19 | 0.00 | 1.96 | UNK_AA833192 | AA833192 |
| *105686_at* | *0.00* | *0.00* | *0.00* | *0.00* | *0.00* | *4.01* | *UNK_AI836126* | *AI836126* |
| 105689_r_at | 0.00 | 0.00 | 0.00 | 0.00 | 0.00 | 2.68 | UNK_AI842855 | AI842855 |
| 106101_at | 0.00 | 0.00 | 0.00 | 1.63 | 0.00 | 2.91 | UNK_AI853221 | AI853221 |
| 106184_at | 0.00 | 0.00 | 0.00 | 0.00 | 0.00 | 2.88 | UNK_AI848994 | AI848994 |
| 106189_at | 0.00 | 0.00 | 0.00 | 0.00 | 0.00 | 2.53 | UNK_AI225382 | AI225382 |
| 106262_at | 0.00 | 0.00 | 0.00 | 0.00 | 0.00 | 2.08 | UNK_AA914186 | AA914186 |
| 106479_at | 0.00 | 0.00 | 0.00 | 0.00 | 0.00 | 2.53 | UNK_AI844057 | AI844057 |
| 106491_at | 0.00 | 0.00 | 0.00 | 0.00 | 0.00 | 2.06 | UNK_AI957035 | AI957035 |
| 106536_f_at | 0.00 | 0.00 | 0.00 | 0.00 | 0.00 | 2.86 | UNK_AI786456 | AI786456 |
| 106616_at | 0.00 | 0.00 | 0.00 | 0.00 | 0.00 | 2.12 | UNK_AA139123 | AA139123 |
| 106617_at | 0.00 | 0.00 | 0.00 | 0.00 | 0.00 | 2.16 | UNK_AW123240 | AW123240 |
| 106635_at | 0.00 | 0.00 | 0.00 | 0.00 | 0.00 | 3.61 | UNK_AA764553 | AA764553 |
| 106637_r_at | 0.00 | 0.00 | 0.00 | 0.00 | 0.00 | 2.79 | UNK_AI647933 | AI647933 |
| 106648_at | 0.00 | 0.00 | 0.00 | 0.00 | 0.00 | 2.85 | UNK_AW045837 | AW045837 |
| 106654_at | 0.00 | 0.00 | 0.00 | 0.00 | 0.00 | 2.82 | UNK_AA647503 | AA647503 |
| 106868_at | 0.00 | 0.00 | 0.00 | 0.00 | 0.00 | 2.33 | UNK_AW048984 | AW048984 |
| 106958_r_at | 0.00 | 0.00 | 0.00 | 0.00 | 0.00 | 3.40 | UNK_AI790368 | AI790368 |
| 107045_at | 0.00 | 1.82 | 0.00 | 0.00 | 0.00 | 2.29 | UNK_AA840458 | AA840458 |
| 107064_at | 0.00 | 0.00 | 1.47 | 0.00 | 0.00 | 2.10 | UNK_AA645686 | AA645686 |
| 107273_at | 0.00 | 0.00 | 0.00 | 0.00 | 0.00 | 2.03 | UNK_AW046853 | AW046853 |
| 107459_at | 0.00 | 0.00 | 0.00 | 0.00 | 0.00 | 3.47 | UNK_AW049987 | AW049987 |
| 107483_at | 0.00 | 0.00 | 0.00 | 0.00 | 0.00 | 2.14 | UNK_AW050172 | AW050172 |
| 107552_at | 0.00 | 0.00 | 0.00 | 0.00 | 0.00 | 2.74 | UNK_AA711627 | AA711627 |
| 107602_at | 0.00 | 0.00 | 0.00 | 0.00 | 0.00 | 3.00 | UNK_AA717340 | AA717340 |
| 107609_at | 0.00 | 0.00 | 0.00 | 0.00 | 0.00 | 3.22 | UNK_AA137485 | AA137485 |
| 107766_at | 0.00 | 0.00 | 0.00 | 0.00 | 0.00 | 2.74 | UNK_AI426461 | AI426461 |
| 107787_at | 0.00 | 0.00 | 0.00 | 0.00 | 0.00 | 2.22 | UNK_AA755149 | AA755149 |
| 107871_at | 0.00 | 1.46 | 0.00 | 0.00 | 0.00 | 2.69 | UNK_AW048252 | AW048252 |
| 107995_at | 0.00 | 0.00 | 0.00 | 0.00 | 0.00 | 2.14 | UNK_AI845884 | AI845884 |
| 108073_at | 0.00 | 0.00 | 0.00 | 0.00 | 0.00 | 2.92 | UNK_AI850676 | AI850676 |
| 108312_at | 0.00 | 0.00 | 0.00 | 0.00 | 0.00 | 2.66 | UNK_AI593736 | AI593736 |
| 108329_at | 0.00 | 0.00 | 0.00 | 0.00 | 0.00 | 2.46 | UNK_AA833472 | AA833472 |
| 108352_at | 0.00 | 0.00 | 0.00 | 0.00 | 0.00 | 2.32 | UNK_AW061021 | AW061021 |
| 108368_at | 0.00 | 0.00 | 0.00 | 0.00 | 0.00 | 2.08 | UNK_AI121297 | AI121297 |
| 108375_at | 0.00 | 0.00 | 0.00 | 0.00 | 0.00 | 2.22 | UNK_AA982346 | AA982346 |
| 108492_at | 0.00 | 0.00 | 0.00 | 1.05 | 0.00 | 4.22 | UNK_AI852003 | AI852003 |
| 108519_at | 0.00 | 0.00 | 0.00 | 0.00 | 0.00 | 2.72 | UNK_AW212926 | AW212926 |
| 108556_at | 0.00 | 0.00 | 0.00 | 0.00 | 0.00 | 2.50 | UNK_AI851581 | AI851581 |
| *108733_at* | *0.00* | *0.00* | *0.00* | *0.00* | *0.00* | *19.06* | *UNK_AW120982* | *AW120982* |
| *109066_at* | *0.00* | *0.00* | *0.00* | *0.00* | *0.00* | *5.85* | *UNK_AA874293* | *AA874293* |
| *109081_at* | *0.00* | *0.00* | *0.00* | *0.00* | *0.00* | *5.41* | *UNK_AI119897* | *AI119897* |
| 109092_at | 0.00 | 0.00 | 0.00 | 0.00 | 0.00 | 2.32 | UNK_AA763190 | AA763190 |
| 109176_at | 0.00 | 0.00 | 0.00 | 0.00 | 0.00 | 2.47 | UNK_AI846059 | AI846059 |
| 109326_at | 0.00 | 0.00 | 0.00 | 0.00 | 0.00 | 2.72 | UNK_AI837923 | AI837923 |
| 109410_at | 0.00 | 0.00 | 0.00 | 0.00 | 0.00 | 2.67 | UNK_AW121121 | AW121121 |
| 109453_at | 0.00 | 0.00 | 0.00 | 0.00 | 0.00 | 2.98 | UNK_AW044905 | AW044905 |
| 109561_at | 0.00 | 0.00 | 0.00 | 1.77 | 0.00 | 2.55 | UNK_AA032690 | AA032690 |
| 109729_at | 0.00 | 0.00 | 0.00 | 0.00 | 0.00 | 3.09 | UNK_AI226312 | AI226312 |
| 109747_at | 0.00 | 0.00 | 0.00 | 0.00 | 0.00 | 2.66 | UNK_AW046149 | AW046149 |
| 109758_at | 0.00 | 0.00 | 0.00 | 0.00 | 0.00 | 2.07 | UNK_AW124910 | AW124910 |
| 109785_at | 0.00 | 0.00 | 0.00 | 0.00 | 0.00 | 2.45 | UNK_AW123736 | AW123736 |
| 109807_f_at | 0.00 | 0.00 | 0.00 | 0.00 | 0.00 | 2.28 | TSGA12 | AI117666 |
| 109813_f_at | 0.00 | 0.00 | 0.00 | 0.00 | 0.00 | 2.10 | UNK_AI413781 | AI413781 |
| 109923_at | 0.00 | 0.00 | 0.00 | 1.67 | 0.00 | 2.09 | UNK_AA792733 | AA792733 |
| *109945_at* | *0.00* | *0.00* | *0.00* | *0.00* | *0.00* | *4.10* | *UNK_AI850918* | *AI850918* |
| 109962_at | 0.00 | 0.00 | 0.00 | 0.00 | 0.00 | 3.36 | UNK_AI314322 | AI314322 |
| 109970_at | 0.00 | 0.00 | 0.00 | 0.00 | 0.00 | 2.61 | UNK_AI843938 | AI843938 |
| 110168_at | 0.00 | 0.00 | 0.00 | 0.00 | 0.00 | 3.15 | UNK_AW124258 | AW124258 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 110331_at | 0.00 | 0.00 | 0.00 | 0.00 | 0.00 | 3.16 | UNK_AI851383 | AI851383 |
| 110355_at | 0.00 | 0.00 | 0.00 | 0.00 | 0.00 | 2.86 | UNK_AW049880 | AW049880 |
| 110374_at | 0.00 | 0.00 | 0.00 | 0.00 | 0.00 | 2.98 | UNK_AI851558 | AI851558 |
| 110396_at | 0.00 | 0.00 | 0.00 | 0.00 | 0.00 | 2.93 | UNK_AW050339 | AW050339 |
| 110472_f_at | 0.00 | 0.00 | 0.00 | 0.00 | 0.00 | 2.23 | UNK_AW121052 | AW121052 |
| 110515_at | 0.00 | 0.00 | 0.00 | 1.94 | 0.00 | 2.61 | UNK_AW123207 | AW123207 |
| 110570_at | 0.00 | 0.00 | 0.00 | 0.00 | 0.00 | 2.39 | UNK_AA118312 | AA118312 |
| 110616_at | 0.00 | 0.00 | 0.00 | 0.00 | 0.00 | 2.28 | UNK_AI646542 | AI646542 |
| 110712_at | 0.00 | 0.00 | 0.00 | 0.00 | 0.00 | 2.14 | UNK_AA863810 | AA863810 |
| 110758_at | 0.00 | 0.00 | 0.00 | 0.00 | 0.00 | 2.61 | UNK_AA915391 | AA915391 |
| 110790_at | 0.00 | −1.32 | 0.00 | 0.00 | 0.00 | 3.19 | UNK_AW121879 | AW121879 |
| 110833_at | 0.00 | 0.00 | 0.00 | 0.00 | 0.00 | 2.59 | UNK_AI847626 | AI847626 |
| 110834_at | 0.00 | 0.00 | 0.00 | 0.00 | 0.00 | 3.53 | UNK_AA919801 | AA919801 |
| *110839_at* | *0.00* | *0.00* | *0.00* | *0.00* | *0.00* | *4.31* | *UNK_AI839647* | *AI839647* |
| 110852_at | 0.00 | 0.00 | 0.00 | 1.38 | 0.00 | 2.51 | UNK_AI226234 | AI226234 |
| 111036_f_at | 0.00 | 0.00 | 0.00 | 0.00 | 0.00 | 3.48 | UNK_AI882445 | AI882445 |
| 111083_at | 0.00 | 0.00 | 0.00 | 0.00 | 0.00 | 3.25 | UNK_AW122341 | AW122341 |
| 111191_at | 0.00 | 0.00 | 0.00 | 0.00 | 0.00 | 3.55 | UNK_AW120521 | AW120521 |
| 111233_at | 0.00 | 0.00 | 0.00 | 0.00 | 0.00 | 3.31 | UNK_AW122352 | AW122352 |
| 111309_at | 0.00 | 0.00 | 0.00 | 0.00 | 0.00 | 2.88 | UNK_AI181332 | AI181332 |
| 111405_at | 0.00 | 0.00 | 0.00 | 0.00 | 0.00 | 2.17 | UNK_AI847396 | AI847396 |
| 111439_at | 0.00 | 0.00 | 0.00 | 0.00 | 0.00 | 2.69 | UNK_AI591562 | AI591562 |
| 111515_at | 0.00 | 0.00 | 0.00 | 0.00 | 0.00 | 3.71 | UNK_AW060320 | AW060320 |
| 111682_at | 0.00 | 0.00 | 0.00 | 0.00 | 0.00 | 2.47 | UNK_AW229627 | AW229627 |
| 111707_at | 0.00 | 0.00 | 0.00 | 0.00 | 0.00 | 2.37 | UNK_AW259521 | AW259521 |
| 111738_at | 0.00 | 0.00 | 0.00 | 0.00 | 0.00 | 2.54 | UNK_AW121627 | AW121627 |
| 111790_at | 0.00 | 0.00 | 0.00 | 0.00 | 0.00 | 2.80 | UNK_AW122322 | AW122322 |
| 111916_at | 0.00 | 0.00 | 0.00 | 0.00 | 0.00 | 2.06 | UNK_AI841396 | AI841396 |
| 111924_at | 0.00 | 0.00 | 0.00 | 0.00 | 0.00 | 2.33 | UNK_AA789586 | AA789586 |
| 112020_g_at | 0.00 | 0.00 | 0.00 | 0.00 | 0.00 | 3.63 | UNK_AA881092 | AA881092 |
| 112084_at | 0.00 | 0.00 | 0.00 | 1.49 | 0.00 | 2.11 | UNK_AI662678 | AI662678 |
| *112351_at* | *0.00* | *0.00* | *0.00* | *0.00* | *0.00* | *4.17* | *UNK_AW048346* | *AW048346* |
| 112388_at | 0.00 | 0.00 | 0.00 | 0.00 | 0.00 | 2.20 | UNK_AW123069 | AW123069 |
| *112435_at* | *0.00* | *0.00* | *0.00* | *0.00* | *0.00* | *4.03* | *UNK_AW061103* | *AW061103* |
| 112802_at | 0.00 | 0.00 | 0.00 | 0.00 | 0.00 | 2.65 | UNK_AW122077 | AW122077 |
| 112858_at | 0.00 | 0.00 | 0.00 | 0.00 | 0.00 | 2.94 | UNK_AI854616 | AI854616 |
| 112918_at | 0.00 | 0.00 | 0.00 | 0.00 | 0.00 | 3.95 | UNK_AI842563 | AI842563 |
| 112944_at | 0.00 | 0.00 | 0.00 | 1.46 | 0.00 | 2.25 | UNK_AI607994 | AI607994 |
| 112949_at | 0.00 | 0.00 | 0.00 | 0.00 | 0.00 | 2.74 | UNK_AA915460 | AA915460 |
| 113019_at | 0.00 | 0.00 | 0.00 | 0.00 | 0.00 | 2.62 | UNK_AA138087 | AA138087 |
| *113020_at* | *0.00* | *0.00* | *0.00* | *0.00* | *0.00* | *4.44* | *UNK_AA967744* | *AA967744* |
| 113044_at | 0.00 | 0.00 | 0.00 | 0.00 | 0.00 | 3.47 | UNK_AA002573 | AA002573 |
| 113130_at | 0.00 | 0.00 | 0.00 | 0.00 | 0.00 | 2.36 | UNK_AI854014 | AI854014 |
| 113131_at | 0.00 | 0.00 | 0.00 | 0.00 | 0.00 | 2.71 | UNK_AW047592 | AW047592 |
| *113171_at* | *0.00* | *0.00* | *0.00* | *0.00* | *0.00* | *4.72* | *UNK_AI849023* | *AI849023* |
| *113227_at* | *0.00* | *0.00* | *0.00* | *0.00* | *0.00* | *6.08* | *UNK_AI854880* | *AI854880* |
| 113240_at | 0.00 | 0.00 | 0.00 | 1.73 | 0.00 | 2.76 | UNK_AA153179 | AA153179 |
| 113246_at | 0.00 | 0.00 | 0.00 | 0.00 | 0.00 | 2.29 | UNK_AI156068 | AI156068 |
| 113287_at | 0.00 | 0.00 | 0.00 | 0.00 | 0.00 | 3.02 | UNK_AI115322 | AI115322 |
| 113311_r_at | 0.00 | 0.00 | 0.00 | 0.00 | 0.00 | 2.64 | UNK_AA175228 | AA175228 |
| 113316_at | 0.00 | 0.00 | 0.00 | 0.00 | 0.00 | 3.21 | UNK_AI841062 | AI841062 |
| 113319_at | 0.00 | 0.00 | 0.00 | 0.00 | 0.00 | 3.04 | UNK_AI786159 | AI786159 |
| 113339_at | 0.00 | 0.00 | 0.00 | 0.00 | 0.00 | 2.24 | UNK_AW046072 | AW046072 |
| 113554_at | 0.00 | 0.00 | 0.00 | 0.00 | 0.00 | 2.53 | UNK_AI840943 | AI840943 |
| 113579_at | 0.00 | 0.00 | 0.00 | 0.00 | 0.00 | 2.33 | UNK_AI842229 | AI842229 |
| 113680_at | 0.00 | 0.00 | 0.00 | 1.91 | 0.00 | 2.52 | UNK_AI846297 | AI846297 |
| 113737_at | 0.00 | 0.00 | 0.00 | 0.00 | 0.00 | 2.30 | UNK_AW122351 | AW122351 |
| 113790_at | 0.00 | 0.00 | 0.00 | 1.63 | 0.00 | 3.67 | UNK_AI194566 | AI194566 |
| 114005_at | 0.00 | 0.00 | 0.00 | 1.75 | 0.00 | 3.24 | UNK_AW215403 | AW215403 |
| 114016_at | 0.00 | 0.00 | 0.00 | 0.00 | 0.00 | 2.30 | UNK_AW124568 | AW124568 |
| 114045_at | 0.00 | 0.00 | 0.00 | 0.00 | 0.00 | 2.70 | UNK_AI877454 | AI877454 |
| 114149_at | 0.00 | 0.00 | 0.00 | 0.00 | 0.00 | 2.05 | UNK_AA596704 | AA596704 |
| *114197_at* | *0.00* | *0.00* | *0.00* | *0.00* | *0.00* | *4.89* | *UNK_AI643902* | *AI643902* |
| 114213_at | 0.00 | 0.00 | 0.00 | 0.00 | 0.00 | 2.45 | UNK_AA242681 | AA242681 |
| *114270_at* | *0.00* | *0.00* | *0.00* | *0.00* | *0.00* | *12.52* | *UNK_AW049906* | *AW049906* |
| 114281_at | 0.00 | 0.00 | 0.00 | 1.98 | 0.00 | 5.21 | UNK_AI593204 | AI593204 |
| 114309_at | 0.00 | 0.00 | 0.00 | 0.00 | 0.00 | 2.11 | UNK_AA716898 | AA716898 |
| *114390_at* | *0.00* | *0.00* | *0.00* | *0.00* | *0.00* | *4.05* | *UNK_AI464339* | *AI464339* |
| 114408_at | 0.00 | 0.00 | 0.00 | 0.00 | 0.00 | 2.77 | UNK_AI843543 | AI843543 |
| 114463_at | 0.00 | 0.00 | 0.00 | 0.00 | 0.00 | 2.40 | UNK_AI585881 | AI585881 |
| 114485_at | 0.00 | 0.00 | 0.00 | 1.71 | 0.00 | 2.72 | UNK_AI596717 | AI596717 |
| 114619_at | 0.00 | 0.00 | 0.00 | 1.83 | 0.00 | 2.26 | UNK_AA797871 | AA797871 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 114686_at | 0.00 | 0.00 | 0.00 | 0.00 | 0.00 | 2.30 | UNK_AW048693 | AW048693 |
| 114716_at | 0.00 | 0.00 | 0.00 | 0.00 | 0.00 | 2.26 | UNK_AI181770 | AI181770 |
| 114752_at | 0.00 | −2.01 | 0.00 | 0.00 | 0.00 | 2.84 | UNK_AI843572 | AI843572 |
| 114755_at | 0.00 | 0.00 | 0.00 | 0.00 | 0.00 | 2.34 | UNK_AI844350 | AI844350 |
| 114804_at | 0.00 | 0.00 | 0.00 | 0.00 | 0.00 | 2.22 | NNAT | AI154029 |
| *114836_at* | *0.00* | *0.00* | *0.00* | *0.00* | *0.00* | *4.17* | *UNK_AI536480* | *AI536480* |
| *114854_at* | *0.00* | *0.00* | *0.00* | *0.00* | *0.00* | *5.39* | *UNK_AI843070* | *AI843070* |
| *114917_at* | *0.00* | *0.00* | *0.00* | *0.00* | *0.00* | *4.31* | *UNK_AI118679* | *AI118679* |
| 114980_at | 0.00 | 0.00 | 0.00 | 0.00 | 0.00 | 2.28 | UNK_AI854024 | AI854024 |
| 115004_at | 0.00 | 0.00 | 0.00 | 0.00 | 0.00 | 2.23 | UNK_AI788664 | AI788664 |
| 115017_at | 0.00 | 0.00 | 0.00 | 1.79 | 0.00 | 2.11 | UNK_AI848298 | AI848298 |
| 115058_at | 0.00 | 0.00 | 0.00 | 0.00 | 0.00 | 3.62 | UNK_AA756546 | AA756546 |
| 115110_at | 0.00 | 0.00 | 0.00 | 0.00 | 0.00 | 2.93 | UNK_AA250358 | AA250358 |
| 115114_at | 0.00 | 0.00 | 0.00 | 0.00 | 0.00 | 3.74 | UNK_AW047112 | AW047112 |
| *115202_at* | *0.00* | *0.00* | *0.00* | *0.00* | *0.00* | *5.05* | *UNK_AI851969* | *AI851969* |
| 115398_at | 0.00 | 0.00 | 0.00 | 0.00 | 0.00 | 2.07 | UNK_AA990038 | AA990038 |
| *115612_at* | *0.00* | *0.00* | *0.00* | *0.00* | *0.00* | *9.42* | *UNK_AA175284* | *AA175284* |
| 115664_at | 0.00 | 0.00 | 0.00 | 0.00 | 0.00 | 2.15 | UNK_AA222756 | AA222756 |
| 115679_at | 0.00 | 0.00 | 0.00 | 0.00 | 0.00 | 2.09 | UNK_AA174839 | AA174839 |
| 115692_r_at | 0.00 | 0.00 | 0.00 | 0.00 | 0.00 | 2.88 | UNK_AA396015 | AA396015 |
| 115741_at | 0.00 | 0.00 | 0.00 | 0.00 | 0.00 | 2.52 | UNK_AW125843 | AW125843 |
| 116096_at | 0.00 | 0.00 | 0.00 | 0.00 | 0.00 | 2.33 | UNK_AA718043 | AA718043 |
| *116113_at* | *0.00* | *0.00* | *0.00* | *0.00* | *0.00* | *4.05* | *UNK_AI790538* | *AI790539* |
| *116149_at* | *0.00* | *0.00* | *0.00* | *0.00* | *0.00* | *4.15* | *UNK_AI155421* | *AI155421* |
| 116337_at | 0.00 | 0.00 | 0.00 | 0.00 | 0.00 | 3.22 | UNK_AI390374 | AI390374 |
| *116346_at* | *0.00* | *0.00* | *0.00* | *0.00* | *0.00* | *6.82* | *UNK_AI843913* | *AI843913* |
| 116380_at | 0.00 | 0.00 | 0.00 | 0.00 | 0.00 | 2.70 | UNK_AI227104 | AI227104 |
| 116408_at | 0.00 | 0.00 | 0.00 | 0.00 | 0.00 | 3.16 | UNK_AI851073 | AI851073 |
| *116488_f_at* | *0.00* | *0.00* | *0.00* | *0.00* | *0.00* | *5.95* | *UNK_AA178300* | *AA178300* |
| 116489_r_at | 0.00 | 0.00 | 0.00 | 0.00 | 0.00 | 2.99 | UNK_AA178300 | AA178300 |
| *116526_at* | *0.00* | *0.00* | *0.00* | *0.00* | *0.00* | *8.92* | *UNK_AW121457* | *AW121457* |
| *116629_at* | *0.00* | *0.00* | *0.00* | *0.00* | *0.00* | *6.07* | *UNK_AW215503* | *AW215503* |
| *116642_f_at* | *0.00* | *0.00* | *0.00* | *0.00* | *0.00* | *5.54* | *UNK_AI852563* | *AI852563* |
| 116672_at | 0.00 | 0.00 | 0.00 | 0.00 | 0.00 | 3.31 | UNK_AA611861 | AA611861 |
| 116755_at | 0.00 | 0.00 | 0.00 | 0.00 | 0.00 | 2.12 | UNK_AI835947 | AI835947 |
| *116786_at* | *0.00* | *0.00* | *0.00* | *0.00* | *0.00* | *9.07* | *UNK_AI850351* | *AI850351* |
| 116936_f_at | 0.00 | 0.00 | 0.00 | 0.00 | 0.00 | 2.55 | UNK_AI847709 | AI847709 |
| 117043_at | 0.00 | 0.00 | 0.00 | 0.00 | 0.00 | 2.19 | UNK_AI851915 | AI851915 |
| 117056_at | 0.00 | 0.00 | 0.00 | 0.00 | 0.00 | 2.24 | UNK_AI837103 | AI837103 |
| 117120_at | 0.00 | 0.00 | 0.00 | 0.00 | 0.00 | 3.42 | UNK_AW124145 | AW124145 |
| 117263_at | 0.00 | 0.00 | 0.00 | 0.00 | 0.00 | 2.90 | UNK_AI850544 | AI850544 |
| 117297_at | 0.00 | 0.00 | 0.00 | 0.00 | 0.00 | 2.56 | UNK_AI846211 | AI846211 |
| 117302_at | 0.00 | 0.00 | 0.00 | 0.00 | 0.00 | 2.95 | UNK_AI847477 | AI847477 |
| *128837_f_at* | *0.00* | *0.00* | *0.00* | *0.00* | *0.00* | *4.79* | *UNK_AA726602* | *AA726602* |
| *129125_at* | *0.00* | *0.00* | *0.00* | *0.00* | *0.00* | *5.05* | *UNK_AA475062* | *AA475062* |
| 129284_at | 0.00 | 0.00 | 0.00 | 0.00 | 0.00 | 3.32 | UNK_AA154872 | AA154872 |
| 129320_at | 0.00 | 0.00 | 0.00 | 0.00 | 0.00 | 3.25 | UNK_AI593773 | AI593773 |
| 130499_at | 0.00 | −1.75 | 0.00 | 0.00 | 0.00 | 2.16 | UNK_AW108404 | AW108404 |
| 132374_at | 0.00 | 0.00 | 0.00 | 0.00 | 0.00 | 2.21 | UNK_AI467276 | AI467276 |
| 133489_f_at | 0.00 | 0.00 | 0.00 | 1.65 | 0.00 | 2.50 | UNK_AI449387 | AI449387 |
| 133743_at | 0.00 | 0.00 | 0.00 | 0.00 | 0.00 | 3.92 | UNK_AI467607 | AI467607 |
| 133851_s_at | 0.00 | 0.00 | 0.00 | 1.80 | 0.00 | 2.39 | UNK_AU019736 | AU019736 |
| 134141_at | 0.00 | 0.00 | 0.00 | 0.00 | 0.00 | 3.08 | UNK_AA189644 | AA189644 |
| 135248_at | 0.00 | 0.00 | 0.00 | 0.00 | 0.00 | 3.48 | UNK_AI843905 | AI843905 |
| *135716_f_at* | *0.00* | *0.00* | *0.00* | *0.00* | *0.00* | *37.37* | *UNK_AI836970* | *AI836970* |
| 136580_at | 0.00 | 1.40 | 0.00 | 2.03 | 0.00 | 1.59 | UNK_AI428854 | AI428854 |
| 136798_at | 0.00 | 0.00 | 0.00 | 0.00 | 0.00 | 2.31 | UNK_AI536255 | AI536255 |
| *137203_f_at* | *0.00* | *0.00* | *0.00* | *0.00* | *0.00* | *5.09* | *UNK_AI661008* | *AI661008* |
| 137569_at | 0.00 | 0.00 | 0.00 | 0.00 | 0.00 | 2.28 | UNK_AI605650 | AI605650 |
| 139200_at | 0.00 | 0.00 | 0.00 | 0.00 | 0.00 | 2.05 | UNK_AW045408 | AW045408 |
| 140629_s_at | 0.00 | 0.00 | 0.00 | 1.28 | 0.00 | 2.38 | UNK_AI506220 | AI506220 |
| *140759_at* | *0.00* | *0.00* | *0.00* | *0.00* | *0.00* | *5.94* | *UNK_AI646554* | *AI646554* |
| 140820_at | 0.00 | 0.00 | 0.00 | 0.00 | 0.00 | 2.91 | UNK_AI662586 | AI662586 |
| 140840_at | 0.00 | 0.00 | 0.00 | 0.00 | 0.00 | 2.96 | UNK_AI791094 | AI791094 |
| 94079_at | 0.00 | 0.00 | 0.00 | 0.00 | 0.00 | 2.57 | homolog (Drosophila); Pnutl2 | X61452 |
| 110428_at | 0.00 | 0.00 | 0.00 | 1.81 | 0.00 | 2.31 | UNK_AA797538 | AA797538 |
| 112746_at | 0.00 | 0.00 | 0.00 | 0.00 | 0.00 | 2.54 | UNK_AW260381 | AW260381 |
| 102873_at | 0.00 | 0.00 | 0.00 | 1.90 | 0.00 | 2.96 | TAP2 | U60091 |
| 98859_at | 0.00 | 0.00 | 0.00 | 7.40 | 5.86 | 101.96 | tartrate resistant; Acp5 | M99054 |
| 99104_at | 0.00 | −0.86 | 0.00 | 0.00 | 0.00 | 2.83 | ACRP30 | U49915 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 98589_at | 0.00 | 1.38 | 0.00 | 2.93 | 0.00 | 2.22 | differentiation related protein; Adfp | M93275 |
| 99559_at | 0.00 | 0.00 | 0.00 | 0.00 | 0.00 | 2.62 | dehydrogenase family 3, subfamily A2; Aldh3a2 | U14390 |
| 93354_at | 0.00 | 0.00 | 0.00 | 0.00 | 0.00 | 3.14 | Apoc1 | Z22661 |
| 104155_f_at | 0.00 | 0.00 | 0.00 | 0.00 | 0.00 | 2.14 | transcription factor 3; Atf3 | U19118 |
| *95744_at* | *0.00* | *0.00* | *0.00* | *0.00* | *0.00* | *6.19* | *ATPase, H+ transporting, lysosomal (vacuolar proton pump), alpha 70 kDa, isoform 2;* | *U13837* |
| *92597_s_at* | *0.00* | *0.00* | *0.00* | *0.00* | *0.00* | *7.95* | *ATPase, H+ transporting, lysosomal (vacuolar proton pump), beta 56/58 kDa, isoform 2;* | *U13838* |
| *92598_at* | *0.00* | *0.00* | *0.00* | *0.00* | *0.00* | *5.12* | *ATP6B2* | *AI843029* |
| 94532_at | 0.00 | 0.00 | 0.00 | 0.00 | 0.00 | 2.12 | transporting lysosomal (vacuolar proton pump), 32 kDa; Atp6e | U13841 |
| 103205_at | 0.00 | 0.00 | 0.00 | 7.48 | 7.29 | 36.60 | ATP6I | AI286861 |
| 130186_f_at | 0.00 | 0.00 | 0.00 | 0.00 | 0.00 | 2.13 | ATP6I | AW211999 |
| 96919_at | 0.00 | 0.00 | 0.00 | 0.00 | 0.00 | 2.22 | vacuolar proton channel; Atpl | M64298 |
| 94043_at | 0.00 | 0.00 | 0.00 | 0.00 | 0.00 | 2.47 | ATP6S1 | AB031290 |
| 112716_at | 0.00 | 0.00 | 0.00 | 0.00 | 0.00 | 2.06 | UNK_AW122682 | AW122682 |
| 94189_at | 0.00 | 0.00 | 0.00 | 0.00 | 0.00 | 2.17 | BAZF | AB011665 |
| 100336_s_at | 0.00 | 0.00 | 0.00 | 0.00 | 7.91 | 53.48 | BGLAP1 | L24431 |
| *93605_r_at* | *−1.20* | *0.00* | *0.00* | *0.00* | *0.00* | *4.12* | *BL2* | *AF061260* |
| 92982_at | 0.00 | 0.00 | 0.00 | 0.00 | 0.00 | 2.65 | bone morphogenetic protein 8a; Bmp8a | M97017 |
| 96255_at | 0.00 | 0.00 | 0.00 | 0.00 | 0.00 | 2.02 | BNIP3L | AF067395 |
| 92668_at | 0.00 | 2.99 | 1.99 | 1.78 | 0.00 | 3.12 | agammaglobulinemia tyrosine kinase; Btk | L10627 |
| 106304_at | 0.00 | 0.00 | 0.00 | 0.00 | 0.00 | 2.83 | C1S | AW215831 |
| 112110_at | 0.00 | 0.00 | 0.00 | 0.00 | 0.00 | 2.07 | CAMKK | AI843712 |
| 92642_at | 0.00 | 0.00 | −2.16 | 0.00 | −2.62 | 5.27 | CAR2 | M25944 |
| 102905_at | 0.00 | 1.80 | 0.00 | 2.52 | 0.00 | 1.94 | CASP11 | Y13089 |
| *98437_at* | *0.00* | *0.00* | *0.00* | *0.00* | *0.00* | *7.81* | *CASP3* | *U63720* |
| 98498_at | 0.00 | 0.00 | 0.00 | 1.75 | 0.00 | 2.28 | CASP7 | D86353 |
| 97832_at | 0.00 | 0.00 | 0.00 | 0.00 | 0.00 | 2.22 | CD97 | AA754887 |
| 98447_at | 0.00 | 1.36 | 1.37 | 1.74 | 0.00 | 2.25 | binding protein (C/EBP), alpha; Cebpa | M62362 |
| 114787_at | 0.00 | 0.00 | 0.00 | 0.00 | 0.00 | 2.46 | UNK_AW107224 | AW107224 |
| 102027_s_at | 0.00 | 0.00 | 0.00 | 0.00 | 0.00 | 2.16 | CHETK | AA204010 |
| 92694_at | 2.21 | 2.77 | 2.17 | 0.00 | 0.00 | 3.52 | Chi3l3 | M94584 |
| 99070_at | 0.00 | 0.00 | 1.95 | 2.74 | 0.00 | 2.05 | conserved helix-loop-helix ubiquitous kinase; Chuk | U12473 |
| 137242_f_at | 0.00 | 0.00 | 0.00 | 0.00 | 0.00 | 27.84 | CKB | AI836689 |
| 93595_at | 0.00 | 0.00 | 0.00 | 0.00 | 0.00 | 2.11 | CLN2 | AF111172 |
| 99413_at | 2.76 | 5.61 | 2.96 | 3.04 | 2.59 | 16.03 | CMKBR1 | U29678 |
| 134879_at | 0.00 | 0.00 | 0.00 | 0.00 | 0.00 | 2.62 | COL11A2 | AI324726 |
| 98782_at | 0.00 | 0.00 | 0.00 | 0.00 | 0.00 | 2.10 | complexin 2; Cplx2 | D38613 |
| 93198_at | 0.00 | 0.00 | 0.00 | 0.00 | 0.00 | 3.45 | colony stimulating factor 3 receptor (granulocyte); Csf3r | M58288 |
| 95608_at | 0.00 | 1.92 | 2.08 | 3.00 | 0.00 | 2.77 | CTSB | AI851255 |
| 104696_at | 0.00 | 0.00 | 0.00 | 0.00 | 0.00 | 2.99 | CTSE | AJ009840 |
| 97336_at | 0.00 | −2.65 | 0.00 | 0.00 | 0.00 | 2.12 | UNK_AJ131851 | AJ131851 |
| 100069_at | 0.00 | 0.00 | 0.00 | 0.00 | 0.00 | 3.27 | cytochrome P450, 2f2; Cyp2f2 | M77497 |
| 97526_at | 0.00 | 0.00 | 0.00 | 0.00 | 0.00 | 2.67 | LOC55946 | AW123294 |
| 101960_at | 0.00 | 0.00 | 0.00 | 2.59 | 0.00 | 1.98 | D10WSU52E | AI842208 |
| 114696_at | 0.00 | 0.00 | 0.00 | 0.00 | 0.00 | 2.72 | UNK_AW046335 | AW046335 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 112306_at | 0.00 | 0.00 | 0.00 | 0.00 | 0.00 | 2.37 | UNK_AW121212 | AW121212 |
| 92610_at | 0.00 | 0.00 | 0.00 | 2.19 | 0.00 | 2.64 | DNA segment, Chr 17, human D6S45; D17H6S45 | M21332 |
| 104391_s_at | 0.00 | 0.00 | 0.00 | 0.00 | 0.00 | 2.95 | D17WSU51E | AI850563 |
| *115816_at* | *0.00* | *0.00* | *0.00* | *0.00* | *0.00* | *5.54* | *UNK_AA869817* | *AA869817* |
| 103877_at | 0.00 | 0.00 | 0.00 | 0.00 | 0.00 | 2.28 | D2WSU58E | AW060485 |
| 99143_at | 0.00 | 0.00 | 0.00 | 0.00 | 0.00 | 2.35 | TTGN1 | AA614914 |
| 113046_at | 0.00 | 0.00 | 0.00 | 0.00 | 0.00 | 2.45 | TTGN1 | AI842091 |
| 96561_at | 0.00 | 0.00 | 0.00 | 0.00 | 0.00 | 2.30 | UNK_AI157475 | AI157475 |
| *108293_at* | *0.00* | *0.00* | *0.00* | *0.00* | *0.00* | *4.29* | *UNK_AI592230* | *AI592230* |
| 97863_at | 0.00 | 0.00 | 0.00 | 0.00 | 0.00 | 2.09 | UNK_AW125274 | AW125274 |
| 110406_at | 0.00 | 0.00 | 0.00 | 0.00 | 0.00 | 2.63 | UNK_AA958839 | AA958839 |
| 99506_at | 0.00 | 0.00 | 0.00 | 0.00 | 0.00 | 2.25 | DAPK2 | AB018002 |
| 99025_at | 0.00 | 0.00 | 0.00 | 0.00 | 0.00 | 3.32 | Ala-Asp/His) box polypeptide 19; Ddx19 | L25125 |
| 104371_at | 0.00 | 0.00 | 0.00 | 0.00 | 0.00 | 2.06 | DGAT | AF078752 |
| 99881_at | 0.00 | 0.00 | 0.00 | 0.00 | 0.00 | 3.49 | DKK1 | AF030433 |
| 99328_at | 0.00 | 0.00 | 0.00 | 0.00 | 0.00 | 3.37 | distal-less homeobox 3; Dlx3 | U79738 |
| 99903_at | 0.00 | 0.00 | 0.00 | 0.00 | 9.98 | 51.29 | DMP1 | AJ242625 |
| 114809_at | 0.00 | 0.00 | 0.00 | 0.00 | 0.00 | 3.58 | DOKL-PENDING | AW046136 |
| 94052_at | 0.00 | 0.00 | 0.00 | 0.00 | 0.00 | 2.34 | DPM2 | AB013360 |
| 92535_at | 0.00 | 0.00 | 0.00 | 0.00 | 0.00 | 3.27 | Ebf | L12147 |
| 104492_at | 0.00 | 0.00 | 0.00 | 0.00 | 0.00 | 2.18 | early B-cell factor 3; Ebf3 | U92702 |
| 102996_at | 0.00 | 0.00 | 0.00 | 0.00 | 0.00 | 2.11 | lysine-rich leukemia gene; Ell | U80227 |
| 92207_at | 0.00 | 0.00 | 0.00 | 0.00 | 0.00 | 3.03 | elastin; Eln | U08210 |
| 107900_at | 0.00 | 0.00 | 0.00 | 2.56 | 0.00 | 2.12 | UNK_AW123554 | AW123554 |
| 102771_at | 0.00 | 0.00 | 0.00 | 0.00 | 0.00 | 2.62 | ESET | AF091628 |
| 107996_at | 0.00 | 0.00 | 0.00 | 0.00 | 0.00 | 2.27 | ESTM573010 | AW049050 |
| *92267_at* | *0.00* | *0.00* | *0.00* | *0.00* | *0.00* | *5.46* | *F2R* | *L03529* |
| 94307_at | 0.00 | 0.00 | 0.00 | 0.00 | 0.00 | 3.38 | fibulin 1; Fbln1 | X70854 |
| 100928_at | −4.16 | 0.00 | 0.00 | 2.21 | −0.01 | 19.58 | fibulin 2; Fbln2 | X75285 |
| 102366_at | 0.00 | 0.00 | −5.06 | −3.75 | 0.00 | 2.31 | UNK_AA718169 | AA718169 |
| 95295_s_at | 0.00 | 0.00 | 0.00 | 0.00 | 0.00 | 2.74 | FMS-like tyrosine kinase 3; Flt3 | X59398 |
| 101422_at | 0.00 | 0.00 | 0.00 | 0.00 | 0.00 | 2.07 | FNBP4 | AW121377 |
| 92959_at | 0.00 | 0.00 | 0.00 | 0.00 | 0.00 | 2.21 | B-cell src-homology tyrosine kinase; Frk | Z48757 |
| 102016_at | 0.00 | −1.46 | 0.00 | 0.00 | 0.00 | 3.68 | fat specific gene 27; Fsp27 | M61737 |
| 94966_at | 0.00 | 1.70 | 0.00 | 1.97 | 0.00 | 2.99 | phosphate dehydrogenase X-linked; G6pdx | Z11911 |
| 100407_at | 0.00 | 0.00 | 0.00 | 0.00 | 0.00 | 2.99 | galanin; Gal | L38580 |
| *96998_at* | *0.00* | *0.00* | *0.00* | *0.00* | *0.00* | *7.44* | *UNK_AJ133523* | *AJ133523* |
| 94813_at | 0.00 | 0.00 | 0.00 | 0.00 | 0.00 | 2.85 | growth arrest specific 1; Gas1 | X65128 |
| 104597_at | 0.00 | 0.00 | 3.30 | 2.90 | 0.00 | 6.62 | GBP2 | AJ007970 |
| 104134_at | 0.00 | 0.00 | 0.00 | 0.00 | 0.00 | 2.51 | GDAP2 | Y17851 |
| 92534_at | 0.00 | 0.00 | 0.00 | 0.00 | 0.00 | 2.86 | (gene overexpressed in skeletal muscle); | U10551 |
| 102968_at | 0.00 | 0.00 | 0.00 | 0.00 | 0.00 | 3.69 | GGTLA1 | AF077765 |
| 97384_at | 0.00 | 2.67 | 3.42 | 0.00 | 0.00 | 2.09 | UNK_AA791012 | AA791012 |
| 100514_at | 0.00 | 0.00 | 0.00 | 0.00 | 0.00 | 2.43 | guanine nucleotide binding protein, alpha 13; Gna13 | M63660 |
| 93080_at | 0.00 | 0.00 | 0.00 | 0.00 | 0.00 | 3.13 | GNG3LG | AF069954 |
| 97385_at | 0.00 | 0.00 | 0.00 | 0.00 | 0.00 | 2.76 | GNK-PENDING | AJ242909 |
| 100565_at | 0.00 | 1.93 | 2.25 | 2.33 | 0.00 | 2.45 | GNPI | AW123396 |
| 96553_at | 0.00 | 2.13 | 3.60 | 0.00 | 0.00 | 1.56 | G-protein coupled receptor 25; Gpcr25 | U39827 |
| 100594_at | 0.00 | 0.00 | 0.00 | 2.29 | 0.00 | 2.00 | glycosylphosphatidyl inositol 1 homolog (human); Gpi1h | AB008895 |
| 104256_at | 1.79 | 1.75 | 0.00 | 0.00 | 0.00 | 2.53 | UNK_AI120844 | AI120844 |
| 102995_s_at | 0.00 | 0.00 | 0.00 | 0.00 | 0.00 | 2.21 | GZMA | M13226 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 93092_at | 0.00 | 1.49 | 0.00 | 0.00 | 0.00 | 4.62 | histocompatibility 2, class II, locus Dma, histocompatibility 2, class II, locus Mb1, histocompatibility 2, class II, locus Mb2, proteosome (prosome, macropain) subunit, beta type 9 (large multifunctional protease 2); H2-DMa, H2-DMb1, H2- | U35323 |
| 93120_f_at | 0.00 | 0.00 | 0.00 | 2.02 | 0.00 | 2.69 | H2-K | V00746 |
| 101876_s_at | 0.00 | 0.00 | 1.96 | 2.42 | 0.00 | 2.64 | UNK_M35247 | M35247 |
| *98284_f_at* | *0.00* | *0.00* | *0.00* | *0.00* | *0.00* | *5.93* | *H2-T18* | *X03052* |
| 101523_at | 0.00 | 0.00 | 0.00 | 2.34 | 0.00 | 1.86 | H3F3A | AW046194 |
| 111423_at | 0.00 | 0.00 | 0.00 | 0.00 | 0.00 | 3.30 | UNK_AI852812 | AI852812 |
| 100966_at | 0.00 | 0.00 | 0.00 | 0.00 | 0.00 | 3.32 | Hcf2 | U07425 |
| 104194_at | 0.00 | 0.00 | 0.00 | 0.00 | 0.00 | 2.51 | HEPH | AF082567 |
| *104502_f_at* | *0.00* | *0.00* | *0.00* | *0.00* | *0.00* | *4.35* | *HES6* | *AI414025* |
| 107620_at | 0.00 | 0.00 | 0.00 | 0.00 | 0.00 | 2.16 | HIPK1 | AW125573 |
| 98038_at | 0.00 | 0.00 | 0.00 | 2.31 | 0.00 | 3.06 | HMG4 | AF022465 |
| 93378_at | 0.00 | 0.00 | 0.00 | 0.00 | 0.00 | 3.93 | Hoxc8 | X07439 |
| 103835_f_at | 0.00 | 0.00 | 0.00 | 0.00 | 0.00 | 3.00 | HPCAL1 | AF085192 |
| *98962_at* | *0.00* | *0.00* | *0.00* | *0.00* | *0.00* | *4.30* | *hepatic lipase; Hpl* | *X58426* |
| 96144_at | 0.00 | 0.00 | 0.00 | 0.00 | 0.00 | 2.40 | IDB4 | AJ001972 |
| 104500_at | 0.00 | 0.00 | 0.00 | 0.00 | 0.00 | 2.01 | Idua | L34111 |
| 92773_at | 0.00 | 0.00 | 0.00 | 1.95 | 0.00 | 2.30 | IER5 | AF079528 |
| 97409_at | 0.00 | 0.00 | 2.03 | 3.55 | 0.00 | 2.64 | interferon inducible protein 1; Ifi1 | U19119 |
| 93321_at | 0.00 | 0.00 | 0.00 | 2.88 | 0.00 | 2.59 | interferon activated gene 203; Ifi203 | AF022371 |
| 103963_f_at | 0.00 | 0.00 | 6.13 | 0.00 | 0.00 | 12.91 | UNK_AA914345 | AA914345 |
| 137251_f_at | 0.00 | 0.00 | 0.00 | 0.00 | 0.00 | 3.68 | UNK_AI449282 | AI449282 |
| 94398_s_at | 0.00 | 0.00 | 0.00 | 0.00 | 0.00 | 2.79 | INPP5B | AF040094 |
| 99034_at | 0.00 | 0.00 | 0.00 | 0.00 | 0.00 | 2.23 | IRX3 | Y15001 |
| 98828_at | 1.64 | 3.70 | 0.00 | 1.93 | 0.00 | 1.84 | integrin alpha M (Cd11b); Itgam | X07640 |
| 99904_at | 0.00 | 0.00 | 0.00 | 0.00 | 0.00 | 2.18 | ITGB3 | AF026509 |
| *100906_at* | *0.00* | *0.00* | *0.00* | *0.00* | *0.00* | *4.05* | *ITGB7* | *M68903* |
| 99577_at | 0.00 | 0.00 | 0.00 | 0.00 | 0.00 | 2.21 | KITL | M57647 |
| 97761_f_at | 0.00 | 0.00 | 0.00 | 0.00 | 0.00 | 2.29 | killer cell lectin-like receptor, subfamily A, member 7; Klra7 | U10094 |
| 97762_f_at | 0.00 | 0.00 | 0.00 | 0.00 | 0.00 | 2.56 | KLRA7 | U12890 |
| 99993_at | 0.00 | 0.00 | 0.00 | 0.00 | 0.00 | 2.25 | leucine arylaminopeptidase 1, intestinal; Lap1 | U77083 |
| 104658_at | 0.00 | 0.00 | 0.00 | 0.00 | 1.22 | 12.86 | LIFR | D17444 |
| 96810_at | 0.00 | 0.00 | 0.00 | 0.00 | 0.00 | 2.15 | LMO2 | AI154017 |
| 97980_at | 0.00 | 0.00 | 0.00 | 0.00 | 0.00 | 2.54 | LTBR | L38423 |
| 92401_at | 0.00 | 0.00 | 0.00 | 0.00 | 0.00 | 2.01 | leukotriene C4 synthase; Ltc4s | U27195 |
| 96089_at | 0.00 | 0.00 | 0.00 | 0.00 | 0.00 | 2.20 | UNK_AI255972 | AI255972 |
| 93454_at | 0.00 | 1.58 | 0.00 | 2.37 | 0.00 | 2.17 | LY68 | AF081789 |
| 92216_at | 4.83 | 3.87 | 2.49 | 0.00 | 0.00 | 1.72 | MADH7 | AF015260 |
| 103020_s_at | 0.00 | 0.00 | 0.00 | 0.00 | 0.00 | 2.15 | MAP3K1 | AI317205 |
| 101834_at | 0.00 | 0.00 | 0.00 | 2.51 | 0.00 | 3.21 | protein kinase 3; Mapk3 | Z14249 |
| 96003_at | 0.00 | 0.00 | 0.00 | 0.00 | 0.00 | 2.67 | MATA1L1 | AW048332 |
| 96310_at | 0.00 | 0.00 | 0.00 | 0.00 | 0.00 | 2.98 | MBP | L07508 |
| 101070_at | 0.00 | 0.00 | 0.00 | 0.00 | 0.00 | 2.92 | MKRN1 | AW125438 |
| 100484_at | 0.00 | 0.00 | 0.00 | 1.38 | 21.43 | 135.83 | metalloproteinase 13; Mmp13 | X66473 |
| 100414_s_at | 0.00 | 0.00 | −1.84 | 0.00 | 0.00 | 2.69 | MPO | X15313 |
| *97719_at* | *0.00* | *0.00* | *0.00* | *0.00* | *0.00* | *9.46* | *ROW* | *X74736* |
| 95340_at | 0.00 | 0.00 | 0.00 | 0.00 | 0.00 | 3.06 | Mt3 | M93310 |
| 102096_f_at | 0.00 | 0.00 | −2.42 | 0.00 | 0.00 | 3.13 | MUP1 | AI255271 |
| 101909_f_at | 0.00 | 0.00 | −4.14 | 0.00 | 0.00 | 3.70 | MUP3 | M16357 |
| 101910_f_at | 0.00 | 0.00 | 0.00 | 0.00 | 0.00 | 3.19 | major urinary protein 3; Mup3 | M16359 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 101682_f_at | 0.00 | 0.00 | 0.00 | 0.00 | 0.00 | 3.68 | major urinary protein 4; Mup4 | M16358 |
| 94122_at | 7.47 | 3.44 | 2.58 | 0.00 | −3.81 | −1.94 | MYOC | AF041335 |
| 103662_at | 2.05 | 2.83 | 5.66 | 5.71 | 0.00 | 5.18 | neutrophil cytosolic factor 4; Ncf4 | U59488 |
| 97843_at | 0.00 | 0.00 | 0.00 | 0.00 | 0.00 | 2.39 | UNK__AI834866 | AI834866 |
| 101554_at | 0.00 | 0.00 | 0.00 | 9.53 | 0.00 | 3.44 | NFKBIA | U57524 |
| 104149_at | 0.00 | 0.00 | 0.00 | 1.87 | 0.00 | 2.95 | NFKBIA | AI642048 |
| 100120_at | 0.00 | 0.00 | 0.00 | 0.00 | 0.00 | 2.41 | NID1 | L17324 |
| 94982_f_at | 0.00 | 0.00 | 0.00 | 0.00 | 0.00 | 2.13 | UNK__AI852470 | AI852470 |
| 97497_at | 0.00 | 0.00 | 0.00 | 0.00 | 0.00 | 3.34 | 1, (Drosophila); Notch 1 | Z11886 |
| 95016_at | 0.00 | 1.82 | 1.85 | 2.13 | 0.00 | 2.03 | neuropilin; Nrp | D50086 |
| 100436_at | 0.00 | 0.00 | 0.00 | 0.00 | 0.00 | 2.35 | Orm1 | M27008 |
| 103029_at | 0.00 | 0.00 | 0.00 | 0.00 | 0.00 | 2.74 | programmed cell death 4; Pdcd4 | D86344 |
| 95040_at | 0.00 | 0.00 | 0.00 | 0.00 | 0.00 | 2.02 | UNK__AI840810 | AI840810 |
| 95079_at | 0.00 | 0.00 | 0.00 | 0.00 | 0.00 | 3.53 | PDGFRA | M57683 |
| 93039_at | 0.00 | 0.00 | 0.00 | 0.00 | 0.00 | 2.50 | HLS2 | AF009513 |
| 96502_at | 0.00 | 0.00 | 0.00 | 0.00 | 0.00 | 2.85 | regulating neutral endopeptidases on the X chromosome; Phex | U75646 |
| 130145_i_at | 0.00 | 0.00 | 0.00 | 0.00 | 1.36 | 25.36 | PHEX | AI481510 |
| 130146_f_at | 0.00 | 0.00 | 0.00 | 0.00 | 1.68 | 14.49 | PHEX | AI481510 |
| 103573_at | 0.00 | 0.00 | 0.00 | 0.00 | 0.00 | 3.43 | 4-phosphate 5-kinase, type 1 alpha; Pip5k1a | D86176 |
| *101865_at* | *0.00* | *0.00* | *0.00* | *0.00* | *0.00* | *4.51* | *PIP5K2A* | *AB009615* |
| *99510_at* | *0.00* | *0.00* | *0.00* | *0.00* | *0.00* | *4.15* | *PKCB* | *X59274* |
| 99916_at | 0.00 | 0.00 | 0.00 | 0.00 | 0.00 | 3.44 | protein kinase C, eta; Pkch | D90242 |
| 100707_at | 0.00 | 0.00 | 0.00 | 0.00 | 0.00 | 2.05 | UNK__AF030131 | AF030131 |
| 97926_s_at | 0.00 | 0.00 | 2.03 | 0.00 | 0.00 | 2.82 | PPARG | U10374 |
| 113154_at | 0.43 | 0.00 | −2.71 | −1.11 | −2.08 | 2.44 | UNK__AI854500 | AI854500 |
| 92904_at | 0.00 | 0.00 | 0.00 | 0.00 | 0.00 | 3.09 | containing 1, with ZNF domain; Prdm1 | U08185 |
| 110362_at | 0.00 | 0.00 | 0.00 | 0.00 | 0.00 | 2.90 | UNK__AW046410 | AW046410 |
| 94085_at | 0.00 | 0.00 | 0.00 | 0.00 | 0.00 | 2.37 | PRG | M34603 |
| 96957_at | 0.00 | 0.00 | 0.00 | 0.00 | 0.00 | 3.05 | PENDING | AB006463 |
| 94454_at | 0.00 | 0.00 | 0.00 | 2.36 | 0.00 | 1.70 | PRTB | AF085348 |
| 101486_at | 0.00 | 0.00 | 0.00 | 0.00 | 0.00 | 2.88 | PSMB10 | Y10875 |
| 93085_at | 0.00 | 3.16 | 6.20 | 5.37 | 0.00 | 6.03 | PSMB9 | D44456 |
| 112345_at | 0.00 | 0.00 | 0.00 | 0.00 | 0.00 | 2.81 | UNK__AI841610 | AI841610 |
| *92356_at* | *0.00* | *0.00* | *0.00* | *0.00* | *0.00* | *5.19* | *phosphatase, non-receptor type 8; Ptpn8* | *M90388* |
| 101932_at | 0.00 | 0.00 | 0.00 | 2.02 | 0.00 | 3.46 | PTPRE | D83484 |
| 92309_i_at | 0.00 | 0.00 | 0.00 | 0.00 | 0.00 | 2.50 | phosphatase, receptor-type, M; Ptprm | X58287 |
| 92854_at | 0.00 | 1.77 | 0.00 | 2.37 | 0.00 | 1.82 | RAS oncogene family; Rab11a | D50500 |
| 100459_at | 0.00 | 0.00 | 0.00 | 0.00 | 0.00 | 2.57 | RAD50 homolog (*S. cerevisiae*); Rad50 | U66887 |
| 99032_at | 0.00 | 0.00 | 0.00 | 0.00 | 0.00 | 2.73 | dexamethasone-induced 1; Rasd1 | AF009246 |
| 104618_at | 0.00 | 0.00 | 0.00 | 0.00 | 0.00 | 2.22 | RBBP9 | AI845819 |
| 97848_at | 0.00 | 0.00 | 0.00 | 0.00 | 0.00 | 2.19 | RBMX | AJ237846 |
| 100530_at | 0.00 | 0.00 | 0.00 | 0.00 | 0.00 | 2.57 | nucleotide dissociation stimulator; Rgds | L07924 |
| 97844_at | 0.00 | 0.00 | 2.15 | 2.25 | 0.00 | 3.16 | protein signaling 2; Rgs2 | U67187 |
| 102762_r_at | 0.00 | 0.00 | 0.00 | 0.00 | 0.00 | 2.08 | RHAG | AF057527 |
| 100980_at | 0.00 | 0.00 | 0.00 | 0.00 | 0.00 | 2.13 | Rho-associated coiled-coil forming kinase 1; Rock1 | U58512 |
| 93839_at | 0.00 | 0.00 | 0.00 | 0.00 | 0.00 | 2.28 | RTN3 | AI854888 |
| 102336_at | 0.00 | 0.00 | 0.00 | 0.00 | 0.00 | 2.06 | RW1 | AF060565 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 103448_at | 0.00 | 2.51 | -4.75 | -1.37 | -6.47 | 3.81 | binding protein A8 (calgranulin A); S100a8 | M83218 |
| 103887_at | 4.41 | 0.00 | -8.99 | -5.52 | -6.50 | 5.43 | binding protein A9 (calgranulin B); S100a9 | M83219 |
| 103715_at | 0.00 | 0.00 | 0.00 | 0.00 | 0.00 | 3.21 | scinderin; Scin | U04354 |
| 101436_at | 0.00 | 0.00 | 3.77 | 3.82 | 0.00 | 6.09 | cytokine B subfamily (Cys-X-Cys), member 9; Scyb9 | M34815 |
| *100112_at* | *0.00* | *0.00* | *0.00* | *0.00* | *0.00* | *5.61* | *derived factor 1; Sdf1* | *L12030* |
| 103488_at | 0.00 | 1.89 | 2.03 | 2.49 | 0.00 | 6.53 | selectin) ligand; Selpl | X91144 |
| *92469_at* | *0.00* | *0.00* | *0.00* | *0.00* | *0.00* | *6.76* | *SFRP4* | *AF117709* |
| *96126_at* | *0.00* | *0.00* | *0.00* | *0.00* | *0.00* | *4.16* | *SGPL1* | *AF036894* |
| 96682_at | 0.00 | 0.00 | 0.00 | 0.00 | 0.00 | 3.69 | SIAT7D | Y15780 |
| 102318_at | 0.00 | 0.00 | 0.00 | 0.00 | 0.00 | 3.68 | sialyltransferase 8 (alpha-2, 8-sialytransferase) D; Siat8d | X86000 |
| 110381_at | 0.00 | 0.00 | 0.00 | 1.54 | 0.00 | 2.32 | SLAP | AI120030 |
| 92582_at | 0.00 | 0.00 | 0.00 | 0.00 | 0.00 | 2.81 | solute carrier family 1, member 7; Slc1a7 | L42115 |
| 103347_at | 0.00 | 0.00 | 0.00 | 0.00 | 0.00 | 2.45 | UNK_AI852548 | AI852548 |
| 109069_at | 0.00 | -2.82 | -2.00 | 0.00 | 0.00 | 3.28 | SLC39A1 | AI255982 |
| 98299_s_at | 2.97 | 0.00 | 0.00 | 2.13 | 0.00 | 1.52 | SLFN3 | AF099974 |
| 115731_at | 0.00 | 0.00 | 0.00 | 0.00 | 0.00 | 2.37 | UNK_AA896535 | AA896535 |
| 100422_i_at | 0.00 | 0.00 | 0.00 | 0.00 | 0.00 | 2.96 | STAT5A | AJ237939 |
| 93680_at | 0.00 | 0.00 | 0.00 | 0.00 | 0.00 | 2.99 | STK10 | D89728 |
| 100425_at | 0.00 | 1.48 | 0.00 | 0.00 | 0.00 | 3.69 | SYK | U25685 |
| 95066_at | 0.00 | 0.00 | 0.00 | 0.00 | 0.00 | 2.20 | Taldo1 | U67611 |
| 103328_at | 0.00 | 0.00 | 0.00 | 2.54 | 0.00 | 2.23 | TANK | U59864 |
| 98087_at | 0.00 | 0.00 | 0.00 | 1.88 | 0.00 | 2.80 | UNK_AW048562 | AW048562 |
| 92387_at | 0.00 | 0.00 | 0.00 | 0.00 | 0.00 | 2.03 | synthase 1, platelet; Tbxas1 | L18868 |
| *103539_at* | *0.00* | *0.00* | *0.00* | *0.00* | *0.00* | *4.07* | *cytoplasmic tyrosine kinase, Dscr28C related (Drosophila); Tec* | *X55663* |
| 92427_at | 0.00 | 0.00 | 0.00 | 0.00 | 0.00 | 2.71 | transforming growth factor, beta receptor I; Tgfbr1 | D25540 |
| *102637_at* | *0.00* | *0.00* | *0.00* | *0.00* | *0.00* | *6.10* | *TGFBR3* | *AF039601* |
| 113920_at | -1.60 | 0.00 | 0.00 | 0.00 | 0.00 | 2.12 | UNK_AI021069 | AI021069 |
| 102906_at | 0.00 | 0.00 | 2.95 | 3.25 | 0.00 | 9.29 | T-cell specific GTPase; Tgtp | L38444 |
| 99602_at | 0.00 | 1.29 | 0.00 | 2.02 | 0.00 | 1.67 | TIEG | AF064088 |
| 101964_at | 0.00 | 0.00 | -2.16 | 0.00 | 0.00 | 3.47 | transketolase; Tkt | U05809 |
| 97893_at | 0.00 | 0.00 | 0.00 | 0.00 | 0.00 | 2.01 | TLP | AB017697 |
| 111478_at | 0.00 | 0.00 | 0.00 | 1.96 | 0.00 | 2.34 | UNK_AI047601 | AI047601 |
| 96700_r_at | 0.00 | 0.00 | 0.00 | 0.00 | 0.00 | 2.46 | UBL1A2-PENDING | AW060594 |
| 99580_s_at | 0.00 | 1.50 | 0.00 | 1.61 | 0.00 | 2.44 | UGT1A1 | U16818 |
| 92760_at | 0.00 | 5.57 | 3.44 | 0.00 | 0.00 | 4.76 | WASP | U42471 |
| 94704_at | 2.27 | 0.00 | 0.00 | 0.00 | 0.00 | 9.98 | WISP2 | AF100778 |
| 97950_at | 0.00 | 0.00 | 0.00 | 2.32 | 0.00 | 2.77 | xanthine dehydrogenase; Xdh | X75129 |
| 98053_at | 0.00 | 1.87 | 0.00 | 2.77 | 0.00 | 2.11 | YWHAB | AF058797 |
| 97060_at | 0.00 | 0.00 | 0.00 | 0.00 | 0.00 | 2.95 | YWHAQ | AW215489 |
| 93013_at | 3.57 | 3.97 | 3.52 | 5.65 | 7.05 | 6.32 | IDB2 | AF077861 |
| 96331_at | 2.04 | 2.99 | 2.67 | 3.12 | 2.54 | 2.59 | UNK_AI842754 | AI842754 |
| 99051_at | 2.16 | 3.59 | 4.32 | 7.61 | 3.35 | 4.76 | S100A4 | M36579 |
| 102104_f_at | 2.36 | 3.77 | 6.03 | 8.42 | 3.97 | 5.52 | UNK_AI504305 | AI504305 |
| 109403_at | 2.15 | 3.73 | 5.34 | 10.02 | 4.37 | 19.28 | UNK_AW121933 | AW121933 |
| 114810_at | 2.97 | 9.08 | 11.55 | 9.62 | 8.54 | 4.12 | UNK_AI447446 | AI447446 |
| 130509_at | 2.64 | 4.77 | 7.87 | 6.94 | 2.24 | 2.18 | UNK_AI851996 | AI851996 |
| 92820_at | 0.00 | 3.05 | 4.26 | 5.46 | 10.73 | 9.24 | UNK_AI842259 | AI842259 |
| 92850_at | 0.00 | 2.42 | 2.43 | 6.71 | 9.75 | 6.66 | UNK_AI836446 | AI836446 |
| 93548_at | 0.00 | 2.61 | 2.07 | 3.67 | 4.32 | 2.86 | UNK_AW122942 | AW122942 |
| 93829_at | 0.00 | 2.05 | 3.42 | 3.58 | 3.28 | 5.01 | UNK_AW107884 | AW107884 |
| 93842_at | 0.00 | 2.97 | 3.69 | 7.34 | 12.44 | 11.01 | UNK_AI196645 | AI196645 |
| 94792_at | 3.10 | 5.07 | 4.52 | 4.71 | 2.76 | 0.00 | UNK_AI447305 | AI447305 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 95102_at | 0.00 | 2.19 | 2.59 | 3.61 | 3.09 | 3.88 | UNK_AW123754 | AW123754 |
| 95152_g_at | 0.00 | 3.22 | 2.73 | 3.00 | 4.27 | 4.52 | UNK_AW061307 | AW061307 |
| 95417_at | 0.00 | 2.59 | 3.27 | 3.18 | 3.80 | 3.54 | UNK_AI117848 | AI117848 |
| 95466_at | 0.00 | 5.84 | 6.73 | 4.76 | 5.82 | 4.94 | UNK_AI837006 | AI837006 |
| 95542_at | 0.00 | 2.62 | 2.69 | 4.54 | 5.75 | 4.80 | UNK_AI835858 | AI835858 |
| 95543_at | 0.00 | 3.08 | 3.87 | 4.77 | 4.36 | 4.23 | UNK_AI843046 | AI843046 |
| 95647_f_at | 0.00 | 2.65 | 2.69 | 3.32 | 3.84 | 4.28 | UNK_AI465845 | AI465845 |
| 95654_at | 0.00 | 3.23 | 3.45 | 5.80 | 4.72 | 5.58 | UNK_AF109905 | AF109905 |
| 95673_s_at | 0.00 | 2.31 | 2.83 | 5.79 | 6.60 | 5.31 | UNK_AW124113 | AW124113 |
| 95749_at | 0.00 | 2.30 | 2.14 | 5.13 | 4.36 | 3.10 | UNK_AW122364 | AW122364 |
| 95940_f_at | 1.92 | 3.66 | 5.69 | 6.58 | 4.38 | 7.39 | UNK_AW047237 | AW047237 |
| 96135_at | 0.00 | 2.38 | 3.85 | 7.06 | 6.16 | 10.09 | UNK_AA833425 | AA833425 |
| 96168_at | 0.00 | 3.47 | 4.05 | 3.80 | 5.45 | 3.82 | UNK_AI591702 | AI591702 |
| 96319_at | 0.00 | 5.82 | 5.05 | 13.49 | 5.11 | 6.19 | UNK_AW061324 | AW061324 |
| 96333_g_at | 0.00 | 2.97 | 2.46 | 3.17 | 2.53 | 2.19 | UNK_AW259199 | AW259199 |
| 96784_at | 0.00 | 4.17 | 5.63 | 6.89 | 5.90 | 3.14 | UNK_AW123269 | AW123269 |
| 96811_at | 1.20 | 4.20 | 5.77 | 6.75 | 9.85 | 12.17 | UNK_AW049806 | AW049806 |
| 96834_at | 0.00 | 2.06 | 2.03 | 3.08 | 3.82 | 4.91 | UNK_AI843586 | AI843586 |
| 96885_at | 0.00 | 5.55 | 6.66 | 17.42 | 21.15 | 8.95 | UNK_AW122271 | AW122271 |
| 96886_at | 0.00 | 3.53 | 3.88 | 3.89 | 3.05 | 3.28 | UNK_AW060556 | AW060556 |
| 97444_at | 0.00 | 4.08 | 4.33 | 11.02 | 8.47 | 20.65 | UNK_AI844520 | AI844520 |
| 97527_at | 0.00 | 4.63 | 5.52 | 9.52 | 8.69 | 5.59 | UNK_AA681998 | AA681998 |
| 97838_at | 0.00 | 2.19 | 3.16 | 3.46 | 5.45 | 3.88 | UNK_AA684508 | AA684508 |
| 98076_at | 0.00 | 2.21 | 3.02 | 6.55 | 5.41 | 5.24 | UNK_AI835644 | AI835644 |
| 98915_at | 0.00 | 5.42 | 4.17 | 5.26 | 4.08 | 4.94 | UNK_AI849082 | AI849082 |
| 99849_at | 0.00 | 2.58 | 2.39 | 3.64 | 2.12 | 4.11 | UNK_C85523 | C85523 |
| 100116_at | 0.00 | 3.92 | 4.43 | 5.52 | 8.26 | 3.36 | UNK_AI122538 | AI122538 |
| 100511_at | 0.00 | 3.60 | 4.84 | 3.90 | 2.10 | 3.63 | UNK_AI154249 | AI154249 |
| 101061_at | 0.00 | 2.33 | 2.52 | 5.11 | 5.20 | 4.85 | UNK_AI845293 | AI845293 |
| 101464_at | 1.63 | 7.86 | 6.79 | 16.41 | 14.96 | 19.13 | metalloproteinase; Timp | V00755 |
| 101912_at | 0.00 | 4.12 | 4.68 | 7.62 | 13.31 | 6.66 | UNK_AI019679 | AI019679 |
| 101956_at | 0.00 | 4.37 | 3.27 | 7.15 | 8.46 | 8.94 | UNK_AI834849 | AI834849 |
| 102056_f_at | 0.00 | 2.01 | 2.37 | 3.49 | 4.61 | 4.59 | UNK_AA839379 | AA839379 |
| 102108_f_at | 0.00 | 2.23 | 2.51 | 3.59 | 3.19 | 3.25 | UNK_AI505453 | AI505453 |
| 102907_at | 0.00 | 2.60 | 6.00 | 11.32 | 13.64 | 4.29 | UNK_AW125043 | AW125043 |
| 103017_at | 0.00 | 2.12 | 3.20 | 5.24 | 4.49 | 20.95 | D13ABB1E | AI060729 |
| 103723_at | 0.00 | 2.32 | 2.67 | 3.04 | 3.60 | 3.21 | 0 | AA608387 |
| 104023_at | 0.00 | 2.89 | 3.42 | 5.91 | 4.20 | 5.95 | UNK_AW060457 | AW060457 |
| 104389_at | 0.00 | 2.65 | 3.70 | 4.62 | 5.54 | 7.36 | UNK_AW049360 | AW049360 |
| 104464_s_at | 0.00 | 2.24 | 3.48 | 10.84 | 18.75 | 9.30 | UNK_AI642389 | AI642389 |
| 105606_at | 1.75 | 2.68 | 2.44 | 2.77 | 6.16 | 5.68 | UNK_AW210072 | AW210072 |
| 105881_at | 0.00 | 2.16 | 2.37 | 3.53 | 5.35 | 24.32 | UNK_AI847606 | AI847606 |
| 106310_at | 0.00 | 3.45 | 3.22 | 2.71 | 2.82 | 3.11 | UNK_AI843606 | AI843606 |
| 106619_at | 2.41 | 2.32 | 0.00 | 2.78 | 3.02 | 3.67 | UNK_AW060770 | AW060770 |
| 107510_at | 0.00 | 8.81 | 6.27 | 8.47 | 8.55 | 5.39 | UNK_AW049506 | AW049506 |
| 107935_at | 0.00 | 2.29 | 4.62 | 10.35 | 26.40 | 9.69 | UNK_AI450518 | AI450518 |
| 108018_at | 0.00 | 2.98 | 3.50 | 5.18 | 16.34 | 11.82 | UNK_AA959436 | AA959436 |
| 108477_at | 0.00 | 3.49 | 3.67 | 6.12 | 15.44 | 10.74 | UNK_AA692253 | AA692253 |
| 109103_f_at | 0.00 | 2.58 | 3.05 | 3.95 | 4.48 | 3.00 | UNK_AI841088 | AI841088 |
| 109669_at | 0.00 | 2.64 | 3.10 | 5.19 | 15.50 | 11.17 | UNK_AA796759 | AA796759 |
| 109737_at | 0.00 | 3.30 | 3.69 | 7.52 | 10.54 | 18.42 | UNK_AI836805 | AI836805 |
| 109982_at | 0.00 | 3.10 | 2.97 | 3.92 | 5.94 | 12.35 | UNK_AI851247 | AI851247 |
| 110160_at | 0.00 | 3.54 | 6.56 | 5.47 | 2.73 | 3.51 | UNK_AI510217 | AI510217 |
| 110187_at | 0.00 | 2.20 | 2.36 | 2.56 | 2.44 | 3.74 | UNK_AA624041 | AA624041 |
| 110334_at | 0.00 | 2.05 | 2.27 | 6.10 | 4.52 | 6.30 | UNK_AI852289 | AI852289 |
| 110848_at | 0.00 | 3.74 | 4.17 | 8.73 | 18.05 | 9.18 | UNK_AI851487 | AI851487 |
| 111125_at | 0.00 | 2.32 | 2.83 | 2.54 | 3.64 | 7.94 | UNK_AI391368 | AI391368 |
| 111225_at | 0.00 | 2.83 | 2.56 | 3.59 | 6.73 | 3.30 | UNK_AW121825 | AW121825 |
| 111350_at | 0.00 | 2.33 | 3.71 | 2.48 | 5.40 | 4.17 | UNK_AI462022 | AI462022 |
| 111841_at | 0.00 | 3.34 | 4.66 | 5.84 | 4.01 | 7.21 | UNK_AI527656 | AI527656 |
| 112039_at | 0.00 | 2.69 | 2.34 | 2.25 | 2.25 | 3.88 | UNK_AA178128 | AA178128 |
| 112322_at | 0.00 | 3.84 | 2.74 | 2.31 | 2.17 | 3.75 | UNK_AA931004 | AA931004 |
| 112383_at | 0.00 | 2.92 | 5.72 | 9.18 | 4.14 | 6.63 | UNK_AI155444 | AI155444 |
| 112687_at | 0.00 | 2.10 | 2.91 | 2.49 | 3.33 | 3.44 | UNK_AA683840 | AA683840 |
| 112763_at | 0.00 | 3.08 | 2.52 | 3.95 | 5.44 | 2.31 | UNK_AI788757 | AI788757 |
| 112807_at | 0.00 | 2.55 | 3.32 | 3.33 | 5.30 | 3.44 | UNK_AI891565 | AI891565 |
| 113750_at | 1.90 | 3.09 | 3.33 | 3.67 | 2.95 | 4.78 | UNK_AA881110 | AA881110 |
| 113932_g_at | 0.00 | 3.21 | 3.06 | 5.89 | 6.81 | 3.86 | UNK_AW230677 | AW230677 |
| 114025_at | 1.61 | 6.05 | 10.16 | 14.50 | 25.81 | 11.77 | UNK_AI643935 | AI643935 |
| 114303_at | 1.50 | 8.14 | 14.58 | 11.85 | 13.19 | 2.02 | UNK_AW107218 | AW107218 |
| 114498_at | 0.00 | 3.36 | 3.84 | 3.78 | 4.04 | 3.68 | UNK_AW215808 | AW215808 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 114701_at | 1.81 | 2.80 | 2.37 | 5.00 | 12.96 | 7.64 | UNK_AI425702 | AI425702 |
| 116159_at | 0.00 | 3.76 | 4.87 | 3.67 | 2.28 | 3.06 | UNK_AA823048 | AA823048 |
| 116414_at | 0.00 | 3.28 | 3.48 | 5.32 | 3.90 | 7.35 | UNK_AI180528 | AI180528 |
| 116943_at | 0.00 | 2.38 | 2.30 | 4.09 | 3.55 | 4.14 | UNK_AI852450 | AI852450 |
| 116969_at | 0.00 | 2.04 | 2.14 | 2.52 | 2.63 | 3.29 | UNK_AI843050 | AI843050 |
| 117049_at | 0.00 | 2.11 | 2.62 | 2.33 | 2.62 | 3.41 | UNK_AI848494 | AI848494 |
| 135169_at | 0.00 | 2.79 | 3.47 | 3.44 | 2.37 | 2.14 | UNK_AA509929 | AA509929 |
| 137100_at | 2.43 | 4.34 | 4.00 | 4.39 | 1.80 | 3.84 | UNK_AW214591 | AW214591 |
| 139422_at | 0.00 | 2.58 | 3.05 | 5.10 | 2.06 | 3.16 | UNK_AW212694 | AW212694 |
| 92185_at | 0.00 | 0.00 | 2.80 | 3.37 | 5.13 | 2.63 | UNK_AI846023 | AI846023 |
| 92787_at | 0.00 | 2.76 | 0.00 | 2.66 | 3.64 | 2.18 | UNK_AI845902 | AI845902 |
| 92800_i_at | 0.00 | 1.89 | 2.06 | 3.12 | 3.93 | 5.57 | UNK_AI836694 | AI836694 |
| 93037_i_at | 0.00 | 2.22 | 0.00 | 3.35 | 2.89 | 4.40 | LPC1 | M69260 |
| 93327_at | 0.00 | 0.00 | 4.87 | 5.05 | 4.80 | 4.81 | UNK_AI842665 | AI842665 |
| 94273_at | 0.00 | 1.93 | 2.18 | 4.60 | 6.39 | 4.24 | UNK_AI849067 | AI849067 |
| 94330_at | 0.00 | 5.76 | 2.95 | 4.18 | 2.28 | 0.00 | UNK_AA710564 | AA710564 |
| 94486_at | 0.00 | 1.87 | 2.21 | 3.22 | 3.76 | 2.56 | UNK_AW125178 | AW125178 |
| 94549_at | 0.00 | 2.24 | 0.00 | 2.48 | 2.75 | 2.12 | UNK_AI315650 | AI315650 |
| 94830_at | 0.00 | 2.01 | 0.00 | 2.55 | 2.23 | 2.09 | UNK_AI854300 | AI854300 |
| 94992_at | 0.00 | 1.93 | 2.08 | 3.30 | 5.15 | 4.11 | UNK_AI840667 | AI840667 |
| 95590_at | 0.00 | 0.00 | 2.08 | 3.19 | 3.55 | 4.06 | UNK_AA615951 | AA615951 |
| 95648_at | 0.00 | 1.92 | 2.17 | 2.65 | 2.60 | 3.36 | UNK_AA655507 | AA655507 |
| 95885_at | 0.00 | 1.53 | 2.21 | 3.06 | 3.95 | 2.16 | UNK_AA177621 | AA177621 |
| 96004_at | 0.00 | 6.08 | 0.00 | 5.08 | 7.87 | 7.33 | UNK_AI851641 | AI851641 |
| 96262_at | 0.00 | 4.44 | 3.02 | 1.84 | 2.66 | 3.32 | UNK_AI836812 | AI836812 |
| 96605_at | 0.00 | 1.99 | 8.89 | 9.27 | 26.99 | 8.68 | UNK_AI787183 | AI787183 |
| 96708_at | 0.00 | 1.59 | 2.40 | 3.97 | 4.47 | 4.62 | UNK_AW120643 | AW120643 |
| 97211_at | 0.00 | 0.00 | 2.92 | 5.48 | 8.89 | 5.70 | UNK_AI747444 | AI747444 |
| 97425_at | 0.00 | 3.99 | 4.68 | 0.00 | 15.01 | 10.66 | UNK_AI840191 | AI840191 |
| 97456_at | 0.00 | 3.00 | 1.91 | 3.34 | 2.85 | 4.04 | UNK_AI838021 | AI838021 |
| 97811_at | 0.00 | 2.45 | 0.00 | 6.99 | 21.66 | 12.97 | UNK_AI844507 | AI844507 |
| 97947_at | 0.00 | 1.70 | 2.19 | 2.39 | 2.35 | 3.32 | UNK_AI836959 | AI836959 |
| 97964_at | 0.00 | 0.00 | 4.12 | 10.11 | 19.39 | 10.90 | UNK_AW122851 | AW122851 |
| 98107_at | 0.00 | 1.89 | 2.26 | 4.29 | 5.16 | 5.87 | UNK_AW123801 | AW123801 |
| 98346_at | 0.00 | 0.00 | 2.40 | 3.53 | 8.88 | 9.07 | UNK_AI593759 | AI593759 |
| 98440_at | 0.00 | 0.00 | 3.53 | 3.85 | 3.62 | 3.27 | UNK_AA596710 | AA596710 |
| 99149_at | 0.00 | 1.63 | 2.59 | 2.83 | 3.43 | 2.04 | UNK_AI851230 | AI851230 |
| 99191_at | 0.00 | 1.66 | 2.04 | 2.42 | 2.86 | 2.36 | UNK_AI844939 | AI844939 |
| 99366_at | 0.00 | 1.74 | 2.18 | 2.99 | 3.04 | 7.11 | UNK_AI553536 | AI553536 |
| 99505_at | 0.00 | 2.50 | 0.00 | 4.22 | 2.83 | 2.64 | UNK_AI844664 | AI844664 |
| 100611_at | 0.00 | 1.75 | 2.16 | 2.76 | 2.14 | 3.06 | lysozyme; Lyzs | M21050 |
| 102936_at | 0.00 | 2.24 | 2.95 | 2.51 | 2.80 | 0.00 | UNK_AW125314 | AW125314 |
| 103435_at | 0.00 | 2.05 | 0.00 | 4.32 | 4.31 | 6.16 | UNK_AW045910 | AW045910 |
| 103525_at | 0.00 | 0.00 | 2.54 | 2.48 | 2.46 | 2.26 | UNK_AA981725 | AA981725 |
| 103570_at | 1.36 | 0.00 | 3.57 | 8.33 | 32.50 | 24.51 | UNK_AI315647 | AI315647 |
| 103605_g_at | 0.00 | 2.34 | 0.00 | 2.72 | 3.09 | 3.43 | UNK_AW231026 | AW231026 |
| 103606_r_at | 0.00 | 0.00 | 3.31 | 5.63 | 5.50 | 5.04 | UNK_AW121438 | AW121438 |
| 103607_at | 0.00 | 1.91 | 2.63 | 4.83 | 7.58 | 4.57 | UNK_AI882309 | AI882309 |
| 103905_at | 0.00 | 1.30 | 2.12 | 4.42 | 2.69 | 2.19 | UNK_AI314958 | AI314958 |
| 104315_at | 0.00 | 0.00 | 2.66 | 3.65 | 5.15 | 4.85 | UNK_AI846773 | AI846773 |
| 104322_at | 0.00 | 2.76 | −0.53 | 8.24 | 10.40 | 4.90 | UNK_AI121796 | AI121796 |
| 104578_f_at | 0.00 | 1.68 | 2.43 | 4.41 | 6.50 | 5.77 | UNK_AI195392 | AI195392 |
| 104735_at | 0.00 | 1.83 | 3.51 | 4.53 | 7.04 | 7.68 | UNK_AI842065 | AI842065 |
| 104792_at | 0.00 | 0.00 | 3.24 | 2.74 | 2.85 | 2.31 | UNK_AI504064 | AI504064 |
| 106007_at | 0.00 | 0.00 | 2.18 | 2.81 | 4.75 | 4.24 | UNK_AA798398 | AA798398 |
| 106215_at | 0.00 | 2.75 | 3.03 | 0.00 | 3.77 | 4.25 | UNK_AI839767 | AI839767 |
| 106281_f_at | 0.00 | 0.00 | 2.58 | 4.87 | 12.31 | 6.40 | UNK_AI851600 | AI851600 |
| 106287_at | 0.00 | 0.00 | 3.09 | 3.01 | 2.93 | 4.46 | UNK_AW124686 | AW124686 |
| 106984_at | 0.00 | 0.00 | 4.71 | 3.16 | 2.02 | 3.27 | UNK_AA655780 | AA655780 |
| 107043_at | 0.00 | 2.49 | 0.00 | 2.68 | 4.39 | 10.55 | UNK_AA770975 | AA770975 |
| 107063_at | 0.00 | 0.00 | 2.56 | 4.20 | 9.80 | 9.48 | UNK_AI852358 | AI852358 |
| 107406_at | 0.00 | 0.00 | 2.34 | 2.06 | 5.20 | 3.73 | UNK_AW048981 | AW048981 |
| 107408_at | 1.42 | 2.22 | 0.00 | 3.13 | 4.06 | 3.64 | UNK_AW049048 | AW049048 |
| 107520_at | 0.00 | 0.00 | 2.20 | 2.65 | 2.60 | 7.04 | UNK_AI846038 | AI846038 |
| 107917_at | 0.00 | 2.57 | 0.00 | 3.20 | 7.84 | 6.47 | UNK_AA796707 | AA796707 |
| 108048_at | 0.00 | 0.00 | 2.60 | 2.63 | 5.24 | 2.87 | UNK_AI836268 | AI836268 |
| 108889_at | 0.00 | 2.27 | 0.00 | 2.74 | 7.67 | 8.01 | UNK_AA870215 | AA870215 |
| 109021_at | 0.00 | 0.00 | 4.01 | 3.06 | 2.13 | 3.35 | UNK_AW214142 | AW214142 |
| 109033_at | 0.00 | 2.56 | 0.00 | 3.78 | 6.98 | 5.70 | UNK_AW122053 | AW122053 |
| 109169_at | 0.00 | 0.00 | 2.18 | 2.74 | 2.66 | 2.83 | UNK_AI841448 | AI841448 |
| 109330_at | 0.00 | 1.86 | 2.26 | 3.04 | 8.08 | 4.45 | UNK_AI195395 | AI195395 |
| 109554_at | 0.00 | 3.33 | 3.40 | 2.32 | 1.66 | 2.64 | UNK_AA611111 | AA611111 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 109709_at | 0.00 | 0.00 | 4.62 | 6.04 | 6.21 | 5.36 | UNK_AW124034 | AW124034 |
| 109989_at | 0.00 | 2.30 | 0.00 | 2.23 | 3.21 | 2.82 | UNK_AW124029 | AW124029 |
| 110124_at | 0.00 | 1.81 | 2.27 | 2.56 | 2.86 | 2.77 | UNK_AI647471 | AI647471 |
| 110319_at | 0.00 | 0.00 | 2.77 | 3.82 | 6.37 | 7.50 | UNK_AW215732 | AW215732 |
| 110351_at | 0.00 | 0.00 | 2.46 | 2.37 | 2.59 | 3.02 | UNK_AI842140 | AI842140 |
| 110429_at | 0.00 | 0.00 | 2.59 | 4.62 | 5.25 | 11.50 | UNK_AW060321 | AW060321 |
| 110853_at | 0.00 | 1.86 | 3.15 | 3.52 | 4.37 | 5.49 | UNK_AW124968 | AW124968 |
| 111044_f_at | 0.00 | 1.72 | 3.54 | 3.57 | 2.88 | 4.78 | UNK_AA175250 | AA175250 |
| 111229_at | 0.00 | 2.14 | 0.00 | 2.59 | 3.44 | 3.06 | UNK_AW123416 | AW123416 |
| 111624_at | 0.00 | 0.00 | 2.65 | 4.22 | 4.19 | 4.97 | UNK_AI843542 | AI843542 |
| 111628_at | 0.00 | 1.82 | 2.88 | 2.96 | 3.56 | 3.44 | UNK_AA415523 | AA415523 |
| 111680_at | 0.00 | 0.00 | 3.55 | 2.66 | 3.45 | 4.18 | UNK_AA681812 | AA681812 |
| 111965_at | 0.00 | 1.88 | 5.19 | 12.18 | 16.02 | 7.92 | UNK_AA869027 | AA869027 |
| 112062_at | 0.00 | 0.00 | 2.60 | 4.10 | 8.79 | 9.97 | UNK_AA989939 | AA989939 |
| 112349_at | 0.00 | 3.23 | 0.00 | 4.74 | 4.11 | 7.10 | UNK_AW048860 | AW048860 |
| 112373_at | 0.00 | 3.42 | 0.00 | 3.33 | 3.07 | 9.92 | UNK_AI840826 | AI840826 |
| 112386_at | 0.00 | 0.00 | 2.10 | 6.36 | 5.47 | 5.04 | UNK_AI838633 | AI838633 |
| 112411_at | 0.00 | 3.41 | 0.00 | 3.71 | 5.34 | 5.90 | UNK_AW229681 | AW229681 |
| 112445_at | 0.00 | 4.88 | 0.00 | 4.11 | 5.78 | 7.36 | UNK_AI156718 | AI156718 |
| 112464_at | 0.00 | 0.00 | 2.20 | 2.19 | 5.18 | 3.92 | UNK_AI194396 | AI194396 |
| 112465_at | 0.00 | 0.00 | 3.34 | 2.83 | 3.08 | 4.56 | UNK_AI226955 | AI226955 |
| 112766_at | 0.00 | 0.00 | 2.32 | 2.86 | 4.43 | 2.35 | UNK_AI788798 | AI788798 |
| 112996_at | 0.00 | 1.91 | 3.42 | 3.15 | 2.25 | 3.79 | UNK_AA170203 | AA170203 |
| 113036_at | 0.00 | 0.00 | 9.63 | 27.96 | 22.87 | 15.50 | UNK_AW120709 | AW120709 |
| 113196_at | 0.00 | 0.00 | 2.73 | 5.42 | 19.47 | 19.66 | UNK_AW124306 | AW124306 |
| 113268_s_at | 0.00 | 0.00 | 2.94 | 4.41 | 4.90 | 6.78 | UNK_AI835128 | AI835128 |
| 113302_at | 0.00 | 0.00 | 3.92 | 4.35 | 2.37 | 2.39 | UNK_AA967902 | AA967902 |
| 113322_at | 0.00 | 4.17 | 3.83 | 2.29 | 1.80 | 3.97 | UNK_AI116109 | AI116109 |
| 113989_at | 0.00 | 1.53 | 2.26 | 3.83 | 2.32 | 2.71 | UNK_AW209554 | AW209554 |
| 113995_at | 0.00 | 0.00 | 2.09 | 3.10 | 7.68 | 8.85 | UNK_AW061313 | AW061313 |
| 114602_at | 0.00 | 0.00 | 2.53 | 4.43 | 5.72 | 4.29 | UNK_AW228836 | AW228836 |
| 114633_at | 0.00 | 1.95 | 2.18 | 2.85 | 2.34 | 2.13 | UNK_AA895405 | AA895405 |
| 114635_at | 0.00 | 0.00 | 3.64 | 5.07 | 2.28 | 3.67 | UNK_AA960121 | AA960121 |
| 114849_at | 0.00 | 0.00 | 2.04 | 2.51 | 2.21 | 2.98 | UNK_AI462265 | AI462265 |
| 115057_at | 0.00 | 3.81 | 0.00 | 4.34 | 6.22 | 9.28 | UNK_AI591439 | AI591439 |
| 115463_at | 0.00 | 1.89 | 2.87 | 3.42 | 3.47 | 3.30 | UNK_AI118729 | AI118729 |
| 115786_at | 0.00 | 2.74 | 4.53 | 4.67 | 5.11 | 0.00 | UNK_AI563688 | AI563688 |
| 115795_at | 0.00 | 1.66 | 2.14 | 2.42 | 2.02 | 2.38 | UNK_AI851830 | AI851830 |
| 115800_at | 0.00 | 0.00 | 2.19 | 2.85 | 3.72 | 4.95 | UNK_AW125385 | AW125385 |
| 115840_at | 0.00 | 3.42 | 0.00 | 4.03 | 7.10 | 8.17 | UNK_AA756752 | AA756752 |
| 116382_at | 0.00 | 2.11 | 0.00 | 3.91 | 8.77 | 15.59 | UNK_AW046112 | AW046112 |
| 117179_at | 0.00 | 1.97 | 8.96 | 15.72 | 41.33 | 9.71 | UNK_AI852894 | AI852894 |
| 130969_at | 0.00 | 0.00 | 2.19 | 2.47 | 2.21 | 3.14 | UNK_AI844373 | AI844373 |
| 135177_at | 0.00 | 3.65 | 0.00 | 5.69 | 3.01 | 3.18 | UNK_AI882074 | AI882074 |
| 135189_f_at | 0.00 | 0.00 | 2.54 | 5.92 | 8.57 | 7.44 | UNK_AI481498 | AI481498 |
| 135257_at | 0.00 | 1.76 | 2.12 | 3.83 | 3.13 | 5.08 | UNK_AI848406 | AI848406 |
| 137034_f_at | 0.00 | 2.01 | 0.00 | 3.48 | 3.35 | 3.21 | UNK_AI480781 | AI480781 |
| 137656_s_at | 2.10 | 4.17 | 0.00 | 3.83 | 1.46 | 2.66 | UNK_AI195998 | AI195998 |
| 92268_at | 0.00 | 0.00 | 0.00 | 2.96 | 2.58 | 2.60 | UNK_AI854851 | AI854851 |
| 92279_at | 0.00 | 0.00 | 0.00 | 3.35 | 3.86 | 2.45 | UNK_AW121320 | AW121320 |
| 92831_at | 0.00 | 1.64 | 0.00 | 2.11 | 2.74 | 4.13 | UNK_AI846308 | AI846308 |
| 93174_at | 0.00 | 0.00 | 0.00 | 3.77 | 9.21 | 14.95 | UNK_AI593640 | AI593640 |
| 93236_s_at | 0.00 | 1.84 | 2.29 | 2.54 | 3.78 | 1.95 | thymidylate synthase; Tyms | M13352 |
| 93443_at | 0.00 | −1.73 | 0.00 | 2.28 | 4.61 | 2.81 | UNK_AW212271 | AW212271 |
| 93472_at | 0.00 | 0.00 | 0.00 | 5.12 | 7.16 | 5.99 | UNK_AA796989 | AA796989 |
| 93714_f_at | 0.00 | 0.00 | 0.00 | 2.75 | 2.14 | 2.74 | UNK_AI117211 | AI117211 |
| 93747_at | 0.00 | 0.00 | 0.00 | 2.11 | 2.53 | 2.90 | UNK_AW122599 | AW122599 |
| 93830_at | 0.00 | 0.00 | 0.00 | 2.26 | 2.94 | 2.21 | UNK_AI851199 | AI851199 |
| 93831_at | 0.00 | 0.00 | 0.00 | 2.37 | 3.09 | 2.39 | UNK_AI316087 | AI316087 |
| 93974_at | 0.00 | 0.00 | 1.65 | 4.60 | 2.63 | 5.21 | 33 POLYPEPTIDE [R. NORVEGICUS] | AW212475 |
| 93999_at | 0.00 | 1.56 | 1.86 | 2.43 | 2.61 | 2.30 | CD8B | AW060597 |
| 94041_at | 0.00 | 0.00 | 1.71 | 2.39 | 2.63 | 2.32 | UNK_AI840643 | AI840643 |
| 94060_at | 0.00 | 0.00 | 0.00 | 2.72 | 3.43 | 2.97 | UNK_AI852623 | AI852623 |
| 94289_r_at | 0.00 | 0.00 | 0.00 | 5.89 | 6.92 | 5.31 | UNK_AI851574 | AI851574 |
| 94415_at | 0.00 | 1.93 | 0.00 | 3.04 | 2.62 | 2.30 | 0 | AA710439 |
| 94445_at | 0.00 | 0.00 | 0.00 | 2.05 | 3.55 | 3.58 | UNK_AW125273 | AW125273 |
| 94470_i_at | 0.00 | 0.00 | 0.00 | 2.09 | 3.10 | 3.00 | UNK_AW045974 | AW045974 |
| 94473_at | 0.00 | 0.00 | 0.00 | 2.23 | 2.77 | 3.60 | UNK_AW047951 | AW047951 |
| 94503_at | 0.00 | 0.00 | 0.00 | 5.46 | 4.11 | 4.57 | UNK_AI842492 | AI842492 |
| 94511_at | 0.00 | 0.00 | 1.98 | 3.57 | 4.92 | 3.27 | UNK_AI850546 | AI850546 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 94784_at | 0.00 | 0.00 | 2.33 | 2.63 | 2.69 | 0.00 | UNK_AI593484 | AI593484 |
| 94931_at | 0.00 | 0.00 | 1.55 | 2.64 | 4.46 | 2.36 | UNK_AI851104 | AI851104 |
| 95020_at | 0.00 | 1.59 | 0.00 | 2.17 | 2.56 | 3.30 | UNK_AI848868 | AI848868 |
| 95042_at | 0.00 | 0.00 | 0.00 | 2.81 | 3.92 | 3.09 | UNK_AI839770 | AI839770 |
| 95091_at | 0.00 | 0.00 | 0.00 | 2.19 | 3.07 | 2.05 | UNK_AI839895 | AI839895 |
| 95151_at | 0.00 | 0.00 | 1.55 | 2.53 | 10.58 | 4.87 | UNK_AW061307 | AW061307 |
| 95400_i_at | 0.00 | 0.00 | 0.00 | 2.02 | 2.63 | 3.14 | UNK_AI447783 | AI447783 |
| 95404_at | 0.00 | 0.00 | 0.00 | 2.20 | 2.89 | 2.95 | UNK_AW123453 | AW123453 |
| 95405_at | 0.00 | 0.00 | 0.00 | 2.32 | 2.36 | 2.24 | UNK_AW045534 | AW045534 |
| 95609_at | 0.00 | 0.00 | 1.63 | 2.66 | 2.03 | 2.61 | UNK_AA869927 | AA869927 |
| 95637_at | 0.00 | 0.00 | 0.00 | 5.65 | 6.59 | 4.70 | UNK_AI838592 | AI838592 |
| 96117_r_at | 0.00 | 1.70 | 1.72 | 4.04 | 6.17 | 3.16 | UNK_AI843732 | AI843732 |
| 96207_at | 0.00 | 1.93 | 0.00 | 2.38 | 2.45 | 2.47 | UNK_AW046449 | AW046449 |
| 96249_at | 0.00 | 0.00 | 0.00 | 2.41 | 2.55 | 2.39 | UNK_AW122105 | AW122105 |
| 96271_at | 0.00 | 0.00 | 0.00 | 2.11 | 2.16 | 2.61 | UNK_AA914105 | AA914105 |
| 96288_at | 0.00 | 0.00 | 0.00 | 2.42 | 2.50 | 2.26 | UNK_AI648831 | AI648831 |
| 96524_at | 0.00 | 0.00 | 0.00 | 7.01 | 7.10 | 6.99 | UNK_AI157060 | AI157060 |
| 96526_at | 0.00 | 0.00 | 1.78 | 2.38 | 4.26 | 4.98 | UNK_AW228840 | AW228840 |
| 96603_at | 0.00 | 0.00 | 1.45 | 3.17 | 7.47 | 6.26 | UNK_AW123556 | AW123556 |
| 96610_at | 0.00 | 1.73 | 0.00 | 2.37 | 2.33 | 3.57 | UNK_AW046442 | AW046442 |
| 96831_at | 0.00 | 0.00 | 0.00 | 4.14 | 9.52 | 4.49 | UNK_AA755004 | AA755004 |
| 96855_at | 0.00 | 0.00 | 0.00 | 4.41 | 2.28 | 3.04 | UNK_AI839946 | AI839946 |
| 97322_at | 1.42 | 2.58 | 4.12 | 2.93 | 1.61 | 1.47 | UNK_AI835093 | AI835093 |
| 97360_at | 0.00 | 0.00 | 0.00 | 4.98 | 8.63 | 6.80 | UNK_AI841689 | AI841689 |
| 97374_at | 0.00 | 0.00 | 0.00 | 4.28 | 5.95 | 5.36 | UNK_AI840458 | AI840458 |
| 97387_at | 0.00 | 0.00 | 0.00 | 3.29 | 6.53 | 6.82 | UNK_AI847879 | AI847879 |
| 97420_at | 0.00 | 1.86 | 2.49 | 3.68 | 2.46 | 0.00 | UNK_AW230891 | AW230891 |
| 97492_at | 0.00 | 0.00 | 0.00 | 2.77 | 2.23 | 2.14 | UNK_AW121746 | AW121746 |
| 97496_f_at | 0.00 | 1.85 | 1.97 | 3.37 | 3.29 | 3.18 | UNK_AW048944 | AW048944 |
| 97711_at | 4.97 | 7.08 | 9.21 | 0.00 | 0.00 | −1.58 | UNK_AI606967 | AI606967 |
| 97770_s_at | 0.00 | 0.00 | 0.00 | 2.02 | 2.40 | 2.53 | UNK_AA733372 | AA733372 |
| 97818_at | 0.00 | 0.00 | 0.00 | 2.30 | 2.75 | 2.58 | UNK_AI838691 | AI838691 |
| 97885_at | 0.00 | 0.00 | 0.00 | 2.89 | 3.28 | 3.88 | UNK_AB031386 | AB031386 |
| 97918_at | 0.00 | 0.00 | 0.00 | 2.13 | 2.36 | 2.81 | UNK_AA623587 | AA623587 |
| 98042_at | 0.00 | 0.00 | 0.00 | 4.50 | 7.72 | 7.38 | UNK_AW049787 | AW049787 |
| 98083_at | 0.00 | 0.00 | 0.00 | 2.45 | 2.40 | 2.85 | UNK_AW049031 | AW049031 |
| 98594_at | 0.00 | 0.00 | 0.00 | 2.89 | 4.90 | 5.86 | UNK_AW125453 | AW125453 |
| 98615_at | 0.00 | 0.00 | 1.63 | 2.53 | 2.51 | 2.12 | UNK_AW049570 | AW049570 |
| 98917_at | 0.00 | 0.00 | 0.00 | 2.09 | 2.77 | 3.39 | UNK_AA823202 | AA823202 |
| 98931_at | 0.00 | 0.00 | 0.00 | 2.18 | 2.06 | 4.22 | UNK_AW123589 | AW123589 |
| 98956_at | 0.00 | 1.91 | 0.00 | 4.40 | 4.62 | 4.19 | UNK_AI844979 | AI844979 |
| 98975_at | 0.00 | 0.00 | 0.00 | 2.13 | 2.85 | 3.32 | UNK_AI019999 | AI019999 |
| 99378_f_at | 0.00 | 0.00 | 0.00 | 3.06 | 2.42 | 4.09 | UNK_M18837 | M18837 |
| 100074_at | 0.00 | 0.00 | 0.00 | 4.44 | 3.57 | 2.83 | UNK_AW046723 | AW046723 |
| 100100_at | 0.00 | 6.72 | 5.24 | 5.35 | 0.00 | 0.00 | UNK_AA762212 | AA762212 |
| 100471_at | 0.00 | 0.00 | 1.84 | 5.94 | 20.39 | 6.44 | UNK_AW048916 | AW048916 |
| 100915_at | 0.00 | 1.46 | 1.50 | 3.52 | 2.39 | 3.61 | UNK_AW125698 | AW125698 |
| 100974_at | 0.00 | 0.00 | 2.13 | 1.44 | 2.13 | 3.27 | UNK_AI844250 | AI844250 |
| 101001_at | 0.00 | 0.00 | 0.00 | 2.97 | 4.32 | 3.67 | UNK_AI647612 | AI647612 |
| 101084_f_at | 0.00 | 0.00 | 0.00 | 4.39 | 4.47 | 3.59 | UNK_AI527477 | AI527477 |
| 101441_i_at | 0.00 | 0.00 | 0.00 | 3.13 | 2.07 | 2.48 | ITPR5 | AF031127 |
| 101856_at | 0.00 | 0.00 | 0.00 | 2.71 | 2.82 | 2.13 | UNK_AI836771 | AI836771 |
| 102279_at | 0.00 | 0.00 | 1.71 | 4.39 | 5.91 | 9.29 | UNK_AW046479 | AW046479 |
| 102354_at | 0.00 | 1.81 | 2.65 | 0.00 | 3.39 | 2.56 | UNK_AI049398 | AI049398 |
| 102812_i_at | 0.00 | 0.00 | 0.00 | 2.63 | 2.76 | 2.35 | UNK_AW210346 | AW210346 |
| 102813_f_at | 0.00 | 0.00 | 0.00 | 3.19 | 3.50 | 3.42 | UNK_AW210346 | AW210346 |
| 103056_at | 0.00 | 0.00 | 0.00 | 2.34 | 2.20 | 2.30 | UNK_AI849721 | AI849721 |
| 103071_at | 0.00 | 0.00 | 2.37 | 2.05 | 2.42 | 0.00 | UNK_AI843655 | AI843655 |
| 103345_at | 0.00 | 0.00 | 0.00 | 2.50 | 5.36 | 3.40 | UNK_AW046708 | AW046708 |
| 103381_at | 0.00 | 0.00 | 0.00 | 3.22 | 3.91 | 3.29 | UNK_AI838735 | AI838735 |
| 103491_at | 0.00 | 0.00 | 0.00 | 2.34 | 2.48 | 3.21 | UNK_AA968123 | AA968123 |
| 103556_at | 0.00 | 0.00 | 1.92 | 4.21 | 4.47 | 2.64 | ARP2-PENDING | AI840158 |
| 103708_at | 0.00 | 1.72 | 2.04 | 3.24 | 3.11 | 0.00 | UNK_AI132207 | AI132207 |
| 103709_at | 0.00 | 0.00 | 0.00 | 3.82 | 2.14 | 2.74 | UNK_AA763466 | AA763466 |
| 103726_at | 0.00 | 1.67 | 0.00 | 3.54 | 3.48 | 2.76 | UNK_AI842264 | AI842264 |
| 103748_at | 0.00 | 0.00 | 3.05 | 0.00 | 6.47 | 4.96 | UNK_AW125627 | AW125627 |
| 103863_at | 0.00 | 1.56 | 0.00 | 2.29 | 2.39 | 2.32 | UNK_AW049769 | AW049769 |
| 104188_at | 0.00 | 1.72 | 0.00 | 3.24 | 4.10 | 4.01 | UNK_AI853703 | AI853703 |
| 104250_at | 0.00 | 0.00 | 0.00 | 2.04 | 3.44 | 3.33 | UNK_AW121353 | AW121353 |
| 104386_f_at | 0.00 | 0.00 | 0.00 | 2.79 | 2.29 | 4.39 | UNK_AI843901 | AI843901 |
| 104399_at | 0.00 | 1.79 | 0.00 | 2.21 | 2.47 | 2.45 | UNK_AI850965 | AI850965 |
| 104427_at | 0.00 | 1.64 | 0.00 | 2.13 | 2.42 | 2.92 | UNK_AA930526 | AA930526 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 104435_at | 0.00 | 0.00 | 0.00 | 2.52 | 4.50 | 4.08 | UNK_AI644072 | AI644072 |
| 104544_at | 0.00 | 1.92 | 2.25 | 2.22 | 2.98 | 0.00 | UNK_AA675604 | AA675604 |
| 104579_r_at | 0.00 | 1.68 | 0.00 | 4.11 | 3.04 | 4.02 | UNK_AI195392 | AI195392 |
| 104677_at | 0.00 | 0.00 | 0.00 | 2.37 | 3.06 | 2.31 | UNK_AI852008 | AI852008 |
| 104766_at | 0.00 | 2.25 | 0.00 | 3.53 | 3.02 | 1.54 | UNK_AI851198 | AI851198 |
| 105411_at | 0.00 | 1.86 | 0.00 | 2.61 | 4.05 | 4.05 | UNK_AI842846 | AI842846 |
| 105451_at | 0.00 | 0.00 | 0.00 | 3.53 | 9.33 | 5.81 | UNK_AI153747 | AI153747 |
| 105585_at | 0.00 | 0.00 | 0.00 | 2.17 | 2.27 | 2.37 | UNK_AI466953 | AI466953 |
| 106051_at | 0.00 | 0.00 | 0.00 | 3.22 | 11.40 | 8.03 | UNK_AI838192 | AI838192 |
| 106198_at | 0.00 | 0.00 | 0.00 | 2.10 | 3.50 | 2.96 | UNK_AI847104 | AI847104 |
| 106222_at | 0.00 | 0.00 | 0.00 | 3.02 | 10.05 | 8.98 | UNK_AW050335 | AW050335 |
| 106260_at | 0.00 | 0.00 | 0.00 | 3.66 | 5.37 | 3.81 | UNK_AW123372 | AW123372 |
| 106294_at | 0.00 | 0.00 | 0.00 | 2.34 | 2.47 | 2.79 | UNK_AI834916 | AI834916 |
| 106469_at | 0.00 | 3.06 | 2.69 | 5.69 | 0.00 | 0.00 | UNK_AI835918 | AI835918 |
| 106554_at | 0.00 | 0.00 | 0.00 | 2.16 | 2.03 | 2.55 | UNK_AI854833 | AI854833 |
| 106569_at | 0.00 | 0.00 | 0.00 | 2.30 | 2.04 | 2.34 | UNK_AA611588 | AA611588 |
| 106581_at | 0.00 | 0.00 | 0.00 | 2.22 | 2.23 | 2.53 | UNK_AW049498 | AW049498 |
| 106596_at | 0.00 | 0.00 | 0.00 | 2.79 | 2.50 | 5.15 | UNK_AW046788 | AW046788 |
| 106623_at | 0.00 | 0.00 | 0.00 | 3.01 | 5.89 | 20.01 | UNK_AI180489 | AI180489 |
| 106638_at | 0.00 | 0.00 | 0.00 | 2.26 | 2.86 | 5.68 | UNK_AA762192 | AA762192 |
| 107099_at | 0.00 | 0.00 | −2.37 | 3.85 | 3.65 | 3.57 | UNK_AA792731 | AA792731 |
| 107124_at | 0.00 | 0.00 | 2.17 | 0.00 | 2.98 | 2.82 | UNK_AI848296 | AI848296 |
| 107515_at | 0.00 | 0.00 | 0.00 | 2.35 | 5.98 | 4.81 | UNK_AI152665 | AI152665 |
| 107519_at | 0.00 | 1.66 | 0.00 | 2.83 | 3.62 | 7.65 | UNK_AW122581 | AW122581 |
| 107521_at | 0.00 | 0.00 | 0.00 | 2.38 | 3.00 | 3.81 | UNK_AI853924 | AI853924 |
| 107553_at | 0.00 | 0.00 | 1.28 | 2.76 | 3.62 | 3.25 | UNK_AW047590 | AW047590 |
| 107575_at | 0.00 | 0.00 | 0.00 | 3.06 | 4.02 | 3.94 | UNK_AA980835 | AA980835 |
| 107587_at | 0.00 | 0.45 | 0.00 | 2.13 | 4.88 | 3.39 | UNK_AI035938 | AI035938 |
| 107599_at | 0.00 | 0.00 | 0.00 | 2.18 | 2.13 | 2.08 | UNK_AI121363 | AI121363 |
| 107959_at | 0.00 | 0.00 | 0.00 | 2.33 | 4.89 | 5.30 | UNK_AA980253 | AA980253 |
| 108008_at | 0.00 | 0.00 | 2.96 | 0.00 | 4.43 | 7.06 | UNK_AI551848 | AI551848 |
| 108049_at | 0.00 | 0.00 | 0.00 | 7.17 | 8.21 | 5.99 | UNK_AW121296 | AW121296 |
| 108105_at | 0.00 | 0.00 | 5.44 | 4.71 | 1.58 | 5.04 | UNK_AA839380 | AA839380 |
| 108382_at | 0.00 | 0.00 | 0.00 | 5.21 | 5.76 | 6.53 | UNK_AW259632 | AW259632 |
| 108383_at | 0.00 | 0.00 | 0.00 | 3.99 | 5.62 | 7.43 | UNK_AA066623 | AA066623 |
| 108384_g_at | 0.00 | 0.00 | 0.00 | 4.00 | 6.89 | 6.79 | UNK_AA066623 | AA066623 |
| 108466_at | 0.00 | 0.00 | 3.44 | 0.00 | 3.36 | 5.90 | UNK_AI596076 | AI596076 |
| 108532_at | 0.00 | 0.00 | 0.00 | 2.66 | 4.30 | 3.67 | UNK_AW122038 | AW122038 |
| 108541_at | 0.00 | 0.00 | 0.00 | 2.03 | 2.62 | 2.82 | UNK_AW048008 | AW048008 |
| 108568_at | 0.00 | 0.00 | 0.00 | 2.42 | 2.63 | 2.64 | UNK_AI155631 | AI155631 |
| 108820_at | 0.00 | 0.00 | 0.00 | 3.58 | 4.40 | 3.77 | UNK_AW049198 | AW049198 |
| 109051_at | 0.00 | 0.00 | 0.00 | 2.66 | 4.11 | 4.07 | UNK_AI157102 | AI157102 |
| 109059_at | 0.00 | 0.00 | 0.00 | 2.98 | 6.09 | 4.59 | UNK_AI594658 | AI594658 |
| 109090_at | 0.00 | 0.00 | 2.21 | 0.00 | 2.45 | 2.26 | UNK_AA032312 | AA032312 |
| 109120_at | 0.00 | 0.00 | 0.00 | 2.42 | 5.70 | 4.73 | UNK_AI157108 | AI157108 |
| 109178_g_at | 0.00 | 0.00 | 0.00 | 3.12 | 3.11 | 4.12 | UNK_AW122327 | AW122327 |
| 109352_s_at | 0.00 | 0.00 | 0.00 | 2.01 | 2.51 | 3.11 | UNK_AI840133 | AI840133 |
| 109368_at | 0.00 | 0.00 | 0.00 | 2.40 | 8.63 | 10.05 | UNK_AI840476 | AI840476 |
| 109387_f_at | 0.00 | 0.00 | 0.00 | 2.55 | 3.54 | 4.69 | UNK_AA960590 | AA960590 |
| 109553_at | 0.00 | 0.00 | 0.00 | 3.76 | 4.23 | 5.14 | UNK_AI645484 | AI645484 |
| 109652_at | 0.00 | 0.00 | 0.00 | 4.42 | 10.57 | 4.83 | UNK_AI596121 | AI596121 |
| 109682_at | 0.00 | 1.47 | 0.00 | 2.80 | 3.58 | 3.26 | UNK_AW046087 | AW046087 |
| 109722_at | 0.00 | 0.00 | 0.00 | 3.76 | 3.11 | 5.30 | UNK_AI843690 | AI843690 |
| 109728_at | 0.00 | 0.00 | 0.00 | 2.72 | 3.41 | 4.91 | UNK_AI848741 | AI848741 |
| 109733_at | 0.00 | 0.00 | 0.00 | 2.11 | 3.48 | 4.36 | UNK_AW121434 | AW121434 |
| 109757_at | 0.00 | 0.00 | 0.00 | 2.45 | 2.41 | 5.31 | UNK_AW122156 | AW122156 |
| 110225_at | 0.00 | 0.00 | 0.00 | 2.35 | 3.42 | 3.96 | UNK_AI646302 | AI646302 |
| 110228_at | 0.00 | 0.00 | 0.00 | 3.63 | 17.05 | 10.06 | UNK_AI197339 | AI197339 |
| 110318_at | 0.00 | 0.00 | 0.00 | 2.36 | 3.20 | 7.36 | UNK_AA866881 | AA866881 |
| 110382_at | 0.00 | 0.00 | 0.00 | 2.35 | 2.14 | 3.23 | UNK_AW215580 | AW215580 |
| 110713_at | 0.00 | 0.00 | 0.00 | 2.31 | 4.34 | 3.18 | UNK_AW124288 | AW124288 |
| 110728_at | 0.00 | 2.05 | 2.30 | 1.91 | 1.98 | 2.38 | UNK_AA959412 | AA959412 |
| 110835_at | 0.00 | 0.00 | 0.00 | 2.96 | 3.58 | 3.92 | UNK_AW122399 | AW122399 |
| 111029_at | 0.00 | 0.00 | 2.83 | 2.65 | 5.89 | 1.80 | UNK_AW060610 | AW060610 |
| 111272_at | 0.00 | 1.98 | 0.00 | 2.45 | 3.49 | 3.79 | UNK_AI006978 | AI006978 |
| 111552_at | 0.00 | 5.28 | 0.00 | 9.85 | 3.20 | 0.00 | UNK_AA645952 | AA645952 |
| 111684_at | 0.00 | 0.00 | 0.00 | 4.50 | 7.26 | 4.83 | UNK_AA856145 | AA856145 |
| 111816_at | 0.00 | 0.00 | 0.00 | 2.08 | 2.78 | 3.47 | UNK_AI853182 | AI853182 |
| 111831_at | 0.00 | 0.00 | 2.34 | 1.99 | 2.46 | 3.35 | UNK_AA759455 | AA759455 |
| 111909_f_at | 0.00 | 0.00 | 0.00 | 5.45 | 5.79 | 4.68 | UNK_AW047813 | AW047813 |
| 112321_at | 0.00 | 0.00 | 0.00 | 2.25 | 2.63 | 3.38 | UNK_AA198542 | AA198542 |
| 112350_at | 0.00 | 0.00 | 0.00 | 2.05 | 3.09 | 3.70 | UNK_AA739089 | AA739089 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 112375_at | 0.00 | 0.00 | 0.00 | 2.44 | 3.43 | 3.62 | UNK_AI850477 | AI850477 |
| 112379_at | 0.00 | 0.00 | 2.65 | 0.00 | 4.96 | 3.46 | UNK_AI851953 | AI851953 |
| 112394_at | 0.00 | 1.50 | 1.92 | 2.81 | 3.97 | 5.52 | UNK_AI790592 | AI790592 |
| 112453_at | 0.00 | 0.00 | 0.00 | 3.38 | 3.38 | 5.27 | UNK_AW048464 | AW048464 |
| 112509_at | 0.00 | 0.00 | 0.00 | 2.47 | 9.02 | 2.08 | UNK_AW125633 | AW125633 |
| 112661_at | 0.00 | 0.00 | 0.00 | 3.24 | 3.61 | 3.86 | UNK_AI877116 | AI877116 |
| 112679_at | 0.00 | 0.00 | 6.56 | 5.10 | 4.31 | 0.00 | UNK_AA867783 | AA867783 |
| 112684_at | 0.00 | 0.00 | 0.00 | 2.54 | 2.50 | 2.46 | UNK_AI853966 | AI853966 |
| 112831_at | 0.00 | 0.00 | 0.00 | 6.83 | 5.69 | 5.51 | UNK_AI845409 | AI845409 |
| 112910_f_at | 0.00 | 0.00 | 0.00 | 2.28 | 10.24 | 2.63 | UNK_AW229261 | AW229261 |
| 112922_i_at | 0.00 | 0.00 | 0.00 | 5.39 | 12.82 | 7.06 | UNK_AI173274 | AI173274 |
| 112929_at | 0.00 | 2.83 | 0.00 | 0.00 | 5.12 | 3.45 | UNK_AA711463 | AA711463 |
| 112988_at | 0.00 | 0.00 | 0.00 | 3.10 | 5.72 | 4.74 | UNK_AI006418 | AI006418 |
| 113050_at | 0.00 | 0.00 | 0.00 | 2.00 | 2.17 | 3.46 | UNK_AI846034 | AI846034 |
| 113122_i_at | 0.00 | 2.46 | 0.73 | 2.33 | 3.55 | 0.00 | UNK_AI843040 | AI843040 |
| 113297_at | 0.00 | 1.78 | 0.00 | 2.94 | 3.25 | 2.48 | UNK_AW125352 | AW125352 |
| 113335_at | 0.00 | 0.00 | 0.00 | 3.40 | 7.49 | 12.56 | UNK_AI876264 | AI876264 |
| 113549_at | 0.00 | 0.00 | 0.00 | 2.76 | 2.88 | 3.00 | UNK_AI849286 | AI849286 |
| 113622_at | 0.00 | 0.00 | 1.78 | 2.89 | 3.75 | 7.10 | UNK_AW046166 | AW046166 |
| 113734_at | 0.00 | 1.78 | 2.06 | 0.00 | 2.17 | 3.62 | UNK_AA940541 | AA940541 |
| 113743_at | 0.00 | 0.00 | 0.00 | 3.40 | 3.14 | 3.99 | UNK_AI854778 | AI854778 |
| 113808_at | 1.65 | 2.82 | 3.65 | 3.78 | 1.94 | 0.00 | UNK_AA930477 | AA930477 |
| 113914_at | 0.00 | 0.00 | 0.00 | 3.60 | 4.87 | 4.90 | UNK_AW121680 | AW121680 |
| 113921_at | 0.00 | 2.71 | 0.00 | 6.11 | 5.22 | 0.00 | UNK_AW121531 | AW121531 |
| 113931_at | 0.00 | 0.00 | 0.00 | 5.86 | 20.80 | 7.34 | UNK_AW230677 | AW230677 |
| 113933_at | 0.00 | 1.99 | 0.00 | 3.12 | 4.60 | 3.14 | UNK_AI789270 | AI789270 |
| 114091_at | 0.00 | 4.16 | 4.06 | 2.47 | 1.71 | 0.00 | UNK_AI450598 | AI450598 |
| 114212_at | 0.00 | 0.00 | 0.00 | 2.37 | 3.27 | 10.38 | MRC2 | AI430350 |
| 114240_at | 0.00 | 0.00 | 0.00 | 2.57 | 3.20 | 3.35 | UNK_AA816087 | AA816087 |
| 114345_at | 0.00 | 0.00 | 1.93 | 3.11 | 2.71 | 2.08 | UNK_AI595956 | AI595956 |
| 114362_at | 1.85 | 0.00 | 4.86 | 4.77 | 2.19 | 0.00 | UNK_AW208678 | AW208678 |
| 114456_i_at | 0.00 | 0.00 | 0.00 | 2.18 | 2.05 | 2.78 | UNK_AI845540 | AI845540 |
| 114457_f_at | 0.00 | 0.00 | 0.00 | 2.03 | 2.05 | 2.60 | UNK_AI845540 | AI845540 |
| 114625_at | 0.00 | 0.00 | 0.00 | 2.00 | 3.47 | 7.02 | UNK_AI851509 | AI851509 |
| 114639_at | 0.00 | 1.75 | 0.00 | 3.14 | 6.05 | 5.01 | UNK_AI317333 | AI317333 |
| 114671_at | 0.00 | 0.00 | 0.00 | 2.08 | 2.22 | 2.52 | UNK_AI841352 | AI841352 |
| 114704_at | 0.00 | 0.00 | 0.00 | 3.00 | 2.86 | 3.76 | UNK_AA822693 | AA822693 |
| 114749_at | 0.00 | 0.00 | 0.00 | 2.16 | 2.72 | 2.70 | UNK_AW107659 | AW107659 |
| 114807_at | 0.00 | 0.00 | 2.23 | 2.33 | 1.46 | 2.09 | UNK_AI627083 | AI627083 |
| 114838_at | 0.00 | 0.00 | 0.00 | 2.76 | 2.51 | 2.30 | UNK_AA624264 | AA624264 |
| 114850_at | 0.00 | 4.93 | 20.51 | 5.87 | 0.00 | 0.00 | UNK_AA138065 | AA138065 |
| 115423_at | 0.00 | 0.00 | 0.00 | 2.19 | 3.32 | 3.16 | UNK_AW045388 | AW045388 |
| 115489_at | 0.00 | 1.75 | 1.96 | 2.11 | 2.67 | 3.02 | UNK_AI851130 | AI851130 |
| 115529_at | 0.00 | 0.00 | 0.00 | 4.30 | 23.77 | 11.55 | UNK_AI853798 | AI853798 |
| 115530_at | 0.00 | 0.00 | 2.66 | 0.00 | 4.19 | 2.70 | UNK_AA034718 | AA034718 |
| 115558_at | 0.00 | −1.22 | 0.00 | 5.43 | 15.06 | 4.67 | UNK_AI549722 | AI549722 |
| 115710_at | 0.00 | 1.71 | 0.00 | 2.33 | 3.51 | 2.87 | UNK_AW048553 | AW048553 |
| 115782_at | 0.00 | 0.00 | 0.00 | 2.58 | 3.24 | 2.25 | UNK_AI845269 | AI845269 |
| 115861_at | 0.00 | 0.00 | 0.00 | 2.56 | 4.71 | 5.81 | UNK_AA544955 | AA544955 |
| 116019_at | 0.00 | 0.00 | 0.00 | 2.31 | 4.51 | 4.20 | UNK_AA646779 | AA646779 |
| 116304_at | 0.00 | 0.00 | 0.00 | 2.62 | 2.71 | 4.84 | UNK_AI848982 | AI848982 |
| 116342_at | 0.00 | 0.00 | 1.99 | 2.40 | 2.04 | 2.09 | UNK_AI605037 | AI605037 |
| 116361_at | 0.00 | 0.00 | 0.00 | 5.08 | 2.90 | 4.34 | UNK_AW120661 | AW120661 |
| 116371_at | 0.00 | 1.76 | 2.58 | 1.92 | 2.39 | 2.10 | UNK_AA184363 | AA184363 |
| 116605_at | 0.00 | 0.00 | 0.00 | 3.18 | 9.23 | 12.30 | UNK_AI846130 | AI846130 |
| 116807_at | 0.00 | 0.00 | 0.00 | 2.83 | 8.66 | 13.74 | UNK_AI846342 | AI846342 |
| 116890_at | 0.00 | 0.00 | 0.00 | 2.33 | 3.60 | 2.63 | UNK_AW124225 | AW124225 |
| 116956_at | 0.00 | 0.00 | 0.00 | 3.64 | 7.36 | 6.60 | UNK_AI848366 | AI848366 |
| 116979_at | 0.00 | 0.00 | 0.00 | 2.07 | 2.07 | 3.57 | UNK_AW123277 | AW123277 |
| 117071_at | 0.00 | 0.00 | 0.00 | 2.46 | 6.44 | 10.77 | UNK_AA796399 | AA796399 |
| 117257_at | 0.00 | 0.00 | 0.00 | 2.38 | 2.89 | 4.95 | UNK_AI853746 | AI853746 |
| 117317_at | 0.00 | 0.00 | 0.00 | 5.30 | 7.21 | 4.70 | UNK_AI851921 | AI851921 |
| 128809_at | 0.00 | 0.00 | 0.00 | 2.30 | 5.74 | 5.68 | UNK_AA606775 | AA606775 |
| 129315_at | 0.00 | 0.00 | 0.00 | 2.13 | 2.07 | 2.28 | UNK_AI122193 | AI122193 |
| 129444_f_at | 0.00 | 2.18 | 0.00 | 0.00 | 3.74 | 5.87 | UNK_AW215481 | AW215481 |
| 131513_s_at | 0.00 | 0.00 | 0.00 | 2.13 | 2.35 | 5.06 | UNK_AI415094 | AI415094 |
| 134041_at | 0.00 | 2.25 | 0.00 | 2.69 | 1.52 | 2.01 | UNK_AA267733 | AA267733 |
| 137130_at | 0.00 | 0.00 | 0.00 | 3.26 | 3.04 | 4.23 | UNK_AI662755 | AI662755 |
| 92350_at | 0.00 | 1.66 | 0.00 | 0.00 | 2.28 | 2.81 | UNK_AA165759 | AA165759 |
| 92778_i_at | 0.00 | 0.00 | 0.00 | 0.00 | 2.57 | 2.94 | virus locus 43; Mtv43 | Z22552 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 92836_at | 0.00 | 0.00 | 0.00 | 0.00 | 2.68 | 4.38 | UNK_AA919594 | AA919594 |
| 93376_at | 0.00 | 2.10 | 2.01 | 0.00 | 1.58 | 1.62 | 0 | AA673486 |
| 93437_f_at | 0.00 | 0.00 | 1.17 | 0.00 | 2.71 | 3.32 | UNK_AI850509 | AI850509 |
| 93439_f_at | 0.00 | 0.00 | 0.00 | 0.00 | 7.78 | 4.37 | UNK_AA260005 | AA260005 |
| 93440_at | 0.00 | 0.00 | 0.00 | 0.00 | 2.55 | 2.36 | 0 | AA692530 |
| 93480_at | 0.00 | 0.00 | 0.00 | 1.72 | 3.43 | 2.21 | UNK_AI845559 | AI845559 |
| 93485_at | 0.00 | 0.00 | 0.00 | 0.00 | 4.92 | 6.45 | UNK_AI844911 | AI844911 |
| 93496_at | 0.00 | 0.00 | 0.00 | 1.93 | 2.03 | 2.48 | UNK_AI852098 | AI852098 |
| 93774_at | 0.00 | 0.00 | 0.00 | 6.70 | 7.93 | 0.00 | UNK_AW049040 | AW049040 |
| 93835_at | 0.00 | 0.00 | 0.00 | 0.00 | 3.31 | 3.09 | UNK_AI843222 | AI843222 |
| 94024_at | 0.00 | 0.00 | 1.12 | 1.99 | 2.02 | 2.42 | UNK_AA671429 | AA671429 |
| 94081_at | 0.00 | 0.00 | 0.00 | 3.48 | 2.65 | 0.00 | UNK_AW124390 | AW124390 |
| 94211_at | 0.00 | 0.00 | 0.00 | 0.00 | 3.56 | 3.72 | UNK_AA959180 | AA959180 |
| 94332_at | 0.00 | 0.00 | 0.00 | 0.00 | 2.04 | 2.61 | UNK_AI882555 | AI882555 |
| 94340_at | 0.00 | 0.00 | 0.00 | 0.00 | 4.53 | 3.65 | UNK_AW124224 | AW124224 |
| 94374_at | 0.00 | 0.00 | 0.00 | 2.30 | 1.99 | 2.48 | UNK_AI850378 | AI850378 |
| 94377_at | 0.00 | 0.00 | 0.00 | 0.00 | 2.16 | 2.62 | UNK_AI854793 | AI854793 |
| 94395_at | 0.00 | 0.00 | 0.00 | 1.91 | 2.23 | 3.23 | UNK_AI194254 | AI194254 |
| 94441_at | 0.00 | 0.00 | 0.00 | 0.00 | 3.02 | 2.46 | UNK_AW061237 | AW061237 |
| 94506_at | 0.00 | 0.00 | 2.59 | 0.00 | 2.93 | 1.86 | UNK_AI853113 | AI853113 |
| 94509_at | 0.00 | 0.00 | 0.00 | 2.02 | 2.30 | 0.00 | UNK_AI851207 | AI851207 |
| 94548_at | 0.00 | 1.28 | 1.48 | 2.07 | 1.86 | 2.36 | UNK_AI790537 | AI790537 |
| 94556_at | 0.00 | 0.00 | 0.00 | 1.89 | 2.41 | 11.99 | UNK_AI746846 | AI746846 |
| 94689_at | 0.00 | 0.00 | 0.00 | 0.00 | 2.23 | 2.86 | UNK_C79248 | C79248 |
| 94743_f_at | 0.00 | 0.00 | 0.00 | 0.00 | 2.32 | 7.35 | 0 | M29009 |
| 94814_at | 0.00 | 1.90 | 1.70 | 0.00 | 3.26 | 3.29 | UNK_AI957190 | AI957190 |
| 94971_at | 0.00 | 0.00 | 3.21 | 0.00 | 2.70 | 0.00 | UNK_AI317217 | AI317217 |
| 94989_at | 0.00 | 0.00 | 0.00 | 2.00 | 2.33 | 2.29 | UNK_AI848984 | AI848984 |
| 94991_at | 0.00 | 0.00 | 0.00 | 0.00 | 3.63 | 3.44 | UNK_AW046661 | AW046661 |
| 94993_f_at | 0.00 | 0.00 | 0.00 | 0.00 | 2.61 | 11.61 | UNK_M29010 | M29010 |
| 95037_at | 0.00 | 0.00 | 0.00 | 2.96 | 3.93 | 0.00 | UNK_AW046639 | AW046639 |
| 95118_r_at | 0.00 | 0.00 | 0.00 | 0.00 | 5.66 | 4.58 | UNK_AI131895 | AI131895 |
| 95135_at | 0.00 | 2.06 | 1.73 | 3.10 | 1.99 | 0.00 | UNK_AI844396 | AI844396 |
| 95150_at | 0.00 | 2.53 | 0.00 | 2.86 | 1.48 | 1.58 | UNK_AI852196 | AI852196 |
| 95153_at | 0.00 | 0.00 | 0.00 | 0.00 | 2.28 | 2.00 | UNK_AI845988 | AI845988 |
| 95288_i_at | 0.00 | 0.00 | 0.00 | 1.42 | 2.84 | 2.83 | 0 | AA189811 |
| 95387_f_at | 0.00 | 0.00 | 0.00 | 0.00 | 3.38 | 2.85 | 0 | AA266467 |
| 95420_at | 0.00 | 0.00 | 0.00 | 0.00 | 2.57 | 3.47 | UNK_AW120625 | AW120625 |
| 95474_at | 0.00 | 0.00 | 0.00 | 0.00 | 2.67 | 5.20 | UNK_AW123850 | AW123850 |
| 95496_at | 0.00 | 0.00 | 0.00 | 0.00 | 4.46 | 3.06 | UNK_AI848866 | AI848866 |
| 95523_at | 0.00 | 0.00 | 0.00 | 0.00 | 2.13 | 2.82 | UNK_AI839718 | AI839718 |
| 95593_at | 0.00 | 0.00 | 0.00 | 1.98 | 5.35 | 4.42 | UNK_AW125446 | AW125446 |
| 95612_at | 0.00 | 1.74 | 3.56 | 0.00 | 3.63 | 0.00 | UNK_AA667128 | AA667128 |
| 95656_i_at | 0.00 | 2.27 | 2.14 | 0.00 | 0.00 | 0.00 | D13WSU177E | AW125164 |
| 95677_at | 0.00 | 0.00 | 0.00 | 0.00 | 2.40 | 2.21 | UNK_AA881621 | AA881621 |
| 95723_r_at | 0.00 | 0.00 | 0.00 | 1.53 | 2.04 | 2.07 | SUPT6H | AI841464 |
| 95732_at | 0.00 | 0.00 | 0.00 | 2.19 | 2.49 | 0.00 | UNK_AW047746 | AW047746 |
| 95881_f_at | 0.00 | 0.00 | 0.00 | 0.00 | 3.08 | 2.41 | UNK_AI447783 | AI447783 |
| 96132_at | 0.00 | 0.00 | 1.29 | 0.00 | 3.66 | 4.28 | UNK_AB023957 | AB023957 |
| 96154_at | 0.00 | 0.00 | 0.00 | 3.17 | 1.96 | 4.47 | UNK_AA600645 | AA600645 |
| 96200_at | 0.00 | 1.80 | 0.00 | 2.95 | 5.39 | 0.00 | UNK_AI838344 | AI838344 |
| 96236_at | 0.00 | 0.00 | 0.00 | 2.36 | 3.17 | 1.99 | UNK_AW122965 | AW122965 |
| 96264_at | 0.00 | 0.00 | 0.00 | 2.56 | 4.65 | 0.00 | UNK_AW061235 | AW061235 |
| 96266_at | 0.00 | 0.00 | 1.86 | 2.85 | 2.40 | 1.74 | UNK_AI841982 | AI841982 |
| 96272_at | 0.00 | 0.00 | 0.00 | 0.00 | 4.76 | 4.20 | UNK_AI848471 | AI848471 |
| 96336_at | 0.00 | 1.53 | 0.00 | 2.46 | 2.17 | 0.00 | UNK_AI844626 | AI844626 |
| 96360_at | 0.00 | 1.65 | 0.00 | 0.00 | 3.16 | 3.53 | UNK_AW125498 | AW125498 |
| 96464_at | 0.00 | 0.00 | 0.00 | 1.94 | 2.50 | 2.50 | 0 | N28179 |
| 96602_g_at | 0.00 | 0.00 | 0.00 | 0.00 | 4.91 | 4.54 | UNK_AW045751 | AW045751 |
| 96716_at | 0.00 | 0.00 | 0.00 | 0.00 | 2.39 | 2.46 | UNK_AW121102 | AW121102 |
| 96818_at | 0.00 | 0.00 | 0.00 | 0.00 | 2.72 | 2.98 | UNK_AA762522 | AA762522 |
| 96832_at | 0.00 | 0.00 | 0.00 | 2.05 | 1.96 | 2.56 | UNK_AA606878 | AA606878 |
| 96896_at | 0.00 | 1.77 | 0.00 | 2.42 | 1.85 | 2.35 | UNK_AW214159 | AW214159 |
| 96924_at | 0.00 | 0.00 | 0.00 | 0.00 | 2.43 | 2.83 | UNK_AI849719 | AI849719 |
| 96925_at | 0.00 | 0.00 | 0.00 | 3.83 | 4.12 | 1.93 | UNK_AW122429 | AW122429 |
| 97163_g_at | 0.00 | 0.00 | 0.00 | 0.00 | 2.04 | 3.16 | UNK_AI563699 | AI563699 |
| 97269_f_at | 0.00 | 0.00 | 0.00 | 2.11 | 2.23 | 1.88 | UNK_AI848699 | AI848699 |
| 97311_at | 0.00 | 0.00 | 0.00 | 2.11 | 2.02 | 1.97 | UNK_AI836509 | AI836509 |
| 97329_at | 0.00 | 0.00 | 0.00 | 0.00 | 2.18 | 2.05 | UNK_AW124061 | AW124061 |
| 97349_at | 0.00 | 0.00 | 0.00 | 0.00 | 3.35 | 5.09 | UNK_AA727410 | AA727410 |
| 97398_at | 0.00 | 0.00 | 0.00 | 0.00 | 6.60 | 6.60 | UNK_AI849831 | AI849831 |
| 97451_at | 0.00 | 2.12 | 0.00 | 2.88 | 1.85 | 1.82 | UNK_AI837599 | AI837599 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 97560_at | 0.00 | 0.00 | 0.00 | 0.00 | 2.40 | 2.30 | UNK_AF037437 | AF037437 |
| 97809_at | 0.00 | 0.00 | 0.00 | 1.83 | 2.19 | 2.27 | UNK_AF109906 | AF109906 |
| 97919_at | 0.00 | 0.00 | 0.00 | 0.00 | 2.28 | 2.08 | UNK_AI837467 | AI837467 |
| 98060_at | 0.00 | 0.00 | 2.93 | 0.00 | 4.09 | 0.00 | lamin A; Lmna | D49733 |
| 98355_at | 0.00 | 0.00 | 0.00 | 0.00 | 2.92 | 6.08 | 0 | AA544993 |
| 98492_at | 0.00 | 1.34 | 0.00 | 0.00 | 2.63 | 2.76 | UNK_AA920419 | AA920419 |
| 98515_at | 0.00 | 1.85 | 0.00 | 0.00 | 3.10 | 2.80 | UNK_AI844392 | AI844392 |
| 98633_at | 0.00 | 0.00 | 0.00 | 2.17 | 2.06 | 1.93 | UNK_AI854863 | AI854863 |
| 99156_at | 0.00 | 0.00 | 0.00 | 0.00 | 2.24 | 2.28 | UNK_AI853370 | AI853370 |
| 99163_at | 0.00 | 0.00 | 0.00 | 0.00 | 6.28 | 3.78 | UNK_AI844232 | AI844232 |
| 99168_at | 0.00 | 0.00 | 0.00 | 0.00 | 3.58 | 3.28 | UNK_AW047128 | AW047128 |
| 99338_at | 0.00 | 0.00 | 0.00 | 0.00 | 4.39 | 4.16 | UNK_AA674798 | AA674798 |
| 99451_at | 0.00 | 0.00 | 0.00 | 0.00 | 12.07 | 9.19 | UNK_AW060510 | AW060510 |
| 99467_at | 0.00 | 0.00 | 0.00 | 0.00 | 2.01 | 2.13 | UNK_AI846922 | AI846922 |
| 99645_at | 0.00 | 0.00 | 0.00 | 0.00 | 2.10 | 3.75 | UNK_AW048484 | AW048484 |
| 99992_at | 0.00 | 2.80 | 0.00 | 0.00 | 2.29 | 0.00 | IL17R | AI286698 |
| 100466_f_at | 0.00 | 0.00 | 0.00 | 0.00 | 3.15 | 4.34 | UNK_AA655823 | AA655823 |
| 100979_at | 0.00 | 0.00 | 0.00 | 0.00 | 2.36 | 3.04 | UNK_AW209763 | AW209763 |
| 100988_at | 0.00 | 0.00 | 0.00 | 0.00 | 2.12 | 4.41 | UNK_AA796690 | AA796690 |
| 101426_at | 0.00 | 0.00 | 0.00 | 0.00 | 3.70 | 4.09 | UNK_AW125333 | AW125333 |
| 101432_at | 0.00 | 0.00 | 0.00 | 0.00 | 3.51 | 3.76 | UNK_AI504100 | AI504100 |
| 101505_at | 0.00 | 0.00 | 0.00 | 0.00 | 3.05 | 2.74 | UNK_AW121234 | AW121234 |
| 101851_at | 0.00 | 0.00 | 0.00 | 0.00 | 3.98 | 4.82 | MOX2 | AF029215 |
| 101882_s_at | 0.00 | 0.00 | 0.00 | 0.00 | 6.36 | 2.59 | procollagen, type XV, procollagen, type XVIII, alpha 1; Col15a1, Col18a1 | U03715 |
| 102099_f_at | 0.00 | 0.00 | 0.00 | 1.68 | 5.10 | 3.69 | UNK_AI843637 | AI843637 |
| 102331_at | 0.00 | 0.00 | 0.00 | 2.40 | 2.51 | 0.00 | UNK_AW120586 | AW120586 |
| 102352_at | 0.00 | 0.00 | 0.00 | 0.00 | 6.99 | 3.33 | UNK_AW121380 | AW121380 |
| 102370_at | 0.00 | 0.00 | 0.00 | 2.09 | 1.71 | 4.73 | UNK_AA822174 | AA822174 |
| 102562_at | 0.00 | 0.00 | 0.00 | 0.00 | 2.02 | 2.12 | UNK_Z80833 | Z80833 |
| 102848_f_at | 0.00 | 0.00 | 0.00 | 0.00 | 8.43 | 5.42 | UNK_AI840577 | AI840577 |
| 102942_at | 0.00 | 0.00 | 0.00 | 0.00 | 2.12 | 4.85 | UNK_AA683785 | AA683785 |
| 103082_at | 0.00 | 0.00 | 1.69 | 1.90 | 2.78 | 3.55 | UNK_AI847507 | AI847507 |
| 103100_at | 0.00 | 0.00 | 0.00 | 0.00 | 3.42 | 2.16 | UNK_AI788543 | AI788543 |
| 103218_at | 0.00 | 0.00 | 1.24 | 0.00 | 2.76 | 4.58 | 0 | J04761 |
| 103260_at | 0.00 | 1.71 | 0.00 | 2.55 | 1.53 | 5.42 | UNK_AI838553 | AI838553 |
| 103400_at | 0.00 | 0.00 | 0.00 | 1.70 | 2.18 | 2.55 | Unknown | D50523 |
| 103402_at | 0.00 | 0.00 | 0.00 | 0.00 | 3.66 | 4.38 | UNK_AI848522 | AI848522 |
| 103415_at | 0.00 | 0.00 | 0.00 | 0.00 | 2.85 | 2.49 | UNK_AI840925 | AI840925 |
| 103459_at | 0.00 | 1.44 | 0.00 | 0.00 | 3.28 | 2.82 | UNK_AW124544 | AW124544 |
| 103460_at | 0.00 | 0.00 | 0.00 | 0.00 | 8.28 | 9.43 | UNK_AI849939 | AI849939 |
| 103462_at | 0.00 | 2.50 | 2.95 | 0.00 | 1.56 | 1.78 | UNK_AW122239 | AW122239 |
| 103529_at | 0.00 | 0.00 | 0.00 | 0.00 | 3.16 | 3.32 | UNK_AW125505 | AW125505 |
| 103545_at | 0.00 | 0.00 | 1.85 | 2.19 | 2.94 | 1.98 | UNK_AA240695 | AA240695 |
| 103631_at | 0.00 | 0.00 | 0.00 | 2.14 | 2.17 | 0.00 | UNK_AA985795 | AA985795 |
| 103635_at | 0.00 | 0.00 | 0.00 | 0.00 | 2.73 | 2.60 | UNK_AI648925 | AI648925 |
| 103643_at | 0.00 | 0.00 | 0.00 | 2.11 | 2.07 | 0.00 | UNK_AI844784 | AI844784 |
| 103717_at | 0.00 | 0.00 | 0.00 | 2.44 | 4.25 | 0.00 | UNK_AA921411 | AA921411 |
| 103736_at | 0.00 | 0.00 | 1.88 | 2.30 | 1.99 | 3.39 | UNK_AI837786 | AI837786 |
| 103752_r_at | 0.00 | 0.00 | 0.00 | 0.00 | 2.43 | 2.39 | UNK_AW227545 | AW227545 |
| 103891_i_at | 0.00 | 0.00 | 0.00 | 0.00 | 3.19 | 2.98 | UNK_AI197161 | AI197161 |
| 103892_r_at | 0.00 | 0.00 | 0.00 | 0.00 | 3.23 | 3.91 | UNK_AI197161 | AI197161 |
| 103932_at | 0.00 | 1.87 | 0.00 | 2.20 | 2.21 | 1.71 | UNK_AA655311 | AA655311 |
| 103989_at | 0.00 | 0.00 | 0.00 | 1.71 | 2.99 | 2.62 | UNK_AI314715 | AI314715 |
| 104002_at | 0.00 | 0.00 | 0.00 | 0.00 | 4.37 | 2.28 | UNK_AI153693 | AI153693 |
| 104004_at | 0.00 | 0.00 | 0.00 | 0.00 | 3.04 | 4.20 | UNK_AI931876 | AI931876 |
| 104065_at | 0.00 | 1.42 | 1.95 | 0.00 | 2.82 | 3.61 | UNK_AW212878 | AW212878 |
| 104105_at | 0.00 | 0.00 | 0.00 | 0.00 | 3.30 | 3.23 | UNK_AI854665 | AI854665 |
| 104119_at | 0.00 | 0.00 | 0.00 | 0.00 | 2.19 | 3.50 | UNK_AI845028 | AI845028 |
| 104306_at | 0.00 | 0.00 | 0.00 | 3.41 | 3.36 | 0.00 | UNK_AI847886 | AI847886 |
| 104350_at | 0.00 | 0.00 | 0.00 | 0.00 | 2.43 | 3.37 | UNK_AI050321 | AI050321 |
| 104412_at | 0.00 | 0.00 | 0.00 | 0.00 | 3.91 | 5.94 | UNK_AI153412 | AI153412 |
| 104559_at | 0.00 | 0.00 | 0.00 | 0.00 | 2.03 | 2.13 | UNK_AI848162 | AI848162 |
| 104573_at | 0.00 | 1.68 | 0.00 | 2.24 | 2.03 | 0.00 | UNK_AA921069 | AA921069 |
| 104576_at | 0.00 | 0.00 | 0.00 | 2.05 | 1.69 | 2.10 | [H. SAPIENS] | AW212397 |
| 104620_at | 0.00 | 0.00 | 0.00 | 0.00 | 3.31 | 2.61 | UNK_AW123402 | AW123402 |
| 104697_at | 0.00 | 0.00 | 0.00 | 0.00 | 2.23 | 2.13 | UNK_AW121127 | AW121127 |
| 104761_at | 0.00 | 0.00 | 0.00 | 0.00 | 2.03 | 3.75 | UNK_AA612450 | AA612450 |
| 104932_at | 0.00 | 0.00 | 0.00 | 1.83 | 4.86 | 3.78 | UNK_AA197852 | AA197852 |
| 104948_at | 0.00 | 0.00 | 0.00 | 0.00 | 2.26 | 2.71 | UNK_AI591666 | AI591666 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 104983_at | 0.00 | 0.00 | 0.00 | 1.68 | 4.08 | 2.97 | UNK_AA611753 | AA611753 |
| 105012_at | 0.00 | 0.00 | 0.00 | 1.94 | 3.33 | 2.51 | UNK_AI225316 | AI225316 |
| 105453_at | 0.00 | 0.00 | 0.00 | 0.00 | 2.88 | 6.18 | UNK_AI606622 | AI606622 |
| 105500_at | 0.00 | 0.00 | 0.00 | 1.94 | 3.03 | 7.55 | UNK_AA389264 | AA389264 |
| 105538_at | 0.00 | 0.00 | 0.00 | 0.00 | 2.54 | 3.39 | UNK_AA125182 | AA125182 |
| 105580_at | 0.00 | 0.00 | 0.00 | 0.00 | 2.51 | 2.56 | UNK_AA517795 | AA517795 |
| 105647_at | 0.00 | 0.00 | 0.00 | 0.00 | 7.93 | 3.57 | UNK_AI785246 | AI785246 |
| 105659_f_at | 0.00 | 0.00 | 0.00 | 1.50 | 2.02 | 2.83 | UNK_AI789447 | AI789447 |
| 105797_at | 0.00 | 2.70 | 0.00 | 2.84 | 0.00 | 0.00 | UNK_AI842817 | AI842817 |
| 105858_at | 0.00 | 1.49 | 1.76 | 3.05 | 5.07 | 0.00 | UNK_AI847445 | AI847445 |
| 105859_at | 0.00 | 0.00 | 0.00 | 0.00 | 2.11 | 3.34 | UNK_AI834985 | AI834985 |
| 105893_at | 0.00 | 0.00 | 0.00 | 0.00 | 2.08 | 2.51 | UNK_AI852905 | AI852905 |
| 106033_at | 0.00 | 0.00 | 0.00 | 1.47 | 2.68 | 2.69 | UNK_AW125624 | AW125624 |
| 106046_at | 0.00 | 0.00 | 0.00 | 1.57 | 3.54 | 2.03 | UNK_AI847176 | AI847176 |
| 106072_at | 0.00 | 0.00 | 0.00 | 2.01 | 2.17 | 0.00 | UNK_AW122135 | AW122135 |
| 106085_at | 0.00 | 0.00 | 0.00 | 0.00 | 2.40 | 2.34 | UNK_AI850834 | AI850834 |
| 106150_at | 0.00 | 0.00 | 0.00 | 0.00 | 3.81 | 6.45 | UNK_AI840953 | AI840953 |
| 106152_at | 0.00 | 0.00 | 0.00 | 0.00 | 3.62 | 4.07 | UNK_AI845991 | AI845991 |
| 106153_g_at | 0.00 | 0.00 | 0.00 | 1.63 | 2.98 | 3.81 | UNK_AI845991 | AI845991 |
| 106195_at | 0.00 | −1.73 | 0.00 | 0.00 | 4.88 | 2.93 | UNK_AI851948 | AI851948 |
| 106196_at | 0.00 | 0.00 | 0.00 | 0.00 | 3.65 | 3.47 | UNK_AW060432 | AW060432 |
| 106237_at | 0.00 | 0.00 | 0.00 | 0.00 | 3.40 | 3.75 | UNK_AI841243 | AI841243 |
| 106256_at | 0.00 | 1.29 | 2.14 | 1.85 | 2.23 | 1.17 | UNK_AA624068 | AA624068 |
| 106274_at | 0.00 | 0.00 | 0.00 | 2.03 | 1.90 | 2.61 | UNK_AI835482 | AI835482 |
| 106280_at | 0.00 | 0.00 | 0.00 | 0.00 | 2.19 | 2.21 | UNK_AW124976 | AW124976 |
| 106508_at | 0.00 | 0.00 | 0.00 | 0.00 | 2.37 | 2.30 | UNK_AA833228 | AA833228 |
| 106568_at | 0.00 | 0.00 | 0.00 | 0.00 | 2.62 | 2.80 | UNK_AW121589 | AW121589 |
| 106575_at | 0.00 | 0.00 | 0.00 | 0.00 | 2.21 | 2.02 | UNK_AI837294 | AI837294 |
| 106593_g_at | 0.00 | 0.00 | 0.00 | 0.00 | 3.66 | 2.41 | UNK_AI115629 | AI115629 |
| 106602_at | 0.00 | 3.16 | 0.00 | 0.00 | 3.00 | 0.00 | UNK_AA638815 | AA638815 |
| 106892_at | 0.00 | 0.00 | 0.00 | 0.00 | 3.46 | 5.31 | UNK_AW124490 | AW124490 |
| 106927_at | 0.00 | 0.00 | 0.00 | 0.00 | 3.65 | 3.89 | UNK_AI882582 | AI882582 |
| 106930_at | 0.00 | 0.00 | 0.00 | 1.93 | 5.20 | 2.02 | UNK_AW123721 | AW123721 |
| 106941_at | 0.00 | 0.00 | 0.00 | 2.08 | 1.82 | 2.75 | UNK_AA839645 | AA839645 |
| 106997_at | 0.00 | 0.00 | 0.00 | 2.35 | 1.77 | 2.72 | UNK_AI463148 | AI463148 |
| 107009_at | 0.00 | 0.00 | 0.00 | 0.00 | 7.44 | 2.74 | UNK_AI842805 | AI842805 |
| 107042_at | 0.00 | 0.00 | 0.00 | 0.00 | 2.60 | 3.78 | UNK_AW045813 | AW045813 |
| 107112_at | 0.00 | 0.00 | 0.00 | 0.00 | 3.76 | 10.09 | UNK_AI121797 | AI121797 |
| 107378_at | 0.00 | 0.00 | 0.00 | 0.00 | 2.15 | 3.49 | UNK_AW050170 | AW050170 |
| 107399_at | 0.00 | 0.00 | 0.00 | 0.00 | 2.49 | 6.12 | UNK_AW060961 | AW060961 |
| 107423_at | 0.00 | 0.00 | 0.00 | 0.00 | 2.48 | 2.26 | UNK_AI852884 | AI852884 |
| 107438_at | 0.00 | 0.00 | 0.00 | 0.00 | 3.20 | 4.12 | UNK_AI838142 | AI838142 |
| 107518_at | 0.00 | 0.00 | 0.00 | 0.00 | 2.38 | 2.62 | UNK_AA832766 | AA832766 |
| 107581_at | 0.00 | 0.00 | 0.00 | 2.32 | 2.35 | 0.00 | UNK_AI843686 | AI843686 |
| 107596_at | 0.00 | 0.00 | 0.00 | −1.14 | 9.07 | 4.95 | UNK_AW125675 | AW125675 |
| 107598_at | 0.00 | 0.00 | 0.00 | 1.92 | 5.33 | 5.65 | UNK_AW047810 | AW047810 |
| 107830_at | 0.00 | 0.00 | 0.00 | 0.00 | 3.29 | 4.02 | UNK_AI390404 | AI390404 |
| 107916_at | 0.00 | 0.00 | 0.00 | 0.00 | 2.76 | 2.66 | UNK_AA790833 | AA790833 |
| 107994_at | 0.00 | 0.00 | 0.00 | 1.31 | 3.83 | 6.08 | UNK_AI842351 | AI842351 |
| 108014_at | 0.00 | 0.00 | 0.00 | 0.00 | 2.07 | 3.81 | UNK_AI551155 | AI551155 |
| 108330_at | 0.00 | 0.00 | 0.00 | 0.00 | 2.71 | 4.28 | UNK_AI197423 | AI197423 |
| 108339_at | 0.00 | 0.00 | 0.00 | 0.00 | 2.25 | 2.80 | UNK_AI552478 | AI552478 |
| 108365_at | 0.00 | 0.00 | 0.00 | 2.22 | 2.71 | 0.00 | UNK_AA981778 | AA981778 |
| 108367_at | 0.00 | 0.00 | 0.00 | 1.62 | 2.34 | 2.24 | UNK_AI842852 | AI842852 |
| 108478_f_at | 0.00 | 0.00 | 0.00 | 0.00 | 4.66 | 11.84 | UNK_AI785264 | AI785264 |
| 108504_at | 0.00 | 0.00 | 0.00 | 0.00 | 2.43 | 3.32 | UNK_AA795013 | AA795013 |
| 108565_at | 0.00 | −2.68 | −2.95 | 0.00 | 2.66 | 4.55 | UNK_AI853095 | AI853095 |
| 108575_at | 0.00 | 0.00 | 0.00 | 0.00 | 3.01 | 2.34 | UNK_AI842010 | AI842010 |
| 108734_at | 0.00 | 0.00 | 0.00 | 0.00 | 4.10 | 8.50 | UNK_AI853716 | AI853716 |
| 108783_at | 0.00 | 0.00 | 0.00 | 0.00 | 6.00 | 11.46 | UNK_AI835933 | AI835933 |
| 108784_at | 0.00 | 0.00 | 0.00 | 0.00 | 8.87 | 8.96 | UNK_AI427138 | AI427138 |
| 108811_at | 0.00 | 1.85 | 2.48 | 2.14 | 0.00 | 0.00 | UNK_AA981032 | AA981032 |
| 108969_at | 0.00 | 0.00 | 0.00 | 0.00 | 3.24 | 2.99 | UNK_AA220091 | AA220091 |
| 108973_at | 0.00 | 0.00 | 0.00 | 0.00 | 2.39 | 2.49 | UNK_AA958878 | AA958878 |
| 109013_at | 0.00 | 0.00 | 0.00 | 0.00 | 2.37 | 4.57 | UNK_AA710128 | AA710128 |
| 109040_at | 0.00 | 0.00 | 0.00 | 0.00 | 3.68 | 2.21 | UNK_AW213256 | AW213256 |
| 109104_at | 0.00 | 0.00 | 0.00 | 0.00 | 2.21 | 2.65 | UNK_AI853670 | AI853670 |
| 109114_at | 0.00 | 0.00 | 0.00 | 2.29 | 2.25 | 0.00 | UNK_AA792643 | AA792643 |
| 109123_at | 0.00 | 0.00 | 0.00 | 0.00 | 5.75 | 10.65 | UNK_AI839366 | AI839366 |
| 109135_at | 0.00 | 0.00 | 0.00 | 0.00 | 4.42 | 3.77 | UNK_AA645519 | AA645519 |
| 109144_at | 0.00 | 0.00 | 0.00 | 0.00 | 6.29 | 4.92 | UNK_AI852146 | AI852146 |
| 109163_f_at | 0.00 | 0.00 | 0.00 | 0.00 | 4.48 | 3.62 | UNK_AI847246 | AI847246 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 109164_r_at | 0.00 | 0.00 | 0.00 | 1.81 | 2.47 | 3.32 | UNK_AI847246 | AI847246 |
| 109177_at | 0.00 | 0.00 | 0.00 | 4.70 | 6.77 | 0.00 | UNK_AW122327 | AW122327 |
| 109184_at | 0.00 | 1.79 | 0.00 | 0.00 | 2.84 | 2.26 | UNK_AI036137 | AI036137 |
| 109337_at | 0.00 | 0.00 | 0.00 | 0.00 | 2.29 | 2.89 | UNK_AW215538 | AW215538 |
| 109341_at | 0.00 | 0.00 | 0.00 | 0.00 | 2.59 | 4.05 | UNK_AW124078 | AW124078 |
| 109358_f_at | 0.00 | 0.00 | 0.00 | 1.22 | 3.44 | 4.46 | UNK_AI854068 | AI854068 |
| 109359_r_at | 0.00 | −1.18 | 0.00 | 0.00 | 2.84 | 3.91 | UNK_AI854068 | AI854068 |
| 109385_at | 0.00 | 0.00 | 4.32 | 3.49 | 0.00 | 0.00 | UNK_AI315194 | AI315194 |
| 109490_at | 0.00 | 0.00 | 0.00 | 0.00 | 3.14 | 8.37 | UNK_AI646305 | AI646305 |
| 109622_at | 0.00 | 0.00 | 0.00 | 0.00 | 7.24 | 4.22 | UNK_AI594717 | AI594717 |
| 109643_at | 0.00 | 0.00 | 0.00 | 0.00 | 4.67 | 4.71 | UNK_AA170471 | AA170471 |
| 109689_at | 0.00 | 0.00 | 0.00 | 0.00 | 2.74 | 4.09 | UNK_AI115717 | AI115717 |
| 109739_at | 0.00 | 2.73 | 0.00 | 0.00 | 4.00 | 0.00 | UNK_AI853736 | AI853736 |
| 109744_at | 0.00 | 2.54 | 0.00 | 4.22 | 0.00 | 0.00 | UNK_AW046698 | AW046698 |
| 109749_at | 0.00 | 0.00 | 0.00 | 1.65 | 2.85 | 5.82 | UNK_AW125440 | AW125440 |
| 109762_at | 0.00 | 0.00 | 0.00 | 0.00 | 4.69 | 2.51 | UNK_AI854227 | AI854227 |
| 109775_at | 0.00 | 0.00 | 0.00 | 2.41 | 4.00 | 0.00 | UNK_AI842966 | AI842966 |
| 109776_at | 0.00 | 0.00 | 0.00 | 1.93 | 2.82 | 3.21 | UNK_AI849150 | AI849150 |
| 109824_f_at | 0.00 | 0.00 | 1.81 | 2.63 | 1.78 | 2.24 | UNK_AI835703 | AI835703 |
| 109911_at | 0.00 | 0.00 | 0.00 | 1.78 | 2.49 | 2.74 | UNK_AW107484 | AW107484 |
| 110076_at | 0.00 | 0.00 | 0.00 | 0.00 | 2.82 | 3.16 | UNK_AI646560 | AI646560 |
| 110107_at | 0.00 | 0.00 | 0.00 | 0.00 | 2.36 | 2.13 | UNK_AI036500 | AI036500 |
| 110145_at | 0.00 | 0.00 | 0.00 | 0.00 | 2.50 | 2.23 | UNK_AW061334 | AW061334 |
| 110147_at | 0.00 | 0.00 | 0.00 | 0.00 | 2.43 | 2.54 | UNK_AW227605 | AW227605 |
| 110181_at | 0.00 | 2.33 | 0.00 | 0.00 | 1.85 | 3.45 | UNK_AW123683 | AW123683 |
| 110229_at | 0.00 | 5.00 | 3.44 | 1.99 | 0.00 | 0.00 | UNK_AA959125 | AA959125 |
| 110259_at | 0.00 | 0.00 | 0.00 | 0.00 | 2.31 | 3.82 | UNK_AA057986 | AA057986 |
| 110262_at | 0.00 | 0.00 | 0.00 | −1.18 | 2.16 | 3.05 | UNK_AI154379 | AI154379 |
| 110295_at | 0.00 | 0.00 | 0.00 | 0.00 | 2.84 | 10.26 | UNK_AW046707 | AW046707 |
| 110322_at | 0.00 | 0.00 | 0.00 | 1.21 | 2.91 | 2.45 | UNK_AI846841 | AI846841 |
| 110324_at | 0.00 | 0.00 | 0.00 | 0.00 | 3.04 | 2.32 | UNK_AI155963 | AI155963 |
| 110328_at | 0.00 | 0.00 | 0.00 | 0.00 | 3.87 | 2.83 | UNK_AI842437 | AI842437 |
| 110329_at | 0.00 | 0.00 | 0.00 | 2.01 | 1.72 | 2.38 | UNK_AI430629 | AI430629 |
| 110372_at | 0.00 | 0.00 | 1.88 | 2.66 | 2.07 | 0.00 | UNK_AI834822 | AI834822 |
| 110435_at | 0.00 | 0.00 | 0.00 | 0.00 | 2.57 | 2.67 | UNK_AI851412 | AI851412 |
| 110437_at | 0.00 | 0.00 | 0.00 | 2.01 | 3.19 | 0.00 | UNK_AW108175 | AW108175 |
| 110443_at | 0.00 | 0.00 | 0.00 | 0.09 | 3.58 | 3.70 | UNK_AW123547 | AW123547 |
| 110585_at | 0.00 | 0.00 | 0.00 | 0.00 | 2.40 | 2.22 | UNK_AA221341 | AA221341 |
| 110591_at | 0.00 | 0.00 | 0.00 | 0.00 | 3.39 | 4.94 | UNK_AA270831 | AA270831 |
| 110632_at | 0.00 | 0.00 | 0.00 | 1.79 | 2.14 | 3.87 | UNK_AI021658 | AI021658 |
| 110634_at | 0.00 | 0.00 | 0.00 | 0.00 | 2.32 | 2.37 | UNK_AA644787 | AA644787 |
| 110732_at | 0.00 | 0.00 | 0.00 | 0.00 | 2.42 | 2.39 | UNK_AA763948 | AA763948 |
| 110738_at | 0.00 | 0.00 | 0.00 | 1.87 | 2.37 | 2.59 | UNK_AA867029 | AA867029 |
| 110743_at | 0.00 | 0.00 | 0.00 | 0.00 | 4.96 | 6.38 | UNK_AW121291 | AW121291 |
| 110810_at | 0.00 | 0.00 | 0.00 | 2.02 | 1.67 | 2.82 | UNK_AI844703 | AI844703 |
| 111072_at | 0.00 | 0.00 | 0.00 | 1.36 | 2.20 | 2.36 | UNK_AA739282 | AA739282 |
| 111080_at | 0.00 | 0.00 | 0.00 | 0.00 | 2.24 | 3.71 | UNK_AA762313 | AA762313 |
| 111124_at | 0.00 | 0.00 | 0.00 | 1.48 | 3.16 | 3.45 | UNK_AA472921 | AA472921 |
| 111209_at | 0.00 | 0.00 | 0.00 | 3.55 | 2.55 | 0.00 | UNK_AW122433 | AW122433 |
| 111336_at | 0.00 | 0.00 | 0.00 | 0.00 | 19.09 | 8.17 | UNK_AI841087 | AI841087 |
| 111358_at | 0.00 | 0.00 | 0.00 | 0.00 | 2.87 | 4.47 | UNK_AI785284 | AI785284 |
| 111383_at | 0.00 | 0.00 | 0.00 | 0.00 | 2.10 | 2.13 | UNK_AI848661 | AI848661 |
| 111412_at | 0.00 | 0.00 | 0.00 | 0.00 | 4.68 | 11.73 | UNK_AW123189 | AW123189 |
| 111429_f_at | 0.00 | 0.00 | 0.00 | 0.00 | 3.32 | 3.05 | UNK_AW011836 | AW011836 |
| 111447_at | 0.00 | 0.00 | 0.00 | 2.15 | 1.70 | 2.18 | UNK_AI837588 | AI837588 |
| 111476_at | 0.00 | 0.00 | 0.00 | 0.00 | 4.26 | 5.02 | UNK_AW045512 | AW045512 |
| 111695_at | 0.00 | 0.00 | 0.00 | 2.23 | 4.07 | 0.00 | UNK_AW125745 | AW125745 |
| 111698_at | 0.00 | 0.00 | 0.00 | 0.00 | 2.31 | 2.74 | UNK_AW121218 | AW121218 |
| 111735_at | 0.00 | 0.00 | 0.00 | 2.98 | 1.45 | 2.74 | UNK_AI061010 | AI061010 |
| 111747_at | 0.00 | 0.00 | 0.00 | 0.00 | 2.44 | 2.94 | UNK_AW215531 | AW215531 |
| 111809_r_at | 0.00 | 0.00 | 0.00 | 0.00 | 6.07 | 5.28 | UNK_AW049301 | AW049301 |
| 111820_at | 0.00 | 0.00 | 0.00 | 0.00 | 2.28 | 2.14 | UNK_AI225827 | AI225827 |
| 111842_at | 0.00 | 0.00 | 0.00 | 0.00 | 2.39 | 2.76 | UNK_AW121081 | AW121081 |
| 111887_at | 0.00 | 0.00 | 0.00 | 0.00 | 2.19 | 2.38 | UNK_AA726802 | AA726802 |
| 111975_at | 0.00 | 0.00 | 0.00 | 0.00 | 6.01 | 5.95 | UNK_AI844650 | AI844650 |
| 111998_at | 0.00 | 0.00 | 0.00 | 0.00 | 2.61 | 2.22 | UNK_AI606832 | AI606832 |
| 112002_at | 0.00 | 0.00 | 0.00 | 0.00 | 4.22 | 2.88 | UNK_AI641819 | AI641819 |
| 112019_at | 0.00 | 0.00 | 0.00 | 0.00 | 3.76 | 4.45 | UNK_AA881092 | AA881092 |
| 112245_at | 0.00 | 0.00 | 0.00 | 0.00 | 4.57 | 5.35 | UNK_AW122302 | AW122302 |
| 112257_at | 0.00 | 0.00 | 0.00 | 1.84 | 2.97 | 6.53 | UNK_AA958476 | AA958476 |
| 112284_at | 0.00 | 0.00 | 0.00 | 0.00 | 3.54 | 8.72 | UNK_AW124683 | AW124683 |
| 112288_at | 0.00 | 0.00 | 0.00 | 0.00 | 8.31 | 6.31 | UNK_AW120568 | AW120568 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 112289_g_at | 0.00 | 0.00 | 0.00 | 1.34 | 3.02 | 3.48 | UNK_AW120568 | AW120568 |
| 112337_at | 0.00 | 0.00 | 0.00 | 0.00 | 2.56 | 2.03 | UNK_AW045621 | AW045621 |
| 112355_at | 0.00 | 0.00 | 0.00 | 0.00 | 2.23 | 2.45 | UNK_AI156083 | AI156083 |
| 112358_at | 0.00 | 0.00 | 0.00 | 0.00 | 2.24 | 4.50 | UNK_AA681243 | AA681243 |
| 112374_at | 0.00 | 0.00 | 0.00 | 5.63 | 2.94 | 0.00 | UNK_AW046652 | AW046652 |
| 112378_at | 0.00 | 0.00 | 0.00 | 2.04 | 1.86 | 2.06 | UNK_AI842868 | AI842868 |
| 112431_at | 0.00 | 0.00 | 0.00 | 1.58 | 2.09 | 2.91 | UNK_AI853946 | AI853946 |
| 112472_at | 0.00 | 0.00 | 0.00 | 0.00 | 2.38 | 3.08 | UNK_AI286746 | AI286746 |
| 112482_at | 0.00 | 0.00 | 0.00 | 1.29 | 2.05 | 2.04 | UNK_AW208789 | AW208789 |
| 112704_at | 0.00 | 0.00 | 0.00 | 1.67 | 2.06 | 2.33 | UNK_AW228808 | AW228808 |
| 112706_at | 0.00 | 0.00 | 0.00 | 1.69 | 6.43 | 5.73 | UNK_AW212497 | AW212497 |
| 112718_at | 0.00 | 1.41 | 0.00 | 2.02 | 2.27 | 0.00 | UNK_AW230461 | AW230461 |
| 112743_at | 0.00 | 0.00 | 0.00 | 0.00 | 2.31 | 2.41 | UNK_AI157595 | AI157595 |
| 112747_at | 0.00 | 1.77 | 1.64 | 2.12 | 1.86 | 2.04 | UNK_AW106365 | AW106365 |
| 112768_at | 0.00 | 0.00 | 0.00 | 0.00 | 2.01 | 2.45 | UNK_AI227355 | AI227355 |
| 112792_at | 1.77 | 1.62 | 0.00 | 2.00 | 1.83 | 2.40 | UNK_AI843762 | AI843762 |
| 112794_at | 0.00 | 0.00 | 0.00 | 0.00 | 2.12 | 4.37 | UNK_AI844497 | AI844497 |
| 112877_at | 0.00 | 0.00 | 0.00 | 0.00 | 9.13 | 6.99 | UNK_AW228014 | AW228014 |
| 112892_at | 0.00 | 0.00 | 0.00 | 0.00 | 3.90 | 2.90 | UNK_AI316340 | AI316340 |
| 112911_r_at | 0.00 | 0.00 | 0.00 | 1.98 | 7.48 | 2.42 | UNK_AW229261 | AW229261 |
| 112924_at | 0.00 | 0.00 | 0.00 | 0.00 | 2.19 | 3.79 | UNK_AI842606 | AI842606 |
| 112934_at | 0.00 | 0.00 | 0.00 | 1.94 | 5.22 | 4.57 | UNK_AI845672 | AI845672 |
| 112943_at | 0.00 | 0.00 | 0.00 | 1.58 | 2.45 | 2.73 | UNK_AI462057 | AI462057 |
| 112955_at | 0.00 | 0.00 | 0.00 | 0.00 | 26.37 | 10.55 | UNK_AW122703 | AW122703 |
| 112993_at | 0.00 | 0.00 | 0.00 | 0.00 | 4.43 | 2.63 | UNK_AA798461 | AA798461 |
| 113033_at | 0.00 | 0.00 | 0.00 | 2.25 | 1.72 | 2.00 | UNK_AW049519 | AW049519 |
| 113048_at | 0.00 | 0.00 | 0.00 | 1.46 | 2.11 | 3.42 | UNK_AA717403 | AA717403 |
| 113114_at | 0.00 | 0.00 | 0.00 | 0.00 | 8.30 | 7.15 | UNK_AI842299 | AI842299 |
| 113142_at | 0.00 | 1.46 | 0.00 | 1.82 | 4.37 | 4.99 | UNK_AI854696 | AI854696 |
| 113145_at | 0.00 | 0.00 | 0.00 | 0.00 | 2.61 | 3.12 | UNK_AI838163 | AI838163 |
| 113198_at | 0.00 | 0.00 | 1.66 | 2.26 | 2.60 | 0.00 | UNK_AI851615 | AI851615 |
| 113250_at | 0.00 | 0.00 | 0.00 | 0.00 | 2.13 | 2.69 | UNK_AI847212 | AI847212 |
| 113286_at | 0.00 | 0.00 | 0.00 | 2.66 | 1.54 | 2.22 | UNK_AI845147 | AI845147 |
| 113442_at | 0.00 | 0.00 | 2.13 | 2.10 | 1.47 | 0.00 | UNK_AI613741 | AI613741 |
| 113495_at | 0.00 | 0.00 | 0.00 | 0.00 | 2.21 | 3.10 | UNK_AI595304 | AI595304 |
| 113575_at | 0.00 | 0.00 | 0.00 | 2.14 | 3.04 | 0.00 | UNK_AI931943 | AI931943 |
| 113590_at | 0.00 | 0.00 | 0.00 | 0.00 | 2.10 | 2.13 | UNK_AI931548 | AI931548 |
| 113640_at | 0.00 | 0.00 | 0.00 | 0.00 | 13.54 | 17.72 | UNK_AW045201 | AW045201 |
| 113650_at | 0.00 | 0.00 | 0.00 | 0.00 | 8.85 | 9.09 | UNK_AW049728 | AW049728 |
| 113674_at | 0.00 | 0.00 | 1.00 | 0.00 | 3.44 | 3.04 | UNK_AI505611 | AI505611 |
| 113692_at | 0.00 | 0.00 | 0.00 | 1.90 | 2.09 | 3.43 | UNK_AA666755 | AA666755 |
| 113749_at | 0.00 | 0.00 | 0.00 | 0.00 | 2.85 | 3.63 | UNK_AA960059 | AA960059 |
| 113766_at | 0.00 | 0.00 | 0.00 | 0.00 | 2.74 | 3.34 | UNK_AI854004 | AI854004 |
| 113851_at | 0.00 | 0.00 | 0.00 | 0.00 | 3.25 | 5.14 | UNK_AA204063 | AA204063 |
| 113912_at | 0.00 | 0.00 | 0.00 | 0.00 | 2.91 | 4.00 | UNK_AW123902 | AW123902 |
| 113926_at | 0.00 | 0.00 | 0.00 | 0.00 | 2.31 | 2.82 | UNK_AW228609 | AW228609 |
| 113970_at | 0.00 | 0.00 | 0.00 | 1.16 | 2.89 | 2.02 | UNK_AW229038 | AW229038 |
| 114199_at | 0.00 | 0.00 | 0.00 | 1.61 | 4.96 | 4.23 | UNK_AA215054 | AA215054 |
| 114224_at | 0.00 | 0.00 | 0.00 | 0.00 | 8.65 | 10.01 | UNK_AI425989 | AI425989 |
| 114254_at | 0.00 | 0.00 | 0.00 | 0.00 | 3.94 | 2.14 | UNK_AA183037 | AA183037 |
| 114271_at | 0.00 | 0.00 | 0.00 | 0.00 | 3.02 | 2.28 | UNK_AA794755 | AA794755 |
| 114420_at | 0.00 | -3.91 | -3.29 | 0.00 | 3.25 | 4.37 | UNK_AA734866 | AA734866 |
| 114426_at | 0.00 | 0.00 | 0.00 | 0.00 | 3.18 | 3.42 | UNK_AI480529 | AI480529 |
| 114468_at | 0.00 | 0.00 | 0.00 | 0.00 | 3.35 | 2.89 | UNK_AI845124 | AI845124 |
| 114475_at | 0.00 | 0.00 | 0.00 | 0.00 | 2.43 | 2.28 | UNK_AI839459 | AI839459 |
| 114483_at | 0.00 | 0.00 | 0.00 | 0.00 | 3.83 | 4.62 | UNK_AW122384 | AW122384 |
| 114562_at | 0.00 | -1.08 | 0.00 | 0.00 | 6.04 | 7.48 | UNK_AA710515 | AA710515 |
| 114589_at | 0.00 | 0.00 | 0.00 | 1.96 | 2.17 | 3.62 | UNK_AA792890 | AA792890 |
| 114689_at | 0.00 | 0.00 | 0.00 | 2.80 | 3.79 | 0.00 | UNK_AW045811 | AW045811 |
| 114694_at | 0.00 | 0.00 | 0.00 | 0.00 | 2.21 | 2.96 | UNK_AI848139 | AI848139 |
| 114750_at | 0.00 | 0.00 | 1.76 | 1.57 | 2.37 | 2.13 | UNK_AW046379 | AW046379 |
| 114774_at | 0.00 | 0.00 | 0.00 | 0.00 | 2.22 | 3.98 | TCF7L2 | AW211815 |
| 114790_at | 0.00 | 0.00 | 0.00 | 0.00 | 2.64 | 3.20 | UNK_AI594026 | AI594026 |
| 114791_at | 0.00 | 0.00 | 0.00 | 0.00 | 3.14 | 4.04 | UNK_AI834978 | AI834978 |
| 114795_at | 0.00 | 0.00 | 0.00 | 0.00 | 2.26 | 2.83 | UNK_AI158227 | AI158227 |
| 114815_at | 0.00 | 0.00 | 0.00 | 0.00 | 3.31 | 2.88 | UNK_AI155547 | AI155547 |
| 114857_at | 0.00 | 0.00 | 0.00 | 2.87 | 3.49 | 0.00 | UNK_AW048104 | AW048104 |
| 114994_at | 0.00 | 0.00 | 0.00 | 0.00 | 2.80 | 2.87 | UNK_AW050047 | AW050047 |
| 115028_at | 0.00 | 0.00 | 0.00 | 0.09 | 2.64 | 6.54 | UNK_AA711308 | AA711308 |
| 115033_f_at | 0.00 | 0.00 | 0.00 | 2.17 | 3.65 | 0.00 | UNK_AI848847 | AI848847 |
| 115107_at | 0.00 | 0.00 | 0.00 | 1.26 | 17.16 | 2.58 | UNK_AW125312 | AW125312 |
| 115116_at | 1.39 | 0.00 | 0.00 | 0.00 | 2.02 | 2.17 | UNK_AW121890 | AW121890 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 115145_at | 0.00 | 0.00 | 0.00 | 2.13 | 2.14 | 0.00 | UNK_AA789611 | AA789611 |
| 115185_at | 0.00 | 0.00 | 0.00 | 2.52 | 3.20 | 0.00 | UNK_AW124312 | AW124312 |
| 115200_at | 0.00 | 0.00 | 0.00 | 0.00 | 3.56 | 2.19 | UNK_AI643806 | AI643806 |
| 115210_at | 0.00 | 0.00 | 0.00 | 0.00 | 7.58 | 2.25 | UNK_AA985762 | AA985762 |
| 115219_at | 0.00 | 0.00 | 0.00 | 0.00 | 5.64 | 5.93 | UNK_AI607010 | AI607010 |
| 115315_at | 0.00 | 0.00 | 0.00 | 0.00 | 2.12 | 2.43 | UNK_AA068501 | AA068501 |
| 115361_at | 0.00 | 0.00 | 0.00 | 1.31 | 2.33 | 2.22 | UNK_AU045961 | AU045961 |
| 115543_at | 0.00 | 0.00 | 0.00 | 0.00 | 2.32 | 2.45 | UNK_AW120607 | AW120607 |
| 115570_f_at | 0.00 | 0.00 | 0.00 | 1.83 | 2.15 | 3.21 | UNK_AI428995 | AI428995 |
| 115776_at | 0.00 | 0.00 | 0.00 | 0.00 | 3.11 | 2.09 | UNK_AI132212 | AI132212 |
| 115811_at | 0.00 | 0.00 | 0.00 | 0.00 | 16.04 | 6.53 | UNK_AA795075 | AA795075 |
| 115820_at | 0.00 | 0.00 | 0.00 | 0.00 | 2.27 | 4.56 | UNK_AI852255 | AI852255 |
| 115859_at | 0.00 | 0.00 | 0.00 | 2.76 | 6.40 | 0.00 | UNK_AI159157 | AI159157 |
| 115926_at | 0.00 | 0.00 | 0.00 | 0.00 | 21.98 | 21.56 | UNK_AA839289 | AA839289 |
| 115932_at | 0.00 | 0.00 | 0.00 | 0.00 | 3.54 | 3.31 | UNK_AW047504 | AW047504 |
| 115956_at | 0.00 | 0.00 | 0.00 | 1.73 | 2.39 | 4.92 | UNK_AA472455 | AA472455 |
| 115962_at | 0.00 | 0.00 | 0.00 | 0.00 | 14.87 | 7.81 | UNK_AI615325 | AI615325 |
| 116031_at | 0.00 | 0.00 | 0.00 | 0.00 | 2.05 | 2.39 | UNK_AI843837 | AI843837 |
| 116072_at | 0.00 | 0.00 | 0.00 | 2.47 | 2.74 | 0.00 | UNK_AI853043 | AI853043 |
| 116124_at | 0.00 | 0.00 | 0.00 | 0.00 | 2.83 | 3.36 | UNK_AI466198 | AI466198 |
| 116132_at | 0.00 | 0.00 | 0.00 | 2.75 | 3.17 | 0.00 | UNK_AI851807 | AI851807 |
| 116197_at | 0.00 | 0.00 | 0.00 | 2.33 | 2.24 | 0.00 | UNK_AI132005 | AI132005 |
| 116253_at | 0.00 | 0.00 | 0.00 | 0.00 | 2.67 | 3.74 | UNK_AI843499 | AI843499 |
| 116303_at | 0.00 | 0.00 | 0.00 | 1.58 | 3.25 | 2.23 | UNK_AA592780 | AA592780 |
| 116432_at | 0.00 | 0.00 | 0.00 | 1.91 | 4.84 | 3.49 | UNK_AI845744 | AI845744 |
| 116470_at | 0.00 | 0.00 | 0.00 | 0.00 | 2.21 | 4.31 | UNK_AW047556 | AW047556 |
| 116594_at | 0.00 | 0.00 | 0.00 | 1.94 | 5.23 | 4.43 | UNK_AW047008 | AW047008 |
| 116600_at | 0.51 | 0.00 | 0.00 | 0.00 | 6.42 | 2.37 | UNK_AI848448 | AI848448 |
| 116612_at | 0.00 | 0.00 | 0.00 | 0.00 | 3.08 | 3.73 | UNK_AI854230 | AI854230 |
| 116627_at | 0.00 | 0.00 | 0.00 | 0.00 | 2.11 | 2.05 | UNK_AI608135 | AI608135 |
| 116659_at | 0.00 | 0.00 | 0.00 | 0.00 | 2.73 | 3.51 | UNK_AI854578 | AI854578 |
| 116678_at | 0.00 | 0.00 | 0.00 | 2.39 | 2.23 | 1.68 | UNK_AI256490 | AI256490 |
| 116719_at | 0.00 | 0.00 | 1.74 | 2.05 | 1.88 | 2.31 | UNK_AI850429 | AI850429 |
| 116806_at | 0.00 | −0.05 | 1.09 | 0.64 | 12.02 | 5.79 | UNK_AI481202 | AI481202 |
| 116809_at | 0.00 | 0.00 | 0.00 | 0.00 | 3.34 | 4.18 | UNK_AW120749 | AW120749 |
| 116823_at | 0.00 | 0.00 | 0.00 | 0.00 | 2.68 | 3.08 | UNK_AI314071 | AI314071 |
| 116837_at | 0.00 | 0.00 | 0.00 | 0.00 | 3.43 | 3.94 | UNK_AI839054 | AI839054 |
| 116860_at | 0.00 | 0.00 | 0.00 | 0.00 | 2.22 | 2.51 | UNK_AA929441 | AA929441 |
| 116908_at | 0.00 | 0.00 | 0.00 | 0.00 | 2.52 | 2.30 | UNK_AA692402 | AA692402 |
| 116942_at | 0.00 | 0.00 | 0.00 | 1.90 | 2.63 | 2.14 | UNK_AI838939 | AI838939 |
| 116963_at | 0.00 | 0.00 | 0.00 | 2.77 | 3.27 | 0.00 | UNK_AW125370 | AW125370 |
| 116989_at | 0.00 | 0.00 | 0.00 | 0.00 | 3.12 | 3.03 | UNK_AI852587 | AI852587 |
| 117030_at | 0.00 | 0.00 | 0.00 | 0.00 | 5.28 | 4.57 | UNK_AI838603 | AI838603 |
| 117099_at | 0.00 | 0.00 | 0.00 | 0.00 | 2.08 | 2.57 | UNK_AI851714 | AI851714 |
| 117145_at | 0.00 | 0.00 | 0.00 | 0.00 | 4.05 | 3.74 | UNK_AI850896 | AI850896 |
| 117183_at | 0.00 | 0.00 | 0.00 | 1.96 | 2.07 | 2.56 | UNK_AI842864 | AI842864 |
| 117207_at | 0.00 | 0.00 | 0.00 | 0.00 | 6.29 | 4.16 | UNK_AI854445 | AI854445 |
| 117270_at | 0.00 | 0.00 | 0.00 | 2.36 | 2.16 | 0.00 | UNK_AI843596 | AI843596 |
| 117277_at | 0.00 | 0.00 | 0.00 | 1.82 | 5.08 | 7.60 | UNK_AI850694 | AI850694 |
| 129639_at | 0.00 | 0.00 | 0.00 | 0.00 | 5.71 | 10.00 | UNK_AW214378 | AW214378 |
| 130183_at | 0.00 | 0.00 | 0.00 | 2.33 | 1.64 | 3.07 | UNK_AI643934 | AI643934 |
| 130391_at | 0.00 | 0.00 | 0.00 | 0.00 | 2.13 | 4.79 | UNK_AI042932 | AI042932 |
| 130507_at | 0.00 | 0.00 | 0.00 | 0.00 | 2.01 | 3.69 | UNK_AI846909 | AI846909 |
| 131792_s_at | 0.00 | 0.00 | 0.00 | 0.00 | 5.10 | 6.58 | UNK_AI850822 | AI850822 |
| 133116_at | 0.00 | 0.00 | 0.00 | 0.00 | 3.46 | 5.36 | UNK_AA754682 | AA754682 |
| 134513_f_at | 0.00 | 0.00 | 0.00 | 1.81 | 2.12 | 3.20 | UNK_AI852600 | AI852600 |
| 134631_at | 0.00 | 2.91 | 0.00 | 3.80 | 0.00 | 0.00 | UNK_AI154756 | AI154756 |
| 134747_at | 0.00 | 0.00 | 0.00 | 0.00 | 8.56 | 7.68 | UNK_AI662497 | AI662497 |
| 135131_at | 0.00 | 0.00 | 0.00 | 0.00 | 5.42 | 5.34 | UNK_AI508877 | AI508877 |
| 135201_at | 0.00 | −3.44 | −2.08 | 0.00 | 2.29 | 3.08 | UNK_AA420078 | AA420078 |
| 135263_at | 0.00 | 0.00 | 0.00 | 0.00 | 2.50 | 10.32 | UNK_AI850317 | AI850317 |
| 135433_at | 0.00 | 0.00 | 0.00 | 2.53 | 2.11 | 1.80 | UNK_AI529496 | AI529496 |
| 135743_at | 0.00 | 0.00 | 0.00 | 0.00 | 6.47 | 10.98 | UNK_AI849654 | AI849654 |
| 136618_at | 0.00 | 0.00 | 0.00 | 2.36 | 2.06 | 0.00 | UNK_AW121395 | AW121395 |
| 137046_s_at | 0.00 | 1.74 | 0.00 | 0.00 | 4.40 | 7.29 | UNK_AI854440 | AI854440 |
| 138476_at | 0.00 | 0.00 | 0.00 | 0.00 | 2.20 | 2.62 | UNK_AI851865 | AI851865 |
| 139147_at | 0.00 | 0.00 | 0.00 | 0.00 | 3.32 | 7.41 | UNK_AW121331 | AW121331 |
| 139184_at | 0.00 | 0.00 | 0.00 | 1.70 | 2.72 | 3.87 | UNK_AI851432 | AI851432 |
| 140220_r_at | 0.00 | 0.00 | 0.00 | 3.07 | 2.67 | 0.00 | UNK_AI846774 | AI846774 |
| 140833_at | 0.00 | 0.00 | 0.00 | 3.27 | 1.92 | 5.46 | UNK_AI427839 | AI427839 |
| 92233_at | 0.00 | 0.00 | 0.00 | 1.91 | 1.90 | 2.14 | UNK_AI098965 | AI098965 |
| 92280_at | 0.00 | 0.00 | 0.00 | 0.00 | 2.51 | 1.66 | UNK_AA867778 | AA867778 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 93018_at | 0.00 | 0.00 | 0.00 | 0.00 | 3.93 | 0.00 | UNK_AI790103 | AI790103 |
| 93184_at | 0.00 | 0.00 | 0.00 | 0.00 | 1.97 | 3.33 | UNK_AI596362 | AI596362 |
| 93187_at | 0.00 | 1.31 | 0.00 | 1.91 | 1.60 | 2.47 | UNK_AW048347 | AW048347 |
| 93270_at | 0.00 | 0.00 | 0.00 | 0.00 | 2.13 | 0.00 | UNK_AI839918 | AI839918 |
| 93283_at | 0.00 | 0.00 | 0.00 | 0.00 | 2.65 | 0.00 | UNK_AA869401 | AA869401 |
| 93336_at | 0.00 | 0.00 | 0.00 | 1.85 | 2.26 | 1.90 | UNK_AW121539 | AW121539 |
| 93471_at | 0.00 | 1.62 | 0.00 | 0.00 | 1.78 | 2.03 | UNK_AI594427 | AI594427 |
| 93609_at | 0.00 | 0.00 | 0.00 | 0.00 | 2.72 | 0.00 | UNK_AA797709 | AA797709 |
| 93719_at | 0.00 | 0.00 | 0.00 | 0.00 | 1.88 | 5.54 | UNK_AA050273 | AA050273 |
| 93724_at | 0.00 | 0.00 | 0.00 | 0.00 | 2.22 | 1.81 | NTRKR2 | AI596034 |
| 93805_at | 0.00 | 0.00 | 0.00 | 0.00 | 2.64 | 1.86 | UNK_AW121164 | AW121164 |
| 93821_at | 0.00 | 0.00 | 0.00 | 0.00 | 1.66 | 2.29 | UNK_AW046101 | AW046101 |
| 94019_at | 0.00 | 0.00 | 0.00 | 1.98 | 1.94 | 2.15 | UNK_AI852534 | AI852534 |
| 94245_at | 0.00 | 0.00 | 0.00 | 0.00 | 2.32 | 1.77 | UNK_AW125865 | AW125865 |
| 94253_at | 0.00 | 0.00 | 0.00 | 2.26 | 1.54 | 0.00 | UNK_AW061243 | AW061243 |
| 94286_at | 0.00 | 0.00 | 0.00 | 2.18 | 1.84 | 1.93 | UNK_AW050340 | AW050340 |
| 94367_at | 0.00 | 1.90 | 1.65 | 0.00 | 2.11 | 0.00 | UNK_AI850362 | AI850362 |
| 94433_at | 0.00 | 1.59 | 0.00 | 0.00 | 1.88 | 2.17 | UNK_AW060684 | AW060684 |
| 94514_s_at | 0.00 | 0.00 | 0.00 | 0.00 | 2.14 | 1.91 | UNK_AI853439 | AI853439 |
| 94537_at | 0.00 | 0.00 | 0.00 | 1.34 | 1.36 | 2.15 | UNK_AI838859 | AI838859 |
| 94771_at | 0.00 | 2.20 | 0.00 | 0.00 | 0.00 | 0.00 | 0 | AA178600 |
| 94842_at | 0.00 | 0.00 | 0.00 | 0.00 | 2.22 | 0.00 | UNK_AI853630 | AI853630 |
| 94876_f_at | 0.00 | 0.00 | 0.00 | 2.09 | 1.87 | 0.00 | UNK_AI849207 | AI849207 |
| 94963_at | 0.00 | 0.00 | 0.00 | 2.09 | 1.75 | 0.00 | UNK_AI462105 | AI462105 |
| 95029_at | 0.00 | 0.00 | 0.00 | 0.00 | 3.06 | 0.00 | UNK_AW046747 | AW046747 |
| 95094_g_at | 0.00 | 0.00 | 0.00 | 0.00 | 2.20 | 1.98 | UNK_AI035334 | AI035334 |
| 95147_at | 0.00 | 0.00 | 0.00 | 1.58 | 2.20 | 1.92 | UNK_AI843795 | AI843795 |
| 95393_at | 0.00 | 0.00 | 0.00 | 0.00 | 2.53 | 0.00 | UNK_AI503362 | AI503362 |
| 95415_f_at | 0.00 | 0.00 | 0.00 | 0.00 | 1.87 | 2.19 | C1R | AI132585 |
| 95444_at | 0.00 | 0.00 | 0.00 | 2.06 | 1.86 | 1.68 | UNK_AW122274 | AW122274 |
| 95604_at | 0.00 | 0.00 | 0.00 | 0.00 | 3.22 | 0.00 | UNK_AI843294 | AI843294 |
| 95643_at | 0.00 | 0.00 | 0.00 | 0.00 | 4.39 | 0.00 | UNK_AW050287 | AW050287 |
| 95675_at | 0.00 | 0.00 | 0.00 | 0.00 | 1.94 | 2.96 | UNK_AW121182 | AW121182 |
| 95714_at | 0.00 | 2.17 | 0.00 | 0.00 | 1.95 | 1.66 | UNK_AI226264 | AI226264 |
| 95939_i_at | 0.00 | 3.03 | 0.00 | 0.00 | 1.49 | 0.00 | UNK_AW047237 | AW047237 |
| 96029_at | 0.00 | 0.00 | 0.00 | 2.23 | 1.82 | 0.00 | UNK_AI020542 | AI020542 |
| 96155_at | 0.00 | 0.00 | 0.00 | 0.00 | 3.63 | 0.00 | UNK_AW049359 | AW049359 |
| 96186_at | 0.00 | 0.00 | 0.00 | 0.00 | 1.78 | 3.07 | UNK_AI839286 | AI839286 |
| 96269_at | 0.00 | 0.00 | 1.65 | 2.04 | 0.00 | 0.00 | UNK_AA716963 | AA716963 |
| 96278_at | 0.00 | 0.00 | 0.00 | 0.00 | 1.86 | 2.11 | UNK_AI846553 | AI846553 |
| 96329_at | 0.00 | 0.00 | 0.00 | 2.29 | 1.95 | 0.00 | UNK_AI837793 | AI837793 |
| 96342_at | 0.00 | 0.00 | 0.00 | 2.02 | 1.83 | 1.77 | UNK_AI846320 | AI846320 |
| 96516_at | 0.00 | 0.00 | 0.00 | 0.00 | 2.55 | 0.00 | UNK_AA960459 | AA960459 |
| 96533_at | 0.00 | 0.00 | 0.00 | 2.02 | 0.00 | 0.00 | UNK_AI508931 | AI508931 |
| 96609_at | 0.00 | 0.00 | 0.00 | 2.00 | 1.79 | 1.94 | UNK_AW122195 | AW122195 |
| 96640_at | 0.00 | 0.00 | 0.00 | 0.00 | 1.83 | 3.26 | UNK_AI644158 | AI644158 |
| 96698_at | 0.00 | 0.00 | 0.00 | 0.00 | 2.18 | 0.00 | UNK_AI835520 | AI835520 |
| 96725_at | 0.00 | 1.54 | 0.00 | 0.00 | 1.66 | 2.27 | UNK_AI838398 | AI838398 |
| 96739_at | 0.00 | 0.00 | 0.00 | 0.00 | 3.08 | 0.00 | UNK_AI852409 | AI852409 |
| 96748_i_at | 0.00 | 0.00 | 1.18 | 0.00 | 2.53 | 1.86 | UNK_AA619554 | AA619554 |
| 96762_at | 0.00 | 0.00 | 0.00 | 0.00 | 1.87 | 2.00 | UNK_AW046160 | AW046160 |
| 96763_at | 0.00 | 0.00 | 0.00 | 0.00 | 2.13 | 1.88 | UNK_AI839995 | AI839995 |
| 96773_at | 0.00 | 0.00 | 0.00 | 2.49 | 1.75 | 0.00 | UNK_AW125408 | AW125408 |
| 96791_at | 0.00 | 0.00 | 0.00 | 0.00 | 2.06 | 1.97 | UNK_AW047875 | AW047875 |
| 96827_at | 0.00 | 0.00 | 0.00 | 0.00 | 4.81 | 0.00 | UNK_AW061272 | AW061272 |
| 96833_at | 0.00 | 0.00 | 0.00 | 0.00 | 2.26 | 0.00 | UNK_AW048468 | AW048468 |
| 96854_at | 0.00 | 0.00 | 0.00 | 1.95 | 2.13 | 1.77 | COPA | AJ010391 |
| 97199_at | 0.00 | 0.00 | 0.00 | 1.54 | 1.63 | 2.21 | UNK_AI854767 | AI854767 |
| 97217_at | 0.00 | 0.00 | 0.00 | 1.78 | 1.76 | 2.16 | UNK_AI842095 | AI842095 |
| 97268_i_at | 0.00 | 0.00 | 0.00 | 1.85 | 2.67 | 1.96 | UNK_AI848699 | AI848699 |
| 97359_at | 0.00 | 0.00 | 0.00 | 0.00 | 2.10 | 1.85 | UNK_AI851160 | AI851160 |
| 97364_at | 0.00 | 0.00 | 0.00 | 0.00 | 3.61 | 0.00 | UNK_AW213865 | AW213865 |
| 97423_at | 0.00 | 0.00 | 0.00 | 0.00 | 2.28 | 0.00 | UNK_AI839819 | AI839819 |
| 97486_at | 0.00 | 1.48 | 0.00 | 2.11 | 0.00 | 0.00 | UNK_AA693246 | AA693246 |
| 97704_at | 0.00 | 0.00 | 0.00 | 0.00 | 3.14 | 0.00 | 0 | AA414990 |
| 97713_at | 0.00 | 0.00 | 0.00 | 0.00 | 2.23 | 0.00 | UNK_AW214336 | AW214336 |
| 97839_at | 0.00 | 1.91 | 0.00 | 2.32 | 1.80 | 1.97 | UNK_AI841960 | AI841960 |
| 97865_g_at | 0.00 | 0.00 | 0.00 | 0.00 | 1.98 | 3.57 | UNK_AW258842 | AW258842 |
| 97892_at | 0.00 | 0.00 | 0.00 | 0.00 | 2.06 | 0.00 | UNK_AI844732 | AI844732 |
| 97903_at | 0.00 | 0.00 | 0.00 | 0.00 | 3.15 | 0.00 | UNK_AW050078 | AW050078 |
| 97949_at | 0.00 | 1.62 | 0.00 | 2.03 | 0.00 | 0.00 | fibrinogen-like protein 2; Fgl2 | M16238 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 97960_at | 0.00 | 0.00 | 0.00 | 0.00 | 2.65 | 1.44 | UNK_AW125800 | AW125800 |
| 98051_at | 0.00 | 0.00 | 0.00 | 0.00 | 1.60 | 2.00 | GS15 | AI852808 |
| 98431_at | 0.00 | 0.00 | 0.00 | 0.00 | 3.32 | 0.00 | UNK_AW049275 | AW049275 |
| 98495_at | 0.00 | 0.00 | 0.00 | 1.96 | 2.51 | 1.95 | UNK_AI846906 | AI846906 |
| 98528_at | 0.00 | 0.00 | 0.00 | 0.00 | 2.15 | 1.48 | UNK_AI854901 | AI854901 |
| 98896_at | 0.00 | 0.00 | 0.00 | 0.00 | 1.56 | 2.34 | UNK_AW 122980 | AW122980 |
| 98948_at | 0.00 | 0.00 | 0.00 | 0.00 | 2.77 | 0.00 | UNK_AI785289 | AI785289 |
| 98957_at | 0.00 | 0.00 | 0.00 | 0.00 | 2.14 | 0.00 | UNK_AI850297 | AI850297 |
| 99062_at | 0.00 | 0.00 | 0.00 | 0.00 | 3.03 | 1.64 | UNK_AI891912 | AI891912 |
| 99085_at | 0.00 | 0.00 | 0.00 | 0.00 | 4.22 | 0.00 | UNK_AI021421 | AI021421 |
| 99949_at | 0.00 | 0.00 | 0.00 | 0.00 | 2.36 | 0.00 | UNK_AW060324 | AW060324 |
| 99964_at | 0.00 | 0.00 | 0.00 | 0.00 | 1.24 | 4.52 | VDR | AW061016 |
| 100013_at | 0.00 | 0.00 | 0.00 | 4.01 | 0.00 | 0.00 | UNK_AW121732 | AW121732 |
| 101291_at | 0.00 | 0.00 | 0.00 | 0.00 | 3.69 | 0.00 | UNK_Z83956 | Z83956 |
| 101380_at | 0.00 | 0.00 | 0.00 | 0.00 | 2.23 | 0.00 | UNK_AW048282 | AW048282 |
| 101591_at | 0.00 | 0.00 | 0.00 | 0.00 | 2.20 | 1.69 | UNK_AI852589 | AI852589 |
| 102225_at | 0.00 | 0.00 | 0.00 | 0.00 | 1.76 | 2.07 | UNK_AA163268 | AA163268 |
| 102360_at | 0.00 | 0.00 | 0.00 | 0.00 | 2.84 | 1.89 | UNK_AW214225 | AW214225 |
| 102409_at | 0.00 | 0.00 | 0.00 | 2.06 | 1.68 | 1.65 | UNK_AW046963 | AW046963 |
| 102421_at | 0.00 | 0.00 | 0.00 | 0.00 | 2.16 | 0.00 | UNK_AI847950 | AI847950 |
| 102784_at | 0.00 | 0.00 | 0.00 | 0.00 | 4.12 | 0.00 | UNK_AI843949 | AI843949 |
| 102870_at | 0.00 | 0.00 | 0.00 | 0.00 | 2.37 | 1.98 | UNK_AW125272 | AW125272 |
| 102920_at | 0.00 | 0.00 | 0.00 | 0.00 | 1.92 | 2.11 | UNK_AW215585 | AW215585 |
| 103079_at | 0.00 | 0.00 | 0.00 | 0.00 | 1.91 | 2.50 | UNK_AA982208 | AA982208 |
| 103081_at | 0.00 | 0.00 | 0.00 | 0.00 | 2.32 | 0.00 | UNK_AA863928 | AA863928 |
| 103203_f_at | 0.00 | 0.00 | 0.00 | 0.00 | 2.37 | 0.00 | UNK_AW259499 | AW259499 |
| 103256_at | 0.00 | 0.00 | 3.13 | 0.00 | 0.00 | 0.00 | UNK_AI509811 | AI509811 |
| 103308_at | 0.00 | 0.00 | 0.00 | 0.00 | 4.17 | 0.00 | UNK_AI450597 | AI450597 |
| 103366_at | 0.00 | 0.00 | 0.00 | 0.00 | 2.23 | 0.00 | UNK_AI117236 | AI117236 |
| 103562_f_at | 0.00 | 0.00 | 0.00 | 0.00 | 2.69 | 0.00 | 0 | M26005 |
| 103615_at | 0.00 | 0.00 | 2.04 | 2.00 | 0.00 | 0.00 | UNK_AA727023 | AA727023 |
| 103711_at | 0.00 | 0.00 | 1.74 | 0.00 | 1.84 | 2.04 | UNK_AI115399 | AI115399 |
| 103721_at | 0.00 | 0.00 | 0.00 | 0.00 | 1.99 | 2.90 | UNK_AA592182 | AA592182 |
| 103734_at | 0.00 | 0.00 | 0.00 | 0.00 | 2.20 | 1.58 | UNK_AA985771 | AA985771 |
| 103739_at | 0.00 | 0.00 | 1.58 | 2.30 | 0.00 | 0.00 | UNK_AW230977 | AW230977 |
| 103744_at | 0.00 | 0.00 | 0.00 | 0.00 | 2.22 | 1.40 | UNK_AI852760 | AI852760 |
| 103753_at | 0.00 | 0.00 | 0.00 | 0.00 | 1.22 | 2.05 | UNK_AI159572 | AI159572 |
| 103890_at | 0.00 | 0.00 | 0.00 | 0.00 | 3.96 | 0.00 | UNK_AW050153 | AW050153 |
| 103907_at | 0.00 | 4.07 | 0.00 | 0.00 | 0.00 | 0.00 | UNK_AW108492 | AW108492 |
| 103916_at | 0.00 | 0.00 | 0.00 | 0.00 | 2.19 | 1.81 | UNK_AI850713 | AI850713 |
| 104030_at | 0.00 | 0.00 | 0.00 | 0.00 | 8.28 | 0.00 | UNK_AI848841 | AI848841 |
| 104042_at | 0.00 | 0.00 | 0.00 | 0.00 | 3.78 | 0.00 | UNK_AI842275 | AI842275 |
| 104091_at | 0.00 | 2.03 | 0.00 | 0.00 | 0.00 | 0.00 | UNK_AW122563 | AW122563 |
| 104110_at | 0.00 | 0.00 | 0.00 | 0.00 | 2.15 | 1.59 | UNK_AW060515 | AW060515 |
| 104147_at | 0.00 | 0.00 | 0.00 | 0.00 | 3.95 | 0.00 | UNK_AW122052 | AW122052 |
| 104179_at | 0.00 | 1.51 | 1.70 | 1.78 | 2.12 | 1.67 | UNK_AI788669 | AI788669 |
| 104207_at | 0.00 | 0.00 | 0.00 | 0.00 | 3.49 | 1.90 | UNK_AI430272 | AI430272 |
| 104222_f_at | 0.00 | 0.00 | 0.00 | 0.00 | 2.00 | 0.00 | 0 | C79210 |
| 104287_at | 0.00 | 0.00 | 0.00 | 2.23 | 1.96 | 0.00 | UNK_AI853807 | AI853807 |
| 104303_i_at | 0.00 | 0.00 | 0.00 | 0.00 | 2.18 | 0.00 | UNK_AW124151 | AW124151 |
| 104335_at | 0.00 | 0.00 | 0.00 | 0.00 | 2.39 | 0.00 | UNK_AW124084 | AW124084 |
| 104339_at | 0.00 | 0.00 | 0.00 | 0.00 | 2.57 | 0.00 | UNK_AW060236 | AW060236 |
| 104341_at | 0.00 | 1.31 | 0.00 | 0.00 | 1.72 | 2.10 | UNK_AW121406 | AW121406 |
| 104351_at | 0.00 | 0.00 | 0.00 | 0.00 | 9.17 | 0.00 | UNK_AW120925 | AW120925 |
| 104467_at | 0.00 | 0.00 | 1.38 | 1.98 | 2.11 | 1.98 | UNK_AA763004 | AA763004 |
| 104525_at | 0.00 | 0.00 | 0.00 | 0.00 | 1.67 | 2.50 | UNK_AW124812 | AW124812 |
| 104534_at | 0.00 | 0.00 | 0.00 | 0.00 | 1.96 | 2.16 | UNK_AA623874 | AA623874 |
| 104561_at | 0.00 | 0.00 | 0.00 | 0.00 | 4.63 | 0.00 | UNK_AW120990 | AW120990 |
| 104624_at | 0.00 | 0.00 | 0.00 | 0.00 | 2.06 | 1.94 | UNK_AI851539 | AI851539 |
| 104634_at | 0.00 | 0.00 | 0.00 | 2.03 | 1.40 | 1.80 | UNK_AA874589 | AA874589 |
| 104693_at | 0.00 | 0.00 | 0.00 | 0.00 | 2.11 | 1.72 | UNK_AA260145 | AA260145 |
| 105160_at | 0.00 | 0.00 | 0.00 | 0.00 | 2.09 | 1.80 | UNK_AA739142 | AA739142 |
| 105162_at | 0.00 | 0.00 | 0.00 | 0.00 | 2.05 | 0.00 | UNK_AW122704 | AW122704 |
| 105165_at | 0.00 | 0.00 | 0.00 | 1.77 | 4.74 | 0.00 | UNK_AI562171 | AI562171 |
| 105173_at | 0.00 | 0.00 | 0.00 | 0.00 | 1.93 | 2.05 | UNK_AI303628 | AI303628 |
| 105184_at | 0.00 | 0.00 | 0.00 | 0.00 | 2.19 | 1.69 | UNK_AI639898 | AI639898 |
| 105188_at | 0.00 | 0.00 | 1.61 | 0.00 | 2.18 | 0.00 | UNK_AI195930 | AI195930 |
| 105209_at | 0.00 | 0.00 | 0.00 | 0.00 | 1.48 | 2.54 | UNK_AI159074 | AI159074 |
| 105217_at | 0.00 | 0.00 | 0.00 | 0.00 | 2.83 | 0.00 | UNK_AI851943 | AI851943 |
| 105326_at | 0.00 | 0.00 | 0.00 | 0.00 | 1.57 | 2.06 | UNK_AI836944 | AI836944 |
| 105484_at | 0.00 | 0.00 | 0.00 | 0.00 | 2.44 | 0.00 | UNK_AW049561 | AW049561 |
| 105506_at | 0.00 | 0.00 | 0.00 | 2.62 | 0.00 | 0.00 | UNK_AA217898 | AA217898 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 105529_at | 0.00 | 0.00 | 0.00 | 1.21 | 2.88 | 0.00 | UNK_AW122385 | AW122385 |
| 105688_f_at | 0.00 | 0.00 | 0.00 | 2.07 | 1.60 | 0.00 | UNK_AI842855 | AI842855 |
| 105829_at | 0.00 | 0.00 | 0.00 | 1.25 | 2.43 | 1.54 | UNK_AW121238 | AW121238 |
| 105842_at | 0.00 | 0.00 | 0.00 | 0.00 | 3.02 | 0.00 | UNK_AI841683 | AI841683 |
| 105871_at | 0.00 | 0.00 | 0.00 | 0.00 | 1.79 | 7.08 | UNK_AI844617 | AI844617 |
| 105953_at | 0.00 | 0.00 | 0.00 | 0.00 | 1.91 | 2.74 | UNK_AI839641 | AI839641 |
| 105977_f_at | 0.00 | 1.73 | 3.22 | 0.00 | 0.00 | 0.00 | UNK_AA692591 | AA692591 |
| 106019_f_at | 0.00 | 0.00 | 0.00 | 0.00 | 2.36 | 0.00 | UNK_AA823762 | AA823762 |
| 106039_at | 0.00 | 0.00 | 0.00 | 0.00 | 3.72 | 0.00 | UNK_AA683764 | AA683764 |
| 106113_at | 0.00 | 0.00 | 0.00 | 0.00 | 2.04 | 0.00 | UNK_AI850393 | AI850393 |
| 106138_at | 1.72 | 2.31 | 0.00 | 0.00 | 0.00 | 0.00 | UNK_AA797808 | AA797808 |
| 106175_at | 0.00 | 0.00 | 0.00 | 0.00 | 1.73 | 4.48 | UNK_AI851974 | AI851974 |
| 106178_at | 0.00 | 0.00 | 0.00 | 0.00 | 1.97 | 2.51 | UNK_AW122268 | AW122268 |
| 106208_at | 0.00 | 0.00 | 0.00 | 0.00 | 2.84 | 0.00 | UNK_AW123433 | AW123433 |
| 106219_at | 0.00 | 0.00 | 0.00 | 0.00 | 2.45 | 2.00 | UNK_AW045938 | AW045938 |
| 106263_at | 0.00 | 0.00 | 0.00 | 0.00 | 2.84 | 1.79 | UNK_AA591294 | AA591294 |
| 106282_r_at | 0.00 | 0.00 | 0.00 | 0.00 | 3.50 | 0.00 | UNK_AI851600 | AI851600 |
| 106538_at | 0.00 | 0.00 | 0.00 | 2.68 | 1.80 | 0.00 | UNK_AI647881 | AI647881 |
| 106570_at | 0.00 | 0.00 | 0.00 | 1.45 | 2.35 | 1.76 | UNK_AI606458 | AI606458 |
| 106574_at | 0.00 | 0.00 | 0.00 | 1.71 | 2.03 | 0.00 | UNK_AI837536 | AI837536 |
| 106580_at | 0.00 | 0.00 | 0.00 | 0.00 | 3.19 | 0.00 | UNK_AI834858 | AI834858 |
| 106592_at | 0.00 | 0.00 | 0.00 | 2.22 | 0.00 | 0.00 | UNK_AI115629 | AI115629 |
| 106609_at | 0.00 | 0.00 | 1.32 | 0.00 | 2.57 | 0.00 | UNK_AA867207 | AA867207 |
| 106650_at | 0.00 | 0.00 | 0.00 | 2.17 | 0.00 | 0.00 | UNK_AI841093 | AI841093 |
| 106651_at | 0.00 | 0.00 | 0.00 | 1.63 | 1.74 | 2.14 | ADNP | AA790780 |
| 106673_at | 0.00 | 0.00 | 0.00 | 0.00 | 2.65 | 0.00 | UNK_AI839746 | AI839746 |
| 106956_at | 0.00 | 0.00 | 0.00 | 0.00 | 1.81 | 2.13 | UNK_AW125566 | AW125566 |
| 106998_at | 0.00 | 0.00 | 0.00 | 0.00 | 5.51 | 0.00 | UNK_AI845825 | AI845825 |
| 107051_at | 0.00 | 0.00 | 0.00 | 1.89 | 2.00 | 1.97 | UNK_AI848855 | AI848855 |
| 107067_at | 0.00 | 0.00 | 0.00 | 0.00 | 3.06 | 0.00 | UNK_AW047122 | AW047122 |
| 107081_at | 0.00 | 1.45 | 1.79 | 1.43 | 2.11 | 0.00 | UNK_AA691890 | AA691890 |
| 107105_at | 0.00 | 0.00 | 0.00 | 1.82 | 1.64 | 2.54 | UNK_AI159649 | AI159649 |
| 107292_at | 0.00 | 0.00 | 2.80 | 0.00 | 0.00 | 0.00 | UNK_AW049900 | AW049900 |
| 107348_at | 0.00 | 0.00 | 0.00 | 0.00 | 2.06 | 0.00 | UNK_AW050370 | AW050370 |
| 107393_at | 0.00 | 0.00 | 0.00 | 1.73 | 1.90 | 2.53 | UNK_AI502997 | AI502997 |
| 107412_at | 0.00 | 0.00 | 0.00 | 0.00 | 4.17 | 0.00 | UNK_AW048881 | AW048881 |
| 107477_at | 0.00 | 0.00 | 0.00 | 0.00 | 2.20 | 0.00 | UNK_AW045655 | AW045655 |
| 107478_at | 0.00 | 2.14 | 0.00 | 0.00 | 0.00 | 0.00 | UNK_AW048523 | AW048523 |
| 107523_at | 0.00 | 1.46 | 2.88 | 0.00 | 1.96 | 0.00 | UNK_AW209229 | AW209229 |
| 107558_at | 0.00 | 0.00 | 0.00 | 0.00 | 3.76 | 0.00 | UNK_AA833488 | AA833488 |
| 107564_at | 0.00 | 0.00 | 0.00 | 0.00 | 2.56 | 1.62 | UNK_AW123129 | AW123129 |
| 107571_at | 0.00 | 0.00 | 0.00 | 2.21 | 1.65 | 0.00 | UNK_AW122430 | AW122430 |
| 107582_at | 0.00 | 0.00 | 0.00 | 2.28 | 0.00 | 0.00 | UNK_AW050026 | AW050026 |
| 107617_at | 0.00 | 0.00 | 0.00 | 0.00 | 2.66 | 0.00 | UNK_AI851968 | AI851968 |
| 107619_s_at | 0.00 | 0.00 | 0.00 | 0.00 | 2.03 | 1.68 | UNK_AW120573 | AW120573 |
| 107677_at | 0.00 | 0.00 | 0.00 | 0.00 | 2.58 | 0.00 | UNK_AU023434 | AU023434 |
| 107774_at | 0.00 | 0.00 | 0.00 | 1.44 | 2.40 | 0.00 | UNK_AI836428 | AI836428 |
| 107810_at | 0.00 | 0.00 | 0.00 | 0.00 | 2.27 | 0.00 | UNK_AI847267 | AI847267 |
| 107897_at | 0.00 | 0.00 | 0.00 | 2.28 | 1.75 | 0.00 | UNK_AI607556 | AI607556 |
| 107938_at | 0.00 | 0.00 | 0.00 | 1.58 | 2.31 | 0.00 | UNK_AA881991 | AA881991 |
| 107954_at | 0.00 | 0.00 | 0.00 | 0.00 | 2.15 | 0.00 | HOXA7 | AW125404 |
| 107983_at | 0.00 | 0.00 | 0.00 | 0.00 | 4.50 | 0.00 | UNK_AI666712 | AI666712 |
| 107988_at | 0.00 | 0.00 | 0.00 | 0.00 | 2.07 | 0.00 | UNK_AI849414 | AI849414 |
| 108024_at | 0.00 | 1.68 | 0.00 | 1.75 | 2.61 | 0.00 | UNK_AA764623 | AA764623 |
| 108028_at | 0.00 | 0.00 | 0.00 | 0.00 | 2.41 | 0.00 | UNK_AI606099 | AI606099 |
| 108059_at | 0.00 | 0.00 | 0.00 | 0.00 | 4.96 | 0.00 | UNK_AI851960 | AI851960 |
| 108087_at | 0.00 | 0.00 | 0.00 | 0.00 | 1.59 | 2.07 | UNK_AI837854 | AI837854 |
| 108094_at | 0.00 | 0.00 | 0.00 | 0.00 | 10.12 | 0.00 | UNK_AI593656 | AI593656 |
| 108302_at | 0.00 | 0.00 | 0.00 | 0.00 | 2.11 | 0.00 | PKCM | AW121285 |
| 108371_at | 0.00 | 0.00 | 0.00 | 0.00 | 1.96 | 2.45 | UNK_AA710403 | AA710403 |
| 108420_at | 0.00 | 0.00 | 0.00 | 0.00 | 4.97 | 0.00 | UNK_AI036798 | AI036798 |
| 108497_at | 0.00 | 0.00 | 0.00 | 1.90 | 1.86 | 3.24 | UNK_AW124152 | AW124152 |
| 108536_at | 0.00 | 0.00 | 0.00 | 0.00 | 2.28 | 0.00 | UNK_AI850994 | AI850994 |
| 108562_at | 0.00 | 0.00 | 0.00 | 1.34 | 2.14 | 1.56 | UNK_AI195240 | AI195240 |
| 108957_at | 0.00 | 0.00 | 0.00 | 0.00 | 2.01 | 1.43 | UNK_AA419670 | AA419670 |
| 109007_at | 0.00 | 0.00 | 0.00 | 0.00 | 2.08 | 0.00 | UNK_AA738680 | AA738680 |
| 109012_at | 0.00 | 0.00 | 0.00 | 0.00 | 2.34 | 0.00 | UNK_AA000177 | AA000177 |
| 109089_at | 0.00 | 0.00 | 0.00 | 0.00 | 1.77 | 2.77 | UNK_AA798970 | AA798970 |
| 109360_at | 0.00 | 0.00 | 0.00 | 0.00 | 3.03 | 0.00 | UNK_AA170489 | AA170489 |
| 109363_at | 0.00 | 0.00 | 0.00 | 0.05 | 1.43 | 4.09 | UNK_AI847526 | AI847526 |
| 109380_at | 0.00 | 0.00 | 0.00 | 3.87 | 0.00 | 0.00 | UNK_AA638457 | AA638457 |
| 109391_at | 0.00 | 0.00 | 0.00 | 2.10 | 1.86 | 1.92 | UNK_AI852273 | AI852273 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 109407_at | 0.00 | 0.00 | 0.00 | 0.00 | 2.41 | 0.00 | UNK_AW121433 | AW121433 |
| 109416_at | 0.00 | 0.00 | 0.00 | 0.00 | 3.05 | 0.00 | UNK_AI835646 | AI835646 |
| 109491_at | 0.00 | 0.00 | 0.00 | 2.02 | 1.52 | 1.87 | UNK_AA759948 | AA759948 |
| 109509_at | 0.00 | 0.00 | 0.00 | 1.95 | 3.55 | 0.00 | UNK_AI593229 | AI593229 |
| 109512_at | 0.00 | 0.00 | 0.00 | 6.81 | 0.00 | 0.00 | UNK_AA185047 | AA185047 |
| 109521_at | 0.00 | 0.00 | 0.00 | 0.00 | 4.10 | 0.00 | UNK_AW123386 | AW123386 |
| 109603_at | 0.00 | 0.00 | 0.00 | 0.00 | 2.06 | 1.91 | UNK_AW214377 | AW214377 |
| 109607_at | 0.00 | 0.00 | 0.00 | 1.79 | 1.91 | 2.49 | UNK_AW108059 | AW108059 |
| 109616_f_at | 0.00 | 0.00 | 0.00 | 1.79 | 2.16 | 0.00 | UNK_AA681095 | AA681095 |
| 109623_at | 0.00 | 0.00 | 0.00 | 0.00 | 3.31 | 0.00 | UNK_AA105708 | AA105708 |
| 109640_at | 0.00 | 0.00 | 0.00 | 0.00 | 1.81 | 3.66 | UNK_AW124435 | AW124435 |
| 109658_at | 0.00 | 0.00 | 0.00 | 0.00 | 5.20 | 0.00 | UNK_AA869355 | AA869355 |
| 109721_at | 0.00 | 0.00 | 0.00 | 0.00 | 3.40 | 0.00 | UNK_AI839609 | AI839609 |
| 109745_at | 0.00 | 0.00 | 0.00 | 2.12 | 1.79 | 1.92 | UNK_AI837264 | AI837264 |
| 109791_at | 0.00 | 0.00 | 0.00 | 0.00 | 4.95 | 0.00 | UNK_AI605156 | AI605156 |
| 109910_at | 0.00 | 0.00 | 0.00 | 0.00 | 1.78 | 2.57 | UNK_AW123519 | AW123519 |
| 109918_at | 0.00 | 0.00 | 0.00 | 0.00 | 1.27 | 3.04 | UNK_AI427170 | AI427170 |
| 110009_at | 0.00 | 0.00 | 0.00 | 0.00 | 4.01 | 0.00 | UNK_AI551083 | AI551083 |
| 110015_at | 0.00 | 0.00 | 0.00 | 0.00 | 2.46 | 0.00 | UNK_AI385637 | AI385637 |
| 110128_at | 0.00 | 0.00 | 0.00 | 0.00 | 1.66 | 2.28 | UNK_AI664407 | AI664407 |
| 110184_at | 0.00 | 0.00 | 2.39 | 1.96 | 0.00 | 0.00 | UNK_AW123961 | AW123961 |
| 110204_at | 0.00 | 0.00 | 0.00 | 0.00 | 1.79 | 2.89 | UNK_AW123924 | AW123924 |
| 110341_at | 0.00 | 0.00 | 0.00 | 0.00 | 2.26 | 0.00 | UNK_AI851727 | AI851727 |
| 110344_at | 0.00 | 0.00 | 0.00 | 0.00 | 5.37 | 0.00 | UNK_AW123792 | AW123792 |
| 110422_at | 0.00 | 0.00 | 0.00 | 0.00 | 2.24 | 0.00 | UNK_AA896206 | AA896206 |
| 110449_f_at | 0.00 | 0.00 | 0.00 | 1.33 | 1.85 | 2.18 | UNK_AI154580 | AI154580 |
| 110541_at | 0.00 | 0.00 | 0.00 | 0.00 | 1.90 | 2.62 | UNK_AI643915 | AI643915 |
| 110650_at | 0.00 | 0.00 | 0.00 | 0.00 | 1.72 | 2.11 | UNK_AA959574 | AA959574 |
| 110689_at | 0.00 | 0.00 | 0.00 | 0.00 | 2.46 | 0.00 | ADSL | AI391284 |
| 110693_at | 0.00 | 0.00 | 0.00 | 0.00 | 2.41 | 0.00 | UNK_AW121941 | AW121941 |
| 110719_at | 0.00 | 0.00 | 0.00 | 2.30 | 0.00 | 0.00 | UNK_AI839189 | AI839189 |
| 110824_at | 0.00 | 0.00 | 0.00 | 0.00 | 2.62 | 0.00 | UNK_AW121315 | AW121315 |
| 110830_at | 0.00 | 1.67 | 0.00 | 2.06 | 0.00 | 0.00 | UNK_AI021707 | AI021707 |
| 111203_at | 0.00 | 0.00 | 0.00 | 0.00 | 2.25 | 0.00 | UNK_AI614021 | AI614021 |
| 111262_at | 0.00 | 0.00 | 0.00 | 0.00 | 1.91 | 2.61 | UNK_AW061180 | AW061180 |
| 111294_at | 0.00 | 1.68 | 0.00 | 0.00 | 1.89 | 3.19 | UNK_AA175446 | AA175446 |
| 111312_at | 0.00 | 0.00 | 0.00 | 0.00 | 3.20 | 0.00 | UNK_AA693306 | AA693306 |
| 111319_at | 0.00 | 0.00 | 0.00 | 2.37 | 0.00 | 0.00 | UNK_AW124761 | AW124761 |
| 111322_at | 0.00 | 0.00 | 0.00 | 0.00 | 1.52 | 2.36 | UNK_AI842842 | AI842842 |
| 111343_i_at | 0.00 | 0.00 | 0.00 | 2.05 | 1.92 | 0.00 | UNK_AI853582 | AI853582 |
| 111352_at | 0.00 | 0.00 | 0.00 | 2.36 | 1.72 | 0.00 | UNK_AW215724 | AW215724 |
| 111379_at | 0.00 | 0.00 | 0.00 | 2.26 | 1.74 | 0.00 | UNK_AI846352 | AI846352 |
| 111397_at | 0.00 | 0.00 | 0.00 | 0.00 | 3.13 | 0.00 | UNK_AI844734 | AI844734 |
| 111417_at | 0.00 | 0.00 | 0.00 | 0.00 | 2.29 | 0.00 | UNK_AA980507 | AA980507 |
| 111428_at | 0.00 | 0.00 | 0.00 | 0.00 | 3.95 | 0.00 | UNK_AW226863 | AW226863 |
| 111430_r_at | 0.00 | 0.00 | 0.00 | 0.00 | 3.43 | 0.00 | UNK_AW011836 | AW011836 |
| 111459_at | 0.00 | 0.00 | 0.00 | 0.00 | 5.62 | 0.00 | UNK_AI429433 | AI429433 |
| 111475_at | 0.00 | 0.00 | 0.00 | 1.97 | 2.16 | 0.00 | UNK_AA880439 | AA880439 |
| 111533_at | 0.00 | 0.00 | 0.00 | 0.00 | 3.92 | 1.16 | UNK_AI843308 | AI843308 |
| 111535_at | 0.00 | 0.00 | 0.00 | 0.00 | 2.17 | 0.00 | UNK_AI226156 | AI226156 |
| 111543_at | 0.00 | 0.00 | 0.00 | 0.00 | 2.28 | 0.00 | UNK_AW122303 | AW122303 |
| 111572_at | 0.00 | 0.00 | 0.00 | 0.00 | 2.53 | 0.00 | UNK_AA096501 | AA096501 |
| 111578_at | 0.00 | 0.00 | 0.00 | 1.97 | 2.98 | 0.00 | UNK_AA110885 | AA110885 |
| 111647_at | 0.00 | 3.03 | 0.00 | 0.00 | 0.00 | 0.00 | UNK_AI156274 | AI156274 |
| 111685_at | 0.00 | 0.00 | 0.00 | 0.00 | 3.14 | 0.00 | UNK_AW228742 | AW228742 |
| 111741_at | 0.00 | 0.00 | 0.00 | 2.39 | 0.00 | 0.00 | UNK_AW123268 | AW123268 |
| 111772_at | 0.00 | 0.00 | 0.00 | 0.00 | 3.96 | 0.00 | UNK_AI122096 | AI122096 |
| 111793_at | 0.00 | 0.00 | 0.00 | 0.00 | 1.64 | 2.34 | UNK_AA940547 | AA940547 |
| 111800_at | 0.00 | 0.00 | 0.00 | 0.00 | 1.63 | 2.14 | UNK_AI839784 | AI839784 |
| 111829_at | 0.00 | 0.00 | 0.00 | 2.17 | 0.00 | 0.00 | UNK_AW122867 | AW122867 |
| 111850_at | 0.00 | 1.74 | 0.00 | 0.00 | 3.22 | 0.00 | UNK_AI839747 | AI839747 |
| 111931_at | 0.00 | 0.00 | 0.00 | 0.00 | 1.81 | 2.75 | UNK_AW125297 | AW125297 |
| 111939_at | 0.00 | 0.00 | 0.00 | 0.00 | 2.02 | 0.00 | UNK_AI286751 | AI286751 |
| 111952_at | 0.00 | 0.00 | 0.00 | 6.16 | 0.00 | 0.00 | UNK_AW046394 | AW046394 |
| 112018_at | 0.00 | 0.00 | 0.00 | 1.59 | 2.06 | 0.00 | UNK_AW049226 | AW049226 |
| 112031_g_at | 0.00 | 0.00 | 0.00 | 0.00 | 2.04 | 0.00 | UNK_AW048852 | AW048852 |
| 112032_at | 0.00 | 0.00 | 0.00 | 0.00 | 1.43 | 4.48 | UNK_AI838644 | AI838644 |
| 112082_at | 0.00 | 0.00 | 0.00 | 0.00 | 5.39 | 0.00 | UNK_AI591941 | AI591941 |
| 112091_at | 0.00 | 0.00 | 0.00 | 0.00 | 4.52 | 0.00 | UNK_AI426016 | AI426016 |
| 112167_f_at | 0.00 | 0.00 | 0.00 | 0.00 | 2.50 | 0.00 | UNK_W96857 | W96857 |
| 112209_at | 0.00 | 0.00 | 0.00 | 0.00 | 2.64 | 0.00 | UNK_AW122818 | AW122818 |
| 112269_at | 0.00 | 0.00 | 0.00 | 0.00 | 1.77 | 2.67 | UNK_AW123962 | AW123962 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 112291_r_at | 0.00 | 1.64 | 1.80 | 0.00 | 2.57 | 1.43 | UNK_AA655542 | AA655542 |
| 112333_at | 0.00 | 0.00 | 0.00 | 2.17 | 0.00 | 0.00 | UNK_AI835570 | AI835570 |
| 112338_at | 0.00 | 0.00 | 0.00 | 0.00 | 3.04 | 0.00 | UNK_AI846227 | AI846227 |
| 112402_at | 0.00 | 0.00 | 0.00 | 0.00 | 2.30 | 0.00 | UNK_AW045953 | AW045953 |
| 112404_at | 0.00 | 0.00 | 0.00 | 0.00 | 2.70 | 0.00 | UNK_AI844302 | AI844302 |
| 112488_at | 0.00 | 0.00 | 0.00 | 0.00 | 1.88 | 3.93 | UNK_AW120970 | AW120970 |
| 112499_at | 0.00 | 0.00 | 0.00 | 0.00 | 4.01 | 0.00 | UNK_AI172791 | AI172791 |
| 112652_at | 0.00 | 0.00 | 0.00 | 0.00 | 3.04 | 0.00 | UNK_AA636643 | AA636643 |
| 112703_at | 0.00 | 0.00 | 0.00 | 0.00 | 2.26 | 0.00 | UNK_AI846613 | AI846613 |
| 112729_at | 0.00 | 0.00 | 0.00 | 0.00 | 1.50 | 2.17 | UNK_AA644819 | AA644819 |
| 112733_at | 0.00 | 4.52 | 0.00 | 0.00 | 0.00 | 0.00 | UNK_AW212343 | AW212343 |
| 112795_at | 0.00 | 0.00 | 0.00 | 1.99 | 1.74 | 2.51 | UNK_AI854434 | AI854434 |
| 112827_at | 0.00 | 0.00 | 0.00 | 2.50 | 0.00 | 0.00 | UNK_AI847696 | AI847696 |
| 112847_at | 0.00 | 0.00 | 0.00 | 0.00 | 5.12 | 0.00 | UNK_AW123508 | AW123508 |
| 112857_g_at | 0.00 | 0.00 | 0.00 | 0.00 | 1.74 | 3.22 | UNK_AI852143 | AI852143 |
| 112981_at | 0.00 | 0.00 | 0.00 | 0.00 | 3.36 | 0.00 | UNK_AW060744 | AW060744 |
| 112989_at | 0.00 | 0.00 | 0.00 | 0.00 | 2.84 | 0.00 | UNK_AA940527 | AA940527 |
| 113018_at | 0.00 | 0.00 | 0.00 | 0.00 | 2.51 | 0.00 | UNK_AA855540 | AA855540 |
| 113021_at | 0.00 | 0.00 | 0.00 | 1.68 | 1.90 | 2.98 | UNK_AI840910 | AI840910 |
| 113027_at | 0.00 | 0.00 | 0.00 | 0.00 | 2.41 | 1.83 | UNK_AA816040 | AA816040 |
| 113043_at | 0.00 | 1.39 | 2.10 | 1.81 | 1.90 | 0.00 | UNK_AI429002 | AI429002 |
| 113119_at | 0.00 | 0.00 | 0.00 | 2.06 | 0.00 | 0.00 | UNK_AI835854 | AI835854 |
| 113186_at | 0.00 | 0.00 | 0.00 | 0.00 | 1.98 | 2.98 | UNK_AI852046 | AI852046 |
| 113226_at | 0.00 | 0.00 | 0.00 | 0.00 | 1.46 | 2.36 | UNK_AW230690 | AW230690 |
| 113228_at | 0.00 | 0.00 | 0.00 | 3.05 | 0.00 | 0.00 | UNK_AW120751 | AW120751 |
| 113239_at | 0.00 | 0.00 | 0.00 | 0.00 | 2.39 | 0.00 | UNK_AW213684 | AW213684 |
| 113285_at | 0.00 | 0.00 | 0.00 | 0.00 | 5.51 | 0.00 | UNK_AI850452 | AI850452 |
| 113288_at | 0.00 | 0.00 | 1.97 | 0.00 | 1.78 | 3.18 | UNK_AA967846 | AA967846 |
| 113328_at | 0.00 | 0.00 | 0.00 | 1.93 | 1.72 | 2.18 | UNK_AW214631 | AW214631 |
| 113333_at | 0.00 | 0.00 | 1.64 | 1.58 | 1.86 | 2.27 | UNK_AA793994 | AA793994 |
| 113443_r_at | 0.00 | 0.00 | 0.00 | 1.85 | 2.32 | 0.00 | UNK_AI429737 | AI429737 |
| 113541_at | 0.00 | 0.00 | 0.00 | 2.43 | 0.00 | 0.00 | UNK_AI843578 | AI843578 |
| 113548_at | 0.00 | 0.00 | 0.00 | 0.00 | 2.22 | 1.41 | UNK_AI844170 | AI844170 |
| 113550_at | 0.00 | 0.00 | 0.00 | 0.00 | 2.03 | 0.00 | UNK_AI846429 | AI846429 |
| 113574_at | 0.00 | 0.00 | 0.00 | 0.00 | 3.35 | 0.00 | UNK_AW049388 | AW049388 |
| 113620_at | 0.00 | 0.00 | 0.00 | 0.00 | 4.93 | 0.00 | UNK_AW047525 | AW047525 |
| 113629_at | 0.00 | 0.00 | 0.00 | 0.00 | 2.74 | 0.00 | UNK_AW047341 | AW047341 |
| 113656_at | 0.00 | 0.00 | 0.00 | 0.00 | 2.02 | 0.00 | UNK_AW050247 | AW050247 |
| 113657_at | 0.00 | 0.00 | 0.00 | 0.00 | 2.44 | 0.00 | UNK_AW048440 | AW048440 |
| 113695_at | 0.00 | 0.00 | 0.00 | 0.00 | 4.37 | 0.00 | UNK_AW120861 | AW120861 |
| 113728_at | 0.00 | 0.00 | 0.00 | 0.00 | 1.99 | 2.07 | UNK_AA915716 | AA915716 |
| 113777_at | 0.00 | 0.00 | 1.73 | 1.61 | 1.91 | 3.04 | UNK_AW048627 | AW048627 |
| 113863_at | 0.00 | 0.00 | 0.00 | 0.00 | 3.00 | 0.00 | UNK_AA014260 | AA014260 |
| 113896_at | 0.00 | 0.00 | 0.00 | 1.74 | 2.37 | 0.00 | UNK_AI425640 | AI425640 |
| 114001_at | 0.00 | 2.63 | 0.00 | 0.00 | 0.00 | 0.00 | UNK_AW211307 | AW211307 |
| 114102_at | 0.00 | 1.37 | 0.00 | 1.47 | 1.81 | 2.47 | UNK_AW061165 | AW061165 |
| 114140_at | 0.00 | 0.00 | 0.00 | 0.00 | 2.55 | 0.00 | UNK_AW214473 | AW214473 |
| 114168_at | 0.00 | 0.00 | 0.00 | 0.00 | 2.43 | 0.00 | UNK_AW121266 | AW121266 |
| 114323_at | 0.00 | 0.00 | 0.00 | 0.00 | 3.13 | 0.00 | UNK_AA756403 | AA756403 |
| 114379_at | 0.00 | 0.42 | 2.02 | 1.46 | 0.00 | 0.00 | UNK_AI050351 | AI050351 |
| 114461_at | 0.00 | 0.00 | 1.58 | 1.62 | 2.81 | 0.00 | UNK_AI874945 | AI874945 |
| 114525_at | 0.00 | 1.28 | 0.00 | 0.00 | 2.05 | 1.73 | UNK_AA290482 | AA290482 |
| 114667_at | 0.00 | 0.00 | 0.00 | 0.00 | 2.62 | 1.66 | UNK_AA399878 | AA399878 |
| 114695_at | 0.00 | 0.00 | 2.00 | 0.00 | 0.00 | 0.00 | UNK_AI842428 | AI842428 |
| 114698_at | 0.00 | 0.00 | 0.00 | 2.51 | 0.00 | 0.00 | UNK_AW120476 | AW120476 |
| 114709_at | 0.00 | 0.00 | 0.00 | 0.00 | 2.24 | 0.00 | UNK_AI847047 | AI847047 |
| 114718_at | 0.00 | 0.00 | 0.00 | 0.00 | 2.28 | 0.00 | UNK_AI267112 | AI267112 |
| 114747_at | 0.00 | 0.00 | 0.00 | 2.24 | 1.87 | 0.00 | UNK_AI851384 | AI851384 |
| 114830_at | 0.00 | 0.00 | 0.00 | 1.59 | 1.90 | 2.41 | UNK_AI847957 | AI847957 |
| 114880_at | 0.00 | 0.00 | 2.18 | 1.92 | 1.39 | 1.80 | UNK_AW123237 | AW123237 |
| 114955_at | 0.00 | 0.00 | 0.00 | 0.00 | 1.75 | 2.50 | UNK_AI314760 | AI314760 |
| 114996_at | 0.00 | 0.00 | 0.00 | 0.00 | 2.00 | 0.00 | UNK_AA967301 | AA967301 |
| 115032_i_at | 0.00 | 0.00 | 0.00 | 1.76 | 2.89 | 1.84 | UNK_AI848847 | AI848847 |
| 115064_at | 0.00 | 0.00 | 0.00 | 0.00 | 2.36 | 0.00 | UNK_AI573356 | AI573356 |
| 115091_at | 0.00 | 0.00 | 0.00 | 3.34 | 0.00 | 0.00 | UNK_AA647787 | AA647787 |
| 115093_at | 0.00 | 0.00 | 0.00 | 0.00 | 1.90 | 3.27 | UNK_AI606104 | AI606104 |
| 115112_at | 0.00 | 0.00 | 0.00 | 0.00 | 5.07 | 0.00 | UNK_AW050362 | AW050362 |
| 115140_at | 0.00 | 0.00 | 0.00 | 0.00 | 2.84 | 0.00 | UNK_AW124719 | AW124719 |
| 115153_at | 0.00 | 0.00 | 0.00 | 0.00 | 1.70 | 2.94 | UNK_AI789647 | AI789647 |
| 115195_at | 0.00 | 0.00 | 0.00 | 1.66 | 11.32 | 0.00 | UNK_AI838694 | AI838694 |
| 115212_at | 0.00 | 0.00 | 0.00 | 2.24 | 0.00 | 0.00 | UNK_AA856478 | AA856478 |
| 115266_at | 0.00 | 0.00 | 0.00 | 0.00 | 3.97 | 0.00 | UNK_AI152744 | AI152744 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 115333_at | 0.00 | 0.00 | 0.00 | 1.27 | 6.94 | 0.00 | UNK_AI593245 | AI593245 |
| 115338_at | 0.00 | 0.00 | 2.06 | 0.00 | 0.00 | 0.00 | UNK_AI158964 | AI158964 |
| 115354_at | 0.00 | 0.00 | 0.00 | 0.00 | 3.71 | 0.00 | UNK_AA895031 | AA895031 |
| 115371_at | 0.00 | 0.00 | 0.00 | 0.00 | 1.99 | 7.39 | UNK_AI465535 | AI465535 |
| 115402_at | 0.00 | 0.00 | 0.00 | 0.00 | 2.68 | 0.00 | UNK_AW120513 | AW120513 |
| 115416_at | 0.00 | 0.00 | 0.00 | 0.00 | 3.28 | 0.00 | UNK_AA645547 | AA645547 |
| 115449_at | 0.00 | 0.00 | 0.00 | 0.00 | 1.77 | 5.16 | UNK_AW049627 | AW049627 |
| 115481_at | 0.00 | 0.00 | 0.00 | 0.00 | 2.75 | 0.00 | UNK_AI256692 | AI256692 |
| 115506_at | 0.00 | 0.00 | 0.00 | 0.00 | 1.60 | 2.05 | UNK_AW048699 | AW048699 |
| 115652_at | 0.00 | 2.11 | 0.00 | 1.53 | 0.00 | 0.00 | UNK_AI450439 | AI450439 |
| 115885_at | 0.00 | 0.00 | 0.00 | 0.00 | 2.93 | 0.00 | UNK_AW211469 | AW211469 |
| 115891_at | 0.00 | 0.00 | 0.00 | 0.00 | 1.97 | 2.64 | UNK_AI481691 | AI481691 |
| 115898_at | 0.00 | 0.00 | 0.00 | 0.00 | 3.98 | 0.00 | UNK_AA739008 | AA739008 |
| 115904_at | 0.00 | 0.00 | 0.00 | 0.00 | 1.82 | 2.84 | UNK_AI788994 | AI788994 |
| 115916_at | 0.00 | 0.00 | 0.00 | 0.00 | 1.32 | 2.42 | UNK_AA691429 | AA691429 |
| 115917_at | 0.00 | 0.00 | 1.70 | 1.88 | 2.26 | 0.00 | UNK_AA874421 | AA874421 |
| 116044_at | 0.00 | 0.00 | 0.00 | 1.94 | 2.10 | 0.00 | UNK_AA824110 | AA824110 |
| 116102_at | 0.00 | 0.00 | 0.00 | 0.00 | 3.55 | 0.00 | UNK_AW261562 | AW261562 |
| 116139_at | 0.00 | 0.00 | 0.00 | 0.00 | 3.24 | 0.00 | UNK_AA838903 | AA838903 |
| 116166_at | 0.00 | 0.00 | 0.00 | 0.00 | 1.95 | 3.46 | UNK_AI853928 | AI853928 |
| 116286_at | 0.00 | 0.00 | 0.00 | 2.20 | 1.92 | 0.00 | UNK_AI553581 | AI553581 |
| 116320_at | 0.00 | 0.00 | 0.00 | 0.00 | 1.60 | 3.82 | UNK_AW124054 | AW124054 |
| 116345_at | 0.00 | 0.00 | 1.80 | 1.61 | 2.25 | 0.00 | UNK_AI854429 | AI854429 |
| 116379_at | 0.00 | 0.00 | 0.00 | 0.00 | 2.14 | 0.00 | UNK_AA178683 | AA178683 |
| 116386_at | 0.00 | 0.00 | 0.00 | 0.00 | 3.10 | 0.00 | UNK_AA981888 | AA981888 |
| 116426_at | 0.00 | 0.00 | 0.00 | 0.00 | 2.50 | 0.00 | UNK_AW212535 | AW212535 |
| 116431_at | 0.00 | 0.00 | 0.00 | 0.00 | 2.17 | 0.00 | UNK_AI316839 | AI316839 |
| 116451_at | 0.00 | 0.00 | 0.00 | 0.00 | 4.73 | 1.71 | UNK_AA615200 | AA615200 |
| 116562_at | 0.00 | 2.64 | 0.00 | 0.00 | 0.00 | 0.00 | UNK_AI451360 | AI451360 |
| 116576_at | 0.00 | 0.00 | 0.00 | 0.00 | 1.76 | 2.03 | UNK_AI451563 | AI451563 |
| 116582_at | 0.00 | 0.00 | 0.00 | 0.00 | 2.90 | 0.00 | UNK_AI987726 | AI987726 |
| 116671_at | 0.00 | 0.00 | 0.00 | 0.00 | 1.75 | 2.22 | UNK_AW123023 | AW123023 |
| 116831_at | 0.00 | 0.00 | 0.00 | 0.00 | 2.29 | 0.00 | UNK_AI747220 | AI747220 |
| 116858_at | 0.00 | 0.00 | 1.49 | 1.78 | 1.76 | 7.51 | MAFB | AI849704 |
| 116955_at | 0.00 | 0.00 | 0.00 | 0.00 | 2.46 | 0.00 | UNK_AI847605 | AI847605 |
| 116986_at | 0.00 | 0.00 | 0.00 | 0.00 | 2.28 | 0.00 | UNK_AW120935 | AW120935 |
| 117186_at | 0.00 | 1.72 | 1.60 | 2.17 | 1.62 | 0.00 | UNK_AI847496 | AI847496 |
| 117196_at | 0.00 | 0.00 | 0.00 | 0.00 | 1.80 | 4.64 | UNK_AI840220 | AI840220 |
| 117218_at | 0.00 | 0.00 | 0.00 | 0.00 | 3.04 | 0.00 | UNK_AI848424 | AI848424 |
| 117235_at | 0.00 | 1.18 | 0.00 | 1.34 | 2.48 | 0.00 | UNK_AI843866 | AI843866 |
| 117260_at | 0.00 | 0.00 | 0.00 | 0.00 | 4.03 | 0.00 | UNK_AI841583 | AI841583 |
| 117276_at | 0.00 | 0.00 | 0.00 | 0.00 | 2.92 | 0.00 | UNK_AI849085 | AI849085 |
| 117310_at | 0.00 | 0.00 | 0.00 | 0.00 | 3.99 | 0.00 | UNK_AI835269 | AI835269 |
| 129180_f_at | 0.00 | 0.00 | 0.00 | 0.00 | 1.87 | 3.06 | UNK_AW214234 | AW214234 |
| 129925_at | 0.00 | 0.00 | 0.00 | 0.00 | 1.88 | 3.42 | UNK_AW212719 | AW212719 |
| 129983_at | 0.00 | 1.93 | 1.73 | 3.10 | 1.52 | 1.45 | UNK_AA795716 | AA795716 |
| 130549_f_at | 0.00 | 6.37 | 0.00 | 0.00 | 0.00 | 0.00 | UNK_AU018276 | AU018276 |
| 130719_at | 0.00 | 0.00 | 0.00 | 1.99 | 1.42 | 4.14 | UNK_AW045814 | AW045814 |
| 130804_at | 0.00 | 0.00 | 0.00 | 1.73 | 2.86 | 0.00 | UNK_AU024135 | AU024135 |
| 132172_at | 0.00 | 0.00 | 2.03 | 1.88 | 0.00 | 0.00 | UNK_AI195127 | AI195127 |
| 132364_i_at | 0.00 | 0.00 | 0.00 | 0.00 | 2.40 | 0.00 | UNK_AI594430 | AI594430 |
| 132365_r_at | 0.00 | 0.00 | 0.00 | 0.00 | 1.89 | 2.06 | UNK_AI594430 | AI594430 |
| 133139_at | 0.00 | 0.00 | 0.00 | 3.87 | 1.76 | 0.00 | UNK_AW122295 | AW122295 |
| 133799_at | 0.00 | 0.00 | 0.00 | 0.00 | 4.06 | 0.00 | UNK_AI131700 | AI131700 |
| 133901_f_at | 0.00 | 0.00 | 0.00 | 1.64 | 0.46 | 2.10 | UNK_AI481837 | A1481837 |
| 134388_at | 0.00 | 1.21 | 0.00 | 0.00 | 1.88 | 2.31 | UNK_AI536536 | AI536536 |
| 134515_at | 0.00 | 0.00 | 0.00 | 0.00 | 1.93 | 2.29 | UNK_AI874652 | AI874652 |
| 134531_at | 0.00 | 0.00 | 0.00 | 0.00 | 4.11 | 1.62 | UNK_AW121822 | AW121822 |
| 134597_at | 0.00 | 0.00 | 0.00 | 0.00 | 4.14 | 0.00 | UNK_AI643832 | AI643832 |
| 134660_at | 0.00 | 0.00 | 0.00 | 2.17 | 1.73 | 0.00 | UNK_AA793588 | AA793588 |
| 134662_f_at | 0.00 | 0.00 | 0.00 | 2.20 | 1.47 | 1.48 | UNK_AI585590 | AI585590 |
| 135172_at | 0.00 | 0.00 | 0.00 | 0.00 | 1.32 | 2.79 | UNK_AI480578 | AI480578 |
| 135314_at | 0.00 | 0.00 | 1.79 | 1.78 | 2.48 | 2.00 | UNK_AI842058 | AI842058 |
| 135355_at | 0.00 | 0.00 | 0.00 | 0.00 | 1.91 | 3.47 | UNK_AW228646 | AW228646 |
| 135552_f_at | 0.00 | 2.62 | 0.00 | 0.00 | 0.00 | 0.00 | UNK_AI646499 | AI646499 |
| 135655_at | 0.00 | 0.00 | 0.00 | 2.23 | 0.00 | 0.00 | UNK_AI447921 | AI447921 |
| 135812_at | 0.00 | 0.00 | 0.00 | 0.00 | 2.23 | 0.00 | UNK_AI848262 | AI848262 |
| 135888_at | 0.00 | 0.00 | 0.00 | 1.83 | 1.89 | 2.00 | UNK_AI153331 | AI153331 |
| 136132_at | 0.00 | 1.92 | 2.10 | 1.78 | 0.00 | 0.00 | UNK_AI853191 | AI853191 |
| 136191_at | 0.00 | 2.22 | 0.00 | 0.00 | 0.00 | 0.00 | UNK_AI852455 | AI852455 |
| 136558_at | 0.00 | 0.00 | 0.00 | 0.00 | 1.01 | 2.20 | UNK_AI465462 | AI465462 |
| 137699_at | 0.00 | 2.23 | 0.00 | 0.00 | 1.35 | 0.00 | UNK_AW045500 | AW045500 |

TABLE 1-continued

| | Treatment Time | | | | | | | |
|---|---|---|---|---|---|---|---|---|
| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
| 138079_at | 0.00 | 0.00 | 0.00 | 0.00 | 1.62 | 2.50 | UNK_AI849673 | AI849673 |
| 138945_at | 0.00 | 2.27 | 0.11 | 0.00 | 0.00 | 0.00 | UNK_AI843433 | AI843433 |
| 138960_f_at | 0.00 | 0.00 | 0.00 | 0.00 | 1.25 | 2.04 | UNK_AI841128 | AI841128 |
| 140441_at | 0.00 | 2.51 | 0.00 | 0.00 | 0.00 | 0.00 | UNK_AW105899 | AW105899 |
| 140654_at | 0.00 | 0.00 | 0.00 | 0.00 | 1.49 | 2.03 | UNK_AA967374 | AA967374 |
| 140760_at | 0.00 | 0.00 | 0.00 | 0.00 | 2.05 | 0.00 | UNK_AI648116 | AI648116 |
| 140893_at | 0.00 | 0.00 | 0.00 | 1.17 | 2.24 | 0.00 | UNK_AW123714 | AW123714 |
| 140999_at | 0.00 | 1.68 | 1.97 | 2.74 | 1.61 | 1.53 | UNK_AA561076 | AA561076 |
| 141179_at | 0.00 | 2.26 | 0.00 | 0.00 | 0.00 | 0.00 | UNK_AI645500 | AI645500 |
| 97543_at | 0.00 | 0.00 | 0.00 | 2.96 | 1.83 | 2.01 | expressed, developmentally down-regulated gene 5; Nedd5 | D49382 |
| 96337_at | 0.00 | 0.00 | 0.00 | 0.00 | 6.05 | 6.35 | PNUTL1 | AF033350 |
| 98609_at | 0.00 | 0.00 | 0.00 | 3.74 | 5.09 | 4.97 | MSF | AJ250723 |
| 98149_s_at | 0.00 | 2.78 | 2.86 | 6.13 | 9.13 | 4.99 | UNK_AW046496 | AW046496 |
| 110272_at | 0.00 | 2.06 | 5.37 | 4.90 | 3.35 | 3.49 | UNK_AA636558 | AA636558 |
| 92459_at | 0.00 | 4.73 | 9.59 | 15.62 | 24.77 | 14.53 | UNK_AB023418 | AB023418 |
| 97198_at | 0.00 | 0.00 | 0.00 | 3.04 | 2.54 | 4.37 | cassette, sub-family A (ABC1), member 1; Abca1 | X75926 |
| 103035_at | 0.00 | 1.73 | 2.92 | 4.20 | 2.83 | 4.90 | TAP1 | U60020 |
| 98402_at | 0.00 | 0.00 | 0.00 | 2.12 | 2.32 | 2.07 | ACLP7 | AI843799 |
| 92688_at | 0.00 | 2.01 | 2.65 | 2.91 | 2.26 | 2.58 | acid phosphatase 2, lysosomal; Acp2 | X57199 |
| 97904_at | 0.00 | 1.93 | 1.98 | 3.64 | 2.94 | 3.68 | UNK_AW123953 | AW123953 |
| 96573_at | 0.00 | 1.69 | 0.00 | 2.54 | 1.91 | 2.14 | actin, gamma, cytoplasmic, actin-like; Actg, Actl | M21495 |
| 96343_at | 0.00 | 1.72 | 1.82 | 3.41 | 3.64 | 3.03 | UNK_AI836968 | AI836968 |
| 93100_at | 0.00 | 0.00 | 0.00 | 3.39 | 4.40 | 2.27 | vascular smooth muscle; Actvs | X13297 |
| 93460_at | 0.00 | 0.00 | 0.00 | 0.00 | 2.49 | 1.93 | activin A receptor, type 1; Acvr1 | L15436 |
| 100751_at | 0.00 | 0.00 | 0.00 | 0.00 | 2.25 | 2.76 | metalloprotease domain (ADAM) 10; Adam10 | AF011379 |
| 92414_at | 0.00 | 1.50 | 0.00 | 5.97 | 9.93 | 8.83 | a disintegrin and metalloproteinase domain 12 (meltrin alpha); Adam12 | D50411 |
| 103554_at | 0.00 | 0.00 | 2.63 | 3.50 | 5.47 | 3.45 | a disintegrin and metalloproteinase domain 19 (meltrin beta); Adam 19 | AA726223 |
| 103024_at | 6.28 | 10.02 | 5.98 | 4.43 | 4.10 | 2.38 | ADAM8 | X13335 |
| 103392_at | 0.00 | 0.00 | 2.42 | 3.39 | 3.92 | 3.18 | adenylate cyclase 7; Adcy7 | U12919 |
| 94535_at | 0.00 | 0.00 | 0.00 | 0.00 | 2.19 | 0.00 | ADD1 | AW121844 |
| 100903_at | 0.00 | 0.00 | 0.00 | 2.36 | 1.77 | 1.90 | ADPRT2 | AJ007780 |
| 99038_at | 0.00 | 0.00 | 0.00 | 3.40 | 4.12 | 3.85 | adenylosuccinate synthetase 2, non muscle; Adss2 | L24554 |
| 99039_g_at | 0.00 | 1.47 | 0.00 | 2.78 | 2.26 | 2.44 | adenylosuccinate synthetase 2, non muscle; Adss2 | L24554 |
| 100412_g_at | 0.00 | 0.00 | 0.00 | 2.85 | 2.62 | 0.00 | AEBP1 | AF053943 |
| 136586_at | 0.00 | 3.12 | 3.56 | 5.26 | 6.60 | 6.27 | UNK_AA960336 | AA960336 |
| 96357_at | 0.00 | 1.61 | 1.85 | 2.83 | 3.78 | 4.62 | AF007010 | AW212775 |
| 104205_at | 0.00 | 0.00 | 0.00 | 3.25 | 19.16 | 4.89 | aggrecan, structural proteoglycan of cartilage; Agc | L07049 |
| 92210_at | 0.00 | 0.00 | 0.00 | 0.00 | 2.69 | 7.02 | Agpt2 | AF004326 |
| 96025_g_at | 0.00 | 0.00 | 2.18 | 2.51 | 0.00 | 0.00 | adenosylhomocysteine hydrolase; Ahcy | L32836 |
| 103551_at | 0.00 | 0.00 | 0.00 | 0.00 | 2.39 | 4.11 | UNK_AW124208 | AW124208 |
| 116577_at | 0.00 | 0.00 | 0.00 | 0.00 | 2.86 | 3.71 | UNK_AI450355 | AI450355 |
| 107536_at | 0.00 | 0.00 | 2.87 | 4.47 | 3.94 | 4.08 | UNK_AI851964 | AI851964 |
| 104415_at | 0.00 | 0.00 | 0.00 | 0.00 | 2.85 | 0.00 | UNK_AA833293 | AA833293 |
| 103911_at | 0.00 | 0.00 | 0.00 | 0.00 | 2.57 | 2.19 | UNK_AI851573 | AI851573 |
| 102330_at | 2.21 | 4.90 | 6.74 | 9.69 | 5.41 | 3.36 | AIF1 | D86382 |
| 103443_at | 0.00 | 2.98 | 0.00 | 0.00 | 2.23 | 0.00 | UNK_AA711704 | AA711704 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 95148_at | 0.00 | 0.00 | 1.83 | 3.07 | 3.90 | 5.63 | AK2 | AB020202 |
| 92796_at | 0.00 | 0.00 | 4.88 | 10.36 | 57.57 | 19.90 | phosphatase 2, liver; Akp2 | J02980 |
| 96888_at | 0.00 | 0.00 | 0.00 | 2.21 | 2.04 | 2.03 | UNK_AI839814 | AI839814 |
| 100970_at | 0.00 | 0.00 | 0.00 | 2.56 | 2.72 | 2.86 | thymoma viral proto-oncogene; Akt | X65687 |
| 98372_at | 0.00 | 2.97 | 0.00 | 5.29 | 2.86 | 0.00 | UNK_AW050387 | AW050387 |
| 96243_f_at | 0.00 | 1.81 | 0.00 | 0.00 | 2.32 | 3.58 | UNK_AW120804 | AW120804 |
| 102048_at | 4.83 | 7.77 | 16.74 | 18.48 | 10.36 | 4.40 | ALRP | AF041847 |
| 94392_f_at | 0.00 | 2.01 | 1.70 | 2.55 | 2.32 | 0.00 | angiogenin; Ang | U22516 |
| 102054_at | 0.00 | 2.71 | 0.00 | 2.96 | 2.56 | 2.75 | ANKHZN | AB011370 |
| 93038_f_at | 0.00 | 2.05 | 2.40 | 3.64 | 3.20 | 3.58 | LPC1 | M69260 |
| 100569_at | 2.07 | 2.76 | 2.79 | 4.54 | 4.52 | 4.67 | annexin A2; Anxa2 | M14044 |
| 101393_at | 2.43 | 0.00 | 0.00 | 2.45 | 2.13 | 0.00 | ANXA3 | AJ001633 |
| 100584_at | 0.00 | 0.00 | 1.67 | 2.84 | 2.85 | 4.02 | annexin A4; Anxa4 | U72941 |
| 93083_at | 0.00 | 0.00 | 0.00 | 2.67 | 2.69 | 2.86 | ANXA5 | D63423 |
| 93587_at | 0.00 | 0.00 | 0.00 | 3.45 | 0.00 | 0.00 | annexin A7; Anxa7 | L13129 |
| 97529_at | 0.00 | 2.06 | 0.00 | 5.97 | 8.79 | 7.30 | annexin A8; Anxa8 | AJ002390 |
| 102327_at | 0.00 | 0.00 | 2.07 | 2.55 | 3.01 | 3.11 | AOC3 | AF078705 |
| 103242_at | 0.00 | 0.00 | 0.00 | 1.94 | 2.49 | 2.90 | UNK_AW123834 | AW123834 |
| 103878_at | 0.00 | 0.00 | 0.00 | 2.13 | 2.21 | 2.07 | AP3B1 | AF103809 |
| 103796_at | 0.00 | 0.00 | 0.00 | 3.99 | 3.27 | 3.46 | APAF1 | AF064071 |
| 102710_at | 2.15 | 2.86 | 3.37 | 3.90 | 3.45 | 5.22 | precursor protein-binding, family B, member 1 interacting protein; Apbb1ip-pending | AF020313 |
| 101035_at | 0.00 | 0.00 | 2.01 | 0.00 | 1.84 | 2.15 | apoptosis inhibitor 5; Api5 | U35846 |
| 98398_s_at | 0.00 | 2.97 | 3.11 | 3.55 | 2.15 | 2.64 | APOBEC1 | U22262 |
| 95356_at | 0.00 | 1.46 | 1.78 | 2.38 | 2.50 | 3.08 | Apoe | D00466 |
| 93700_at | 0.00 | 0.00 | 0.00 | 0.00 | 2.47 | 2.59 | SIAT9 | AI838022 |
| 96587_at | 0.00 | 0.00 | 0.00 | 0.00 | 3.15 | 2.61 | ADP-ribosylation factor 3; Arf3 | D87900 |
| 92968_at | 0.00 | 0.00 | 0.00 | 0.00 | 2.14 | 0.00 | ADP-ribosylation factor 5; Arf5 | D87902 |
| 93097_at | 0.00 | 6.15 | 1.74 | 1.71 | 0.00 | 0.00 | Arg1 | U51805 |
| 101030_at | 0.00 | 0.00 | 0.00 | 1.85 | 2.12 | 3.24 | homolog B (RhoB); Arhb | X99963 |
| 96056_at | 0.00 | 0.00 | 0.00 | 3.00 | 3.64 | 4.22 | homolog 9 (RhoC); Arhc | X80638 |
| 95547_at | 0.00 | 0.00 | 0.00 | 0.00 | 5.84 | 3.99 | homolog D (RhoD); Arhd | D89821 |
| 98001_at | 0.00 | 0.00 | 2.06 | 1.83 | 2.85 | 2.92 | nucleotide exchange factor (GEF) 1; Arhgef1 | U58203 |
| 101439_at | 0.00 | 0.00 | 0.00 | 0.00 | 2.72 | 2.07 | UNK_AW122716 | AW122716 |
| 115479_at | 0.00 | 0.00 | 2.38 | 5.55 | 5.94 | 3.35 | ARP2-PENDING | AA792177 |
| 95434_at | 0.00 | 2.17 | 2.13 | 2.92 | 2.24 | 2.57 | UNK_AI851740 | AI851740 |
| 100931_at | 0.00 | 0.00 | 0.00 | 0.00 | 4.46 | 4.79 | arylsulfatase A; As2 | X73230 |
| 94282_at | 0.00 | 1.86 | 0.00 | 3.66 | 3.84 | 3.64 | UNK_AW124297 | AW124297 |
| 95133_at | 0.00 | 0.00 | 0.00 | 0.00 | 5.31 | 0.00 | asparagine synthetase; Asns | U38940 |
| 101984_at | 0.00 | 0.00 | 0.00 | 1.79 | 2.04 | 2.76 | ATX1 (antioxidant protein 1) homolog 1 (yeast); Atox1 | AF004591 |
| 99579_at | 0.00 | 1.58 | 0.00 | 2.44 | 2.72 | 3.30 | beta 3 polypeptide; Atp1b3 | U59761 |
| 98126_s_at | 0.00 | 0.00 | 0.00 | 0.00 | 2.12 | 0.00 | ATPase, Ca++ transporting, cardiac muscle, fast twitch 1; Atp2a1 | X67140 |
| 95746_at | 0.00 | 1.51 | 0.00 | 2.69 | 2.20 | 7.69 | ATP6A2 | AW123765 |
| 95745_g_at | 0.00 | 1.35 | 0.00 | 1.80 | 1.68 | 6.74 | transporting, lysosomal (vacuolar proton pump), alpha 70 kDa, isoform 2; | U13837 |
| 94301_at | 0.00 | 2.37 | 2.07 | 3.22 | 5.34 | 8.96 | ATP6K | AI843269 |
| 102854_s_at | 0.00 | 2.19 | 0.00 | 0.00 | 0.00 | 0.00 | ATPase, Cu++ transporting, alpha polypeptide; Atp7a | U03434 |
| 93984_at | 0.00 | 1.88 | 2.24 | 3.26 | 3.23 | 3.67 | Atpi | AF002718 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 98960_s_at | 0.00 | 0.00 | 0.00 | 1.73 | 2.48 | 1.89 | UNK_AF029792 | AF029792 |
| 103002_at | 0.00 | 0.00 | 0.00 | 1.95 | 2.15 | 1.84 | B4GALT1 | M27923 |
| 104005_at | 0.00 | 0.00 | 0.00 | 0.00 | 5.00 | 2.43 | B4GALT2 | AB019541 |
| 111981_at | 0.00 | 0.00 | 0.00 | 0.00 | 2.02 | 0.00 | BACE2 | AW122959 |
| 99670_at | 0.00 | 0.00 | 0.00 | 0.00 | 3.45 | 2.81 | Bcl-associated death promoter; Bad | L37296 |
| 93536_at | 0.00 | 0.00 | 0.00 | 3.00 | 3.22 | 2.81 | Bcl2-associated X protein; Bax | L22472 |
| 93252_at | 0.00 | 0.00 | 0.00 | 0.00 | 2.57 | 0.00 | B-cell receptor-associated protein 31; Bcap31 | X81816 |
| 100026_at | 0.00 | 0.00 | 0.00 | 5.43 | 16.18 | 0.00 | BCAT1 | U42443 |
| 94448_at | 0.00 | 0.00 | 0.00 | 2.85 | 1.58 | 2.13 | BCL10 | AJ006289 |
| 102914_s_at | 0.00 | 0.00 | 0.00 | 0.00 | 5.13 | 13.02 | BCL2A1B | U23778 |
| 93869_s_at | 0.00 | 0.00 | 0.00 | 2.68 | 3.36 | 9.35 | BCL2A1D | U23781 |
| 101748_at | 0.00 | 0.00 | 0.00 | 0.00 | 13.92 | 0.00 | bradykinin receptor, beta; Bdkrb | U47281 |
| 101514_at | 0.00 | 0.00 | 0.00 | 2.06 | 3.68 | 2.34 | BET3-PENDING | AF041433 |
| 103647_at | 0.00 | 0.00 | 3.61 | 2.66 | 5.42 | 16.86 | beta-galactosidase complex; Bgl | M57734 |
| 96049_at | 0.00 | 2.06 | 2.40 | 4.02 | 3.69 | 4.37 | BGN | X53928 |
| 98433_at | 0.00 | 2.16 | 0.00 | 0.00 | 1.45 | 2.01 | domain death agonist; Bid | U75506 |
| 101521_at | 0.00 | 4.32 | 4.05 | 5.67 | 5.14 | 3.35 | AP14 | AB013819 |
| 95803_at | 0.00 | 3.17 | 0.00 | 3.77 | 3.63 | 5.29 | BIT | D85785 |
| 95804_g_at | 0.00 | 5.17 | 0.00 | 0.00 | 8.80 | 10.32 | BIT | D85785 |
| 93604_f_at | 0.00 | 0.00 | 0.00 | 0.00 | 2.95 | 14.19 | BL2 | AF061260 |
| 93606_s_at | 0.00 | 0.00 | 0.00 | 0.00 | 3.11 | 11.25 | BL2 | AB021966 |
| 95557_at | 0.00 | 0.00 | 0.00 | 6.05 | 10.83 | 17.24 | bone morphogenetic protein 1; Bmp1 | L24755 |
| 92701_at | 0.00 | 0.00 | 0.00 | 0.00 | 8.10 | 7.21 | BMP1 | AA518586 |
| 95012_at | 0.00 | 0.00 | 0.00 | 0.00 | 1.54 | 4.40 | UNK_AB012808 | AB012808 |
| 98031_at | 0.00 | 0.00 | 0.00 | 0.00 | 9.58 | 0.00 | BOKL-PENDING | AF027707 |
| 94036_at | 0.00 | 0.00 | 0.00 | 0.00 | 5.14 | 4.93 | UNK_AI844806 | AI844806 |
| 93324_at | 0.00 | 0.00 | 0.00 | 3.98 | 3.49 | 3.40 | butyrate response factor 1; Brf1 | M58566 |
| 93104_at | 0.00 | 2.95 | 2.80 | 4.02 | 4.75 | 5.01 | BTG1 | Z16410 |
| 96146_at | 0.00 | 0.00 | 0.00 | 3.56 | 6.34 | 5.24 | BTG3 | D83745 |
| 104097_at | 0.00 | 0.00 | 1.72 | 2.12 | 1.86 | 0.00 | budding uninhibited by benzimidazoles 1 homolog (S. cerevisiae); Bub1 | AF002823 |
| 109165_at | 0.00 | 0.00 | 0.00 | 0.00 | 2.63 | 0.00 | BUB1B | AW049504 |
| 93042_at | 0.00 | 1.80 | 0.00 | 2.82 | 2.69 | 3.24 | benzodiazepine receptor, peripheral; Bzrp | D21207 |
| 96718_at | 0.00 | 0.00 | 0.00 | 0.00 | 1.79 | 2.12 | UNK_AB012727 | AB012727 |
| 98562_at | 0.00 | 2.80 | 3.66 | 5.77 | 3.76 | 4.31 | component 1, q subcomponent, alpha polypeptide; | X58861 |
| 96020_at | 0.00 | 2.88 | 4.26 | 6.67 | 4.45 | 4.01 | component 1, q subcomponent, beta polypeptide; C1qb | M22531 |
| 92223_at | 0.00 | 1.85 | 2.43 | 4.07 | 2.93 | 2.85 | component 1, q subcomponent, c polypeptide; C1qc | X66295 |
| 103707_at | 0.00 | 2.61 | 3.37 | 4.05 | 3.10 | 2.93 | C3AR1 | U77461 |
| 103033_at | 0.00 | 0.00 | 1.67 | 2.36 | 3.44 | 3.66 | C4 | X06454 |
| 101728_at | 0.00 | 2.20 | 0.00 | 0.12 | 3.09 | 0.00 | C5R1 | S46665 |
| 98483_at | 0.00 | 0.00 | 0.00 | 0.00 | 5.67 | 7.91 | CACNB3 | X94404 |
| 95423_at | 0.00 | 2.15 | 2.96 | 5.11 | 3.94 | 3.37 | CAI | Y00884 |
| 100155_at | 3.86 | 2.01 | 2.63 | 4.29 | 1.65 | 0.00 | Cak | L57509 |
| 101107_at | 0.00 | 0.00 | 0.00 | 3.14 | 3.16 | 2.78 | calumenin; Calu | U81829 |
| 104529_at | 0.00 | 0.00 | 1.88 | 1.93 | 2.26 | 2.09 | calcium modulating ligand; Caml | U21960 |
| 101040_at | 0.00 | 1.47 | 1.28 | 2.06 | 1.74 | 2.07 | calpain 2; Capn2 | D38117 |
| 97942_g_at | −1.56 | 0.00 | 0.00 | 6.16 | 40.88 | 8.57 | CAPN6 | Y12582 |
| 97941_at | 0.00 | 0.00 | 0.00 | 0.00 | 8.69 | 2.20 | CAPN6 | Y12582 |
| 97943_at | 0.00 | 0.00 | 0.00 | 1.98 | 4.94 | 2.50 | CAPN6 | AI747133 |
| 93499_at | 0.00 | 3.32 | 1.92 | 3.16 | 4.17 | 4.70 | capping protein alpha 1; Cappa1 | U16740 |
| 102248_f_at | 0.00 | 1.87 | 0.00 | 2.83 | 3.31 | 2.91 | CASK | Y17138 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 102064_at | 0.00 | 1.72 | 0.00 | 2.05 | 1.38 | 2.48 | CASP1 | L28095 |
| 99049_at | 0.00 | 0.00 | 0.00 | 0.00 | 2.36 | 3.08 | caspase 2; Casp2 | D28492 |
| 98436_s_at | 0.00 | 0.00 | 2.32 | 3.29 | 4.63 | 3.72 | apoptosis related cysteine protease; Casp3 | U54803 |
| 94458_at | 0.00 | 0.00 | 0.00 | 0.00 | 3.24 | 3.31 | CASP6 | Y13087 |
| 102328_at | 1.67 | 0.00 | 3.82 | 0.00 | 5.01 | 4.40 | CASP8 | AJ007749 |
| 93364_at | 0.00 | 1.84 | 0.00 | 2.26 | 2.32 | 2.91 | CATNA1 | X59990 |
| 98151_s_at | 0.00 | 0.00 | 0.00 | 0.00 | 1.80 | 3.29 | catenin src; Catns | Z17804 |
| 94817_at | 0.00 | 2.19 | 2.44 | 4.38 | 4.24 | 4.34 | CBP1 | X60676 |
| 93697_at | 0.00 | 0.00 | 0.00 | 0.00 | 1.72 | 3.53 | CBX4 | U63387 |
| 99186_at | 0.00 | 8.48 | 3.62 | 3.94 | 5.08 | 3.50 | CCNA2 | X75483 |
| 94294_at | 0.00 | 2.93 | 3.54 | 5.89 | 5.22 | 5.58 | cyclin B2; Ccnb2 | X66032 |
| 94232_at | 0.00 | 2.12 | 1.47 | 1.84 | 2.61 | 2.72 | CCND1 | AI849928 |
| 99535_at | 2.08 | 1.94 | 0.00 | 0.00 | 0.00 | 0.00 | CCR4 | AW047630 |
| 98153_at | 0.00 | 0.00 | 0.00 | 2.04 | 1.83 | 0.00 | chaperonin subunit 3 (gamma); Cct3 | L20509 |
| 98446_s_at | 0.00 | 1.83 | 1.75 | 2.36 | 1.70 | 0.00 | EPHB4 | U06834 |
| 98088_at | 0.00 | 0.00 | 1.54 | 0.00 | 2.87 | 0.00 | CD14 antigen; Cd14 | X13333 |
| 103422_at | 0.00 | 0.00 | 0.00 | 0.00 | 2.42 | 7.86 | Cd1d1 | M63695 |
| 101897_g_at | 0.00 | 0.00 | 0.00 | 0.00 | 2.31 | 5.91 | Cd1d2 | M63697 |
| 103005_s_at | 2.64 | 4.50 | 2.70 | 3.84 | 3.12 | 5.15 | CD44 | X66084 |
| 114697_at | 2.65 | 4.08 | 3.95 | 6.25 | 8.24 | 22.18 | CD44 | AI594062 |
| 103089_at | 0.00 | 4.30 | 5.56 | 6.22 | 5.21 | 4.03 | CD48 antigen; Cd48 | X53526 |
| 104606_at | 2.11 | 3.68 | 3.52 | 4.72 | 4.14 | 7.46 | CD52 antigen; Cd52 | M55561 |
| 94939_at | 2.23 | 3.23 | 3.49 | 4.50 | 3.47 | 5.59 | CD53 antigen; Cd53 | X97227 |
| 103016_s_at | 0.00 | 2.52 | 3.48 | 6.07 | 4.53 | 15.71 | CD68 | X68273 |
| 101878_at | 0.00 | 2.02 | 3.26 | 3.66 | 4.16 | 3.58 | CD72 antigen; Cd72 | J04170 |
| 99584_at | 0.00 | 2.17 | 0.00 | 3.40 | 2.84 | 2.83 | CD82 antigen; Cd82 | D14883 |
| 103040_at | 0.00 | 0.00 | 0.00 | 0.00 | 1.56 | 2.15 | CD83 | AI837100 |
| 95661_at | 0.00 | 0.00 | 0.00 | 0.00 | 1.33 | 2.18 | CD9 | L08115 |
| 102934_s_at | 0.00 | 1.60 | 0.00 | 2.80 | 2.37 | 0.00 | CDC25C | L16926 |
| 100128_at | 0.00 | 8.81 | 12.87 | 15.86 | 16.72 | 6.21 | CDC2A | M38724 |
| 103821_at | 0.00 | 1.77 | 1.70 | 1.97 | 2.01 | 0.00 | CDC6 | AJ223087 |
| 100006_at | 0.00 | 0.00 | 0.00 | 0.00 | 6.64 | 5.01 | CDH11 | D21253 |
| 102852_at | 0.00 | 0.00 | 0.00 | 0.00 | 7.68 | 9.75 | cadherin 2; Cdh2 | M31131 |
| 94412_at | 0.00 | 0.00 | 0.00 | 0.00 | 2.88 | 3.60 | CDK2 | AJ223733 |
| 101017_at | 0.00 | 0.00 | 0.00 | 0.00 | 3.17 | 2.52 | CDK4 | AA791962 |
| 100444_at | 0.00 | 0.00 | 0.00 | 0.00 | 3.47 | 0.00 | cyclin-dependent kinase 5; Cdk5 | D29678 |
| 94881_at | 0.00 | 0.00 | 0.00 | 0.00 | 3.11 | 0.00 | CDKN1A | AW048937 |
| 98067_at | 0.00 | 0.00 | 0.00 | 0.00 | 5.18 | 0.00 | cyclin-dependent kinase inhibitor 1A (P21); Cdkn1a | U09507 |
| 95471_at | 0.00 | −2.68 | −2.76 | 0.00 | 2.10 | 1.92 | cyclin-dependent kinase inhibitor 1C (P57); Cdkn1c | U22399 |
| 101900_at | 0.00 | 0.00 | 0.00 | 0.00 | 6.10 | 1.30 | CDKN2B | AF059567 |
| 93094_at | 0.00 | 0.00 | 0.00 | 0.00 | 3.46 | 3.26 | degeneration-related 2; Cdr2 | U88588 |
| 109137_at | 0.00 | 0.00 | 0.00 | 0.00 | 3.39 | 3.25 | CDYL | AI157065 |
| 100616_at | 0.00 | 0.00 | 0.00 | 0.00 | 2.44 | 0.00 | CENPA | AF012710 |
| 98770_at | 0.00 | 0.00 | 0.00 | 0.00 | 2.24 | 0.00 | CENPC | AF012708 |
| 107597_f_at | 0.00 | 0.00 | 4.29 | 2.70 | 3.37 | 0.00 | UNK_AA637016 | AA637016 |
| 92788_f_at | 0.00 | 0.00 | 0.00 | 2.36 | 2.67 | 2.72 | CETN3 | Y12474 |
| 93784_at | 0.00 | 0.00 | 0.00 | 2.99 | 3.88 | 2.71 | CFDP | AB010828 |
| 101853_f_at | 0.00 | 0.00 | 0.00 | 0.00 | 3.42 | 11.91 | component factor h; Cfh | M12660 |
| 92291_f_at | 0.00 | 0.00 | 0.00 | 0.00 | 3.05 | 13.62 | related protein; CFHRB | M29008 |
| 99119_at | 0.00 | 2.89 | 3.39 | 4.99 | 6.15 | 6.26 | cofilin 1, non-muscle; Cfl1 | D00472 |
| 99120_f_at | 0.00 | 0.00 | 0.00 | 2.06 | 2.24 | 1.88 | cofilin 1 , non-muscle; Cfl1 | R75450 |
| 104509_at | 0.00 | 1.89 | 0.00 | 0.00 | 2.34 | 0.00 | CH25H-PENDING | AF059213 |
| 101459_at | 0.00 | 0.00 | 0.00 | 0.00 | 1.60 | 2.02 | helicase DNA binding protein 1; Chd1 | L10410 |
| 103088_at | 0.00 | 3.21 | 2.88 | 0.00 | 0.00 | 0.00 | close homolog of L1; Chl1 | X94310 |
| 100021_at | 0.00 | 0.00 | 2.97 | 7.77 | 7.91 | 0.00 | ACRA | M17640 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 96549_at | 0.00 | 0.00 | 0.00 | 0.00 | 3.62 | 0.00 | acetylcholine receptor delta; Acrd | L10076 |
| 102639_at | 0.00 | 0.00 | 1.92 | 2.41 | 2.72 | 2.04 | CHTS2 | AB011451 |
| 92832_at | 0.00 | 0.00 | 0.00 | 0.00 | 4.30 | 0.00 | CISH1 | U88325 |
| 92232_at | 6.68 | 28.29 | 0.00 | 13.77 | 17.42 | 5.49 | cytokine inducible SH2-containing protein 3; Cish3 | U88328 |
| 93126_at | 0.00 | 0.00 | 0.00 | 0.00 | 2.57 | 10.46 | creatine kinase, brain; Ckb | X04591 |
| 97468_at | 0.00 | 6.71 | 10.12 | 11.31 | 13.78 | 6.31 | CKS1 | AB025409 |
| 92762_at | 2.53 | 6.19 | 4.80 | 3.95 | 2.46 | 3.99 | CLECSF6 | AJ133533 |
| 94256_at | 0.00 | 2.07 | 2.20 | 3.05 | 4.36 | 3.47 | CLIC4 | AI849533 |
| 94254_at | 0.00 | 0.00 | 1.62 | 2.70 | 2.24 | 3.40 | CLIC4 | AI845237 |
| 94255_g_at | 0.00 | 1.55 | 1.90 | 2.51 | 1.93 | 3.71 | CLIC4 | AI845237 |
| 103346_at | 0.00 | 0.00 | 0.00 | 0.00 | 2.31 | 2.73 | CLK2 | AF033564 |
| 100579_s_at | 0.00 | 2.13 | 2.05 | 2.61 | 2.89 | 3.28 | polypeptide (Lca); Clta | U91848 |
| 95286_at | 0.00 | 1.77 | 0.00 | 2.24 | 0.00 | 0.00 | CLU | D14077 |
| 102794_at | 0.00 | 0.00 | 1.89 | 2.10 | 1.38 | 1.53 | CMKAR4 | Z80112 |
| 93397_at | 2.34 | 4.18 | 3.03 | 4.05 | 2.45 | 3.21 | chemokine (C—C) receptor 2; Cmkbr2 | U56819 |
| 102718_at | 2.24 | 3.99 | 3.37 | 0.00 | 2.71 | 0.00 | CMKBR5 | AF022990 |
| 102719_f_at | 1.75 | 3.77 | 2.23 | 2.28 | 2.38 | 1.33 | chemokine (C—C) receptor 5; Cmkbr5 | X94151 |
| 94004_at | 0.00 | 0.00 | 0.00 | 3.43 | 10.86 | 9.73 | calponin 2; Cnn2 | Z19543 |
| 100481_at | 0.00 | 0.00 | 0.00 | 0.00 | 20.07 | 11.26 | procollagen. type XI, alpha 1; Col11a1 | D38162 |
| 103616_at | 0.00 | 0.00 | 0.00 | 0.00 | 25.14 | 34.25 | UNK_AF100956 | AF100956 |
| 92314_at | 0.00 | 0.00 | 0.00 | 0.00 | 10.67 | 0.00 | XII, alpha 1; Col12a1 | U25652 |
| 102261_f_at | 0.00 | 0.00 | 0.00 | 0.00 | 2.65 | 4.65 | COL13A1 | U30292 |
| 102262_r_at | 0.00 | 0.00 | 0.00 | 0.00 | 4.29 | 6.76 | COL13A1 | U30292 |
| 99476_at | 0.00 | 0.00 | 0.00 | 1.84 | 2.80 | 2.91 | COL14A1 | AJ131395 |
| 99637_at | 0.00 | 0.00 | 0.00 | 2.41 | 2.14 | 2.67 | srocollagen, type XV; Col15a1 | AF011450 |
| 99638_at | 0.00 | 0.00 | 0.00 | 3.24 | 5.40 | 5.62 | procollagen, type XV; Col15a1 | D17546 |
| 101881_g_at | 0.00 | 0.00 | 0.00 | 4.81 | 10.82 | 10.32 | COL18A1 | L22545 |
| 102990_at | 0.00 | 2.15 | 3.36 | 6.99 | 10.03 | 12.96 | COL3A1 | AA655199 |
| 98331_at | 0.00 | 0.00 | 0.00 | 2.60 | 3.93 | 4.38 | procollagen, type III, alpha 1; Col3a1 | X52046 |
| 101093_at | 0.00 | 0.00 | 0.00 | 2.28 | 2.02 | 2.23 | COL4A1 | M15832 |
| 101080_at | 0.00 | 1.80 | 3.49 | 9.91 | 19.47 | 13.93 | COL5A1 | AB009993 |
| 101906_at | 0.00 | 2.48 | 3.11 | 5.07 | 3.93 | 3.93 | COL5A2 | AA032310 |
| 92567_at | 0.00 | 1.92 | 2.95 | 6.03 | 7.55 | 9.22 | procollagen, type V, alpha 2; Col5a2 | L02918 |
| 113235_at | 0.00 | 0.00 | 0.00 | 2.96 | 1.95 | 3.12 | COL5A3 | AA734782 |
| 95493_at | 0.00 | 0.00 | 0.00 | 3.72 | 3.84 | 3.50 | procollagen, type VI, alpha 1; Col6a1 | X66405 |
| 93517_at | 0.00 | 0.00 | 1.99 | 4.43 | 6.38 | 5.80 | COL6A2 | Z18272 |
| 101110_at | 0.00 | 0.00 | 2.32 | 5.51 | 6.14 | 5.80 | COL6A3 | AF064749 |
| 100308_at | 0.00 | 2.74 | 2.14 | 6.75 | 37.35 | 14.46 | procollagen, type VIII, alpha 1; Col8a1 | X66976 |
| 104483_at | 0.00 | 0.00 | 0.00 | 0.00 | 32.61 | 0.00 | COL9A1 | L12215 |
| 98027_at | 0.00 | 0.00 | 0.00 | 0.00 | 4.61 | 0.00 | procollagen, type IX, alpha 2; Col9a2 | Z22923 |
| 102070_at | 0.00 | 0.00 | 0.00 | 0.00 | 13.24 | 0.00 | UNK_AW212495 | AW212495 |
| 94305_at | 0.00 | 0.00 | 0.00 | 2.82 | 0.00 | 0.00 | COLA1 | U03419 |
| 93340_f_at | 0.00 | 0.00 | 0.00 | 4.50 | 3.30 | 2.24 | COPB2 | AF043120 |
| 93341_r_at | 0.00 | 0.00 | 0.00 | 2.46 | 2.84 | 1.83 | COPB2 | AF043120 |
| 98930_at | 0.00 | 0.00 | 0.00 | 0.00 | 2.06 | 0.00 | UNK_AI844701 | AI844701 |
| 110860_at | 0.00 | 0.00 | 3.09 | 3.85 | 1.24 | 3.46 | COPEB | AI846501 |
| 94427_at | 0.00 | 0.00 | 0.00 | 2.68 | 4.76 | 3.81 | COPG1 | AI841737 |
| 96936_at | 0.00 | 0.00 | 0.00 | 2.28 | 4.10 | 2.32 | COPG1 | AI020792 |
| 95149_at | 0.00 | 0.00 | 0.00 | 2.58 | 1.86 | 2.06 | UNK_AW121088 | AW121088 |
| 104143_at | 0.00 | 0.00 | 0.00 | 2.36 | 3.59 | 3.04 | UNK_AI843212 | AI843212 |
| 96648_at | 0.00 | 13.50 | 4.26 | 0.00 | 5.51 | 6.88 | CORO1A | AW122039 |
| 98928_at | 0.00 | 1.68 | 0.00 | 3.37 | 5.06 | 5.56 | CORO1B | AW122820 |
| 99631_f_at | 0.00 | 1.54 | 0.00 | 2.84 | 2.08 | 3.07 | COX6A1 | U08440 |
| 92851_at | 0.00 | 0.00 | 0.00 | 0.00 | 2.49 | 8.74 | ceruloplasmin; Cp | U49430 |
| 95514_at | 0.00 | 0.00 | 0.00 | 2.96 | 4.71 | 2.89 | UNK_AI846302 | AI846302 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 93320_at | 0.00 | 1.78 | 2.64 | 3.70 | 2.65 | 3.94 | carnitine palmitoyltransferase 1, liver; Cpt1a | AF017175 |
| 103492_at | 0.00 | 0.00 | 0.00 | 0.00 | 10.90 | 5.75 | UNK_AF077738 | AF077738 |
| 98415_at | 0.00 | 0.00 | 0.00 | 0.00 | 1.35 | 2.34 | CREME9-PENDING | AF046060 |
| 98395_at | 2.46 | 1.94 | 0.00 | 0.00 | 0.00 | 0.00 | CRHR2 | U21729 |
| 94061_at | 0.00 | 0.00 | 0.00 | 2.64 | 1.93 | 2.29 | intestinal protein; Crip | M13018 |
| 101879_s_at | 0.00 | 0.00 | 0.00 | 0.00 | 1.75 | 2.34 | CRRY | M23529 |
| 103817_at | 0.00 | 2.19 | 2.37 | 5.07 | 8.57 | 7.80 | UNK_AJ006469 | AJ006469 |
| 92506_at | 0.00 | 0.00 | 0.00 | 0.00 | 8.84 | 0.00 | CRTL1 | AF098460 |
| 101450_at | 2.70 | 2.74 | 0.00 | 0.00 | 2.07 | 3.42 | factor 1 (macrophage); Csf1 | M21952 |
| 104354_at | 0.00 | 2.65 | 3.08 | 4.25 | 2.85 | 6.88 | factor 1 receptor; Csf1r | X06368 |
| 99330_at | 0.00 | 2.37 | 2.21 | 3.33 | 2.11 | 4.32 | factor 2 receptor, alpha, low-affinity (granulocyte-macrophage); | M85078 |
| 94284_at | 0.00 | 0.00 | 0.39 | 3.31 | 2.27 | 2.13 | UNK_AW122731 | AW122731 |
| 103210_at | 0.00 | 0.00 | 0.00 | 2.89 | 1.78 | 2.62 | factor 2 receptor, beta 2, low-affinity (granulocyte-macrophage); | M29855 |
| 104248_at | 0.00 | 0.00 | 0.00 | 2.35 | 2.26 | 2.03 | CSNK | AW227650 |
| 104249_g_at | 0.00 | 0.00 | 0.00 | 1.76 | 2.15 | 1.71 | CSNK | AW227650 |
| 100019_at | 6.42 | 11.38 | 13.27 | 12.75 | 12.15 | 9.66 | proteoglycan 2; Cspg2 | D45889 |
| 92608_at | 0.00 | 0.00 | 2.71 | 4.25 | 5.49 | 2.97 | cysteine rich protein; Csrp | D88793 |
| 93550_at | 0.00 | 2.70 | 4.70 | 12.96 | 26.37 | 8.78 | cysteine-rich protein 2; Csrp2 | D88792 |
| 100581_at | 0.00 | 1.94 | 2.02 | 3.94 | 2.84 | 7.19 | cystatin B; Cstb | U59807 |
| 92554_at | 0.00 | 0.00 | 0.00 | 1.95 | 2.32 | 2.05 | CTBP2 | AF059735 |
| 100148_at | 0.00 | 0.00 | 0.00 | 0.00 | 2.25 | 0.00 | CCCTC-binding factor; Ctcf | U51037 |
| 96912_s_at | 0.00 | 2.20 | 1.97 | 3.68 | 2.78 | 4.45 | lymphocyte-associated protein 2 alpha; Ctla2a | X15591 |
| 103518_at | 0.00 | 3.44 | 3.65 | 4.74 | 0.00 | 0.00 | lymphocyte-associated protein 2 beta; Ctla2b | X15592 |
| 103341_at | 0.00 | 1.78 | 2.25 | 2.07 | 1.92 | 0.00 | triphosphate synthase; Ctps | U49350 |
| 101019_at | 2.09 | 3.57 | 4.51 | 4.05 | 2.09 | 2.70 | CTSC | U74683 |
| 101020_at | 0.00 | 3.36 | 5.06 | 4.28 | 2.46 | 3.04 | CTSC | AI842667 |
| 94834_at | 0.00 | 1.76 | 2.32 | 4.76 | 5.57 | 5.93 | cathepsin H; Ctsh | U06119 |
| 98543_at | 0.00 | 1.80 | 2.38 | 3.24 | 2.52 | 4.10 | CTSS | AJ223208 |
| 92633_at | 0.00 | 1.52 | 2.44 | 2.98 | 2.97 | 6.50 | D2WSU143E | AJ242663 |
| 94054_at | 0.00 | 0.00 | 0.00 | 2.97 | 4.15 | 3.29 | CTTN | AI841808 |
| 94055_at | 0.00 | 0.00 | 2.52 | 0.00 | 5.91 | 4.16 | cortactin; Cttn | U03184 |
| 97013_f_at | 0.00 | 2.71 | 3.17 | 4.89 | 4.48 | 5.87 | CYBA | AW046124 |
| 100059_at | 0.00 | 2.19 | 2.49 | 3.52 | 3.30 | 4.51 | alpha polypeptide; Cyba | M31775 |
| 100300_at | 0.00 | 0.00 | 1.71 | 2.50 | 2.50 | 3.11 | beta polypeptide; Cybb | U43384 |
| 99979_at | 1.51 | 4.39 | 2.85 | 5.07 | 6.42 | 9.91 | CYP1B1 | X78445 |
| 94916_at | 0.00 | 1.59 | 0.00 | 2.47 | 2.67 | 0.00 | UNK_AW122260 | AW122260 |
| 92777_at | 0.00 | 2.49 | 3.85 | 4.95 | 3.04 | 1.84 | cysteine rich protein 61; Cyr61 | M32490 |
| 98619_at | 0.00 | 0.00 | 0.00 | 0.00 | 3.27 | 0.00 | UNK_AW121709 | AW121709 |
| 106255_at | 0.00 | 2.41 | 2.03 | 4.64 | 4.43 | 4.94 | UNK_AI840993 | AI840993 |
| 104358_at | 0.00 | 0.00 | 0.00 | 1.86 | 5.05 | 0.00 | UNK_AI853668 | AI853668 |
| 107526_at | 0.00 | 0.00 | 0.00 | 0.00 | 1.84 | 2.42 | UNK_AA710084 | AA710084 |
| 111683_at | 0.00 | 0.00 | 0.00 | 2.21 | 2.79 | 4.85 | D10UCLA1 | AA153345 |
| 112407_at | 0.00 | 0.00 | 0.00 | 0.00 | 2.20 | 3.03 | D10UCLA1 | AI021470 |
| 97824_at | 0.00 | 1.87 | 2.19 | 2.60 | 2.50 | 1.64 | UNK_AW121031 | AW121031 |
| 94339_at | 0.00 | 0.00 | 0.00 | 0.00 | 2.33 | 1.99 | UNK_AI841330 | AI841330 |
| 94242_at | 0.00 | 0.00 | 0.00 | 2.16 | 1.70 | 1.68 | UNK_AA881309 | AA881309 |
| 93427_at | 0.00 | 0.00 | 0.00 | 2.34 | 6.05 | 11.04 | UNK_AW122310 | AW122310 |
| 95480_at | 0.00 | 0.00 | 0.00 | 0.00 | 2.18 | 0.00 | D11WSU68E | AI847163 |
| 107600_at | 0.00 | 0.00 | 0.00 | 1.79 | 2.58 | 0.00 | UNK_AI838753 | AI838753 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 111518_at | 0.00 | 0.00 | 0.00 | 0.00 | 2.20 | 3.30 | UNK_AA170647 | AA170647 |
| 93775_at | 0.00 | 0.00 | 0.00 | 1.81 | 1.83 | 2.23 | UNK_AI841894 | AI841894 |
| 98061_at | 0.00 | 0.00 | 0.00 | 0.00 | 3.19 | 2.83 | UNK_AI841192 | AI841192 |
| 104558_at | 0.00 | 0.00 | 0.00 | 0.00 | 4.22 | 3.13 | D12WSU95E | AA867123 |
| 101372_at | 0.00 | 0.00 | 0.00 | 2.81 | 2.01 | 0.00 | UNK_AI852645 | AI852645 |
| 98918_at | 0.00 | 0.00 | 0.00 | 4.35 | 5.87 | 3.22 | D13WSU115E | AI841920 |
| 94452_g_at | 0.00 | 0.00 | 1.63 | 2.11 | 2.04 | 0.00 | D13WSU123E | AI787627 |
| 94450_at | 0.00 | 0.00 | 1.73 | 2.44 | 0.00 | 0.00 | D13WSU123E | AI854202 |
| 94502_at | 0.00 | 1.78 | 0.00 | 4.75 | 3.35 | 3.47 | D13WSU50E | AW125724 |
| 104419_at | 0.00 | 1.94 | 0.00 | 0.00 | 2.42 | 3.99 | UNK_AI132380 | AI132380 |
| 97325_at | 0.00 | 0.00 | 0.00 | 2.68 | 2.67 | 2.97 | UNK_AA881294 | AA881294 |
| 94561_at | 0.00 | 0.00 | 0.00 | 3.23 | 4.12 | 3.13 | UNK_AI836140 | AI836140 |
| 110414_at | 0.00 | 0.00 | 0.00 | 2.05 | 5.26 | 3.81 | UNK_AI594455 | AI594455 |
| 111499_at | 0.00 | 0.00 | 0.00 | 1.56 | 1.93 | 2.42 | UNK_AW046236 | AW046236 |
| 98013_at | 0.00 | 1.88 | 2.52 | 0.00 | 3.28 | 3.54 | UNK_AA666464 | AA666464 |
| 114305_at | 0.00 | 0.00 | 0.00 | 0.00 | 4.13 | 5.18 | UNK_AA739238 | AA739238 |
| 104633_at | 0.00 | 4.17 | 3.44 | 3.82 | 3.73 | 2.71 | D15WSU122E | AW123921 |
| 97822_at | 0.00 | 0.00 | 0.00 | 0.00 | 3.38 | 2.85 | UNK_AW122689 | AW122689 |
| 97821_at | 0.00 | 0.00 | 0.00 | 2.99 | 0.00 | 0.00 | UNK_AI646056 | AI646056 |
| 97823_g_at | 0.00 | 0.00 | 0.00 | 0.00 | 1.81 | 2.08 | UNK_AW122689 | AW122689 |
| 95063_at | 0.00 | 0.00 | 0.00 | 2.11 | 2.59 | 1.68 | UNK_AI606257 | AI606257 |
| 95137_at | 0.00 | 3.19 | 3.65 | 7.69 | 11.28 | 4.71 | UNK_AI852985 | AI852985 |
| 97921_at | 0.00 | 0.00 | 0.00 | 0.00 | 2.36 | 0.00 | UNK_AI846279 | AI846279 |
| 110388_at | 0.00 | 0.00 | 0.00 | 0.00 | 2.12 | 0.00 | UNK_AW213204 | AW213204 |
| 115074_at | 0.00 | 2.62 | 2.33 | 3.85 | 12.14 | 4.46 | UNK_AI197311 | AI197311 |
| 111433_at | 0.00 | 0.00 | 0.00 | 2.83 | 5.30 | 0.00 | UNK_AA795610 | AA795610 |
| 109692_at | 0.00 | 0.00 | 2.28 | 1.49 | 0.00 | 0.00 | UNK_AI848006 | AI848006 |
| 104333_at | 0.00 | 6.18 | 7.27 | 7.18 | 9.71 | 6.35 | DMA segment, Chr 17, human D6S56E 5; D17H6S56E-5 | U69488 |
| 96318_at | 0.00 | 0.00 | 0.00 | 3.10 | 4.21 | 3.13 | D17WSU104E | AW045739 |
| 134595_at | 0.00 | 0.00 | 0.00 | 2.88 | 2.15 | 2.49 | UNK_AI006117 | AI006117 |
| 100154_at | 0.00 | 0.00 | 0.00 | 2.77 | 1.72 | 2.56 | D17WSU91E | AI836367 |
| 104090_at | 0.00 | 0.00 | 0.00 | 0.00 | 2.38 | 2.01 | UNK_AA657164 | AA657164 |
| 96346_at | 0.00 | −1.46 | −2.12 | 0.00 | 2.45 | 5.93 | D18UCLA3 | AI854020 |
| 94967_at | 0.00 | 0.00 | 0.00 | 0.00 | 1.66 | 3.20 | UNK_AI851365 | AI851365 |
| 96838_at | 0.00 | 0.00 | 0.00 | 0.00 | 4.46 | 0.00 | RCE1 | AI851223 |
| 107005_at | 0.00 | 0.00 | 0.00 | 1.90 | 3.19 | 0.00 | UNK_AI853916 | AI853916 |
| 113182_at | 0.00 | 0.00 | 0.00 | 1.92 | 2.43 | 0.00 | UNK_AI844871 | AI844871 |
| 112787_f_at | 0.00 | 0.00 | 0.00 | 2.64 | 2.54 | 2.82 | UNK_AI838572 | AI838572 |
| 112786_i_at | 0.00 | 0.00 | 0.00 | 4.53 | 3.47 | 0.00 | UNK_AI838572 | AI838572 |
| 103310_at | 0.00 | 0.00 | 0.00 | 0.00 | 2.12 | 1.91 | 0 | AA220427 |
| 104740_at | 0.00 | 0.00 | 0.00 | 0.00 | 2.41 | 2.78 | UNK_AW125318 | AW125318 |
| 95428_at | 0.00 | 0.00 | 2.83 | 0.00 | 1.99 | 0.00 | D1WSU40E | AA688761 |
| 104602_at | 0.00 | 1.59 | 0.00 | 0.00 | 1.70 | 3.29 | UNK_AW121972 | AW121972 |
| 104640_f_at | 0.00 | 0.00 | 0.00 | 2.44 | 2.40 | 2.19 | UNK_AI464596 | AI464596 |
| 104639_i_at | 0.00 | 0.00 | 0.00 | 2.93 | 2.83 | 0.00 | UNK_AI464596 | AI464596 |
| 104225_at | 0.00 | 0.00 | 0.00 | 0.00 | 2.10 | 2.21 | UNK_AI645050 | AI645050 |
| 100054_s_at | 0.00 | 0.00 | 0.00 | 0.00 | 2.09 | 0.00 | ENDOG | AW123127 |
| 107513_at | 0.00 | 0.00 | 0.00 | 2.31 | 3.11 | 2.79 | UNK_AW123087 | AW123087 |
| 95708_at | 0.00 | 2.11 | 3.22 | 5.70 | 7.02 | 8.87 | UNK_AI843466 | AI843466 |
| 98016_at | 0.00 | 0.00 | 0.00 | 2.43 | 0.00 | 0.00 | D3WSU161E | AA981268 |
| 95477_at | 0.00 | 0.00 | 0.00 | 0.00 | 2.08 | 2.36 | UNK_AW125185 | AW125185 |
| 99621_s_at | 0.00 | 2.08 | 2.54 | 2.56 | 2.88 | 2.85 | splicing factor proline/glutamine rich (polypyrimidine tract-binding protein-associated) (human) | AA690583 |
| 97295_at | 0.00 | 2.47 | 4.02 | 4.10 | 3.48 | 2.80 | UNK_AW122331 | AW122331 |
| 104116_at | 2.55 | 2.60 | 2.64 | 1.68 | 0.00 | 0.00 | UNK_AW124049 | AW124049 |
| 107574_at | 0.00 | 0.00 | 0.00 | 2.45 | 2.15 | 3.00 | UNK_AI836723 | AI836723 |
| 98092_at | 3.04 | 3.06 | 5.10 | 7.71 | 4.52 | 10.69 | D5WSU111E | AA790307 |
| 104176_at | 0.00 | 0.00 | 0.00 | 0.00 | 4.07 | 3.97 | UNK_AI850941 | AI850941 |
| 96675_at | 0.00 | 0.00 | 0.00 | 1.94 | 2.68 | 2.48 | UNK_AW124245 | AW124245 |
| 104168_at | 0.00 | 2.74 | 2.34 | 3.99 | 2.65 | 3.50 | UNK_AA791742 | AA791742 |
| 94237_at | 0.00 | 2.35 | 3.47 | 5.76 | 4.82 | 3.95 | D6WSU137E | AI846708 |
| 95541_at | 0.00 | 2.27 | 0.00 | 4.67 | 5.62 | 5.12 | D6WSU176E | AW125506 |
| 104300_at | 0.00 | 1.95 | 2.90 | 6.09 | 4.75 | 5.14 | IQGAP1 | AI117936 |
| 95032_at | 0.00 | 3.40 | 3.29 | 6.75 | 7.34 | 1.97 | PRC1 | AA856349 |
| 103871_at | 0.00 | 0.00 | 0.00 | 3.06 | 3.70 | 1.44 | UNK_AW123729 | AW123729 |
| 110005_at | 0.00 | 1.94 | 0.00 | 3.25 | 7.31 | 5.69 | UNK_AA839741 | AA839741 |
| 103862_r_at | 0.00 | 0.00 | 0.00 | 2.45 | 2.02 | 2.13 | D7WSU128E | AA388099 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 103861_s_at | 0.00 | 0.00 | 0.00 | 2.07 | 2.29 | 0.00 | D7WSU128E | AA388099 |
| 95709_at | 0.00 | 0.00 | 0.00 | 3.89 | 6.25 | 6.07 | D7WSU86E | AW012491 |
| 106634_at | 0.00 | 0.00 | 0.00 | 2.10 | 0.00 | 0.00 | UNK_AW123293 | AW123293 |
| 96325_at | 0.00 | 0.00 | 0.00 | 0.00 | 1.66 | 2.12 | D8WSU108E | AW124874 |
| 95430_f_at | 0.00 | 1.77 | 0.00 | 2.65 | 2.71 | 3.32 | D9WSU18E | AI854154 |
| 98045_s_at | 2.72 | 5.83 | 3.95 | 5.13 | 4.15 | 3.08 | disabled homolog 2 (Drosophila); Dab2 | U18869 |
| 98044_at | 1.21 | 2.07 | 0.00 | 0.00 | 1.74 | 0.00 | disabled homolog 2 (Drosophila); Dab2 | U18869 |
| 96008_at | 0.00 | 0.00 | 0.00 | 1.99 | 2.36 | 0.00 | DAD1 | U81052 |
| 117012_g_at | 0.00 | 0.00 | 0.00 | 4.00 | 7.90 | 3.56 | UNK_AW105743 | AW105743 |
| 117011_at | 0.00 | 0.00 | 0.00 | 0.00 | 3.01 | 0.00 | UNK_AW105743 | AW105743 |
| 103430_at | 0.00 | 0.00 | 0.00 | 0.00 | 2.05 | 0.00 | UNK_AW124952 | AW124952 |
| 95529_at | 0.00 | 1.86 | 2.09 | 5.10 | 2.54 | 3.94 | drebrin-like; Dbnl | U58884 |
| 98071_f_at | 0.00 | 2.00 | 3.67 | 3.69 | 3.07 | 3.72 | deoxycytidine kinase; Dck | X77731 |
| 101104_at | 0.00 | 0.00 | 0.00 | 1.46 | 1.46 | 2.07 | critical region gene a; Dcra | AB001990 |
| 96636_at | 0.00 | 1.43 | 1.65 | 2.07 | 1.84 | 1.97 | UNK_AI852649 | AI852649 |
| 95682_at | 0.00 | 0.00 | 0.00 | 2.05 | 2.47 | 1.54 | DDB1 | AB026432 |
| 95683_g_at | 0.00 | 0.00 | 0.00 | 1.88 | 2.50 | 1.80 | DDB1 | AB026432 |
| 100513_at | 0.00 | 0.00 | 0.00 | 1.68 | 4.36 | 3.45 | DDEF1 | AF075461 |
| 101074_at | 0.00 | 0.00 | 2.79 | 4.38 | 3.63 | 2.36 | phosphooligosaccharide-protein glycotransferase; Ddost | D89063 |
| 103598_at | 0.00 | 1.59 | 0.00 | 3.29 | 2.24 | 2.18 | DDX9 | U91922 |
| 131478_at | 0.00 | 0.00 | 0.00 | 0.00 | 3.96 | 3.79 | DECR2 | AW120654 |
| 95688_at | 0.00 | 1.75 | 1.72 | 2.39 | 2.05 | 2.52 | spermatocyte homolog (Drosophila); Degs | Y08460 |
| 93188_at | 0.00 | 0.00 | 0.00 | 4.20 | 11.48 | 5.36 | DKK3 | AJ243964 |
| 102207_at | 0.00 | 0.00 | 0.00 | 0.00 | 3.35 | 3.26 | UNK_AW123249 | AW123249 |
| 101975_at | 0.00 | 0.00 | 0.00 | 0.00 | 1.62 | 3.17 | DLK1 | Z12171 |
| 92332_at | 0.00 | 0.00 | 2.88 | 0.00 | 2.22 | 0.00 | distal-less homeobox 2; Dlx2 | M80540 |
| 92930_at | 0.00 | 0.00 | 0.00 | 0.00 | 8.22 | 7.47 | distal-less homeobox 5; Dlx5 | U67840 |
| 96703_at | 0.00 | 1.79 | 3.01 | 7.33 | 9.33 | 5.98 | UNK_AB029448 | AB029448 |
| 103344_at | 0.00 | 0.00 | 0.00 | 0.00 | 2.04 | 2.64 | DnaJ-like protein 1; Dnajl1 | L16953 |
| 99184_at | 0.00 | 0.00 | 0.00 | 0.00 | 1.89 | 2.60 | DNASE2 | AW120896 |
| 96298_f_at | 0.00 | 1.82 | 1.92 | 3.10 | 3.96 | 3.65 | UNK_AF020185 | AF020185 |
| 103030_at | 0.00 | 0.00 | 0.00 | 4.57 | 7.87 | 4.91 | dynamin; Dnm | L31397 |
| 103031_g_at | 0.00 | 0.00 | 0.00 | 0.00 | 3.09 | 3.12 | dynamin; Dnm | L31397 |
| 101445_at | 0.00 | 2.65 | 0.00 | 0.00 | 0.00 | 0.00 | DNMT | AF036008 |
| 113211_at | 0.00 | 0.00 | 3.68 | 4.25 | 6.78 | 3.64 | DNT-PENDING | AW049974 |
| 102896_at | 0.00 | 0.00 | 2.04 | 3.64 | 4.81 | 3.43 | tyrosine kinase 1; Dok1 | U78818 |
| 102334_at | 3.08 | 3.91 | 0.00 | 0.00 | 0.00 | 0.00 | DOK2 | AF059583 |
| 101503_at | 3.58 | 3.12 | 4.04 | 8.95 | 7.81 | 5.99 | dihydropyrimidinase-like 3; Dpysl3 | X87817 |
| 102374_at | 0.00 | 0.00 | 0.00 | 0.00 | 4.74 | 4.92 | DSCR1L2 | AI847661 |
| 97341_at | 0.00 | 2.40 | 3.13 | 6.07 | 15.30 | 4.95 | DXIMX39E | AW124082 |
| 96813_f_at | 0.00 | 0.00 | 1.72 | 2.21 | 1.85 | 2.48 | DXIMX46E | AI852973 |
| 112941_f_at | 0.00 | 1.46 | 2.93 | 3.92 | 4.37 | 4.97 | UNK_AA960514 | AA960514 |
| 112940_i_at | 0.00 | 0.00 | 0.00 | 2.74 | 5.32 | 7.05 | UNK_AA960514 | AA960514 |
| 115503_at | 0.00 | 0.00 | 0.00 | 2.37 | 0.00 | 0.00 | UNK_AI536452 | AI536452 |
| 93306_at | 0.00 | 1.46 | 0.00 | 2.07 | 1.87 | 1.74 | polyposis coli binding protein Eb1; Eb1 | U51196 |
| 96627_at | 0.00 | 2.70 | 0.00 | 4.71 | 4.42 | 3.78 | Ca2+ antagonist (emopamil) binding protein; Ebp | X97755 |
| 97411_at | 0.00 | 2.04 | 3.41 | 2.85 | 4.03 | 1.78 | ect2 oncogene; Ect2 | L11316 |
| 92352_at | 0.00 | 0.00 | 0.00 | 0.00 | 2.00 | 3.30 | EDG3 | AF108021 |
| 92867_at | 0.00 | 0.00 | 0.00 | 4.47 | 3.82 | 0.00 | EDR2 | AF060076 |
| 113230_at | 0.00 | 12.60 | 18.55 | 27.29 | 46.06 | 32.08 | UNK_AW210333 | AW210333 |
| 98407_at | 0.00 | 0.00 | 0.00 | 0.00 | 4.30 | 3.00 | ephrin B1; Efhb1 | U07602 |
| 96195_at | 0.00 | 0.00 | 0.00 | 0.00 | 2.74 | 5.31 | embryonal Fyn-associated substrate; Efs | U57686 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 101842_g_at | 0.00 | 0.00 | 0.00 | 0.00 | 2.82 | 0.00 | EGFR | AW049716 |
| 115396_at | 0.00 | 0.00 | 0.00 | 0.00 | 4.40 | 0.00 | UNK_AW212285 | AW212285 |
| 93058_at | 0.00 | 2.41 | 2.49 | 4.00 | 4.26 | 3.39 | UNK_AF026481 | AF026481 |
| 103537_at | 0.00 | 1.28 | 0.00 | 0.00 | 1.95 | 2.34 | EIF2AK3 | AF076681 |
| 99101_at | 0.00 | 0.00 | 0.00 | 2.72 | 2.29 | 0.00 | EIF3S7 | AB012580 |
| 92816_r_at | 0.00 | 1.75 | 1.97 | 0.00 | 2.95 | 2.45 | EIF4A1 | X03039 |
| 93783_at | 0.00 | 0.00 | 0.00 | 0.00 | 2.98 | 0.00 | 0 | M27347 |
| 99984_at | 0.00 | 0.00 | 0.00 | 0.00 | 2.33 | 2.51 | ELK3 | L19953 |
| 101560_at | 2.84 | 8.50 | 10.71 | 11.39 | 7.26 | 13.98 | EMB | AW061330 |
| 97426_at | 0.00 | 1.52 | 2.41 | 2.31 | 3.42 | 2.86 | EMP1 | X98471 |
| 93593_f_at | 2.04 | 3.04 | 3.13 | 4.60 | 5.82 | 4.88 | EMP3 | U87948 |
| 103507_at | 0.00 | 4.51 | 20.15 | 12.03 | 5.17 | 6.40 | containing, mucin-like, hormone receptor-like sequence 1; Emr1 | X93328 |
| 100134_at | 0.00 | 0.00 | 0.00 | 4.01 | 4.92 | 4.32 | endoglin; Eng | X77952 |
| 106642_at | 0.00 | 0.00 | 1.68 | 0.00 | 3.70 | 1.79 | UNK_AW260744 | AW260744 |
| 104174_at | 0.00 | 0.00 | 0.00 | 5.50 | 8.69 | 10.09 | phosphodiesterase I/nucleotide pyrophosphatase 1; Pdnp1 | J02700 |
| 115369_at | 0.00 | 0.00 | 2.74 | 4.43 | 7.92 | 3.04 | EPB4.1L3 | AI835976 |
| 96623_at | 0.00 | 2.54 | 2.75 | 4.70 | 5.02 | 3.50 | EPCS21-PENDING | AI853172 |
| 103980_at | 0.00 | 0.00 | 0.00 | 0.00 | 4.49 | 0.00 | Epha2 | U07634 |
| 95298_at | 0.00 | 0.00 | 0.00 | 0.00 | 3.47 | 1.35 | Epha3 | M68513 |
| 93469_at | 0.00 | 0.00 | 0.00 | 0.00 | 6.34 | 0.00 | EPHB3 | Z49086 |
| 104482_at | 0.00 | 0.00 | 0.00 | 0.00 | 6.75 | 0.00 | epimorphin; Epim | D10475 |
| 98992_at | 0.00 | 0.00 | 0.00 | 2.10 | 3.71 | 0.00 | EPPB9-PENDING | AB030483 |
| 104006_at | 0.00 | 2.64 | 0.00 | 0.00 | 0.00 | 0.00 | factor receptor pathway substrate 15; Eps15 | L21768 |
| 93670_at | 0.00 | 0.00 | 0.00 | 4.02 | 4.90 | 3.90 | ERF | AW048233 |
| 94040_at | 0.00 | 1.72 | 0.00 | 2.76 | 2.29 | 1.74 | rudimentary homolog (Drosophila); Erh | D73368 |
| 98129_at | 0.00 | 1.68 | 0.00 | 4.36 | 7.07 | 5.75 | UNK_AI852553 | AI852553 |
| 113283_at | 0.00 | 0.00 | 2.92 | 3.42 | 2.28 | 4.63 | ESTM25 | AI036047 |
| 113563_at | 0.00 | 0.00 | 0.00 | 0.00 | 2.14 | 2.15 | ESTM3 | AI845154 |
| 100348_at | 0.00 | 0.00 | 3.31 | 0.00 | 3.48 | 2.28 | ESTM4 | AW214136 |
| 98025_at | 1.99 | 3.06 | 3.68 | 5.90 | 5.31 | 4.61 | integration site 2; Evi2 | M34896 |
| 98026_g_at | 0.00 | 2.64 | 3.50 | 4.48 | 4.34 | 4.88 | integration site 2; Evi2 | M34896 |
| 94810_at | 0.00 | 1.61 | 0.00 | 2.32 | 2.75 | 2.25 | Ewing sarcoma homolog; Ewsh | X79233 |
| 102811_at | 0.00 | 1.49 | 2.88 | 2.92 | 4.07 | 10.13 | exostoses (multiple) 1; Ext1 | X96639 |
| 141160_f_at | 0.00 | 0.00 | 0.00 | 10.92 | 7.94 | 16.18 | EXT1 | AA710704 |
| 99929_at | 0.00 | 0.00 | 0.00 | 0.00 | 2.47 | 2.05 | EXT2 | U72141 |
| 99917_at | 0.00 | 0.00 | 2.33 | 2.28 | 2.10 | 0.00 | enhancer of zeste homolog 2 (Drosophila); Ezh2 | U52951 |
| 95313_at | 0.00 | 0.00 | 0.00 | 0.00 | 2.80 | 5.33 | UNK_AW046032 | AW046032 |
| 98967_at | 0.00 | 6.61 | 7.73 | 7.50 | 4.13 | 2.08 | protein 7, brain; Fabp7 | U04827 |
| 98588_at | 0.00 | 0.00 | 0.00 | 2.92 | 5.68 | 4.75 | FAH | Z11774 |
| 92441_at | 0.00 | 0.00 | 0.00 | 1.93 | 5.31 | 12.02 | FAP | Y10007 |
| 96119_s_at | 0.00 | 0.00 | 0.00 | 0.00 | 3.68 | 4.93 | UNK_AA797604 | AA797604 |
| 102114_f_at | 0.00 | 0.00 | 0.00 | 0.00 | 3.74 | 7.50 | UNK_AI326963 | AI326963 |
| 94309_g_at | 0.00 | 0.00 | 0.00 | 0.00 | 1.66 | 2.46 | fibulin 1; Fbln1 | X70853 |
| 101090_at | 0.00 | 1.63 | 0.00 | 3.44 | 2.92 | 3.24 | fibrillin 1; Fbn1 | L29454 |
| 103623_at | 0.00 | 0.00 | 0.00 | −0.04 | 3.50 | 0.00 | fibrillin 2; Fbn2 | L39790 |
| 130689_at | 0.00 | 1.99 | 0.00 | 4.20 | 3.52 | 0.00 | FBXO17 | AI957104 |
| 102879_s_at | 2.15 | 2.81 | 3.04 | 3.28 | 2.15 | 0.00 | Fc receptor, IgG, high affinity I; Fcgr1 | M31314 |
| 101793_at | 9.28 | 18.31 | 11.96 | 6.48 | 1.72 | 0.00 | FCGR1 | X70980 |
| 102337_s_at | 0.00 | 6.07 | 3.61 | 4.74 | 4.61 | 2.61 | FCGR2B | M31312 |
| 97327_at | 0.00 | 2.17 | 3.19 | 3.45 | 1.91 | 0.00 | specific endonuclease 1; | L26320 |
| 92188_s_at | 0.00 | 0.00 | 0.00 | 1.71 | 2.16 | 2.22 | feline sarcoma oncogene; Fes | X12616 |

TABLE 1-continued

| | Treatment Time | | | | | | | |
|---|---|---|---|---|---|---|---|---|
| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
| 93674_at | 0.00 | 0.00 | 0.00 | 2.36 | 3.64 | 0.00 | dysplasia homolog; Fgd1 | U22325 |
| 115755_g_at | 0.00 | 0.00 | 2.87 | 3.03 | 0.00 | 0.00 | FGD2 | AA958624 |
| 97509_f_at | 0.00 | 0.00 | 0.00 | 0.00 | 2.00 | 2.61 | FGFR1 | U22324 |
| 93090_at | 0.00 | 2.25 | 0.00 | 0.00 | 15.83 | 12.11 | FGFR2 | M23362 |
| 93091_s_at | 0.00 | 0.00 | 0.00 | 0.00 | 12.79 | 8.09 | factor receptor 2; Fgfr2 | M63503 |
| 100884_at | 0.00 | 8.62 | 5.24 | 11.29 | 12.67 | 10.44 | factor regulated protein; Fgfrp | U04204 |
| 108539_at | 1.30 | 2.97 | 3.41 | 3.92 | 1.57 | 0.00 | FGFRP2-PENDING | AI853558 |
| 100986_at | 0.00 | 0.00 | 0.00 | 1.61 | 2.26 | 2.55 | FHL2 | AF055889 |
| 99176_at | 0.00 | 0.00 | 0.00 | 0.00 | 2.80 | 2.04 | UNK_AI843393 | AI843393 |
| 97421_at | 0.00 | 3.18 | 3.75 | 4.37 | 5.50 | 2.59 | factor inducible 16; Fin16 | U42385 |
| 93294_at | 6.49 | 4.31 | 6.60 | 6.52 | 9.13 | 4.84 | secreted protein; Fisp12 | M70642 |
| 103248_at | 0.00 | 0.00 | 0.00 | 0.00 | 4.54 | 0.00 | FKBP1B | AF060872 |
| 99546_at | 0.00 | 2.31 | 0.00 | 3.07 | 2.84 | 2.41 | protein 2 (13 kDa); Fkbp2 | M77831 |
| 99082_at | 0.00 | 2.02 | 2.88 | 8.30 | 16.01 | 13.94 | protein 6 (65 kDa); Fkbp6 | L07063 |
| 104746_at | 0.00 | 0.00 | 0.00 | 4.08 | 8.21 | 6.92 | FKBP7 | AF040252 |
| 93731_at | 0.00 | 0.00 | 0.00 | 2.75 | 3.90 | 3.42 | FKBP9 | AF090334 |
| 98441_at | 0.00 | 2.19 | 2.46 | 3.50 | 3.23 | 2.83 | retardation syndrome 1 homolog; Fmr1 | L23971 |
| 104172_at | 0.00 | 1.74 | 2.18 | 2.78 | 1.72 | 0.00 | folate binding protein 2; Folbp2 | M64817 |
| 92838_at | 0.00 | 0.00 | 0.00 | 0.00 | 2.65 | 0.00 | FSCN1 | L33726 |
| 98817_at | 0.00 | 2.64 | 0.00 | 0.00 | 4.80 | 0.00 | follistatin; Fst | Z29532 |
| 105369_at | 0.00 | 0.00 | 2.20 | 2.45 | 3.39 | 3.07 | UNK_AW123943 | AW123943 |
| 94833_at | 0.00 | 1.28 | 0.00 | 3.60 | 2.58 | 3.49 | follistatin-like; Fstl | M91380 |
| 103394_at | 1.84 | 3.58 | 3.01 | 6.10 | 4.57 | 16.04 | containing ion transport regulator 5; Fxyd5 | U72680 |
| 100133_at | 0.00 | 0.00 | 0.00 | 2.50 | 2.89 | 3.88 | FYN | M27266 |
| 93681_at | 0.00 | 0.00 | 0.00 | 5.25 | 7.24 | 0.00 | UNK_AW123618 | AW123618 |
| 97531_at | 0.00 | 0.00 | 0.00 | 15.58 | 0.00 | 0.00 | G0/G1 switch gene 2; G0s2 | X95280 |
| 97516_at | 0.00 | 2.18 | 2.47 | 4.38 | 4.79 | 5.05 | alpha glucosidase 2, alpha neutral subunit; G2an | U92793 |
| 101294_g_at | 0.00 | 3.52 | 2.38 | 0.00 | 1.94 | 3.20 | G6PD2 | Z84471 |
| 102292_at | 2.03 | 2.13 | 1.47 | 0.00 | 0.00 | 0.00 | DDIT1 | U00937 |
| 101979_at | 2.21 | 2.10 | 0.00 | 2.23 | 2.97 | 0.00 | GADD45G | AF055638 |
| 109336_at | 0.00 | 0.00 | 0.00 | 0.00 | 3.83 | 0.00 | GADD45G | AI035425 |
| 103367_at | 0.00 | 2.04 | 0.00 | 0.00 | 2.18 | 2.73 | UDP-N-acetyl-alpha-D-galactosamine: (N-acetylneuraminyl)-galactosylglucosyl-ceramide-beta-1, 4-N-acetylgalactosaminyl transferase; Galgt1 | U18975 |
| 115517_at | 0.00 | 1.62 | 0.00 | 0.00 | 3.39 | 3.09 | GALNS | AI845504 |
| 94338_g_at | 0.00 | 0.00 | 0.00 | 0.00 | 2.27 | 0.00 | growth arrest specific 2; Gas2 | M21828 |
| 98530_at | 0.00 | 0.00 | 0.00 | 0.00 | 3.47 | 2.41 | GAS5 | AI849615 |
| 98531_g_at | 0.00 | 0.00 | 0.00 | 2.10 | 2.16 | 1.73 | GAS5 | AI849615 |
| 99067_at | 0.00 | 1.65 | 1.75 | 2.27 | 2.93 | 2.61 | growth arrest specific 6; Gas6 | X59846 |
| 100488_at | 0.00 | 0.00 | 0.00 | 2.15 | 2.08 | 2.54 | acid beta glucosidase; Gba | M24119 |
| 103202_at | 0.00 | 0.00 | 3.29 | 4.08 | 1.83 | 3.84 | GBP3 | AW047476 |
| 114351_at | 0.00 | 0.00 | 0.00 | 1.71 | 2.75 | 4.42 | GCL | AA727943 |
| 92655_at | 0.00 | 0.00 | 0.00 | 2.20 | 1.93 | 0.00 | glucosaminyl (N-acetyl) transferase 1, core 2; Gcnt1 | U19265 |
| 109332_at | 0.00 | 0.00 | 0.00 | 1.55 | 2.61 | 0.00 | UNK_AW046226 | AW046226 |
| 103590_at | 0.00 | 0.00 | 0.00 | 2.29 | 5.83 | 3.68 | UNK_AI507104 | AI507104 |
| 93575_at | 0.00 | 0.00 | 0.00 | 0.00 | 2.41 | 3.91 | GGH | AF051102 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 102993_at | 0.00 | 0.00 | 0.00 | 3.30 | 3.20 | 2.75 | glycoprotein galactosyltransferase alpha 1, 3; Ggta1 | M85153 |
| 100064_f_at | 0.00 | 2.51 | 1.94 | 4.11 | 5.60 | 7.77 | GJA1 | M63801 |
| 100065_r_at | 0.00 | 2.36 | 1.96 | 3.86 | 7.28 | 15.07 | GJA1 | M63801 |
| 104016_at | 0.00 | 2.45 | 0.00 | 0.00 | 0.00 | 0.00 | gap junction membrane channel protein beta 5; Gjb5 | M91236 |
| 100395_at | 0.00 | 0.00 | 0.00 | 0.00 | 2.10 | 0.00 | GLI-Kruppel family member GLI2; Gli2 | X99104 |
| 97820_at | 0.00 | 0.00 | 2.46 | 3.78 | 9.89 | 2.84 | GLK | AB027012 |
| 99141_at | 0.00 | 0.00 | 0.00 | 1.91 | 1.71 | 4.95 | activator protein; Gm2a | U09816 |
| 111347_at | 0.00 | 0.00 | 0.00 | 2.18 | 2.61 | 3.02 | UNK_AI842321 | AI842321 |
| 112203_at | 0.00 | 0.00 | 2.28 | 0.00 | 3.41 | 3.74 | UNK_AI159117 | AI159117 |
| 97227_at | 0.00 | 0.00 | 0.00 | 0.00 | 2.05 | 0.00 | guanine nucleotide binding protein, alpha 12; Gna12 | M63659 |
| 97195_at | 0.00 | 0.00 | 0.00 | 0.00 | 1.55 | 2.31 | binding protein, alpha inhibiting 1; Gnai1 | U38501 |
| 99597_at | 0.00 | 3.19 | 1.89 | 3.28 | 2.96 | 3.96 | GNAI2 | AI841629 |
| 99596_f_at | 0.00 | 1.55 | 0.00 | 2.57 | 2.74 | 2.78 | binding protein, alpha inhibiting 2; Gnai2 | M13963 |
| 99598_g_at | 0.00 | 1.78 | 1.70 | 2.78 | 2.19 | 2.94 | GNAI2 | AI841629 |
| 98403_at | 0.00 | 0.00 | 0.00 | 0.00 | 2.76 | 0.00 | binding protein, related sequence 1; Gna-rs1 | X65026 |
| 94854_g_at | 0.00 | 0.00 | 1.55 | 2.04 | 2.09 | 2.16 | guanine nucleotide binding protein, beta 1; Gnb1 | U29055 |
| 97458_at | 0.00 | 0.00 | 0.00 | 2.21 | 2.02 | 2.23 | GNB1 | AI845935 |
| 94853_at | 0.00 | 0.00 | 0.00 | 2.38 | 1.75 | 2.56 | guanine nucleotide binding protein, beta 1; Gnb1 | U29055 |
| 96911_at | 0.00 | 1.70 | 0.00 | 2.58 | 2.86 | 2.20 | guanine nucleotide binding protein, beta 2; Gnb2 | U34960 |
| 107026_at | 0.00 | 0.00 | 1.56 | 1.38 | 2.66 | 2.01 | UNK_AW123052 | AW123052 |
| 93949_at | 0.00 | 0.00 | 0.00 | 1.26 | 2.32 | 1.69 | guanine nucleotide binding protein, beta 4; Gnb4 | M63658 |
| 99175_at | 0.00 | 1.95 | 0.00 | 3.06 | 3.53 | 3.40 | GNG10 | AI843396 |
| 100418_at | 0.00 | 0.00 | 0.00 | 0.00 | 2.34 | 0.00 | GNG2 | AW123750 |
| 104469_at | 0.00 | 3.50 | 3.20 | 3.84 | 3.87 | 3.68 | Gp38 | M73748 |
| 100325_at | 2.62 | 2.49 | 3.65 | 4.12 | 4.79 | 5.72 | glycoprotein 49 A, glycoprotein 49 B; Gp49a, Gp49b | M65027 |
| 92217_s_at | 2.14 | 2.62 | 2.84 | 3.41 | 3.42 | 3.67 | Gp49b | U05265 |
| 100435_at | 0.00 | 0.00 | 0.00 | 0.00 | 6.50 | 2.76 | GPCR26 | U13370 |
| 96978_at | 0.00 | 0.00 | 0.00 | 0.00 | 2.31 | 2.20 | GPH-PENDING | AB025258 |
| 92611_at | 0.00 | 1.62 | 2.76 | 2.64 | 3.18 | 2.91 | P137 | U18773 |
| 102040_at | 0.00 | 0.00 | 0.00 | 0.00 | 6.38 | 0.00 | GPRK6 | Y15798 |
| 104257_g_at | 1.81 | 3.32 | 4.39 | 2.84 | 3.70 | 4.44 | UNK_AI120844 | AI120844 |
| 93690_at | 0.00 | 0.00 | 0.00 | 0.00 | 5.63 | 2.81 | GRB10 | AF022072 |
| 93691_s_at | 0.00 | 0.00 | 0.00 | 1.82 | 5.28 | 2.39 | receptor bound protein 10; Grb10 | U18996 |
| 92263_at | 0.00 | 0.00 | 0.00 | 3.94 | 7.69 | 6.29 | leucine rich protein, B7 gene; Lrpb7 | AC002397 |
| 94217_f_at | 0.00 | 1.72 | 0.00 | 2.30 | 2.06 | 1.45 | leucine rich protein, B7 gene; Lrpb7 | AC002397 |
| 103993_at | 0.00 | 0.00 | 0.00 | 0.00 | 4.50 | 3.02 | leucine rich protein, B7 gene; Lrpb7 | AC002397 |
| 130710_at | 0.00 | 0.00 | 0.00 | 0.00 | 2.21 | 3.04 | UNK_AA869432 | AA869432 |
| 93066_at | 0.00 | 2.00 | 3.08 | 4.01 | 3.19 | 5.73 | CRN | D16195 |
| 95348_at | 0.00 | 3.06 | 0.00 | 0.00 | 0.00 | 0.00 | Gro1 | J04596 |
| 108045_at | 0.00 | 0.00 | 4.00 | 8.85 | 37.24 | 14.80 | UNK_AA798520 | AA798520 |
| 101060_at | 0.00 | 1.98 | 2.32 | 4.79 | 4.52 | 3.76 | reticulum protein; Erp | M73329 |
| 98052_at | 0.00 | 0.00 | 0.00 | 2.10 | 3.20 | 2.28 | GS15 | AF003999 |
| 94369_at | 0.00 | 0.00 | 0.00 | 0.00 | 2.95 | 3.81 | GSNPAT-PENDING | AW123026 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 94811_s_at | 0.00 | 0.00 | 0.00 | 3.37 | 1.72 | 0.00 | factor IIH, polypeptide 1 (62 kD subunit); Gtf2h1 | AJ002366 |
| 93588_at | 0.00 | 0.00 | 0.00 | 3.44 | 3.31 | 4.17 | Gtl3 | Z54179 |
| 98410_at | 0.00 | 0.00 | 0.00 | 2.35 | 1.93 | 2.75 | GTPI | AJ007972 |
| 98950_at | 0.00 | 0.00 | 0.00 | 1.95 | 1.89 | 2.29 | GTR2 | AB017616 |
| 103038_at | 0.00 | 0.00 | 0.00 | 1.95 | 2.54 | 2.11 | guanylate cyclase activator 1a (retina); Guca1a | L36860 |
| 97538_at | 0.00 | 2.21 | 3.31 | 4.47 | 4.17 | 7.37 | GUS-S | M19279 |
| 102688_f_at | 0.00 | 0.00 | 0.00 | 0.00 | 17.31 | 0.00 | GZMD | X56990 |
| 102728_f_at | 0.00 | 0.00 | 0.00 | 0.00 | 15.71 | 0.00 | GZME | M36901 |
| 92866_at | 0.00 | 2.07 | 0.00 | 2.67 | 2.11 | 4.52 | H2-AA | X52643 |
| 100998_at | 0.00 | 3.08 | 0.00 | 3.81 | 2.27 | 3.97 | H2-AB1 | M21932 |
| 94805_f_at | 0.00 | 2.32 | 2.24 | 3.40 | 2.34 | 1.33 | UNK_M33988 | M33988 |
| 93019_at | 0.00 | 0.00 | 1.29 | 2.00 | 3.96 | 1.92 | HIST5-2AX | Z35401 |
| 101954_at | 0.00 | 0.00 | 0.00 | 2.47 | 2.13 | 1.72 | H2afz | U70494 |
| 97541_f_at | 0.00 | 0.00 | 0.00 | 2.94 | 2.21 | 4.21 | D region locus 1; H2-D | X00246 |
| 97540_f_at | 0.00 | 0.00 | 0.00 | 2.17 | 1.64 | 2.90 | D region locus 1; H2-D | M69069 |
| 101886_f_at | 0.00 | 1.56 | 1.67 | 2.67 | 2.22 | 3.64 | H2-L | X52490 |
| 98035_s_at | 0.00 | 4.04 | 0.00 | 0.00 | 2.47 | 9.55 | H2-DMB1 | U35330 |
| 98034_at | 0.00 | 1.58 | 0.00 | 0.00 | 2.12 | 0.00 | H2-DMB1 | U35330 |
| 94285_at | 0.00 | 2.10 | 0.00 | 2.71 | 2.02 | 3.96 | class II antigen E beta; H2-Eb1 | X00958 |
| 97173_f_at | 0.00 | 0.00 | 0.00 | 4.33 | 2.95 | 7.12 | H2-K2 | M27134 |
| 103371_at | 0.00 | 0.00 | 0.00 | 2.62 | 3.44 | 2.54 | UNK_AF100956 | AF100956 |
| 102161_f_at | 0.00 | 1.46 | 0.00 | 3.22 | 2.08 | 4.39 | H2-Q2 | X58609 |
| 98438_f_at | 0.00 | 0.00 | 0.00 | 2.74 | 1.78 | 3.55 | H2-Q7 | X16202 |
| 93865_s_at | 0.00 | 0.00 | 2.00 | 2.91 | 2.15 | 2.95 | histocompatibility 2, T region locus 10, histocompatibility 2, T region locus 17, histocompatibility 2, T region locus 22, histocompatibility 2, T region locus 9; H2-T10, H2-T17, H2-T22, H2-T9 | M35244 |
| 98472_at | 0.00 | 0.00 | 2.30 | 3.40 | 2.50 | 4.96 | H2-T23 | Y00629 |
| 100708_at | 0.00 | 0.00 | 0.00 | 2.88 | 2.50 | 2.60 | H3 histone, family 3B; H3f3b | X13605 |
| 111734_at | 0.00 | 0.00 | 0.00 | 3.21 | 3.18 | 4.05 | UNK_AW121301 | AW121301 |
| 104125_at | 0.00 | 0.00 | 0.00 | 2.35 | 1.70 | 1.64 | HAIR-PENDING | AA763673 |
| 92580_at | 0.00 | 0.00 | 0.00 | 2.68 | 0.00 | 0.00 | histidyl tRNA synthetase; Hars | U39473 |
| 98865_at | 0.00 | 2.65 | 0.00 | 3.33 | 3.29 | 0.00 | hyaluronan synthase 2; Has2 | U52524 |
| 105550_at | 0.00 | 1.93 | 2.61 | 2.31 | 2.78 | 0.00 | HAS2 | AI122156 |
| 103286_at | 0.00 | 0.00 | 0.00 | 2.02 | 3.13 | 0.00 | UNK_AB012611 | AB012611 |
| 93483_at | 2.86 | 5.24 | 2.12 | 3.21 | 10.07 | 3.83 | lemopoietic cell kinase; Hck | J03023 |
| 99461_at | 1.98 | 5.10 | 3.27 | 2.70 | 2.63 | 0.00 | hematopoietic cell specific Lyn substrate 1; Hcls1 | X84797 |
| 102851_s_at | 0.00 | 2.75 | 5.77 | 5.45 | 2.90 | 4.43 | HCPH | M68902 |
| 96046_at | 0.00 | 0.00 | 0.00 | 2.52 | 1.79 | 0.00 | HDAC1 | X98207 |
| 92730_at | 0.00 | 0.00 | 0.00 | 2.16 | 0.00 | 0.00 | epidermal growth factor-like growth factor; Hegfl | L07264 |
| 97334_at | 0.00 | 1.95 | 0.00 | 0.00 | 4.41 | 0.00 | HES6 | AW048812 |
| 94840_at | 0.00 | 0.00 | 0.00 | 2.49 | 2.45 | 7.00 | Hexa | U05837 |
| 101913_at | 0.00 | 2.34 | 0.00 | 3.35 | 3.35 | 1.98 | HEY1 | AW214298 |
| 98628_f_at | 0.00 | 1.91 | 0.00 | 3.83 | 3.98 | 3.08 | factor 1, alpha subunit; Hif1a | AF003695 |
| 98629_f_at | 0.00 | 1.97 | 0.00 | 3.82 | 3.68 | 3.30 | HIF1A | Y09085 |
| 93250_r_at | 0.00 | 4.01 | 0.00 | 7.33 | 4.74 | 4.32 | HMG2 | X67668 |
| 104285_at | 0.00 | 0.00 | 0.00 | 0.00 | 4.78 | 0.00 | methylglutaryl-Coenzyme A reductase; Hmgcr | M62766 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 96699_at | 0.00 | 1.71 | 1.85 | 3.26 | 3.43 | 2.91 | high mobility group protein 14; Hmg14 | X53476 |
| 101589_at | 0.00 | 2.37 | 2.80 | 4.52 | 3.86 | 3.35 | high mobility group protein 17; Hmg17 | X12944 |
| 93276_at | 0.00 | 1.63 | 2.23 | 2.32 | 2.69 | 2.00 | neurological expressed sequence 1; Hn1 | U90123 |
| 97272_at | 0.00 | 1.75 | 2.19 | 3.44 | 4.86 | 3.11 | HNRPA1 | M99167 |
| 94303_at | 0.00 | 0.57 | 2.05 | 0.00 | 1.69 | 3.51 | nuclear ribonucleoprotein D; Hnrpd | U11274 |
| 101485_at | 0.00 | 0.00 | 0.00 | 5.33 | 3.02 | 2.04 | HNRPDL | AW124859 |
| 93990_at | 0.00 | 0.00 | 0.00 | 2.21 | 1.76 | 1.61 | 0 | Y14196 |
| 95232_at | 0.00 | 0.00 | 0.00 | 1.94 | 1.75 | 2.79 | HNRPL | AB009392 |
| 96092_at | 0.00 | 5.71 | 8.04 | 13.88 | 15.44 | 15.06 | haptoglobin; Hp | M96827 |
| 93351_at | 0.00 | 0.00 | 0.00 | 0.00 | 4.99 | 7.54 | hydroxyprostaglandin dehydrogenase 15 (NAD); Hpgd | U44389 |
| 102306_at | 0.00 | 0.00 | 0.00 | 3.65 | 4.58 | 3.02 | HS2ST1 | AF060178 |
| 101962_at | 0.00 | 0.00 | 0.00 | 0.00 | 1.86 | 2.30 | HSC70 | AI854884 |
| 97261_at | 0.00 | 1.77 | 0.00 | 0.00 | 2.16 | 2.28 | HSJ2 | AF055664 |
| 100353_g_at | 0.00 | 2.82 | 0.00 | 0.00 | 2.79 | 0.00 | HSPA4 | AA919208 |
| 99816_at | 0.00 | 0.00 | 0.00 | 0.00 | 2.43 | 0.00 | heat shock protein, 70 kDa 2; Hsp70-2 | M20567 |
| 95282_at | 0.00 | 2.04 | 0.00 | 2.82 | 1.71 | 1.47 | heat shock protein, 86 kDa 1; Hsp86-1 | J04633 |
| 101955_at | 0.00 | 1.92 | 1.98 | 3.00 | 2.30 | 1.78 | GRP78 | AJ002387 |
| 96254_at | 0.00 | 1.99 | 0.00 | 0.00 | 3.44 | 3.03 | HSPF1 | AB028272 |
| 101399_at | 0.00 | 0.00 | 0.00 | 0.00 | 2.72 | 0.00 | pertecan (heparan sulfate proteoglycan 2); Hspg2 | M77174 |
| 94236_at | 0.00 | 0.00 | 0.00 | 0.00 | 2.44 | 1.97 | UNK_AI838152 | AI838152 |
| 100476_at | 0.00 | 0.00 | 0.00 | 0.82 | 135.39 | 85.11 | IBSP | L20232 |
| 100050_at | 2.63 | 14.09 | 11.54 | 10.70 | 4.20 | 6.22 | inhibitor of DNA binding 1; Idb1 | M31885 |
| 92614_at | 4.55 | 9.82 | 5.87 | 7.78 | 9.53 | 9.08 | inhibitor of DNA binding 3; Idb3 | M60523 |
| 99109_at | 0.00 | 0.00 | 0.00 | 3.13 | 2.22 | 1.86 | immediate early response 2; Ier2 | M59821 |
| 94384_at | 0.00 | 1.56 | 0.00 | 3.55 | 1.73 | 2.13 | immediate early response 3; Ier3 | X67644 |
| 92251_f_at | 0.00 | 1.84 | 2.88 | 3.49 | 2.71 | 3.51 | UNK_AA960657 | AA960657 |
| 94224_s_at | 0.00 | 2.12 | 3.85 | 3.55 | 2.35 | 2.62 | UNK_M74123 | M74123 |
| 98465_f_at | 0.00 | 2.15 | 4.38 | 5.23 | 3.24 | 3.50 | interferon activated gene 204; Ifi204 | M31419 |
| 104750_at | 0.00 | 3.40 | 7.66 | 4.69 | 2.10 | 4.67 | interferon gamma inducible protein, 47 kDa; Ifi47 | M63630 |
| 100981_at | 0.00 | 0.00 | 8.75 | 0.00 | 3.37 | 2.08 | interferon-induced protein with tetratricopeptide repeats 1; Ifit1 | U43084 |
| 112340_at | 0.00 | 0.00 | 4.49 | 1.51 | 0.00 | 0.00 | UNK_AA178653 | AA178653 |
| 103639_at | 0.00 | 0.00 | 4.82 | 7.01 | 2.67 | 2.35 | interferon-induced protein with tetratricopeptide repeats 2; Ifit2 | U43085 |
| 93956_at | 0.00 | 0.00 | 4.25 | 6.35 | 0.00 | 0.00 | IFIT3 | U43086 |
| 100483_at | 0.00 | 0.00 | 2.24 | 3.74 | 4.92 | 4.19 | interferon (alpha and beta) receptor Ifnar | M89641 |
| 101014_at | 0.00 | 0.00 | 3.34 | 0.00 | 2.93 | 3.31 | IFNAR2 | Y09864 |
| 101015_s_at | 0.00 | 2.18 | 1.84 | 1.70 | 3.80 | 5.13 | IFNAR2 | AF013486 |
| 100552_at | 0.00 | 0.00 | 0.00 | 3.89 | 1.88 | 2.16 | IFNGR | M28233 |
| 95546_g_at | 0.00 | 0.00 | 0.00 | 3.10 | 6.23 | 5.82 | insulin-like growth factor 1; Igf1 | X04480 |
| 98623_g_at | 0.00 | 0.00 | 0.00 | 0.00 | 3.20 | 2.42 | IGF2 | X71922 |
| 95082_at | 0.00 | 0.00 | 0.00 | 0.00 | 2.92 | 4.18 | IGFBP3 | AI842277 |
| 95083_at | 0.00 | 0.00 | 0.00 | 0.00 | 7.76 | 6.72 | factor binding protein 3; Igfbp3 | X81581 |
| 101571_g_at | 0.00 | 0.00 | 0.00 | 3.58 | 7.05 | 8.40 | IGFBP4 | X76066 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 103949_at | 0.00 | 0.00 | 0.00 | 0.00 | 3.03 | 0.00 | Indian hedgehog homolog, (Drosophila); Ihh | X76291 |
| 101054_at | 0.00 | 1.83 | 0.00 | 2.41 | 2.02 | 3.39 | Ia-associated invariant chain; Ii | X00496 |
| 96764_at | −2.18 | 0.00 | 4.23 | 4.92 | 2.47 | 10.03 | UNK__AJ007971 | AJ007971 |
| 111615_at | 0.00 | 0.00 | 0.00 | 0.00 | 3.13 | 0.00 | IKBKB | AW209118 |
| 99491_at | 0.00 | 2.16 | 1.76 | 1.96 | 3.49 | 3.19 | interleukin 10 receptor, beta; Il10rb | U53696 |
| 99991_at | 0.00 | 2.79 | 0.00 | 0.00 | 1.72 | 3.32 | interleukin 17 receptor; Il17r | U31993 |
| 103486_at | 0.63 | 2.39 | 2.75 | 3.67 | 2.17 | 4.47 | Il1b | M15131 |
| 93914_at | 0.00 | 4.38 | 0.00 | 3.94 | 3.09 | 3.44 | interleukin 1 receptor, type I; Il1r1 | M20658 |
| 93871_at | 0.00 | 0.00 | 0.00 | 4.89 | 1.33 | 3.75 | IL1RN | L32838 |
| 102021_at | 3.54 | 27.39 | 6.36 | 13.28 | 10.97 | 6.34 | interleukin 4 receptor, alpha; Il4ra | M27960 |
| 102218_at | 0.00 | 2.71 | 0.00 | 1.55 | 0.00 | 0.00 | interleukin 6; Il6 | X54542 |
| 101499_at | 0.00 | 0.00 | 0.00 | 3.26 | 2.76 | 2.65 | ILK | U94479 |
| 100277_at | 0.00 | 0.00 | 2.28 | 5.04 | 4.35 | 0.00 | inhibin beta-A; Inhba | X69619 |
| 94399_at | 0.00 | 0.00 | 0.00 | 0.00 | 1.14 | 2.02 | INPP5B | AI843172 |
| 102884_at | 0.00 | 2.24 | 1.00 | 2.31 | 1.62 | 1.57 | polyphosphate-5-phosphatase, 145 kDa; Inpp5d | U51742 |
| 100561_at | 0.00 | 1.75 | 1.98 | 2.97 | 3.51 | 4.48 | IQGAP1 | AW209098 |
| 99103_at | 0.00 | 0.00 | 0.00 | 0.00 | 2.24 | 0.00 | IRF3 | AF036341 |
| 93425_at | 0.00 | 0.00 | 0.00 | 2.88 | 0.00 | 0.00 | interferon regulatory factor 5; Irf5 | AF028725 |
| 104669_at | 0.00 | 0.00 | 1.37 | 2.31 | 3.90 | 2.76 | interferon regulatory factor 7; Irf7 | U73037 |
| 98822_at | 1.83 | 2.50 | 7.89 | 17.45 | 7.07 | 5.85 | protein (15 kDa); Isg15 | X56602 |
| 103634_at | 0.00 | 2.12 | 0.00 | 3.40 | 4.00 | 3.66 | interferon dependent positive acting transcription factor 3 gamma; Isgf3g | U51992 |
| 99010_at | 0.00 | 1.49 | 0.00 | 2.51 | 4.56 | 3.66 | ISLR | AB024538 |
| 98366_at | 0.00 | 0.00 | 0.00 | 0.00 | 2.16 | 3.20 | integrin alpha V (Cd51); Itgav | U14135 |
| 100124_r_at | 0.00 | 0.00 | 0.00 | 2.19 | 1.92 | 2.34 | ITGB1 | X15202 |
| 102353_at | 1.84 | 2.21 | 2.43 | 2.51 | 3.29 | 7.22 | ITGB2 | M31039 |
| 94826_at | 0.00 | 1.64 | 1.82 | 2.47 | 2.59 | 1.69 | ITGB4BP | Y11460 |
| 100601_at | 0.00 | 0.00 | 0.00 | 0.00 | 2.93 | 0.00 | ITGB5 | AF022110 |
| 103611_at | 0.00 | 1.73 | 0.00 | 2.11 | 2.33 | 2.77 | ITGP | AB012693 |
| 98922_at | 0.00 | 0.00 | 0.00 | 0.00 | 2.69 | 2.27 | intergral membrane protein 1; Itm1 | L34260 |
| 93511_at | 0.00 | 0.00 | 0.00 | 0.00 | 2.04 | 0.00 | integral membrane protein 2; Itm2 | L38971 |
| 96283_at | 0.00 | 0.00 | 0.00 | 4.19 | 9.42 | 7.02 | UNK__AI849180 | AI849180 |
| 99509_s_at | 0.00 | 0.00 | 0.00 | 0.00 | 6.28 | 0.00 | JAK3 | L40172 |
| 103816_at | 0.00 | 0.00 | 0.00 | 1.96 | 1.74 | 2.64 | JCAM | U89915 |
| 102362_i_at | 2.25 | 5.90 | 2.20 | 8.24 | 4.87 | 0.00 | Junb | U20735 |
| 102363_r_at | 0.00 | 6.13 | 3.53 | 14.86 | 4.92 | 0.00 | Junb | U20735 |
| 102364_at | 0.00 | 0.00 | 0.00 | 0.00 | 2.24 | 2.09 | JUND1 | J04509 |
| 114683_at | 0.00 | 0.00 | 0.00 | 0.00 | 2.12 | 4.85 | KAP | AW125126 |
| 102892_at | 0.00 | 2.18 | 0.00 | 0.00 | 1.30 | 1.61 | KCNAB2 | U65592 |
| 109931_at | 0.00 | 0.00 | 0.00 | 0.00 | 4.27 | 2.96 | UNK__AW214619 | AW214619 |
| 102335_at | 0.00 | 0.00 | 0.00 | 0.00 | 4.22 | 5.08 | KCNK1 | AF033017 |
| 104652_at | 0.00 | 0.00 | 0.00 | 0.00 | 1.71 | 3.71 | KCNK2 | AI849601 |
| 102198_at | 0.00 | 5.02 | 4.23 | 5.49 | 6.12 | 6.03 | KCNN4 | AF042487 |
| 102644_at | 0.00 | 2.13 | 2.16 | 3.29 | 3.28 | 4.38 | derived transcript 1; Kdt1 | U13371 |
| 106026_at | 0.00 | 0.00 | 0.00 | 2.22 | 1.11 | 0.00 | KELCHL | AI845205 |
| 99541_at | 0.00 | 0.00 | 2.42 | 2.19 | 2.31 | 1.50 | KIFL1 | AJ223293 |
| 94276_at | 0.00 | 2.50 | 0.00 | 2.52 | 1.93 | 2.89 | UNK__AF064635 | AF064635 |
| 100010_at | 0.00 | 0.00 | 0.00 | 0.00 | 2.38 | 2.04 | Kruppel-like factor 3 (basic); Klf3 | U36340 |
| 99622_at | 0.00 | 0.00 | 0.00 | 0.00 | 2.46 | 2.79 | Kruppel-like factor 4 (gut); Klf4 | U20344 |
| 102707_f_at | 0.00 | 0.00 | 3.80 | 0.00 | 0.00 | 0.00 | kallikrein binding protein; Klkbp | X61597 |
| 93677_at | 0.00 | 0.00 | 0.00 | 1.68 | 2.07 | 1.74 | KLRD1 | AF030311 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 92790_at | 0.00 | 3.36 | 3.06 | 3.84 | 3.02 | 2.72 | (importin) alpha 2; Kpna2 | D55720 |
| 97991_at | 0.00 | 2.56 | 0.00 | 0.00 | 2.22 | 0.00 | Kirsten rat sarcoma oncogene 2, expressed; Kras2 | X02452 |
| 97909_at | 0.00 | 5.50 | 6.71 | 11.66 | 11.44 | 8.79 | UNK_AI838080 | AI838080 |
| 104587_at | 0.00 | 0.00 | 0.00 | 3.06 | 4.57 | 4.63 | Lama4 | U69176 |
| 101948_at | 0.00 | 0.00 | 0.00 | 2.83 | 5.29 | 1.96 | LAMB1-1 | X05212 |
| 140322_at | 0.00 | 0.00 | 2.48 | 2.50 | 2.39 | 2.59 | LAMP2 | AW018326 |
| 100136_at | 0.00 | 0.00 | 0.00 | 2.49 | 2.82 | 2.87 | LAMP2 | M32017 |
| 100012_at | 0.00 | 2.03 | 3.10 | 3.09 | 4.43 | 8.86 | associated protein transmembrane 5; Laptm5 | U29539 |
| 93793_at | 0.00 | 1.73 | 1.73 | 3.30 | 4.36 | 5.96 | LASP1 | AW122780 |
| 93930_at | 0.00 | 0.00 | 0.00 | 1.83 | 4.32 | 4.37 | LIM and SH3 protein 1; Lasp1 | U58882 |
| 114629_at | 0.00 | 0.68 | 2.63 | 3.49 | 1.80 | 2.04 | UNK_AW124408 | AW124408 |
| 102957_at | 0.00 | 3.04 | 0.00 | 3.19 | 2.47 | 4.63 | lymphocyte cytosolic protein 2; Lcp2 | U20159 |
| 93682_at | 0.00 | 0.00 | 0.00 | 0.00 | 2.02 | 1.93 | LDB3 | U89489 |
| 93797_g_at | 0.00 | 2.55 | 1.84 | 3.48 | 3.05 | 2.86 | TCFL1 | AW123952 |
| 93798_at | 0.00 | 2.67 | 0.00 | 3.36 | 3.02 | 3.32 | TCFL1 | AI839988 |
| 93600_at | 0.00 | 1.83 | 2.22 | 2.93 | 3.37 | 4.78 | LEPR | AJ011565 |
| 100431_at | 0.00 | 0.00 | 0.00 | 0.00 | 4.53 | 5.21 | leptin receptor Lepr | U42467 |
| 95706_at | 0.00 | 0.00 | 1.74 | 4.15 | 3.83 | 10.29 | binding, soluble 3; Lgals3 | X16834 |
| 103335_at | 0.00 | 1.81 | 2.08 | 2.99 | 2.89 | 2.47 | binding, soluble 9; Lgals9 | U55060 |
| 104659_g_at | 0.00 | 0.00 | 0.00 | 0.00 | 5.33 | 11.04 | LIFR | D17444 |
| 104657_at | 0.00 | 0.00 | 0.00 | 0.00 | 1.77 | 3.26 | leukemia inhibitory factor receptor; Lifr | D26177 |
| 102123_at | 0.00 | 0.00 | 0.00 | 3.18 | 1.67 | 3.11 | UNK_Z31689 | Z31689 |
| 98059_s_at | 0.00 | 2.68 | 2.74 | 4.63 | 3.92 | 2.97 | lamin A; Lmna | D49733 |
| 93666_at | 0.00 | 0.00 | 0.00 | 0.00 | 2.00 | 0.00 | LMO2 | M64360 |
| 95069_at | 0.00 | 0.00 | 0.00 | 0.00 | 3.14 | 2.18 | UNK_AA940430 | AA940430 |
| 98122_at | 0.00 | 0.00 | 0.00 | 0.00 | 2.19 | 1.94 | LMO4 | AF074600 |
| 93939_at | 0.00 | 0.00 | 0.00 | 0.00 | 3.16 | 1.74 | LNK | U89993 |
| 93885_g_at | 0.00 | 0.00 | 0.00 | 0.00 | 1.92 | 3.59 | LOC53423 | AB034693 |
| 94997_at | 0.00 | 0.00 | 0.00 | 0.00 | 1.76 | 2.65 | LOC53423 | AF060883 |
| 101518_at | 0.00 | 0.00 | 0.00 | 3.58 | 5.95 | 4.14 | uterine protein; LOC55978 | U38981 |
| 92569_f_at | 0.00 | 0.00 | 2.09 | 2.56 | 2.98 | 0.00 | LOC55989 | AF053232 |
| 115414_at | 0.00 | 2.55 | 0.00 | 2.70 | 0.00 | 0.00 | UNK_AI849017 | AI849017 |
| 104524_at | 0.00 | 1.64 | 1.93 | 0.00 | 2.21 | 3.77 | UNK_AI842825 | AI842825 |
| 96260_at | 0.00 | 0.00 | 1.44 | 2.63 | 2.92 | 3.01 | UNK_AB021491 | AB021491 |
| 116843_at | 0.00 | 0.00 | 0.00 | 0.06 | 2.61 | 2.86 | UNK_AW045920 | AW045920 |
| 93753_at | 0.00 | 1.85 | 1.80 | 3.48 | 2.78 | 4.85 | UNK_AI852632 | AI852632 |
| 109105_i_at | 0.00 | 0.00 | 0.00 | 1.57 | 4.79 | 4.72 | UNK_AW122202 | AW122202 |
| 109106_f_at | 0.00 | 0.00 | 0.00 | 2.28 | 2.86 | 1.89 | UNK_AW122202 | AW122202 |
| 111200_at | 0.00 | 0.00 | 0.00 | 0.00 | 2.70 | 0.00 | UNK_AA726446 | AA726446 |
| 96139_at | 0.00 | 0.00 | 0.00 | 0.00 | 6.31 | 0.00 | UNK_AF001797 | AF001797 |
| 113180_at | 0.00 | 0.00 | 0.00 | 0.00 | 2.75 | 0.00 | UNK_AW125855 | AW125855 |
| 113101_f_at | 0.00 | 0.00 | 0.00 | 0.00 | 2.07 | 0.00 | UNK_AI644869 | AI644869 |
| 113215_i_at | 0.00 | 0.00 | 0.00 | 0.00 | 2.52 | 1.42 | UNK_AI850449 | AI850449 |
| 113231_at | 0.00 | 0.00 | 0.00 | 2.09 | 2.43 | 2.31 | UNK_AI854099 | AI854099 |
| 111385_at | 0.00 | 0.00 | 0.00 | 0.00 | 3.75 | 0.00 | UNK_AA734127 | AA734127 |
| 138455_at | 0.00 | 0.00 | 0.00 | 4.25 | 4.54 | 7.46 | UNK_AI847317 | AI847317 |
| 107403_at | 0.00 | 0.00 | 0.00 | 0.00 | 5.41 | 2.12 | UNK_AW047735 | AW047735 |
| 111239_at | 0.00 | 0.00 | 0.00 | 1.67 | 3.73 | 1.58 | UNK_AI428160 | AI428160 |
| 100408_at | 0.00 | 0.00 | 0.00 | 0.00 | 2.27 | 0.00 | UNK_AA839465 | AA839465 |
| 116332_at | 0.00 | 0.00 | 0.00 | 0.00 | 2.64 | 0.00 | UNK_AW228823 | AW228823 |
| 111391_at | 0.00 | 2.16 | 0.00 | 2.12 | 4.09 | 3.51 | UNK_AI846729 | AI846729 |
| 101073_at | 0.00 | 0.00 | 0.00 | 1.86 | 1.89 | 2.07 | low density lipoprotein receptor related protein; Lrp | X67469 |
| 92564_at | 0.00 | 0.00 | 0.00 | 0.00 | 2.44 | 1.96 | LRRFIP1 | AI891475 |
| 104093_at | 0.00 | 1.65 | 0.00 | 3.08 | 7.88 | 3.15 | LSP1 | D49691 |
| 103571_at | 0.00 | 2.58 | 2.53 | 4.71 | 12.61 | 7.37 | LST1 | U72644 |
| 100540_at | 0.00 | 0.00 | 0.00 | 1.94 | 2.39 | 2.10 | leukotriene A4 hydrolase; Lta4h | M63848 |
| 103209_at | 0.00 | 0.00 | 0.00 | 0.00 | 2.04 | 0.00 | UNK_AF022889 | AF022889 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 92335_at | 2.27 | 5.35 | 4.42 | 7.37 | 8.46 | 3.49 | growth factor beta binding protein 2; Ltbp2 | AF004874 |
| 96090_a_at | 0.00 | 0.00 | 0.00 | 0.00 | 1.48 | 2.59 | UNK_AI255972 | AI255972 |
| 93353_at | 0.00 | 0.00 | 0.00 | 2.37 | 4.25 | 4.32 | lumican; Lum | AF013262 |
| 96065_at | 0.00 | 2.48 | 2.99 | 4.79 | 10.45 | 4.81 | latexin; Lxn | D88769 |
| 114822_f_at | 0.00 | 0.00 | 0.00 | 2.23 | 1.71 | 2.53 | UNK_AA762251 | AA762251 |
| 100771_at | 0.00 | 2.32 | 0.00 | 3.22 | 2.64 | 0.00 | LY57 | AF068182 |
| 100772_g_at | 0.00 | 0.00 | 0.00 | 3.32 | 3.38 | 0.00 | LY57 | AF068182 |
| 93078_at | 0.00 | 0.00 | 0.00 | 2.01 | 0.00 | 0.00 | LY6 | X04653 |
| 101487_f_at | 0.00 | 1.52 | 1.77 | 2.89 | 2.34 | 2.43 | LY6E | U47737 |
| 94425_at | 0.00 | 2.66 | 1.85 | 3.26 | 2.53 | 2.88 | LY86 | AB007599 |
| 100468_g_at | 0.00 | 1.84 | 2.02 | 2.66 | 1.65 | 2.94 | lymphoblastomic leukemia; Lyl1 | X57687 |
| 100467_at | 0.00 | 0.00 | 2.64 | 0.00 | 0.00 | 0.00 | lymphoblastomic leukemia; Lyl1 | X57687 |
| 103349_at | 0.00 | 2.70 | 2.60 | 0.00 | 4.26 | 0.00 | viral (v-yes-1) oncogene homolog; Lyn | M57696 |
| 101753_s_at | 0.00 | 1.77 | 2.34 | 3.14 | 2.90 | 3.36 | LZP-S | X51547 |
| 100477_at | 0.00 | 3.23 | 0.00 | 7.39 | 9.49 | 5.76 | hypothetical protein 19.5; p19.5 | M32486 |
| 92847_s_at | 0.00 | 1.93 | 1.57 | 3.01 | 1.89 | 3.90 | M6PR | X56831 |
| 96865_at | 0.00 | 0.00 | 1.70 | 2.61 | 3.59 | 3.60 | alanine rich protein kinase C substrate; Macs | M60474 |
| 99632_at | 0.00 | 3.64 | 3.71 | 5.79 | 4.99 | 3.29 | MAD2L1 | U83902 |
| 99024_at | 0.00 | 0.00 | 0.00 | 2.37 | 3.96 | 3.22 | Max dimerization protein 4; Mad4 | U32395 |
| 102983_at | 0.00 | 0.00 | 0.00 | 2.26 | 2.67 | 2.46 | MADH1 | U58992 |
| 102984_g_at | 0.00 | 0.00 | 0.00 | 0.00 | 2.46 | 2.38 | MADH1 | U58992 |
| 104536_at | 0.00 | 0.00 | 0.00 | 2.18 | 2.08 | 2.27 | MADH2 | U60530 |
| 104220_at | 2.64 | 2.73 | 2.60 | 2.03 | 1.86 | 1.93 | MADH6 | AF010133 |
| 114338_at | 0.00 | 2.06 | 2.77 | 3.20 | 3.21 | 4.58 | MAFB | AI642664 |
| 102204_at | 0.00 | 2.04 | 0.00 | 1.93 | 3.78 | 3.95 | musculoaponeurotic fibrosarcoma oncogene family, protein B (avian); Mafb | L36435 |
| 117143_s_at | 0.00 | 0.00 | 0.00 | 2.70 | 2.61 | 3.69 | MAFB | AW213708 |
| 117144_r_at | 0.00 | 0.00 | 0.00 | 0.00 | 4.02 | 3.31 | MAFB | AW213708 |
| 105228_at | 0.00 | 1.54 | 0.00 | 1.91 | 3.85 | 3.66 | MAN1B | AI528764 |
| 110305_at | 0.00 | 0.00 | 0.00 | 0.00 | 4.70 | 3.60 | MAN1B | AA960561 |
| 104628_at | 0.00 | 1.85 | 0.00 | 4.09 | 2.33 | 3.10 | mannosidase 2, alpha 1; Man2a1 | X61172 |
| 99562_at | 0.00 | 2.00 | 2.50 | 3.15 | 3.16 | 4.31 | MAN2B1 | U87240 |
| 102195_at | 0.00 | 0.00 | 2.76 | 2.19 | 2.65 | 3.58 | protein kinase kinase kinase kinase 4; Map4k4 | U88984 |
| 103416_at | 0.00 | 0.00 | 0.00 | 2.14 | 1.55 | 1.98 | MAPK6 | AI844810 |
| 98475_at | 0.00 | 0.00 | 0.00 | 3.59 | 8.68 | 5.06 | matrilin 2; Matn2 | U69262 |
| 102089_at | 0.00 | 0.00 | 0.00 | 0.00 | 11.72 | 0.00 | MATN3 | Y10521 |
| 96835_at | 0.00 | 0.00 | 0.00 | 0.00 | 23.39 | 8.68 | MATN4 | AJ010984 |
| 99095_at | 0.00 | 0.00 | 0.00 | 1.82 | 2.24 | 2.47 | Max protein; Max | M63903 |
| 96767_at | 0.00 | 1.83 | 1.99 | 3.73 | 4.04 | 3.18 | MBC2 | AF098633 |
| 100062_at | 0.00 | 2.91 | 3.11 | 3.83 | 3.44 | 2.47 | maintenance deficient (S. cerevisiae); Mcmd | X62154 |
| 93112_at | 0.00 | 0.00 | 1.92 | 0.00 | 2.36 | 0.00 | MCMD2 | D86725 |
| 93041_at | 0.00 | 7.24 | 7.49 | 6.58 | 4.25 | 2.16 | maintenance deficient 4 homolog (S. cerevisiae); Mcmd4 | D26089 |
| 100156_at | 0.00 | 7.39 | 9.72 | 7.89 | 7.48 | 2.57 | maintenance deficient 5 (S. cerevisiae); Mcmd5 | D26090 |
| 93356_at | 0.00 | 0.00 | 0.00 | 0.00 | 2.28 | 2.63 | maintenance deficient 7 (S. cerevisiae); Mcmd7 | D26091 |
| 99133_at | 0.00 | 2.08 | 1.76 | 3.23 | 3.10 | 2.32 | monoclonal antibodies 4F2; Mdu1 | X14309 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 103584_at | 0.00 | 2.17 | 2.27 | 3.29 | 4.01 | 4.66 | UNK_AW124334 | AW124334 |
| 92607_at | 0.00 | 0.00 | 0.00 | 4.80 | 35.79 | 13.98 | MEST | AF017994 |
| 101095_at | 0.00 | 0.00 | 0.00 | 0.00 | 7.21 | 12.75 | associated protein 2; Mfap2 | L23769 |
| 131248_at | 1.92 | 0.00 | 0.00 | 2.86 | 4.34 | 2.62 | MFAP5-PENDING | AI608002 |
| 99518_at | 1.91 | 0.00 | 0.00 | 2.66 | 2.54 | 1.97 | MFAP5-PENDING | AW121179 |
| 92880_at | 0.00 | 0.00 | 0.00 | 0.00 | 2.78 | 1.95 | factor 8 protein; Mfge8 | M38337 |
| 103080_at | 0.00 | 2.28 | 3.11 | 3.79 | 2.29 | 3.86 | IFN-gamma induced; Mg11 | U15635 |
| 110672_at | 0.00 | 0.00 | 0.00 | 2.18 | 0.00 | 0.00 | MGL | AW049068 |
| 93866_s_at | 0.00 | 0.00 | 0.00 | 0.00 | 2.01 | 2.44 | matrix gamma-carboxyglutamate (gla) protein; Mglap | D00613 |
| 104410_at | 0.00 | 0.00 | 0.00 | 3.62 | 2.31 | 2.44 | UNK_AW124785 | AW124785 |
| 99457_at | 0.00 | 4.86 | 5.97 | 6.25 | 6.68 | 4.02 | antigen identified by monoclonal antibody Ki 67; Mki67 | X82786 |
| 101069_g_at | 0.00 | 1.70 | 0.00 | 0.00 | 2.03 | 3.10 | MKRN1 | AA656621 |
| 97203_at | 0.00 | 4.21 | 3.45 | 4.84 | 7.71 | 7.84 | MLP | X61399 |
| 92331_at | 0.00 | 0.00 | 0.00 | 0.00 | 5.67 | 3.92 | endopeptidase; Mme | M81591 |
| 98280_at | 0.00 | 0.00 | 0.00 | 0.00 | 1.80 | 2.98 | UNK_AB021228 | AB021228 |
| 112880_at | 0.00 | 0.00 | 0.00 | 2.93 | 7.30 | 4.28 | MMP23 | AA144420 |
| 98833_at | 0.00 | 0.00 | 0.00 | 0.00 | 0.53 | 2.49 | metalloproteinase 3; Mmp3 | X66402 |
| 99957_at | 0.00 | 0.00 | 0.00 | 39.03 | 26.93 | 96.46 | MMP9 | X72795 |
| 95045_at | 0.00 | 1.45 | 0.00 | 3.50 | 3.07 | 2.57 | UNK_AI844469 | AI844469 |
| 131220_f_at | 0.00 | 0.00 | 0.00 | 0.00 | 2.24 | 0.00 | UNK_AW123699 | AW123699 |
| 95951_at | 0.00 | 3.67 | 2.20 | 3.26 | 2.12 | 1.72 | MPCL | AF061272 |
| 99071_at | 0.00 | 1.53 | 2.18 | 3.44 | 4.43 | 9.63 | expressed gene 1; Mpeg1 | L20315 |
| 94857_at | 0.00 | 0.00 | 0.00 | 0.00 | 2.55 | 2.53 | N-methylpurine-DNA glycosylase; Mpg | U10420 |
| 97803_at | 0.00 | 2.84 | 3.15 | 3.77 | 2.11 | 3.63 | membrane protein, palmitoylated (55 kDa); Mpp1 | U38196 |
| 103226_at | 3.09 | 5.30 | 3.98 | 3.64 | 2.84 | 2.41 | mannose receptor, C type 1; Mrc1 | Z11974 |
| 100759_at | 0.00 | 0.00 | 0.00 | 0.00 | 7.71 | 3.67 | mannose receptor, C type 2; Mrc2 | U56734 |
| 96633_s_at | 0.00 | 0.00 | 0.00 | 2.25 | 2.20 | 2.01 | Sid393p; Sid393p | AA529583 |
| 96632_at | 0.00 | 0.00 | 0.00 | 2.23 | 1.96 | 1.69 | UNK_AB025049 | AB025049 |
| 96120_at | 0.00 | 0.00 | 0.00 | 2.06 | 1.64 | 1.99 | MRJ-PENDING | AW124750 |
| 98373_at | 0.00 | 2.29 | 3.59 | 2.69 | 0.00 | 0.00 | UNK_AI462516 | AI462516 |
| 93234_at | 0.00 | 0.00 | 0.00 | 0.00 | 3.55 | 0.00 | MSC | AF087035 |
| 93602_at | 0.00 | 2.16 | 0.00 | 0.00 | 3.26 | 2.23 | UNK_AF074714 | AF074714 |
| 93573_at | 0.00 | 2.93 | 2.31 | 8.18 | 4.56 | 10.01 | Mt1 | V00835 |
| 101561_at | 0.00 | 2.89 | 2.70 | 5.96 | 4.03 | 7.42 | Mt2 | K02236 |
| 108780_at | 0.00 | 2.32 | 2.52 | 3.20 | 4.77 | 3.11 | UNK_AI845395 | AI845395 |
| 100046_at | 0.00 | 0.00 | 3.84 | 6.20 | 4.36 | 3.26 | folate dehydrogenase (NAD+ dependent), methenyltetrahydro-folate | J04627 |
| 98417_at | 2.13 | 0.00 | 2.31 | 2.78 | 1.96 | 1.90 | MX1 | M21038 |
| 96285_at | 0.00 | 1.55 | 1.71 | 3.13 | 2.84 | 2.61 | MYADM | AJ001616 |
| 104712_at | 0.00 | 2.70 | 2.99 | 2.96 | 4.49 | 2.41 | myelocytomatosis oncogene; Myc | L00039 |
| 102430_at | 0.00 | 4.68 | 0.00 | 4.96 | 6.64 | 4.14 | differentiation primary response gene 88; Myd88 | X51397 |
| 106557_at | 0.00 | 0.00 | 0.00 | 3.15 | 5.61 | 4.03 | UNK_AI132668 | AI132668 |
| 100923_at | 0.00 | 0.00 | 0.00 | 0.00 | 1.80 | 2.22 | MYO10 | AJ249706 |
| 98409_at | 0.00 | 0.00 | 1.41 | 2.83 | 7.66 | 9.17 | myosin Ib; Myo1b | L00923 |
| 95506_at | 0.00 | 0.00 | 0.00 | 0.00 | 2.37 | 0.00 | MYO1C | U96723 |
| 101708_at | 0.00 | 0.00 | 0.00 | 0.00 | 1.61 | 2.32 | myosin If; Myo1f | X97650 |
| 98968_at | 0.00 | 1.84 | 2.19 | 1.68 | 1.71 | 2.15 | myosin Va; Myo5a | X57377 |
| 94713_at | 0.00 | 0.00 | 0.00 | 0.00 | 2.66 | 4.15 | myosin VIIa; Myo7a | U81453 |
| 114776_at | 0.00 | 0.00 | 0.00 | 3.11 | 8.64 | 5.61 | MYO9B | AA739159 |
| 102986_at | 3.53 | 3.84 | 2.32 | 2.76 | 2.31 | 0.00 | MYOD1 | M18779 |
| 103053_at | 0.00 | 3.08 | 0.00 | 8.00 | 4.91 | 0.00 | MYOG | X15784 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 94408_at | 0.00 | 0.00 | 0.00 | 2.01 | 2.30 | 3.18 | Ngfi-A binding protein 1; Nab1 | U47008 |
| 100962_at | 0.00 | 0.00 | 1.99 | 2.66 | 3.48 | 3.63 | Ngfi-A binding protein 2; Nab2 | U47543 |
| 103637_at | 0.00 | 0.00 | 0.00 | 0.00 | 4.22 | 4.03 | NAGA | AJ223966 |
| 93373_at | 0.00 | 0.00 | 0.00 | 0.00 | 3.21 | 6.08 | alpha-N-acetylglucosaminidase (Sanfilippo disease IIIB); Naglu | U85247 |
| 98587_at | 0.00 | 1.60 | 2.17 | 2.65 | 2.40 | 1.80 | assembly protein 1-like 1; Nap1l1 | X61449 |
| 101108_at | 0.00 | 4.08 | 0.00 | 0.00 | 0.00 | 0.00 | autoantigenic sperm protein (histone-binding); Nasp | AF034610 |
| 100153_at | 0.00 | 0.00 | 1.32 | 4.10 | 4.06 | 2.79 | neural cell adhesion molecule; Ncam | X15052 |
| 99633_at | 0.00 | 0.00 | 0.00 | 0.00 | 2.26 | 0.00 | NCDN-PENDING | AB017608 |
| 102326_at | 0.00 | 4.13 | 0.00 | 0.00 | 1.95 | 2.92 | NCF2 | AB002664 |
| 100144_at | 0.00 | 0.00 | 0.00 | 2.36 | 2.06 | 0.00 | nucleolin; Ncl | X07699 |
| 94047_at | 0.00 | 1.49 | 0.00 | 2.17 | 2.44 | 3.23 | UNK_AW122935 | AW122935 |
| 101059_at | 0.00 | 0.00 | 0.00 | 2.49 | 2.14 | 0.00 | NDN | D76440 |
| 100472_at | 0.00 | 0.00 | 0.00 | 3.04 | 2.49 | 1.99 | NPC derived proline rich protein 1; Ndpp1 | D10727 |
| 107467_at | 0.00 | 0.00 | 0.00 | 2.05 | 2.13 | 1.80 | UNK_AW047444 | AW047444 |
| 92518_at | 0.00 | 0.00 | 0.00 | 0.00 | 2.48 | 0.00 | NEO1 | Y09535 |
| 103549_at | 0.00 | 0.00 | 0.00 | 1.88 | 2.33 | 0.00 | NES | AW061260 |
| 115217_at | 0.00 | 0.00 | 0.00 | 0.00 | 2.02 | 3.11 | NFAT5 | AI852272 |
| 102209_at | 0.00 | 0.00 | 3.02 | 6.06 | 3.92 | 12.16 | NFATC1 | AF087434 |
| 115215_at | 0.00 | 0.00 | 0.00 | 5.96 | 7.00 | 13.80 | UNK_AA638441 | M638441 |
| 98427_s_at | 0.00 | 0.00 | 0.00 | 2.48 | 1.83 | 2.18 | NFKB1 | M57999 |
| 100469_at | 0.00 | 0.00 | 0.00 | 2.00 | 2.53 | 3.49 | NFYA | D78642 |
| 93563_s_at | 0.00 | 2.18 | 3.71 | 4.33 | 5.30 | 3.48 | NID2 | AB017202 |
| 93318_at | 0.00 | 0.00 | 3.63 | 0.00 | 1.52 | 0.00 | NINJ1 | U91513 |
| 92794_f_at | 0.00 | 0.00 | 1.84 | 0.00 | 2.49 | 1.46 | NME1 | M35970 |
| 102047_at | 0.00 | 0.00 | 0.00 | 2.17 | 0.00 | 0.00 | NMT1 | AF043326 |
| 101473_at | 0.00 | 0.00 | 0.00 | 0.00 | 7.66 | 5.81 | NNMT | U86108 |
| 104132_at | 0.00 | 0.00 | 0.00 | 2.32 | 3.69 | 0.00 | NOC4 | AW047276 |
| 106115_at | 0.00 | 0.00 | 0.00 | 2.39 | 2.08 | 0.00 | UNK_AI849335 | AI849335 |
| 102028_at | 0.00 | 0.00 | 0.00 | 4.05 | 2.85 | 3.43 | NORE1 | AF053959 |
| 100507_at | 0.00 | 0.00 | 0.00 | 2.01 | 4.45 | 6.67 | nephroblastoma overexpressed gene; Nov | Y09257 |
| 114812_at | 0.00 | 0.00 | 0.00 | 2.08 | 6.43 | 3.89 | UNK_AA869278 | AA869278 |
| 99564_at | 0.00 | 3.62 | 3.98 | 4.26 | 2.21 | 2.67 | NP95 | D87908 |
| 92626_at | 0.00 | 0.00 | 0.00 | 3.12 | 3.55 | 2.70 | differentiation and control gene 1; Npdc1 | X67209 |
| 101634_at | 0.00 | 0.00 | 1.77 | 2.55 | 2.14 | 0.00 | Npm1 | M33212 |
| 102796_at | 0.00 | 3.11 | 0.00 | 0.00 | 0.00 | 0.00 | Npm3 | U64450 |
| 101168_at | 0.00 | 0.00 | 0.00 | 2.07 | 2.52 | 1.94 | neoplastic progression 1; Npn1 | Z31360 |
| 93202_at | 0.00 | 0.00 | 0.00 | 0.00 | 2.18 | 1.62 | 5' nucleotidase; Nt5 | L12059 |
| 96666_at | 0.00 | 0.00 | 0.00 | 0.00 | 4.20 | 0.00 | N-terminal Asn amidase; Ntan1 | U57692 |
| 94528_at | 1.73 | 3.32 | 1.59 | 1.72 | 1.90 | 0.00 | NUBP1 | AI846206 |
| 94839_at | 0.00 | 0.00 | 2.37 | 2.60 | 2.29 | | nucleobindin; Nucb | M96823 |
| 102197_at | 0.00 | 0.00 | 0.00 | 2.38 | 3.20 | 2.50 | NUCB2 | AJ222586 |
| 101593_at | 0.00 | 0.00 | 0.00 | 0.00 | 3.55 | 0.00 | UNK_AI851454 | AI851454 |
| 108579_at | 0.00 | 2.97 | 0.00 | 2.53 | 5.55 | 2.93 | NUDT5 | AI854177 |
| 93046_at | 0.00 | 0.00 | 0.00 | 0.00 | 3.03 | 1.95 | UNK_AW045233 | AW045233 |
| 102231_at | 0.00 | 0.00 | 0.00 | 0.00 | 7.53 | 3.00 | OASIS-PENDING | AB017614 |
| 107525_at | 0.00 | 2.46 | 5.90 | 6.26 | 4.94 | 5.61 | OASL | AW211637 |
| 101002_at | 0.00 | 2.02 | 0.00 | 2.36 | 1.89 | 1.67 | decarboxylase antizyme inhibitor; | AF032128 |
| 99549_at | 0.00 | −3.17 | 0.00 | 0.00 | 3.34 | 2.12 | osteoglycin; Ogn | D31951 |
| 93369_at | 0.00 | 0.00 | 0.00 | 0.00 | 9.11 | 5.81 | osteomodulin; Omd | AB007848 |
| 95712_at | 0.00 | 2.64 | 0.00 | 3.22 | 2.28 | 1.84 | UNK_AW045261 | AW045261 |
| 96093_at | 0.00 | 0.00 | 0.00 | 3.36 | 0.00 | 0.00 | UNK_AI842705 | AI842705 |
| 117253_at | 0.00 | 0.00 | 0.00 | 1.90 | 3.19 | 0.00 | UNK_AI845729 | AI845729 |
| 100437_g_at | 0.00 | 0.00 | 0.00 | 3.83 | 0.00 | 0.00 | Orm1 | M27008 |
| 92593_at | 2.42 | 2.26 | 4.11 | 5.43 | 13.56 | 19.79 | osteoblast specific factor 2; OSF-2 | D13664 |

TABLE 1-continued

| Affymetrix Qualifier | Treatment Time | | | | | | Gene Name | Genbank Accession # |
|---|---|---|---|---|---|---|---|---|
| | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | | |
| 102255_at | 0.00 | 0.00 | 0.00 | 3.29 | 2.68 | 3.26 | OSMR | AB015978 |
| 100138_f_at | 0.00 | 1.82 | 2.20 | 0.00 | 2.88 | 0.00 | similar to human SYK interacting protein; p16K | X52102 |
| 95586_at | 0.00 | 0.00 | 3.82 | 3.90 | 3.26 | 1.84 | P2RX4 | AF089751 |
| 96016_at | 0.00 | 2.47 | 0.00 | 6.19 | 4.91 | 2.57 | P40-8 | AW045665 |
| 104139_at | 0.00 | 0.00 | 0.00 | 1.90 | 2.21 | 1.82 | 2-oxoglutarate 4-dioxygenase (proline 4-hydroxylase), alpha 1 polypeptide; P4ha1 | U16162 |
| 98983_at | 0.00 | 0.00 | 0.00 | 2.64 | 5.05 | 2.80 | 2-oxoglutarate 4-dioxygenase (proline 4-hydroxylase), alpha II polypeptide; P4ha2 | U16163 |
| 100720_at | 0.00 | 1.59 | 2.28 | 2.36 | 3.73 | 2.53 | protein, cytoplasmic 1; Pabpc1 | X65553 |
| 98021_at | 0.00 | 0.00 | 0.00 | 0.00 | 2.39 | 0.00 | 0 | D14336 |
| 99023_at | 0.00 | 1.65 | 0.00 | 4.28 | 2.73 | 0.00 | factor acetylhydrolase, isoform 1b, alpha2 subunit; Pafah1b2 | U57747 |
| 100576_at | 0.00 | 0.00 | 0.00 | 1.95 | 2.29 | 2.64 | factor acetylhydrolase, isoform 1b, alpha1 subunit; Pafah1b3 | U57746 |
| 114355_at | 0.00 | 0.00 | 2.27 | 5.58 | 4.79 | 0.00 | PANX1 | AI847747 |
| 93298_at | 0.00 | 0.00 | 0.00 | 0.00 | 3.57 | 3.43 | phosphoadenosine 5'-phosphosulfate synthase 1; Papss1 | U34883 |
| 96713_at | 0.00 | 0.00 | 0.00 | 0.00 | 5.09 | 4.94 | PAPSS2 | AF052453 |
| 93615_at | 0.00 | 1.75 | 0.00 | 2.33 | 2.68 | 2.35 | pre B-cell leukemia transcription factor 3; Pbx3 | AF020200 |
| 94449_at | 0.00 | 0.00 | 0.00 | 0.00 | 2.50 | 3.46 | PCDH13 | AI854522 |
| 102280_at | 0.00 | 0.00 | 0.00 | 0.00 | 1.82 | 3.45 | PCDH7 | AB006758 |
| 102781_at | 0.00 | 0.00 | 0.00 | 0.00 | 2.31 | 2.76 | enhanced expression; PCEE | U37351 |
| 109761_g_at | 0.00 | 0.00 | 0.00 | 2.91 | 5.10 | 0.00 | UNK_AI848972 | AI848972 |
| 101065_at | 0.00 | 3.07 | 2.87 | 3.72 | 2.58 | 2.41 | PCNA | X57800 |
| 93349_at | 0.00 | 0.00 | 0.00 | 3.50 | 6.60 | 6.15 | proteinase enhancer protein; Pcolce | X57337 |
| 92192_s_at | 0.00 | 0.00 | 2.04 | 3.28 | 4.63 | 2.79 | PCSK5 | D12619 |
| 101196_at | 0.00 | 0.00 | 0.00 | 0.00 | 2.74 | 3.02 | convertase subtilisin/kexin type 6; Pcsk6 | D50060 |
| 95412_at | 0.00 | 0.00 | 0.00 | 2.35 | 2.36 | 2.10 | programmed cell death 6; Pdcd6 | U49112 |
| 96252_at | 0.00 | 1.55 | 0.00 | 2.17 | 2.00 | 1.80 | PDCD6IP | AJ005073 |
| 93382_at | 0.00 | 0.00 | 0.00 | 0.00 | 2.51 | 0.00 | PDE1B1 | AF023343 |
| 116964_at | 0.00 | 0.00 | 0.00 | 6.04 | 14.08 | 9.38 | UNK_AI851805 | AI851805 |
| 93574_at | 0.00 | 0.00 | 1.71 | 3.31 | 3.42 | 4.08 | SDF3 | AF036164 |
| 115553_at | 0.00 | 0.00 | 2.11 | 2.15 | 0.00 | 0.00 | UNK_AI841779 | AI841779 |
| 101451_at | 0.00 | 0.00 | 0.00 | 2.15 | 2.01 | 3.16 | PEG3 | AF038939 |
| 96765_at | 0.00 | 0.00 | 0.00 | 2.41 | 2.67 | 1.76 | PEG3 | AW120874 |
| 94516_f_at | 0.00 | 0.00 | 0.00 | 0.00 | 5.97 | 3.99 | PENK2 | M55181 |
| 101468_at | 2.20 | 3.94 | 4.04 | 4.10 | 3.07 | 1.92 | properdin factor, complement; Pfc | X12905 |
| 97834_g_at | 0.00 | 2.07 | 2.29 | 3.11 | 2.38 | 2.29 | UNK_AI853802 | AI853802 |
| 97833_at | 0.00 | 0.00 | 0.00 | 2.77 | 2.41 | 0.00 | UNK_AI853802 | AI853802 |
| 93421_at | 0.00 | 3.19 | 0.00 | 3.98 | 5.66 | 4.45 | PFTAIRE protein kinase 1; Pftk1 | AF033655 |
| 101585_at | 0.00 | 0.00 | 2.28 | 2.71 | 5.13 | 6.27 | PGRMC-PENDING | AF042491 |
| 94406_at | 0.00 | 0.00 | 0.00 | 0.00 | 6.01 | 4.58 | PHTF | AJ242864 |
| 93708_at | 0.00 | 0.00 | 0.00 | 0.00 | 2.16 | 1.78 | PIAS3 | AF034080 |
| 92312_at | 0.00 | 0.00 | 0.00 | 0.00 | 3.14 | 0.00 | PIK3C2A | U55772 |
| 96592_at | 0.00 | 0.00 | 1.93 | 0.00 | 2.15 | 2.21 | phosphatidylinositol 3-kinase, regulatory subunit, polypeptide 1 (p85 alpha); Pik3r1 | U50413 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 101926_at | 0.00 | 0.00 | 0.00 | 0.00 | 2.74 | 0.00 | proviral integration site 2; Pim2 | L41495 |
| 95358_at | 0.00 | 0.00 | 0.00 | 1.63 | 1.80 | 2.05 | UNK_AI843864 | AI843864 |
| 100328_s_at | 4.40 | 8.50 | 5.17 | 12.16 | 2.38 | 11.48 | PIRA3 | U96684 |
| 98003_at | 0.00 | 2.48 | 0.00 | 3.55 | 3.42 | 3.45 | PIRB | AF038149 |
| 102696_s_at | 0.00 | 0.00 | 2.49 | 0.00 | 2.01 | 2.44 | UNK_AI747899 | AI747899 |
| 101461_f_at | 0.00 | 0.00 | 0.00 | 2.09 | 2.39 | 2.19 | PJA1 | U06944 |
| 104531_at | 0.00 | 1.31 | 1.42 | 1.63 | 2.40 | 2.42 | protein kinase C, delta; Pkcd | X60304 |
| 97375_at | 0.00 | 0.00 | 0.00 | 0.00 | 2.90 | 3.20 | disease 1 homolog; Pkd1 | U70209 |
| 100951_at | 0.00 | 0.00 | 0.00 | 2.13 | 3.19 | 3.22 | polycystic kidney disease 2; Pkd2 | AF014010 |
| 99513_at | 1.58 | 5.00 | 0.00 | 10.15 | 10.27 | 5.24 | phospholipase A2, group 4; Pla2g4 | M72394 |
| 94147_at | 4.28 | 9.58 | 8.85 | 11.13 | 4.61 | 4.14 | activator inhibitor, type I; Planh1 | M33960 |
| 102663_at | 0.00 | 0.00 | 0.00 | 5.52 | 8.24 | 0.00 | PLAUR | X62700 |
| 104580_at | 0.00 | 0.00 | 0.00 | 0.00 | 13.32 | 9.79 | UNK_U85711 | U85711 |
| 100607_at | 0.00 | 0.00 | 6.30 | 10.02 | 22.31 | 16.77 | Pld3 | AF026124 |
| 112083_at | 0.00 | 3.60 | 4.03 | 3.29 | 3.72 | 4.57 | PLEK | AA389905 |
| 116483_at | 0.00 | 2.51 | 0.00 | 1.45 | 1.58 | 1.45 | PLEK | AA178053 |
| 93099_f_at | 0.00 | 0.00 | 5.64 | 0.00 | 7.14 | 0.00 | homolog, (Drosophila); Plk | U01063 |
| 101350_g_at | 0.00 | 0.00 | 0.00 | 2.69 | 3.15 | 0.00 | PLK-PS1 | U73170 |
| 112304_at | 0.00 | 0.00 | 0.00 | 2.53 | 2.40 | 3.41 | PLOD1 | AI854890 |
| 114376_at | 0.00 | 0.00 | 0.00 | 10.32 | 19.49 | 16.29 | PLOD2 | AW259579 |
| 95009_at | 0.00 | 0.00 | 0.00 | 3.52 | 2.66 | 0.00 | PLOD3 | AW107836 |
| 108848_g_at | 0.00 | 2.15 | 2.34 | 3.50 | 3.60 | 3.50 | UNK_AW261779 | AW261779 |
| 93323_at | 0.00 | 1.77 | 1.99 | 4.35 | 4.15 | 3.14 | UNK_AB031292 | AB031292 |
| 94278_at | 2.52 | 5.35 | 7.31 | 6.59 | 8.70 | 23.61 | plastin 2, L; Pls2 | D37837 |
| 102839_at | 0.00 | 0.00 | 0.00 | 0.00 | 2.71 | 0.00 | scramblase 1; Plscr1 | D78354 |
| 100927_at | 0.00 | 1.61 | 2.29 | 3.88 | 3.87 | 3.35 | PLTP | U28960 |
| 97900_at | 0.00 | 0.00 | 0.00 | 2.38 | 0.00 | 0.00 | PLUNC | AI845714 |
| 93290_at | 0.00 | 3.58 | 4.71 | 4.54 | 4.00 | 4.14 | PNP | U35374 |
| 103207_at | 0.00 | 0.00 | 0.00 | 1.97 | 2.15 | 1.44 | POLA1 | D13543 |
| 93940_at | 0.00 | 0.00 | 0.00 | 0.00 | 2.74 | 2.18 | Pon3 | L76193 |
| 98508_s_at | 0.00 | 0.00 | 0.00 | 2.11 | 1.67 | 1.47 | PPAP2A | D84376 |
| 109095_at | 0.00 | 0.00 | 0.00 | 0.00 | 1.61 | 4.80 | PPAP2C | AI837099 |
| 101055_at | 0.00 | 0.00 | 0.00 | 1.90 | 2.19 | 4.26 | beta-galactosidase; Ppgb | J05261 |
| 101207_at | 0.00 | 1.60 | 1.73 | 2.43 | 2.37 | 2.22 | peptidylprolyl isomerase A; Ppia | X52803 |
| 94915_at | 0.00 | 2.15 | 2.53 | 4.59 | 5.13 | 5.64 | PPIB | X58990 |
| 100089_at | 0.00 | 0.00 | 0.00 | 2.99 | 6.25 | 8.51 | peptidylprolyl isomerase C; Ppic | M74227 |
| 97507_at | 0.00 | 1.87 | 3.36 | 5.70 | 2.90 | 4.09 | isomerase C-associated protein; Ppicap | X67809 |
| 98993_at | 0.00 | 2.04 | 0.00 | 3.07 | 3.11 | 3.12 | protein phosphatase 2, regulatory subunit B (B56), gamma isoform; Ppp2r5c | U59418 |
| 95631_at | 0.00 | 1.74 | 1.72 | 2.71 | 2.96 | 2.24 | UNK_AF088911 | AF088911 |
| 93495_at | 0.00 | 3.41 | 3.81 | 6.33 | 10.88 | 6.68 | Prdx4 | U96746 |
| 95549_at | 0.00 | 0.00 | 0.00 | 0.00 | 2.83 | 0.00 | PRIM2 | D13545 |
| 100684_at | 0.00 | 0.00 | 1.65 | 2.87 | 2.86 | 2.56 | substrate 80K-H; Prkcsh | U92794 |
| 102414_i_at | 0.00 | 1.63 | 1.80 | 2.44 | 2.02 | 1.69 | interferon inducible double stranded RNA dependent inhibitor; Prkri | U28423 |
| 102415_r_at | 0.00 | 0.00 | 0.00 | 0.00 | 2.50 | 0.00 | interferon inducible double stranded RNA dependent inhibitor; Prkri | U28423 |
| 104728_at | 0.00 | 2.54 | 0.00 | 3.40 | 4.10 | 4.80 | Pros1 | L27439 |
| 103327_at | 3.94 | 5.14 | 4.58 | 8.52 | 7.86 | 5.35 | paired related homeobox 2; Prrx2 | X52875 |
| 93261_at | 0.00 | 3.35 | 4.35 | 6.68 | 5.66 | 3.99 | PRSC1 | AJ000990 |
| 96920_at | 0.00 | −1.76 | 0.00 | 0.00 | 3.99 | 3.39 | PRSS11 | AW125478 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 104102_at | 0.00 | 0.00 | 0.00 | 0.00 | 5.09 | 0.00 | UNK_AW047978 | AW047978 |
| 103433_at | 0.00 | 0.00 | 0.00 | 0.00 | 2.56 | 2.17 | PSCD3 | AI846077 |
| 102791_at | 0.00 | 2.23 | 2.86 | 4.09 | 2.59 | 4.48 | PSMB8 | U22033 |
| 100588_at | 0.00 | 0.00 | 0.00 | 2.43 | 1.91 | 2.49 | PSME2 | U60329 |
| 103946_at | 0.00 | 3.04 | 0.00 | 5.29 | 5.18 | 14.26 | threonine phosphatase-interacting protein 1; | U87814 |
| 102105_f_at | 0.00 | 0.00 | 0.00 | 0.00 | 3.33 | 0.00 | PTGDS | AI840733 |
| 103362_at | 0.00 | 1.42 | 0.00 | 1.93 | 3.68 | 0.00 | receptor EP4 subtype; Ptgerep4 | D13458 |
| 104406_at | 0.00 | 0.00 | 0.00 | 0.00 | 3.15 | 1.63 | UNK_AI060798 | AI060798 |
| 104538_at | 0.00 | 0.00 | 0.00 | 0.00 | 8.77 | 10.57 | prostaglandin I2 (prostacyclin) synthase; Ptgis | AB001607 |
| 104647_at | 1.32 | 4.33 | 7.11 | 10.53 | 8.79 | 1.69 | prostaglandin-endoperoxide synthase 2; Ptgs2 | M88242 |
| 98482_at | 0.00 | 0.00 | 0.00 | 4.76 | 34.85 | 20.48 | PTHR | X78936 |
| 93646_at | 0.00 | 1.74 | 0.00 | 0.00 | 4.58 | 2.84 | PTK9 | U82324 |
| 100718_at | 0.00 | 2.16 | 2.29 | 3.42 | 3.73 | 4.16 | Ptma | X56135 |
| 96426_at | 0.00 | 1.32 | 1.37 | 1.69 | 2.19 | 1.80 | PTMB4 | U38967 |
| 97474_r_at | 0.00 | 0.00 | 0.00 | 0.00 | 2.93 | 1.82 | pleiotrophin; Ptn | D90225 |
| 94929_at | 0.00 | 2.13 | 0.00 | 2.61 | 2.81 | 4.92 | PTPN1 | M97590 |
| 98424_at | 0.00 | 0.00 | 0.00 | 0.00 | 3.23 | 7.57 | PTPN13 | D83966 |
| 92273_at | 1.97 | 3.65 | 0.00 | 3.39 | 0.00 | 0.00 | PTPN18 | U49853 |
| 101996_at | 0.00 | 1.60 | 0.00 | 0.00 | 2.29 | 1.61 | PTPN2 | M80739 |
| 100976_at | 0.00 | 2.38 | 0.00 | 3.41 | 4.06 | 2.87 | protein-tyrosine phosphatase; Ptpn9 | AF013490 |
| 103070_at | 0.00 | 3.60 | 4.76 | 6.60 | 10.28 | 10.14 | PTPNS1 | AB018194 |
| 100908_at | 0.00 | 0.00 | 0.00 | 2.22 | 6.03 | 10.00 | phosphatase, receptor type, A; Ptpra | M36033 |
| 101048_at | 0.00 | 2.63 | 0.00 | 4.79 | 2.56 | 4.70 | phosphatase, receptor type, C; Ptprc | M14343 |
| 101298_g_at | 0.00 | 3.11 | 0.00 | 0.00 | 1.43 | 2.85 | PTPRC | M23158 |
| 93896_at | 0.00 | 0.00 | 0.00 | 0.00 | 5.11 | 6.76 | phosphatase, receptor type, D; Ptprd | D13903 |
| 100427_at | 0.00 | 2.56 | 2.33 | 2.28 | 1.23 | 2.61 | phosphatase, receptor type, O; Ptpro | U37465 |
| 92731_at | 3.07 | 17.44 | 6.55 | 6.96 | 5.75 | 0.00 | pentaxin related gene; Ptx3 | X83601 |
| 96719_at | 0.00 | 0.00 | 0.00 | 0.00 | 2.58 | 0.00 | parvalbumin; Pva | X59382 |
| 97415_at | 0.00 | 0.00 | 0.00 | 0.00 | 3.23 | 4.63 | RAS oncogene family; Rab3d | M89777 |
| 103579_at | 0.00 | 1.69 | 0.00 | 0.00 | 1.72 | 5.55 | RAS-related C3 botulinum substrate 2; Rac2 | X53247 |
| 97319_at | 0.00 | 3.34 | 3.30 | 9.39 | 11.41 | 5.14 | UNK_AF084466 | AF084466 |
| 96104_at | 0.00 | 0.00 | 0.00 | 2.14 | 2.20 | 3.10 | RAD23B | AI047107 |
| 104527_at | 0.00 | 0.00 | 2.19 | 2.89 | 2.79 | 0.00 | RAD51 | D13803 |
| 93676_at | 0.00 | 0.00 | 0.00 | 0.00 | 2.01 | 0.00 | RAD51AP1 | U93583 |
| 102649_s_at | 0.00 | 2.14 | 0.00 | 2.23 | 2.22 | 1.59 | RAET1C | D64162 |
| 106071_at | 0.00 | 5.58 | 0.00 | 6.56 | 5.61 | 3.57 | RALY | AI852199 |
| 103299_at | 1.92 | 0.00 | 2.97 | 3.91 | 4.13 | 3.15 | UNK_AW123773 | AW123773 |
| 114344_at | 0.00 | 0.00 | 0.00 | 2.22 | 3.25 | 3.57 | UNK_AA882453 | AA882453 |
| 101254_at | 0.00 | 0.00 | 0.00 | 2.17 | 0.00 | 0.00 | oncogene family; Ran | L32751 |
| 98573_r_at | 0.00 | 2.30 | 2.42 | 3.53 | 2.49 | 2.60 | RAN binding protein 1; Ranbp1 | X56045 |
| 93319_at | 0.00 | 1.64 | 2.16 | 2.61 | 4.49 | 5.27 | RAS p21 protein activator 3; Rasa3 | U20238 |
| 102821_s_at | 0.00 | 0.00 | 0.00 | 2.31 | 0.00 | 0.00 | RAS-like, family 2, locus 9; Rasl2-9 | L32752 |
| 102379_at | 0.00 | 3.37 | 2.64 | 3.54 | 0.00 | 0.00 | UNK_AW049415 | AW049415 |
| 104476_at | 0.00 | 0.00 | 0.00 | 2.96 | 2.77 | 2.03 | retinoblastoma-like 1 (p107); Rbl1 | U27177 |
| 96041_at | 0.00 | 2.15 | 2.72 | 3.76 | 2.78 | 2.42 | RBM3 | AB016424 |
| 97254_at | 0.00 | 0.00 | 0.00 | 2.49 | 1.83 | 0.00 | UNK_AA690061 | AA690061 |
| 94972_at | 0.00 | 0.00 | 0.00 | 0.00 | 3.12 | 0.00 | UNK_AB026569 | AB026569 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 97847_at | 0.00 | 0.00 | 0.00 | 0.00 | 4.07 | 0.00 | RBMX | AJ237847 |
| 104716_at | 0.00 | 0.00 | 0.00 | 3.52 | 4.52 | 2.49 | protein 1, cellular; Rbp1 | X60367 |
| 96047_at | 0.00 | 0.00 | 0.00 | 0.00 | 3.29 | 3.03 | protein 4, plasma; Rbp4 | U63146 |
| 103804_at | 0.00 | 0.00 | 0.00 | 0.00 | 3.42 | 2.10 | ST15 | AB006960 |
| 102960_at | 0.00 | 0.00 | 0.00 | 2.03 | 2.18 | 2.31 | recombination activating gene 1 gene activation; Rga | X96618 |
| 94378_at | 0.00 | 0.00 | 0.00 | 0.00 | 3.49 | 0.00 | protein signaling 16; Rgs16 | U94828 |
| 94899_at | 0.00 | 0.00 | 0.00 | 0.00 | 2.08 | 2.09 | protein 3; Rhoip3-pending | U73200 |
| 104094_at | 0.00 | 0.00 | 0.00 | 0.00 | 2.15 | 0.00 | LIM gene; Ril-pending | Y08361 |
| 114018_at | 0.00 | 2.49 | 1.95 | 4.66 | 6.14 | 0.00 | UNK_AI504675 | AI504675 |
| 97091_at | 0.00 | 0.00 | 0.00 | 0.00 | 3.11 | 2.05 | interacting serine-threonine kinase 1; Ripk1 | U25995 |
| 96038_at | 0.00 | 1.76 | 0.00 | 2.90 | 2.58 | 2.66 | UNK_AI840339 | AI840339 |
| 93164_at | 0.00 | 0.00 | 0.00 | 0.00 | 2.18 | 2.16 | ring finger protein 2; Rnf2 | Y12783 |
| 93782_at | 0.00 | 1.68 | 1.84 | 3.36 | 3.67 | 3.28 | RNF4 | AI844517 |
| 93453_at | 0.00 | 0.00 | 0.00 | 0.00 | 2.62 | 0.00 | rod outer segment membrane protein 1; Rom1 | M96760 |
| 100711_at | 0.00 | 0.00 | 0.00 | 2.10 | 1.93 | 0.00 | ribosomal protein L10A; Rpl10a | U12403 |
| 92834_at | 0.00 | 2.71 | 3.10 | 4.50 | 4.86 | 3.15 | ribosomal protein L13a; Rpl13a | X51528 |
| 94208_at | 0.00 | 2.29 | 3.47 | 4.81 | 4.93 | 2.77 | RPL27A | AW045202 |
| 94209_g_at | 0.00 | 2.19 | 4.15 | 3.80 | 4.81 | 2.50 | RPL27A | AW045202 |
| 94207_at | 0.00 | 2.31 | 2.67 | 4.56 | 2.55 | 0.00 | RPL27A | AI842377 |
| 95418_at | 0.00 | 0.00 | 0.00 | 0.00 | 2.52 | 0.00 | UNK_AI848851 | AI848851 |
| 100734_at | 0.00 | 2.31 | 2.75 | 3.97 | 3.44 | 4.20 | ribosomal protein L3; Rpl3 | Y00225 |
| 108097_at | 0.00 | 0.00 | 0.00 | 0.00 | 2.70 | 4.31 | UNK_AW121237 | AW121237 |
| 99624_at | 0.00 | 0.00 | 0.00 | 2.07 | 2.20 | 2.07 | UNK_AW125517 | AW125517 |
| 92325_at | 0.00 | 0.00 | 0.00 | 0.00 | 3.50 | 2.79 | RPL7A | AI326889 |
| 96295_at | 0.00 | 2.06 | 2.94 | 4.52 | 9.84 | 5.38 | RPMS7 | AW122030 |
| 94076_i_at | 0.00 | 1.53 | 1.91 | 3.06 | 2.69 | 2.95 | ribophorin; Rpn | D31717 |
| 94077_f_at | 0.00 | 0.00 | 0.00 | 2.44 | 2.46 | 2.44 | ribophorin; Rpn | D31717 |
| 98081_at | 0.00 | 0.00 | 0.00 | 2.75 | 3.10 | 2.31 | RPO1-3 | AI853173 |
| 113001_at | 0.00 | 0.00 | 0.00 | 2.04 | 1.65 | 0.00 | RPS12 | AI643492 |
| 101922_at | 0.00 | 1.67 | 1.76 | 4.37 | 4.88 | 4.01 | RPS8 | AW123408 |
| 100612_at | 0.00 | 0.00 | 2.89 | 0.00 | 0.00 | 0.00 | ribonucleotide reductase M1; Rrm1 | K02927 |
| 102001_at | 0.00 | 4.09 | 4.93 | 4.37 | 4.89 | 2.47 | ribonucleotide reductase M2; Rrm2 | M14223 |
| 101584_at | 0.00 | 0.00 | 0.00 | 0.00 | 2.07 | 2.03 | Ras suppressor protein 1; Rsu1 | X63039 |
| 92399_at | 1.56 | 5.32 | 7.63 | 16.64 | 13.11 | 6.52 | ranscription factor 1; Runx1 | D26532 |
| 92676_at | 0.00 | 1.60 | 2.51 | 4.67 | 13.58 | 14.15 | transcription factor 2; Runx2 | D14636 |
| 92539_at | 0.00 | 2.45 | 2.84 | 3.90 | 5.12 | 4.18 | protein A11 (calgizzarin); S100a10 | M16465 |
| 98600_at | 1.80 | 2.47 | 2.93 | 4.55 | 7.43 | 6.03 | binding protein A11; S100a11 | U41341 |
| 100959_at | 0.00 | 1.56 | 0.00 | 2.63 | 2.65 | 2.69 | binding protein A13; S100a13 | X99921 |
| 100960_g_at | 0.00 | 0.00 | 0.00 | 1.80 | 2.42 | 2.42 | binding protein A13; S100a13 | X99921 |
| 92770_at | 0.00 | 0.00 | 1.83 | 2.72 | 2.37 | 2.61 | protein A6 (calcyclin); S100a6 | X66449 |
| 95754_at | 0.00 | 0.00 | 0.00 | 0.00 | 2.08 | 2.47 | UNK_AI838216 | AI838216 |
| 102712_at | −3.84 | 2.96 | 4.98 | 8.61 | 4.23 | 0.00 | Saa3 | X03505 |
| 102012_at | 0.00 | 3.45 | 2.78 | 6.04 | 4.14 | 5.35 | SAPS | AB014485 |
| 97340_at | 0.00 | 0.00 | 0.00 | 0.00 | 9.89 | 4.81 | SART3 | AI839599 |
| 96657_at | 0.00 | 0.00 | 2.35 | 3.95 | 3.54 | 3.47 | N1-acetyl transferase; Sat | L10244 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 99127_at | 0.00 | 0.00 | 0.00 | 2.14 | 2.18 | 2.16 | ataxia 10 homolog (human); Sca10 | X61506 |
| 95758_at | 0.00 | 0.00 | 1.71 | 3.17 | 5.87 | 3.76 | A desaturase 2; Scd2 | M26270 |
| 103244_at | 0.00 | 2.16 | 1.90 | 6.42 | 14.12 | 8.60 | SCGF | AB009245 |
| 101132_at | 0.00 | 0.00 | 0.00 | 0.00 | 2.13 | 0.00 | voltage-gated, type VI, alpha polypeptide; Scn6a | L36179 |
| 92755_f_at | 0.00 | 0.00 | 0.00 | 3.02 | 0.00 | 0.00 | secretin; Sct | X73580 |
| 94140_at | 0.48 | 2.44 | −2.79 | 0.00 | 0.00 | 0.00 | SCVR | M59446 |
| 93717_at | 2.82 | 3.56 | −0.43 | 1.69 | 2.72 | −0.33 | cytokine A12; Scya12 | U50712 |
| 102736_at | 2.71 | 5.21 | 6.15 | 9.01 | 7.67 | 2.10 | small inducible cytokine A2; Scya2 | M19681 |
| 92849_at | 2.26 | 2.31 | 0.00 | 0.00 | 0.00 | 0.00 | small inducible cytokine A6; Scya6 | M58004 |
| 94761_at | 3.20 | 6.30 | 7.57 | 6.75 | 7.08 | 0.00 | SCYA7 | X70058 |
| 104388_at | 2.37 | 2.97 | 2.84 | 3.61 | 2.34 | 5.38 | SCYA9 | U49513 |
| 93858_at | 0.00 | 0.00 | 4.64 | 3.50 | 1.42 | 1.46 | cytokine B subfamily (Cys-X-Cys), member 10; Scyb10 | M33266 |
| 96953_at | 0.00 | 3.54 | 0.00 | 2.92 | 2.95 | 0.00 | KEC | AW120786 |
| 98772_at | 3.38 | 5.10 | 0.00 | 2.26 | 0.00 | 0.00 | cytokine B subfamily, member 5; Scyb5 | U27267 |
| 98008_at | 0.00 | 0.00 | 0.00 | 0.00 | 5.32 | 0.00 | cytokine subfamily D, 1; Scyd1 | U92565 |
| 96033_at | 0.00 | 0.00 | 0.00 | 0.00 | 3.39 | 3.96 | syndecan 1; Sdc1 | Z22532 |
| 95104_at | 0.00 | 0.00 | 0.00 | 0.00 | 7.78 | 5.08 | syndecan 2; Sdc2 | U00674 |
| 98590_at | 0.00 | 1.50 | 0.00 | 0.00 | 5.17 | 2.08 | syndecan 4; Sdc4 | D89571 |
| 93017_at | 0.00 | 2.05 | 2.50 | 2.98 | 2.03 | 2.97 | SDCBP | AF077527 |
| 110314_at | 0.00 | 0.00 | 0.00 | 3.88 | 0.00 | 0.00 | UNK_AA939505 | AA939505 |
| 93503_at | 3.23 | 2.68 | 3.83 | 5.83 | 5.65 | 6.03 | SDF5 | U88567 |
| 103421_at | 0.00 | 0.00 | 0.00 | 2.75 | 2.23 | 4.03 | factor receptor 2; Sdfr2 | D50464 |
| 102319_at | 0.00 | 0.00 | 0.00 | 0.00 | 2.38 | 0.00 | SDP8 | AF062484 |
| 110816_at | 0.00 | 1.86 | 2.60 | 3.96 | 4.31 | 4.31 | SEC22L1 | AI836222 |
| 103953_at | 0.00 | 0.00 | 0.00 | 4.26 | 4.62 | 2.88 | trafficking protein-like 1 (S. cerevisiae); Sec22l1 | U91538 |
| 93711_at | 0.00 | 0.00 | 0.00 | 0.00 | 2.09 | 0.00 | SEC23A (S. cerevisiae); Sec23a | D12713 |
| 98944_at | 0.00 | 2.50 | 3.56 | 6.12 | 3.76 | 3.03 | UNK_AI848343 | AI848343 |
| 97882_at | 0.00 | 2.61 | 2.86 | 6.48 | 9.11 | 5.92 | SEC61A | AB032902 |
| 92870_at | 0.00 | 0.00 | 0.00 | 2.77 | 0.00 | 0.00 | SEL1H | AF063095 |
| 100457_at | 0.00 | 0.00 | 0.00 | 2.17 | 2.21 | 2.29 | selectin, endothelial cell, ligand; Selel | X84037 |
| 104692_at | 0.00 | 2.30 | 0.00 | 0.00 | 0.00 | 0.00 | SELP | M72332 |
| 94063_at | 0.00 | 0.00 | 0.00 | 0.00 | 4.29 | 0.00 | immunoglobulin domain (Ig), transmembrane domain (TM) and short cytoplasmic domain, (semaphorin) 4A; | X85991 |
| 103094_at | 0.00 | 0.00 | 0.00 | 0.00 | 5.61 | 4.54 | SERF1 | AI036894 |
| 102641_at | 0.00 | 7.13 | 3.23 | 5.34 | 3.39 | 11.03 | SFPI1 | L03215 |
| 97997_at | 0.00 | 4.24 | 6.40 | 9.69 | 9.18 | 2.33 | secreted frizzled-related sequence protein 1; Sfrp1 | U88566 |
| 104672_at | 0.00 | 0.00 | 0.00 | 0.00 | 12.10 | 0.00 | secreted frizzled-related sequence protein 3; Sfrp3 | U68058 |
| 95791_s_at | 0.00 | 0.00 | 0.00 | 2.66 | 2.33 | 0.00 | arginine/serine-rich 10, splidng factor, arginine/serine-rich 2 (SC-35); Sfrs10, Sfrs2 | U14648 |
| 94017_s_at | 0.00 | 0.00 | 0.00 | 2.08 | 0.00 | 0.00 | SFRS2 | X98511 |
| 101004_f_at | 0.00 | 2.16 | 2.00 | 2.68 | 2.36 | 2.18 | splicing factor, arginine/serine-rich 3 (SRp20); Sfrs3 | X91656 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 101861_at | 0.00 | 0.00 | 0.00 | 0.00 | 2.24 | 2.47 | SGCE | AF031919 |
| 96127_at | 0.00 | 2.31 | 2.89 | 3.47 | 3.36 | 6.40 | SGPL1 | AW048730 |
| 93806_at | 0.00 | 2.17 | 2.28 | 2.89 | 3.44 | 5.41 | UNK_AI848671 | AI848671 |
| 92975_at | 0.00 | 2.44 | 2.15 | 2.25 | 2.45 | 3.07 | SH3-domain binding protein 2; Sh3bp2 | L14543 |
| 103755_at | 0.00 | 0.00 | 0.00 | 2.54 | 5.91 | 3.28 | SH3 domain protein D19; Sh3d19 | D89677 |
| 93275_at | 0.00 | 0.50 | 0.00 | 2.58 | 5.00 | 4.00 | SH3 domain protein 2B; Sh3d2b | U58885 |
| 99158_at | 0.00 | 1.76 | 1.70 | 3.10 | 2.59 | 2.16 | SH3 domain protein 3; Sh3d3 | U58888 |
| 95456_r_at | 0.00 | 0.00 | 0.00 | 0.00 | 2.03 | 1.83 | deleted gene 1; Shfdg1 | U41626 |
| 99042_s_at | 0.00 | 0.00 | 0.00 | 2.57 | 4.04 | 6.81 | SHOX2 | U66918 |
| 102752_at | 0.00 | 2.08 | 2.08 | 3.26 | 1.98 | 2.62 | SHYC | AF072697 |
| 94432_at | 0.00 | 0.00 | 0.00 | 0.00 | 2.68 | 3.64 | UNK_AI117157 | AI117157 |
| 99847_at | 0.00 | 0.00 | 0.00 | 0.00 | 3.29 | 3.93 | Siat4 | X73523 |
| 95599_at | 0.00 | 0.00 | 0.00 | 0.00 | 4.82 | 3.35 | sialyltransferase 4c; Siat4c | D28941 |
| 94492_at | 0.00 | 0.00 | 0.00 | 2.96 | 3.59 | 4.98 | UNK_AB025406 | AB025406 |
| 99655_at | 0.00 | 0.00 | 0.00 | 2.64 | 2.61 | 2.30 | UNK_AB025405 | AB025405 |
| 95144_at | 0.00 | 0.00 | 0.00 | 2.28 | 1.75 | 1.94 | UNK_AB024984 | AB024984 |
| 97489_at | 0.00 | 0.00 | 0.00 | 0.00 | 2.58 | 3.90 | UNK_AI846739 | AI846739 |
| 93789_s_at | 0.00 | 1.63 | 0.00 | 2.55 | 3.08 | 3.28 | SIN3B | AF038848 |
| 92450_at | 0.00 | 0.00 | 0.00 | 0.00 | 2.37 | 2.54 | SLC12A4 | AF047339 |
| 104719_at | 0.00 | 2.21 | 0.00 | 0.00 | 3.05 | 2.14 | SLC12A7 | AI182203 |
| 100491_at | 0.00 | 0.00 | 0.00 | 1.90 | 2.76 | 0.00 | SLC16A2 | AF045692 |
| 100943_at | 0.00 | 0.00 | 0.00 | 7.00 | 7.27 | 2.37 | neutral amino acid transporter; Slc1a4 | U75215 |
| 103065_at | 0.00 | 1.93 | 0.00 | 4.69 | 6.26 | 3.25 | 20, member 1; Slc20a1 | M73696 |
| 99112_at | 0.00 | 0.00 | 0.00 | 0.00 | 1.63 | 3.71 | SLC25A10 | AA683883 |
| 97473_at | 0.00 | 8.03 | 4.82 | 19.23 | 14.32 | 7.15 | SLC25A17 | AW124470 |
| 97472_at | 0.00 | 0.00 | 0.00 | 2.35 | 2.52 | 0.00 | SLC25A17 | AJ006341 |
| 100618_f_at | 0.00 | 0.00 | 0.00 | 5.23 | 4.78 | 7.59 | 25 (mitochondrial carrier; adenine nucleotide translocator), member 5; Slc25a5 | AA062013 |
| 97957_at | 0.00 | 0.00 | 0.00 | 0.00 | 2.19 | 0.00 | SLC27A4 | AF072759 |
| 95733_at | 0.00 | 0.00 | 0.00 | 0.00 | 3.22 | 3.31 | UNK_AI838274 | AI838274 |
| 95571_at | 0.00 | 0.00 | 0.00 | 0.00 | 1.83 | 2.40 | SLC30A4 | AF004100 |
| 101877_at | 0.00 | 1.78 | 1.74 | 2.74 | 3.70 | 3.40 | SLC31A1 | AI854432 |
| 103845_at | 0.00 | 0.00 | 0.00 | 2.78 | 2.72 | 0.00 | UNK_AI839005 | AI839005 |
| 93558_at | 0.00 | 0.00 | 0.00 | 2.33 | 3.66 | 2.36 | SLC35A2 | AB027147 |
| 100020_at | 0.00 | 0.00 | 0.00 | 0.00 | 3.18 | 6.84 | solute carrier family 4 (anion exchanger), member 2; Slc4a2 | J04036 |
| 103818_at | 0.00 | 3.94 | 0.00 | 0.00 | 7.66 | 4.45 | SLC7A7 | AJ012754 |
| 104214_at | 0.00 | 2.48 | 0.00 | 0.00 | 0.00 | 0.00 | SLC7A8 | AW122706 |
| 99524_at | 0.00 | 0.00 | 0.00 | 2.03 | 0.00 | 0.00 | solute carrier family 8 (sodium/calcium exchanger), member 1; Slc8a1 | AF004666 |
| 102264_at | 2.09 | 0.00 | 2.47 | 2.09 | 1.99 | 2.48 | SLFN1 | AF099972 |
| 92472_f_at | 2.33 | 3.93 | 4.37 | 4.87 | 3.05 | 3.83 | SLFN2 | AF099973 |
| 92471_i_at | 0.00 | 3.71 | 3.39 | 5.90 | 8.39 | 4.15 | SLFN2 | AF099973 |
| 92858_at | 0.00 | 4.23 | 2.55 | 6.22 | 7.43 | 3.89 | SLPI | AF002719 |
| 99552_at | 3.78 | 17.54 | 20.88 | 10.28 | 11.85 | 25.49 | slug, chicken homolog; Slugh | U79550 |
| 96050_at | 0.00 | 0.00 | 0.00 | 7.04 | 4.66 | 0.00 | SMARCB1 | AJ011740 |
| 102062_at | 0.00 | 0.00 | 4.08 | 0.00 | 4.73 | 3.19 | matrix associated, actin dependent regulator of chromatin, subfamily c, member 1; | U85614 |
| 106277_at | 0.00 | 0.00 | 0.00 | 2.18 | 2.30 | 3.29 | UNK_AW120530 | AW120530 |
| 96812_at | 0.00 | 0.00 | 0.00 | 2.57 | 6.03 | 2.71 | SMOH | AF089721 |
| 103830_at | 0.00 | 2.85 | 0.00 | 0.00 | 3.62 | 1.44 | snail homolog, Drosophila); Sna | M95604 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 101530_at | 0.00 | 0.00 | 0.00 | 2.32 | 2.60 | 1.69 | ribonucleoprotein 116 kDa; Snrp116-pending | U97079 |
| 101506_at | 0.00 | 0.00 | 0.00 | 2.55 | 0.00 | 0.00 | UNK_AW227345 | AW227345 |
| 100577_at | 0.00 | 0.00 | 2.41 | 0.00 | 2.31 | 2.11 | small nuclear ribonucleoprotein D1; Snrpd1 | M58558 |
| 112282_s_at | 0.00 | 3.18 | 4.02 | 4.54 | 4.18 | 4.52 | UNK_AI154073 | AH 54073 |
| 112283_at | 1.68 | 2.68 | 0.00 | 3.14 | 7.08 | 5.94 | UNK_AA718584 | AA718584 |
| 94550_at | 0.00 | 2.19 | 1.41 | 1.85 | 1.56 | 2.92 | UNK_AW121324 | AW121324 |
| 94902_at | 0.00 | 1.87 | 0.00 | 2.17 | 2.23 | 1.87 | dismutase 3, extracellular; Sod3 | U38261 |
| 111853_at | 0.00 | 0.00 | 0.00 | 1.50 | 4.58 | 3.78 | SOUL-PENDING | AA726177 |
| 104408_s_at | 0.00 | 0.00 | 0.00 | 0.00 | 2.29 | 2.61 | SRY-box containing gene 18; Sox18 | L35032 |
| 101430_at | 0.00 | 0.00 | 0.00 | 2.09 | 4.36 | 6.01 | SOX4 | AW124153 |
| 100032_at | 0.00 | 0.00 | 0.00 | 2.03 | 2.18 | 0.00 | transcription factor 1; Sp1 | X60136 |
| 113152_at | 0.00 | 0.00 | 0.00 | 1.99 | 2.66 | 0.00 | SPAK-PENDING | AI850672 |
| 97160_at | 0.00 | 0.00 | 0.00 | 3.53 | 3.24 | 3.71 | cysteine rich glycoprotein; Sparc | X04017 |
| 97817_at | 0.00 | 1.94 | 1.93 | 3.63 | 3.06 | 3.46 | UNK_AW121136 | AW121136 |
| 104374_at | 0.00 | 5.69 | 5.43 | 8.11 | 4.63 | 0.00 | serine protease inhibitor 2-2; Spi2-2 | M64086 |
| 96060_at | 0.00 | 0.00 | 0.00 | 2.21 | 1.73 | 1.92 | serine protease inhibitor 3; Spi3 | U25844 |
| 97487_at | 0.00 | 0.00 | 0.00 | 0.00 | 2.61 | 6.46 | serine protease inhibitor 4; Spi4 | X70296 |
| 98405_at | 0.00 | 0.00 | 0.00 | 0.00 | 5.15 | 0.00 | serine protease inhibitor 6; Spi6 | U96700 |
| 102125_f_at | 0.00 | 0.00 | 1.30 | 0.00 | 2.11 | 0.00 | SPI6 | AI838923 |
| 99528_at | 0.00 | 0.00 | 0.00 | 0.00 | 1.58 | 2.19 | SPIN | AW122015 |
| 99563_at | 0.00 | 0.00 | 0.00 | 0.00 | 1.95 | 2.49 | SPIN | AW124681 |
| 97519_at | 2.00 | 2.60 | 5.99 | 14.15 | 24.33 | 29.32 | SPP1 | X13986 |
| 94322_at | 0.00 | 2.38 | 2.44 | 0.00 | 3.97 | 0.56 | squalene epoxidase; Sqle | D42048 |
| 100095_at | 0.00 | 0.00 | 0.00 | 1.76 | 1.71 | 2.24 | scavenger receptor class B1; Srb1 | U37799 |
| 96712_at | 0.00 | 0.00 | 0.00 | 5.45 | 0.00 | 0.00 | UNK_AI848508 | AI848508 |
| 92540_f_at | 0.00 | 2.10 | 2.30 | 7.95 | 5.95 | 3.58 | SRM | Z67748 |
| 103568_at | 0.00 | 2.43 | 4.42 | 4.07 | 17.64 | 6.56 | SRPX-PENDING | AB028049 |
| 92265_f_at | 0.00 | 0.00 | 0.00 | 0.00 | 1.91 | 3.63 | SSA2 | AF042139 |
| 99610_at | 0.00 | 0.00 | 0.00 | 0.00 | 1.96 | 2.34 | synovial sarcoma, translocated to X chromosome; Ssxt | X93357 |
| 101465_at | 0.00 | 0.00 | 0.00 | 3.32 | 2.28 | 4.66 | signal transducer and activator of transcription 1; Stat1 | U06924 |
| 115806_at | 0.00 | 0.00 | 3.13 | 2.81 | 0.00 | 0.00 | UNK_AI851966 | AI851966 |
| 99100_at | 0.00 | 0.00 | 0.00 | 0.00 | 2.73 | 0.00 | STATS | AI837104 |
| 94331_at | 0.00 | 2.04 | 0.00 | 0.00 | 2.15 | 2.15 | signal transducer and activator of transcription 6; Stat6 | L47650 |
| 93272_at | 0.00 | 0.00 | 0.00 | 0.00 | 2.30 | 2.62 | STK16 | AF062076 |
| 98996_at | 0.00 | 2.59 | 2.69 | 3.64 | 4.59 | 2.59 | STK18 | L29480 |
| 92639_at | 0.00 | 1.93 | 0.00 | 2.47 | 2.35 | 0.00 | serine/threonine kinase 6; Stk6 | U80932 |
| 96076_at | 0.00 | 0.00 | 0.00 | 2.18 | 3.12 | 2.49 | UNK_AW121716 | AW121716 |
| 99146_at | 0.00 | 0.00 | 0.00 | 1.89 | 3.17 | 3.15 | UNK_AW124355 | AW124355 |
| 97983_s_at | 0.00 | 0.00 | 0.00 | 0.00 | 2.13 | 0.00 | syntaxin binding protein 1; Stxbp1 | D45903 |
| 95703_at | 0.00 | 0.00 | 0.00 | 3.28 | 1.98 | 1.70 | UNK_AB024303 | AB024303 |
| 101901_at | 0.00 | 0.00 | 2.31 | 2.55 | 1.48 | 1.72 | SUPL15H | AB024713 |
| 96542_at | 0.00 | 0.00 | 0.00 | 0.00 | 4.43 | 4.05 | surfeit gene 4; Surf4 | M62606 |
| 97238_at | 0.00 | 1.75 | 2.05 | 1.79 | 1.87 | 0.00 | TACC3 | AW209238 |
| 93541_at | 0.00 | 0.00 | 0.00 | 2.16 | 3.73 | 0.00 | TAGLN | Z68618 |
| 93333_at | 0.00 | 0.00 | 2.00 | 2.33 | 2.00 | 2.02 | Tbca | U05333 |
| 98937_at | 0.00 | 0.00 | 1.55 | 3.06 | 3.36 | 2.94 | TBRG1 | AW049795 |
| 104655_at | 0.00 | 0.00 | 0.00 | 0.00 | 1.42 | 2.13 | UNK_AA755817 | AA755817 |
| 97994_at | 0.00 | 0.00 | 0.00 | 0.00 | 8.61 | 7.06 | TCF7 | AI019193 |
| 97995_at | 0.00 | 0.00 | 0.00 | 0.00 | 2.94 | 2.18 | 7, T-cell specific; Tcf7 | X61385 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 97901_at | 0.00 | 0.00 | 0.00 | 0.00 | 3.66 | 0.00 | transcription factor UBF; Tcfubf | X60831 |
| 93736_at | 0.00 | 0.00 | 0.00 | 0.00 | 1.97 | 3.23 | TCN2 | AF090686 |
| 101540_at | 0.00 | 0.00 | 0.00 | 1.89 | 2.12 | 1.40 | TDG | AF069519 |
| 108581_at | 0.00 | 0.00 | 0.00 | 0.00 | 2.46 | 4.50 | UNK_AI835817 | AI835817 |
| 116324_g_at | 0.00 | 0.00 | 0.00 | 0.00 | 1.48 | 2.45 | TEDP2-PENDING | AI851893 |
| 93367_at | 0.00 | 0.00 | 0.00 | 2.20 | 3.14 | 3.08 | associated protein 1; Tep1 | U86137 |
| 103385_at | 0.00 | 0.00 | 0.00 | 1.97 | 2.16 | 1.87 | teratocarcinoma expressed, serine rich; Tera | U64033 |
| 99138_at | 0.00 | 2.50 | 0.00 | 2.37 | 2.41 | 2.06 | TFG | AA756292 |
| 98514_at | 0.00 | 0.00 | 0.00 | 3.17 | 4.49 | 2.87 | TFPI | AF004833 |
| 94383_at | 0.00 | 0.00 | 0.00 | 4.72 | 5.97 | 5.52 | pathway inhibitor 2; Tfpi2 | D50586 |
| 101918_at | 0.00 | 0.00 | 0.00 | 0.00 | 11.46 | 8.03 | TGFB1 | AJ009862 |
| 98019_at | 0.00 | 0.00 | 0.00 | 0.00 | 8.41 | 3.84 | factor beta 1 induced transcript 1; Tgfb1i1 | L22482 |
| 93728_at | 0.00 | 2.12 | 2.20 | 3.09 | 3.15 | 2.65 | factor beta 1 induced transcript 4; Tgfb1i4 | X62940 |
| 93300_at | 0.00 | 0.00 | 0.00 | 0.00 | 3.26 | 0.00 | transforming growth factor, beta 2; Tgfb2 | X57413 |
| 102751_at | 0.00 | 0.00 | 0.00 | 3.15 | 3.21 | 1.80 | transforming growth factor, beta 3; Tgfb3 | M32745 |
| 92877_at | 2.66 | 4.57 | 4.66 | 7.44 | 3.85 | 2.47 | transforming growth factor, beta induced, 68 kDa; Tgfbi | L19932 |
| 101502_at | 0.00 | 0.00 | 2.62 | 4.72 | 4.01 | 3.84 | TG interacting factor; Tgif | X89749 |
| 104601_at | 0.00 | 2.79 | 0.00 | 0.00 | 2.21 | 0.00 | Thbd | X14432 |
| 94930_at | 0.00 | 0.00 | 0.00 | 6.81 | 11.52 | 6.37 | Thbs2 | L07803 |
| 103869_at | 0.00 | 0.00 | 4.33 | 17.37 | 14.36 | 8.82 | protein, mucin 1, transmembrane, thrombospondin 3; LOC54129, Muc1, Thbs3 | U16175 |
| 99057_at | 0.00 | 1.45 | 0.00 | 2.57 | 3.87 | 1.98 | THY1 | M12379 |
| 93071_at | 0.00 | 0.00 | 0.00 | 2.37 | 2.57 | 1.98 | TIF1B | X99644 |
| 93507_at | 0.00 | 0.00 | 0.00 | 0.00 | 3.00 | 3.30 | tissue inhibitor of metalloproteinase 2; Timp2 | X62622 |
| 103671_at | 0.00 | 0.00 | 0.00 | 0.00 | 3.68 | 2.01 | TIP30-PENDING | AF061972 |
| 102273_at | 0.00 | 0.00 | 0.00 | 1.73 | 2.46 | 1.93 | TJ6 | M31226 |
| 99935_at | 0.00 | 0.00 | 0.00 | 0.00 | 2.21 | 2.70 | tight junction protein 1; Tjp1 | D14340 |
| 96081_at | 0.00 | 0.00 | 0.67 | 0.00 | 8.09 | 0.00 | TK1 | X60980 |
| 110423_at | 0.00 | 0.00 | 0.00 | 0.00 | 6.50 | 2.22 | UNK_AA895554 | AA895554 |
| 104623_at | 0.00 | 0.00 | 0.00 | 0.00 | 2.35 | 3.25 | enhancer of split 3, homolog of Drosophila E(spl); | X73360 |
| 98304_at | 0.00 | 1.55 | 0.00 | 2.11 | 1.46 | 1.57 | TLR6 | AB020808 |
| 92555_at | 0.00 | 0.00 | 2.39 | 3.84 | 11.52 | 5.85 | UNK_AF053454 | AF053454 |
| 100039_at | 0.00 | 0.00 | 0.00 | 2.65 | 5.36 | 3.33 | UNK_AW125880 | AW125880 |
| 115179_at | 0.00 | 2.54 | 0.00 | 0.00 | 0.00 | 0.00 | UNK_AA718842 | AA718842 |
| 99013_f_at | 0.00 | 1.67 | 0.00 | 2.36 | 3.05 | 3.11 | TMOD3 | AI846797 |
| 115913_at | 0.00 | 0.00 | 0.00 | 2.69 | 4.01 | 3.29 | TMOD3 | AI526875 |
| 101993_at | 0.00 | 3.87 | 7.79 | 16.34 | 19.51 | 19.59 | tenascin C; Tnc | X56304 |
| 98474_r_at | 0.00 | 1.62 | 2.24 | 1.98 | 1.85 | 2.10 | factor induced protein 6; Tnfip6 | U83903 |
| 102887_at | 0.00 | 0.00 | 0.00 | 0.00 | 10.64 | 3.70 | OPG | U94331 |
| 92793_at | 0.00 | 3.30 | 0.00 | 2.34 | 3.22 | 2.94 | TNFRSF1A | X57796 |
| 94928_at | 0.00 | 1.58 | 2.10 | 2.39 | 1.72 | 3.94 | TNFRSF1B | X87128 |
| 93416_at | 0.00 | 1.93 | 1.50 | 0.00 | 2.12 | 4.02 | factor (ligand) superfamily, member 11; Tnfsf 11 | AF019048 |
| 100593_at | 0.00 | 0.00 | 0.00 | 0.00 | 12.73 | 3.78 | TNNT2 | L47600 |
| 99578_at | 0.00 | 1.98 | 3.26 | 3.07 | 3.45 | 1.98 | TOP2A | U01915 |
| 95505_at | 0.00 | 0.00 | 0.00 | 2.60 | 0.00 | 0.00 | TOR1B | AW060509 |
| 97557_at | 0.00 | 0.00 | 0.00 | 0.00 | 3.90 | 0.00 | TOR2A | AI841457 |
| 95345_at | 0.00 | 0.00 | 0.00 | 1.80 | 3.25 | 2.14 | TPBG | AJ012160 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 103032_at | 0.00 | 0.00 | 0.00 | 0.00 | 2.37 | 2.26 | TPST1 | AF038008 |
| 94948_at | 0.00 | 0.00 | 0.00 | 0.00 | 4.95 | 4.19 | TRIP6 | AF097511 |
| 104154_at | 0.00 | 2.21 | 0.00 | 0.00 | 4.07 | 0.00 | TRP53 | AB021961 |
| 104275_g_at | 0.00 | 0.00 | 0.00 | 0.00 | 2.73 | 0.00 | TRP53 | AB021961 |
| 96183_at | 0.00 | 0.00 | 2.23 | 0.00 | 2.20 | 2.47 | UNK__AW122985 | AW122985 |
| 93538_at | 0.00 | 0.00 | 0.00 | 2.02 | 0.00 | 0.00 | TTRAP-PENDING | AW228036 |
| 100342_i_at | 0.00 | 2.12 | 2.24 | 4.45 | 5.18 | 2.86 | TUBA1 | M28729 |
| 100343_f_at | 0.00 | 1.98 | 2.03 | 3.13 | 2.91 | 2.34 | TUBA1 | M28729 |
| 98759_f_at | 0.00 | 2.05 | 1.98 | 3.16 | 3.39 | 2.73 | TUBA2 | M28727 |
| 101543_f_at | 0.00 | 2.06 | 2.24 | 3.40 | 3.14 | 2.65 | TUBA6 | M13441 |
| 94835_f_at | 0.00 | 2.92 | 2.73 | 4.98 | 5.58 | 3.49 | Tubb2 | M28739 |
| 94788_f_at | 0.00 | 3.11 | 3.62 | 5.63 | 6.28 | 4.29 | Tubb5 | X04663 |
| 94789_r_at | 0.00 | 7.98 | 8.12 | 78.06 | 13.75 | 7.31 | Tubb5 | X04663 |
| 98028_at | 0.00 | 0.00 | 1.73 | 1.28 | 5.13 | 7.55 | TWIST | M63649 |
| 92807_at | 0.00 | 1.60 | 2.05 | 2.73 | 2.29 | 2.42 | TXN | X77585 |
| 93237_s_at | 0.00 | 1.82 | 0.00 | 0.00 | 4.28 | 3.89 | TYMS | AU044050 |
| 100397_at | 2.04 | 3.39 | 3.70 | 5.63 | 5.00 | 12.41 | TYROBP | AF024637 |
| 97304_at | 0.00 | 0.00 | 0.00 | 0.00 | 2.07 | 2.44 | UBP1 | AI836100 |
| 98972_at | 0.00 | 0.00 | 0.00 | 0.00 | 5.36 | 2.56 | UNK__AI574262 | AI574262 |
| 94197_at | 0.00 | 3.03 | 0.00 | 2.40 | 3.38 | 0.00 | UGCG | D89866 |
| 102322_at | 2.51 | 2.38 | 2.67 | 3.94 | 4.24 | 4.11 | UGDH | AF061017 |
| 95024_at | 1.90 | 0.00 | 3.20 | 3.26 | 2.42 | 0.00 | USP18 | AW047653 |
| 93305_f_at | 0.00 | 0.00 | 5.69 | 4.47 | 3.95 | 3.50 | VAMP8 | AF053724 |
| 100345_f_at | 0.00 | 0.00 | 0.00 | 2.62 | 2.67 | 2.60 | VAMP8 | W65964 |
| 101982_at | 0.00 | 1.36 | 0.00 | 2.45 | 2.66 | 2.27 | stimulated phosphoprotein; | X98475 |
| 99799_at | 1.44 | 3.13 | 0.00 | 2.64 | 2.99 | 2.40 | vav oncogene; Vav | X64361 |
| 96511_s_at | 0.00 | 0.00 | 0.00 | 0.00 | 2.07 | 0.00 | vav oncogene; Vav | D83266 |
| 95490_at | 0.00 | 0.00 | 0.00 | 2.26 | 3.00 | 2.09 | UNK__AW120891 | AW120891 |
| 92558_at | 0.00 | 3.13 | 0.00 | 4.11 | 5.49 | 11.07 | VCAM1 | M84487 |
| 92559_at | 1.22 | 1.55 | 0.00 | 0.00 | 2.01 | 2.67 | VCAM1 | U12884 |
| 92560_g_at | 0.00 | 0.00 | 0.00 | 0.00 | 3.35 | 4.56 | VCAM1 | U12884 |
| 100084_at | 0.00 | 0.00 | 0.00 | 0.00 | 2.73 | 3.56 | villin 2; Vil2 | X60671 |
| 101047_at | 0.00 | 0.00 | 0.00 | 0.00 | 2.12 | 1.73 | VIM | AW123697 |
| 93337_at | 0.00 | 0.00 | 0.00 | 2.13 | 1.83 | 2.11 | sorting 4b (yeast); Vps4b | U10119 |
| 98963_at | 0.00 | 2.85 | 0.00 | 0.00 | 4.71 | 3.54 | VRL1 | AB021665 |
| 100522_s_at | 0.00 | 0.00 | 0.00 | 3.20 | 3.75 | 3.21 | WW domain binding protein 5; Wbp5 | U92454 |
| 100523_r_at | 0.00 | 0.00 | 0.00 | 2.41 | 3.13 | 2.02 | WW domain binding protein 5; Wbp5 | U92454 |
| 103690_at | 0.00 | 3.29 | 2.41 | 5.12 | 3.55 | 5.88 | UNK__AW125574 | AW125574 |
| 96075_at | 0.00 | 2.11 | 0.00 | 3.70 | 2.89 | 3.37 | WDR1 | AW060876 |
| 92262_at | 0.00 | 0.00 | 0.00 | 0.00 | 3.19 | 0.00 | WIG1 | AF012923 |
| 102044_at | 0.00 | 2.42 | 3.42 | 11.06 | 23.81 | 19.33 | ELM1 | AF100777 |
| 102891_at | 0.00 | 0.00 | 0.00 | 1.63 | 2.46 | 2.59 | WRN | D86527 |
| 113110_at | 0.00 | 0.00 | 0.00 | 0.00 | 2.42 | 3.11 | WRN | AA960405 |
| 98946_at | 0.00 | 1.87 | 0.00 | 4.72 | 3.95 | 3.55 | UNK__AF033186 | AF033186 |
| 113094_at | 0.00 | 0.00 | 0.00 | 0.00 | 3.83 | 0.00 | UNK__AA175692 | AA175692 |
| 100958_at | 0.00 | 0.00 | 0.00 | 0.00 | 4.56 | 7.64 | UNK__AI647003 | AI647003 |
| 99126_at | 0.00 | 0.00 | 0.00 | 0.00 | 2.03 | 3.61 | inactive X specific transcripts; Xist | L04961 |
| 92665_f_at | 0.00 | 0.00 | 0.00 | 0.00 | 1.94 | 2.01 | regulated complex; Xlr | X07967 |
| 100015_at | 0.00 | 0.00 | 0.00 | 0.00 | 2.30 | 0.00 | viral (v-yes) oncogene homolog; Yes | X67677 |
| 104400_at | 0.00 | 2.18 | 0.00 | 2.06 | 3.18 | 2.96 | UNK__AF076956 | AF076956 |
| 97229_at | 0.00 | 0.00 | 0.00 | 2.05 | 0.00 | 0.00 | UNK__AW061042 | AW061042 |
| 97535_at | 0.00 | 1.63 | 2.14 | 2.89 | 2.41 | 2.21 | monooxygenase/tryptophan 5-monooxygenase activation protein, eta polypeptide; | D87661 |
| 97061_g_at | 0.00 | 1.94 | 2.17 | 2.75 | 3.19 | 3.36 | YWHAQ | AW215489 |
| 97544_at | 0.00 | 1.72 | 0.00 | 2.31 | 3.14 | 2.92 | YWHAZ | D83037 |
| 92501_s_at | 0.00 | 0.00 | 0.00 | 0.00 | 5.24 | 4.39 | ZAC1 | X95503 |
| 92502_at | 0.00 | 0.00 | 0.00 | 1.40 | 7.40 | 6.62 | ZAC1 | X95504 |
| 100475_at | 0.00 | 0.00 | 0.00 | 3.36 | 2.20 | 2.88 | zinc finger protein 147; Zfp147 | D63902 |
| 92771_at | 0.00 | 0.00 | 0.00 | 0.00 | 2.13 | 1.97 | ZFP207 | AB013357 |
| 102277_at | 0.00 | 0.00 | 0.00 | 0.00 | 2.59 | 0.00 | ZFP26 | M36514 |

TABLE 1-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day14 Avg. Fold Change | Gene Name | Genbank Accession # |
|---|---|---|---|---|---|---|---|---|
| 92934_at | 0.00 | 0.00 | 0.00 | 0.00 | 2.66 | 0.00 | zinc finger protein 90; Zfp90 | X79828 |
| 103676_at | 0.00 | 0.00 | 0.00 | 0.00 | 2.06 | 2.03 | UNK_AI551306 | AI551306 |

TABLE 2

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 115844_at | −2.74 | −4.65 | −3.15 | −2.76 | −2.12 | −2.10 | UNK_AI847028 | AI847028 |
| 103494_at | 0.00 | −2.50 | −3.42 | −2.87 | −4.24 | −2.99 | UNK_AI047972 | AI047972 |
| 104342_i_at | 0.00 | −4.22 | −3.45 | −5.08 | −10.18 | −4.00 | UNK_AI845798 | AI845798 |
| 107074_at | 0.00 | −2.55 | −2.53 | −3.42 | −4.39 | −2.24 | UNK_AI838083 | AI838083 |
| 133738_at | 0.00 | −2.30 | −2.02 | −3.17 | −4.39 | −3.23 | UNK_AI467229 | AI467229 |
| 133932_at | 0.00 | −2.17 | −2.06 | −3.16 | −4.05 | −2.76 | UNK_AI503993 | AI503993 |
| 133951_at | 0.00 | −3.22 | −3.10 | −10.36 | −6.86 | −2.39 | UNK_AI504979 | AI504979 |
| 94534_at | 0.00 | −2.04 | −2.11 | 0.00 | −4.07 | −2.36 | UNK_AI835446 | AI835446 |
| 94790_at | 0.00 | −2.24 | −2.48 | 0.00 | −3.80 | −2.57 | UNK_AA681807 | AA681807 |
| 95468_at | 0.00 | −2.15 | −1.91 | −2.63 | −4.12 | −2.55 | BTD | AI850202 |
| 96391_at | 0.00 | −2.96 | −2.60 | −1.90 | −3.00 | −2.41 | EST; unknown | C80836 |
| 105638_at | 0.00 | −3.95 | −4.59 | 0.00 | −10.36 | −2.07 | UNK_AA896641 | AA896641 |
| 106963_at | 0.00 | −2.48 | −2.10 | 0.00 | −3.26 | −3.68 | UNK_AW050323 | AW050323 |
| 107282_at | 0.00 | −2.07 | −2.27 | 0.00 | −4.69 | −4.22 | UNK_AW047933 | AW047933 |
| 107418_at | 0.00 | −2.16 | 0.00 | −3.07 | −5.71 | −2.08 | UNK_AW046245 | AW046245 |
| 107952_i_at | 0.00 | −2.62 | −2.43 | 0.00 | −2.93 | −2.12 | UNK_AA606601 | AA606601 |
| 109968_at | 0.00 | −5.91 | −3.57 | 0.00 | −8.76 | −2.67 | UNK_AA771415 | AA771415 |
| 110269_at | −2.16 | −5.45 | −2.93 | 0.00 | −3.03 | 0.00 | UNK_AW045975 | AW045975 |
| 115109_at | 0.00 | −2.05 | −1.79 | −4.17 | −4.31 | −2.28 | UNK_AI838503 | AI838503 |
| 115246_at | 0.00 | −1.95 | −2.61 | −3.31 | −5.64 | −2.62 | UNK_AA790442 | AA790442 |
| 116614_at | 0.00 | −2.54 | −2.37 | 0.00 | −3.72 | −2.01 | UNK_AA647405 | AA647405 |
| 129661_at | 0.00 | −2.57 | −3.45 | 0.00 | −3.41 | −2.12 | UNK_AA792999 | AA792999 |
| 130718_at | 0.00 | −2.98 | −2.27 | 0.00 | −2.50 | −2.32 | UNK_AI844247 | AI844247 |
| 133977_at | 0.00 | −3.33 | −2.14 | −3.11 | −2.79 | −1.68 | UNK_AI506633 | AI506633 |
| 135609_at | 0.00 | −2.66 | 0.00 | −2.42 | −4.25 | −2.42 | UNK_AI505553 | AI505553 |
| 93514_at | 0.00 | −2.76 | −1.94 | 0.00 | −4.77 | −5.23 | MYLC | X12972 |
| 94418_at | 0.00 | −2.71 | −8.42 | 0.00 | −2.51 | −0.63 | UNK_AI839004 | AI839004 |
| 94908_r_at | 0.00 | 0.00 | −2.19 | 0.00 | −4.76 | −2.57 | UNK_AW045632 | AW045632 |
| 95587_at | 0.00 | −2.33 | −2.23 | 0.00 | −2.97 | −1.80 | UNK_AI837204 | AI837204 |
| 98942_r_at | 0.00 | −2.33 | −3.05 | 0.00 | −3.93 | −1.78 | UNK_AW125284 | AW125284 |
| 102862_at | 0.00 | 0.00 | −3.42 | 0.00 | −3.42 | −3.17 | UNK_AA873956 | AA873956 |
| 102916_s_at | 0.00 | −4.25 | −3.83 | 0.00 | −2.86 | 0.00 | UNK_AB010266 | AB010266 |
| 102922_at | 0.00 | −3.08 | −2.52 | 0.00 | −2.84 | −1.50 | UNK_AI851387 | AI851387 |
| 105610_at | 0.00 | 0.00 | −2.89 | 0.00 | −4.34 | −2.22 | UNK_AA388982 | AA388982 |
| 106934_at | 0.00 | 0.00 | −2.79 | 0.00 | −10.65 | −4.94 | UNK_AW047806 | AW047806 |
| 107569_at | 0.00 | −2.01 | 0.00 | 0.00 | −2.37 | −2.03 | UNK_AA738625 | AA738625 |
| 110774_at | 0.00 | −3.03 | −2.48 | 0.00 | −2.45 | −1.51 | UNK_AI852667 | AI852667 |
| 111228_at | 0.00 | −1.68 | −2.69 | 0.00 | −2.72 | −2.01 | UNK_AW122874 | AW122874 |
| 111254_at | 0.00 | −2.06 | −2.12 | 0.00 | −3.40 | −1.69 | UNK_AA735016 | AA735016 |
| 111260_at | 0.00 | 0.00 | −2.66 | 0.00 | −3.27 | −3.11 | UNK_AI843809 | AI843809 |
| 112012_at | 0.00 | −2.13 | −2.12 | 0.00 | −4.16 | −1.67 | UNK_AI875092 | AI875092 |
| 113124_at | 0.00 | −4.08 | 0.00 | 0.00 | −8.64 | −2.40 | UNK_AI852911 | AI852911 |
| 113806_at | 0.00 | 0.00 | −2.69 | 0.00 | −2.68 | −2.20 | UNK_AW121611 | AW121611 |
| 114138_at | 0.00 | 0.00 | −2.00 | 0.00 | −5.82 | −2.95 | UNK_AI643851 | AI643851 |
| 114297_f_at | 0.00 | −1.96 | −2.03 | 0.00 | −4.33 | −2.31 | UNK_AI021087 | AI021087 |
| 114466_at | 0.00 | −1.89 | −2.07 | 0.00 | −3.21 | −2.18 | UNK_AA197511 | AA197511 |
| 116583_at | 0.00 | −2.08 | −1.70 | 0.00 | −3.36 | −2.23 | UNK_AW121389 | AW121389 |
| 116792_at | 0.00 | −1.94 | −3.96 | 0.00 | −4.51 | −3.31 | UNK_AI480742 | AI480742 |
| 129309_at | 0.00 | −2.55 | −1.92 | 0.00 | −3.86 | −2.58 | UNK_AI596885 | AI596885 |
| 129952_at | 0.00 | 0.00 | −2.17 | 0.00 | −2.85 | −2.68 | UNK_AI595378 | AI595378 |
| 135181_f_at | 0.00 | −1.74 | −1.70 | −2.21 | −3.48 | −2.24 | UNK_AW125817 | AW125817 |
| 139035_at | 0.00 | −2.05 | 0.00 | −2.09 | −2.40 | 0.00 | UNK_AI846518 | AI846518 |
| 140572_at | 0.00 | −2.94 | −2.45 | 0.00 | −2.88 | 0.00 | UNK_AW125201 | AW125201 |
| 92202_g_at | 0.00 | 0.00 | 0.00 | 0.00 | −3.21 | −2.40 | UNK_AI553024 | AI553024 |
| 92941_at | 0.00 | 0.00 | 0.00 | 0.00 | −3.70 | −2.71 | UNK_AA833509 | AA833509 |
| 93177_at | 0.00 | 0.00 | 0.00 | 0.00 | −3.03 | −2.08 | UNK_AW121661 | AW121661 |
| 93780_at | 0.00 | −2.35 | −1.92 | 0.00 | −2.37 | −1.95 | UNK_AW060827 | AW060827 |
| 95376_at | 0.00 | 0.00 | 0.00 | 0.00 | −5.44 | −5.10 | UNK_AJ011107 | AJ011107 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 95518_at | 0.00 | −2.12 | −1.76 | 0.00 | −2.06 | 0.00 | UNK__AW122893 | AW122893 |
| 96211_at | 0.00 | 0.00 | 0.00 | −2.61 | −4.19 | 0.00 | UNK__AI846896 | AI846896 |
| 99331_at | 0.00 | 0.00 | 0.00 | 0.00 | −3.02 | −4.46 | UNK__AW125581 | AW125581 |
| 99503_at | 0.00 | −2.49 | 0.00 | 0.00 | −2.85 | −1.74 | UNK__AW045204 | AW045204 |
| 100058_at | 0.00 | 0.00 | 0.00 | 0.00 | −2.34 | −3.75 | UNK__AW047776 | AW047776 |
| 103257_at | 0.00 | 0.00 | −1.75 | 0.00 | −2.96 | −2.37 | UNK__AA690483 | AA690483 |
| 103665_at | 0.00 | −2.26 | −5.60 | 0.00 | −1.79 | −0.73 | UNK__AW122523 | AW122523 |
| 104153_at | 0.00 | 0.00 | 0.00 | 0.00 | −3.18 | −2.04 | UNK__AW047743 | AW047743 |
| 104293_at | 0.00 | 0.00 | −1.95 | 0.00 | −2.61 | −2.73 | UNK__AI882440 | AI882440 |
| 104445_at | −1.69 | −3.53 | −2.56 | 0.00 | −1.65 | 0.00 | UNK__AW046694 | AW046694 |
| 104491_at | 0.00 | −1.77 | −2.21 | 0.00 | −2.08 | 0.00 | UNK__AI509330 | AI509330 |
| 104804_at | 0.00 | −1.61 | 0.00 | 0.00 | −2.94 | −2.31 | UNK__AI504570 | AI504570 |
| 104944_at | 0.00 | 0.00 | 0.00 | 0.00 | −2.25 | −2.14 | UNK__AA619815 | AA619815 |
| 105168_at | 0.00 | −1.76 | 0.00 | 0.00 | −2.67 | −2.61 | UNK__AI847519 | AI847519 |
| 105569_at | 0.00 | 0.00 | −1.98 | 0.00 | −3.12 | −3.32 | UNK__AI605044 | AI605044 |
| 105619_at | 0.00 | 0.00 | 0.00 | 0.00 | −20.58 | −7.69 | UNK__AI849242 | AI849242 |
| 105706_at | 0.00 | 0.00 | 0.00 | 0.00 | −3.77 | −2.26 | UNK__AI847342 | AI847342 |
| 106065_at | 0.00 | −2.29 | 0.00 | 0.00 | −2.40 | 0.00 | UNK__AI849096 | AI849096 |
| 106297_at | 0.00 | −2.02 | 0.00 | 0.00 | −2.32 | 0.00 | UNK__AI841521 | AI841521 |
| 106439_at | 0.00 | 0.00 | 0.00 | 0.00 | −3.25 | −3.88 | UNK__AI851838 | AI851838 |
| 106505_at | 0.00 | −1.79 | 0.00 | 0.00 | −2.85 | −2.52 | UNK__AI844271 | AI844271 |
| 106521_at | 0.00 | −2.23 | 0.00 | 0.00 | −4.38 | 0.00 | UNK__AI987764 | AI987764 |
| 106896_at | 0.00 | 0.00 | 0.00 | 0.00 | −2.96 | −2.16 | UNK__AW049892 | AW049892 |
| 107400_at | 0.00 | −2.00 | −2.22 | 0.00 | −1.83 | 0.00 | UNK__AW048204 | AW048204 |
| 107427_at | 0.00 | −1.59 | 0.00 | 0.00 | −3.02 | −2.22 | UNK__AW122504 | AW122504 |
| 107428_at | 0.00 | 0.00 | 0.00 | 0.00 | −2.66 | −2.13 | UNK__AW046414 | AW046414 |
| 108010_at | 0.00 | 0.00 | 0.00 | 0.00 | −3.82 | −2.72 | UNK__AW210455 | AW210455 |
| 108069_at | 0.00 | 0.00 | 0.00 | 0.00 | −2.51 | −2.13 | UNK__AI642606 | AI642606 |
| 108488_at | 0.00 | 0.00 | 0.00 | 0.00 | −2.80 | −2.49 | UNK__AI838112 | AI838112 |
| 108565_at | 0.00 | −2.68 | −2.95 | 0.00 | 2.66 | 4.55 | UNK__AI853095 | AI853095 |
| 108767_at | 0.00 | −2.42 | 0.00 | 0.00 | −3.47 | 0.00 | UNK__AI448797 | AI448797 |
| 108822_at | 0.00 | 0.00 | 0.00 | −3.70 | −3.72 | 0.00 | UNK__AI615758 | AI615758 |
| 109049_at | 0.00 | 0.00 | 0.00 | 0.00 | −3.89 | −2.60 | UNK__AI643675 | AI643675 |
| 109086_at | 0.00 | 0.00 | −1.83 | 0.00 | −3.02 | −2.24 | UNK__AI463271 | AI463271 |
| 109488_at | 0.00 | 0.00 | 0.00 | 0.00 | −3.72 | −3.74 | UNK__AW123076 | AW123076 |
| 109774_at | 0.00 | −1.85 | −1.71 | 0.00 | −3.33 | −2.06 | PDK2 | AI848783 |
| 110330_at | 0.00 | −1.52 | 0.00 | 0.00 | −4.15 | −2.08 | UNK__AI843917 | AI843917 |
| 111483_at | 0.00 | −1.37 | 0.00 | 0.00 | −4.16 | −3.11 | UNK__AI451767 | AI451767 |
| 111525_at | 0.00 | 0.00 | 0.00 | 0.00 | −2.70 | −2.28 | UNK__AA289880 | AA289880 |
| 111547_at | 0.00 | 0.00 | 0.00 | 0.00 | −3.17 | −2.26 | UNK__AI851666 | AI851666 |
| 111970_at | 0.00 | −1.51 | 0.00 | 0.00 | −4.74 | −3.89 | UNK__AI616223 | AI616223 |
| 112392_at | 0.00 | 0.00 | 0.00 | 0.00 | −4.82 | −2.89 | UNK__AI834768 | AI834768 |
| 112405_at | 0.00 | 0.00 | 0.00 | 0.00 | −5.07 | −3.81 | UNK__AI557974 | AI557974 |
| 112864_at | 0.00 | −1.75 | −2.07 | 0.00 | −2.50 | 0.00 | UNK__AI849524 | AI849524 |
| 112986_at | 0.00 | 0.00 | 0.00 | 0.00 | −5.51 | −5.79 | UNK__AI849914 | AI849914 |
| 113545_at | 0.00 | −1.47 | 0.00 | 0.00 | −2.87 | −2.16 | UNK__AI847141 | AI847141 |
| 113691_at | 0.00 | 0.00 | 0.00 | 0.00 | −3.69 | −2.65 | UNK__AW049533 | AW049533 |
| 114315_at | 0.00 | 0.00 | 0.00 | 0.00 | −2.70 | −2.60 | UNK__AW048818 | AW048818 |
| 114394_at | 0.00 | −2.13 | 0.00 | 0.00 | −2.20 | 0.00 | UNK__AW121080 | AW121080 |
| 114420_at | 0.00 | −3.91 | −3.29 | 0.00 | 3.25 | 4.37 | UNK__AA734866 | AA734866 |
| 114453_at | 0.00 | 0.00 | 0.00 | 0.00 | −4.76 | −5.72 | UNK__AI848077 | AI848077 |
| 114514_at | 0.00 | 0.00 | 0.00 | −2.37 | −2.33 | −1.99 | UNK__AI605635 | AI605635 |
| 114553_at | 0.00 | 0.00 | 0.00 | 0.00 | −2.81 | −2.15 | UNK__AI414584 | AI414584 |
| 114556_at | 0.00 | −1.81 | −1.54 | 0.00 | −2.17 | −2.03 | UNK__AI451747 | AI451747 |
| 114685_at | 0.00 | −2.08 | 0.00 | 0.00 | −2.83 | 0.00 | UNK__AW123120 | AW123120 |
| 114743_at | 0.00 | 0.00 | 0.00 | 0.00 | −4.86 | −4.13 | UNK__AI591553 | AI591553 |
| 114775_at | 0.00 | 0.00 | 0.00 | 0.00 | −4.72 | −2.22 | UNK__AI005882 | AI005882 |
| 115070_at | 0.00 | 0.00 | −1.91 | 0.00 | −4.34 | −2.05 | UNK__AA711252 | AA711252 |
| 115155_at | 0.00 | 0.00 | −1.72 | 0.00 | −4.16 | −3.45 | UNK__AI853189 | AI853189 |
| 115199_at | 0.00 | 0.00 | 0.00 | 0.00 | −3.57 | −2.34 | UNK__AA667270 | AA667270 |
| 115201_at | 0.00 | 0.00 | 0.00 | 0.00 | −2.39 | −2.04 | UNK__AI851486 | AI851486 |
| 115236_at | 0.00 | −2.07 | 0.00 | 0.00 | −3.28 | −1.93 | UNK__AA824120 | AA824120 |
| 115360_at | 0.00 | −1.81 | 0.00 | 0.00 | −3.33 | −2.68 | UNK__AI839569 | AI839569 |
| 115467_at | 0.00 | 0.00 | 0.00 | 0.00 | −2.94 | −2.13 | UNK__AI852809 | AI852809 |
| 115539_at | 0.00 | −2.59 | −1.92 | 0.00 | −3.44 | −1.93 | UNK__AW045801 | AW045801 |
| 115575_at | 0.00 | 0.00 | 0.00 | 0.00 | −2.04 | −2.26 | UNK__AI853953 | AI853953 |
| 116042_at | 0.00 | 0.00 | −1.84 | 0.00 | −3.19 | −2.15 | UNK__AI591726 | AI591726 |
| 116350_at | 0.00 | 0.00 | 0.00 | 0.00 | −5.09 | −3.88 | UNK__AA981270 | AA981270 |
| 116390_at | 0.00 | 0.00 | 0.00 | 0.00 | −3.43 | −2.26 | UNK__AI647836 | AI647836 |
| 116644_at | 0.00 | 0.00 | −1.97 | 0.00 | −2.74 | −2.31 | UNK__AI882312 | AI882312 |
| 116747_at | 0.00 | −1.82 | 0.00 | 0.00 | −3.27 | −2.54 | UNK__AI505458 | AI505458 |
| 116826_at | 0.00 | −1.98 | −2.47 | 0.00 | −4.71 | −1.89 | UNK__AA616199 | AA616199 |
| 117128_at | 0.00 | 0.00 | 0.00 | 0.00 | −2.27 | −2.06 | UNK__AI851602 | AI851602 |
| 117208_at | 0.00 | −1.93 | −1.88 | 0.00 | −3.27 | −2.57 | UNK__AI838208 | AI838208 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 117242_at | 0.00 | 0.00 | 0.00 | 0.00 | −5.22 | −2.68 | UNK_AI835553 | AI835553 |
| 117280_at | 0.00 | 0.00 | 0.00 | 0.00 | −4.97 | −5.55 | UNK_AI835075 | AI835075 |
| 128785_r_at | 0.00 | −2.02 | 0.00 | 0.00 | −4.18 | −1.97 | UNK_AI049307 | AI049307 |
| 128829_at | 0.00 | −1.71 | 0.00 | −1.71 | −2.81 | −2.11 | UNK_AA624027 | AA624027 |
| 129503_at | 0.00 | −1.69 | 0.00 | 0.00 | −3.59 | −2.12 | UNK_AI893884 | AI893884 |
| 129544_at | 0.00 | 0.00 | 0.00 | 0.00 | −3.45 | −2.71 | UNK_AI156198 | AI156198 |
| 130460_at | 0.00 | 0.00 | 0.00 | 0.00 | −2.29 | −2.22 | UNK_AI836434 | AI836434 |
| 130990_at | 0.00 | 0.00 | 0.00 | 0.00 | −2.19 | −2.38 | UNK_AW047063 | AW047063 |
| 131264_f_at | 0.00 | 0.00 | 0.00 | 0.00 | −2.03 | −2.23 | UNK_AA466676 | AA466676 |
| 132021_at | 0.00 | 0.00 | 0.00 | 0.00 | −2.04 | −2.33 | UNK_AI429239 | AI429239 |
| 132820_at | 0.00 | −2.10 | 0.00 | −2.44 | 0.00 | 0.00 | UNK_AI639670 | AI639670 |
| 133719_f_at | 0.00 | 0.00 | 0.00 | 0.00 | −2.62 | −2.46 | UNK_AI463563 | AI463563 |
| 133720_at | 0.00 | −1.88 | 0.00 | 0.00 | −2.73 | −3.37 | UNK_AI464129 | AI464129 |
| 133838_at | 0.00 | −1.90 | 0.00 | −2.11 | −2.82 | 0.00 | UNK_AA420328 | AA420328 |
| 134116_at | 0.00 | 0.00 | 0.00 | 0.00 | −2.70 | −2.28 | UNK_AI255188 | AI255188 |
| 135201_at | 0.00 | −3.44 | −2.08 | 0.00 | 2.29 | 3.08 | UNK_AA420078 | AA420078 |
| 136068_at | 0.00 | 0.00 | 0.00 | 0.00 | −2.93 | −2.72 | UNK_AI551047 | AI551047 |
| 136348_at | 0.00 | 0.00 | −1.98 | 0.00 | −3.82 | −3.36 | UNK_AW146057 | AW146057 |
| 136535_at | 0.00 | 0.00 | −1.79 | 0.00 | −2.03 | −2.06 | UNK_AI642422 | AI642422 |
| 137185_i_at | 0.00 | 0.00 | 0.00 | 0.00 | −2.57 | −2.24 | UNK_AI840674 | AI840674 |
| 138502_at | 0.00 | 0.00 | 0.00 | 0.00 | −2.66 | −3.02 | UNK_AI847438 | AI847438 |
| 139022_at | 0.00 | 0.00 | −1.88 | 0.00 | −3.62 | −2.20 | UNK_AI427762 | AI427762 |
| 140015_at | 0.00 | 0.00 | 0.00 | 0.00 | −2.30 | −2.18 | UNK_AW215832 | AW215832 |
| 92786_at | 0.00 | 0.00 | 0.00 | 0.00 | −2.31 | 0.00 | UNK_AI626942 | AI626942 |
| 92845_at | 0.00 | 0.00 | 0.00 | 0.00 | −2.11 | 0.00 | UNK_AI843232 | AI843232 |
| 93138_at | 0.00 | 0.00 | 0.00 | 0.00 | −2.26 | 0.00 | UNK_AI853219 | AI853219 |
| 93464_at | 0.00 | 0.00 | 0.00 | 0.00 | −2.24 | 0.00 | UNK_AI561567 | AI561567 |
| 93478_at | 0.00 | 0.00 | 0.00 | −1.69 | −1.83 | −2.11 | UNK_AA612483 | AA612483 |
| 93481_at | 0.00 | 0.00 | 0.00 | 0.00 | 0.00 | −2.06 | UNK_AI846720 | AI846720 |
| 93560_at | 0.00 | −1.90 | 0.00 | 0.00 | −2.31 | −1.66 | UNK_AI845882 | AI845882 |
| 93584_at | 0.00 | 0.00 | 0.00 | 0.00 | −2.69 | −1.71 | IGH-6 | V00821 |
| 93815_at | 0.00 | 0.00 | 0.00 | 0.00 | −2.17 | 0.00 | UNK_AI839425 | AI839425 |
| 94010_g_at | 0.00 | 0.00 | 0.00 | 0.00 | −2.07 | 0.00 | UNK_AI848888 | AI848888 |
| 94057_g_at | −1.44 | −2.04 | 0.00 | 0.00 | −2.00 | 0.00 | stearoyl-Coenzyme A desaturase 1; Scd1 | M21285 |
| 94080_at | 0.00 | 0.00 | 0.00 | 0.00 | −2.49 | 0.00 | UNK_AI835718 | AI835718 |
| 94481_at | 0.00 | 0.00 | 0.00 | 0.00 | −2.14 | −1.86 | UNK_AI851321 | AI851321 |
| 94531_at | 0.00 | 0.00 | 0.00 | 0.00 | −3.06 | −1.99 | UNK_AW124582 | AW124582 |
| 94554_at | 0.00 | 0.00 | 0.00 | 0.00 | −2.75 | 0.00 | UNK_AW120965 | AW120965 |
| 94663_at | 0.00 | 0.00 | 0.00 | 0.00 | −2.21 | 0.00 | 0 | AA407151 |
| 94806_at | 0.00 | 0.00 | 0.00 | 0.00 | −2.11 | 0.00 | UNK_AW125336 | AW125336 |
| 94807_at | 0.00 | 0.00 | −2.25 | 0.00 | 0.00 | 0.00 | UNK_AI848354 | AI848354 |
| 94870_f_at | 0.00 | 0.00 | 0.00 | 0.00 | −2.62 | −1.84 | UNK_AW124226 | AW124226 |
| 94871_r_at | 0.00 | 0.00 | 0.00 | 0.00 | −4.12 | 0.00 | UNK_AW124226 | AW124226 |
| 94907_f_at | 0.00 | 0.00 | 0.00 | 0.00 | −2.76 | −1.89 | UNK_AW045632 | AW045632 |
| 95026_at | 0.00 | 0.00 | 0.00 | 0.00 | −2.74 | 0.00 | UNK_AW047688 | AW047688 |
| 95031_at | 0.00 | 0.00 | 0.00 | 0.00 | −2.05 | −1.89 | UNK_AW060212 | AW060212 |
| 95058_f_at | 0.00 | 0.00 | 0.00 | 0.00 | −2.18 | 0.00 | UNK_AW121984 | AW121984 |
| 95120_at | 0.00 | 0.00 | 0.00 | 0.00 | −2.27 | 0.00 | UNK_AI837621 | AI837621 |
| 95440_at | 0.00 | 0.00 | 0.00 | 0.00 | −2.82 | 0.00 | UNK_AI846093 | AI846093 |
| 95577_at | 0.00 | 0.00 | 0.00 | 0.00 | −2.67 | −1.99 | UNK_AW049625 | AW049625 |
| 95905_at | 0.00 | 0.00 | 0.00 | 0.00 | 0.00 | −2.38 | UNK_AI118078 | AH18078 |
| 95952_at | 0.00 | −1.84 | −1.82 | −1.27 | −2.86 | −1.99 | UNK_AW124781 | AW124781 |
| 96095_i_at | 0.00 | 0.00 | 0.00 | 0.00 | −2.47 | 0.00 | UNK_AI648018 | AI648018 |
| 96096_f_at | 0.00 | 0.00 | 0.00 | 0.00 | −2.58 | 0.00 | UNK_AI648018 | AI648018 |
| 96122_at | 0.00 | −1.93 | 0.00 | 0.00 | −2.80 | 0.00 | UNK_AW049373 | AW049373 |
| 96158_at | 0.00 | 0.00 | −1.77 | 0.00 | −2.05 | −1.69 | UNK_AW123477 | AW123477 |
| 96205_at | 0.00 | 0.00 | −1.84 | 0.00 | −2.56 | −1.72 | SH3BGR | AW048272 |
| 96212_at | 0.00 | 0.00 | −1.93 | 0.00 | −3.14 | −1.65 | UNK_AI853918 | AI853918 |
| 96291_f_at | 0.00 | 0.00 | 0.00 | 0.00 | −2.41 | −1.88 | UNK_AI835847 | AI835847 |
| 96572_at | 0.00 | 0.00 | 0.00 | 0.00 | −2.71 | 0.00 | UNK_AW047232 | AW047232 |
| 96634_at | 0.00 | 0.00 | 0.00 | 0.00 | −2.92 | 0.00 | UNK_AI850090 | AI850090 |
| 96670_at | 0.00 | 0.00 | 0.00 | 0.00 | −2.97 | −1.69 | UNK_AI841295 | AI841295 |
| 96676_at | 0.00 | 0.00 | 0.00 | 0.00 | −2.01 | 0.00 | UNK_AW121875 | AW121875 |
| 96688_at | 0.00 | 0.00 | 0.00 | 0.00 | −2.29 | 0.00 | UNK_AI845463 | AI845463 |
| 96746_at | 0.00 | 0.00 | −1.92 | 0.00 | −2.21 | 0.00 | UNK_AW124813 | AW124813 |
| 96747_at | 0.00 | 0.00 | 0.00 | 0.00 | −2.42 | 0.00 | UNK_AW121294 | AW121294 |
| 96756_at | 0.00 | 0.00 | 0.00 | 0.00 | −2.18 | 0.00 | 0 | AA693236 |
| 96879_at | 0.00 | 0.00 | 0.00 | 0.00 | −2.07 | 0.00 | UNK_AI852338 | AI852338 |
| 96899_at | 0.00 | 0.00 | 0.00 | 0.00 | −2.32 | 0.00 | UNK_AW123802 | AW123802 |
| 96909_at | 0.00 | 0.00 | 0.00 | 0.00 | −2.23 | 0.00 | UNK_AI849803 | AI849803 |
| 96947_at | 0.00 | 0.00 | 0.00 | 0.00 | −2.18 | 0.00 | UNK_AW046273 | AW046273 |
| 97201_s_at | 0.00 | 0.00 | 0.00 | 0.00 | −2.03 | 0.00 | UNK_AA823381 | AA823381 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 97204_s_at | 0.00 | 0.00 | 0.00 | 0.00 | −2.02 | 0.00 | UNK_AI850983 | AI850983 |
| 97242_at | 0.00 | 0.00 | 0.00 | 0.00 | −2.05 | −1.78 | UNK_AI849011 | AI849011 |
| 97447_at | 0.00 | 0.00 | 0.00 | 0.00 | −2.07 | 0.00 | UNK_AI836718 | AI836718 |
| 97773_at | 0.00 | 0.00 | −2.54 | 0.00 | 0.00 | 0.00 | UNK_AI173145 | AI173145 |
| 97869_at | 0.00 | 0.00 | −1.78 | 0.00 | −2.27 | 0.00 | UNK_AI844043 | AI844043 |
| 98924_at | 0.00 | 0.00 | 0.00 | 0.00 | −3.31 | −1.92 | UNK_Y08027 | Y08027 |
| 99159_at | 0.00 | 0.00 | 0.00 | 0.00 | −2.29 | 0.00 | UNK_AI842675 | AI842675 |
| 99441_at | 0.00 | 0.00 | 0.00 | 0.00 | −2.03 | −1.79 | UNK_AW123852 | AW123852 |
| 99618_at | 0.00 | 0.00 | 0.00 | 0.00 | −2.07 | 0.00 | UNK_AI853523 | AI853523 |
| 99658_f_at | 0.00 | 0.00 | 0.00 | 0.00 | −2.32 | 0.00 | UNK_AW047907 | AW047907 |
| 99988_at | 0.00 | 0.00 | 0.00 | 0.00 | −2.14 | −1.75 | UNK_AW122115 | AW122115 |
| 100042_at | 0.00 | 0.00 | −1.69 | 0.00 | −2.14 | 0.00 | UNK_AI837921 | AI837921 |
| 100628_at | 0.00 | 0.00 | 0.00 | 0.00 | −2.01 | 0.00 | UNK_AI840263 | AI840263 |
| 100878_at | 0.00 | 0.00 | 0.00 | 0.00 | −2.22 | 0.00 | UNK_AW124985 | AW124985 |
| 100892_at | 0.00 | 0.00 | 0.00 | 0.00 | −2.38 | 0.00 | UNK_AI850186 | AI850186 |
| 101525_at | 0.00 | 0.00 | 0.00 | 0.00 | −2.24 | 0.00 | UNK_AI848871 | AI848871 |
| 101929_at | 0.00 | 0.00 | 0.00 | 0.00 | −2.09 | −1.63 | UNK_AI836322 | AI836322 |
| 102000_f_at | 0.00 | 0.00 | 0.00 | 0.00 | −2.69 | 0.00 | UNK_AI842835 | AI842835 |
| 102022_at | 0.00 | 0.00 | −1.98 | 0.00 | −2.33 | 0.00 | UNK_AW124555 | AW124555 |
| 102128_f_at | 0.00 | 0.00 | 0.00 | 0.00 | −2.27 | 0.00 | UNK_C77227 | C77227 |
| 102163_at | 0.00 | 0.00 | 0.00 | 0.00 | −4.48 | 0.00 | UNK_X60388 | X60388 |
| 102702_at | 0.00 | 0.00 | 0.00 | 0.00 | −2.14 | −0.66 | UNK_AI841487 | AI841487 |
| 102845_at | 0.00 | 0.00 | 0.00 | 0.00 | −1.66 | −2.14 | UNK_AI836034 | AI836034 |
| 103300_at | 0.00 | 0.00 | 0.00 | 0.00 | −2.06 | 0.00 | UNK_AW124239 | AW124239 |
| 103331_at | 0.00 | 0.00 | 0.00 | 0.00 | −1.61 | −2.20 | UNK_AI854450 | AI854450 |
| 103484_at | 0.00 | 0.00 | 0.00 | 0.00 | −1.84 | −2.16 | UNK_AA619442 | AA619442 |
| 103552_at | 0.00 | 0.00 | −2.03 | 0.00 | 0.00 | 0.00 | UNK_AW046470 | AW046470 |
| 103780_at | 0.00 | 0.00 | 0.00 | 0.00 | −2.47 | 0.00 | UNK_AW049510 | AW049510 |
| 103939_at | 0.00 | 0.00 | 0.00 | 0.00 | −2.16 | 0.00 | UNK_AW121399 | AW121399 |
| 103957_at | 0.00 | 0.00 | 0.00 | 0.00 | −2.38 | 2.04 | transferrin receptor; Trfr | X57349 |
| 103998_at | 0.00 | −1.74 | 0.00 | 0.00 | −2.23 | 0.00 | UNK_AW122699 | AW122699 |
| 103999_at | 0.00 | 0.00 | 0.00 | 0.00 | −1.59 | −2.39 | UNK_AI852034 | AI852034 |
| 104034_at | 0.00 | 0.00 | 0.00 | 0.00 | −2.16 | −1.70 | UNK_AI846672 | AI846672 |
| 104066_at | 0.00 | 0.00 | −1.97 | 0.00 | 0.00 | −2.12 | UNK_AI842192 | AI842192 |
| 104212_at | 0.00 | 0.00 | 0.00 | 0.00 | −2.20 | 0.00 | UNK_AA607767 | AA607767 |
| 104229_at | 0.00 | 0.00 | 0.00 | 0.00 | −2.42 | 0.00 | UNK_AI840035 | AI840035 |
| 104258_at | 0.00 | 0.00 | 0.00 | 0.00 | −3.02 | −1.84 | UNK_AA881576 | AA881576 |
| 104343_f_at | 0.00 | 0.00 | 0.00 | 0.00 | −2.20 | −1.54 | UNK_AI845798 | AI845798 |
| 104356_at | 0.00 | 0.00 | 0.00 | 0.00 | 0.00 | −2.87 | UNK_AI465543 | AI465543 |
| 104745_at | 0.00 | 0.00 | 0.00 | 0.00 | −2.39 | −1.80 | UNK_AA763874 | AA763874 |
| 104869_at | 0.00 | 0.00 | 0.00 | 0.00 | −3.21 | 0.00 | UNK_AW049126 | AW049126 |
| 104958_at | 0.00 | −1.85 | 0.00 | 0.00 | −3.70 | −1.99 | UNK_AA170343 | AA170343 |
| 105301_at | 0.00 | −1.94 | 0.00 | 0.00 | −5.40 | −1.39 | UNK_AW121997 | AW121997 |
| 105367_at | 0.00 | −1.91 | 0.00 | 0.00 | −2.71 | −1.86 | UNK_AI605428 | AI605428 |
| 105393_at | 0.00 | 0.00 | 0.00 | 0.00 | 0.00 | −3.00 | UNK_AA416072 | AA416072 |
| 105583_at | 0.00 | 0.00 | 0.00 | 0.00 | −3.25 | −1.67 | UNK_AI838647 | AI838647 |
| 105635_at | 0.00 | 0.00 | 0.00 | 0.00 | −2.31 | −1.66 | UNK_AA920824 | AA920824 |
| 105733_at | 0.00 | 0.00 | −1.87 | 0.00 | −2.68 | −1.62 | UNK_AI844638 | AI844638 |
| 105804_at | 0.00 | 0.00 | 0.00 | 0.00 | −2.78 | 0.00 | UNK_AI847122 | AI847122 |
| 105815_at | 0.00 | 0.00 | 0.00 | 0.00 | 0.00 | −2.97 | UNK_AI851880 | AI851880 |
| 106109_at | 0.00 | 0.00 | 0.00 | 0.00 | −2.98 | 0.00 | UNK_AI843976 | AI843976 |
| 106135_at | 0.00 | 0.00 | 0.00 | 0.00 | −2.34 | −1.82 | UNK_AI852401 | AI852401 |
| 106225_at | 0.00 | 0.00 | 0.00 | 0.00 | −2.77 | −1.69 | UNK_AW048096 | AW048096 |
| 106267_s_at | 0.00 | 0.00 | 0.00 | 0.00 | −2.06 | −1.55 | UNK_AW124033 | AW124033 |
| 106268_at | 0.00 | −1.61 | 0.00 | 0.00 | −2.23 | −1.75 | UNK_AI788609 | AI788609 |
| 106573_at | 0.00 | −2.38 | 0.00 | 0.00 | 0.00 | 0.00 | UNK_AW122342 | AW122342 |
| 106600_at | 0.00 | 0.00 | 0.00 | 0.00 | −5.18 | 0.00 | UNK_AW047323 | AW047323 |
| 106815_at | 0.00 | 0.00 | 0.00 | −1.27 | −2.07 | 0.00 | UNK_AW047326 | AW047326 |
| 106925_at | 0.00 | 0.00 | 0.00 | 0.00 | −2.61 | −1.62 | UNK_AW125887 | AW125887 |
| 107001_at | 0.00 | 0.00 | −1.55 | 0.00 | −3.54 | −1.85 | UNK_AW125170 | AW125170 |
| 107002_at | 0.00 | 0.00 | 0.00 | 0.00 | −2.61 | 0.00 | UNK_AI265696 | AI265696 |
| 107085_at | 0.00 | 0.00 | 0.00 | 0.00 | −2.01 | 0.00 | UNK_AW122784 | AW122784 |
| 107099_at | 0.00 | 0.00 | −2.37 | 3.85 | 3.65 | 3.57 | UNK_AA792731 | AA792731 |
| 107139_at | 0.00 | 0.00 | 0.00 | 0.00 | −2.06 | −1.58 | UNK_AW123545 | AW123545 |
| 107332_at | 0.00 | 0.00 | 0.00 | 0.00 | −3.03 | −1.79 | UNK_AW125461 | AW125461 |
| 107534_at | 0.00 | 0.00 | 0.00 | 0.00 | −2.47 | 0.00 | UNK_AI877261 | AI877261 |
| 107545_at | 0.00 | −2.13 | 0.00 | 0.00 | 0.00 | 0.00 | UNK_AI195408 | AI195408 |
| 107555_at | 0.00 | 0.00 | 0.00 | 0.00 | −2.07 | 0.00 | UNK_AW049421 | AW049421 |
| 107626_at | 0.00 | 0.00 | 0.00 | 0.00 | −2.07 | 0.00 | UNK_AA174516 | AA174516 |
| 107817_at | 0.00 | −1.80 | −1.98 | 0.00 | −2.62 | −1.77 | UNK_AI481808 | AI481808 |
| 107865_at | 0.00 | 0.00 | 0.00 | 0.00 | −2.55 | −1.93 | UNK_AW212116 | AW212116 |
| 107953_r_at | 0.00 | 0.00 | 0.00 | 0.00 | −2.97 | −1.99 | UNK_AA606601 | AA606601 |
| 107976_at | 0.00 | 0.00 | 0.00 | 0.00 | −2.37 | −1.86 | UNK_AI877204 | AI877204 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 108032_at | 0.00 | −1.55 | 0.00 | 0.00 | −2.52 | −1.56 | UNK_AI850652 | AI850652 |
| 108084_at | 0.00 | −1.76 | 0.00 | 0.00 | −2.45 | −1.41 | UNK_AA674925 | AA674925 |
| 108095_at | 0.00 | −1.77 | 0.00 | 0.00 | −2.32 | −1.50 | UNK_AW124440 | AW124440 |
| 108357_at | 0.00 | 0.00 | 0.00 | 0.00 | 0.00 | −2.14 | UNK_AA611398 | AA611398 |
| 108493_at | 0.00 | −1.92 | 0.00 | 0.00 | −2.21 | −1.38 | UNK_AI852390 | AI852390 |
| 108537_at | 0.00 | −1.86 | −1.87 | 0.00 | −3.15 | −1.61 | UNK_AI846354 | AI846354 |
| 108560_at | 0.00 | −1.66 | 0.00 | 0.00 | −2.49 | −1.49 | UNK_AI849518 | AI849518 |
| 108742_at | 0.00 | 0.00 | 0.00 | 0.00 | −2.00 | −2.05 | UNK_AA619412 | M619412 |
| 108753_at | 0.00 | 0.00 | 0.00 | 0.00 | −2.11 | 0.00 | UNK_AW048441 | AW048441 |
| 108770_at | 0.00 | 0.00 | 0.00 | 0.00 | −2.36 | −1.57 | UNK_AW124553 | AW124553 |
| 108855_at | 0.00 | 0.00 | 0.00 | 0.00 | −5.20 | 0.00 | UNK_AI647526 | AI647526 |
| 109016_at | 0.00 | −1.69 | −1.87 | 0.00 | −3.06 | −1.74 | UNK_AI891634 | AI891634 |
| 109047_at | 0.00 | 0.00 | 0.00 | 0.00 | −2.25 | 0.00 | UNK_AI850557 | AI850557 |
| 109124_at | 0.00 | 0.00 | 0.00 | 0.00 | −2.11 | 0.00 | UNK_AW125343 | AW125343 |
| 109348_at | 0.00 | 0.00 | 0.00 | 0.00 | −2.06 | 0.00 | UNK_AI850333 | AI850333 |
| 109361_at | 0.00 | −1.38 | 0.00 | 0.00 | −2.31 | −1.38 | UNK_AA170632 | AA170632 |
| 109386_at | 0.00 | 0.00 | −4.41 | 0.00 | 0.00 | 0.00 | UNK_AA614943 | AA614943 |
| 109390_at | 0.00 | −1.75 | 0.00 | 0.00 | −2.84 | −1.53 | UNK_AW049308 | AW049308 |
| 109415_at | 0.00 | 0.00 | 0.00 | 0.00 | 0.00 | −2.85 | UNK_AI646948 | AI646948 |
| 109570_at | 0.00 | 0.00 | 0.00 | 0.00 | −2.02 | 0.00 | UNK_AA763178 | AA763178 |
| 109575_at | 0.00 | 0.00 | 0.00 | 0.00 | −2.11 | 0.00 | UNK_AI155995 | AH55995 |
| 109655_at | 0.00 | −1.68 | −1.90 | 0.00 | −2.13 | −1.65 | UNK_W08276 | W08276 |
| 109662_at | 0.00 | 0.00 | 0.00 | 0.00 | −2.84 | 0.00 | UNK_AW122695 | AW122695 |
| 109681_at | 0.00 | 0.00 | 0.00 | 0.00 | −2.17 | −1.60 | UNK_AI838049 | AI838049 |
| 109738_at | 0.00 | 0.00 | 0.00 | 0.00 | −3.12 | −1.76 | UNK_AI099014 | AI099014 |
| 109755_at | 0.00 | 0.00 | 0.00 | 0.00 | −2.03 | 0.00 | UNK_AW047377 | AW047377 |
| 109773_at | 0.00 | 0.00 | −2.04 | 0.00 | 0.00 | 0.00 | UNK_AI852349 | AI852349 |
| 109820_f_at | 0.00 | 0.00 | 0.00 | 0.00 | −2.03 | 0.00 | UNK_AI840770 | AI840770 |
| 109938_at | 0.00 | −1.55 | −1.73 | 0.00 | −2.46 | −1.92 | UNK_AA986399 | AA986399 |
| 109955_at | 0.00 | 0.00 | 0.00 | 0.00 | −2.04 | −1.73 | UNK_AW122907 | AW122907 |
| 109958_at | 0.00 | −1.50 | 0.00 | 0.00 | −2.36 | −1.91 | UNK_AI503400 | AI503400 |
| 110069_at | 0.00 | −1.80 | 0.00 | 0.00 | −2.21 | 0.00 | UNK_AW123500 | AW123500 |
| 110092_at | 0.00 | 0.00 | 0.00 | 0.00 | −2.07 | −1.74 | UNK_AW050361 | AW050361 |
| 110096_at | 0.00 | 0.00 | 0.00 | 0.00 | −1.54 | −2.02 | UNK_AA718224 | AA718224 |
| 110122_at | 0.00 | −1.49 | 0.00 | 0.00 | −2.59 | −1.94 | UNK_AA762771 | AA762771 |
| 110140_f_at | 0.00 | 0.00 | 0.00 | 0.00 | −2.59 | 0.00 | UNK_AW060592 | AW060592 |
| 110286_at | 0.00 | −1.78 | 0.00 | 0.00 | −2.53 | 0.00 | UNK_AI194762 | AI194762 |
| 110290_at | 0.00 | 0.00 | 0.00 | 0.00 | 0.00 | −3.55 | UNK_AW122616 | AW122616 |
| 110292_at | 0.00 | 0.00 | 0.00 | 0.00 | −2.79 | 0.00 | D9UCLA2 | AI839742 |
| 110361_at | 0.00 | −1.63 | −1.39 | 0.00 | −3.08 | −1.93 | UNK_AI839531 | AI839531 |
| 110442_at | 0.00 | 0.00 | 0.00 | 0.00 | −2.09 | −1.65 | UNK_AA960476 | AA960476 |
| 110529_at | 0.00 | 0.00 | 0.00 | 0.00 | −2.21 | −1.70 | UNK_AI594683 | AI594683 |
| 110644_s_at | 0.00 | −1.12 | −5.38 | 0.00 | 0.00 | 0.00 | UNK_AI593562 | AI593562 |
| 110673_at | 0.00 | 0.00 | 0.00 | 0.00 | −2.03 | 0.00 | UNK_W53698 | W53698 |
| 110755_at | 0.00 | 0.00 | −2.59 | 0.00 | −1.61 | 0.00 | UNK_AI842126 | AI842126 |
| 110757_at | 0.00 | 0.00 | 0.00 | 0.00 | −2.17 | −1.85 | UNK_AI847218 | AI847218 |
| 110770_at | 0.00 | 0.00 | 0.00 | 0.00 | −2.06 | 0.00 | UNK_AW045392 | AW045392 |
| 110812_at | 0.00 | 0.00 | 0.00 | 0.00 | −2.87 | −1.60 | UNK_AI836721 | AI836721 |
| 110826_at | 0.00 | 0.00 | −1.80 | 0.00 | −2.02 | −1.66 | UNK_AW122152 | AW122152 |
| 110972_at | 0.00 | 0.00 | 0.00 | −1.92 | −2.38 | −1.71 | UNK_AI848760 | AI848760 |
| 111305_at | 0.00 | −1.67 | 0.00 | 0.00 | −2.84 | −1.80 | UNK_AW121459 | AW121459 |
| 111359_at | 0.00 | −1.57 | 0.00 | 0.00 | −3.83 | −1.58 | UNK_AW108291 | AW108291 |
| 111382_at | 0.00 | 0.00 | 0.00 | 0.00 | −2.03 | 0.00 | UNK_AI835341 | AI835341 |
| 111431_at | 0.00 | −1.91 | −1.68 | 0.00 | −4.69 | −1.78 | UNK_AI836555 | AI836555 |
| 111445_at | 0.00 | 0.00 | 0.00 | 0.00 | −2.41 | −1.61 | UNK_AW046417 | AW046417 |
| 111517_at | 0.00 | 0.00 | 0.00 | 0.00 | −2.09 | 0.00 | UNK_AA983096 | AA983096 |
| 111548_g_at | 0.00 | 0.00 | 0.00 | 0.00 | −2.90 | −2.00 | UNK_AI851666 | AI851666 |
| 111613_at | 0.00 | −1.36 | 0.00 | 0.00 | −2.33 | −1.44 | UNK_AW228205 | AW228205 |
| 111689_at | 0.00 | 0.00 | 0.00 | 0.00 | −2.18 | 0.00 | UNK_AW060751 | AW060751 |
| 111690_at | 0.00 | 0.00 | 0.00 | 0.00 | −2.27 | 0.00 | UNK_AW125187 | AW125187 |
| 111947_at | 0.00 | 0.00 | 0.00 | 0.00 | −2.29 | 0.00 | UNK_AA789365 | AA789365 |
| 112029_at | 0.00 | 0.00 | 0.00 | 0.00 | −2.61 | −1.65 | UNK_AA821545 | AA821545 |
| 112063_at | 0.00 | 0.00 | 0.00 | 0.00 | −2.86 | 0.00 | UNK_AA420218 | AA420218 |
| 112073_at | 0.00 | 0.00 | 0.00 | 0.00 | −3.03 | 0.00 | UNK_AA242716 | AA242716 |
| 112081_at | 0.00 | 0.00 | 0.00 | 0.00 | −2.25 | −1.64 | UNK_AI510428 | AI510428 |
| 112220_at | 0.00 | 0.00 | −2.37 | 0.00 | 0.00 | 0.00 | UNK_AA763894 | AA763894 |
| 112318_at | 0.00 | 0.00 | 0.00 | 0.00 | −2.38 | −1.55 | UNK_AW122090 | AW122090 |
| 112336_at | 0.00 | −2.56 | 0.00 | 0.00 | 0.00 | 0.00 | UNK_AI854546 | AI854546 |
| 112352_at | 0.00 | 0.00 | 0.00 | 0.00 | −2.08 | 0.00 | UNK_AI841571 | AI841571 |
| 112363_at | 0.00 | 0.00 | 0.00 | 0.00 | −3.06 | −1.80 | UNK_AW048194 | AW048194 |
| 112381_at | 0.00 | −1.69 | −2.32 | 0.00 | 0.00 | 0.00 | UNK_AA863867 | AA863867 |
| 112398_at | 0.00 | 0.00 | 0.00 | 0.00 | −4.67 | 0.00 | UNK_AW045591 | AW045591 |
| 112406_at | 0.00 | 0.00 | 0.00 | 0.00 | −2.71 | −1.61 | UNK_AI851470 | AI851470 |
| 112415_at | 0.00 | 0.00 | 0.00 | 0.00 | −2.06 | −1.58 | UNK_AI604376 | AI604376 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 112432_at | 0.00 | 0.00 | 0.00 | 0.00 | −2.38 | 0.00 | UNK_AW045567 | AW045567 |
| 112668_at | 0.00 | 0.00 | 0.00 | 0.00 | −2.48 | 0.00 | UNK_AW261533 | AW261533 |
| 112722_at | 0.00 | 0.00 | 0.00 | 0.00 | 0.00 | −2.59 | UNK_AW124381 | AW124381 |
| 112820_at | 0.00 | −1.53 | 0.00 | 0.00 | −3.27 | −1.49 | UNK_AW045244 | AW045244 |
| 112920_at | 0.00 | 0.00 | 0.00 | 0.00 | −7.87 | 0.00 | UNK_AW125065 | AW125065 |
| 112947_at | 0.00 | 0.00 | 0.00 | 0.00 | −3.08 | −1.87 | UNK_AA693298 | AA693298 |
| 113012_at | 0.00 | −1.77 | −1.53 | 0.00 | −4.20 | −1.84 | UNK_AI846919 | AI846919 |
| 113210_at | 0.00 | −1.92 | 0.00 | 0.00 | −2.72 | −0.66 | UNK_AI841042 | AI841042 |
| 113232_at | 0.00 | 0.00 | 0.00 | 0.00 | −2.36 | 0.00 | UNK_AI841061 | AI841061 |
| 113314_at | 0.00 | 0.00 | 0.00 | 0.00 | −2.73 | −1.77 | UNK_AI840767 | AI840767 |
| 113318_at | 0.00 | 0.00 | 0.00 | 0.00 | −2.72 | −1.78 | UNK_AW261686 | AW261686 |
| 113330_at | 0.00 | 0.00 | 0.00 | 0.00 | −2.01 | −0.45 | UNK_AI527630 | AI527630 |
| 113565_at | 0.00 | 0.00 | 0.00 | 0.00 | −2.22 | 0.00 | UNK_AW049089 | AW049089 |
| 113604_at | 0.00 | −1.61 | 0.00 | 0.00 | −2.40 | 0.00 | UNK_AI847956 | AI847956 |
| 113638_at | 0.00 | 0.00 | 0.00 | 0.00 | −2.45 | −1.83 | UNK_AW045993 | AW045993 |
| 113715_at | 0.00 | −1.98 | 0.00 | 0.00 | −2.01 | −1.62 | UNK_AA822301 | AA822301 |
| 113785_at | 0.00 | 0.00 | −1.72 | 0.00 | −2.43 | −1.66 | UNK_AI850504 | AI850504 |
| 113901_at | 0.00 | 0.00 | 0.00 | 0.00 | −1.89 | −2.14 | UNK_AI593827 | AI593827 |
| 113938_at | 0.00 | 0.00 | 0.00 | 0.00 | −4.11 | 0.00 | UNK_AI842866 | AI842866 |
| 113985_at | −2.17 | 0.00 | 0.00 | 0.00 | 0.00 | 0.00 | UNK_AI838258 | AI838258 |
| 113986_at | 0.00 | −1.99 | 0.00 | 0.00 | −2.92 | 0.00 | UNK_AI510303 | AI510303 |
| 113990_at | 0.00 | 0.00 | 0.00 | 0.00 | −2.03 | 0.00 | UNK_AA763276 | AA763276 |
| 113998_at | 0.00 | 0.00 | 0.00 | 0.00 | 0.00 | −2.00 | UNK_AA416235 | AA416235 |
| 114069_at | 0.00 | 0.00 | 0.00 | 0.00 | −2.72 | −1.86 | UNK_AI844797 | AI844797 |
| 114093_at | 0.00 | 0.00 | 0.00 | 0.00 | −2.00 | 0.00 | UNK_AI852806 | AI852806 |
| 114143_at | 0.00 | 0.00 | 0.00 | 0.00 | −2.11 | 0.00 | UNK_AI853600 | AI853600 |
| 114296_at | 0.00 | 0.00 | 0.00 | 0.00 | −2.72 | −1.42 | UNK_AA823920 | AA823920 |
| 114316_at | 0.00 | 0.00 | 0.00 | 0.00 | −2.92 | −1.69 | UNK_AI605358 | AI605358 |
| 114392_at | 0.00 | 0.00 | 0.00 | 0.00 | −2.85 | 0.00 | UNK_AW120619 | AW120619 |
| 114416_at | 0.00 | 0.00 | 0.00 | 0.00 | 0.00 | −3.51 | UNK_AW045985 | AW045985 |
| 114418_at | 0.00 | 0.00 | 0.00 | 0.00 | −2.38 | 0.00 | UNK_AI854454 | AI854454 |
| 114476_at | 0.00 | 0.00 | 0.00 | 0.00 | −2.89 | 0.00 | UNK_AI482420 | AI482420 |
| 114478_at | 0.00 | 0.00 | 0.00 | 0.00 | 0.00 | −3.17 | UNK_AA061949 | AA061949 |
| 114706_at | 0.00 | 0.00 | 0.00 | 0.00 | −2.32 | −1.36 | UNK_AW049085 | AW049085 |
| 114752_at | 0.00 | −2.01 | 0.00 | 0.00 | 0.00 | 2.84 | UNK_AI843572 | AI843572 |
| 114794_at | 0.00 | −1.73 | 0.00 | 0.00 | −2.33 | −1.39 | UNK_AA693185 | AA693185 |
| 114982_at | 0.00 | −1.59 | 0.00 | 0.00 | −3.53 | −1.98 | UNK_AA959852 | AA959852 |
| 115077_f_at | 0.00 | 0.00 | 0.00 | 0.00 | −2.03 | 0.00 | DBT | AA896722 |
| 115078_r_at | 0.00 | 0.00 | 0.00 | 0.00 | −2.52 | 0.00 | DBT | AA896722 |
| 115106_at | 0.00 | −1.49 | 0.00 | 0.00 | −2.69 | −1.92 | UNK_AI851210 | AI851210 |
| 115169_at | 0.00 | 0.00 | 0.00 | 0.00 | −2.15 | 0.00 | UNK_AW047351 | AW047351 |
| 115323_at | 0.00 | 0.00 | −1.34 | 0.00 | −2.07 | −1.72 | UNK_AA107507 | AA107507 |
| 115370_at | 0.00 | 0.00 | 0.00 | 0.00 | −2.38 | 0.00 | UNK_AI527642 | AI527642 |
| 115376_at | 0.00 | 0.00 | 0.00 | 0.00 | −2.23 | 0.00 | UNK_AI850511 | AI850511 |
| 115428_at | 0.00 | 0.00 | −1.95 | 0.00 | −3.82 | 0.00 | UNK_AA673260 | M673260 |
| 115437_at | 0.00 | −1.66 | 0.00 | 0.00 | −2.21 | −1.37 | UNK_AW049924 | AW049924 |
| 115545_at | 0.00 | 0.00 | 0.00 | 0.00 | −2.29 | 0.00 | UNK_AA940371 | M940371 |
| 115629_at | 0.00 | 0.00 | 0.00 | 0.00 | 0.00 | −3.06 | UNK_AA183896 | AA183896 |
| 115640_at | 0.00 | 0.00 | 0.00 | 0.00 | −2.88 | −0.66 | UNK_AI451541 | AI451541 |
| 115686_at | 0.00 | 0.00 | 0.00 | 0.00 | −3.34 | 0.00 | UNK_AI853521 | AI853521 |
| 115845_at | 0.00 | 0.00 | 0.00 | 0.00 | −2.24 | −1.49 | UNK_AW107813 | AW107813 |
| 115847_i_at | 0.00 | 0.00 | 0.00 | 0.00 | −2.07 | −1.59 | UNK_AI327072 | AI327072 |
| 116046_at | 0.00 | 0.00 | 0.00 | 0.00 | −2.42 | 0.00 | UNK_AI848153 | AI848153 |
| 116151_at | 0.00 | 0.00 | −2.09 | 0.00 | 0.00 | 0.00 | UNK_AI845734 | AI845734 |
| 116152_at | 0.00 | 0.00 | 0.00 | 0.00 | −5.30 | −1.89 | UNK_AI840320 | AI840320 |
| 116263_at | 0.00 | 0.00 | 0.00 | 0.00 | −2.20 | −1.49 | UNK_AW060609 | AW060609 |
| 116349_at | 0.00 | 0.00 | 0.00 | 0.00 | −2.01 | 0.00 | UNK_AI155885 | AI155885 |
| 116406_at | 0.00 | 0.00 | 0.00 | 0.00 | 0.00 | −2.81 | UNK_AW050231 | AW050231 |
| 116438_at | 0.00 | 0.00 | 0.00 | 0.00 | 0.00 | −2.92 | UNK_AI853912 | AI853912 |
| 116466_at | 0.00 | 0.00 | 0.00 | 0.00 | −2.94 | −1.80 | UNK_AI591541 | AI591541 |
| 116661_at | 0.00 | 0.00 | 0.00 | 0.00 | −2.81 | 0.00 | UNK_AI594516 | AI594516 |
| 116771_at | 0.00 | 0.00 | 0.00 | 0.00 | −2.16 | −1.56 | UNK_AI843862 | AI843862 |
| 116856_at | 0.00 | 0.00 | 0.00 | 0.00 | −2.08 | 0.00 | UNK_AW122439 | AW122439 |
| 116887_at | 0.00 | 0.00 | 0.00 | 0.00 | −2.49 | 0.00 | UNK_AI848169 | AI848169 |
| 116919_f_at | 0.00 | 0.00 | 0.00 | 0.00 | −3.43 | −1.62 | UNK_AI837430 | AI837430 |
| 116949_at | 0.00 | 0.00 | 0.00 | 0.00 | −2.30 | −1.95 | UNK_AI835398 | AI835398 |
| 116967_at | 0.00 | 0.00 | 0.00 | 0.00 | −2.74 | −1.58 | UNK_AI851900 | AI851900 |
| 116975_at | 0.00 | 0.00 | 0.00 | 0.00 | 0.00 | −2.24 | UNK_AI848908 | AI848908 |
| 117008_at | 0.00 | 0.00 | 0.00 | 0.00 | −2.41 | 0.00 | UNK_AI836364 | AI836364 |
| 117080_at | 0.00 | 0.00 | 0.00 | 0.00 | −4.41 | −1.77 | UNK_AW046827 | AW046827 |
| 117107_at | 0.00 | −1.73 | −1.97 | 0.00 | −3.77 | −1.76 | UNK_AI837768 | AI837768 |
| 117123_at | 0.00 | −2.18 | 0.00 | 0.00 | −1.51 | 0.00 | UNK_AI840704 | AI840704 |
| 117125_at | 0.00 | 0.00 | −0.03 | 0.00 | −3.36 | −0.88 | UNK_AI835705 | AI835705 |
| 117178_at | 0.00 | 0.00 | 0.00 | 0.00 | −2.32 | −1.81 | UNK_AI844448 | AI844448 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 117206_at | 0.00 | 0.00 | 0.00 | 0.00 | −5.29 | 0.00 | UNK__AW122028 | AW122028 |
| 117213_at | 0.00 | −1.74 | 0.00 | 0.00 | −3.01 | −1.60 | UNK__AI850929 | AI850929 |
| 117307_at | 0.00 | 0.00 | 0.00 | 0.00 | −3.93 | 0.00 | UNK__AI844588 | AI844588 |
| 117308_at | 0.00 | 0.00 | 0.00 | 0.00 | −2.09 | 0.00 | UNK__AI835357 | AI835357 |
| 128879_f_at | 0.00 | 0.00 | 0.00 | 0.00 | −3.24 | 0.00 | UNK__AI838074 | AI838074 |
| 129016_f_at | 0.00 | 0.00 | 0.00 | 0.00 | −1.50 | −2.09 | UNK__AI596402 | AI596402 |
| 129176_at | 0.00 | 0.00 | 0.00 | 0.00 | 0.00 | −13.63 | UNK__AI607324 | AI607324 |
| 129231_at | 0.00 | −5.11 | 0.00 | 0.00 | 0.00 | 0.00 | UNK__AW046840 | AW046840 |
| 129306_r_at | 0.00 | 0.00 | 0.00 | 0.00 | −2.42 | −1.86 | UNK__AI606549 | AI606549 |
| 129582_at | 0.00 | 0.00 | 0.00 | 0.00 | −2.32 | −1.74 | UNK__AI465103 | AI465103 |
| 130312_at | 0.00 | 0.00 | 0.00 | 0.00 | −1.96 | −2.85 | UNK__AW215796 | AW215796 |
| 130512_at | 0.00 | −1.69 | 0.00 | 0.00 | −2.50 | −1.87 | UNK__AI848603 | AI848603 |
| 130696_f_at | 0.00 | 0.00 | 0.00 | −3.94 | 0.00 | 0.00 | UNK__AW210623 | AW210623 |
| 130730_f_at | 0.00 | 0.00 | 0.00 | 0.00 | −1.91 | −2.09 | UNK__AA270325 | AA270325 |
| 132118_at | 0.00 | −1.73 | 0.00 | −2.16 | −1.93 | −1.94 | UNK__AI642706 | AI642706 |
| 133171_at | 0.00 | −2.00 | −1.80 | 0.00 | 0.00 | 0.00 | UNK__AA683786 | AA683786 |
| 133759_at | 0.00 | 0.00 | 0.00 | 0.00 | −2.61 | 0.00 | UNK__AI480951 | AI480951 |
| 133886_at | 0.00 | 0.00 | 0.00 | 0.00 | −4.76 | 0.00 | UNK__AA168908 | AA168908 |
| 134047_at | 0.00 | −1.88 | 0.00 | 0.00 | −2.17 | −1.74 | UNK__AW123320 | AW123320 |
| 134281_at | 0.00 | 0.00 | 0.00 | 0.00 | −2.51 | 0.00 | UNK__AI551165 | AI551165 |
| 134622_f_at | −2.30 | 0.00 | 0.00 | 0.00 | 0.00 | 0.00 | UNK__AI641962 | AI641962 |
| 134778_at | 0.00 | −1.98 | −1.91 | 0.00 | −2.80 | −1.87 | UNK__AI666678 | AI666678 |
| 135643_at | 0.00 | −2.73 | 0.00 | 0.00 | 0.00 | 0.00 | UNK__AA396310 | AA396310 |
| 135691_at | 0.00 | −1.77 | 0.00 | 0.00 | −2.36 | −1.46 | UNK__AA882067 | AA882067 |
| 136174_at | 0.00 | 0.00 | −1.68 | 0.00 | −2.11 | −1.50 | UNK__AW048956 | AW048956 |
| 136545_at | 0.00 | −4.44 | −1.77 | 0.00 | −1.82 | 0.00 | UNK__AA982069 | AA982069 |
| 136719_at | 0.00 | 0.00 | 0.00 | 0.00 | −2.50 | 0.00 | UNK__AI847908 | AI847908 |
| 137973_at | 0.00 | −1.94 | −1.65 | 0.00 | −3.24 | −1.85 | UNK__AI843877 | AI843877 |
| 137979_at | 0.00 | −2.19 | 0.00 | 0.00 | 0.00 | 0.00 | UNK__AI848070 | AI848070 |
| 138060_at | 0.00 | 0.00 | 0.00 | 0.00 | −2.00 | 0.00 | UNK__AW122571 | AW122571 |
| 138086_f_at | 0.00 | 0.00 | 0.00 | 0.00 | −1.73 | −2.25 | UNK__AW122816 | AW122816 |
| 138556_at | 0.00 | 0.00 | 0.00 | 0.00 | 0.00 | −2.27 | UNK__AI874931 | AI874931 |
| 139522_at | 0.00 | −1.48 | 0.00 | 0.00 | −2.07 | −1.56 | UNK__AW046420 | AW046420 |
| 139980_g_at | 0.00 | 0.00 | 0.00 | 0.00 | −3.05 | −1.67 | UNK__AI450646 | AI450646 |
| 140519_at | 0.00 | 0.00 | 0.00 | 0.00 | −2.66 | −1.97 | UNK__AI642378 | AI642378 |
| 140861_at | 0.00 | −2.29 | 0.00 | 0.00 | −1.43 | 0.00 | UNK__AI645591 | AI645591 |
| 104962_at | 0.00 | 0.00 | 0.00 | 0.00 | 0.78 | −3.35 | AA450473 | AA450473 |
| 93316_at | 0.00 | 0.00 | 0.00 | 0.00 | −2.00 | 0.00 | UNK__AB017026 | AB017026 |
| 97172_s_at | 0.00 | 0.00 | 0.00 | 0.00 | −2.07 | 0.00 | ABCC9 | D86037 |
| 95425_at | 0.00 | 0.00 | 0.00 | 0.00 | −2.24 | 0.00 | acetyl-Coenzyme A dehydrogenase, long chain; Acadl | U21489 |
| 92581_at | 0.00 | 0.00 | −1.93 | 0.00 | −2.49 | 0.00 | acetyl-Coenzyme A dehydrogenase, medium chain; Acadm | U07159 |
| 106070_at | 0.00 | 0.00 | −3.56 | 0.00 | −4.60 | 0.00 | UNK__AI854239 | AI854239 |
| 104650_at | 0.00 | 0.00 | 0.00 | 0.00 | 0.00 | −8.36 | acetylcholinesterase; Ache | X56518 |
| 101515_at | 0.00 | 0.00 | 0.00 | 0.00 | −2.32 | 0.00 | acyl-Coenzyme A oxidase; Acox-pending | AF006688 |
| 101028_i_at | 0.00 | −1.72 | −3.47 | 0.00 | −3.72 | −2.05 | actin, alpha, cardiac; Actc1 | M15501 |
| 93903_at | 0.00 | 0.00 | 0.00 | 0.00 | −3.07 | 0.00 | activin receptor IIB; Acvr2b | M84120 |
| 99671_at | 0.00 | −1.93 | −2.01 | 0.00 | 0.00 | 1.51 | adipsin; Adn | X04673 |
| 98999_at | 0.00 | 0.00 | 0.00 | 0.00 | −2.64 | −1.88 | ADSL | AA606587 |
| 98435_at | 0.00 | 0.00 | 0.00 | 0.00 | −2.43 | −2.03 | adenylosuccinate synthetase 1, muscle; Adss1 | M74495 |
| 111708_at | 0.00 | 0.00 | 0.00 | 0.00 | −2.33 | −1.94 | AF180471 | AA709944 |
| 97279_at | 0.00 | 0.00 | 0.00 | 0.00 | −2.14 | 0.00 | UNK__AI837615 | AI837615 |
| 110392_at | 0.00 | 0.00 | 0.00 | 0.00 | −2.20 | 0.00 | UNK__AA789854 | AA789854 |
| 112429_at | −1.97 | −1.95 | −1.77 | 0.00 | −2.77 | 0.00 | UNK__AI462012 | AI462012 |
| 112387_at | 0.00 | −2.45 | 0.00 | 0.00 | −3.22 | −2.31 | UNK__AI747215 | AI747215 |
| 99521_at | 0.00 | 0.00 | 0.00 | 0.00 | −2.53 | 0.00 | AK4 | AB020239 |
| 92768_s_at | 0.00 | 0.00 | −2.85 | −2.29 | 0.00 | 0.00 | aminolevulinic acid synthase 2, erythroid; Alas2 | M15268 |
| 93500_at | 0.00 | 0.00 | 0.00 | 0.00 | −2.08 | 0.00 | 0 | M63245 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 100068_at | 0.00 | −1.88 | 0.00 | 0.00 | −3.32 | −1.91 | alcohol dehydrogenase family 1, subfamily A2; Aldh1a2 | M74570 |
| 101489_at | 0.00 | 0.00 | 0.00 | 0.00 | −2.09 | −2.05 | AMD1 | D12780 |
| 100323_at | 0.00 | 0.00 | −1.91 | 0.00 | −2.12 | 0.00 | AMD2 | Z23077 |
| 100324_g_at | 0.00 | 0.00 | 0.00 | 0.00 | −2.21 | −1.84 | AMD2 | Z23077 |
| 101058_at | 0.00 | 0.00 | −2.85 | 0.00 | −2.87 | −2.06 | AMY1 | J00356 |
| 100440_f_at | 0.00 | 0.00 | 0.00 | 0.00 | −3.30 | −2.28 | ANK1 | U76758 |
| 100441_s_at | 0.00 | 0.00 | 0.00 | 0.00 | −5.39 | −2.20 | ANK1 | X69064 |
| 100439_i_at | 0.00 | 0.00 | 0.00 | 0.00 | −2.65 | −1.95 | ANK1 | U76758 |
| 98476_at | 0.00 | 0.00 | −1.74 | 0.00 | −2.10 | 0.00 | ANK3 | L40631 |
| 98477_s_at | 0.00 | −1.84 | 0.00 | 0.00 | −3.34 | −1.89 | ankyrin 3, epithelial; AnK3 | L40632 |
| 97786_at | −1.75 | 0.00 | 0.00 | 0.00 | −2.14 | −1.51 | UNK_AJ011118 | AJ011118 |
| 97235_f_at | 0.00 | −1.80 | −2.29 | 0.00 | −3.50 | 0.00 | APOBEC2 | AW124988 |
| 93592_at | −1.50 | −3.36 | 0.00 | 0.00 | 0.00 | 0.00 | apolipoprotein D; Apod | X82648 |
| 109808_at | 0.00 | 0.00 | 0.00 | 0.00 | −3.03 | 0.00 | APOE | AI504617 |
| 102704_at | −0.92 | −4.95 | −3.29 | −4.01 | −5.56 | −3.77 | aquaporin 4; Aqp4 | U88623 |
| 102703_s_at | 0.00 | −2.91 | 0.00 | 0.00 | −3.94 | −2.23 | AQP4 | U48398 |
| 102382_at | 0.00 | 0.00 | 0.00 | 0.00 | 0.00 | −2.46 | ARNTL | AB014494 |
| 99481_at | 0.00 | 0.00 | −1.98 | 0.00 | −2.90 | −2.33 | UNK_AI839697 | AI839697 |
| 93664_at | 0.00 | 0.00 | 0.00 | 0.00 | 0.00 | −2.07 | ATP1B2 | X16645 |
| 99570_s_at | 0.00 | −2.68 | −1.76 | −2.81 | −1.98 | 0.00 | ATP2A2 | AF029982 |
| 103699_i_at | 0.00 | −2.48 | −3.08 | 0.00 | −3.36 | −2.40 | UNK_AI646638 | AI646638 |
| 96035_at | 0.00 | 0.00 | −2.13 | 0.00 | −2.59 | −1.68 | branched chain ketoacid dehydrogenase E1, alpha polypeptide; Bckdha | L47335 |
| 102302_at | 0.00 | 0.00 | −1.89 | 0.00 | −2.21 | 0.00 | BCKDHB | L16992 |
| 103015_at | 0.00 | 0.00 | 0.00 | 0.00 | −2.04 | 0.00 | B-cell leukemia/lymphoma 6; Bcl6 | U41465 |
| 93836_at | 0.00 | −2.58 | −2.53 | 0.00 | −3.95 | −1.74 | BNIP3 | AF041054 |
| 101903_at | 0.00 | 0.00 | 0.00 | 0.00 | −3.93 | −2.66 | CD8beta opposite strand; Bop | U76371 |
| 94815_at | 0.00 | −1.91 | −2.05 | 0.00 | −3.33 | 0.00 | 2,3-bisphosphoglycerate mutase; Bpgm | X13586 |
| 113861_at | 0.00 | 0.00 | 0.00 | 0.00 | −2.15 | −1.61 | BVES-PENDING | AI152383 |
| 101128_at | 0.00 | 0.00 | 0.00 | 0.00 | −2.93 | −2.12 | calcium channel, voltage-dependent, L type, alpha 1S subunit; Cacna1s | L06234 |
| 99812_at | 0.00 | −1.79 | 0.00 | 0.00 | −2.40 | −2.09 | calpain 3; Capn3 | X92523 |
| 99813_g_at | 0.00 | 0.00 | 0.00 | 0.00 | −2.54 | −2.11 | calpain 3; Capn3 | X92523 |
| 98079_at | −2.36 | −4.93 | 0.00 | 0.00 | −13.32 | −6.68 | CAR14 | AB005450 |
| 92642_at | 0.00 | 0.00 | −2.16 | 0.00 | −2.62 | 5.27 | CAR2 | M25944 |
| 100600_at | 0.00 | 0.00 | 0.00 | 0.00 | −2.40 | −2.04 | CD24A | M58661 |
| 93332_at | 0.00 | 0.00 | 0.00 | 0.00 | −2.65 | −1.74 | CD36 antigen; Cd36 | L23108 |
| 101516_at | 0.00 | 0.00 | −2.01 | 0.00 | 0.00 | 0.00 | CD59 | U60473 |
| 104743_at | 0.00 | 0.00 | 0.00 | 0.00 | −2.26 | −2.14 | UNK_AB022100 | AB022100 |
| 95471_at | 0.00 | −2.68 | −2.76 | 0.00 | 2.10 | 1.92 | cyclin-dependent kinase inhibitor 1C (P57); Cdkn1c | U22399 |
| 104209_at | 0.00 | 0.00 | 0.00 | 0.00 | −6.63 | −3.70 | CHRP | AI847016 |
| 99994_at | 0.00 | 0.00 | −2.89 | 0.51 | −3.44 | 0.00 | CIDEA | AF041376 |
| 94463_at | 0.00 | 0.00 | 0.00 | 0.00 | −5.15 | 0.00 | chloride channel 3; Clcn3 | X78874 |
| 94464_at | 0.00 | −1.75 | 0.00 | 0.00 | −2.12 | −1.59 | CLCN3 | AF029347 |
| 94465_g_at | 0.00 | 0.00 | 0.00 | 0.00 | −2.01 | −1.32 | CLCN3 | AF029347 |
| 92322_at | 0.00 | 0.00 | −2.94 | −1.65 | −2.57 | 0.00 | cathelin-like protein; Cnlp | X94353 |
| 93582_at | 0.00 | 0.00 | 0.00 | 0.00 | −2.10 | 0.00 | COQ7 | AF080580 |
| 102749_at | 0.00 | 0.00 | −1.45 | 0.00 | −2.37 | −1.32 | COX7A1 | AF037370 |
| 113828_at | 0.00 | −2.35 | −2.07 | 0.00 | −4.31 | −2.24 | CPT1B | AA189179 |
| 102951_at | 0.00 | 0.00 | 0.00 | 0.00 | 0.00 | −2.03 | CRADD | AJ224738 |
| 103646_at | 0.00 | 0.00 | −1.75 | 0.00 | −2.43 | −1.81 | carnitine acetyltransferase; Crat | X85983 |
| 99065_at | 0.00 | 0.00 | 0.00 | −2.08 | 0.00 | 0.00 | casein kappa; Csnk | M10114 |
| 97336_at | 0.00 | −2.65 | 0.00 | 0.00 | 0.00 | 2.12 | UNK_AJ131851 | AJ131851 |

TABLE 2-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 98132_at | 0.00 | 0.00 | 0.00 | 0.00 | −3.97 | 0.00 | cytochrome c, somatic; Cycs | X01756 |
| 93996_at | 0.00 | −4.02 | −5.63 | −4.92 | −3.73 | 0.00 | CYP2E1 | X01026 |
| 94526_at | 0.00 | 0.00 | 0.00 | 0.00 | −2.34 | 0.00 | UNK__AI848453 | AI848453 |
| 96757_at | 0.00 | 0.00 | −2.06 | 0.00 | −3.05 | −1.95 | D10JHU81E | AI852165 |
| 109645_at | 0.00 | 0.00 | 0.00 | 0.00 | −2.03 | −1.59 | UNK__AW123377 | AW123377 |
| 113324_at | 0.00 | 0.00 | 0.00 | 0.00 | −2.47 | 0.00 | UNK__AI121830 | AI121830 |
| 96803_at | 0.00 | 0.00 | 0.00 | 0.00 | −2.32 | 0.00 | UNK__AW210370 | AW210370 |
| 96346_at | 0.00 | −1.46 | −2.12 | 0.00 | 2.45 | 5.93 | D18UCLA3 | AI854020 |
| 133703_at | 0.00 | 0.00 | 0.00 | 0.00 | −2.52 | −2.07 | UNK__AI462192 | AI462192 |
| 95594_at | 0.00 | −2.01 | −2.26 | 0.00 | −2.86 | −2.01 | UNK__AI847486 | AI847486 |
| 93614_at | 0.00 | 0.00 | 0.00 | 0.00 | −4.05 | −4.34 | UNK__AA600647 | AA600647 |
| 99959_at | 0.00 | 0.00 | 0.00 | 0.00 | −2.42 | 0.00 | UNK__AW061337 | AW061337 |
| 97397_at | 0.00 | 0.00 | 0.00 | 0.00 | −2.35 | −1.50 | UNK__AI848344 | AI848344 |
| 113212_at | 0.00 | 0.00 | 0.00 | 0.00 | −4.09 | −1.85 | UNK__AI848538 | AI848538 |
| 102859_at | 0.00 | −1.90 | 0.00 | 0.00 | −2.02 | −1.80 | UNK__AW121304 | AW121304 |
| 96112_at | 0.00 | 0.00 | 0.00 | 0.00 | −2.15 | 0.00 | UNK__AI851178 | AI851178 |
| 112421_at | 0.00 | −2.29 | 0.00 | 0.00 | −6.07 | −3.49 | UNK__AI838528 | AI838528 |
| 103617_at | 0.00 | 0.00 | 0.00 | 0.00 | −2.42 | 0.00 | decay accelerating factor 1; Daf1 | D63679 |
| 98966_at | 0.00 | 0.00 | 0.00 | 0.00 | −2.58 | −0.74 | dihydrolipoamide branched chain transacylase E2; Dbt | L42996 |
| 98527_at | 0.00 | −2.22 | 0.00 | 0.00 | −3.37 | −2.02 | dodecenoyl-Coenzyme A delta isomerase (3,2 trans-enoyl-Coenyme A isomerase); Dci | Z14050 |
| 95478_at | 0.00 | 0.00 | 0.00 | 0.00 | −2.07 | −1.81 | DEB1 | AW124231 |
| 99485_at | 0.00 | 0.00 | 0.00 | 0.00 | −2.08 | 0.00 | DFFA | AB009376 |
| 108255_at | 0.00 | 0.00 | 0.00 | 0.00 | −2.29 | −2.60 | DUSP13 | AA144705 |
| 100311_f_at | 0.00 | 0.00 | −2.37 | 0.00 | 0.00 | 0.00 | EAR1 | U72032 |
| 103240_f_at | 0.00 | 0.00 | −3.40 | 0.00 | 0.00 | 0.00 | EAR3 | AF017258 |
| 93754_at | 0.00 | 0.00 | 0.00 | 0.00 | −2.05 | 0.00 | enoyl coenzyme A hydratase 1, peroxisomal; Ech1 | AF030343 |
| 102774_at | 0.00 | −1.77 | 0.00 | 0.00 | −2.89 | −1.98 | epidermal growth factor; Egf | V00741 |
| 94353_at | 0.00 | 0.00 | 0.00 | 0.00 | 0.00 | −2.24 | eukaryotic translation initiation factor 4E binding protein 2; Eif4ebp2 | U75530 |
| 93051_at | 0.00 | −2.61 | 0.00 | 0.00 | −2.14 | 0.00 | EPHX2 | Z37107 |
| 101538_i_at | 0.00 | −4.79 | −3.78 | 0.00 | −7.47 | −1.63 | ES1 | AW226939 |
| 101539_f_at | 0.00 | −3.93 | −3.37 | 0.00 | −7.31 | 0.00 | ES1 | AW226939 |
| 103964_at | 0.00 | −1.62 | −1.63 | 0.00 | −2.22 | 0.00 | estrogen related receptor, alpha; Esrra | U85259 |
| 115969_at | 0.00 | 0.00 | 0.00 | 0.00 | −2.50 | 0.00 | EXTL1 | AI850861 |
| 94214_at | 0.00 | −2.71 | 0.00 | 0.00 | −3.30 | 0.00 | FABP3 | X14961 |
| 94507_at | 0.00 | 0.00 | 0.00 | 0.00 | −2.62 | 0.00 | fatty acid Coenzyme A ligase, long chain 2; Facl2 | U15977 |
| 98575_at | 0.00 | −1.34 | −3.15 | −2.39 | −3.33 | 0.00 | fatty acid synthase; Fasn | X13135 |
| 100928_at | −4.16 | 0.00 | 0.00 | 2.21 | −0.01 | 19.58 | fibulin 2; Fbln2 | X75285 |
| 97379_at | −0.89 | −3.22 | −4.99 | 0.00 | −7.21 | −4.72 | fructose bisphosphatase 2; Fbp2 | D42083 |
| 97518_at | 0.00 | −3.76 | −2.66 | 0.00 | −2.48 | −1.86 | farnesyl diphosphate farnesyl transferase 1; Fdft1 | D29016 |
| 92587_at | 0.00 | 0.00 | 0.00 | 0.00 | −2.01 | 0.00 | ferredoxin 1; Fdx1 | L29123 |
| 97213_at | 0.00 | −2.01 | −2.18 | 0.00 | −3.49 | −2.34 | FEM1A | AF064447 |
| 100494_at | 0.00 | 0.00 | 0.00 | 0.00 | −3.74 | 0.00 | FGF1 | M30641 |
| 103995_at | 0.00 | 0.00 | 0.00 | 0.00 | −2.00 | −2.32 | FGFBP1 | AF065441 |
| 102366_at | 0.00 | 0.00 | −5.06 | −3.75 | 0.00 | 2.31 | UNK__AA718169 | AA718169 |
| 101991_at | 0.00 | 0.00 | −2.61 | 0.00 | −1.59 | 1.77 | flavin containing monooxygenase 1; Fmo1 | D16215 |
| 104607_at | 0.00 | 0.00 | −1.82 | 0.00 | −2.08 | −1.72 | UNK__AF093624 | AF093624 |

(Treatment Time header spans the fold-change columns)

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 99121_at | 0.00 | 0.00 | 0.00 | 0.00 | −2.20 | 0.00 | fragile X mental retardation gene, autosomal homolog; Fxr1h | X90875 |
| 97430_at | 0.00 | −2.17 | 0.00 | 0.00 | −3.62 | −2.00 | G6PT1 | AF080469 |
| 104616_g_at | 0.00 | 0.00 | 0.00 | 0.00 | −3.11 | 0.00 | galactose-1-phosphate uridyl transferase; Galt | M96265 |
| 102967_at | 0.00 | 0.00 | 0.00 | −1.64 | −2.62 | −2.68 | GDAP1 | Y17850 |
| 92592_at | 0.00 | 0.00 | 0.00 | 0.00 | −3.62 | −2.07 | GDC1 | M25558 |
| 97155_at | −1.62 | 0.00 | 0.00 | 0.00 | −4.30 | −2.94 | myostatin; Mstn | U84005 |
| 98984_f_at | 0.00 | 0.00 | 0.00 | 0.00 | −5.39 | −2.75 | glycerol phosphate dehydrogenase 1, mitochondrial; Gdm1 | D50430 |
| 99107_at | 0.00 | −2.02 | 0.00 | 0.00 | −1.80 | 0.00 | GHR | M31680 |
| 102060_at | 0.00 | −2.08 | 0.00 | 0.00 | −1.92 | −1.63 | GOLGA4 | AF051357 |
| 100573_f_at | 0.00 | −1.98 | −1.95 | 0.00 | −2.35 | −1.80 | GPI1 | M14220 |
| 113915_at | 0.00 | −2.92 | −3.65 | −4.26 | −4.95 | −3.03 | UNK_AI226254 | AI226254 |
| 93750_at | 0.00 | −2.13 | −2.15 | 0.00 | −1.75 | 0.00 | gelsolin; Gsn | J04953 |
| 112869_at | 0.00 | 0.00 | 0.00 | 0.00 | −2.44 | −2.45 | GSNPAT-PENDING | AI852572 |
| 96085_at | 0.00 | 0.00 | 0.00 | 0.00 | 0.00 | −2.36 | GSTA4 | L06047 |
| 93543_f_at | 0.00 | 0.00 | −1.85 | 0.00 | −2.20 | 0.00 | GSTM1 | J03952 |
| 102094_f_at | 0.00 | 0.00 | 0.00 | 0.00 | −3.22 | −1.46 | GSTM1 | AI841270 |
| 95445_at | 0.00 | 0.00 | 0.00 | 0.00 | −1.96 | −2.10 | GUKMI1 | AW124194 |
| 100597_at | 0.00 | 0.00 | 0.00 | 0.00 | −2.22 | 0.00 | GYG1 | AW049730 |
| 98496_at | 0.00 | −2.01 | 0.00 | 0.00 | −2.49 | −1.83 | GYS3 | U53218 |
| 95485_at | 0.00 | 0.00 | −1.89 | 0.00 | −2.61 | 0.00 | hydroxylacyl-Coenzyme A dehydrogenase-dehydrogenase; Hadh | D29639 |
| 94781_at | −1.29 | −1.94 | −2.84 | −2.71 | −1.65 | 0.00 | hemoglobin alpha, adult chain 1; Hba-a1 | V00714 |
| 103534_at | −1.77 | −1.81 | −3.81 | 0.00 | −2.23 | 1.56 | hemoglobin, beta adult minor chain; Hbb-b2 | V00722 |
| 94375_at | 0.00 | 0.00 | 0.00 | 0.00 | −2.10 | −1.94 | hexokinase 2; Hk2 | Y11666 |
| 92568_at | 0.00 | 0.00 | 0.00 | 0.00 | −1.92 | −2.02 | house-keeping protein 1; Hkp1 | M74555 |
| 102714_at | 0.00 | 0.00 | 0.00 | 0.00 | −1.87 | −2.08 | HSC70T | L27086 |
| 97867_at | 0.00 | −2.03 | 0.00 | 0.00 | 0.00 | 0.00 | hydroxysteroid 11-beta dehydrogenase 1; Hsd11b1 | X83202 |
| 102620_at | 0.00 | 0.00 | 0.00 | 0.00 | −7.64 | −4.63 | UNK_AF088983 | AF088983 |
| 97914_at | 0.00 | 0.00 | 0.00 | 0.00 | −2.02 | −1.92 | heat shock protein, 74 kDa, A; Hspa9a | D17666 |
| 95693_at | 0.00 | −2.56 | −2.35 | 0.00 | −2.04 | −1.82 | isocitrate dehydrogenase 2 (NADP+), mitochondrial; Idh2 | U51167 |
| 93029_at | 0.00 | 0.00 | 0.00 | 0.00 | −2.22 | 0.00 | isocitrate dehydrogenase 3 (NAD+), gamma; Idh3g | U68564 |
| 103904_at | 0.00 | −2.69 | −2.38 | 0.00 | 0.00 | 0.00 | insulin-like growth factor binding protein 6; Igfbp6 | X81584 |
| 96764_at | −2.18 | 0.00 | 4.23 | 4.92 | 2.47 | 10.03 | UNK_AJ007971 | AJ007971 |
| 110795_at | 0.00 | 0.00 | 0.00 | 0.00 | −2.27 | 0.00 | JDP1-PENDING | AI852445 |
| 94193_at | 0.00 | 0.00 | −3.26 | 0.00 | −3.75 | −2.14 | KCNA7 | AF032099 |
| 98787_at | 0.00 | 0.00 | 0.00 | 0.00 | 0.00 | −4.22 | potassium inwardly rectifying channel, subfamily J, member 11; Kcnj11 | D50581 |
| 102849_at | 0.00 | 0.00 | −3.01 | 0.00 | 0.00 | 0.00 | potassium inwardly-rectifying channel, subfamily J, member 8; Kcnj8 | D88159 |
| 94379_at | 0.00 | −2.47 | −1.93 | 0.00 | −2.35 | −2.21 | kinesin heavy chain member 1B; Kif1b | D17577 |
| 93527_at | 0.00 | −2.06 | −2.23 | 0.00 | 0.00 | 0.00 | KLF9 | Y14296 |
| 93528_s_at | 0.00 | −1.98 | 0.00 | 0.00 | −2.51 | 0.00 | KLF9 | AI848050 |

TABLE 2-continued

| Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 94321_at | 0.00 | 0.00 | 0.00 | 0.00 | −2.29 | 0.00 | keratin complex 1, acidic, gene 10; Krt1-10 | V00830 |
| 97976_at | 0.00 | 0.00 | 0.00 | 0.00 | −2.24 | 0.00 | kinectin 1; Ktn1 | L43326 |
| 92366_at | 0.00 | −2.03 | 0.00 | 0.00 | 0.00 | 0.00 | laminin, alpha 2; Lama2 | U12147 |
| 101990_at | 0.00 | −3.06 | −2.70 | 0.00 | −3.72 | −1.80 | lactate dehydrogenase 2, B chain; Ldh2 | X51905 |
| 96608_at | 0.00 | 0.00 | 0.00 | 0.00 | −2.42 | 0.00 | lupus nephritis-associated peptide 1; Lnap1 | AF023463 |
| 113140_at | 0.00 | 0.00 | 0.00 | 0.00 | −3.11 | −2.24 | LOC56046 | AI846417 |
| 103090_at | 0.00 | 0.00 | 0.00 | 0.00 | 0.00 | −2.06 | LOC56046 | AI838742 |
| 99536_at | 0.00 | 0.00 | 0.00 | 0.00 | −2.79 | −2.17 | UNK_AB016080 | AB016080 |
| 112850_at | 0.00 | −1.89 | −1.68 | 0.00 | −2.20 | −2.12 | UNK_AW121352 | AW121352 |
| 101115_at | 0.00 | 0.00 | 0.00 | −2.20 | −2.15 | −0.12 | lactotransferrin; Ltf | J03298 |
| 130772_at | 0.00 | −2.36 | −2.24 | 0.00 | 0.00 | 0.00 | LYNX1 | AI838844 |
| 137205_f_at | 0.00 | 0.00 | 0.00 | 0.00 | −2.71 | 0.00 | LYNX1 | AI839851 |
| 102828_at | 0.00 | 0.00 | 0.00 | 0.00 | −2.31 | −1.54 | mitogen activated protein kinase kinase 6; Map2k6 | U39066 |
| 102829_s_at | 0.00 | 0.00 | 0.00 | 0.00 | −2.06 | 0.00 | MAP2K6 | X97052 |
| 102431_at | 0.00 | 0.00 | 0.00 | 0.00 | −0.45 | −2.09 | MTAPT | M18775 |
| 102742_g_at | 0.00 | 0.00 | 0.00 | 0.00 | −1.89 | −2.98 | MTAPT | M18775 |
| 96311_at | 0.00 | −2.37 | 0.00 | 0.00 | −3.29 | −2.09 | MBP | M11533 |
| 97282_at | −11.15 | 0.00 | 0.00 | 0.00 | 0.00 | 0.00 | MELA | D10049 |
| 103838_at | 0.00 | 0.00 | 0.00 | 0.00 | −2.36 | −1.98 | MG29 | AB010144 |
| 102061_at | 0.00 | −3.00 | −3.32 | −3.75 | −5.64 | −2.29 | MLF1 | AF100171 |
| 103622_at | −1.34 | 0.00 | 0.00 | 0.00 | −2.19 | −1.80 | UNK_AW050255 | AW050255 |
| 96348_at | 0.00 | −2.13 | 0.00 | 0.00 | −2.20 | 0.00 | UNK_AW121217 | AW121217 |
| 101082_at | 0.00 | 0.00 | −2.34 | 0.00 | −2.56 | −1.12 | MOD1 | J02652 |
| 102096_f_at | 0.00 | 0.00 | −2.42 | 0.00 | 0.00 | 3.13 | MUP1 | AI255271 |
| 101909_f_at | 0.00 | 0.00 | −4.14 | 0.00 | 0.00 | 3.70 | MUP3 | M16357 |
| 100017_at | −1.56 | 0.00 | 0.00 | 0.00 | −2.75 | 0.00 | myosin-binding protein H; Mybph | U68267 |
| 97990_at | 0.00 | 0.00 | 0.00 | 0.00 | −2.28 | 0.00 | myosin heavy chain 11, smooth muscle; Myh11 | D85923 |
| 98616_f_at | 0.00 | −8.12 | −2.13 | −32.76 | −4.63 | −4.81 | MYHCB | AJ223362 |
| 93050_at | 0.00 | −2.77 | 0.00 | 0.00 | −2.91 | −2.11 | myosin light chain, phosphorylatable, cardiac ventricles; Mylpc | M91602 |
| 94122_at | 7.47 | 3.44 | 2.58 | 0.00 | −3.81 | −1.94 | MYOC | AF041335 |
| 92407_at | 0.00 | −1.90 | 0.00 | 0.00 | −3.23 | −2.03 | MYOM1 | AJ012072 |
| 102041_at | 0.00 | 0.00 | 0.00 | 0.00 | −2.53 | −1.90 | MYOM2 | AJ001038 |
| 92876_at | 0.00 | 0.00 | 0.00 | 0.00 | −4.44 | −2.04 | NADH dehydrogenase (ubiquinone) Fe—S protein 4 (18 kDa); Ndufs4 | AA590675 |
| 93006_at | 0.00 | 0.00 | 0.00 | 0.00 | −4.91 | −2.79 | NFIC | Y07693 |
| 96153_at | 0.00 | 0.00 | −4.66 | −8.35 | −10.04 | −5.56 | neutrophilic granule protein; Ngp | L37297 |
| 92824_at | 0.00 | 0.00 | 0.00 | 0.00 | −2.29 | −1.91 | NM23-M6 | AF051942 |
| 99009_at | 0.00 | −2.54 | 0.00 | 0.00 | −2.06 | 0.00 | nicotinamide nucleotide transhydrogenase; Nnt | Z49204 |
| 98365_at | 0.00 | 0.00 | 0.00 | 0.00 | 0.00 | −2.02 | nitric oxide synthase 1, neuronal; Nos1 | D14552 |
| 102371_at | 0.00 | 0.00 | 0.00 | 0.00 | −3.52 | −2.20 | nuclear receptor subfamily 4, group A, member 1; Nr4a1 | X16995 |
| 92362_at | 0.00 | 0.00 | 0.00 | 0.00 | 0.00 | −2.83 | NTTP1 | X95518 |
| 99549_at | 0.00 | −3.17 | 0.00 | 0.00 | 3.34 | 2.12 | osteoglycin; Ogn | D31951 |
| 104479_at | 0.00 | 0.00 | 0.00 | 0.00 | −4.22 | −5.06 | purinergic receptor P2Y, G-protein coupled 2; P2ry2 | L14751 |
| 113762_at | 0.00 | 0.00 | 0.00 | 0.00 | −2.71 | 0.00 | UNK_AI510151 | AI510151 |
| 96735_at | 0.00 | 0.00 | 0.00 | 0.00 | 0.00 | −2.76 | UNK_AW049732 | AW049732 |
| 93308_s_at | 0.00 | 0.00 | 0.00 | −1.80 | −4.41 | 0.00 | PCX | M97957 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 100489_at | 0.00 | 0.00 | 0.00 | 0.00 | 0.00 | −2.12 | phosphodiesterase 7A; Pde7a | U68171 |
| 115211_at | 0.00 | 0.00 | 0.00 | 0.00 | −2.66 | −1.52 | PDHX | AA987055 |
| 103526_at | 0.00 | 0.00 | 0.00 | 0.00 | −3.17 | −2.61 | peptidyl arginine deiminase, type II; Pdi2 | D16580 |
| 102049_at | −1.92 | 0.00 | 0.00 | 0.00 | −2.30 | 0.00 | PDK4 | AJ001418 |
| 103297_at | 0.00 | 0.00 | −5.49 | 0.00 | −5.13 | −4.79 | 6-phosphofructo-2-kinase/fructose-2,6-biphosphatase 1; Pfkfb1 | X98848 |
| 93567_at | 0.00 | 0.00 | 0.00 | 0.00 | −2.14 | −1.90 | PFN2 | AW122536 |
| 92599_at | 0.00 | 0.00 | 0.00 | 0.00 | −2.14 | −1.47 | PGAM2 | AF029843 |
| 94733_at | 0.00 | −1.95 | −2.18 | −1.90 | −2.98 | −1.72 | P glycoprotein 2; Pgy2 | J03398 |
| 94855_at | 0.00 | 0.00 | 0.00 | 0.00 | −4.56 | −3.15 | prohibitin; Phb | X78682 |
| 92519_at | 0.00 | −2.02 | −2.13 | 0.00 | −2.66 | −2.06 | phosphorylase kinase alpha 1; Phka1 | X74616 |
| 97094_at | 0.00 | 0.00 | −2.50 | 0.00 | −5.08 | −2.05 | phosphorylase kinase gamma; Phkg | J03293 |
| 107109_at | 0.00 | 0.00 | 0.00 | 0.00 | −4.21 | −2.18 | PHRET1 | AI835608 |
| 104431_at | 0.00 | 0.00 | 0.00 | 0.00 | −3.03 | −1.83 | protein kinase C, theta; Pkcq | D11091 |
| 98004_at | 0.00 | 0.00 | 0.00 | 0.00 | −2.53 | −2.11 | protein kinase inhibitor, alpha; Pkia | M63554 |
| 98005_at | 0.00 | 0.00 | 0.00 | 0.00 | −2.57 | −1.86 | PKIA | AW125442 |
| 113154_at | 0.43 | 0.00 | −2.71 | −1.11 | −2.08 | 2.44 | UNK__AI854500 | AI854500 |
| 96114_at | 0.00 | 0.00 | 0.00 | 0.00 | −2.25 | 0.00 | UNK__AW122076 | AW122076 |
| 93933_at | 0.00 | 0.00 | 0.00 | 0.00 | −2.41 | −2.58 | protein phosphatase 1, regulatory (inhibitor) subunit 5; Ppp1r5 | U89924 |
| 97989_at | 0.00 | 0.00 | 0.00 | 0.00 | −2.59 | −1.60 | protein phosphatase 3, catalytic subunit, beta isoform; Ppp3cb | M81483 |
| 96256_at | 0.00 | 0.00 | 0.00 | 0.00 | −2.17 | 0.00 | peroxiredoxin 3; Prdx3 | M28723 |
| 97096_at | 0.00 | 0.00 | 0.00 | 0.00 | −5.20 | −2.84 | protein kinase, cAMP dependent regulatory, type II alpha; Prkar2a | J02935 |
| 100595_at | 0.00 | 0.00 | 0.00 | 0.00 | −2.33 | 0.00 | PTP4A2 | AF035644 |
| 101027_s_at | 0.00 | −1.93 | 0.00 | 0.00 | −2.20 | −1.52 | PTTG1 | AF069051 |
| 96720_f_at | 0.00 | 0.00 | 0.00 | 0.00 | −2.67 | 0.00 | parvalbumin; Pva | X59382 |
| 104098_at | 0.00 | −2.59 | −2.95 | −3.60 | −3.43 | −2.09 | peroxisomal membrane protein 2, 22 kDa; Pxmp2 | L28835 |
| 92410_at | 0.00 | 0.00 | 0.00 | 0.00 | 0.00 | −2.59 | RAD23a homolog (S. cerevisiae); Rad23a | X92410 |
| 104680_at | 0.00 | −2.27 | −2.19 | 0.00 | 0.00 | 0.00 | RAMP1 | AJ250489 |
| 100562_at | 0.00 | 0.00 | 0.00 | 0.00 | −3.97 | −3.48 | UNK__AI846319 | AI846319 |
| 99951_at | 0.00 | 0.00 | 0.00 | 0.00 | 0.00 | −4.08 | RORC | AF019660 |
| 98464_at | 0.00 | 0.00 | 0.00 | 0.00 | −2.35 | 0.00 | UNK__AW124196 | AW124196 |
| 96296_at | 0.00 | 0.00 | 0.00 | 0.00 | −2.25 | 0.00 | RPML7 | AI843685 |
| 98007_at | 0.00 | −3.41 | −2.82 | −3.72 | −3.18 | −2.45 | RPS6KA2 | AJ131021 |
| 92237_at | 0.00 | 0.00 | 0.00 | 0.00 | −9.91 | −5.35 | retinoid X receptor gamma; Rxrg | X66225 |
| 103448_at | 0.00 | 2.51 | −4.75 | −1.37 | −6.47 | 3.81 | S100 calcium binding protein A8 (calgranulin A); S100a8 | M83218 |
| 103887_at | 4.41 | 0.00 | −8.99 | −5.52 | −6.50 | 5.43 | S100 calcium-binding protein A9 (calgranulin B); S100a9 | M83219 |
| 102763_at | 0.00 | 0.00 | 0.00 | 0.00 | −2.52 | −1.62 | UNK__AF064748 | AF064748 |
| 102712_at | −3.84 | 2.96 | 4.98 | 8.61 | 4.23 | 0.00 | serum amyloid A 3; Saa3 | X03505 |
| 99665_at | 0.00 | 0.00 | −2.09 | −2.05 | −3.58 | −2.00 | special AT-rich sequence binding protein 1; Satb1 | U05252 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 111448_f_at | 0.00 | −1.94 | −1.73 | 0.00 | −2.64 | −1.81 | SATB1 | AI121993 |
| 111449_r_at | 0.00 | 0.00 | 0.00 | 0.00 | −2.19 | 0.00 | SATB1 | AI121993 |
| 103399_at | 0.00 | 0.00 | 0.00 | 0.00 | 0.00 | −2.01 | SCML1 | AI853225 |
| 102808_at | 0.00 | 0.00 | 0.00 | 0.00 | −2.21 | −1.64 | sodium channel, voltage-gated, type I, beta polypeptide; Scn1b | L48687 |
| 94140_at | 0.48 | 2.44 | −2.79 | 0.00 | 0.00 | 0.00 | SCVR | M59446 |
| 92742_at | 0.00 | −4.88 | 0.00 | 0.00 | −2.58 | −1.69 | SCYA11 | U77462 |
| 98624_at | 0.00 | −1.98 | −2.23 | 0.00 | −2.88 | −2.07 | seb4 protein; Seb4 | X75316 |
| 103395_at | 0.00 | 0.00 | 0.00 | 0.00 | −2.03 | −1.79 | SGCA | AF019564 |
| 101394_at | 0.00 | 0.00 | 0.00 | 0.00 | −2.25 | 0.00 | SGCG | AB024922 |
| 96204_at | 0.00 | 0.00 | 0.00 | 0.00 | −2.53 | 0.00 | SH3BGR | AJ239082 |
| 102208_at | 0.00 | −1.79 | −2.13 | 0.00 | −2.43 | 0.00 | ST3GALVI | AI153959 |
| 99320_at | 0.00 | 0.00 | 0.00 | 0.00 | −2.62 | 0.00 | sialyltransferase 8 (alpha 2, 8 sialytransferase) E; Siat8e | X98014 |
| 92722_f_at | 0.00 | 0.00 | 0.00 | 0.00 | −2.03 | 0.00 | sine oculis-related homeobox 1 homolog (Drosophila); Six1 | X80339 |
| 93000_g_at | −2.80 | −2.40 | 0.00 | 0.00 | 0.00 | 0.00 | SIX4 | D50416 |
| 93001_at | −1.65 | 0.00 | 0.00 | 0.00 | −2.44 | 0.00 | sine oculis-related homeobox 4 homolog (Drosophila); Six4 | D50418 |
| 102314_at | 0.00 | −2.97 | 0.00 | 0.00 | −4.23 | −2.74 | solute carrier family 2 (facilitated glucose transporter), member 4; Slc2a4 | M23383 |
| 109069_at | 0.00 | −2.82 | −2.00 | 0.00 | 0.00 | 3.28 | SLC39A1 | AI255982 |
| 96926_at | −2.06 | −2.87 | −2.56 | 0.00 | 0.00 | 0.00 | UNK_AA980164 | AA980164 |
| 96042_at | 0.00 | 0.00 | 0.00 | 0.00 | −2.94 | 0.00 | SOD2 | L35528 |
| 92302_at | 0.00 | 0.00 | −1.87 | 0.00 | −2.80 | 0.00 | Son of sevenless homolog 2. (Drosophila); Sos2 | Z11664 |
| 92726_at | 0.00 | 0.00 | 0.00 | 0.00 | −3.87 | −2.50 | SOX6 | AJ010605 |
| 113125_at | 0.00 | 0.00 | 0.00 | 0.00 | −3.81 | −2.03 | UNK_AI851671 | AI851671 |
| 100952_at | 0.00 | 0.00 | 0.00 | 0.00 | −2.38 | −2.24 | stromal Interaction molecule 1; Stim1 | U47323 |
| 92888_s_at | 0.00 | 0.00 | 0.00 | 0.00 | −2.62 | −1.73 | protein tyrosine phosphatase-like unspliced c-terminal product and spliced c-terminal end STYX; hStyxb | U34973 |
| 93501_f_at | 0.00 | 0.00 | 0.00 | 0.00 | −2.61 | 0.00 | SUCLA2 | AF058955 |
| 93502_r_at | 0.00 | 0.00 | 0.00 | 0.00 | −4.71 | 0.00 | SUCLA2 | AF058955 |
| 96268_at | 0.00 | 0.00 | 0.00 | 0.00 | −2.29 | 0.00 | UNK_AI840979 | AI840979 |
| 100587_f_at | 0.00 | 0.00 | 0.00 | 0.00 | −2.02 | 0.00 | SUPT4H | AI843959 |
| 93994_at | 0.00 | 0.00 | 0.00 | 0.00 | −2.00 | 0.00 | SYCP3 | AW212131 |
| 102221_at | 0.00 | 0.00 | 0.00 | 0.00 | −2.28 | −1.75 | SYNGR1 | AJ002306 |
| 100355_g_at | 0.00 | 0.00 | 0.00 | 0.00 | −2.24 | −1.51 | TBX14 | AF013282 |
| 102256_at | 0.00 | 0.00 | 0.00 | 0.00 | −2.14 | 0.00 | TBX15 | AF041822 |
| 102344_s_at | 0.00 | −2.14 | −2.56 | −4.39 | −4.38 | −2.48 | TCEA3 | AI132239 |
| 97402_at | −2.80 | −5.83 | −4.24 | −3.96 | −4.97 | −2.21 | thioether S-methyltransferase; Temt | M88694 |
| 101964_at | 0.00 | 0.00 | −2.16 | 0.00 | 0.00 | 3.47 | transketolase; Tkt | U05809 |
| 92224_at | 0.00 | −5.01 | 0.00 | 0.00 | 0.00 | 0.00 | tetranectin (plasminogen-binding protein); Tna | X79199 |
| 101063_at | 0.00 | −3.19 | 0.00 | 0.00 | 0.00 | −2.68 | troponin C, cardiac/slow skeletal; Tncc | M29793 |
| 98561_at | 0.00 | −3.08 | 0.00 | 0.00 | 0.00 | −2.24 | UNK_AJ242874 | AJ242874 |
| 93532_at | 0.00 | 0.00 | 0.00 | 0.00 | −2.52 | 0.00 | troponin I, skeletal, fast 2; Tnni2 | J04992 |
| 101383_at | 0.00 | −2.85 | 0.00 | 0.00 | −1.69 | −1.97 | TNNT1 | AJ131711 |
| 99532_at | 0.00 | 0.00 | 0.00 | 0.00 | −2.17 | 0.00 | transducer of ErbB-2.1; Tob1 | D78382 |
| 101446_at | 0.00 | 0.00 | 0.00 | 0.00 | −2.49 | 0.00 | TPD52L1 | AF004428 |

TABLE 2-continued

| Treatment Time Affymetrix Qualifier | BMP2 day 01 Avg. Fold Change | BMP2 day 02 Avg. Fold Change | BMP2 day 03 Avg. Fold Change | BMP2 day 04 Avg. Fold Change | BMP2 day 07 Avg. Fold Change | BMP2 day 14 Avg. Fold Change | Gene Name | Genbank Accession # |
|---|---|---|---|---|---|---|---|---|
| 93266_at | 0.00 | −2.33 | −1.90 | 0.00 | −2.55 | −2.51 | tropomyosin 5; Tpm5 | U04541 |
| 93509_at | 0.00 | 0.00 | −1.82 | 0.00 | −2.58 | −2.00 | UBE2B | U57690 |
| 99507_at | 0.00 | 0.00 | −3.44 | 0.00 | −2.86 | −1.60 | UCP | M21247 |
| 93392_at | −1.48 | −1.66 | 0.00 | 0.00 | −2.72 | −1.67 | UCP3 | AB010742 |
| 95537_at | 0.00 | 0.00 | 0.00 | 0.00 | −2.26 | 0.00 | ULK2 | AB019577 |
| 92820_at | 0.00 | 0.00 | 0.00 | 0.00 | −2.43 | −2.13 | USP2 | AI846522 |
| 92821_at | 0.00 | 0.00 | 0.00 | 0.00 | −2.73 | −1.71 | USP2 | AF079565 |
| 114088_at | 0.00 | 0.00 | 0.00 | 0.00 | −2.55 | −1.55 | VAMP1 | AI850070 |
| 92496_at | 0.00 | 0.00 | 0.00 | 0.00 | 0.00 | −2.59 | VAMP5 | AF035643 |
| 103001_at | 0.00 | −2.17 | −1.96 | 0.00 | −3.42 | −2.12 | vascular endothelial growth factor B; Vegfb | U43836 |
| 98549_at | 0.00 | −1.87 | 0.00 | 0.00 | −2.11 | 0.00 | vitronectin; Vtn | M77123 |
| 115141_at | 0.00 | 0.00 | −3.89 | 0.00 | −5.60 | 0.00 | UNK_AW049840 | AW049840 |
| 103824_at | −1.39 | −2.00 | −2.01 | 0.00 | −1.92 | −1.71 | WFS1 | AF084482 |
| 103238_at | 0.00 | 0.00 | 0.00 | 0.00 | −4.41 | 0.00 | wingless-related MMTV integration site 4; Wnt4 | M89797 |
| 96063_at | 0.00 | 0.00 | 0.00 | 0.00 | −2.02 | 0.00 | X-ray repair complementing defective repair In Chinese hamster cells 5; XrccS | X66323 |
| 99932_at | 0.00 | 0.00 | 0.00 | 0.00 | 0.00 | −6.45 | ZFP100 | U14556 |
| 101456_at | 0.00 | 0.00 | 0.00 | 0.00 | −2.16 | −1.95 | ZFP106 | AF060245 |
| 108046_at | 0.00 | 0.00 | 0.00 | 0.00 | −2.37 | −2.19 | ZFP238 | AI844802 |

TABLE 5

BMP-2-induced changes in the expression of known genes previously associated with bone or cartilage metabolism.

| Gene Title | Symbol | GenBank | Day 1 | Day 2 | Day 3 | Day 4 | Day 7 | Day 14 |
|---|---|---|---|---|---|---|---|---|
| Cell Surface Proteins | | | | | | | | |
| OSTEOBLAST SPECIFIC FACT. 2 | Osf2 | D13664 | 2.1 +/− 0.2 | 4.1 +/− 0.6 | 7.4 +/− 0.2 | 11.6 +/− 0.3 | 64.3 +/− 6.7 | 42.7 +/− 12 |
| MEGAKAR. STIM. FACT. | Prg4 | AB034730 | 0 +/− 0 | 5.6 +/− 0.2 | 4.3 +/− 0.2 | 4.8 +/− 0.1 | 0 +/− 0 | 0 +/− 0 |
| CADHERIN 11 | Cdh11 | D21253 | 0 +/− 0 | 2.1 +/− 0.3 | 2.9 +/− 0 | 5.5 +/− 3.3 | 37.9 +/− 9.6 | 38.2 +/− 7.3 |
| CD44 ANTIGEN | Cd44 | M27129 | 0 +/− 0 | 3.2 +/− 0.5 | 3.9 +/− 0.1 | 4.3 +/− 0.3 | 4.5 +/− 0.2 | 6 +/− 0.6 |
| CADHERIN 2 | Cdh2 | AB008811 | 0 +/− 0 | 0 +/− 0 | 0 +/− 0 | 2.1 +/− 0.5 | 15.9 +/− 1.5 | 14.6 +/− 0.2 |
| SYNDECAN 2 | Sdc2 | U00674 | 0 +/− 0 | 0 +/− 0 | 0 +/− 0 | 0 +/− 0 | 4.1 +/− 1.2 | 4.5 +/− 0.2 |
| INTEGRIN ALPHA V (CD51) | Itgav | U14135 | 0 +/− 0 | 0 +/− 0 | 0 +/− 0 | 0 +/− 0 | 4.4 +/− 1.4 | 5.7 +/− 1 |
| NEURAL CELL ADHESION MOLECULE | Ncam | X07233 | 0 +/− 0 | 0 +/− 0 | 0 +/− 0 | 4 +/− 1.3 | 7.8 +/− 1.9 | 3.4 +/− 0.6 |
| SYNDECAN 1 | Sdc1 | X15487 | 0 +/− 0 | 2 +/− 0.6 | 0 +/− 0 | 0 +/− 0 | 7.2 +/− 1 | 6.9 +/− 0.2 |
| L-34 GALACTOSIDE-BINDING LECTIN. | Lgals3 | X16074 | 0 +/− 0 | 1.6 +/− 0.3 | 2.1 +/− 0.5 | 2.4 +/− 0.5 | 6 +/− 0.9 | 8.4 +/− 0.9 |
| GAP JUNC. MEMB. CHANN. PROT. ALPHA 1 | Gja1 | X61576 | 0 +/− 0 | 2.3 +/− 0.5 | 0 +/− 0 | 4 +/− 0.8 | 8.4 +/− 1.9 | 14.8 +/− 3.6 |

TABLE 5-continued

BMP-2-induced changes in the expression of known genes previously associated with bone or cartilage metabolism.

| Gene Title | Symbol | GenBank | Day 1 | Day 2 | Day 3 | Day 4 | Day 7 | Day 14 |
|---|---|---|---|---|---|---|---|---|
| INTEGRIN BETA 3 (CD61) | Itgb3 | AF026509 | 0 +/− 0 | 0 +/− 0 | 0 +/− 0 | 0 +/− 0 | 0 +/− 0 | 7.2 +/− 1 |
| INTEGRIN BETA 2 (CD18) | Itgb2 | X14951 | 2.6 +/− 0.6 | 3 +/− 0.3 | 2.8 +/− 1.1 | 2.9 +/− 0.3 | 2.9 +/− 1.1 | 8.8 +/− 0.1 |
| VASCULAR CELL ADHESION MOLECULE 1 | Vcam1 | X67783 | 0 +/− 0 | 2.2 +/− 0 | 0 +/− 0 | 2.9 +/− 0.6 | 3.5 +/− 0.9 | 6.8 +/− 1.4 |
| Cytokines | | | | | | | | |
| CONNECTIVE TISSUE GROWTH FACTOR | Ctgf | M70642 | 5.1 +/− 0.8 | 8 +/− 1 | 10.2 +/− 3.1 | 5.8 +/− 1.7 | 19.1 +/− 3.1 | 9.6 +/− 0.5 |
| STROMAL CELL DERIVED FACT. 5 | Sdf5 | D50462 | 2.2 +/− 0.8 | 4.6 +/− 0.5 | 8.3 +/− 2.3 | 10.2 +/− 3.4 | 17.5 +/− 1.6 | 10.1 +/− 1.1 |
| MONO. CHEMOATTRAC. PROT.-2 PRECUR. | Scya8 | AB023418 | 0 +/− 0 | 3.9 +/− 1.8 | 6 +/− 2.3 | 9 +/− 2.3 | 9.4 +/− 1.3 | 4.8 +/− 2 |
| SMALL INDUCIB. CYTOKINE A2 | Scya2 | J04467 | 3.3 +/− 0.6 | 7.4 +/− 1.4 | 8.5 +/− 1.9 | 8.4 +/− 0.6 | 5.9 +/− 0.9 | 1.9 +/− 1 |
| IL-1 BETA | Il1b | M15131 | 1.1 +/− 1.9 | 5.4 +/− 2 | 4.4 +/− 2.1 | 4.3 +/− 1.1 | 0 +/− 0 | 5.4 +/− 0.9 |
| CYSTEINE RICH PROT. 61 | Cyr61 | M32490 | 1.7 +/− 0.5 | 2.6 +/− 0.3 | 5.2 +/− 0.3 | 7.8 +/− 2.3 | 6.4 +/− 1.8 | 2.8 +/− 0.7 |
| TGF, BETA 1 | Tgfb1 | M13177 | 0 +/− 0 | 2.6 +/− 0.5 | 0 +/− 0 | 2.9 +/− 0.7 | 11.3 +/− 0.8 | 7.6 +/− 0.7 |
| MIDKINE | Mdk | M35833 | 0 +/− 0 | 0 +/− 0 | 0 +/− 0 | 0 +/− 0 | 22.2 +/− 1.8 | 10.9 +/− 1.5 |
| INHIBIN BETA-A | Inhba | X69619 | 0 +/− 0 | 1.5 +/− 0.4 | 2 +/− 0.7 | 4.9 +/− 4.4 | 5.2 +/− 2.8 | 0 +/− 0 |
| WNT1 INDUCIB. SIG. PATHWAY PROT. 2 | Wisp2 | AF126063 | 0 +/− 0 | 0 +/− 0 | 0 +/− 0 | 0 +/− 0 | 0 +/− 0 | 4.3 +/− 0.3 |
| STROMAL CELL DERIVED FACT. 1 | Sdf1 | D43805 | 0 +/− 0 | 0 +/− 0 | 0 +/− 0 | 0 +/− 0 | 0 +/− 0 | 6.7 +/− 1 |
| COLONY STIM. FACT. 1 (MACROPHAGE) | Csf1 | M21149 | 2.8 +/− 0.6 | 3 +/− 1 | 1.9 +/− 0.1 | 0 +/− 0 | 3.1 +/− 0.7 | 5.3 +/− 0.7 |
| PDGF, ALPHA | Pdgfa | M29464 | 0 +/− 0 | 0 +/− 0 | 0 +/− 0 | 0 +/− 0 | 5.7 +/− 1.4 | 0 +/− 0 |
| TGF, BETA 3 | Tgfb3 | M32745 | 0 +/− 0 | 0 +/− 0 | 0 +/− 0 | 2.6 +/− 0.3 | 4.1 +/− 1.3 | 1.9 +/− 0.3 |
| BONE MORPHOGENETIC PROT. 8A | Bmp8a | M97017 | 0 +/− 0 | 0 +/− 0 | 0 +/− 0 | 0 +/− 0 | 0 +/− 0 | 5.6 +/− 1.2 |
| TPA REPRESSED GENE 1 | TPAR1 | S74318 | −1.8 +/− 0.1 | 0 +/− 0 | 0 +/− 0 | 0 +/− 0 | 2.2 +/− 0.2 | 9 +/− 1.9 |
| SECRETED FRIZZLED-RELATED PROT. 3 | Sfrp3 | U91905 | 0 +/− 0 | 0 +/− 0 | 0 +/− 0 | 0 +/− 0 | 9.5 +/− 1 | 2.2 +/− 0.8 |
| OSTEOPROTEGERIN | Tnfrsf11b | U94331 | 0 +/− 0 | 0 +/− 0 | 0 +/− 0 | 0 +/− 0 | 5.2 +/− 0.6 | 0 +/− 0 |
| FOLLISTATIN | Fst | Z29532 | 0 +/− 0 | 2.4 +/− 0.3 | 0 +/− 0 | 0 +/− 0 | 4.2 +/− 0.1 | 0 +/− 0 |

TABLE 5-continued

BMP-2-induced changes in the expression of known genes previously associated with bone or cartilage metabolism.

| Gene Title | Symbol | GenBank | Day 1 | Day 2 | Day 3 | Day 4 | Day 7 | Day 14 |
|---|---|---|---|---|---|---|---|---|
| GROWTH DIFFEREN. FACT. 1 | Gdf1 | M62301 | 0 +/− 0 | 0 +/− 0 | 0 +/− 0 | −4.7 +/− 0 | 0 +/− 0 | 0 +/− 0 |
| Extracellular Matrix Proteins | | | | | | | | |
| TENASCIN C | Tnc | X56304 | 0 +/− 0 | 6.6 +/− 1.6 | 14.4 +/− 1.7 | 34.5 +/− 13 | 91.6 +/− 22.7 | 68.9 +/− 7.6 |
| SECRETED PHOSPHO-PROT. 1 | Spp1 | J04806 | 2.4 +/− 0.9 | 3.4 +/− 1.4 | 6 +/− 1 | 15.7 +/− 10.7 | 46.2 +/− 8.7 | 98.3 +/− 5.1 |
| BIGLYCAN | Bgn | X53928 | 1.8 +/− 0.3 | 2.8 +/− 0.5 | 4.2 +/− 0.1 | 5.8 +/− 1 | 11.6 +/− 1.3 | 12.1 +/− 1.4 |
| PROCOLL., TYPE V, ALPHA 1 | Col5a1 | AB009993 | 0 +/− 0 | 0 +/− 0 | 3.1 +/− 0.9 | 9 +/− 2.2 | 17.1 +/− 3.2 | 15.5 +/− 1.5 |
| CHONDROITIN SULFATE PROTEOGLYCAN 2 | Cspg2 | D16263 | 2.4 +/− 1 | 3.1 +/− 0.6 | 4.4 +/− 0.5 | 5.4 +/− 0.4 | 5.1 +/− 1.2 | 2.4 +/− 0.3 |
| PROCOLL., TYPE V, ALPHA 2 | Col5a2 | L02918 | 0 +/− 0 | 2.4 +/− 0.3 | 3.6 +/− 0.5 | 7 +/− 0 | 17.2 +/− 1 | 18.3 +/− 0.4 |
| AGGRECAN | Agc | L07049 | 0 +/− 0 | 0 +/− 0 | 0 +/− 0 | 4.8 +/− 2 | 27.6 +/− 3.4 | 4.7 +/− 0.8 |
| FIBRONECTIN 1 | Fn1 | M18194 | 0 +/− 0 | 3.1 +/− 0.2 | 3 +/− 0.4 | 4.5 +/− 0.4 | 7.8 +/− 0.5 | 6.1 +/− 0.4 |
| ALPHA-1 TYPE-III COLLAGEN | Col3a1 | M18933 | 0 +/− 0 | 2.3 +/− 0.3 | 2.2 +/− 0.3 | 5 +/− 0.2 | 13 +/− 1.2 | 7.9 +/− 0.7 |
| THROMBOSPONDIN 1 | Thbs1 | M87276 | 3 +/− 0.7 | 3.8 +/− 0.8 | 3.9 +/− 1.2 | 9.5 +/− 3.4 | 27.2 +/− 6.4 | 8.5 +/− 2 |
| PROCOLL., TYPE XII, ALPHA 1 | Col12a1 | U25652 | 0.5 +/− 1.4 | 2 +/− 0.3 | 3.9 +/− 0.4 | 7.9 +/− 2.5 | 29.4 +/− 7.5 | 12.1 +/− 1.3 |
| PROCOLL., TYPE VI, ALPHA 2 | Col6a2 | X65582 | 0 +/− 0 | 0 +/− 0 | 0 +/− 0 | 5.6 +/− 0 | 14.1 +/− 2.6 | 9.7 +/− 0.5 |
| COL8A1 | Col8a1 | X66977 | 0 +/− 0 | 2.4 +/− 0.2 | 1.8 +/− 0.1 | 6.8 +/− 1.4 | 23.4 +/− 3.7 | 8.1 +/− 3.1 |
| LUMICAN | Lum | AF013262 | 0 +/− 0 | 0 +/− 0 | 0 +/− 0 | 2.9 +/− 0.5 | 8.5 +/− 0.8 | 7.7 +/− 1 |
| COL11A2 | Col11a2 | AF100956 | 0 +/− 0 | 0 +/− 0 | 0 +/− 0 | 0 +/− 0 | 23.7 +/− 0.2 | 24.2 +/− 9 |
| PROCOLL., TYPE XI, ALPHA 1 | Col11a1 | D38162 | 0 +/− 0 | 0 +/− 0 | 0 +/− 0 | 0 +/− 0 | 79.8 +/− 1.6 | 49.7 +/− 3.7 |
| INTEGRIN BINDING SIALOPROT. | Ibsp | L20232 | 0 +/− 0 | 0 +/− 0 | 0 +/− 0 | 0 +/− 0 | 237.8 +/− 9 | 174.1 +/− 17 |
| BONE GLA. PROT. 1 | Bglap1 | L24431 | 0 +/− 0 | 0 +/− 0 | −4.1 +/− 1 | 0 +/− 0 | 14.9 +/− 4.7 | 59.6 +/− 3.8 |
| PROCOLL., TYPE II, ALPHA 1 | Col2a1 | M65161 | 0 +/− 0 | 0 +/− 0 | −1.8 +/− 0.1 | 0 +/− 0 | 168.1 +/− 24 | 28.9 +/− 3 |
| PROCOLL., TYPE VI, ALPHA 1 | Col6a1 | Z18271 | 0 +/− 0 | 0 +/− 0 | 1.7 +/− 0 | 3.4 +/− 0.1 | 5 +/− 0.3 | 4 +/− 0.4 |
| PROCOLL., TYPE X, ALPHA 1 | Col10a1 | Z21610 | 0 +/− 0 | 0 +/− 0 | 0 +/− 0 | 0 +/− 0 | 45.1 +/− 29.9 | 5.6 +/− 3.2 |
| CARTILAGE OLIGOMERIC MATRIX PROT. | Comp | AF033530 | 0 +/− 0 | 2.2 +/− 0.4 | 0 +/− 0 | 2.3 +/− 0.6 | 10.8 +/− 0.7 | 2.8 +/− 0.4 |
| CARTILAGE LINK PROT. 1 | Crtl1 | AF098460 | 0 +/− 0 | 0 +/− 0 | 0 +/− 0 | 0 +/− 0 | 14.9 +/− 1.1 | 0 +/− 0 |
| PROCOLL., TYPE XIV, ALPHA 1 | Col14a1 | AJ131395 | 0 +/− 0 | 0 +/− 0 | 0 +/− 0 | 0 +/− 0 | 4.1 +/− 0.8 | 2.1 +/− 0.3 |
| PROCOLL., TYPE IX, ALPHA 1 | Col9a1 | D17511 | 0 +/− 0 | 0 +/− 0 | 0 +/− 0 | 0 +/− 0 | 14 +/− 0.7 | 0 +/− 0 |
| PROCOLL., TYPE XV | Col15a1 | D17546 | 0 +/− 0 | 0 +/− 0 | 0 +/− 0 | 0 +/− 0 | 6.9 +/− 0.6 | 3.9 +/− 0.7 |

TABLE 5-continued

BMP-2-induced changes in the expression of known genes previously associated with bone or cartilage metabolism.

| Gene Title | Symbol | GenBank | Day 1 | Day 2 | Day 3 | Day 4 | Day 7 | Day 14 |
|---|---|---|---|---|---|---|---|---|
| BONE GLA. PROT., RELATED SEQ. 1 | Bglap-rs1 | L24430 | 0 +/- 0 | 0 +/- 0 | 0 +/- 0 | 0 +/- 0 | 0 +/- 0 | 77.8 +/- 18.8 |
| EXTRACELLULAR MATRIX PROT. 1 | Ecm1 | L33416 | 0 +/- 0 | 2.4 +/- 0.2 | 2.6 +/- 0.2 | 3 +/- 0.4 | 3.2 +/- 0.6 | 5.1 +/- 0.2 |
| ELASTIN | Eln | U08210 | 0 +/- 0 | 0 +/- 0 | 0 +/- 0 | 0 +/- 0 | 0 +/- 0 | 4.2 +/- 1.8 |
| ALPHA 3 TYPE IX COLLAGEN. | Col9a3 | X91012 | 0 +/- 0 | 0 +/- 0 | 0 +/- 0 | 0 +/- 0 | 9.8 +/- 0.8 | 0 +/- 0 |
| PROCOLL., TYPE IX, ALPHA 2 | Col9a2 | Z22923 | 0 +/- 0 | 0 +/- 0 | 0 +/- 0 | 0 +/- 0 | 4.4 +/- 2.1 | 0 +/- 0 |
| Extracellular Proteins | | | | | | | | |
| NEUROBLASTOMA, SUPP. OF TUMORIGEN. 1 | Nbl1 | D50263 | 0 +/- 0 | 0 +/- 0 | 0 +/- 0 | 0 +/- 0 | 6 +/- 3.7 | 5.5 +/- 1.1 |
| IGF BINDING PROT. 4 | Igfbp4 | X76066 | 0 +/- 0 | 0 +/- 0 | 0 +/- 0 | 0 +/- 0 | 7.1 +/- 1.2 | 5.4 +/- 0.4 |
| APOLIPOPROT. E | Apoe | D00466 | 0 +/- 0 | 1.8 +/- 0.4 | 2.4 +/- 0.1 | 2.7 +/- 0.1 | 3.8 +/- 0.2 | 4.8 +/- 0.3 |
| IGF BINDING PROT. 3 | Igfbp3 | X81581 | 0 +/- 0 | 0 +/- 0 | 0 +/- 0 | 0 +/- 0 | 5 +/- 0.4 | 3.2 +/- 1 |
| VITRONECTIN | Vtn | M77123 | -2.1 +/- 0.2 | -4.2 +/- 1 | -2.3 +/- 0.3 | 0 +/- 0 | 0 +/- 0 | 0 +/- 0 |
| Intracellular Proteins | | | | | | | | |
| CELL DIV. CYCLE 2 HOMOLOG A | Cdc2a | M38724 | 1.6 +/- 0.6 | 7.2 +/- 1.1 | 10.6 +/- 0.9 | 13.4 +/- 3.9 | 12.1 +/- 1.6 | 4 +/- 0.2 |
| LYSYL OXIDASE | Lox | M65142 | 0 +/- 0 | 5.3 +/- 0.7 | 8.9 +/- 1 | 12.6 +/- 0.6 | 22.8 +/- 1.3 | 15.5 +/- 0.9 |
| PROCOLL-LYS., 2-OXOGLUT. 5-DIOXYGEN. 2 | Plod2 | AF080572 | 0 +/- 0 | 2.9 +/- 0.4 | 6.2 +/- 2.6 | 15.2 +/- 4.4 | 13.5 +/- 1.8 | 11.6 +/- 1.7 |
| ALK. PHOSPHATASE 2, LIVER | Akp2 | J02980 | 0 +/- 0 | 0 +/- 0 | 5 +/- 1 | 6.1 +/- 3.6 | 32.6 +/- 2.9 | 18.5 +/- 3.8 |
| HEME OXYGENASE (DECYCLING) 1 | Hmox1 | X13356 | 1.9 +/- 0.3 | 4 +/- 1.5 | 4.5 +/- 1.2 | 7.3 +/- 2.3 | 8.2 +/- 0.3 | 7.6 +/- 1 |
| PROCOLL-LYS., 2-OXOGLUT. 5-DIOXYGEN. 3 | Plod3 | AF046783 | 0 +/- 0 | 3.7 +/- 0.6 | 4.6 +/- 0.2 | 5.1 +/- 0.5 | 8.5 +/- 0.7 | 3.8 +/- 0.9 |
| PHOSPHOLIPASE A2, GROUP 4 | Pla2g4 | M72394 | 0 +/- 0 | 2.6 +/- 0.5 | 3.9 +/- 0.1 | 6.9 +/- 1.8 | 7.2 +/- 0.6 | 4.4 +/- 0.1 |
| ATPASE. H+ TRANSPORTING, LYSOSOMAL I | Tcirg1 | AB022322 | 0 +/- 0 | 0 +/- 0 | 3.1 +/- 0.8 | 0 +/- 0 | 7 +/- 1.4 | 27.8 +/- 2.4 |
| LYSYL OXIDASE-LIKE PROT. 2 | Loxl2 | AF117951 | 0 +/- 0 | 0 +/- 0 | 0 +/- 0 | 7.2 +/- 0.6 | 7.7 +/- 0.8 | 2.1 +/- 0.4 |
| PROSTAGLAN.-ENDOPEROX. SYNTHASE 2 | Ptgs2 | M64291 | 0 +/- 0 | 2.5 +/- 0.3 | 2.3 +/- 0 | 8.9 +/- 3.4 | 5.5 +/- 1.2 | -0.3 +/- 1.6 |

TABLE 5-continued

BMP-2-induced changes in the expression of known genes previously associated with bone or cartilage metabolism.

| Gene Title | Symbol | GenBank | Day 1 | Day 2 | Day 3 | Day 4 | Day 7 | Day 14 |
|---|---|---|---|---|---|---|---|---|
| CREATINE KINASE, BRAIN | Ckb | M74149 | 0 +/− 0 | 0 +/− 0 | 0 +/− 0 | 0 +/− 0 | 4.6 +/− 0.6 | 28.6 +/− 2 |
| CALRETICULIN | Calr | X14926 | 0 +/− 0 | 2.9 +/− 0.2 | 3 +/− 0.3 | 4.1 +/− 0.6 | 5.5 +/− 0.2 | 3.9 +/− 0.3 |
| BCL2-ASSOCIATED X PROT. | Bax | L22472 | 0 +/− 0 | 2.5 +/− 0.4 | 2.1 +/− 0.2 | 0 +/− 0 | 4.9 +/− 0.8 | 0 +/− 0 |
| CARBONIC ANHYDRASE 2 | Car2 | M81022 | 0 +/− 0 | 0 +/− 0 | 0 +/− 0 | 0 +/− 0 | 0.3 +/− 1.4 | 13.8 +/− 3.7 |
| LYSYL OXIDASE-LIKE | Loxl | U79144 | 0 +/− 0 | 2 +/− 0.1 | 0 +/− 0 | 3.5 +/− 0.1 | 4.6 +/− 0.6 | 3.4 +/− 0.3 |
| FATTY ACID SYNTHASE | Fasn | X13135 | 0 +/− 0 | −1.5 +/− 2.6 | −4.4 +/− 0.6 | −3.3 +/− 2.4 | −3.9 +/− 1.2 | −0.2 +/− 2.3 |
| Proteases | | | | | | | | |
| TISSUE INHIB. OF METALLOPROT. | Timp | M17243 | 1.1 +/− 2 | 12.8 +/− 3.2 | 25.4 +/− 7.6 | 48.1 +/− 11.6 | 100.3 +/− 11 | 56 +/− 3.5 |
| SERINE PROTEASE INHIB. 2-2 | Spi2-2 | M64086 | 0 +/− 0 | 6.8 +/− 1.2 | 7.4 +/− 0.8 | 8.3 +/− 2.5 | 7.7 +/− 1.3 | 2.4 +/− 1.1 |
| BONE MORPHOGENETIC PROT. 1 | Bmp1 | L24755 | 0 +/− 0 | 0 +/− 0 | 2.9 +/− 0.5 | 6.8 +/− 1.7 | 23 +/− 4.1 | 18.1 +/− 0.3 |
| MATRIX METALLOPROT. 14 | Mmp14 | U54984 | 0 +/− 0 | 2.8 +/− 0.4 | 2.7 +/− 0 | 7 +/− 1.3 | 23.1 +/− 3.8 | 18.1 +/− 4.6 |
| CATHEPSIN K | Ctsk | X94444 | 0 +/− 0 | 0 +/− 0 | 0 +/− 0 | 6.1 +/− 4 | 11.3 +/− 3.1 | 47 +/− 1.6 |
| MATRIX METALLOPROT. 9 | Mmp9 | Z27231 | 0 +/− 0 | 0 +/− 0 | 0 +/− 0 | 20 +/− 16.8 | 16.3 +/− 12.3 | 221.5 +/− 18 |
| PROCOLL. C-PROT. ENHANCER PROT. | Pcolce | AB008548 | 0 +/− 0 | 0 +/− 0 | 0 +/− 0 | 3.3 +/− 0.5 | 7 +/− 1.2 | 6.7 +/− 0.8 |
| PLASMINOGEN ACT., TISSUE | Plat | J03520 | 0 +/− 0 | 0 +/− 0 | 0 +/− 0 | 0 +/− 0 | 5.3 +/− 1.3 | 4.6 +/− 0.6 |
| MATRIX METALLOPROT. 2 | Mmp2 | M84324 | −2.1 +/− 0.3 | −1.8 +/− 0.1 | 0.1 +/− 1.7 | 2.7 +/− 0.4 | 8.1 +/− 1.1 | 7.2 +/− 0.6 |
| UROKINASE PLASMINOGEN ACT. RECEPT. | Plaur | X62700 | 1.7 +/− 0.3 | 3.1 +/− 0.5 | 0 +/− 0 | 4.4 +/− 1 | 7.8 +/− 0.7 | 2.3 +/− 0.4 |
| MATRIX METALLOPROT. 13 | Mmp 13 | X66473 | 0 +/− 0 | 0 +/− 0 | 0 +/− 0 | 0 +/− 0 | 19.3 +/− 2.5 | 144.8 +/− 24 |
| PLASMINOGEN ACT. INHIB., TYPE I | Serpine 1 | M33960 | 0 +/− 0 | 2.9 +/− 0.7 | 2.8 +/− 0.3 | 5 +/− 1.3 | 3.2 +/− 0.5 | 0 +/− 0 |
| TISSUE INHIB. OF METALLOPROT. 2 | Timp2 | X62622 | 0 +/− 0 | 1.7 +/− 0.1 | 1.8 +/− 0 | 2.6 +/− 0.4 | 4.7 +/− 0.9 | 3.8 +/− 0.5 |
| Receptors | | | | | | | | |
| TGF BETA INDUCED, 68 KDA | Tgfbi | L19932 | 2.8 +/− 0.7 | 6 +/− 2 | 5.6 +/− 0.7 | 7.8 +/− 0.7 | 5.3 +/− 1 | 2 +/− 0.4 |
| PARATHYROID HORMONE RECEPT. | Pthr | X78936 | 0 +/− 0 | 0 +/− 0 | 3 +/− 0.1 | 6 +/− 1.9 | 57.4 +/− 1.3 | 25.5 +/− 1.1 |

TABLE 5-continued

BMP-2-induced changes in the expression of known genes previously associated with bone or cartilage metabolism.

| Gene Title | Symbol | GenBank | Day 1 | Day 2 | Day 3 | Day 4 | Day 7 | Day 14 |
|---|---|---|---|---|---|---|---|---|
| PTP, RECEPT. TYPE, D | Ptprd | D13903 | 0 +/− 0 | 0 +/− 0 | 0 +/− 0 | 1.6 +/− 0.1 | 6.6 +/− 0.4 | 8.7 +/− 2.2 |
| IL-4 RECEPT., ALPHA | Il4ra | M29854 | 0 +/− 0 | 4.8 +/− 1.4 | 2.9 +/− 0.1 | 0 +/− 0 | 8.1 +/− 0.7 | 0 +/− 0 |
| FIBROBL. GROWTH FACT. RECEPT. 2 | Fgfr2 | M86441 | 0 +/− 0 | 0 +/− 0 | 0 +/− 0 | 0 +/− 0 | 15.3 +/− 2.5 | 7.9 +/− 1.3 |
| COLONY STIM. FACT. 1 RECEPT. | Csf1r | X68932 | 1.8 +/− 0.5 | 3.2 +/− 0.4 | 3.3 +/− 0.5 | 4.1 +/− 0.6 | 3.5 +/− 0.6 | 10.9 +/− 0.9 |
| ACTIVIN A RECEPT., TYPE 1 | Acvr1 | L15436 | 0 +/− 0 | 0 +/− 0 | 1.9 +/− 0.2 | 2.7 +/− 0.3 | 4.6 +/− 0.1 | 0 +/− 0 |
| COLONY STIM. FACT. 3 RECEPT. | Csf3r | M58288 | 0 +/− 0 | 0 +/− 0 | 0 +/− 0 | 0 +/− 0 | 0 +/− 0 | 4.9 +/− 0.9 |
| COLONY STIM. FACT. 2 RECEPT., ALPHA | Csf2ra | M85078 | 0 +/− 0 | 2.6 +/− 0.7 | 3.3 +/− 0.3 | 0 +/− 0 | 4.8 +/− 0.8 | 3.9 +/− 0.4 |
| TGF BETA RECEPT. II | Tgfbr2 | S69114 | 0 +/− 0 | 0 +/− 0 | 0 +/− 0 | 0 +/− 0 | 0 +/− 0 | 4.7 +/− 1 |
| Signal Transduction | | | | | | | | |
| C-SRC TYROSINE KINASE | Csk | U05247 | 0 +/− 0 | 2.6 +/− 0.3 | 0 +/− 0 | 2.9 +/− 0.1 | 4.9 +/− 0.4 | 3.6 +/− 0.2 |
| Transcription Factors | | | | | | | | |
| MAD HOMOLOG 6 | Madh6 | AF010133 | 6.7 +/− 3 | 8.1 +/− 1.7 | 9.9 +/− 2.3 | 4.6 +/− 0.9 | 7.7 +/− 2.9 | 5.5 +/− 0.5 |
| INHIB. OF DNA BINDING 1 | Idb1 | M31885 | 3.6 +/− 0.7 | 8.1 +/− 1.9 | 7.6 +/− 0.8 | 4.9 +/− 1.9 | 4.4 +/− 1.7 | 4.9 +/− 0.6 |
| INHIB. OF DNA BINDING 2 | Idb2 | M69293 | 2.4 +/− 0.6 | 4.5 +/− 0.6 | 5.7 +/− 1.4 | 4.8 +/− 0.5 | 11.9 +/− 3.2 | 5.7 +/− 0.7 |
| RUNT RELATED TRANSCRIP. FACT. 2 | Runx2 | D14636 | 0 +/− 0 | 2.6 +/− 0.5 | 3.8 +/− 0.2 | 8.9 +/− 2.7 | 15.8 +/− 1.3 | 20.1 +/− 4.9 |
| JUN-B ONCOGENE | Junb | J03236 | 0.9 +/− 1.7 | 4.4 +/− 0.5 | 2.7 +/− 0 | 3.6 +/− 1.2 | 5.1 +/− 1 | 2.3 +/− 0.4 |
| SCLERAXIS | Scx | S78079 | 0 +/− 0 | 3.8 +/− 1.9 | 6.9 +/− 3.8 | 0 +/− 0 | 19.4 +/− 6 | 0 +/− 0 |
| SIG. TRANS. AND ACT. OF TRANS-CRIP. 1 | Stat1 | U06924 | 0 +/− 0 | 2.2 +/− 0.3 | 3.5 +/− 0.9 | 4.7 +/− 0.3 | 2.7 +/− 0.1 | 5.2 +/− 3.2 |
| DISTAL-LESS HOMEOBOX 5 | Dlx5 | U67840 | 0 +/− 0 | 0 +/− 0 | 0 +/− 0 | 0 +/− 0 | 8.5 +/− 1 | 7.5 +/− 1 |
| NUC. FACT. ACTIV. T-CELLS, CYTOPLAS. 1 | Nfatc1 | AF049606 | 0 +/− 0 | 0 +/− 0 | 0 +/− 0 | 0 +/− 0 | 2.7 +/− 0.8 | 5.2 +/− 0.8 |
| MAD HOMOLOG 2 | Madh2 | U60530 | 0 +/− 0 | 2 +/− 0.3 | 2.5 +/− 0.2 | 0 +/− 0 | 4.5 +/− 0.7 | 0 +/− 0 |
| SLUG | Slugh | U79550 | 0 +/− 0 | 0 +/− 0 | 0 +/− 0 | 0 +/− 0 | 4.4 +/− 3.1 | 0 +/− 0 |
| INHIB. OF DNA BINDING 4 | Idb4 | X75018 | 2.8 +/− 1.4 | 3.5 +/− 0.6 | 3.7 +/− 1.2 | 0 +/− 0 | 1.7 +/− 0.2 | 6 +/− 0.3 |

TABLE 6

BMP-2-induced changes in the expression of known genes not explicitly associated with bone or cartilage metabolism*.

| Gene Title | Symbol | GenBank | Day 1 | Day 2 | Day 3 | Day 4 | Day 7 | Day 14 |
|---|---|---|---|---|---|---|---|---|
| Cell Surface Proteins | | | | | | | | |
| CD68 ANTIGEN | Cd68 | X68273 | 2.2 +/- 0.5 | 3.2 +/- 0.5 | 3.8 +/- 0.6 | 5.1 +/- 0.6 | 6.5 +/- 1.1 | 15.8 +/- 0.5 |
| FIBROBL. ACTIVATION PROT. | Fap | Y10007 | 0 +/- 0 | 0 +/- 0 | 0 +/- 0 | 2.3 +/- 0.1 | 5.6 +/- 0.7 | 10.9 +/- 0.4 |
| CD9 ANTIGEN | Cd9 | L08115 | 0 +/- 0 | 0 +/- 0 | 0 +/- 0 | 0 +/- 0 | 3.5 +/- 0.3 | 4.1 +/- 0.1 |
| HEPATIC LIPASE | Lipc | X58426 | 0 +/- 0 | 0 +/- 0 | 0 +/- 0 | 0 +/- 0 | 0 +/- 0 | 4.5 +/- 0.9 |
| SELECTIN, PLATELET (P-SELECTIN) LIGAND | Selpl | X91144 | 0 +/- 0 | 2.3 +/- 0.2 | 2.5 +/- 0.3 | 3.2 +/- 0.4 | 3.2 +/- 0.3 | 7.2 +/- 0.6 |
| EPHRIN B1 | Efnbl | Z48781 | 0 +/- 0 | 0 +/- 0 | 1.6 +/- 0.1 | 0 +/- 0 | 5.9 +/- 1 | 3.4 +/- 1.2 |
| Cytokines | | | | | | | | |
| MONO. CHEMOTACTIC PROT.-3 | Scya7 | S71251 | 4.1 +/- 0.7 | 9.3 +/- 1.7 | 5.7 +/- 2.3 | 8.1 +/- 2.2 | 6.6 +/- 1.5 | 0 +/- 0 |
| SMALL INDUCIB. CYTOKINE A12 | Scya12 | U50712 | 1.9 +/- 0.1 | 4.1 +/- 2.1 | 5.6 +/- 0.8 | 3.8 +/- 0.1 | 10.7 +/- 2 | 0 +/- 0 |
| SECRETED FRIZZLED-RELATED PROT. 1 | Sfrpl | U88566 | 0 +/- 0 | 2.8 +/- 0.9 | 5.9 +/- 0.5 | 11.4 +/- 5.9 | 9.3 +/- 1.8 | 2.5 +/- 0.5 |
| SMALL INDUCIB. CYTOKINE B MEMBER 9 | Scyb9 | M34815 | 0 +/- 0 | 0 +/- 0 | 3.4 +/- 0.5 | 5.2 +/- 0.4 | 3.6 +/- 0.6 | 7 +/- 7.7 |
| VASCULAR ENDOTHELIAL GROWTH FACT. B | Vegftb | U48800 | 0 +/- 0 | -2.3 +/- 1 | 0 +/- 0 | -9.6 +/- 9.3 | -7.8 +/- 3.9 | -2.7 +/- 0.4 |
| SMALL INDUCIB. CYTOKINE A11 | Scya11 | U40672 | -4.1 +/- 2 | -3.4 +/- 0.4 | 0 +/- 0 | -1.5 +/- 0.3 | -2.6 +/- 1 | -2.4 +/- 0.5 |
| Extracellular Proteins | | | | | | | | |
| LIPOCORTIN 1 | Anxa1 | M24554 | 2 +/- 0.5 | 2.4 +/- 0.2 | 2.7 +/- 0.6 | 3.8 +/- 0.6 | 4.5 +/- 0.8 | 5 +/- 0.2 |
| SECRETED FRIZZLED-RELATED PROT. 4 | Sfrp4 | AF117709 | 0 +/- 0 | -1.3 +/- 0.1 | 0 +/- 0 | 0 +/- 0 | 0 +/- 0 | 12.7 +/- 0.8 |
| SUPEROX. DISMUTASE 3, EXTRACELL. | Sod3 | D50856 | 0 +/- 0 | 4 +/- 1.1 | 3.8 +/- 0.1 | 3.6 +/- 1 | 4.4 +/- 0.8 | 0 +/- 0 |
| ANNEXIN A4 | Anxa4 | U72941 | 0 +/- 0 | 1 +/- 1.8 | 2.1 +/- 0.2 | 2.9 +/- 0.4 | 3.8 +/- 0.9 | 4.2 +/- 0.1 |
| AMYLOID BETA (A4) PRECUR. PROT. | App | U84012 | 0 +/- 0 | 1.8 +/- 0.2 | 1.6 +/- 0.2 | 2.5 +/- 0 | 4 +/- 0.6 | 2.7 +/- 0.4 |
| Intracellular Proteins | | | | | | | | |
| PLASTIN 2, L | Pls2 | D37837 | 0 +/- 0 | 4.5 +/- 0.8 | 4.3 +/- 0.4 | 5.2 +/- 0.3 | 8.1 +/- 0.9 | 11.4 +/- 1.1 |
| CYSTEINE-RICH PROT. 2 | Csrp2 | AF037208 | 0 +/- 0 | 3.8 +/- 0.3 | 8.4 +/- 1.9 | 15.8 +/- 3.4 | 25.8 +/- 7.5 | 6.5 +/- 0.8 |
| FGF REGULATED PROT. | Fgfrp | U04204 | 0 +/- 0 | 3.7 +/- 0.7 | 4 +/- 0.9 | 5.7 +/- 1.4 | 5.6 +/- 0.7 | 5.9 +/- 0.8 |

TABLE 6-continued

BMP-2-induced changes in the expression of known genes not explicitly associated with bone or cartilage metabolism*.

| Gene Title | Symbol | GenBank | Day 1 | Day 2 | Day 3 | Day 4 | Day 7 | Day 14 |
|---|---|---|---|---|---|---|---|---|
| CARBONYL REDUCTASE 2 | Cbr2 | D26123 | 1.6 +/− 0.4 | 4.6 +/− 0.4 | 6.8 +/− 0.5 | 5.1 +/− 0.2 | 2.1 +/− 0.1 | 1.9 +/− 0.2 |
| ENDO-PLASMIC RETICULUM PROT. | Grp58 | M73329 | 0 +/− 0 | 2.8 +/− 0.2 | 2.8 +/− 0.3 | 4.8 +/− 0.8 | 7 +/− 1.6 | 4.3 +/− 0.3 |
| CYCLIN D1 | Cyl-1 | S78355 | 0 +/− 0 | 3.2 +/− 0.1 | 4.5 +/− 0.2 | 0 +/− 0 | 7.2 +/− 0.6 | 6.4 +/− 0.6 |
| TRANSPORTER 1, ATP BINDING CASSETTE | Abcb2 | U60019 | 0 +/− 0 | 1.8 +/− 0.4 | 4.2 +/− 0.2 | 3.7 +/− 0.9 | 4.9 +/− 0.2 | 5.3 +/− 2.9 |
| 2'-5' OLIGOADENYLATE SYNTHETASE 1A | Oas1a | X04958 | 1.8 +/− 0.2 | 2.8 +/− 0.6 | 4.3 +/− 0.7 | 5.8 +/− 1.2 | 5.1 +/− 0.4 | 3.7 +/− 0.5 |
| CALCIUM BIND. PROT. A11 (CALGIZZARIN) | S100a10 | M16465 | 1.9 +/− 0.5 | 2.5 +/− 0.1 | 2.8 +/− 0.5 | 3.4 +/− 0.2 | 4.4 +/− 0.7 | 4.2 +/− 0.3 |
| MYOSIN LIGHT CHAIN, ALKALI, ATRIA | Myla | M19436 | 0 +/− 0 | 0 +/− 0 | 0 +/− 0 | 0 +/− 0 | 8 +/− 2.5 | 5.5 +/− 1.1 |
| RETINOL BINDING PROT. 1, CELLULAR | Rbp1 | X60367 | 0 +/− 0 | 0 +/− 0 | 0 +/− 0 | 4.1 +/− 0.9 | 7.1 +/− 0.8 | 2.4 +/− 0.1 |
| CYCLIN A2 | Ccha2 | Z26580 | 0 +/− 0 | 3.1 +/− 0.5 | 3.6 +/− 0.7 | 4.8 +/− 0.3 | 5.7 +/− 0.3 | 1.9 +/− 0.2 |
| PROCOLL-LYS., 2-OXOGLUT. 5-DIOXYGEN. 1 | Plod1 | AF046782 | 0 +/− 0 | 0 +/− 0 | 0 +/− 0 | 0 +/− 0 | 5.2 +/− 1.1 | 3.4 +/− 0.4 |
| GALACTOSYLTRANSFERASE, POLYPEP. 1 | B4galt1 | J03880 | 0 +/− 0 | 0 +/− 0 | 0 +/− 0 | 0 +/− 0 | 8 +/− 1.8 | 0 +/− 0 |
| RHO, GDP DISSOCIATION INHIB. BETA | Arhgdib | L07918 | 0 +/− 0 | 4 +/− 0.4 | 3.1 +/− 0.3 | 3.3 +/− 0.5 | 4.4 +/− 0.3 | 3.8 +/− 1.2 |
| STEROL O-ACYL-TRANSFERASE 1 | Soat1 | L42293 | 0 +/− 0 | 2.5 +/− 0.6 | 2.2 +/− 0.2 | 3.6 +/− 0.2 | 5.4 +/− 0.9 | 2.9 +/− 0.7 |
| CYCLIN D2 | Ccnd2 | M83749 | 0 +/− 0 | 0 +/− 0 | 0 +/− 0 | 0 +/− 0 | 4.2 +/− 0.1 | 3.7 +/− 0.1 |
| RAT PROTEASOME HOMOLOG | Psmb9 | S59862 | 0 +/− 0 | 2.8 +/− 0.5 | 3.3 +/− 0.4 | 5.5 +/− 0.9 | 0 +/− 0 | 3.8 +/− 4.1 |
| LYMPHOCYTE CYTOSOLIC PROT. 2 | Lcp2 | U20159 | 0 +/− 0 | 2.4 +/− 0.4 | 2.5 +/− 0.3 | 3.1 +/− 0.7 | 3.2 +/− 0.6 | 4.8 +/− 0.2 |
| TRANSPORTER 2, ATP BINDING CASSETTE | Abcb3 | U60087 | 0 +/− 0 | 0 +/− 0 | 0 +/− 0 | 0 +/− 0 | 0 +/− 0 | 4.7 +/− 2.1 |
| CAPPING PROT., GELSOLIN-LIKE | Capg | X54511 | 0 +/− 0 | 2.6 +/− 0.2 | 2.6 +/− 0.4 | 3 +/− 0.1 | 3.8 +/− 0.4 | 4.7 +/− 1 |
| CYCLIN B1, RELATED SEQ. 1 | Ccnb1-rs1 | X58708 | 0+/−0 | 2.4 +/− 0.2 | 3.1 +/− 0.2 | 3.9 +/− 0.4 | 4.1 +/− 0.1 | 1.7 +/− 0.2 |

TABLE 6-continued

BMP-2-induced changes in the expression of known genes not explicitly associated with bone or cartilage metabolism*.

| Gene Title | Symbol | GenBank | Day 1 | Day 2 | Day 3 | Day 4 | Day 7 | Day 14 |
|---|---|---|---|---|---|---|---|---|
| CYCLIN B2 | Ccnb2 | X66032 | 0 +/− 0 | 3.6 +/− 0.5 | 2.7 +/− 0.6 | 4.4 +/− 0.7 | 2.9 +/− 0.2 | 2.2 +/− 0.4 |
| HISTONE DEACETYLASE 1 | Hdac1 | X98207 | 0 +/− 0 | 0 +/− 0 | 3.2 +/− 0.2 | 0 +/− 0 | 7.3 +/− 0.7 | 3.2 +/− 0.3 |
| Proteases | | | | | | | | |
| MATRIX METALLOPROT. 23 | Mmp23 | AF085742 | 0 +/− 0 | 0 +/− 0 | 0 +/− 0 | 11.2 +/− 1 | 39.9 +/− 3 | 15.7 +/− 0.6 |
| CASPASE 6 | Casp6 | Y13087 | 0 +/− 0 | 0 +/− 0 | 2.8 +/− 1.3 | 4.9 +/− 2.1 | 7.6 +/− 1.6 | 7.7 +/− 0.9 |
| CATHEPSIN H | Ctsh | U06119 | 0 +/− 0 | 2.1 +/− 0.4 | 2.3 +/− 0.2 | 3.6 +/− 0.2 | 5.8 +/− 0.8 | 4.4 +/− 0.6 |
| CATHEPSIN S | Ctss | AF03854 | 1.8 +/− 0.3 | 2.8 +/− 0.5 | 3.2 +/− 0.4 | 4 +/− 0 | 3.8 +/− 0.5 | 5.4 +/− 1 |
| PROTEOSOME SUBUNIT, BETA TYPE 8 | Psmb8 | U22032 | 0 +/− 0 | 2.9 +/− 0.4 | 3.5 +/− 0.2 | 3.7 +/− 0.6 | 3.4 +/− 0.3 | 6.3 +/− 4.3 |
| SERINE PROTEASE INHIB. 4 | Serpine2 | X70296 | 0 +/− 0 | 0 +/− 0 | 0 +/− 0 | 0 +/− 0 | 3.4 +/− 0.3 | 8.9 +/− 1.2 |
| Receptors | | | | | | | | |
| IL-2 RECEPT., GAMMA CHAIN | Il2rg | L20048 | 0 +/− 0 | 3.9 +/− 0.7 | 4.7 +/− 0.2 | 5.6 +/− 0.5 | 7.9 +/− 0.8 | 5.3 +/− 0.9 |
| CYTOKINE RECEPT.-LIKE FACT. 1 | Crlf1 | AB04003I | 3 +/− 1.1 | 7.6 +/− 1 | 7.2 +/− 2.9 | 14.7 +/− 6.4 | 8.8 +/− 4 | 2.1 +/− 0.5 |
| FC RECEPT., IGG, HIGH AFFINITY 1 | Fcgr1 | X70980 | 2.7 +/− 0.5 | 7.6 +/− 2.7 | 7.3 +/− 0.6 | 6.7 +/− 1.2 | 4.8 +/− 1.1 | 0 +/− 0 |
| PTP, RECEPT. TYPE, C | Ptprc | M14342 | 2.5 +/− 0.5 | 3.4 +/− 0.4 | 4.3 +/− 1.7 | 5.2 +/− 0.9 | 3.3 +/− 0.8 | 6.8 +/− 0.8 |
| CHEMOKINE (C-C) RECEPT. 2 | Cmkbr2 | U51717 | 2.9 +/− 1 | 6.1 +/− 0.8 | 5.1 +/− 1.3 | 4.2 +/− 0.4 | 3.4 +/− 0.6 | 3.6 +/− 0.4 |
| TNF RECEPT. SUPERFAMILY, MEMBER 1A | Tnfrsf1a | L26349 | 1.4 +/− 0.3 | 2.7 +/− 0.2 | 1.9 +/− 0 | 2.8 +/− 0.1 | 4.1 +/− 0.2 | 4 +/− 0.1 |
| CHEMOKINE (C-C) RECEPT. 1 | Cmkbr1 | U29678 | 3.4 +/− 1.6 | 4.9 +/− 1 | 2.4 +/− 0.7 | 2.8 +/− 0.2 | 1.9 +/− 0.2 | 13.3 +/− 0.6 |
| PDGF RECEPT., BETA POLYPEPTIDE | Pdgfrb | X04367 | 0 +/− 0 | 0 +/− 0 | 0 +/− 0 | 0 +/− 0 | 4.6 +/− 1.5 | 4.8 +/− 1 |
| PTP. RECEPT. TYPE, S | Ptprs | X82288 | 0 +/− 0 | 0 +/− 0 | 0 +/− 0 | 0 +/− 0 | 4.1 +/− 0.7 | 5.4 +/− 0.5 |
| FRIZZLED-1 | Fzd1 | AF054623 | 0 +/− 0 | 0 +/− 0 | 0 +/− 0 | 0 +/− 0 | 5 +/− 1 | 1.4 +/− 0.4 |
| ANGIOTENSIN RECEPT.-LIKE 1 | Agtrl1 | AJ007612 | 0 +/− 0 | 0 +/− 0 | 0 +/− 0 | 0 +/− 0 | 4.2 +/− 0.6 | 2.9 +/− 0.1 |
| LEUKEMIA INHIB. Y FACT. RECEPT. | Lifr | D17444 | 0 +/− 0 | 1.2 +/− 0.1 | 0 +/− 0 | 0 +/− 0 | 3.2 +/− 0.3 | 9.9 +/− 1.3 |
| FC RECEPT., IGG, LOW AFFINITY III | Fcgr3 | M14215 | 0 +/− 0 | 3.6 +/− 0.4 | 3.4 +/− 0.3 | 3.6 +/− 0.2 | 4.2 +/− 0.4 | 0 +/− 0 |

TABLE 6-continued

BMP-2-induced changes in the expression of known genes not explicitly associated with bone or cartilage metabolism*.

| Gene Title | Symbol | GenBank | Day 1 | Day 2 | Day 3 | Day 4 | Day 7 | Day 14 |
|---|---|---|---|---|---|---|---|---|
| PTP. RECEPT. TYPE, A | Ptpra | M36033 | 0 +/− 0 | 0 +/− 0 | 0 +/− 0 | 2.9 +/− 0.1 | 3.9 +/− 0.7 | 4 +/− 0.4 |
| CHEMOKINE (C-C) RECEPT. 5 | Cmkbr5 | U47036 | 2.7 +/− 1 | 4.8 +/− 1.9 | 2.6 +/− 0.1 | 3.5 +/− 0.2 | 3.2 +/− 0.2 | 1.5 +/− 0.2 |
| EPH RECEPT. A2 | Epha2 | X76010 | 0 +/− 0 | 0 +/− 0 | 0 +/− 0 | 0 +/− 0 | 5.1 +/− 0.9 | 3 +/− 0.2 |
| EPH RECEPT. B3 | Ephb3 | Z49086 | 0 +/− 0 | 0 +/− 0 | 0 +/− 0 | 2.5 +/− 1 | 7.1 +/− 1.5 | 2.9 +/− 0.2 |
| RETINOID X RECEPT. GAMMA | Rxrg | X66225 | 0 +/− 0 | 0 +/− 0 | 0 +/− 0 | −4.2 +/− 3.1 | −4.5 +/− 0.4 | −4.6 +/− 2.5 |
| Signal Transduction | | | | | | | | |
| APLYSIA RAS-RELATED HOMOLOG 9 | Arhc | X80638 | 0 +/− 0 | 0 +/− 0 | 3.5 +/− 0.4 | 5.7 +/− 0.3 | 7 +/− 0.8 | 7.6 +/− 0.2 |
| FYN PROTO-ONCOGENE | Fyn | M27266 | 0 +/− 0 | 0 +/− 0 | 1.5 +/− 0.4 | 2.2 +/− 0.1 | 4.2 +/− 0.5 | 4.4 +/− 0.7 |
| RAS P21 PROT. ACT. 3 | Rasa3 | U20238 | 0 +/− 0 | 0 +/− 0 | 0 +/− 0 | 0 +/− 0 | 4.4 +/− 0.4 | 4.7 +/− 0.5 |
| DOWN-STREAM OF TYROSINE KINASE 1 | Dok1 | U78818 | 0 +/− 0 | 1.7 +/− 0.5 | 2.7 +/− 1.1 | 4.5 +/− 1.4 | 5.4 +/− 1.5 | 3.3 +/− 0.1 |
| MITOGEN-ACTIVATED PROT. (KINASE)4 | Map4k4 | U88984 | 0 +/− 0 | 2 +/− 0.3 | 2.6 +/− 0.3 | 3.1 +/− 0.1 | 5.2 +/− 0.5 | 4.9 +/− 0.7 |
| VAV ONCOGENE | Vav | X64361 | 0 +/− 0 | 4.3 +/− 0.4 | 3.2 +/− 0.2 | 4 +/− 0.4 | 2.3 +/− 0.2 | 0 +/− 0 |
| HEMATO. CELL SPECIFIC LYN SUBSTR. 1 | Hcls1 | X84797 | 2.7 +/− 1.3 | 5.6 +/− 1.5 | 4.2 +/− 1.3 | 3.2 +/− 0.6 | 4 +/− 0.9 | 3.1 +/− 0.5 |
| REGULATOR OF G-PROT. SIG. 2 | Rgs2 | AF215668 | 0 +/− 0 | 1.5 +/− 0.4 | 2.9 +/− 0.9 | 3.2 +/− 0.2 | 2.8 +/− 0.6 | 5.6 +/− 0.7 |
| ANNEXIN A8 | Anxa8 | AJ002390 | 0 +/− 0 | 0 +/− 0 | 0 +/− 0 | 0 +/− 0 | 8.3 +/− 1.6 | 3.8 +/− 0.2 |
| CYCLIN-DEPENDENT KINASE 4 | Cdk4 | L01640 | 0 +/− 0 | 2.4 +/− 0.2 | 2.5 +/− 0 | 3.4 +/− 0.7 | 5.2 +/− 0.7 | 3.5 +/− 0.1 |
| INOSITOL POLY-PHOS.-5-PHOS-PHATASE | Inpp5d | U52044 | 0 +/− 0 | 1.9 +/− 0.3 | 1.9 +/− 0.5 | 0 +/− 0 | 3.7 +/− 0.8 | 4.3 +/− 0.4 |
| CYTO. INDUCIB. SH2-CON-TAINING PROT. 3 | Cish3 | U88328 | 0 +/− 0 | 3.6 +/− 0.7 | 0 +/− 0 | 0 +/− 0 | 5.6 +/− 1.5 | 1.8 +/− 0.2 |
| FELINE SARCOMA ONCOGENE | Fes | X12616 | 0 +/− 0 | 0 +/− 0 | 0 +/− 0 | 0 +/− 0 | 7 +/− 1 | 0 +/− 0 |
| PTP. NON-RECEPT. TYPE 12 | Ptpn12 | X86781 | 0 +/− 0 | 0 +/− 0 | 0 +/− 0 | 0 +/− 0 | 3.2 +/− 1.1 | 4.9 +/− 0.5 |
| APLYSIA RAS-RELATED HOMOLOG B | Arhb | X99963 | 0 +/− 0 | 0 +/− 0 | 0 +/− 0 | 0 +/− 0 | 3.5 +/− 0.5 | 4 +/− 0.4 |

TABLE 6-continued

BMP-2-induced changes in the expression of known genes not explicitly associated with bone or cartilage metabolism*.

| Gene Title | Symbol | GenBank | Day 1 | Day 2 | Day 3 | Day 4 | Day 7 | Day 14 |
|---|---|---|---|---|---|---|---|---|
| Structural Proteins | | | | | | | | |
| TROPONIN T2, CARDIAC | Tnnt2 | L47570 | 0 +/− 0 | 0 +/− 0 | −1.3 +/− 0.1 | 4 +/− 2.7 | 12.4 +/− 5.2 | 3.4 +/− 1.6 |
| NESTIN | Nes | AF076623 | 0 +/− 0 | 0 +/− 0 | 0 +/− 0 | 0 +/− 0 | 6.1 +/− 1.2 | 0 +/− 0 |
| CORONIN, ACTIN BINDING PROT. 1A | Coro1a | AF143955 | 1.8 +/− 0.4 | 4.1 +/− 0.8 | 2.9 +/− 0 | 3.3 +/− 0.4 | 3.3 +/− 0.1 | 3.7 +/− 1.1 |
| MYOSIN HEAVY CHAIN, CARDIAC MUSCLE | Myhca | M76601 | 0 +/− 0 | −3.9 +/− 3.9 | 0 +/− 0 | −9.1 +/− 9.4 | −8.9 +/− 6.3 | −6.6 +/− 6 |
| Transcription Factors | | | | | | | | |
| MYOGENIN | Myog | D90156 | 0 +/− 0 | 6.9 +/− 5.1 | 6.6 +/− 2.8 | 17.2 +/− 13.6 | 15.8 +/− 10.6 | 0 +/− 0 |
| MYOGENIC DIFFEREN. 1 | Myod1 | M84918 | 6.4 +/− 0.9 | 7.5 +/− 3.1 | 5.3 +/− 3.6 | 0 +/− 0 | 8 +/− 3.7 | 0 +/− 0 |
| SFFV PROVIRAL INTEGRATION 1 | Sfpi1 | X17463 | 0 +/− 0 | 2.1 +/− 0.6 | 4.2 +/− 0 | 2.8 +/− 0.3 | 4.4 +/− 1 | 8 +/− 1 |
| ELK3, ETS ONCOGENE FAMILY | Elk3 | Z32815 | 0 +/− 0 | 2.4 +/− 0.3 | 2.7 +/− 0.5 | 0 +/− 0 | 6.4 +/− 0.5 | 4.6 +/− 0.5 |
| INS-1 WINGED HELIX | Foxm1 | U83112 | 1.6 +/− 0.5 | 2.6 +/− 0.5 | 0 +/− 0 | 2.4 +/− 0.4 | 3.1 +/− 0.3 | 4.4 +/− 1.8 |
| INTERFERON REG. FACT. 1 | Irf1 | M21065 | 0 +/− 0 | 0 +/− 0 | 0 +/− 0 | 0 +/− 0 | 0 +/− 0 | 5.4 +/− 2.4 |
| T-CELL ACUTE LYMPHOCYTIC LEUKEMIA 1 | Tal1 | U01530 | 4.1 +/− 1.7 | 0 +/− 0 | 0 +/− 0 | 0 +/− 0 | 0 +/− 0 | 0 +/− 0 |
| PEROX. PROLIF. ACTIV. RECEPT. GAMMA | Pparg | U09138 | 0 +/− 0 | 0 +/− 0 | 3.3 +/− 0.4 | 0 +/− 0 | 0 +/− 0 | 4.9 +/− 0.4 |
| NFKB INHIB., ALPHA | Nfkbia | U36277 | 0 +/− 0 | 0 +/− 0 | 0 +/− 0 | 0 +/− 0 | 0 +/− 0 | 4.3 +/− 0.4 |

*Genes were assigned to this table after three searches of the PubMed database. The first search looked for papers in which the gene name OR an MGI alias were used in the title. The second search looked for all papers in which the following terms were used in the title: cartilage OR bone OR chondrogenesis OR osteogenesis OR BMP OR endochondral OR fracture OR osteoblast OR osteoclast. The third search looked for the intersection of searches 1 AND 2. If no records were returned in the third search, then it was determined that there is no explicit association between the gene and bone or cartilage metabolism.

TABLE 7

A correlative analysis of genes having expression profiles similar to selected marker genes.

| Similar to Cyr61 | Similar to Col2a1 | Similar to Runx2 | Similar to Ctsk |
|---|---|---|---|
| Genes from Table 5 | | | |
| Scya8 | Comp | Pcolce | Tcirg1 |
| Cspg2 | Crtl1 | Col5a1 | Itgb3 |
| Cyr61 | Col14a1 | Lum | Ctsk |
| Cdc2a | Col9a1 | Nfatc1 | Sdf1 |
|  | Agc | Apoe | Spp1 |
|  | Pdgfa | Ptprd | Bglap-rs1 |
|  | Mdk | Runx2 | Bglap1 |
|  | Col2a1 | Cdh11 | Ckb |
|  | Fgfr2 | Spp1 | Car2 |
|  | Slugh | Col5a2 | Bmp8a |
|  | Sfrp3 | Bmp1 | Tgfbr2 |
|  | Tnfrsf11b | Csf3r | TPAR1 |
|  | col8a1 | Tgfbr2 | Gja1 |
|  | Pthr | Itgav | Mmp13 |
|  | moucol9a3 | Sdc1 | Mmp9 |
|  | Col10a1 | Bgn |  |
|  | Col9a2 | Gja1 |  |
|  |  | Vcam1 |  |
| Genes from Table 6 | | | |
| Myog | Fzd1 | Pls2 | Fap |
| Sfrp1 | Nes | Cd9 | Sfrp4 |
| Oas1a | Anxa8 | Irf1 | Lifr |
| Ccna2 | Epha2 | Fyn | Lipc |
|  |  | Scyb9 | Serpine2 |
|  |  | Ccnd2 |  |
|  |  | Rasa3 |  |
|  |  | Abcb3 |  |
|  |  | Pdgfrb |  |
|  |  | Ptpn12 |  |
|  |  | Arhb |  |
|  |  | Fap |  |
|  |  | Casp6 |  |

SEQUENCE LISTING

<160> NUMBER OF SEQ ID NOS: 4

<210> SEQ ID NO 1
<211> LENGTH: 1716
<212> TYPE: DNA
<213> ORGANISM: Homo sapiens
<220> FEATURE:
<221> NAME/KEY: CDS
<222> LOCATION: (119)..(1387)
<223> OTHER INFORMATION:

<400> SEQUENCE: 1

```
cgcccagcga cgtgcgggcg gcctggcccg cgccctcccg cgcccggcct gcgtcccgcg      60
ccctgcgcca ccgccgccga gccgcagccc gccgcgcgcc cccggcagcg ccggcccc          118 atg ccc gcc ggc cgc cgg ggc ccc gcc gcc caa tcc gcg cgg cgg ccg      166
Met Pro Ala Gly Arg Arg Gly Pro Ala Ala Gln Ser Ala Arg Arg Pro
1               5                  10                  15 ccg ccg ttg ctg ccc ctg ctg ctg ctc tgc gtc ctc ggg gcg ccg          214
Pro Pro Leu Leu Pro Leu Leu Leu Leu Cys Val Leu Gly Ala Pro
            20                  25                  30 cga gcc gga tca gga gcc cac aca gct gtg atc agt ccc cag gat ccc      262
Arg Ala Gly Ser Gly Ala His Thr Ala Val Ile Ser Pro Gln Asp Pro
        35                  40                  45 acg ctt ctc atc ggc tcc tcc ctg ctg gcc acc tgc tca gtg cac gga      310
Thr Leu Leu Ile Gly Ser Ser Leu Leu Ala Thr Cys Ser Val His Gly
    50                  55                  60 gac cca cca gga gcc acc gcc gag ggc ctc tac tgg acc ctc aac ggg      358
Asp Pro Pro Gly Ala Thr Ala Glu Gly Leu Tyr Trp Thr Leu Asn Gly
65                  70                  75                  80 cgc cgc ctg ccc cct gag ctc tcc cgt gta ctc aac gcc tcc acc ttg      406
Arg Arg Leu Pro Pro Glu Leu Ser Arg Val Leu Asn Ala Ser Thr Leu
                85                  90                  95
```

-continued

```
gct ctg gcc ctg gcc aac ctc aat ggg tcc agg cag cgg tcg ggg gac       454
Ala Leu Ala Leu Ala Asn Leu Asn Gly Ser Arg Gln Arg Ser Gly Asp
            100                 105                 110 aac ctc gtg tgc cac gcc cgt gac ggc agc atc ctg gct ggc tcc tgc       502
Asn Leu Val Cys His Ala Arg Asp Gly Ser Ile Leu Ala Gly Ser Cys
        115                 120                 125 ctc tat gtt ggc ctg ccc cca gag aaa ccc gtc aac atc agc tgc tgg       550
Leu Tyr Val Gly Leu Pro Pro Glu Lys Pro Val Asn Ile Ser Cys Trp
    130                 135                 140 tcc aag aac atg aag gac ttg acc tgc cgc tgg acg cca ggg gcc cac       598
Ser Lys Asn Met Lys Asp Leu Thr Cys Arg Trp Thr Pro Gly Ala His
145                 150                 155                 160 ggg gag acc ttc ctc cac acc aac tac tcc ctc aag tac aag ctt agg       646
Gly Glu Thr Phe Leu His Thr Asn Tyr Ser Leu Lys Tyr Lys Leu Arg
                165                 170                 175 tgg tat ggc cag gac aac aca tgt gag gag tac cac aca gtg ggg ccc       694
Trp Tyr Gly Gln Asp Asn Thr Cys Glu Glu Tyr His Thr Val Gly Pro
            180                 185                 190 cac tcc tgc cac atc ccc aag gac ctg gct ctc ttt acg ccc tat gag       742
His Ser Cys His Ile Pro Lys Asp Leu Ala Leu Phe Thr Pro Tyr Glu
        195                 200                 205 atc tgg gtg gag gcc acc aac cgc ctg ggc tct gcc cgc tcc gat gta       790
Ile Trp Val Glu Ala Thr Asn Arg Leu Gly Ser Ala Arg Ser Asp Val
    210                 215                 220 ctc acg ctg gat atc ctg gat gtg gtg acc acg gac ccc ccg ccc gac       838
Leu Thr Leu Asp Ile Leu Asp Val Val Thr Thr Asp Pro Pro Pro Asp
225                 230                 235                 240 gtg cac gtg agc cgc gtc ggg ggc ctg gag gac cag ctg agc gtg cgc       886
Val His Val Ser Arg Val Gly Gly Leu Glu Asp Gln Leu Ser Val Arg
                245                 250                 255 tgg gtg tcg cca ccc gcc ctc aag gat ttc ctc ttt caa gcc aaa tac       934
Trp Val Ser Pro Pro Ala Leu Lys Asp Phe Leu Phe Gln Ala Lys Tyr
            260                 265                 270 cag atc cgc tac cga gtg gag gac agt gtg gac tgg aag gtg gtg gac       982
Gln Ile Arg Tyr Arg Val Glu Asp Ser Val Asp Trp Lys Val Val Asp
        275                 280                 285 gat gtg agc aac cag acc tcc tgc cgc ctg gcc ggc ctg aaa ccc ggc      1030
Asp Val Ser Asn Gln Thr Ser Cys Arg Leu Ala Gly Leu Lys Pro Gly
    290                 295                 300 acc gtg tac ttc gtg caa gtg cgc tgc aac ccc ttt ggc atc tat ggc      1078
Thr Val Tyr Phe Val Gln Val Arg Cys Asn Pro Phe Gly Ile Tyr Gly
305                 310                 315                 320 tcc aag aaa gcc ggg atc tgg agt gag tgg agc cac ccc aca gcc gcc      1126
Ser Lys Lys Ala Gly Ile Trp Ser Glu Trp Ser His Pro Thr Ala Ala
                325                 330                 335 tcc act ccc cgc agt gag cgc ccg ggc ccg ggc ggc ggg gcg tgc gaa      1174
Ser Thr Pro Arg Ser Glu Arg Pro Gly Pro Gly Gly Gly Ala Cys Glu
            340                 345                 350 ccg cgg ggc gga gag ccg agc tcg ggg ccg gtg cgg cgc gag ctc aag      1222
Pro Arg Gly Gly Glu Pro Ser Ser Gly Pro Val Arg Arg Glu Leu Lys
        355                 360                 365 cag ttc ctg ggc tgg ctc aag aag cac gcg tac tgc tcc aac ctc agc      1270
Gln Phe Leu Gly Trp Leu Lys Lys His Ala Tyr Cys Ser Asn Leu Ser
    370                 375                 380 ttc cgc ctc tac gac cag tgg cga gcc tgg atg cag aag tcg cac aag      1318
Phe Arg Leu Tyr Asp Gln Trp Arg Ala Trp Met Gln Lys Ser His Lys
385                 390                 395                 400 acc cgc aac cag gac gag ggg atc ctg ccc tcg ggc aga cgg ggc acg      1366
Thr Arg Asn Gln Asp Glu Gly Ile Leu Pro Ser Gly Arg Arg Gly Thr
                405                 410                 415
```

-continued

```
gcg aga ggt cct gcc aga taa gctgtaggg ctcaggccac cctccctgcc         1417
Ala Arg Gly Pro Ala Arg
        420 acgtggagac gcagaggccg aacccaaact ggggccacct ctgtaccctc acttcagggc   1477 acctgagcca ccctcagcag gagctggggt ggcccctgag ctccaacggc cataacagct   1537 ctgactccca cgtgaggcca cctttgggtg cacccagtg ggtgtgtgtg tgtgtgtgag    1597 ggttggttga gttgcctaga acccctgcca gggctggggg tgagaagggg agtcattact   1657 ccccattacc tagggcccct ccaaaagagt cctttttaaat aaatgagcta tttaggtgc   1716

<210> SEQ ID NO 2
<211> LENGTH: 422
<212> TYPE: PRT
<213> ORGANISM: Homo sapiens

<400> SEQUENCE: 2

Met Pro Ala Gly Arg Arg Gly Pro Ala Ala Gln Ser Ala Arg Arg Pro
1               5                   10                  15

Pro Pro Leu Leu Pro Leu Leu Leu Leu Cys Val Leu Gly Ala Pro
            20                  25                  30

Arg Ala Gly Ser Gly Ala His Thr Ala Val Ile Ser Pro Gln Asp Pro
        35                  40                  45

Thr Leu Leu Ile Gly Ser Ser Leu Leu Ala Thr Cys Ser Val His Gly
    50                  55                  60

Asp Pro Pro Gly Ala Thr Ala Glu Gly Leu Tyr Trp Thr Leu Asn Gly
65                  70                  75                  80

Arg Arg Leu Pro Pro Glu Leu Ser Arg Val Leu Asn Ala Ser Thr Leu
                85                  90                  95

Ala Leu Ala Leu Ala Asn Leu Asn Gly Ser Arg Gln Arg Ser Gly Asp
            100                 105                 110

Asn Leu Val Cys His Ala Arg Asp Gly Ser Ile Leu Ala Gly Ser Cys
        115                 120                 125

Leu Tyr Val Gly Leu Pro Pro Glu Lys Pro Val Asn Ile Ser Cys Trp
    130                 135                 140

Ser Lys Asn Met Lys Asp Leu Thr Cys Arg Trp Thr Pro Gly Ala His
145                 150                 155                 160

Gly Glu Thr Phe Leu His Thr Asn Tyr Ser Leu Lys Tyr Lys Leu Arg
                165                 170                 175

Trp Tyr Gly Gln Asp Asn Thr Cys Glu Glu Tyr His Thr Val Gly Pro
            180                 185                 190

His Ser Cys His Ile Pro Lys Asp Leu Ala Leu Phe Thr Pro Tyr Glu
        195                 200                 205

Ile Trp Val Glu Ala Thr Asn Arg Leu Gly Ser Ala Arg Ser Asp Val
    210                 215                 220

Leu Thr Leu Asp Ile Leu Asp Val Val Thr Thr Asp Pro Pro Asp
225                 230                 235                 240

Val His Val Ser Arg Val Gly Gly Leu Glu Asp Gln Leu Ser Val Arg
                245                 250                 255

Trp Val Ser Pro Pro Ala Leu Lys Asp Phe Leu Phe Gln Ala Lys Tyr
            260                 265                 270

Gln Ile Arg Tyr Arg Val Glu Asp Ser Val Asp Trp Lys Val Val Asp
        275                 280                 285

Asp Val Ser Asn Gln Thr Ser Cys Arg Leu Ala Gly Leu Lys Pro Gly
    290                 295                 300
```

```
Thr Val Tyr Phe Val Gln Val Arg Cys Asn Pro Phe Gly Ile Tyr Gly
305                 310                 315                 320

Ser Lys Lys Ala Gly Ile Trp Ser Glu Trp Ser His Pro Thr Ala Ala
                325                 330                 335

Ser Thr Pro Arg Ser Glu Arg Pro Gly Pro Gly Gly Ala Cys Glu
                340                 345                 350

Pro Arg Gly Gly Glu Pro Ser Ser Gly Pro Val Arg Arg Glu Leu Lys
                355                 360                 365

Gln Phe Leu Gly Trp Leu Lys Lys His Ala Tyr Cys Ser Asn Leu Ser
370                 375                 380

Phe Arg Leu Tyr Asp Gln Trp Arg Ala Trp Met Gln Lys Ser His Lys
385                 390                 395                 400

Thr Arg Asn Gln Asp Glu Gly Ile Leu Pro Ser Gly Arg Arg Gly Thr
                405                 410                 415

Ala Arg Gly Pro Ala Arg
                420

<210> SEQ ID NO 3
<211> LENGTH: 1246
<212> TYPE: DNA
<213> ORGANISM: Homo sapiens
<220> FEATURE:
<221> NAME/KEY: CDS
<222> LOCATION: (39)..(1211)
<223> OTHER INFORMATION:

<400> SEQUENCE: 3
ctgccccatg cagccctgag ccccacagca agtctgcc atg ggc cgc ggg gcc cgt      56
                                        Met Gly Arg Gly Ala Arg
                                         1               5 gtc ccc tcg gag gcc ccg ggg gca ggc gtc gag cgc cgc tgg ctt gga      104
Val Pro Ser Glu Ala Pro Gly Ala Gly Val Glu Arg Arg Trp Leu Gly
             10                  15                  20 gcc gcg ctg gtc gcc ctg tgc ctc ctc ccc gcg ctg gtg ctg ctg gcc      152
Ala Ala Leu Val Ala Leu Cys Leu Leu Pro Ala Leu Val Leu Leu Ala
         25                  30                  35 cgg ctg ggg gcc ccg gcg gtg ccg gcc tgg agc gca gcg cag gga gac      200
Arg Leu Gly Ala Pro Ala Val Pro Ala Trp Ser Ala Ala Gln Gly Asp
     40                  45                  50 gtc gct gcg ctg ggc ctc tcg gcg gtc ccc ccc acc cgg gtc ccg ggc      248
Val Ala Ala Leu Gly Leu Ser Ala Val Pro Pro Thr Arg Val Pro Gly
 55                  60                  65                  70 cca ctg gcc ccc cgc aga cgc cgc tac acg ctg act cca gcc agg ctg      296
Pro Leu Ala Pro Arg Arg Arg Arg Tyr Thr Leu Thr Pro Ala Arg Leu
                 75                  80                  85 cgc tgg gac cac ttc aac ctc acc tac agg atc ctc tcc ttc ccg cgg      344
Arg Trp Asp His Phe Asn Leu Thr Tyr Arg Ile Leu Ser Phe Pro Arg
             90                  95                 100 aac ctg ctg agc ccg cgg gag acg cgg cgg gcc cta gct gcc gcc ttc      392
Asn Leu Leu Ser Pro Arg Glu Thr Arg Arg Ala Leu Ala Ala Ala Phe
         105                 110                 115 cgc atg tgg agc gac gtg tcc ccc ttc agc ttc cgc gag gtg gcc ccc      440
Arg Met Trp Ser Asp Val Ser Pro Phe Ser Phe Arg Glu Val Ala Pro
     120                 125                 130 gag cag ccc agc gac ctc cgg ata ggc ttc tac ccg atc aac cac acg      488
Glu Gln Pro Ser Asp Leu Arg Ile Gly Phe Tyr Pro Ile Asn His Thr
135                 140                 145                 150 gac tgc ctg gtc tcc gcg ctg cac cac tgc ttc gac ggc ccc acg ggg      536
Asp Cys Leu Val Ser Ala Leu His His Cys Phe Asp Gly Pro Thr Gly
```

```
                155              160              165
gag ctg gcc cac gcc ttc ttc ccc ccg cac ggc ggc atc cac ttc gac    584
Glu Leu Ala His Ala Phe Phe Pro Pro His Gly Gly Ile His Phe Asp
            170              175              180 gac agc gag tac tgg gtc ctg ggc ccc acg cgc tac agc tgg aag aaa    632
Asp Ser Glu Tyr Trp Val Leu Gly Pro Thr Arg Tyr Ser Trp Lys Lys
        185              190              195 ggc gtg tgg ctc acg gac ctg gtg cac gtg gcg gcc cac gag atc ggc    680
Gly Val Trp Leu Thr Asp Leu Val His Val Ala Ala His Glu Ile Gly
    200              205              210 cac gcg ctg ggc ctg atg cac tca caa cac ggc cgg gcg ctc atg cac    728
His Ala Leu Gly Leu Met His Ser Gln His Gly Arg Ala Leu Met His
215              220              225              230 ctg aac gcc acg ctg cgc ggc tgg aag gcg ttg tcc cag gac gag ctg    776
Leu Asn Ala Thr Leu Arg Gly Trp Lys Ala Leu Ser Gln Asp Glu Leu
            235              240              245 tgg ggg ctg cac cgg ctc tac gga tgc ctc gac agg ctg ttc gtg tgc    824
Trp Gly Leu His Arg Leu Tyr Gly Cys Leu Asp Arg Leu Phe Val Cys
        250              255              260 gcg tcc tgg gcg cgg agg ggc ttc tgc gac gct cgc cgg cgg ctc atg    872
Ala Ser Trp Ala Arg Arg Gly Phe Cys Asp Ala Arg Arg Arg Leu Met
    265              270              275 aag agg ctc tgc ccc agc agc tgc gac ttc tgc tac gaa ttc ccc ttc    920
Lys Arg Leu Cys Pro Ser Ser Cys Asp Phe Cys Tyr Glu Phe Pro Phe
280              285              290 ccc acg gtg gcc acc acc cca ccg ccc ccc agg acc aaa acc agg ctg    968
Pro Thr Val Ala Thr Thr Pro Pro Pro Pro Arg Thr Lys Thr Arg Leu
295              300              305              310 gtg ccc gag ggc agg aac gtg acc ttc cgc tgc ggc cag aag atc ctc   1016
Val Pro Glu Gly Arg Asn Val Thr Phe Arg Cys Gly Gln Lys Ile Leu
            315              320              325 cac aag aaa ggg aaa gtg tac tgg tac aag gac cag gag ccc ctg gag   1064
His Lys Lys Gly Lys Val Tyr Trp Tyr Lys Asp Gln Glu Pro Leu Glu
        330              335              340 ttc tcc tac ccc ggc tac ctg gcc ctg ggc gag gcg cac ctg agc atc   1112
Phe Ser Tyr Pro Gly Tyr Leu Ala Leu Gly Glu Ala His Leu Ser Ile
    345              350              355 atc gcc aac gcc gtc aat gag ggc acc tac acc tgc gtg gtg cgc cgc   1160
Ile Ala Asn Ala Val Asn Glu Gly Thr Tyr Thr Cys Val Val Arg Arg
360              365              370 cag cag cgc gtg ctg acc acc tac tcc tgg cga gtc cgt gtg cgg ggc   1208
Gln Gln Arg Val Leu Thr Thr Tyr Ser Trp Arg Val Arg Val Arg Gly
375              380              385              390 tga gcccggctga taaagcactt tctctctgaa aaaaa                         1246

<210> SEQ ID NO 4
<211> LENGTH: 390
<212> TYPE: PRT
<213> ORGANISM: Homo sapiens

<400> SEQUENCE: 4

Met Gly Arg Gly Ala Arg Val Pro Ser Glu Ala Pro Gly Ala Gly Val
1               5                   10                  15

Glu Arg Arg Trp Leu Gly Ala Ala Leu Val Ala Leu Cys Leu Leu Pro
            20                  25                  30

Ala Leu Val Leu Leu Ala Arg Leu Gly Ala Pro Ala Val Pro Ala Trp
        35                  40                  45

Ser Ala Ala Gln Gly Asp Val Ala Ala Leu Gly Leu Ser Ala Val Pro
    50                  55                  60
```

```
Pro Thr Arg Val Pro Gly Pro Leu Ala Pro Arg Arg Arg Tyr Thr
 65              70                  75                  80

Leu Thr Pro Ala Arg Leu Arg Trp Asp His Phe Asn Leu Thr Tyr Arg
             85                  90                  95

Ile Leu Ser Phe Pro Arg Asn Leu Leu Ser Pro Arg Glu Thr Arg Arg
            100                 105             110

Ala Leu Ala Ala Ala Phe Arg Met Trp Ser Asp Val Ser Pro Phe Ser
            115                 120             125

Phe Arg Glu Val Ala Pro Glu Gln Pro Ser Asp Leu Arg Ile Gly Phe
        130                 135             140

Tyr Pro Ile Asn His Thr Asp Cys Leu Val Ser Ala Leu His His Cys
145             150                 155                 160

Phe Asp Gly Pro Thr Gly Glu Leu Ala His Ala Phe Phe Pro Pro His
                165                 170             175

Gly Gly Ile His Phe Asp Asp Ser Glu Tyr Trp Val Leu Gly Pro Thr
            180                 185             190

Arg Tyr Ser Trp Lys Lys Gly Val Trp Leu Thr Asp Leu Val His Val
            195                 200             205

Ala Ala His Glu Ile Gly His Ala Leu Gly Leu Met His Ser Gln His
        210                 215             220

Gly Arg Ala Leu Met His Leu Asn Ala Thr Leu Arg Gly Trp Lys Ala
225             230                 235                 240

Leu Ser Gln Asp Glu Leu Trp Gly Leu His Arg Leu Tyr Gly Cys Leu
                245                 250             255

Asp Arg Leu Phe Val Cys Ala Ser Trp Ala Arg Arg Gly Phe Cys Asp
            260                 265             270

Ala Arg Arg Arg Leu Met Lys Arg Leu Cys Pro Ser Ser Cys Asp Phe
        275                 280             285

Cys Tyr Glu Phe Pro Phe Pro Thr Val Ala Thr Thr Pro Pro Pro Pro
290                 295             300

Arg Thr Lys Thr Arg Leu Val Pro Glu Gly Arg Asn Val Thr Phe Arg
305             310                 315                 320

Cys Gly Gln Lys Ile Leu His Lys Lys Gly Lys Val Tyr Trp Tyr Lys
                325                 330             335

Asp Gln Glu Pro Leu Glu Phe Ser Tyr Pro Gly Tyr Leu Ala Leu Gly
            340                 345             350

Glu Ala His Leu Ser Ile Ile Ala Asn Ala Val Asn Glu Gly Thr Tyr
        355                 360             365

Thr Cys Val Val Arg Arg Gln Gln Arg Val Leu Thr Thr Tyr Ser Trp
370                 375             380

Arg Val Arg Val Arg Gly
385             390
```

The invention claimed is:

1. A method for assessing the efficacy of a treatment for a disease associated with bone or cartilage metabolism in a subject comprising the steps of:
    determining the level of expression of a polynucleotide comprising the nucleic acid sequence set forth in SEQ ID NO:3 in a biological sample or samples from the subject at a time point after initiation of treatment; and
    comparing the level of expression of the polynucleotide in the biological sample with a corresponding reference level of expression of the polynucleotide,
    wherein an increased similarity between the level of expression of the polynucleotide in the biological sample and the reference level of expression of the polynucleotide indicates that the treatment for the disease is efficacious.

2. The method of claim 1, wherein the disease is associated with bone or cartilage formation.

3. The method of claim 1, wherein the disease is associated with bone or cartilage resorption.

4. The method of claim 3, wherein the treatment comprises administration of a polynucleotide comprising the nucleic acid sequence set forth in SEQ ID NO:5 and/or a polypeptide comprising the amino acid sequence set forth in SEQ ID NO:6.

5. A method for monitoring a treatment for a disease associated with bone or cartilage metabolism in a subject comprising the steps of:

determining the level of expression of a polynucleotide comprising the nucleic acid sequence set forth in SEQ ID NO:3 in a biological sample or samples from the subject at a time point or points after initiation of treatment; and comparing the level of expression of the polynucleotide in the biological sample with a corresponding reference level of expression of the polynucleotide, wherein an increased similarity between the level of expression of the polynucleotide in the biological sample or samples and the reference level of expression of the polynucleotide indicates that the treatment is improving or continuing to improve the disease associated with bone or cartilage metabolism in the subject.

6. The method of claim 5, wherein the disease is associated with bone or cartilage formation.

7. The method of claim 5, wherein the disease is associated with bone or cartilage resorption.

8. The method of claim 7, wherein the treatment comprises administration of a polynucleotide comprising the nucleic acid sequence set forth in SEQ ID NO:5 and/or a polypeptide comprising the amino acid sequence set forth in SEQ ID NO:6.

* * * * *

UNITED STATES PATENT AND TRADEMARK OFFICE
CERTIFICATE OF CORRECTION

PATENT NO. : 7,251,568 B2
APPLICATION NO. : 10/329056
DATED : July 31, 2007
INVENTOR(S) : Debra D. Pittman et al.

It is certified that error appears in the above-identified patent and that said Letters Patent is hereby corrected as shown below:

ON COVER PAGE AT (56) OTHER PUBLICATIONS

After "Elson et al." (second occurrence): "TO" should read --to--;
After "Velasco et al.": "Predomonantly" should read --Predominantly--; and
After "Database GenBank,": "eds. Mar. 16, 2000" should read --cds. Mar. 16, 2000--.

COLUMN 2

Line 56, "to," should read --to--.

COLUMN 4

Line 30, "indicates" should read --indicate--.

COLUMN 5

Line 3, "communications" should read --communication--;
Line 15, "indicates" should read --indicate--;
Line 33, "indicates" should read --indicate--; and
Line 59, "indicates" should read --indicate--.

COLUMN 8

Line 5, "that found" should read --that was found--;
Line 7, "Metalloproteinse" should read --Metalloproteinase--; and
Line 52, "reference" should read --references--.

COLUMN 10

Line 13, "a" should be deleted;
Line 54, "asantibodies," should read --antibodies,--; and
Line 61, "Any" should read --any--.

COLUMN 15

Line 56, "cause" should read --caused--.

COLUMN 16

Line 30, "subject" should read --subjects--.

UNITED STATES PATENT AND TRADEMARK OFFICE
CERTIFICATE OF CORRECTION

PATENT NO. : 7,251,568 B2
APPLICATION NO. : 10/329056
DATED : July 31, 2007
INVENTOR(S) : Debra D. Pittman et al.

It is certified that error appears in the above-identified patent and that said Letters Patent is hereby corrected as shown below:

COLUMN 18

Line 8, "describe" should read --describes--;
    Line 17, "has" should read --have--; and
    Line 23, "is" should read --are--.

COLUMN 19

Line 8, "Ophtalmol." should read --Ophthalmol.--; and
    Line 59, "than 106" should read --than $10^6$--.

COLUMN 20

Line 45, "Superscript.™0.11," should read --Superscript.™.II,--; and
    Line 67, "Nphenyl-N-methyl-2-aminoaphthalene-6-sulfonate;" should read
        --N-phenyl-N-methyl-2-aminonaphthalene-6-sulfonate;--.

COLUMN 21

Line 7, "(2--methyl-5-phenyl-oxazolyl))benzene;" should read
        --(2-methyl-5-phenyl-oxazolyl)benzene;--;
    Line 9, "dilodide;" should read --diiodide;--;
    Line 11, "N-(p-(2benzimidazolyl)-phenyl)ma-" should read
        --N-(p-2-benzimidazolyl)-phenyl)ma- --; and
    Line 15, "3(2H)-furanone." should read --3(2H)-furanone--.

COLUMN 22

Line 14, "resoprtion" should read --resorption--.

COLUMN 23

Line 6, "froma" should read --from a--.

COLUMN 24

Line 52, "is" should read --are--; and
    Line 62, "cre" should read --are--.

UNITED STATES PATENT AND TRADEMARK OFFICE
CERTIFICATE OF CORRECTION

PATENT NO. : 7,251,568 B2
APPLICATION NO. : 10/329056
DATED : July 31, 2007
INVENTOR(S) : Debra D. Pittman et al.

It is certified that error appears in the above-identified patent and that said Letters Patent is hereby corrected as shown below:

COLUMN 25

Line 5, "GeneChips®)" should read --GeneChips®).--;
Line 51, "5,631,734 5,143,854" should read --5,631,734; 5,143,854--; and
Line 61, "photolithogaphic" should read --photolithographic--.

COLUMN 26

Line 2, "have" should read --has--; and
Line 29, "on to" should read --onto--.

COLUMN 29

Line 34, "different" should read --the difference--;
Line 45, "fibre" should read --fiber--; and
Line 67, "Windows$^R$" should read --Windows®--.

COLUMN 30

Line 39, "subtrackion" should read --subtraction--.

COLUMN 31

Line 44, "sets" should read --set--.

COLUMN 33

Line 29, "form" should read --from--;
Line 38, "a" should read --an--; and
Line 63, "is" should read --are--.

COLUMN 39

Line 43, "composition" should read --compositions--.

COLUMN 43

Line 25, "preferably" should read --preferable--.

UNITED STATES PATENT AND TRADEMARK OFFICE
CERTIFICATE OF CORRECTION

| | |
|---|---|
| PATENT NO. | : 7,251,568 B2 |
| APPLICATION NO. | : 10/329056 |
| DATED | : July 31, 2007 |
| INVENTOR(S) | : Debra D. Pittman et al. |

It is certified that error appears in the above-identified patent and that said Letters Patent is hereby corrected as shown below:

COLUMN 47

Line 30, "Nature 2001 ;411(6836):494-8)." should read --Nature 2001; 411(6836):494-8).--;and
    Line 39, "Accad." should read --Acad.--.

COLUMN 48

Line 26, "on" should read --one--.

COLUMN 51

Line 13, "couples." should read --coupled.--; and
    Line 38, "mophogenetic" should read --morphogenetic--.

COLUMN 52

Line 32, "degrades" should read --degrade--; and "causes" should read --cause--.

COLUMN 54

Line 37, "efficiency" should read --efficacy--.

COLUMN 55

Line 29, "preformed" should read --performed--.

COLUMN 58

Line 24, "nebuliser," should read --nebulizer,--.

COLUMN 62

Line 7, "muscles The" should read --muscles. ¶The--;
    Line 14, "mice (14" should read --mice (~14--;
    Line 31, "GeneChip" should read --GeneChip®--;
    Line 39, "GeneChip" should read --GeneChip®--; and
    Line 41, "GeneChip" should read --GeneChip®--.

UNITED STATES PATENT AND TRADEMARK OFFICE
CERTIFICATE OF CORRECTION

PATENT NO. : 7,251,568 B2
APPLICATION NO. : 10/329056
DATED : July 31, 2007
INVENTOR(S) : Debra D. Pittman et al.

It is certified that error appears in the above-identified patent and that said Letters Patent is hereby corrected as shown below:

COLUMN 63

Line 40, "osteblasts" should read --osteoblasts--.

COLUMN 73

Table 1,

" 116113_at   0.00   0.00   0.00   0.00   0.00   4.05   UNK_A1790538   A1790539 "

should read

-- 116113_at   0.00   0.00   0.00   0.00   0.00   4.05   UNK_A1790538   A1790538 --.

COLUMN 77

Table 1,

" 100514_at   0.00   0.00   0.00   0.00   0.00   2.43   guanine nucleotide binding protein, alpha 13; Gna13   M63660 "

should read

-- 100514_at   0.00   0.00   0.00   0.00   0.00   2.43   guanine nucleotide binding protein, alpha 13; Gna13   M63660 --.

COLUMN 79

Table 1,

" 97719_at   0.00   0.00   0.00   0.00   0.00   9.46   ROW   X74736 "

should read

-- 97719_at   0.00   0.00   0.00   0.00   0.00   9.46   RON   X74736 --.

UNITED STATES PATENT AND TRADEMARK OFFICE
CERTIFICATE OF CORRECTION

PATENT NO.       : 7,251,568 B2
APPLICATION NO.  : 10/329056
DATED            : July 31, 2007
INVENTOR(S)      : Debra D. Pittman et al.

It is certified that error appears in the above-identified patent and that said Letters Patent is hereby corrected as shown below:

COLUMN 129

Table 1,

" 99637_at  0.00  0.00  0.00  2.41  2.14  2.67  srocollagen, type XV; Col15a1  AF011450 "

should read

-- 99637_at  0.00  0.00  0.00  2.41  2.14  2.67  procollagen, type XV; Col15a1  AF011450 --.

COLUMN 131

Table 1,

" 93320_at  0.00  1.78  2.64  3.70  2.65  3.94  carnitine palmitoyltransferase 1, liver; Cpt1a  AF017175 "

should read

-- 93320_at  0.00  1.78  2.64  3.70  2.65  3.94  carnitine palmitoyltransferase 1, liver; Cpt1a  AF017175 --.

COLUMN 143

Table 1,

" 104125_at  0.00  0.00  0.00  2.35  1.70  1.64  HAIR-PENDING  AA763673 "

should read

-- 104125_at  0.00  0.00  0.00  2.35  1.70  1.64  HAIR-PENDING  AA763673 --.

UNITED STATES PATENT AND TRADEMARK OFFICE
CERTIFICATE OF CORRECTION

PATENT NO. : 7,251,568 B2
APPLICATION NO. : 10/329056
DATED : July 31, 2007
INVENTOR(S) : Debra D. Pittman et al.

It is certified that error appears in the above-identified patent and that said Letters Patent is hereby corrected as shown below:

COLUMN 145

Table 1,

" 100483_at 0.00 0.00 2.24 3.74 4.92 4.19 interferon (alpha and M89641 "
beta) receptor Ifnar should read -- 100483_at 0.00 0.00 2.24 3.74 4.92 4.19 interferon (alpha and M89641 --.
beta) receptor; Ifnar

COLUMN 147

Table 1,

" 98922_at 0.00 0.00 0.00 0.00 2.69 2.27 intergral membrane L34260 "
protein 1; Itm1 should read

-- 98922_at 0.00 0.00 0.00 0.00 2.69 2.27 integral membrane L34260 --.
protein 1; Itm1

COLUMN 151

Table 1,

" 100156_at 0.00 7.39 9.72 7.89 7.48 2.57 maintenance D26090 "
deficient 5 (*S. cerefisiae*); McmdS should read -- 100156_at 0.00 7.39 9.72 7.89 7.48 2.57 maintenance D26090 --.
deficient 5 (*S. cereflsiae*); Mcmd5

UNITED STATES PATENT AND TRADEMARK OFFICE
CERTIFICATE OF CORRECTION

PATENT NO. : 7,251,568 B2
APPLICATION NO. : 10/329056
DATED : July 31, 2007
INVENTOR(S) : Debra D. Pittman et al.

Page 8 of 16

It is certified that error appears in the above-identified patent and that said Letters Patent is hereby corrected as shown below:

COLUMN 165

Table 1,

" 95791_s_at  0.00  0.00  0.00  2.66  2.33  0.00  arginine/serine-rich 10, splidng factor, arginine/serine-rich 2 (SC-35); Sfrs10, Sfrs2   U14648 "

should read

-- 95791_s_at  0.00  0.00  0.00  2.66  2.33  0.00  arginine/serine-rich 10, splicing factor, arginine/serine-rich 2 (SC-35); Sfrs10, Sfrs2   U14648 --.

COLUMN 169

Table 1,

" 112282_s_at  0.00  3.18  4.02  4.54  4.18  4.52  UNK_AI154073  AH 54073 "

should read

-- 112282_s_at  0.00  3.18  4.02  4.54  4.18  4.52  UNK_AI154073  AI 54073 --;

and

" 99100_at  0.00  0.00  0.00  0.00  2.73  0.00  STATS  AI837104 "

should read

-- 99100_at  0.00  0.00  0.00  0.00  2.73  0.00  STAT 5  AI837104 --.

COLUMN 179

Table 2,

" 95905_at  0.00  0.00  0.00  0.00  0.00  -2.38  UNK_AI118078  AH 18078 "

should read

UNITED STATES PATENT AND TRADEMARK OFFICE
CERTIFICATE OF CORRECTION

PATENT NO. : 7,251,568 B2  Page 9 of 16
APPLICATION NO. : 10/329056
DATED : July 31, 2007
INVENTOR(S) : Debra D. Pittman et al.

It is certified that error appears in the above-identified patent and that said Letters Patent is hereby corrected as shown below:

-- 95905_at 0.00 0.00 0.00 0.00 0.00 -2.38 UNK_AI118078 AI118078 --.

COLUMN 183

Table 2,

" 109575__at 0.00 0.00 0.00 0.00 -2.11 0.00 UNK_AI155995 AH 55995 "

should read

-- 109575__at 0.00 0.00 0.00 0.00 -2.11 0.00 UNK_AI155995 AI155995 --.

COLUMN 191

Table 2,

" 97518__at 0.00 -3.76 -2.66 0.00 -2.48 -1.86 farnesyl diphosphate farnesyl transferase 1; Fdft1 D29016 "

should read

-- 97518__at 0.00 -3.76 -2.66 0.00 -2.48 -1.86 farnesyl diphosphate farnesyl transferase 1; Fdft1 D29016 --.

COLUMN 199

Table 2,

" 92302__at 0.00 0.00 -1.87 0.00 -2.80 0.00 Son of sevenless homolog 2. Z11664 "

should read

-- 92302__at 0.00 0.00 -1.87 0.00 -2.80 0.00 Son of sevenless homolog 2, Z11664 --;

UNITED STATES PATENT AND TRADEMARK OFFICE
CERTIFICATE OF CORRECTION

PATENT NO. : 7,251,568 B2  
APPLICATION NO. : 10/329056  
DATED : July 31, 2007  
INVENTOR(S) : Debra D. Pittman et al.

Page 10 of 16

It is certified that error appears in the above-identified patent and that said Letters Patent is hereby corrected as shown below:

and

" 100952_at 0.00 0.00 0.00 0.00 -2.38 -2.24 stromal Interaction molecule 1; Stim 1 U47323 "

should read

100952_at 0.00 0.00 0.00 0.00 -2.38 -2.24 stromal interaction molecule 1; Stim 1 U47323

-- --.

Column 201

Table 2,

" 96063_at 0.00 0.00 0.00 0.00 -2.02 0.00 X-ray repair complementing defective repair In Chinese hamster cells 5; XrccS X66323 "

should read

96063_at 0.00 0.00 0.00 0.00 -2.02 0.00 X-ray repair complementing defective repair in Chinese hamster cells 5; Xrcc5 X66323

-- --.

Column 215

Table 6,

" CYCLIN A2 Ccha2 Z26580 0+/-0 3.1 +/-0.5 3.6 +/- 0.7 4.8 +/- 0.3 5.7 +/- 0.3 1.9 +/- 0.2 "

should read

CYCLIN A2 Ccna2 Z26580 0+/-0 3.1 +/-0.5 3.6 +/- 0.7 4.8 +/- 0.3 5.7 +/- 0.3 1.9 +/- 0.2

-- --.

UNITED STATES PATENT AND TRADEMARK OFFICE
CERTIFICATE OF CORRECTION

| | | |
|---|---|---|
| PATENT NO. | : 7,251,568 B2 | |
| APPLICATION NO. | : 10/329056 | |
| DATED | : July 31, 2007 | |
| INVENTOR(S) | : Debra D. Pittman et al. | |

It is certified that error appears in the above-identified patent and that said Letters Patent is hereby corrected as shown below:

<u>COLUMN 221</u>

Table 6, "*Genes were assigned to this table after three searches of the PubMed database. The first search looked for papers in which the gene name OR an MGI alias were used in the title. The second search looked for all the papers in which the following terms were used in the title: cartilage OR bone OR chondrogenesis OR osteogenesis OR BMP OR endochondral OR fracture OR osteoblast OR osteoclast. The third search looked forthe intersection of searches 1 AND 2. If no records were returned in the third search, then it was determined that there is no explicit association between the gene and bone or cartilage metabolism."

should read

--*Genes were assigned to this table after three searches of the PubMed database. The first search looked for papers in which the gene name OR an MGI alias were used in the title. The second search looked for all the papers in which the following terms were used in the title: cartilage OR bone OR chondrogenesis OR osteogenesis OR BMP OR endochondral OR fracture OR osteoblast OR osteoclast. The third search looked for the intersection of searches 1 AND 2. If no records were returned in the third search, then it was determined that there is no explicit association between the gene and bone or cartilage metabolism.--.

UNITED STATES PATENT AND TRADEMARK OFFICE
CERTIFICATE OF CORRECTION

PATENT NO. : 7,251,568 B2  
APPLICATION NO. : 10/329056  
DATED : July 31, 2007  
INVENTOR(S) : Debra D. Pittman et al.

Page 12 of 16

It is certified that error appears in the above-identified patent and that said Letters Patent is hereby corrected as shown below:

<u>COLUMN 233</u> Insert immediately before the claims:
--

```
<210>  5
<211>  3150
<212>  DNA
<213>  Homo sapiens

<220>
<221>  CDS
<222>  (786)..(1976)
<223>  GeneBank NM_001200

<300>
<301>  Wozney,J.M., Rosen,V., Celeste,A.J., Mitsock,L.M., Whitters,M.J.,
<302>  Novel regulators of bone formation: molecular clones and
       activities
<303>  Science
<304>  242
<305>  4885
<306>  1528-1534
<307>  1988
<308>  NM_001200
<309>  2005-11-27
<313>  (786)..(1976)

<400>  5
ccacaaaggg cacttggccc cagggctagg agagcgaggg gagagcacag ccacccgcct    60
cggcggcccg ggactcggct cgactcgccg gagaatgcgc ccgaggacga cggggcgcca   120
gagccgcggt gctttcaact ggcgagcgcg aatgggggtg cactggagta aggcagagtg   180
atgcggggggg gcaactcgcc tggcaccgag atccgccgcg tgcccttccc tggacccggc   240
gtcgcccagg atggctgccc cgagccatgg gccgcggcgg agctagcgcg gagcgcccga   300
ccctcgaccc ccgagtcccg gagccggccc cgcgcgggc cacgcgtccc tcgggcgctg    360
gttcctaagg aggacgacag caccagcttc tcctttctcc cttcccttcc ctgccccgca   420
ctcctccccc tgctcgctgt tgttgtgtgt cagcacttgg ctggggactt cttgaacttg   480
cagggagaat aacttgcgca ccccactttg cgccggtgcc tttgcccag cggagcctgc    540
ttcgccatct ccgagcccca ccgccctcc actcctcggc cttgcccgac actgagacgc    600
tgttcccagc gtgaaaagag agactgcgcg gccggcaccc gggagaagga ggaggcaaag   660
aaaaggaacg gacattcggt ccttgcgcca ggtcctttga ccagagtttt tccatgtgga   720
cgctctttca atggacgtgt ccccgcgtgc ttcttagacg gactgcggtc tcctaaaggt   780 cgacc atg gtg gcc ggg acc cgc tgt ctt cta gcg ttg ctg ctt ccc cag   830
      Met Val Ala Gly Thr Arg Cys Leu Leu Ala Leu Leu Leu Pro Gln
       1               5                  10                  15 gtc ctc ctg ggc ggc gcg gct ggc ctc gtt ccg gag ctg ggc cgc agg      878
Val Leu Leu Gly Gly Ala Ala Gly Leu Val Pro Glu Leu Gly Arg Arg
                 20                  25                  30 aag ttc gcg gcg gcg tcg tcg ggc cgc ccc tca tcc cag ccc tct gac     926
Lys Phe Ala Ala Ala Ser Ser Gly Arg Pro Ser Ser Gln Pro Ser Asp
                 35                  40                  45
```

UNITED STATES PATENT AND TRADEMARK OFFICE
CERTIFICATE OF CORRECTION

PATENT NO. : 7,251,568 B2
APPLICATION NO. : 10/329056
DATED : July 31, 2007
INVENTOR(S) : Debra D. Pittman et al.

It is certified that error appears in the above-identified patent and that said Letters Patent is hereby corrected as shown below:

```
gag gtc ctg agc gag ttc gag ttg cgg ctg ctc agc atg ttc ggc ctg      974
Glu Val Leu Ser Glu Phe Glu Leu Arg Leu Leu Ser Met Phe Gly Leu
        50              55                  60 aaa cag aga ccc acc ccc agc agg gac gcc gtg gtg ccc ccc tac atg     1022
Lys Gln Arg Pro Thr Pro Ser Arg Asp Ala Val Val Pro Pro Tyr Met
        65              70                  75 cta gac ctg tat cgc agg cac tca ggt cag ccg ggc tca ccc gcc cca     1070
Leu Asp Leu Tyr Arg Arg His Ser Gly Gln Pro Gly Ser Pro Ala Pro
80              85              90                  95 gac cac cgg ttg gag agg gca gcc agc cga gcc aac act gtg cgc agc     1118
Asp His Arg Leu Glu Arg Ala Ala Ser Arg Ala Asn Thr Val Arg Ser
            100             105                 110 ttc cac cat gaa gaa tct ttg gaa gaa cta cca gaa acg agt ggg aaa     1166
Phe His His Glu Glu Ser Leu Glu Glu Leu Pro Glu Thr Ser Gly Lys
                115             120             125 aca acc cgg aga ttc ttc ttt aat tta agt tct atc ccc acg gag gag     1214
Thr Thr Arg Arg Phe Phe Phe Asn Leu Ser Ser Ile Pro Thr Glu Glu
        130             135                 140 ttt atc acc tca gca gag ctt cag gtt ttc cga gaa cag atg caa gat     1262
Phe Ile Thr Ser Ala Glu Leu Gln Val Phe Arg Glu Gln Met Gln Asp
    145                 150             155 gct tta gga aac aat agc agt ttc cat cac cga att aat att tat gaa     1310
Ala Leu Gly Asn Asn Ser Ser Phe His His Arg Ile Asn Ile Tyr Glu
160             165             170             175 atc ata aaa cct gca aca gcc aac tcg aaa ttc ccc gtg acc aga ctt     1358
Ile Ile Lys Pro Ala Thr Ala Asn Ser Lys Phe Pro Val Thr Arg Leu
            180             185             190 ttg gac acc agg ttg gtg aat cag aat gca agc agg tgg gaa agt ttt     1406
Leu Asp Thr Arg Leu Val Asn Gln Asn Ala Ser Arg Trp Glu Ser Phe
            195             200             205 gat gtc acc ccc gct gtg atg cgg tgg act gca cag gga cac gcc aac     1454
Asp Val Thr Pro Ala Val Met Arg Trp Thr Ala Gln Gly His Ala Asn
        210             215             220 cat gga ttc gtg gtg gaa gtg gcc cac ttg gag gag aaa caa ggt gtc     1502
His Gly Phe Val Val Glu Val Ala His Leu Glu Glu Lys Gln Gly Val
        225             230             235 tcc aag aga cat gtt agg ata agc agg tct ttg cac caa gat gaa cac     1550
Ser Lys Arg His Val Arg Ile Ser Arg Ser Leu His Gln Asp Glu His
240             245             250             255 agc tgg tca cag ata agg cca ttg cta gta act ttt ggc cat gat gga     1598
Ser Trp Ser Gln Ile Arg Pro Leu Leu Val Thr Phe Gly His Asp Gly
                260             265             270 aaa ggg cat cct ctc cac aaa aga gaa aaa cgt caa gcc aaa cac aaa     1646
Lys Gly His Pro Leu His Lys Arg Glu Lys Arg Gln Ala Lys His Lys
            275             280             285 cag cgg aaa cgc ctt aag tcc agc tgt aag aga cac cct ttg tac gtg     1694
Gln Arg Lys Arg Leu Lys Ser Ser Cys Lys Arg His Pro Leu Tyr Val
        290             295             300
```

Page 13 of 16

UNITED STATES PATENT AND TRADEMARK OFFICE
CERTIFICATE OF CORRECTION

PATENT NO.      : 7,251,568 B2
APPLICATION NO. : 10/329056
DATED           : July 31, 2007
INVENTOR(S)     : Debra D. Pittman et al.

It is certified that error appears in the above-identified patent and that said Letters Patent is hereby corrected as shown below:

```
gac ttc agt gac gtg ggg tgg aat gac tgg att gtg gct ccc ccg ggg   1742
Asp Phe Ser Asp Val Gly Trp Asn Asp Trp Ile Val Ala Pro Pro Gly
        305                 310                 315 tat cac gcc ttt tac tgc cac gga gaa tgc cct ttt cct ctg gct gat   1790
Tyr His Ala Phe Tyr Cys His Gly Glu Cys Pro Phe Pro Leu Ala Asp
320                 325                 330                 335 cat ctg aac tcc act aat cat gcc att gtt cag acg ttg gtc aac tct   1838
His Leu Asn Ser Thr Asn His Ala Ile Val Gln Thr Leu Val Asn Ser
                340                 345                 350 gtt aac tct aag att cct aag gca tgc tgt gtc ccg aca gaa ctc agt   1886
Val Asn Ser Lys Ile Pro Lys Ala Cys Cys Val Pro Thr Glu Leu Ser
        355                 360                 365 gct atc tcg atg ctg tac ctt gac gag aat gaa aag gtt gta tta aag   1934
Ala Ile Ser Met Leu Tyr Leu Asp Glu Asn Glu Lys Val Val Leu Lys
370                 375                 380 aac tat cag gac atg gtt gtg gag ggt tgt ggg tgt cgc tag           1976
Asn Tyr Gln Asp Met Val Val Glu Gly Cys Gly Cys Arg
        385                 390                 395
```

| | | | |
|---|---|---|---|
| tacagcaaaa | ttaaatacat | aaatatatat | atatatatat | attttagaaa | aaagaaaaaa | 2036 |
| acaaacaaac | aaaaaaaccc | caccccagtt | gacactttaa | tatttcccaa | tgaagacttt | 2096 |
| atttatggaa | tggaatggaa | aaaaaaacag | ctattttgaa | aatatattta | tatctacgaa | 2156 |
| aagaagttgg | gaaaacaaat | attttaatca | gagaattatt | ccttaaagat | ttaaaatgta | 2216 |
| tttagttgta | cattttatat | gggttcaacc | ccagcacatg | aagtataatg | gtcagattta | 2276 |
| ttttgtatct | atttactatt | ataaccactt | tttaggaaaa | aaatagctaa | tttgtattta | 2336 |
| tatgtaatca | aaagaagtat | cgggtttgta | cataattttc | caaaaattgt | agttgttttc | 2396 |
| agttgtgtgt | atttaagatg | aaaagtctac | atggaaggtt | actctggcaa | agtgcttagc | 2456 |
| acgtttgctt | ttttgcagtg | ctactgttga | gttcacaagt | tcaagtccag | aaaaaaaaag | 2516 |
| tggataatcc | actctgctga | ctttcaagat | tattatatta | ttcaattctc | aggaatgttg | 2576 |
| cagagtgatt | gtccaatcca | tgagaattta | catccttatt | aggtggaata | tttggataag | 2636 |
| aaccagacat | tgctgatcta | ttatagaaac | tctcctcctg | ccccttaatt | tacagaaaga | 2696 |
| ataaagcagg | atccatagaa | ataattagga | aaacgatgaa | cctgcaggaa | agtgaatgat | 2756 |
| ggtttgttgt | tcttctttcc | taaattagtg | atcccttcaa | aggggctgat | ctggccaaag | 2816 |
| tattcaataa | aacgtaagat | ttcttcatta | ttgatattgt | ggtcatatat | atttaaaatt | 2876 |
| gatatctcgt | ggccctcatc | aagggttgga | aatttatttg | tgttttacct | ttacctcatc | 2936 |
| tgagagctct | ttattctcca | aagaacccag | ttttctaact | ttttgcccaa | cacgcagcaa | 2996 |
| aattatgcac | atcgtgtttt | ctgcccaccc | tctgttctct | gacctatcag | cttgcttttc | 3056 |
| tttccaaggt | tgtgtgtttg | aacacatttc | tccaaatgtt | aaacctattt | cagataataa | 3116 |
| atatcaaatc | tctggcattt | cattctataa | agtc | | | 3150 |

UNITED STATES PATENT AND TRADEMARK OFFICE
CERTIFICATE OF CORRECTION

| | |
|---|---|
| PATENT NO. | : 7,251,568 B2 |
| APPLICATION NO. | : 10/329056 |
| DATED | : July 31, 2007 |
| INVENTOR(S) | : Debra D. Pittman et al. |

It is certified that error appears in the above-identified patent and that said Letters Patent is hereby corrected as shown below:

```
<210>  6
<211>  396
<212>  PRT
<213>  Homo sapiens

<400>  6

Met Val Ala Gly Thr Arg Cys Leu Leu Ala Leu Leu Leu Pro Gln Val
 1               5                  10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220
```

UNITED STATES PATENT AND TRADEMARK OFFICE
CERTIFICATE OF CORRECTION

PATENT NO.        : 7,251,568 B2
APPLICATION NO.   : 10/329056
DATED             : July 31, 2007
INVENTOR(S)       : Debra D. Pittman et al.

It is certified that error appears in the above-identified patent and that said Letters Patent is hereby corrected as shown below:

```
Gly Phe Val Val Glu Val Ala His Leu Glu Glu Lys Gln Gly Val Ser
225             230             235             240

Lys Arg His Val Arg Ile Ser Arg Ser Leu His Gln Asp Glu His Ser
            245             250             255

Trp Ser Gln Ile Arg Pro Leu Leu Val Thr Phe Gly His Asp Gly Lys
            260             265             270

Gly His Pro Leu His Lys Arg Glu Lys Arg Gln Ala Lys His Lys Gln
            275             280             285

Arg Lys Arg Leu Lys Ser Ser Cys Lys Arg His Pro Leu Tyr Val Asp
    290             295             300

Phe Ser Asp Val Gly Trp Asn Asp Trp Ile Val Ala Pro Pro Gly Tyr
305             310             315             320

His Ala Phe Tyr Cys His Gly Glu Cys Pro Phe Pro Leu Ala Asp His
            325             330             335

Leu Asn Ser Thr Asn His Ala Ile Val Gln Thr Leu Val Asn Ser Val
            340             345             350

Asn Ser Lys Ile Pro Lys Ala Cys Cys Val Pro Thr Glu Leu Ser Ala
    355             360             365

Ile Ser Met Leu Tyr Leu Asp Glu Asn Glu Lys Val Val Leu Lys Asn
    370             375             380

Tyr Gln Asp Met Val Val Glu Gly Cys Gly Cys Arg
385             390             395
```

--.

Signed and Sealed this

Twenty-ninth Day of December, 2009

David J. Kappos
*Director of the United States Patent and Trademark Office*